(12) United States Patent
Damude et al.

(10) Patent No.: US 7,863,502 B2
(45) Date of Patent: Jan. 4, 2011

(54) DELTA-8 DESATURASES AND THEIR USE IN MAKING POLYUNSATURATED FATTY ACIDS

(75) Inventors: Howard Damude, Hockessin, DE (US); Quinn Qun Zhu, West Chester, PA (US); Zhixiong Xue, Chadds Ford, PA (US)

(73) Assignee: E.I. duPont de Nemours and Company, Wilmington, DE (US)

( * ) Notice: Subject to any disclaimer, the term of this patent is extended or adjusted under 35 U.S.C. 154(b) by 583 days.

(21) Appl. No.: 11/876,115

(22) Filed: Oct. 22, 2007

(65) Prior Publication Data

US 2008/0095915 A1    Apr. 24, 2008

Related U.S. Application Data

(60) Provisional application No. 60/853,563, filed on Oct. 23, 2006.

(51) Int. Cl.
```
A01H 5/00      (2006.01)
C12N 15/82     (2006.01)
C12N 5/10      (2006.01)
C07H 21/04     (2006.01)
```
(52) U.S. Cl. .................. 800/298; 800/281; 435/419; 536/23.2
(58) Field of Classification Search ............ None
See application file for complete search history.

(56) References Cited

U.S. PATENT DOCUMENTS

| | | | |
|---|---|---|---|
| 5,968,809 | A | 10/1999 | Knutzon et al. |
| 5,972,664 | A | 10/1999 | Knutzon et al. |
| 6,051,754 | A | 4/2000 | Knutzon |
| 6,075,183 | A | 6/2000 | Knutzon et al. |
| 6,136,574 | A | 10/2000 | Knutzon et al. |
| 6,410,288 | B1 | 6/2002 | Knutzon et al. |
| 6,825,017 | B1 | 11/2004 | Browse et al. |
| 7,256,033 | B2 * | 8/2007 | Damude et al. .......... 435/252.3 |
| 2005/0273885 | A1 | 12/2005 | Singh et al. |
| 2005/0287652 | A1 | 12/2005 | Damude et al. |
| 2007/0118929 | A1 | 5/2007 | Damude et al. |

FOREIGN PATENT DOCUMENTS

| WO | WO98/46763 | 10/1998 |
|---|---|---|
| WO | WO98/46764 | 10/1998 |
| WO | WO00/12720 | 3/2000 |
| WO | WO00/34439 | 6/2000 |
| WO | WO00/40705 | 7/2000 |
| WO | WO2004/057001 | 7/2004 |
| WO | WO2004/071178 | 8/2004 |
| WO | WO2004/071467 | 8/2004 |
| WO | WO2004/101753 | 11/2004 |
| WO | WO2004/101757 | 11/2004 |
| WO | WO2005/012316 | 2/2005 |
| WO | WO2005/103253 | 11/2005 |
| WO | WO2006/012325 | 2/2006 |
| WO | WO2006/012326 | 2/2006 |

OTHER PUBLICATIONS

Thierry Tonon et al., Fatty acid desaturases from the microalga *Thalassiosira pseudonana*, The FEBS Journal, vol. 272, pp. 3401-3412, Jul. 1, 2005.
F. Garcia-Maroto et al., Evolution of 'front-end' desaturases in Echium, Bochemical Systematics and Ecology, vol. 34, pp. 327-337, Apr. 1, 2006.
Maria Alejandra Nudelman, Phylogeny of Euglenophyceae Based on Small Subunit rDNA Sequences: Taxonomic Implications, (2003) J.Phycol. 39:226-235.
U.S. Appl. No. 60/739,989, filed Nov. 23, 2005, E. I. du Pont de Nemours and Company.
U.S. Appl. No. 60/795,810, filed Apr. 28, 2006, E. I. du Pont de Nemours and Company.
U.S. Appl. No. 11/166,003, filed Jun. 24, 2005, E. I. du Pont de Nemours and Company.
U.S. Appl. No. 11/264,737, filed Nov. 1, 2005, E. I. du Pont de Nemours and Company.
U.S. Appl. No. 11/264,784, filed Nov. 1, 2005, E. I. du Pont de Nemours and Company.
U.S. Appl. No. 11/265,761, filed Nov. 2, 2005, E. I. du Pont de Nemours and Company.
U.S. Appl. No. 11/737,772, filed Apr. 20, 2007, E. I. du Pont de Nemours and Company.
U.S. Appl. No. 11/166,993, filed Jun. 24, 2005, E. I. du Pont de Nemours and Company.
Wallis et al., Archives of Biochemistry and Biophysics, vol. 365(2):307-316, 1999, "The Delta8-Desaturase of *Euglena gracilis*:An Alternate Pathway for Synthesis of 20-Carbon Polyunsaturated Fatty Acids".
National Center for Biotechnology Information Database, Accession No. AAD45877 (GI 5639724), Wallis et al., "The Delta8-desaturase of *Euglena gracilis*: an alternate pathway for synthesis of 20-carbon polyunsaturated fatty acids", 1999.
National Center for Biotechnology Information Database, Accession No. AF139720 (GI 5639723), Wallis et al., "The Delta8-desaturase of *Euglena gracilis*: an alternate pathway for synthesis of 20-carbon polyunsaturated fatty acids", 1999.
Sayanova et al. (FEBS Letters, vol. 580, pp. 1946-1952 (2006), "The alternative pathway C20 Delta8-desaturase from the non-photosynthetic organism *Acanthamoeba castellanii* is an atypical cytochrome b5-fusion desaturase".

* cited by examiner

*Primary Examiner*—Elizabeth F McElwain
(74) *Attorney, Agent, or Firm*—Alston & Bird LLP

(57) ABSTRACT

Isolated nucleic acid fragments and recombinant constructs comprising such fragments encoding delta-8 desaturases along with a method of making long-chain polyunsaturated fatty acids (PUFAs) using these delta-8 desaturases in plants and oleaginous yeast.

20 Claims, 23 Drawing Sheets

FIG. 5

Fatty Acid Composition (wt. %)

| Event | 16:0 | 18:0 | 18:1 | LA | GLA | ALA | EDA | DGLA | ERA | ETA | C20 % delta-8 desat | EDA % delta-8 desat | ERA % delta-8 desat | Ratio (EDA/ERA) % desat |
|---|---|---|---|---|---|---|---|---|---|---|---|---|---|---|
| 1974-1-1-1 | 14.5 | 3.6 | 14.9 | 40.3 | 0.0 | 13.4 | 9.9 | 1.2 | 1.7 | 0.4 | 11.8 | 10.7 | 17.9 | 0.6 |
| 1974-1-1-2 | 14.7 | 4.8 | 19.3 | 37.6 | 0.0 | 12.5 | 8.0 | 1.4 | 1.2 | 0.5 | 17.3 | 15.2 | 29.2 | 0.5 |
| 1974-1-1-3 | 14.0 | 3.7 | 14.5 | 39.0 | 0.0 | 12.9 | 11.8 | 1.8 | 1.9 | 0.5 | 14.4 | 13.1 | 22.0 | 0.6 |
| 1974-1-1-4 | 15.9 | 2.7 | 10.5 | 41.9 | 0.0 | 17.0 | 8.0 | 1.7 | 1.5 | 0.7 | 20.1 | 17.8 | 29.9 | 0.6 |
| 1974-1-1-5 | 15.9 | 4.1 | 11.3 | 41.2 | 0.0 | 16.4 | 4.7 | 5.0 | 0.5 | 1.0 | 53.5 | 51.4 | 67.5 | 0.8 |
| 1974-1-1-6 | 15.3 | 3.2 | 10.5 | 40.6 | 0.0 | 15.8 | 9.8 | 2.1 | 1.8 | 0.8 | 19.9 | 17.8 | 29.6 | 0.6 |
| 1974-1-2-1 | 13.8 | 4.0 | 13.8 | 31.2 | 0.0 | 7.1 | 16.1 | 10.0 | 2.1 | 1.9 | 39.7 | 38.3 | 48.6 | 0.8 |
| 1974-1-2-2 | 14.5 | 2.9 | 14.3 | 29.0 | 0.0 | 8.5 | 16.4 | 9.9 | 2.3 | 2.2 | 39.4 | 37.7 | 49.5 | 0.8 |
| 1974-1-2-3 | 14.0 | 4.0 | 11.4 | 36.7 | 0.0 | 9.8 | 15.9 | 4.7 | 2.4 | 1.1 | 24.1 | 23.0 | 30.2 | 0.8 |
| 1974-1-2-4 | 15.2 | 3.1 | 10.9 | 36.7 | 0.0 | 10.3 | 13.5 | 6.7 | 2.0 | 1.6 | 34.8 | 33.1 | 44.3 | 0.7 |
| 1974-1-2-5 | 13.8 | 3.8 | 14.0 | 36.1 | 0.0 | 10.0 | 12.6 | 6.6 | 1.7 | 1.4 | 36.0 | 34.4 | 46.2 | 0.7 |
| 1974-1-2-6 | 13.2 | 2.8 | 14.6 | 35.0 | 0.0 | 8.8 | 17.1 | 4.2 | 3.1 | 1.2 | 21.2 | 19.7 | 28.4 | 0.7 |
| 1974-3-1-1 | 14.7 | 6.2 | 20.1 | 27.9 | 0.0 | 11.6 | 10.5 | 5.0 | 2.1 | 1.8 | 35.0 | 32.3 | 45.4 | 0.7 |
| 1974-3-1-2 | 15.8 | 5.2 | 17.4 | 27.2 | 0.0 | 14.1 | 10.7 | 5.0 | 2.7 | 1.8 | 34.0 | 32.1 | 40.3 | 0.8 |
| 1974-3-1-3 | 15.4 | 5.5 | 18.3 | 27.3 | 0.0 | 12.2 | 12.6 | 4.6 | 2.6 | 1.5 | 28.5 | 26.6 | 36.7 | 0.7 |
| 1974-3-1-4 | 16.2 | 6.2 | 19.7 | 25.1 | 0.0 | 12.8 | 9.7 | 5.5 | 2.7 | 2.1 | 38.0 | 36.2 | 43.5 | 0.8 |
| 1974-3-1-5 | 16.2 | 4.7 | 19.1 | 28.7 | 0.0 | 13.5 | 9.8 | 4.3 | 2.2 | 1.4 | 32.5 | 30.6 | 39.7 | 0.8 |
| 1974-3-1-6 | 15.8 | 5.3 | 19.9 | 26.3 | 0.0 | 13.0 | 9.9 | 5.6 | 2.4 | 1.9 | 37.7 | 36.1 | 43.7 | 0.8 |
| 1974-1-4-1 | 13.6 | 3.2 | 7.0 | 39.4 | 0.0 | 10.2 | 16.8 | 6.3 | 2.3 | 1.1 | 27.7 | 27.2 | 31.1 | 0.9 |
| 1974-1-4-2 | 13.2 | 2.7 | 10.4 | 41.2 | 0.0 | 8.4 | 16.1 | 5.5 | 1.7 | 0.9 | 26.5 | 25.5 | 34.5 | 0.7 |
| 1974-1-4-3 | 13.6 | 3.0 | 8.8 | 36.3 | 0.0 | 7.3 | 17.7 | 9.6 | 2.1 | 1.7 | 36.3 | 35.1 | 44.9 | 0.8 |
| 1974-1-4-4 | 13.6 | 2.9 | 8.2 | 35.8 | 0.0 | 8.4 | 17.8 | 9.3 | 2.4 | 1.6 | 35.1 | 34.2 | 40.6 | 0.8 |
| 1974-1-4-5 | 13.3 | 2.8 | 9.9 | 40.3 | 0.0 | 8.2 | 16.5 | 5.8 | 2.0 | 1.2 | 27.7 | 26.1 | 38.4 | 0.7 |
| 1974-1-4-6 | 13.4 | 4.1 | 10.4 | 41.1 | 0.0 | 9.7 | 13.6 | 4.9 | 1.8 | 1.0 | 27.9 | 26.5 | 36.9 | 0.7 |
| 1974-5-6-1 | 15.3 | 3.8 | 12.5 | 29.6 | 0.0 | 9.0 | 12.2 | 13.7 | 1.1 | 2.9 | 55.5 | 52.9 | 72.7 | 0.7 |
| 1974-5-6-2 | 14.7 | 3.8 | 12.9 | 28.0 | 0.0 | 8.8 | 14.8 | 12.4 | 1.7 | 2.8 | 47.9 | 45.6 | 61.6 | 0.7 |
| 1974-5-6-3 | 15.2 | 3.9 | 9.3 | 27.1 | 0.0 | 9.9 | 14.8 | 14.6 | 1.9 | 3.4 | 52.0 | 49.6 | 64.9 | 0.8 |
| 1974-5-6-4 | 13.4 | 3.9 | 15.0 | 30.3 | 0.1 | 9.4 | 12.1 | 12.0 | 1.2 | 2.6 | 52.2 | 49.7 | 68.1 | 0.7 |
| 1974-5-6-5 | 13.7 | 3.3 | 11.6 | 30.5 | 0.0 | 9.1 | 14.0 | 13.4 | 1.5 | 2.9 | 51.1 | 48.9 | 65.3 | 0.7 |
| 1974-5-6-6 | 15.9 | 2.2 | 8.1 | 30.2 | 0.1 | 12.1 | 15.1 | 11.4 | 2.1 | 2.8 | 45.3 | 43.0 | 57.6 | 0.7 |

FIG. 7A

|  |  |  |  |  |  |  |
|---|---|---|---|---|---|---|
| 1 | MSPKRQAL-PITIDGATYDVSAWVNHHPGGADIIENYRNRDATDAFMVMHSQEAVAKLKR | SEQ ID NO57 (CCMP1491).pro |
| 1 | MSPKREAL-PITIDGTTYDVSAWVNHHPGGADIMENYRNRDATDVFMVMHSHDALNKLKR | SEQ ID NO47 (CCMP389).pro |
| 1 | MSPKRDAL-PLTIDGTTYDVSAWVNHHPGGAQIIENYRNRDATDVFMVMHSQQALNKLKR | SEQ ID NO49 (CCMP1594).pro |
| 1 | MKSKRQALSPLQLMEQTYDV---VNFHPGGAEIIENYQGRDATDAFMVMHFQEAFDKLKR | SEQ ID NO98 (Euglena gracilis).pro |
| 1 | MKSKRQAL-PLTIDGTTYDVSAWVNFHPGGAEIIENYQGRDATDAFMVMHSQEAFDKLKR | SEQ ID NO112 (Euglena gracilis).pro |
| 60 | MPVMEPSSPDTPVAPKPKRDEPQEDFRKLREEFISKGMFETSFLWYFYKTSTTVGLMVLS | SEQ ID NO57 (CCMP1491).pro |
| 60 | MPVMEPTSP---RSPKTPNDEVAEDFRKLRKDMIAKGMFNASPLFYVYKSATTVALGALA | SEQ ID NO47 (CCMP389).pro |
| 60 | MPVMEPSSP---LTPKSPSDDISXDFRKLRNSMVEKGMFNASPLFYVYKSLTTVALGAVG | SEQ ID NO49 (CCMP1594).pro |
| 58 | MPKINPSFE---LPPQAAVNEAQEDFRKLREELIATGMFDASPLWYSYKISTTLGLGVLG | SEQ ID NO98 (Euglena gracilis).pro |
| 60 | MPKINPSSE---LPPQAAVNEAQEDFRKLREELIATGMFDASPLWYSYKISTTLGLGVLG | SEQ ID NO112 (Euglena gracilis).pro |
| 120 | ILMTVYTNWYFTAALVLGVCYQQLGWLSHDYCHHQVFTNRKINDAFGLFFGNVMQGYSQT | SEQ ID NO57 (CCMP1491).pro |
| 117 | ILMVMHLQWYYIPAILLGLCYQQLGWLAHDYCHHQVFSNRAYNNFAGLVFGNVMQGYSGT | SEQ ID NO47 (CCMP389).pro |
| 117 | VLMVMYLQWYYVSAMFLGLCYQQLGWVAHDYAHHQVFTNRDYGNLGGLFFGXLVLQGYSLT | SEQ ID NO49 (CCMP1594).pro |
| 115 | YFLMVQYQMYFIGAVLLGMHYQQMGWLSHDICHHQTFKNRWNNLVGLVFGNGLQGFSVT | SEQ ID NO98 (Euglena gracilis).pro |
| 117 | YFLMVQYQMYFIGAVLLGMHYQQMGWLSHDICHHQTFKNRWNNLVGLVFGNGLQGFSVT | SEQ ID NO112 (Euglena gracilis).pro |
| 180 | WWKDRHNGHHAATNVVGHDPDIDNLPILAWSPEDVKRATPSTRNLIKYQQYYFIPTIASL | SEQ ID NO57 (CCMP1491).pro |
| 177 | WWKDRHNGHHAATNVQGHDPDIDDLPVLAWSPEDVKNAGPTTRKLIKWQQYYFLPTIATL | SEQ ID NO47 (CCMP389).pro |
| 177 | WWKDRHNGHHAATNVQGHDPDIDNLPVLAWSPEDVKNAGPGTRNIIKYQQYYFLPTIAIL | SEQ ID NO49 (CCMP1594).pro |
| 175 | CWKDRHNAHHSATNVQGHDPDIDNLPPLAWSEDDVTRASPISRKLIQFQQYYFLVICILL | SEQ ID NO98 (Euglena gracilis).pro |
| 177 | WWKDRHNAHHSATNVQGHDPDIDNLPLLAWSEDDVTRASPISRKLIQFQQYYFLVICILL | SEQ ID NO112 (Euglena gracilis).pro |

FIG. 7B

```
       250        260        270        280        290        300
240  RFIWCLQSIGGVMSYKSEERNLYYKRRYTKEAIGLALPWVLKATF-YCSAMPSFATGLGC   SEQ ID NO57 (CCMP1491).pro
237  RFIWCFQSILAVMAYKTDARNIYYQRQYAKEAVGLALHWILKGVFMFCY-MPGILTGLAF   SEQ ID NO47 (CCMP389).pro
237  RFIWCFQSILGVMSYKTDSXNLYYKRQYRREAAGLALHWILKSVFLFCY-MPSFLTGLAF   SEQ ID NO49 (CCMP1594).pro
235  RFIWCFQCVLTVRSLK-DRDNQFYRSQYKKEAIGLALHWTLKALFHLFF-MPSILTSLLV   SEQ ID NO98 (Euglena gracilis).pro
237  RFIWCFQSVLTVRSLK-DRDNQFYRSQYKKEAIGLALHWTLKTLFHLFF-MPSILTSLLV   SEQ ID NO112 (Euglena gracilis).pro 310        320        330        340        350        360
299  FLISELLGGFGIAIVVFLNHYPLDKVEETVWDEHGFSASQIHETLNIKPGLLTDWVFGGL   SEQ ID NO57 (CCMP1491).pro
296  FLISECLGGFGIAIVVFLNHYPLEKVEESVWDSHGFCAGQIHTTMNIQRGVIVDWFFGGL   SEQ ID NO47 (CCMP389).pro
296  FLISECLGGFGIAIVVFLNHYPLDKVEESVWDGHGFCAGQILTTMNIQRGLITDWFFGGL   SEQ ID NO49 (CCMP1594).pro
293  FFVSELVGGFGIAIVVFMNHYPLEKIGDPVWDGHGFSVGQIHETMNIRRGIITDWFFGGL   SEQ ID NO98 (Euglena gracilis).pro
295  FFVSELVGGFGIAIVVFMNHYPLEKIGDSVWDGHGFSVGQIHETMNIRRGIITDWFFGGL   SEQ ID NO112 (Euglena gracilis).pro 370        380        390        400        410        420
359  NYQIEHHLWPNMPRHNLTAASLEVQKLCAKHNLPYRAPAIIPGVQKLVSFLGEIAQLA--   SEQ ID NO57 (CCMP1491).pro
356  NYQIEHHLWPTLPRHHLKAASFEVEKICQKHKLPYRAPPMSDGVAQLLGFLGKIAKLA--   SEQ ID NO47 (CCMP389).pro
356  NYQIEHHLWPNLPRHHLKAVSFEVEKLCQKHNLPYRAPPMHTGVAQLLGYLGKIAQLA--   SEQ ID NO49 (CCMP1594).pro
353  NYQIEHHLWPTLPRHNLTAVSYQVEQLCQKHNLPYRNPLPHEGLVILLRYLAVFARMAEK   SEQ ID NO98 (Euglena gracilis).pro
355  NYQIEHHLWPTLPRHNLTAVSYQVEQLCQKHNLPYRNPLPHEGLVILLRYLAVFARMAEK   SEQ ID NO112 (Euglena gracilis).pro 417  ---AVPE     SEQ ID NO57 (CCMP1491).pro
414  ---AVPV     SEQ ID NO47 (CCMP389).pro
414  ---AVPV     SEQ ID NO49 (CCMP1594).pro
413  QPAGKAL     SEQ ID NO98 (Euglena gracilis).pro
415  QP          SEQ ID NO112 (Euglena gracilis).pro
```

FIG. 10

| Event | Fatty acid composition (wt.%) | | | | | | | | | | C20 % delta-8 desat | EDA % delta-8 desat | ERA % delta-8 desat | Ratio (EDA:ERA) % desat |
|---|---|---|---|---|---|---|---|---|---|---|---|---|---|---|
| | 16:0 | 18:0 | 18:1 | LA | GLA | ALA | EDA | DGLA | ERA | ETA | | | | |
| 2024-2-11-1 | 20.3 | 6.6 | 16.3 | 29.6 | 0.0 | 12.3 | 4.9 | 6.7 | 1.0 | 2.4 | 60.7 | 57.7 | 71.1 | 0.8 |
| 2024-2-11-2 | 17.1 | 4.8 | 21.7 | 28.7 | 0.0 | 12.1 | 4.8 | 7.4 | 0.7 | 2.7 | 64.7 | 60.5 | 79.9 | 0.8 |
| 2024-2-11-3 | 18.3 | 5.1 | 17.7 | 30.7 | 0.0 | 13.6 | 4.5 | 6.7 | 0.9 | 2.5 | 63.3 | 60.1 | 74.1 | 0.8 |
| 2024-2-11-4 | 18.9 | 5.0 | 13.2 | 32.5 | 0.0 | 14.7 | 5.0 | 7.2 | 0.9 | 2.7 | 62.6 | 59.0 | 75.1 | 0.8 |
| 2024-2-11-5 | 21.1 | 5.9 | 17.5 | 29.1 | 0.1 | 11.5 | 5.4 | 6.2 | 1.0 | 2.3 | 57.2 | 53.5 | 70.5 | 0.8 |
| 2024-2-11-6 | 19.5 | 6.2 | 17.7 | 29.7 | 0.0 | 11.9 | 5.7 | 6.5 | 0.8 | 2.1 | 57.0 | 53.3 | 72.5 | 0.7 |
| 2024-3-5-1 | 16.9 | 4.9 | 17.2 | 23.2 | 0.0 | 7.5 | 11.8 | 13.2 | 1.7 | 3.8 | 55.7 | 52.8 | 69.4 | 0.8 |
| 2024-3-5-2 | 17.1 | 5.3 | 24.1 | 23.2 | 0.0 | 9.3 | 8.1 | 9.0 | 1.2 | 2.7 | 55.6 | 52.6 | 68.9 | 0.8 |
| 2024-3-5-3 | 15.3 | 6.1 | 34.5 | 16.8 | 0.0 | 6.0 | 7.8 | 9.7 | 1.0 | 3.0 | 59.1 | 55.7 | 73.9 | 0.8 |
| 2024-3-5-4 | 17.4 | 7.2 | 24.5 | 20.8 | 0.0 | 6.5 | 9.0 | 10.7 | 1.3 | 2.5 | 55.9 | 54.1 | 65.2 | 0.8 |
| 2024-3-5-5 | 17.6 | 6.6 | 22.5 | 22.1 | 0.0 | 8.8 | 8.3 | 9.8 | 1.5 | 2.8 | 56.1 | 54.0 | 64.8 | 0.8 |
| 2024-3-5-6 | 17.0 | 6.7 | 23.2 | 19.8 | 0.0 | 6.1 | 10.7 | 11.9 | 1.4 | 3.2 | 55.5 | 52.8 | 68.6 | 0.8 |
| 2024-3-9-1 | 16.9 | 5.1 | 24.7 | 16.5 | 0.0 | 6.2 | 11.2 | 14.1 | 1.5 | 3.7 | 58.3 | 55.7 | 70.8 | 0.8 |
| 2024-3-9-2 | 16.2 | 5.2 | 19.9 | 20.0 | 0.0 | 6.1 | 11.5 | 16.0 | 1.3 | 3.9 | 60.8 | 58.1 | 74.8 | 0.8 |
| 2024-3-9-3 | 16.4 | 5.6 | 25.3 | 17.1 | 0.0 | 5.7 | 10.4 | 14.3 | 1.4 | 3.8 | 60.5 | 57.9 | 73.1 | 0.8 |
| 2024-3-9-4 | 16.3 | 5.5 | 28.7 | 15.9 | 0.0 | 6.4 | 9.2 | 13.1 | 1.3 | 3.7 | 61.4 | 58.7 | 73.2 | 0.8 |
| 2024-3-9-5 | 15.8 | 6.4 | 27.6 | 14.2 | 0.0 | 5.5 | 10.3 | 15.2 | 1.3 | 3.7 | 62.1 | 59.6 | 74.6 | 0.8 |
| 2024-3-9-6 | 16.3 | 5.0 | 22.2 | 17.9 | 0.0 | 5.6 | 11.8 | 15.9 | 1.4 | 3.8 | 59.9 | 57.4 | 73.1 | 0.8 |
| 2024-3-11-1 | 17.9 | 6.5 | 24.3 | 22.9 | 0.0 | 7.9 | 8.1 | 9.1 | 1.0 | 2.3 | 55.5 | 53.1 | 68.2 | 0.8 |
| 2024-3-11-2 | 16.0 | 6.2 | 29.6 | 20.5 | 0.0 | 6.4 | 9.4 | 8.3 | 1.2 | 2.3 | 49.9 | 46.8 | 65.3 | 0.7 |
| 2024-3-11-3 | 18.1 | 7.6 | 24.5 | 18.9 | 0.0 | 5.4 | 9.7 | 11.9 | 1.1 | 2.9 | 57.9 | 55.2 | 72.3 | 0.8 |
| 2024-3-11-4 | 16.3 | 6.5 | 27.0 | 21.7 | 0.0 | 6.7 | 8.2 | 9.8 | 1.1 | 2.5 | 56.7 | 54.3 | 68.5 | 0.8 |
| 2024-3-11-5 | 16.0 | 6.4 | 28.5 | 19.8 | 0.0 | 6.3 | 8.3 | 10.8 | 1.1 | 2.8 | 59.3 | 56.6 | 72.3 | 0.8 |
| 2024-3-11-6 | 17.2 | 7.2 | 29.1 | 19.3 | 0.0 | 5.4 | 8.3 | 9.9 | 1.1 | 2.5 | 56.8 | 54.2 | 69.5 | 0.8 |
| 2024-3-15-1 | 16.9 | 4.3 | 15.7 | 28.9 | 0.3 | 11.0 | 6.9 | 11.5 | 1.1 | 3.4 | 65.0 | 62.4 | 75.9 | 0.8 |
| 2024-3-15-2 | 15.8 | 4.2 | 19.5 | 27.4 | 0.3 | 7.9 | 7.5 | 13.5 | 0.7 | 3.1 | 66.8 | 64.2 | 80.9 | 0.8 |
| 2024-3-15-3 | 19.3 | 7.0 | 19.3 | 22.8 | 0.0 | 9.1 | 11.4 | 6.5 | 2.9 | 1.7 | 36.5 | 36.3 | 37.2 | 1.0 |
| 2024-3-15-4 | 16.9 | 3.7 | 9.6 | 30.2 | 0.2 | 13.2 | 7.4 | 13.4 | 2.0 | 3.2 | 63.7 | 64.4 | 60.8 | 1.1 |
| 2024-3-15-5 | 17.0 | 4.5 | 12.9 | 29.8 | 0.1 | 13.6 | 6.9 | 10.6 | 1.8 | 2.8 | 60.6 | 60.5 | 60.9 | 1.0 |
| 2024-3-15-6 | 17.7 | 5.5 | 20.4 | 25.2 | 0.3 | 10.7 | 5.4 | 10.7 | 1.0 | 3.2 | 68.7 | 66.7 | 76.5 | 0.9 |

FIG. 14

| Event | Fatty acid composition (wt.%) | | | | | | | | | C20 % delta-8 desat | EDA % delta-8 desat | ERA % delta-8 desat | Ratio (EDA/ERA) % desat |
|---|---|---|---|---|---|---|---|---|---|---|---|---|---|
| | 16:0 | 18:0 | 18:1 | LA | ALA | EDA | DGLA | ERA | ETA | | | | |
| 2108-2-2-1 | 16.1 | 3.9 | 15.9 | 25.3 | 10.7 | 8.6 | 13.3 | 1.0 | 5.3 | 66.0 | 60.8 | 84.4 | 0.7 |
| 2108-2-2-2 | 16.1 | 2.8 | 12.0 | 27.9 | 14.1 | 6.9 | 12.8 | 1.1 | 6.3 | 70.4 | 64.9 | 85.0 | 0.8 |
| 2108-2-2-3 | 16.6 | 4.3 | 13.6 | 27.4 | 12.9 | 6.3 | 12.5 | 0.9 | 5.4 | 71.3 | 66.4 | 85.9 | 0.8 |
| 2108-2-2-4 | 16.5 | 4.2 | 14.9 | 25.8 | 12.0 | 8.4 | 11.7 | 1.1 | 5.3 | 64.0 | 58.3 | 82.2 | 0.7 |
| 2108-2-2-5 | 14.9 | 3.1 | 13.5 | 29.1 | 10.9 | 11.3 | 11.1 | 1.4 | 4.7 | 55.5 | 49.5 | 77.3 | 0.6 |
| 2108-5-2-1 | 17.7 | 4.0 | 16.2 | 31.0 | 11.8 | 6.0 | 9.1 | 0.8 | 3.6 | 65.2 | 60.4 | 81.9 | 0.7 |
| 2108-5-2-2 | 15.9 | 3.0 | 12.1 | 33.2 | 12.8 | 6.6 | 11.0 | 0.9 | 4.4 | 67.0 | 62.5 | 82.2 | 0.8 |
| 2108-5-2-3 | 17.2 | 3.4 | 13.9 | 30.8 | 12.4 | 6.5 | 10.2 | 1.0 | 4.4 | 66.0 | 60.9 | 81.3 | 0.7 |
| 2108-5-2-4 | 16.0 | 3.2 | 12.5 | 33.1 | 12.6 | 6.8 | 10.6 | 1.0 | 4.2 | 65.7 | 60.9 | 81.4 | 0.7 |
| 2108-5-2-5 | 15.3 | 2.5 | 11.6 | 33.0 | 14.6 | 6.4 | 11.1 | 0.9 | 4.5 | 68.1 | 63.4 | 83.1 | 0.8 |
| 2108-5-5-1 | 13.9 | 3.0 | 13.1 | 31.1 | 9.7 | 12.5 | 11.1 | 1.4 | 4.3 | 52.6 | 47.0 | 75.6 | 0.6 |
| 2108-5-5-2 | 16.3 | 3.4 | 12.1 | 30.5 | 12.8 | 10.1 | 9.6 | 1.4 | 3.8 | 53.8 | 48.5 | 73.8 | 0.7 |
| 2108-5-5-3 | 14.9 | 3.5 | 13.2 | 29.9 | 9.9 | 11.8 | 11.3 | 1.4 | 4.3 | 54.1 | 48.8 | 75.7 | 0.6 |
| 2108-5-5-4 | 15.0 | 3.7 | 15.0 | 28.3 | 8.9 | 12.4 | 11.2 | 1.4 | 4.1 | 52.6 | 47.4 | 74.8 | 0.6 |
| 2108-5-5-5 | 15.7 | 2.8 | 11.0 | 32.2 | 14.2 | 10.2 | 8.5 | 1.7 | 3.6 | 50.3 | 45.3 | 67.8 | 0.7 |
| 2108-5-9-1 | 20.3 | 5.8 | 14.9 | 23.1 | 9.7 | 9.6 | 10.6 | 1.7 | 4.2 | 56.8 | 52.5 | 71.3 | 0.7 |
| 2108-5-9-2 | 22.4 | 7.3 | 13.7 | 21.5 | 10.9 | 9.3 | 9.7 | 1.3 | 3.8 | 56.0 | 51.1 | 74.8 | 0.7 |
| 2108-5-9-3 | 24.1 | 7.5 | 18.7 | 18.9 | 7.3 | 9.4 | 9.2 | 1.4 | 3.6 | 54.3 | 49.6 | 72.1 | 0.7 |
| 2108-5-9-4 | 20.6 | 4.3 | 11.6 | 23.8 | 11.2 | 11.0 | 10.9 | 2.0 | 4.5 | 54.3 | 50.0 | 68.9 | 0.7 |
| 2108-5-9-5 | 20.6 | 6.0 | 20.9 | 20.8 | 8.5 | 9.7 | 8.5 | 1.6 | 3.5 | 51.4 | 46.8 | 68.1 | 0.7 |
| 2108-6-6-1 | 21.5 | 5.4 | 9.6 | 22.0 | 7.0 | 10.8 | 17.7 | 1.3 | 4.7 | 64.9 | 62.0 | 78.7 | 0.8 |
| 2108-6-6-2 | 25.4 | 7.9 | 17.2 | 19.0 | 7.4 | 8.1 | 10.5 | 1.3 | 3.4 | 59.7 | 56.4 | 72.7 | 0.8 |
| 2108-6-6-3 | 23.9 | 8.4 | 18.4 | 17.1 | 5.5 | 9.0 | 13.1 | 1.1 | 3.5 | 62.3 | 59.3 | 76.6 | 0.8 |
| 2108-6-6-4 | 21.2 | 7.9 | 19.1 | 19.5 | 5.9 | 9.0 | 12.5 | 1.1 | 3.7 | 61.5 | 58.0 | 77.3 | 0.7 |
| 2108-6-6-5 | 20.1 | 5.0 | 10.8 | 23.7 | 10.0 | 10.3 | 14.3 | 1.5 | 4.3 | 61.1 | 58.0 | 74.1 | 0.8 |

FIG. 16

| Event | Fatty acid composition (wt.%) | | | | | | | | | C20 % delta-8 desat | EDA % delta-8 desat | ERA % delta-8 desat | Ratio (EDA/ERA) % desat |
|---|---|---|---|---|---|---|---|---|---|---|---|---|---|
| | 16:0 | 18:0 | 18:1 | LA | ALA | EDA | DGLA | ERA | ETA | | | | |
| 2107-3-5-1 | 17.6 | 4.3 | 12.1 | 30.3 | 15.6 | 8.1 | 7.0 | 1.5 | 3.5 | 52.3 | 46.4 | 70.4 | 0.7 |
| 2107-3-5-2 | 16.4 | 4.6 | 14.9 | 27.4 | 12.1 | 10.1 | 9.4 | 1.3 | 3.8 | 53.5 | 48.1 | 74.1 | 0.6 |
| 2107-3-5-3 | 16.7 | 4.3 | 12.4 | 29.6 | 13.9 | 9.0 | 9.1 | 1.3 | 3.5 | 55.1 | 50.4 | 72.9 | 0.7 |
| 2107-3-5-4 | 16.8 | 3.8 | 13.0 | 28.9 | 12.1 | 9.3 | 11.0 | 1.1 | 4.1 | 59.2 | 54.3 | 78.1 | 0.7 |
| 2107-3-5-5 | 16.6 | 4.3 | 12.8 | 27.1 | 12.8 | 9.0 | 11.7 | 1.3 | 4.6 | 61.4 | 56.5 | 78.5 | 0.7 |
| 2107-3-11-1 | 15.7 | 4.6 | 14.1 | 27.2 | 12.7 | 8.0 | 11.7 | 1.2 | 4.9 | 64.6 | 59.5 | 81.0 | 0.7 |
| 2107-3-11-2 | 17.5 | 5.1 | 13.9 | 26.1 | 13.0 | 7.3 | 11.3 | 1.0 | 4.9 | 66.0 | 60.8 | 82.4 | 0.7 |
| 2107-3-11-3 | 16.5 | 4.9 | 14.9 | 25.1 | 11.4 | 8.5 | 12.3 | 1.2 | 5.1 | 64.0 | 59.1 | 80.2 | 0.7 |
| 2107-3-11-4 | 16.6 | 4.3 | 12.2 | 29.2 | 16.4 | 6.7 | 9.2 | 1.1 | 4.2 | 63.2 | 57.9 | 78.6 | 0.7 |
| 2107-3-11-5 | 16.7 | 4.6 | 12.9 | 27.0 | 13.8 | 7.3 | 11.3 | 1.2 | 5.1 | 65.7 | 60.7 | 80.6 | 0.8 |
| 2107-4-11-1 | 18.1 | 5.5 | 11.2 | 29.0 | 14.0 | 8.4 | 7.9 | 1.7 | 4.2 | 54.6 | 48.6 | 71.1 | 0.7 |
| 2107-4-11-2 | 17.9 | 5.8 | 16.4 | 23.8 | 11.2 | 7.3 | 11.8 | 1.1 | 4.7 | 66.2 | 61.6 | 81.3 | 0.8 |
| 2107-4-11-3 | 16.8 | 6.2 | 15.3 | 26.0 | 10.8 | 12.6 | 5.6 | 3.2 | 3.5 | 36.6 | 30.8 | 52.2 | 0.6 |
| 2107-4-11-4 | 17.5 | 5.4 | 14.7 | 24.3 | 12.4 | 7.6 | 12.1 | 1.1 | 5.0 | 66.2 | 61.6 | 81.2 | 0.8 |
| 2107-4-11-5 | 18.0 | 5.2 | 11.7 | 27.3 | 13.2 | 7.7 | 11.1 | 1.3 | 4.7 | 63.9 | 59.2 | 78.9 | 0.7 |
| 2107-4-14-1 | 19.3 | 5.0 | 11.0 | 22.9 | 11.0 | 7.4 | 16.1 | 1.2 | 6.0 | 72.1 | 68.6 | 83.4 | 0.8 |
| 2107-4-14-2 | 18.6 | 5.1 | 10.3 | 27.7 | 16.6 | 6.0 | 10.0 | 1.1 | 4.6 | 67.5 | 62.6 | 81.1 | 0.8 |
| 2107-4-14-3 | 19.6 | 4.7 | 11.6 | 21.5 | 11.2 | 7.6 | 15.2 | 1.4 | 7.1 | 71.2 | 66.6 | 83.3 | 0.8 |
| 2107-4-14-4 | 18.8 | 6.5 | 11.7 | 32.1 | 16.1 | 4.0 | 6.7 | 0.9 | 3.1 | 66.9 | 62.5 | 78.7 | 0.8 |
| 2107-4-14-5 | 17.7 | 5.7 | 10.6 | 26.3 | 12.0 | 8.6 | 12.6 | 1.2 | 5.3 | 64.8 | 59.6 | 81.9 | 0.7 |
| 2107-5-3-1 | 17.0 | 4.4 | 12.3 | 28.2 | 10.0 | 10.8 | 11.8 | 1.3 | 4.3 | 57.1 | 52.2 | 76.9 | 0.7 |
| 2107-5-3-2 | 16.6 | 4.9 | 13.0 | 27.7 | 9.0 | 10.9 | 12.9 | 1.1 | 3.9 | 58.3 | 54.2 | 77.8 | 0.7 |
| 2107-5-3-3 | 17.4 | 3.7 | 13.4 | 28.4 | 10.0 | 10.6 | 11.4 | 1.3 | 3.8 | 56.0 | 51.7 | 74.3 | 0.7 |
| 2107-5-3-4 | 16.7 | 4.4 | 14.6 | 25.1 | 9.4 | 10.8 | 13.0 | 1.4 | 4.6 | 59.1 | 54.7 | 76.6 | 0.7 |
| 2107-5-3-5 | 19.0 | 3.8 | 12.1 | 37.7 | 18.6 | 3.0 | 4.1 | 0.3 | 1.3 | 62.3 | 58.2 | 79.7 | 0.7 |

FIG. 18

Fatty acid composition (wt. %)

| Event | 16:0 | 18:0 | 18:1 | LA | ALA | 20:0 | 20:1 (11) | EDA | DGLA | ERA | ETA | C20 % delta-8 desat | EDA % delta-8 desat | ERA % delta-8 desat | Ratio (EDA/ERA) % desat |
|---|---|---|---|---|---|---|---|---|---|---|---|---|---|---|---|
| pKR1022R-1 | 7.4 | 2.8 | 16.5 | 26.2 | 10.1 | 1.4 | 15.5 | 12.3 | 2.3 | 5.0 | 0.4 | 13.6 | 15.8 | 7.9 | 2.0 |
| pKR1022R-2 | 7.0 | 2.7 | 18.3 | 26.0 | 11.8 | 1.5 | 17.3 | 7.8 | 3.9 | 3.0 | 0.8 | 30.4 | 33.3 | 21.4 | 1.6 |
| pKR1022R-3 | 9.1 | 3.0 | 16.6 | 20.1 | 7.1 | 1.3 | 13.3 | 13.0 | 8.7 | 5.5 | 2.2 | 37.1 | 40.3 | 28.0 | 1.4 |
| pKR1022R-4 | 7.7 | 3.0 | 16.0 | 27.7 | 12.2 | 1.6 | 16.5 | 8.5 | 2.5 | 3.9 | 0.5 | 19.2 | 22.3 | 11.2 | 2.0 |
| pKR1022R-5 | 8.3 | 2.8 | 15.5 | 28.9 | 12.0 | 1.4 | 16.0 | 8.2 | 2.9 | 3.4 | 0.6 | 22.7 | 25.9 | 14.0 | 1.9 |
| pKR1022R-6 | 8.5 | 3.0 | 17.8 | 32.4 | 16.2 | 1.8 | 17.9 | 2.0 | 0.1 | 0.4 | 0.0 | 4.3 | 5.2 | 0.0 | |
| pKR1022R-7 | 7.8 | 2.6 | 17.6 | 31.8 | 16.6 | 1.7 | 19.6 | 1.9 | 0.0 | 0.4 | 0.0 | 0.0 | 0.0 | 0.0 | |
| pKR1022R-8 | 7.9 | 3.1 | 16.4 | 27.4 | 12.3 | 1.5 | 16.2 | 7.6 | 3.5 | 3.4 | 0.8 | 27.9 | 31.4 | 18.5 | 1.7 |
| pKR1022R-9 | 7.7 | 2.7 | 18.6 | 31.4 | 16.4 | 1.7 | 19.2 | 1.9 | 0.1 | 0.4 | 0.0 | 3.2 | 3.9 | 0.0 | |
| pKR1022R-10 | 8.3 | 2.8 | 15.9 | 25.7 | 11.2 | 1.4 | 15.7 | 8.3 | 5.8 | 3.5 | 1.4 | 38.0 | 41.2 | 28.6 | 1.4 |
| pKR1022R-11 | 8.1 | 3.0 | 15.4 | 27.9 | 13.1 | 1.6 | 16.3 | 8.2 | 2.2 | 3.8 | 0.4 | 17.7 | 20.7 | 10.4 | 2.0 |
| pKR1022R-12 | 7.7 | 2.8 | 16.1 | 28.0 | 11.9 | 1.5 | 16.9 | 8.4 | 2.6 | 3.6 | 0.5 | 20.5 | 23.6 | 12.3 | 1.9 |
| pKR1022R-13 | 8.2 | 3.0 | 14.9 | 27.7 | 12.9 | 1.6 | 16.2 | 7.9 | 3.2 | 3.7 | 0.7 | 25.1 | 28.6 | 16.2 | 1.8 |
| pKR1022R-14 | 8.5 | 3.0 | 14.9 | 27.8 | 12.6 | 1.5 | 15.0 | 8.4 | 3.7 | 4.0 | 0.9 | 26.9 | 30.5 | 18.0 | 1.7 |
| pKR1022R-15 | 8.1 | 2.9 | 15.5 | 28.0 | 13.6 | 1.6 | 16.4 | 7.1 | 2.8 | 3.3 | 0.6 | 25.0 | 28.4 | 16.4 | 1.7 |
| pKR1022R-16 | 8.4 | 3.1 | 16.5 | 23.4 | 10.0 | 1.5 | 15.5 | 9.5 | 6.6 | 3.8 | 1.5 | 38.0 | 41.0 | 28.8 | 1.4 |
| pKR1022R-17 | 8.7 | 2.7 | 17.1 | 27.3 | 14.6 | 1.7 | 17.3 | 5.3 | 2.3 | 2.3 | 0.6 | 27.0 | 29.8 | 19.7 | 1.5 |
| pKR1022R-18 | 8.2 | 2.9 | 16.8 | 25.9 | 10.9 | 1.5 | 16.6 | 8.1 | 4.8 | 3.2 | 1.1 | 34.2 | 37.2 | 25.2 | 1.5 |
| pKR1022R-19 | 8.6 | 3.0 | 15.3 | 28.2 | 12.9 | 1.5 | 15.4 | 7.7 | 3.1 | 3.5 | 0.7 | 25.4 | 28.8 | 16.8 | 1.7 |
| pKR1022R-20 | 7.8 | 3.0 | 16.2 | 28.2 | 12.3 | 1.7 | 16.5 | 8.3 | 2.1 | 3.5 | 0.4 | 17.7 | 20.6 | 10.0 | 2.1 |
| pKR1022R-21 | 8.1 | 3.0 | 15.6 | 26.8 | 9.9 | 1.5 | 15.7 | 9.7 | 4.8 | 3.9 | 1.0 | 29.6 | 32.9 | 19.8 | 1.7 |
| pKR1022R-22 | 8.0 | 3.1 | 16.0 | 26.2 | 10.2 | 1.5 | 16.6 | 9.3 | 4.5 | 3.8 | 0.9 | 29.3 | 32.5 | 20.0 | 1.6 |

FIG. 19

| Event | Fatty acid composition (wt.%) | | | | | | | | | | | | | | C20 delta-8 desat | C20 % delta-8 desat |
|---|---|---|---|---|---|---|---|---|---|---|---|---|---|---|---|---|
| | 16:0 | 18:0 | 18:1 | LA | GLA | ALA | EDA | SCI | DGLA | ARA | ERA | JUP | ETA | EPA | DPA | Other | | |
| AFS 4881-6-5 | 15.2 | 1.8 | 12.3 | 20.9 | 3.0 | 5.9 | 2.8 | 0.0 | 5.8 | 0.1 | 2.0 | 0.3 | 18.3 | 9.5 | 0.1 | 2.2 | 33.7 | 87.5 |
| AFS 4885-1-2 | 14.9 | 3.0 | 14.5 | 20.8 | 1.3 | 4.6 | 8.3 | 0.0 | 8.8 | 0.7 | 1.6 | 0.7 | 6.5 | 12.8 | 0.1 | 1.3 | 28.9 | 74.4 |
| AFS 4829-6-5 | 13.3 | 4.2 | 13.3 | 23.9 | 0.9 | 6.3 | 5.8 | 0.0 | 6.9 | 0.8 | 1.6 | 0.9 | 4.1 | 16.6 | 0.1 | 1.2 | 28.6 | 79.5 |
| AFS 4880-1-8 | 17.7 | 4.1 | 12.6 | 24.8 | 1.0 | 5.3 | 3.7 | 0.0 | 11.6 | 0.5 | 1.4 | 0.3 | 5.3 | 10.1 | 0.3 | 1.1 | 27.9 | 84.6 |
| AFS 4880-8-8 | 16.4 | 3.6 | 13.2 | 26.2 | 1.4 | 8.2 | 1.3 | 0.0 | 11.4 | 6.6 | 0.6 | 0.5 | 2.0 | 7.2 | 0.1 | 1.3 | 27.3 | 93.5 |
| AFS 4882-5-5 | 15.9 | 4.1 | 16.7 | 22.6 | 1.6 | 5.2 | 3.7 | 0.0 | 9.0 | 0.4 | 1.0 | 0.7 | 4.4 | 12.5 | 0.3 | 1.8 | 26.6 | 84.9 |
| AFS 4828-2-22 | 11.0 | 2.1 | 13.1 | 33.3 | 1.2 | 9.9 | 0.9 | 0.0 | 5.1 | 0.8 | 0.7 | 0.4 | 5.0 | 15.1 | 0.2 | 1.4 | 26.2 | 94.3 |
| AFS 4881-4-5 | 15.4 | 3.1 | 18.0 | 22.7 | 1.7 | 7.4 | 3.0 | 0.0 | 10.5 | 0.1 | 1.2 | 0.0 | 12.6 | 3.0 | 0.0 | 1.5 | 26.1 | 86.2 |
| AFS 4829-3-2 | 14.6 | 2.3 | 10.7 | 30.9 | 1.0 | 10.3 | 1.2 | 0.0 | 6.1 | 0.7 | 0.9 | 1.0 | 5.0 | 13.8 | 0.3 | 1.3 | 25.8 | 92.5 |
| AFS 4882-4-6 | 15.8 | 3.9 | 15.2 | 25.3 | 0.9 | 6.7 | 2.7 | 0.0 | 9.1 | 0.4 | 1.3 | 1.2 | 4.4 | 11.3 | 0.3 | 1.8 | 25.5 | 86.6 |
| Average | 15.0 | 3.2 | 14.0 | 25.1 | 1.4 | 7.0 | 3.3 | 0.0 | 8.4 | 1.1 | 1.2 | 0.6 | 6.8 | 11.2 | 0.2 | 1.5 | 27.7 | 86.4 |

FIG. 20

| Event | 16:0 | 18:0 | 18:1 | 18:2 (5,9) | LA | GLA | ALA | 20:1 (11) | EDA | SCI | DGLA | ARA | ERA | JUP | ETA | EPA | DPA | Other | C20 delta-8 desat | C20 % delta-8 desat |
|---|---|---|---|---|---|---|---|---|---|---|---|---|---|---|---|---|---|---|---|---|
| 4882-4-6-1-1 | 11.7 | 3.7 | 11.8 | 0.0 | 56.7 | 0.0 | 15.5 | 0.1 | 0.1 | 0.0 | 0.1 | 0.0 | 0.0 | 0.0 | 0.0 | 0.0 | 0.0 | 0.3 | 0.2 | 63.1 |
| 4882-4-6-1-2 | 13.8 | 2.9 | 35.6 | 7.1 | 13.6 | 1.7 | 2.5 | 1.0 | 1.5 | 0.4 | 5.2 | 0.1 | 0.7 | 0.6 | 2.1 | 10.3 | 0.2 | 1.2 | 18.0 | 88.9 |
| 4882-4-6-1-3 | 11.7 | 2.6 | 36.0 | 11.1 | 12.0 | 1.9 | 2.4 | 1.2 | 1.0 | 0.6 | 5.1 | 0.1 | 0.7 | 0.5 | 2.0 | 10.1 | 0.2 | 1.3 | 17.5 | 91.2 |
| 4882-4-6-1-4 | 24.3 | 7.4 | 19.3 | 6.4 | 15.4 | 1.0 | 6.4 | 0.7 | 3.2 | 0.0 | 3.8 | 0.7 | 1.1 | 0.5 | 2.4 | 6.2 | 0.0 | 1.1 | 13.1 | 75.2 |
| 4882-4-6-1-5 | 12.5 | 3.1 | 36.6 | 8.2 | 13.3 | 1.6 | 2.6 | 1.2 | 1.7 | 0.4 | 5.9 | 0.3 | 0.7 | 0.4 | 2.0 | 8.3 | 0.2 | 1.1 | 16.9 | 87.7 |
| 4882-4-6-1-6 | 13.8 | 2.8 | 35.4 | 18.2 | 5.2 | 2.2 | 2.1 | 1.1 | 0.8 | 1.0 | 2.8 | 0.3 | 0.4 | 0.3 | 1.9 | 9.9 | 0.8 | 2.0 | 15.7 | 92.9 |
| 4882-4-6-1-7 | 15.1 | 2.8 | 18.1 | 4.5 | 18.1 | 2.6 | 2.9 | 0.4 | 1.8 | 0.3 | 5.8 | 0.1 | 0.9 | 0.8 | 2.7 | 21.6 | 0.6 | 1.2 | 30.9 | 91.9 |
| 4882-4-6-1-8 | 13.2 | 2.9 | 32.8 | 8.2 | 12.3 | 2.2 | 2.2 | 1.0 | 1.1 | 0.5 | 6.0 | 0.2 | 0.6 | 0.4 | 2.4 | 12.7 | 0.4 | 1.3 | 21.7 | 93.0 |
| 4882-4-6-1-9 | 11.1 | 3.6 | 12.6 | 0.0 | 56.2 | 0.0 | 16.1 | 0.1 | 0.0 | 0.0 | 0.0 | 0.0 | 0.0 | 0.0 | 0.0 | 0.0 | 0.0 | 0.2 | 0.0 | 44.2 |
| 4882-4-6-1-10 | 12.0 | 4.4 | 13.5 | 0.0 | 54.4 | 0.0 | 15.1 | 0.2 | 0.0 | 0.0 | 0.0 | 0.0 | 0.0 | 0.0 | 0.0 | 0.0 | 0.0 | 0.3 | 0.1 | 60.3 |
| 4882-4-6-2-1 | 11.9 | 4.0 | 15.5 | 0.0 | 53.3 | 0.0 | 14.8 | 0.2 | 0.0 | 0.0 | 0.0 | 0.0 | 0.0 | 0.0 | 0.0 | 0.0 | 0.0 | 0.3 | 0.0 | 57.4 |
| 4882-4-6-2-2 | 10.7 | 3.8 | 49.2 | 13.7 | 7.1 | 0.8 | 1.6 | 2.3 | 0.9 | 0.5 | 2.5 | 0.0 | 0.7 | 0.4 | 1.1 | 3.7 | 0.0 | 1.5 | 7.3 | 81.9 |
| 4882-4-6-2-3 | 12.0 | 3.4 | 40.9 | 9.0 | 10.7 | 1.7 | 1.7 | 1.4 | 1.2 | 0.5 | 5.0 | 0.1 | 0.5 | 0.3 | 2.2 | 8.6 | 0.1 | 1.2 | 16.1 | 90.4 |
| 4882-4-6-2-4 | 12.7 | 3.1 | 32.5 | 11.6 | 9.3 | 2.7 | 2.1 | 1.3 | 0.8 | 0.7 | 4.4 | 0.3 | 0.5 | 0.4 | 2.1 | 14.2 | 0.5 | 1.6 | 21.4 | 94.2 |
| 4882-4-6-2-5 | 15.8 | 2.3 | 22.9 | 9.1 | 12.4 | 3.8 | 2.4 | 0.7 | 0.8 | 0.4 | 6.0 | 0.4 | 0.5 | 0.4 | 2.5 | 18.0 | 0.6 | 1.4 | 27.5 | 95.3 |
| 4882-4-6-2-6 | 10.0 | 5.2 | 58.5 | 9.3 | 5.7 | 0.3 | 1.1 | 3.1 | 0.8 | 0.3 | 1.6 | 0.0 | 0.5 | 0.4 | 0.7 | 1.8 | 0.0 | 1.1 | 4.2 | 76.5 |
| 4882-4-6-2-7 | 10.3 | 3.9 | 55.2 | 10.6 | 6.4 | 0.5 | 1.1 | 2.7 | 0.9 | 0.6 | 2.4 | 0.0 | 0.6 | 0.3 | 0.9 | 2.8 | 0.0 | 1.3 | 6.1 | 80.1 |
| 4882-4-6-2-8 | 11.0 | 3.9 | 50.3 | 10.1 | 7.3 | 0.6 | 1.0 | 2.3 | 1.8 | 0.6 | 3.8 | 0.0 | 0.6 | 0.3 | 1.3 | 4.3 | 0.0 | 1.3 | 9.4 | 79.6 |
| 4882-4-6-2-9 | 12.2 | 5.7 | 57.6 | 8.8 | 3.1 | 0.0 | 1.0 | 2.8 | 0.5 | 0.6 | 2.4 | 0.0 | 0.0 | 0.0 | 1.6 | 2.7 | 0.0 | 1.6 | 6.7 | 92.8 |
| 4882-4-6-2-10 | 12.2 | 3.3 | 18.6 | 0.0 | 52.9 | 0.0 | 12.5 | 0.2 | 0.0 | 0.0 | 0.0 | 0.0 | 0.0 | 0.0 | 0.0 | 0.0 | 0.0 | 0.3 | 0.0 | 0.0 |

FIG. 21

| Event | Fatty acid composition (wt.%) | | | | | | | | | | | | | | | C20 delta-8 desat | C20 % delta-8 desat |
|---|---|---|---|---|---|---|---|---|---|---|---|---|---|---|---|---|---|
| | 16:0 | 18:0 | 18:1 | LA | GLA | ALA | EDA | SCI | DGLA | ARA | ERA | JUP | ETA | EPA | DPA | Other | | |
| AFS 5002-1-4 | 14.8 | 2.9 | 17.7 | 22.1 | 1.0 | 10.1 | 4.7 | 0.6 | 8.0 | 10.3 | 0.9 | 0.8 | 0.9 | 3.3 | 0.2 | 1.7 | 22.7 | 80.2 |
| AFS 5001-7-1 | 15.2 | 2.0 | 25.5 | 17.9 | 1.9 | 9.3 | 1.7 | 0.0 | 2.2 | 0.0 | 1.5 | 0.9 | 11.5 | 7.9 | 0.1 | 2.4 | 21.8 | 87.3 |
| AFS 5006-1-20 | 17.3 | 3.0 | 22.6 | 17.9 | 0.8 | 6.7 | 4.2 | 0.0 | 3.2 | 0.2 | 1.7 | 3.6 | 2.9 | 14.3 | 0.4 | 1.3 | 21.0 | 78.0 |
| AFS 5001-6-25 | 14.3 | 3.4 | 23.1 | 19.2 | 0.6 | 7.4 | 4.1 | 0.0 | 2.1 | 0.0 | 3.1 | 3.0 | 7.7 | 10.2 | 0.2 | 1.6 | 20.2 | 73.6 |
| AFS 5001-3-4 | 13.5 | 2.7 | 17.8 | 27.9 | 0.6 | 8.0 | 6.1 | 0.1 | 6.6 | 1.9 | 1.3 | 1.0 | 2.6 | 8.6 | 0.2 | 1.2 | 19.7 | 72.8 |
| AFS 5001-7-7 | 14.6 | 2.9 | 16.0 | 26.0 | 0.6 | 9.2 | 5.4 | 0.1 | 2.6 | 0.3 | 2.7 | 1.4 | 3.5 | 13.2 | 0.2 | 1.4 | 19.7 | 70.8 |
| AFS 5003-6-12 | 17.9 | 2.4 | 11.8 | 23.3 | 0.8 | 8.8 | 5.8 | 0.1 | 2.8 | 0.1 | 3.3 | 4.7 | 5.3 | 10.8 | 0.1 | 1.7 | 19.2 | 67.7 |
| AFS 5003-1-8 | 14.8 | 3.2 | 18.4 | 24.3 | 0.4 | 6.4 | 6.2 | 0.1 | 2.6 | 0.2 | 2.5 | 3.2 | 3.6 | 12.0 | 0.4 | 1.6 | 18.8 | 68.2 |
| AFS 5003-5-7 | 13.1 | 2.9 | 12.9 | 24.9 | 0.3 | 7.2 | 9.5 | 2.8 | 5.2 | 9.5 | 1.6 | 2.6 | 0.7 | 4.7 | 0.2 | 1.9 | 20.2 | 64.4 |
| AFS 5002-7-2 | 14.2 | 2.9 | 18.7 | 27.5 | 1.6 | 8.0 | 4.3 | 0.2 | 6.9 | 2.6 | 1.1 | 1.8 | 1.4 | 7.4 | 0.3 | 1.4 | 18.4 | 77.5 |
| Average | 15.0 | 2.8 | 18.5 | 23.1 | 0.9 | 8.1 | 5.2 | 0.4 | 4.2 | 2.5 | 2.0 | 2.3 | 4.0 | 9.2 | 0.2 | 1.6 | 20.2 | 74.1 |

FIG. 22

Fatty acid composition (wt.%)

| Event | 16:0 | 18:0 | 18:1 | 18:2 (5,9) | LA | GLA | ALA | 20:1 (11) | EDA | SCI | DGLA | ARA | ERA | JUP | ETA | EPA | DPA | Other | C20 delta-8 desat | C20 % delta-8 desat |
|---|---|---|---|---|---|---|---|---|---|---|---|---|---|---|---|---|---|---|---|---|
| 5003-1-8-1-1 | 11.1 | 2.8 | 21.9 | 0.0 | 50.4 | 0.0 | 13.0 | 0.1 | 0.0 | 0.0 | 0.0 | 0.0 | 0.0 | 0.0 | 0.0 | 0.1 | 0.2 | 0.3 | 0.3 | 100.0 |
| 5003-1-8-1-2 | 12.7 | 2.9 | 12.7 | 0.0 | 49.1 | 0.0 | 21.9 | 0.1 | 0.0 | 0.0 | 0.0 | 0.0 | 0.0 | 0.0 | 0.0 | 0.1 | 0.1 | 0.3 | 0.2 | 100.0 |
| 5003-1-8-1-3 | 16.8 | 3.3 | 50.2 | 2.3 | 7.1 | 0.7 | 6.3 | 0.4 | 0.4 | 0.3 | 1.0 | 0.0 | 0.5 | 0.1 | 3.0 | 4.8 | 0.2 | 2.7 | 9.0 | 91.3 |
| 5003-1-8-1-4 | 14.0 | 3.1 | 41.4 | 1.6 | 9.2 | 0.5 | 13.3 | 0.6 | 1.3 | 0.0 | 1.3 | 0.1 | 0.8 | 0.3 | 2.8 | 6.4 | 0.1 | 3.2 | 10.7 | 83.8 |
| 5003-1-8-1-5 | 14.3 | 4.1 | 36.3 | 2.4 | 9.8 | 1.3 | 10.5 | 0.5 | 1.3 | 0.2 | 2.5 | 0.0 | 0.6 | 0.4 | 4.0 | 9.4 | 0.3 | 2.1 | 16.2 | 89.2 |
| 5003-1-8-1-6 | 15.4 | 4.5 | 49.8 | 2.4 | 6.3 | 1.2 | 2.9 | 0.5 | 0.8 | 0.0 | 1.6 | 0.0 | 0.5 | 0.4 | 4.0 | 7.1 | 0.3 | 2.5 | 13.1 | 91.2 |
| 5003-1-8-1-7 | 12.3 | 2.6 | 21.3 | 0.0 | 49.3 | 0.0 | 13.9 | 0.1 | 0.0 | 0.0 | 0.0 | 0.0 | 0.0 | 0.0 | 0.0 | 0.1 | 0.1 | 0.2 | 0.2 | 100.0 |
| 5003-1-8-1-8 | 12.4 | 4.6 | 54.6 | 2.7 | 8.0 | 0.7 | 1.4 | 1.0 | 2.8 | 0.0 | 2.0 | 0.0 | 0.9 | 0.4 | 2.0 | 4.6 | 0.1 | 1.8 | 8.8 | 70.0 |
| 5003-1-8-1-9 | 11.4 | 6.4 | 45.8 | 2.1 | 13.0 | 0.7 | 1.7 | 0.6 | 5.5 | 0.0 | 1.9 | 0.1 | 1.3 | 0.9 | 1.5 | 5.9 | 0.2 | 1.0 | 9.5 | 58.2 |
| 5003-1-8-1-10 | 13.3 | 4.6 | 53.2 | 2.8 | 7.7 | 0.6 | 1.4 | 1.1 | 3.1 | 0.0 | 1.3 | 0.0 | 1.2 | 0.7 | 2.3 | 5.1 | 0.2 | 1.5 | 8.8 | 67.4 |
| 5003-1-8-2-1 | 16.0 | 3.6 | 42.1 | 2.5 | 8.0 | 1.7 | 6.8 | 0.2 | 0.9 | 0.2 | 1.7 | 0.0 | 0.6 | 0.3 | 3.3 | 8.5 | 0.2 | 3.5 | 13.7 | 90.2 |
| 5003-1-8-2-2 | 12.2 | 3.1 | 21.1 | 0.0 | 47.7 | 0.0 | 15.6 | 0.0 | 0.0 | 0.0 | 0.0 | 0.0 | 0.0 | 0.0 | 0.0 | 0.1 | 0.0 | 0.3 | 0.1 | 100.0 |
| 5003-1-8-2-3 | 9.1 | 3.3 | 28.8 | 0.0 | 47.0 | 0.0 | 10.9 | 0.2 | 0.0 | 0.0 | 0.0 | 0.0 | 0.0 | 0.0 | 0.0 | 0.3 | 0.1 | 0.3 | 0.4 | 96.5 |
| 5003-1-8-2-4 | 13.8 | 3.5 | 14.6 | 0.0 | 53.4 | 0.4 | 14.1 | 0.0 | 0.0 | 0.0 | 0.0 | 0.0 | 0.0 | 0.0 | 0.0 | 0.1 | 0.1 | 0.3 | 0.3 | 100.0 |
| 5003-1-8-2-5 | 11.0 | 3.5 | 50.7 | 2.2 | 11.2 | 0.0 | 1.6 | 1.5 | 7.4 | 0.0 | 1.1 | 0.2 | 1.7 | 1.9 | 1.0 | 3.2 | 0.1 | 1.1 | 5.5 | 37.6 |
| 5003-1-8-2-6 | 10.5 | 3.5 | 22.2 | 0.0 | 37.0 | 0.0 | 25.1 | 0.1 | 0.0 | 0.0 | 0.0 | 0.0 | 0.1 | 0.0 | 0.0 | 0.1 | 0.2 | 1.1 | 0.4 | 84.1 |
| 5003-1-8-2-7 | 13.7 | 3.5 | 40.9 | 2.0 | 9.2 | 0.8 | 13.5 | 0.4 | 1.4 | 0.2 | 1.2 | 0.1 | 0.8 | 0.4 | 1.9 | 6.9 | 0.1 | 3.1 | 10.2 | 82.3 |
| 5003-1-8-2-8 | 12.5 | 2.9 | 15.7 | 0.0 | 47.4 | 0.0 | 20.7 | 0.0 | 0.0 | 0.0 | 0.0 | 0.0 | 0.0 | 0.0 | 0.0 | 0.2 | 0.2 | 0.5 | 0.4 | 100.0 |

US 7,863,502 B2

DELTA-8 DESATURASES AND THEIR USE IN MAKING POLYUNSATURATED FATTY ACIDS

This application claims the benefit of U.S. Provisional Application No. 60/853,563, filed Oct. 23, 2006, the entire contents of which are herein incorporated by reference.

FIELD OF THE INVENTION

This invention is in the field of biotechnology. More specifically, this invention pertains to polynucleotide sequences encoding delta-8 desaturases and the use of these desaturases in making long-chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further elongation and desaturation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg et al., *Amer. J. Clin. Nutr.* 28:958-966 (1975); Dyerberg et al., *Lancet.* 2(8081):117-119 (1978); Shimokawa, H., *World Rev. Nutr. Diet* 88:100-108 (2001); von Schacky et al., *World Rev. Nutr. Diet* 88:90-99 (2001)). Numerous other studies document wide-ranging health benefits conferred by administration of omega-3 and/or omega-6 PUFAs against a variety of symptoms and diseases (e.g., asthma, psoriasis, eczema, diabetes, cancer).

Today, a variety of different hosts including plants, algae, fungi and yeast are being investigated as means for commercial PUFA production via numerous divergent efforts. Although the natural PUFA-producing abilities of the host organisms are sometimes essential to a given methodology, genetic engineering has also proven that the natural abilities of some hosts (even those natively limited to LA and ALA fatty acid production) can be substantially altered to result in high-level production of various long-chain omega-3/omega-6 PUFAs. Whether this effect is the result of natural abilities or recombinant technology, production of arachidonic acid (ARA; 20:4 ω-6), eicosapentaenoic acid (EPA; 20:5 ω-3) and docosahexaenoic acid (DHA; 22:6 ω-3) all require expression of either the delta-9 elongase/delta-8 desaturase pathway (which operates in some organisms, such as euglenoid species and which is characterized by the production of eicosadienoic acid (EDA; 20:2 ω-6) and/or eicosatrienoic acid (ETrA; 20:3 ω-3) or the delta-6 desaturase/delta-6 elongase pathway (which is predominantly found in algae, mosses, fungi, nematodes and humans and which is characterized by the production of γ-linoleic acid (GLA; 18:3 ω-6) and/or stearidonic acid (STA; 18:4 ω-3) (FIG. 6). A delta-6 elongase is also known as a $C_{18/20}$ elongase.

The delta-8 desaturase enzymes identified thus far have the ability to convert both EDA to dihomo-γ-linolenic acid (DGLA; 20:3) and ETrA to eicosatetraenoic acid (ETA; 20:4) (wherein ARA are EPA are subsequently synthesized from DGLA and ETA, respectively, following reaction with a delta-5 desaturase, while DHA synthesis requires subsequent expression of an additional $C_{20/22}$ elongase and a delta-4 desaturase).

Based on the role delta-8 desaturase enzymes play in the synthesis of e.g., ARA, EPA and DHA, there has been considerable effort to identify and characterize these enzymes. Most efforts thus far have focused on the isolation and characterization of delta-8 desaturases from *Euglena gracilis*; and, several sequence variations within the *Euglena gracilis* delta-8 desaturase have been reported (see, e.g., Wallis et al., *Arch. Biochem. and Biophys.* 365(2):307-316 (1999); PCT Publication No. WO 2000/34439; U.S. Pat. No. 6,825,017; PCT Publication No. WO 2004/057001). Also, Applicants' Assignee's co-pending applications having U.S. application Ser. Nos. 11/166,003 and 11/166,993 filed Jun. 24, 2005, respectively (PCT Publication Nos. WO 2006/012325 and WO 2006/012326; both published Feb. 2, 2006)) discloses amino acid and nucleic acid sequences for a *Euglena gracilis* delta-8 desaturase.

More recently, PCT Publication No. WO 2005/103253 (published Apr. 22, 2005) discloses amino acid and nucleic acid sequences for a delta-8 desaturase enzyme from *Pavlova salina* (see also U.S. Publication No. 2005/0273885). Sayanova et al. (*FEBS Lett.* 580:1946-1952 (2006)) describes the isolation and characterization of a cDNA from the free living soil amoeba *Acanthamoeba castellanii* that, when expressed in *Arabidopsis*, encodes a $C_{20}$ delta-8 desaturase. Also, Applicants' Assignee's co-pending application having Provisional Application No. 60/795,810 filed Apr. 28, 2006 discloses amino acid and nucleic acid sequences for a delta-8 desaturase enzyme from *Pavlova lutheri* (CCMP459).

Based on the utility of expressing delta-8 desaturases in conjunction with delta-9 elongases, there has also been considerable effort to identify and characterize delta-9 elongases from various sources. A delta-9 elongase from *Isochrysis galbana* has been publicly available (described in GenBank Accession No. AAL37626, as well as PCT Publication No. WO 02/077213). Applicants' Assignee's co-pending application having U.S. Provisional Application No. 60/739,989 filed Nov. 23, 2005, discloses a delta-9 elongase from *Eulgena gracilis*.

Applicants' Assignee has a number of patent applications concerning the production of PUFAs in oleaginous yeasts (i.e., *Yarrowia lipolytica*), including: PCT Publication Nos. WO 2004/101757 and WO 2004/101753 (both published Nov. 25, 2004); U.S. application Ser. No. 11/265,761 (filed Nov. 2, 2005); U.S. application Ser. No. 11/264,784 (filed Nov. 1, 2005); and U.S. application Ser. No. 11/264,737 (filed Nov. 1, 2005).

Relatedly, PCT Publication No. WO 2004/071467 (published Aug. 26, 2004) concerns the production of PUFAs in plants, while PCT Publication No. WO 2004/071178 (published Aug. 26, 2004) concerns annexin promoters and their use in expression of transgenes in plants; both are Applicants' Assignee's copending applications.

SUMMARY OF THE INVENTION

The present invention concerns an isolated polynucleotide comprising:
(a) a nucleotide sequence encoding a polypeptide having delta-8 desaturase activity, wherein the polypeptide has at least 80% amino acid identity, based on the Clustal V method of alignment, when compared to an amino acid sequence as set forth in SEQ ID NO:47, SEQ ID NO:49 or SEQ ID NO:57;

(b) a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:92, SEQ ID NO:93 or SEQ ID NO:62;

(c) a nucleotide sequence encoding a polypeptide having delta-8 desaturase activity, wherein the nucleotide sequence hybridizes under stringent conditions to a nucleotide sequence as set forth in SEQ ID NO:92, SEQ ID NO:93 or SEQ ID NO:62; or (d) a complement of the nucleotide sequence of (a), (b) or (c), wherein the complement and the nucleotide sequence consist of the same number of nucleotides and are 100% complementary.

In a second embodiment, the invention concerns a recombinant DNA construct comprising any of the isolated polynucleotides of the invention operably linked to at least one regulatory sequence.

In a third embodiment, the invention concerns a cell comprising in its genome the recombinant DNA construct of the invention. Such cells can be plant cells or yeast cells.

In a fourth embodiment, the invention concerns a method for transforming a cell, comprising transforming a cell with a recombinant construct of the invention or an isolated polynucleotide of the invention and selecting those cells transformed with the recombinant construct or the isolated polynucleotide.

In a fifth embodiment, the invention concerns transgenic seed comprising in its genome the recombinant construct of the invention or a transgenic seed obtained from a plant made by a method of the invention. Also of interest is oil or by-products obtained from such transgenic seeds.

In a sixth embodiment, the invention concerns a method for making long-chain polyunsaturated fatty acids in a plant cell comprising:

(a) transforming a cell with the recombinant construct of the invention; and (b) selecting those transformed cells that make long-chain polyunsaturated fatty acids.

In a seventh embodiment, the invention concerns a method for producing at least one polyunsaturated fatty acid in an oilseed plant cell comprising:

(a) transforming an oilseed plant cell with a first recombinant DNA construct comprising an isolated polynucleotide encoding at least one delta-8 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase;

(b) regenerating an oilseed plant from the transformed cell of step (a); and (c) selecting those seeds obtained from the plants of step (b) having an altered level of polyunsaturated fatty acids when compared to the level in seeds obtained from a nontransformed oilseed plant.

In an eighth embodiment, the invention concerns an oilseed plant comprising in its genome the recombinant construct of the invention. Suitable oilseed plants include, but are not limited to, soybean, *Brassica* species, sunflower, maize, cotton, flax and safflower.

In a ninth embodiment, the invention concerns an oilseed plant comprising:

(a) a first recombinant DNA construct comprising an isolated polynucleotide encoding at least one delta-8 desaturase polypeptide, operably linked to at least one regulatory sequence; and (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

Also of interest are transgenic seeds obtained from such oilseed plants as well as oil or by-products obtained from these transgenic seeds. A preferred product is lecithin.

In a tenth embodiment, the invention concerns food or feed incorporating an oil or seed of the invention or food or feed comprising an ingredient derived from the processing of the seeds.

In an eleventh embodiment, the invention concerns a method for making long-chain polyunsaturated fatty acids in a cell having a reduced level of by-product fatty acids, said method comprising:

(a) transforming a host cell with at least one recombinant DNA construct comprising an isolated polynucleotide encoding at least two delta-8 desaturases operably linked to at least one regulatory sequence; and (b) selecting those transformed host cells obtained having a reduced level of by-product fatty acids, when compared to the level of such metabolic by-product fatty acids in a transformed host cell having at least one recombinant DNA construct comprising an isolated polynucleotide encoding one delta-8 desaturase operably linked to a regulatory sequence.

In a twelfth embodiment, the invention concerns progeny plants obtained from obtained from a plant made by the method of the invention or an oilseed plant of the invention.

BIOLOGICAL DEPOSITS

The following plasmid has been deposited with the American Type Culture Collection (ATCC), 10801 University Boulevard, Manassas, Va. 20110-2209, and bears the following designation, Accession Number and date of deposit (Table 1).

TABLE 1

| | ATCC Deposit | |
|---|---|---|
| Plasmid | Accession Number | Date of Deposit |
| pKR72 | PTA-6019 | May 28, 2004 |

BRIEF DESCRIPTION OF THE DRAWINGS AND SEQUENCE LISTINGS

The invention can be more fully understood from the following detailed description and the accompanying drawings and Sequence Listing, which form a part of this application.

FIG. 5 are the lipid profiles of somatic soybean embryos expressing the *Tetruetreptia pomquetensis* CCMP1491 delta-8 desaturase and the *Isochrysis galbana* delta-9 elongase (see Example 10).

FIGS. 7A and 7B show a Clustal V alignment of the delta-8 desaturases from *Tetruetreptia pomquetensis* CCMP1491 (SEQ ID NO:57), *Eutreptiella* sp. CCMP389 (SEQ ID NO:47), *Eutreptiella* cf_*gymnastica* CCMP1594 (SEQ ID NO:49), *Euglena gracilis* (SEQ ID NO:98; NCBI Accession No. AAD45877 (GI 5639724)) and *Euglena gracilis* (SEQ ID NO:112).

Figure 8:
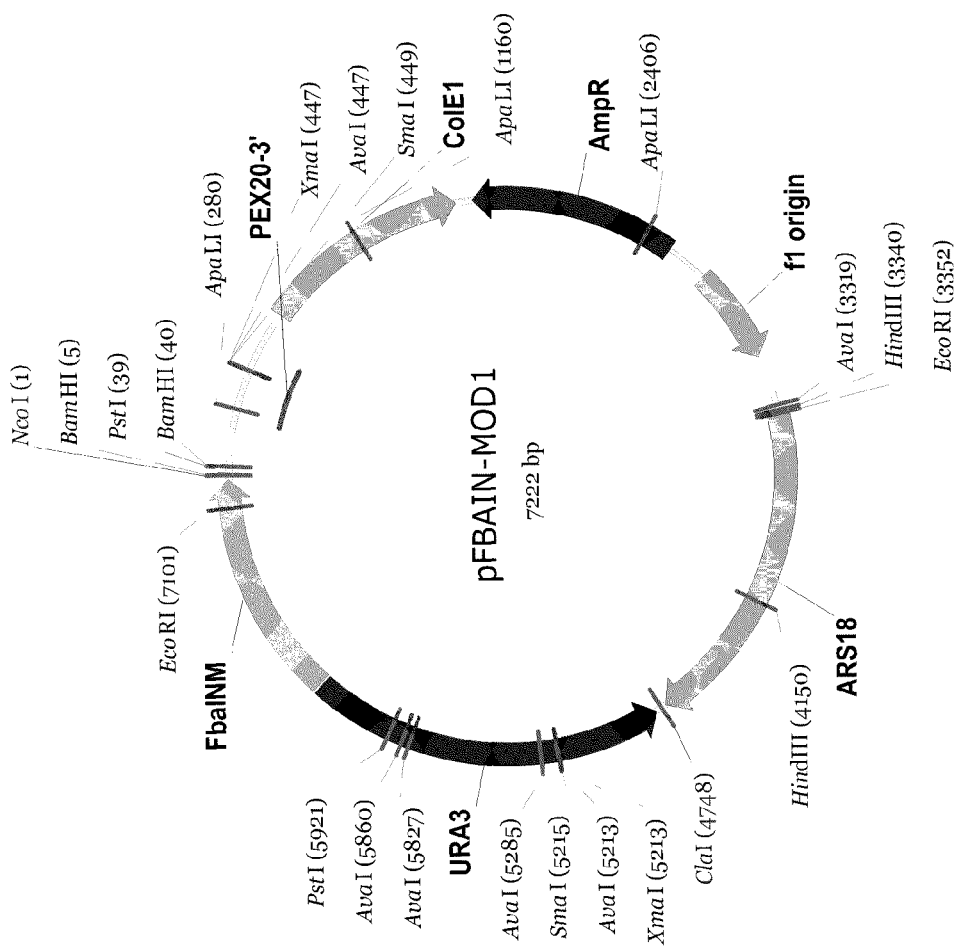

FIG. 8 is a schematic of the *Yarrowia lipolytica* expression vector pFBAIn-MOD1.

Figure 9:
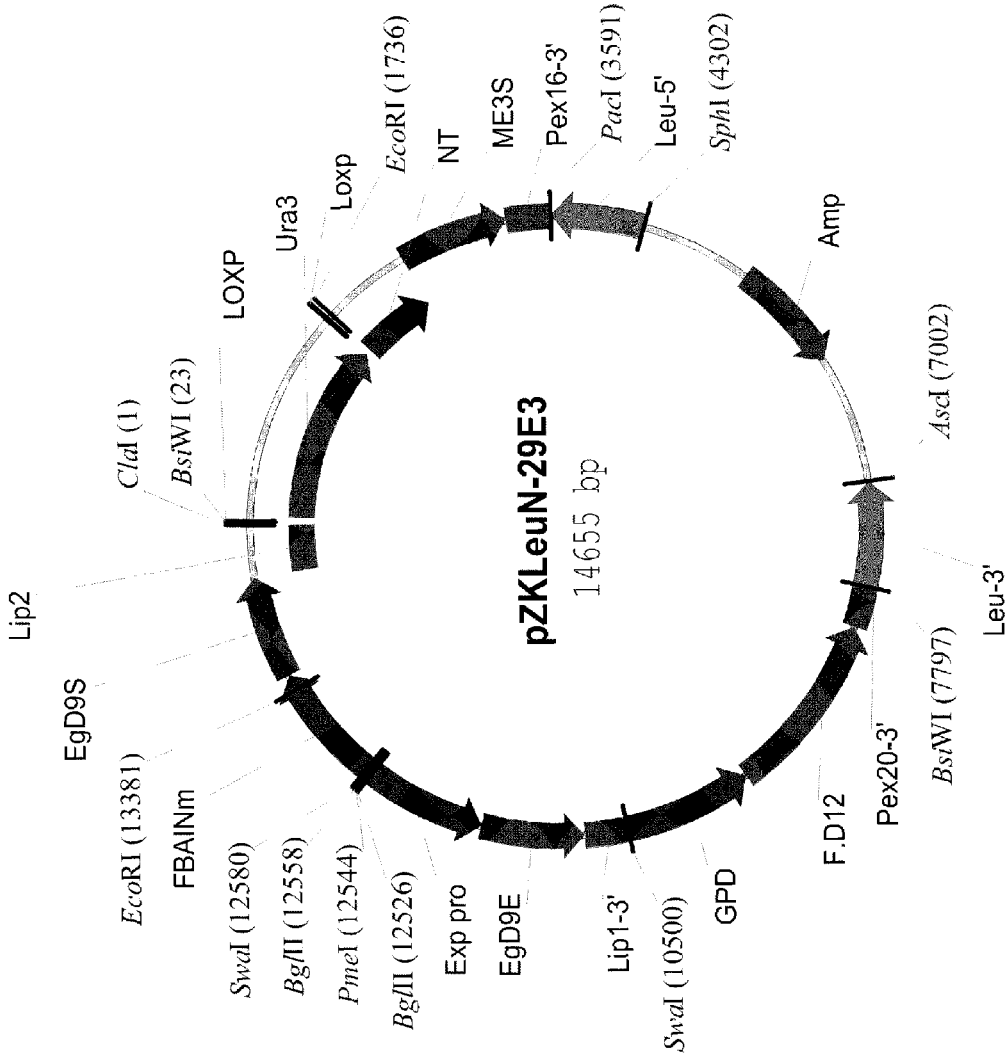

FIG. 9 is a schematic of the construct pZKLeuN-29E3.

FIG. 10 are the lipid profiles of somatic soybean embryos expressing *Tetruetreptia pomquetensis* CCMP1491 (TpomD8) and *Euglena gracilis* delta-9 elongase (EgD9e) for the top 5 events (see Example 12).

Figure 11:
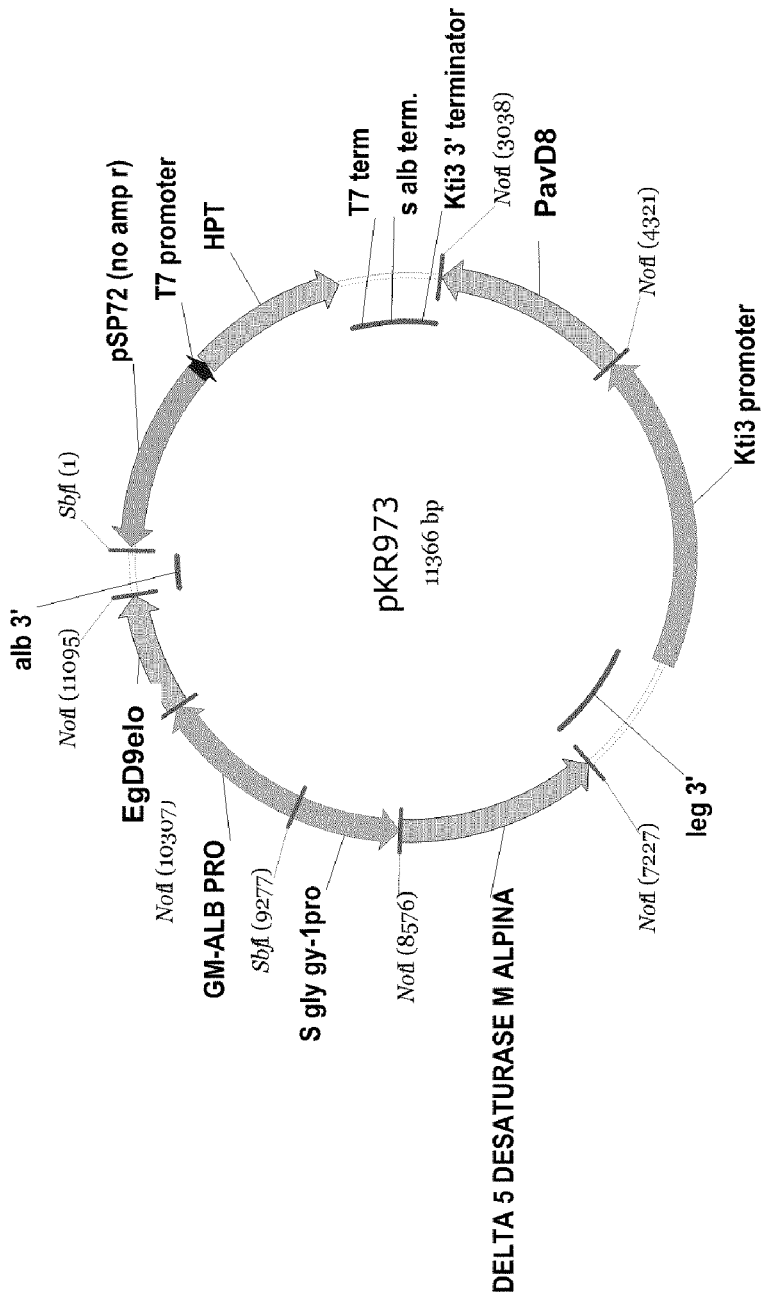

FIG. 11 is the soybean expression vector pKR973.

Figure 12:
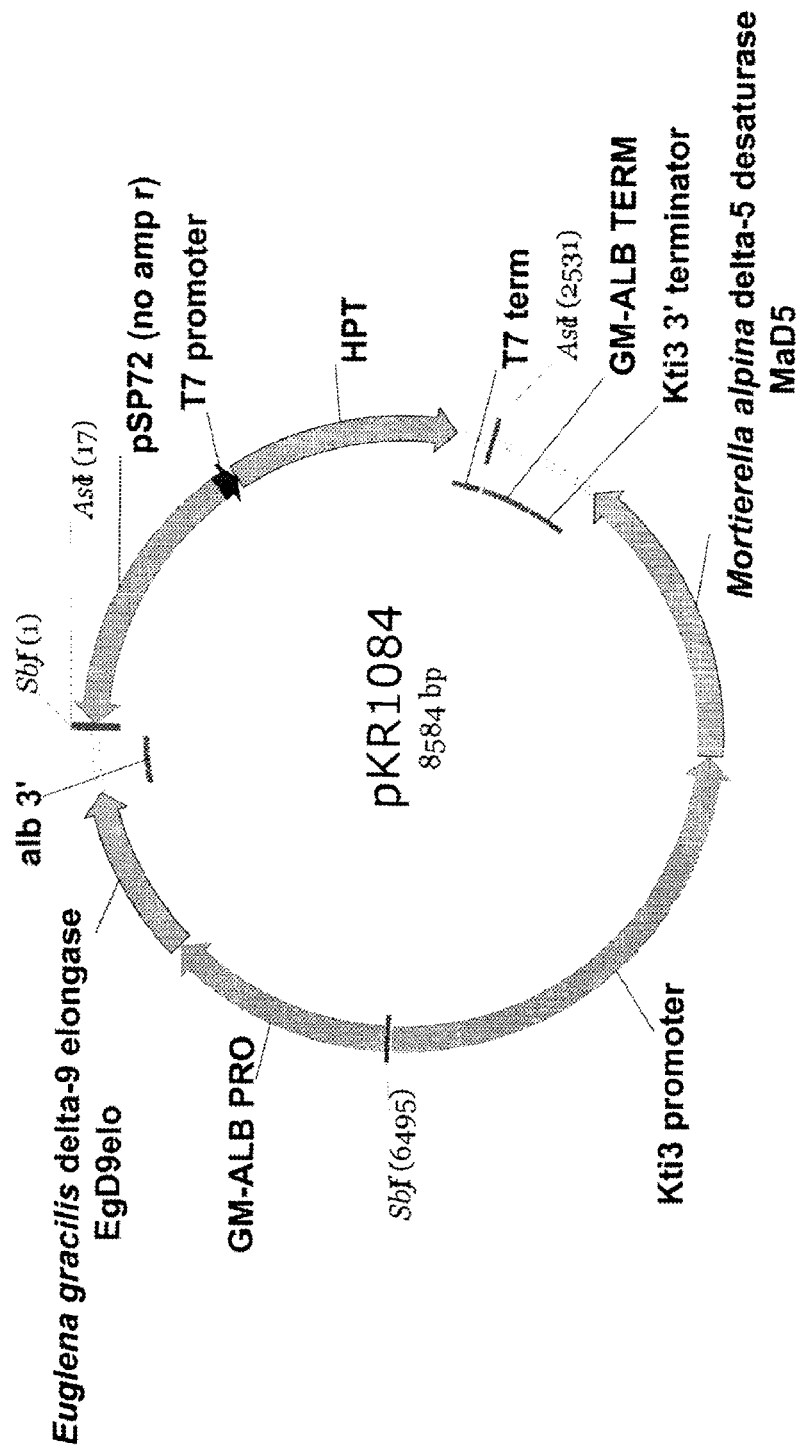

FIG. 12 is the soybean expression vector pKR1084.

Figure 13:
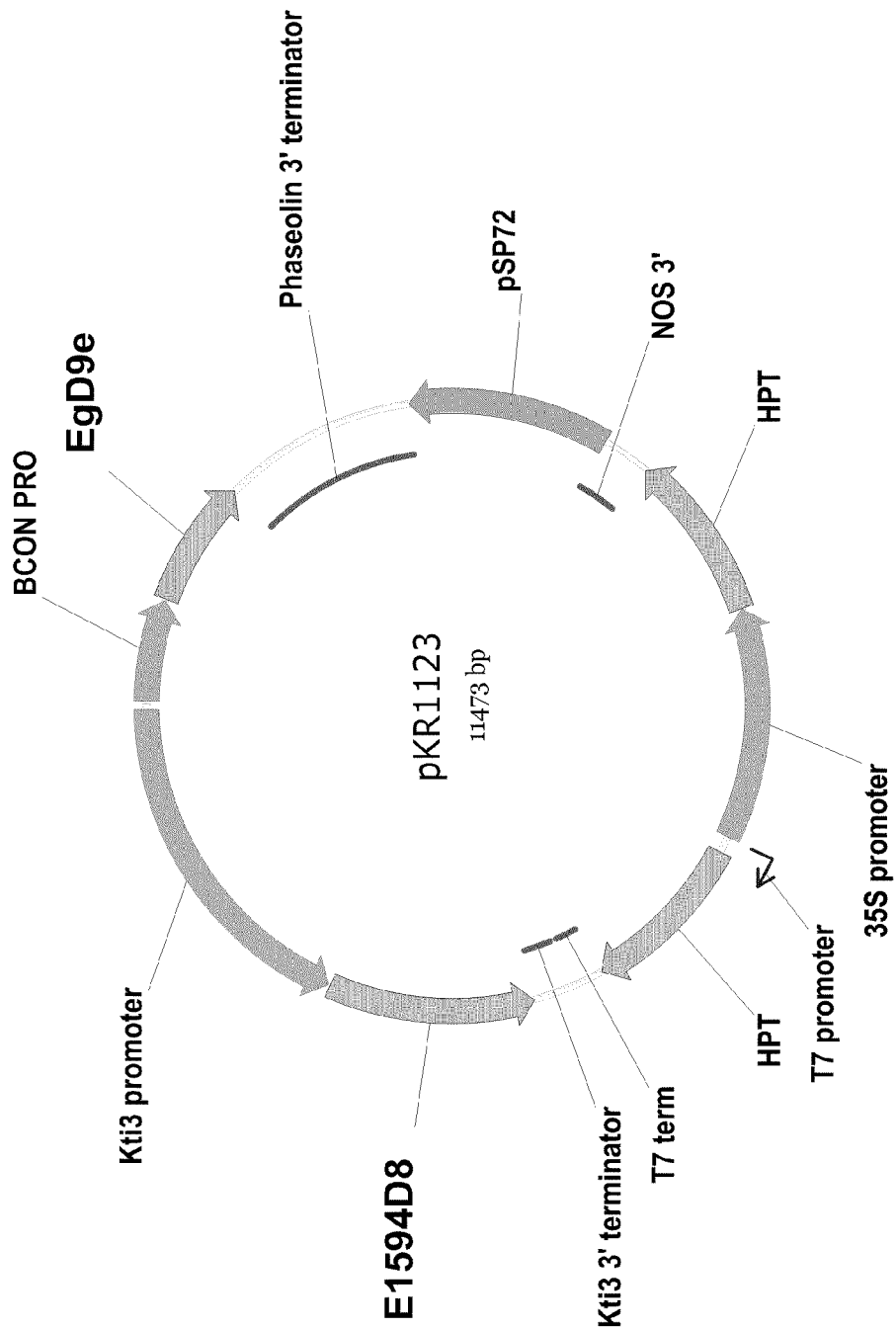

FIG. 13 is the soybean expression vector pKR1123.

FIG. 14 shows the lipid profiles of somatic soybean embryos expressing E1594D8 and EgD9e for the top 5 events. Fatty acids are identified as 16:0 (palmitate), 18:0 (stearic acid), 18:1 (oleic acid), LA, GLA, ALA, EDA, DGLA, ERA and ETA; and, fatty acid compositions listed in FIG. 14 are expressed as a weight percent (wt. %) of total fatty acids. The activity of E1594D8 is expressed as percent desaturation (% desat), calculated according to the following formula: ([product]/[substrate+product])*100. The combined percent desaturation for EDA and ERA is shown as "C20% delta-8 desat". The individual omega-6 delta-8 desaturation ("EDA % delta-8 desat.") was calculated as: ([DGLA]/[DGLA+EDA])*100. Similarly, the individual omega-3 delta-8 desaturation ("ERA % delta-8 desat.") was calculated as: ([ETA]/[ETA+ERA])*100. The ratio of delta-8 desaturation for omega-6 versus omega-3 substrates ("ratio [EDA/ERA] % desat.") was obtained by dividing the EDA % delta-8 desaturation by the ERA % delta-8 desaturation.

Figure 15:
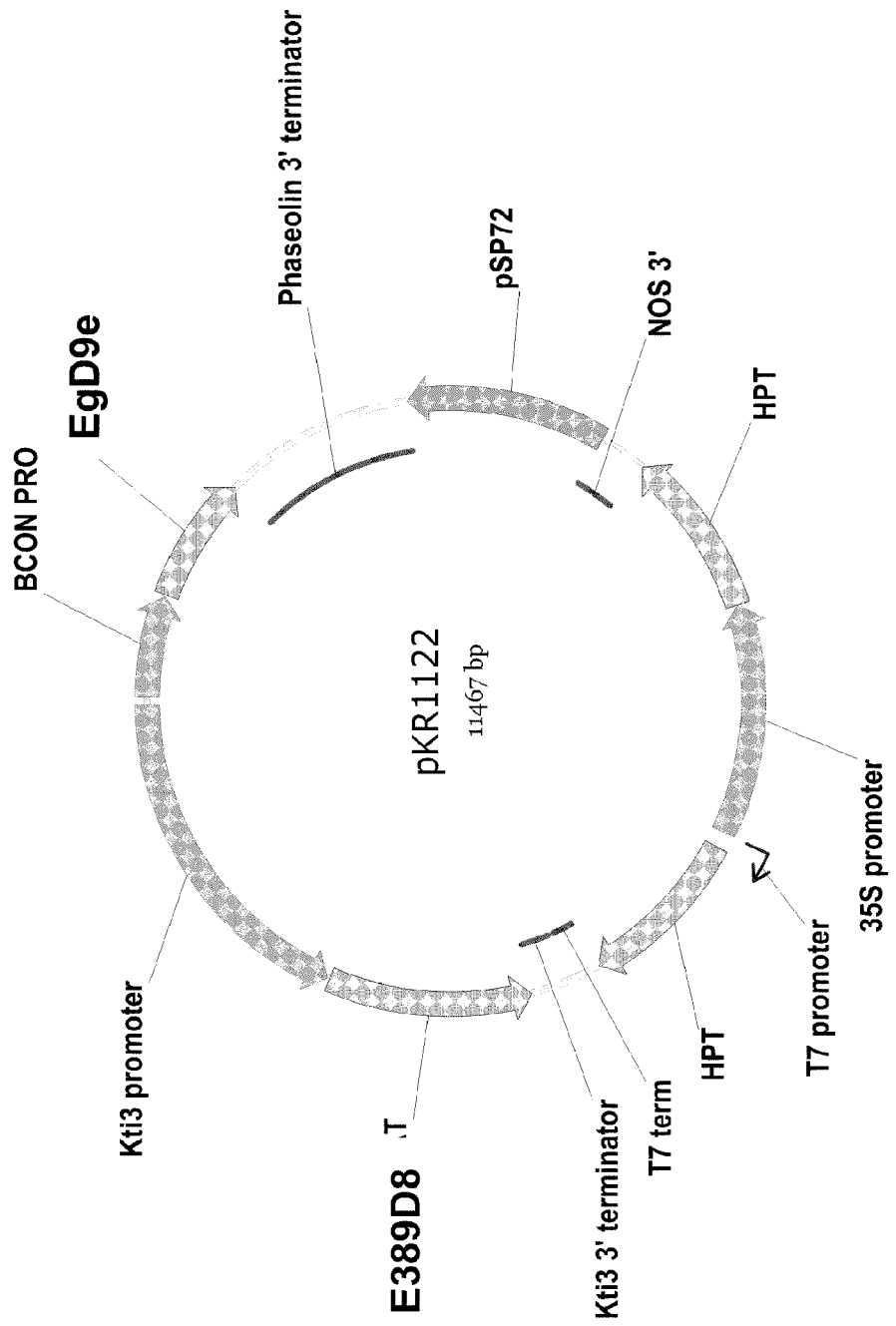

FIG. 15 is the soybean expression vector pKR1122.

FIG. 16 shows the lipid profiles of somatic soybean embryos expressing E389D8 and EgD9e for the top 5 events.

Figure 17:
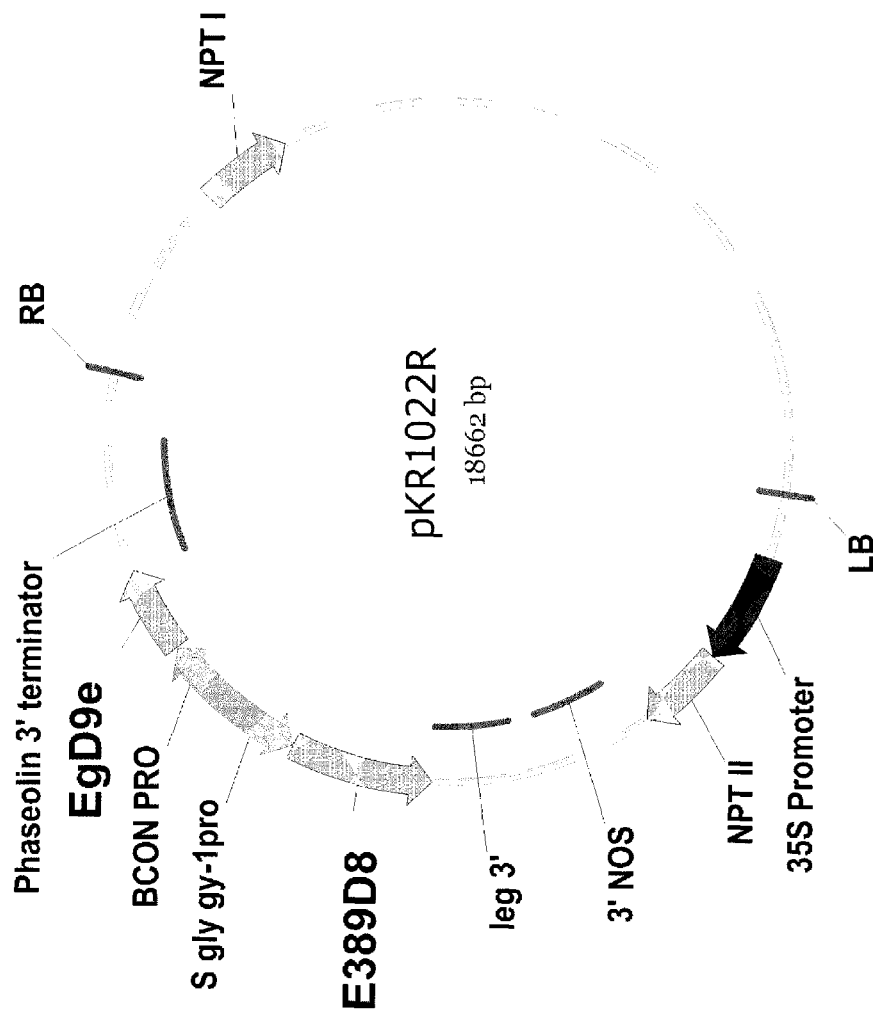

FIG. 17 is the *Arabidopsis* Binary Expression pKR1022R.

FIG. 18 shows the lipid profiles of T2 bulk seed for 22 events where wild-type-*Arabidopsis* was transformed with pKR1022R (SEQ ID NO:141).

Figure 4:
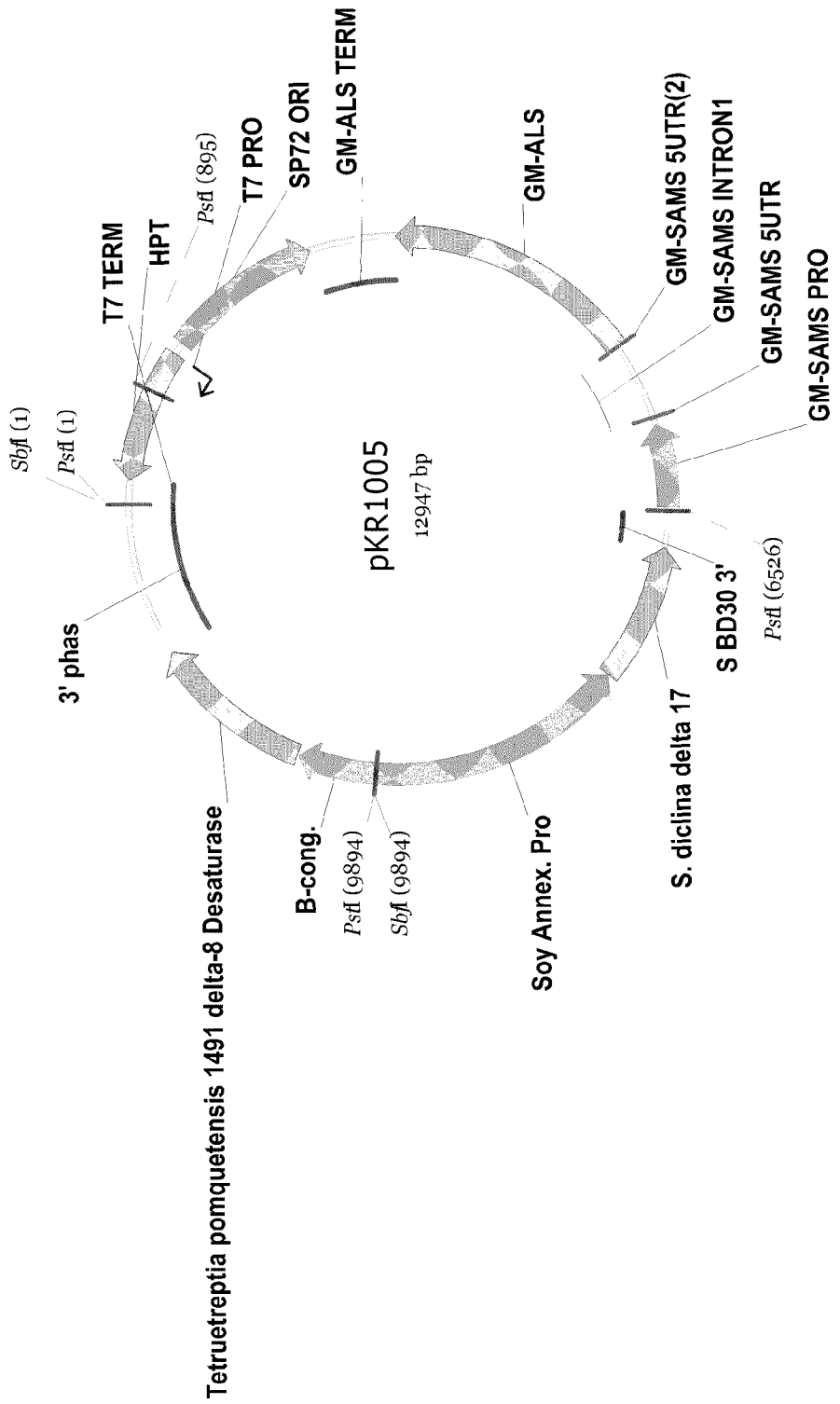
FIG. 4 is the soybean expression vector pKR1005.

FIG. 19 shows the average fatty acid profiles (average of 10 embryos per event) of soybean embryos transformed with the AscI fragments of pKR1005 (SEQ ID NO:90; FIG. 4) and pKR973 (SEQ ID NO:125; FIG. 11), for the 10 events having the highest amounts of delta-8 desaturation products. Fatty acids are identified as 16:0 (palmitate), 18:0 (stearic acid), 18:1 (oleic acid), LA, GLA, ALA, EDA, SCI, DGLA, ARA, ERA, JUP, ETA, EPA and DPA; and are expressed as a weight percent (wt. %) of total fatty acids. Fatty acids listed as "others" include: 18:2 (5,9), STA, 20:0, 20:1(11), 20:2 (7,11) or 20:2 (8,11), and DHA. The total wt. % of fatty acids containing a delta-8 double bond is expressed as C20 delta-8 desat (DGLA+ARA+ETA+EPA+DPA) and the delta-8 desaturase activity is expressed as percent desaturation (C20% delta-8 desat), calculated according to the following formula: ([DGLA+ETA]/[DGLA+ETA+EDA+ERA])*100.

FIG. 20 shows the fatty acid profiles for ten individual T1 seeds from 2 plants from event AFS 4882-4-6 (plant #4882-4-6-1 & #4882-4-6-2) having some of the highest amounts of total delta-8 desaturation products FIG. 21 shows the average fatty acid profiles (average of 10 embryos per event) of soybean embryos transformed with the AscI fragments of pKR1005 (SEQ ID NO:90; FIG. 4) and pKR1084 (SEQ ID NO:129; FIG. 12), for the 10 events having the highest amounts of delta-8 desaturation products. Fatty acids are identified as 16:0 (palmitate), 18:0 (stearic acid), 18:1 (oleic acid), LA, GLA, ALA, EDA, SCI, DGLA, ARA, ERA, JUP, ETA, EPA and DPA; and, fatty acid compositions are expressed as a weight percent (wt. %) of total fatty acids. Fatty acids listed as "others" include: 18:2 (5,9), STA, 20:0, 20:1(11), 20:2 (7,11) or 20:2 (8,11), and DHA. The total wt. % of fatty acids containing a delta-8 double bond is expressed as C20 delta-8 desat (DGLA+ARA+ETA+EPA+DPA) and the delta-8 desaturase activity is expressed as percent desaturation (C20% delta-8 desat), calculated according to the following formula: ([DGLA+ETA]/[DGLA+ETA+EDA+ERA])*100.

FIG. 22 shows the fatty acid profiles for individual T1 seeds from 2 plants from event AFS 5003-1-8 (plant #5003-1-8-1 & #5003-1-8-2) having some of the highest amounts of total delta-8 desaturation products.

The sequence descriptions summarize the Sequences Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

A Sequence Listing is provided herewith on Compact Disk. The contents of the Compact Disk containing the Sequence Listing are hereby incorporated by reference in compliance with 37 C.F.R. §1.52(e).

SEQ ID NOs:1-11 are the nucleotide sequences of primers D8F1, D8F2, D8F3, D8F4, D8F5, D8F6, D8F7, D8F8, D8F9, D8R1 and D8R2, respectively.

SEQ ID NO:12 is the amino acid sequence of primers D8F1 and D8F4.

SEQ ID NO:13 is the amino acid sequence of primers D8F2, D8F3, D8F5 and D8F6.

SEQ ID NO:14 is the amino acid sequence of primers D8F7, D8F8 and D8F9.

SEQ ID NO:15 is the amino acid sequence of primers D8R1 and D8R2.

SEQ ID NO:16 is the partial nucleotide sequence of the delta-8 desaturase from *Tetruetreptia pomquetensis* CCMP1491 using the primer combination D8F4/D8R1 (see Example 1).

SEQ ID NO:17 is the partial nucleotide sequence of the delta-8 desaturase from *Eutreptiella* sp. CCMP389 using the primer combination D8F4/D8R1 (see Example 1).

SEQ ID NO:18 is the partial nucleotide sequence of the delta-8 desaturase from *Eutreptiella* cf_*gymnastica* CCMP1594 using the primer combination D8F4/D8R1 (see Example 1).

SEQ ID NO:19 is the nucleotide sequence of the SMART IV oligonucleotide.

SEQ ID NOs:20-24 are the nucleotide sequences of primers 389D8-3-1, 389D8-3-2, 389D8-5-1, 389D8-5-2 and 389D8-5-3, respectively.

SEQ ID NOs:25-29 are the nucleotide sequences of primers ED8-5-1, ED8-5-2, ED8-5-3, ED8-3-1 and ED8-3-2, respectively.

SEQ ID NO:30 is the nucleotide sequence of CDSIII/3' PCR primer.

SEQ ID NO:31 is the nucleotide sequence of the Adaptor Primer from Invitrogen 3'-RACE kit.

SEQ ID NOs:32-36 are the nucleotide sequences of primers 1594D8-3-1, 1594D8-3-2, 1594D8-5-1, 1594D8-5-2 and 1594D8-5-3, respectively.

SEQ ID NO:37 is the nucleotide sequence of the GenomeWalker adaptor (see also SEQ ID NO:111).

SEQ ID NOs:38 and 39 are the nucleotide sequences of primer AP1 and AP2, respectively.

SEQ ID NO:40 is nucleotide sequence of pCR2.1-TOPO.

SEQ ID NO:41 is the 5'-region nucleotide sequence of the delta-8 desaturase from *Eutreptiella* cf_*gymnastica* CCMP1594 (see Example 2).

SEQ ID NO:42 is the 5'-region nucleotide sequence of the delta-8 desaturase from *Eutreptiella* sp. CCMP389 (see Example 2).

SEQ ID NO:43 is the 3'-region nucleotide sequence of the delta-8 desaturase from *Eutreptiella* sp. CCMP389 (see Example 2).

SEQ ID NO:44 is a 3'-region nucleotide sequence of the delta-8 desaturase from *Eutreptiella* cf_*gymnastica* CCMP1594 (1594D8-3'A) (see Example 2).

SEQ ID NO:45 is a 3'-region nucleotide sequence of the delta-8 desaturase from *Eutreptiella* cf_*gymnastica* CCMP1594 (1594D8-3'B) (see Example 2).

SEQ ID NO:46 is the nucleotide sequence of the delta-8 desaturase from *Eutreptiella* sp. CCMP389 (1963 bp contig).

SEQ ID NO:47 is the amino acid sequence of the delta-8 desaturase from *Eutreptiella* sp. CCMP389 (coding region of SEQ ID NO:46 and SEQ ID NO:92).

SEQ ID NO:48 is the nucleotide sequence of the delta-8 desaturase from *Eutreptiella* cf_*gymnastica* CCMP1594 (2063 bp contig).

SEQ ID NO:49 is the amino acid sequence of the delta-8 desaturase from *Eutreptiella* cf_*gymnastica* CCMP1594 (coding region of SEQ ID NO:48 and SEQ ID NO:93).

SEQ ID NO:50 is the nucleotide sequence of the TOPO linker.

SEQ ID NO:51 is the nucleotide sequence of the LinkAmp primer 1.

SEQ ID NO:52 is the nucleotide sequence of the LinkAmp primer 2.

SEQ ID NO:53 is the 5'-region nucleotide sequence of the delta-8 desaturase from *Tetruetreptia pomquetensis* CCMP1491 (see Example 3).

SEQ ID NO:54 is the nucleotide sequence of primer AUAP.

SEQ ID NO:55 is the 3'-region nucleotide sequence of the delta-8 desaturase from *Tetruetreptia pomquetensis* CCMP1491 (see Example 3).

SEQ ID NO:56 is the nucleotide sequence of the delta-8 desaturase from *Tetruetreptia pomquetensis* CCMP1491 (2233 bp contig).

SEQ ID NO:57 is the amino acid sequence of the delta-8 desaturase from *Tetruetreptia pomquetensis* CCMP1491 (coding region of SEQ ID NO:56 and SEQ ID NO:62).

SEQ ID NOs:58 and 59 are the nucleotide sequences of TpomNot-5 and TpomNot-3, respectively.

SEQ ID NO:60 is the nucleotide sequence of primer T7.

SEQ ID NO:61 is the nucleotide sequence of primer M13-28Rev.

SEQ ID NO:62 is the nucleotide sequence of the coding sequence of *Tetruetreptia pomquetensis* CCMP1491 delta-8 desaturase.

SEQ ID NO:63 is the nucleotide sequence of pLF114-10.

SEQ ID NO:64 is the nucleotide sequence of pY-75.

Figure 1:
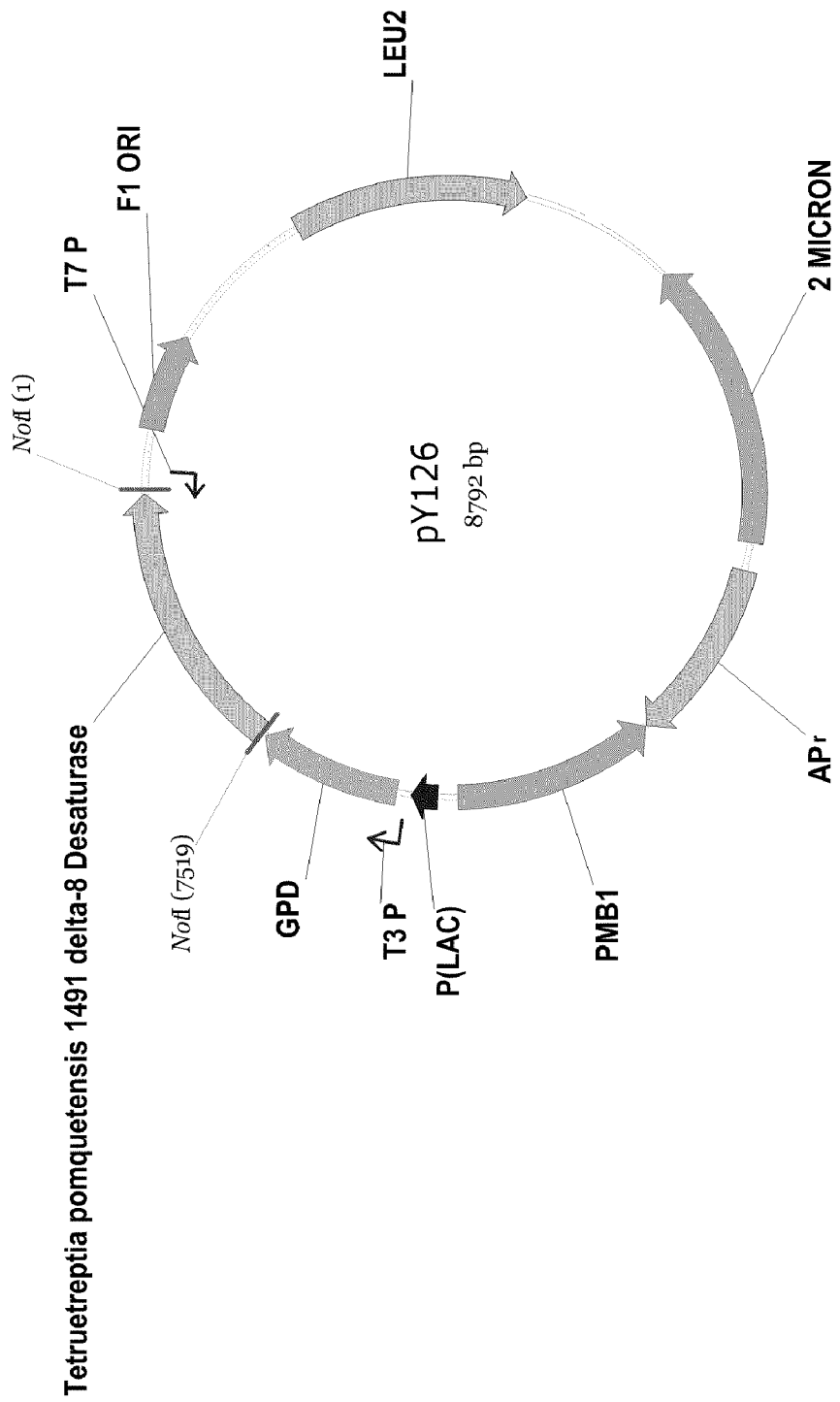
FIG. 1 is the yeast expression vector pY126.

SEQ ID NO:65 is the nucleotide sequence of pY126 (see FIG. 1).

SEQ ID NO:66 is the nucleotide sequence of pKR123r.

SEQ ID NO:67 is the nucleotide sequence of pKR1007.

SEQ ID NO:68 is the nucleotide sequence of pKR607.

Figure 2:
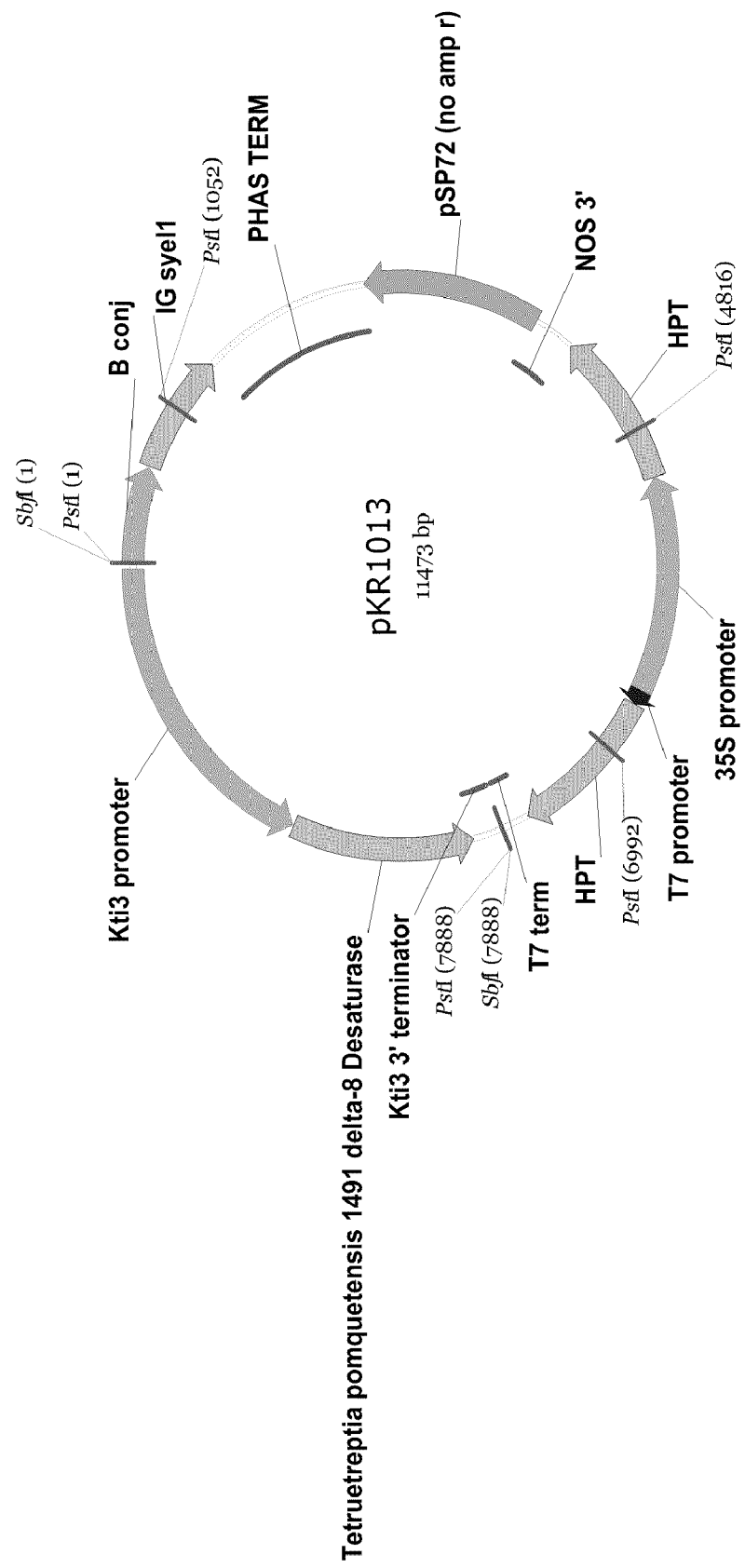
FIG. 2 is the soybean expression vector pKR1013.

SEQ ID NO:69 is the nucleotide sequence of pKR1013 (see FIG. 2).

SEQ ID NO:70 is the nucleotide sequence of the coding sequence of the *Isochrysis galbana* delta-9 elongase (NCBI Accession No. AAL37626 (GI 17226123), locus AAL37626, CDS AF390174; Qi et al., *FEBS Lett.* 510(3):159-165 (2002)).

SEQ ID NO:71 is the sequence of a portion of the cDNA insert from *Euglena gracilis* clone eeg1c.pk001.n5.f (5' end of cDNA insert).

SEQ ID NO:72 is the sequence of a portion of the cDNA insert from clone eeg1c.pk001.n5.f (3' end of cDNA insert).

SEQ ID NO:73 is the sequence of clone eeg1c.pk001.n5.f (5' and 3' sequences were aligned).

SEQ ID NO:74 is the *Euglena gracilis* delta-9 elongase coding sequence from the cDNA in clone eeg1c.pk001.n5.f.

SEQ ID NO:75 is the amino acid sequence of the *Euglena gracilis* delta-9 elongase from clone eeg1c.pk001.n5.f (coding region of SEQ ID NO:74).

SEQ ID NO:76 is the amino acid sequence of the long-chain PUFA elongation enzyme (delta-9 elongase) from *Isochrysis galbana* (NCBI Accession No. AAL37626 (GI 17226123), locus AAL37626, CDS AF390174) (designated "IgD9e").

SEQ ID NOs:77 and 78 are the nucleotide sequences of oligonucleotide primers oEugEL1-1 and oEugEL1-2, respectively.

SEQ ID NO:79 is the nucleotide sequence of pKR906.

SEQ ID NO:80 is the nucleotide sequence of pKR72 (ATCC Accession No. PTA-6019).

SEQ ID NO:81 is the nucleotide sequence of pK912.

Figure 3:
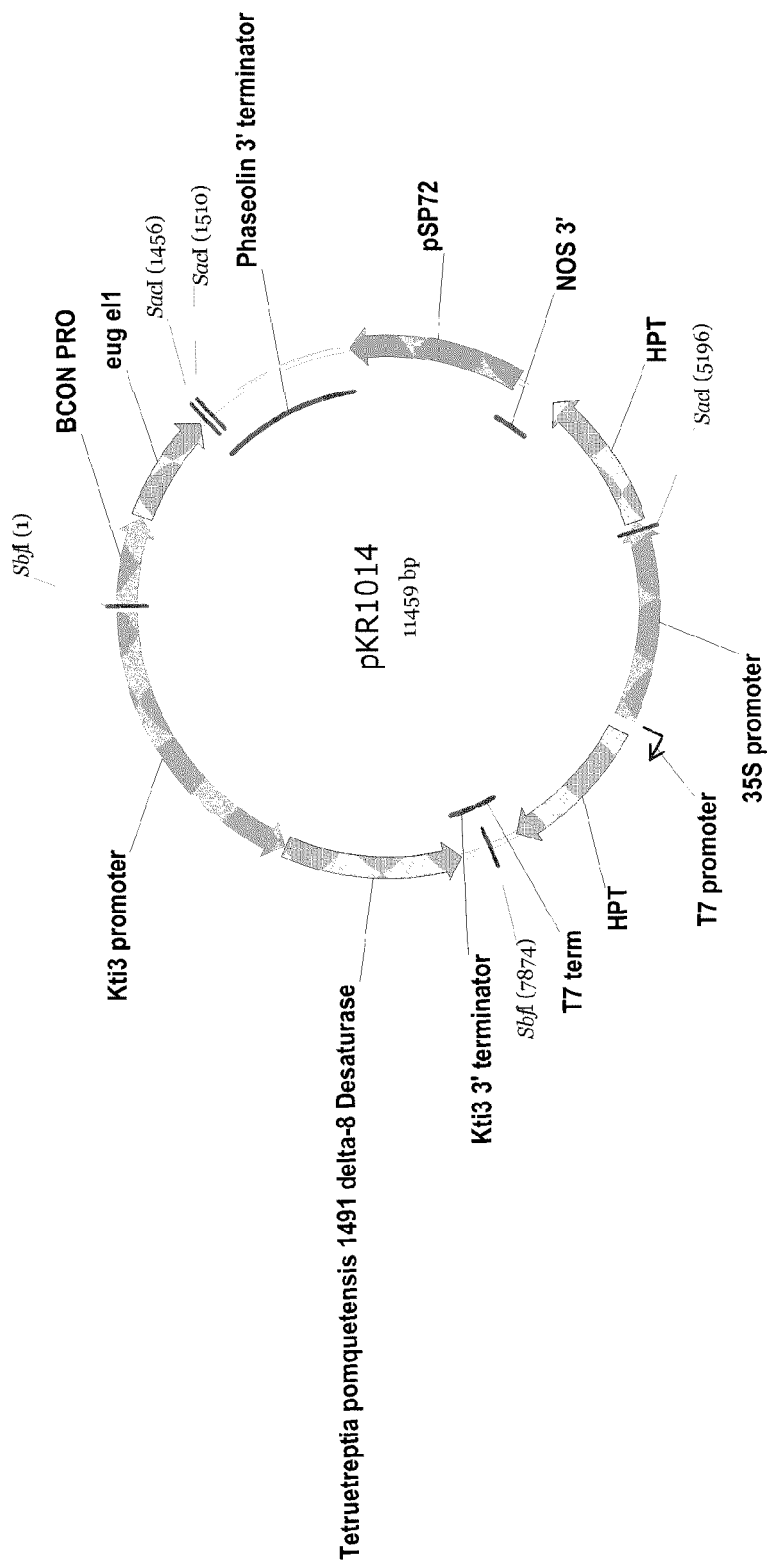
FIG. 3 is the soybean expression vector pKR1014.

SEQ ID NO:82 is the nucleotide sequence of pKR1014 (see FIG. 3).

SEQ ID NO:83 is the nucleotide sequence of pKR271.

SEQ ID NO:84 is the nucleotide sequence of pKR226.

SEQ ID NO:85 is the nucleotide sequence of pKR886r.

SEQ ID NOs:86 and 87 are the nucleotide sequences of oligonucleotide primers oCon1 and oCon2, respectively.

SEQ ID NO:88 is the nucleotide sequence of pKR179.

SEQ ID NO:89 is the nucleotide sequence of pKR1002.

SEQ ID NO:90 is the nucleotide sequence of pKR1005 (see FIG. 4).

SEQ ID NO:91 is the nucleotide sequence of the M13F universal primer.

SEQ ID NO:92 is the nucleotide sequence of the coding sequence of *Eutreptiella* sp. CCMP389 delta-8 desaturase.

SEQ ID NO:93 is the nucleotide sequence of the coding sequence of *Eutreptiella* cf_*gymnastica* CCMP1594 delta-8 desaturase.

SEQ ID NO:94 is the nucleotide sequence of *Yarrowia lipolytica* expression vector pFBAIn-MOD1.

SEQ ID NO:95 is the nucleotide sequence of *Yarrowia lipolytica* expression vector pFBAIn-389D8.

SEQ ID NO:96 is the nucleotide sequence of *Yarrowia lipolytica* expression vector pFBAIn-1594D8.

SEQ ID NO:97 is the nucleotide sequence of *Yarrowia lipolytica* expression vector pFBAIn-1491D8.

SEQ ID NO:98 is the amino acid sequence of the *Euglena gracilis* delta-8 fatty acid desaturase gene (NCBI Accession No. AAD45877 (GI 5639724)). SEQ ID NO:98 is the amino acid sequence encoded by nucleotides 14-1273 of NCBI Accession No. AF139720 (GI 5639723). This delta-8 fatty acid desaturase has been shown to be non-functional.

SEQ ID NOs:99 and 100 are the nucleotide sequences of primers 389D8-F and 389D8-R, respectively.

SEQ ID NOs:101 and 102 are the nucleotide sequences of primers 1491D8-F and 1491D8-R, respectively.

SEQ ID NOs:103 and 104 are the nucleotide sequences of primers 1594D8-F and 1594D8-R, respectively.

SEQ ID NO:105 is the 5' PCR primer used in Example 1.

SEQ ID NO:106 is the nucleotide sequence of plasmid pZKLeuN-29E3 (see FIG. 9).

SEQ ID NO:107 is the nucleotide sequence of a synthetic delta-9 elongase (initially from *Euglena gracilis*—see SEQ ID NO:74) codon-optimized for *Yarrowia lipolytica*; see also U.S. Patent Application No. 60/739,989, filed Nov. 23, 2005 (designated "EgD9E" or "EgD9S")

SEQ ID NO:108 is the nucleotide sequence of the LoxP sequence from *Escherichia coli*.

SEQ ID NO:109 is the nucleotide sequence of a synthetic $C_{16/18}$ elongase (initially from *M. alpina*) codon-optimized for *Yarrowia lipolytica*; see also U.S. patent application Ser. No. 11/253,882, filed Oct. 19, 2005.

SEQ ID NO:110 is the nucleotide sequence of a synthetic delta-9 elongase (initially from *Isochrysis galbana*) codon-optimized for *Yarrowia lipolytica* (designated "IgD9eS").

SEQ ID NO:111 is the nucleotide sequence of the GenomeWalker adaptor (see also SEQ ID NO:37).

SEQ ID NO:112 is the amino acid sequence of *Euglena gracilis* delta-8 desaturase (SEQ ID NO:2 of U.S. Publication No. 20050287652).

SEQ ID NO:113 is the nucleotide sequence of pKR132.

SEQ ID NO:114 is the nucleotide sequence of pKR953.

SEQ ID NO:115 is the nucleotide sequence of pKR287.

SEQ ID NO:116 is the nucleotide sequence of *Mortierella alpina* delta-5 desaturase (which is described in U.S. Pat. No. 6,075,183).

SEQ ID NO:117 is the nucleotide sequence of pKR277.

SEQ ID NO:118 is the nucleotide sequence of pKR952.

SEQ ID NO:119 is the nucleotide sequence of pKR457.

SEQ ID NO:120 is the nucleotide sequence of the modified KtiI-NotI-Kti3'Salb3'cassette.

SEQ ID NO:121 is the nucleotide sequence of the *Pavlova lutheri* Delta-8 Desaturase codon sequence described in U.S. Provisional Application No. 60/795,810 and U.S. patent application Ser. No. 11/737,772.

SEQ ID NO:122 is the nucleotide sequence of oligonucleotide primer PvDES5'Not-1.

SEQ ID NO:123 is the nucleotide sequence of oligonucleotide primer PvDES3'Not-1.

SEQ ID NO:124 is the nucleotide sequence of pKR970.

SEQ ID NO:125 is the nucleotide sequence of pKR973.

SEQ ID NO:126 is the nucleotide sequence of pKS129.

SEQ ID NO:127 is the nucleotide sequence of pKR606.

SEQ ID NO:128 is the nucleotide sequence of pKR804.

SEQ ID NO:129 is the nucleotide sequence of pKR1084.

SEQ ID NO:130 is the nucleotide sequence of pKR908.

SEQ ID NO:131 is the nucleotide sequence of pKR1118.

SEQ ID NO:132 is the nucleotide sequence of pKR1120.

SEQ ID NO:133 is the nucleotide sequence of pKR1123.

SEQ ID NO:134 is the nucleotide sequence of pKR1117.

SEQ ID NO:135 is the nucleotide sequence of pKR1119.

SEQ ID NO:136 is the nucleotide sequence of pKR1122.

SEQ ID NO:137 is the nucleotide sequence of pKR393.

SEQ ID NO:138 is the nucleotide sequence of pKR407.

SEQ ID NO:139 is the nucleotide sequence of pKR1018.

SEQ ID NO:140 is the nucleotide sequence of pKR1020R.

SEQ ID NO:141 is the nucleotide sequence of pKR1022R.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The present invention relates to delta-8 desaturase enzymes and nucleic acid for encoding the same isolated from *Tetruetreptia pomquetensis* CCMP1491, *Eutreptiella* sp. CCMP389 and *Eutreptiella cf_gymnastica* CCMP1594 delta-8. These are useful for, inter alia, for the manipulation of biochemical pathways for the production of healthful PUFAs. Thus, the subject invention finds many applications. PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

In the context of this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Fatty acids are described herein by a simple notation system of "X:Y", wherein X is number of carbon (C) atoms in the particular fatty acid and Y is the number of double bonds. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c,12c), GLA (18:3, 6c,9c,12c) and ALA (18:3, 9c,12c,15c)). Unless otherwise specified, 18:1, 18:2 and 18:3 refer to oleic, LA and ALA fatty acids, respectively. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the table summarizes the common names of omega-3 and omega-6 fatty acids and their precursors, the abbreviations that will be used throughout the remainder of the specification, and each compounds' chemical name.

TABLE 2

Nomenclature of Polyunsaturated Fatty Acids and Precursors

| Common Name | Abbreviation | Chemical Name | Shorthand Notation |
|---|---|---|---|
| myristic | — | tetradecanoic | 14:0 |
| palmitic | PA | hexadecanoic | 16:0 |
| palmitoleic | — | 9-hexadecenoic | 16:1 |
| stearic | — | octadecanoic | 18:0 |
| oleic | — | cis-9-octadecenoic | 18:1 |
| linoleic | LA | cis-9,12-octadecadienoic | 18:2 ω-6 |
| gamma-linolenic | GLA | cis-6,9,12-octadecatrienoic | 18:3 ω-6 |
| eicosadienoic | EDA | cis-11,14-eicosadienoic | 20:2 ω-6 |
| dihomo-gamma-linolenic | DGLA | cis-8,11,14-eicosatrienoic | 20:3 ω-6 |
| sciadonic | SCI | cis-5,11,14-eicosatrienoic | 20:3b ω-6 |
| arachidonic | ARA | cis-5,8,11,14-eicosatetraenoic | 20:4 ω-6 |
| alpha-linolenic | ALA | cis-9,12,15-octadecatrienoic | 18:3 ω-3 |
| stearidonic | STA | cis-6,9,12,15-octadecatetraenoic | 18:4 ω-3 |
| eicosatrienoic | ETrA or ERA | cis-11,14,17-eicosatrienoic | 20:3 ω-3 |
| eicosatetraenoic | ETA | cis-8,11,14,17-eicosatetraenoic | 20:4 ω-3 |
| juniperonic | JUP | cis-5,11,14,17-eicosatrienoic | 20:4b ω-3 |
| eicosapentaenoic | EPA | cis-5,8,11,14,17-eicosapentaenoic | 20:5 ω-3 |
| docosapentaenoic | DPA | cis-7,10,13,16,19-docosapentaenoic | 22:5 ω-3 |
| docosahexaenoic | DHA | cis-4,7,10,13,16,19-docosahexaenoic | 22:6 ω-3 |

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO 2006/052870). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulum membrane. More specifically, "PUFA biosynthetic pathway enzyme" refers to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase.

Figure 6:
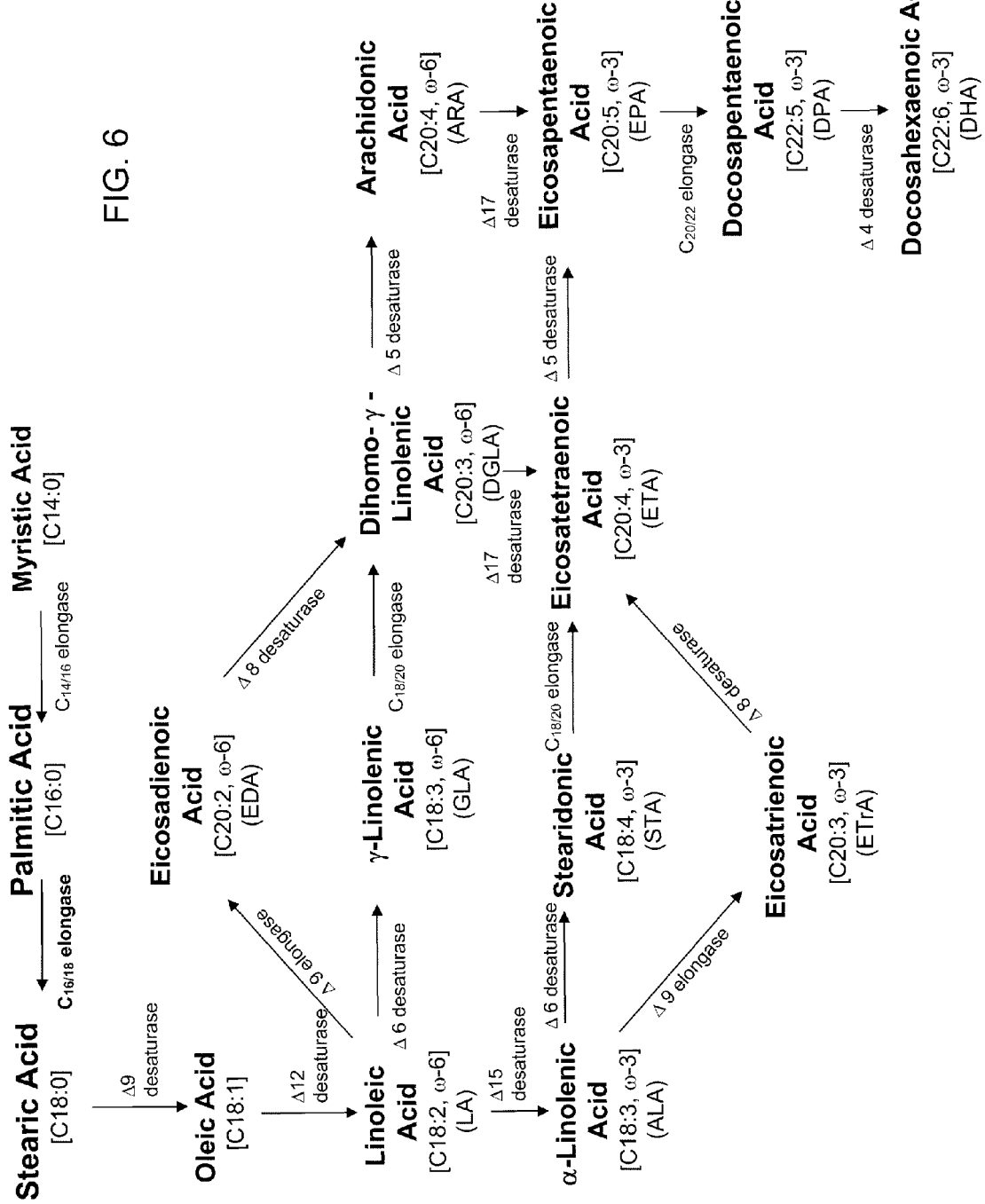
FIG. 6 is a representative omega-3 and omega-6 fatty acid pathway providing for the conversion of myristic acid through various intermediates to DHA.

The term "omega-3/omega-6 fatty acid biosynthetic pathway" refers to a set of genes which, when expressed under the appropriate conditions encode enzymes that catalyze the production of either or both omega-3 and omega-6 fatty acids. Typically the genes involved in the omega-3/omega-6 fatty acid biosynthetic pathway encode PUFA biosynthetic pathway enzymes. A representative pathway is illustrated in FIG. 6, providing for the conversion of myristic acid through various intermediates to DHA, which demonstrates how both omega-3 and omega-6 fatty acids may be produced from a common source. The pathway is naturally divided into two portions where one portion will generate omega-3 fatty acids and the other portion, omega-6 fatty acids.

The term "functional" as used herein in context with the omega-3/omega-6 fatty acid biosynthetic pathway means that some (or all of) the genes in the pathway express active enzymes, resulting in in vivo catalysis or substrate conversion. It should be understood that "omega-3/omega-6 fatty acid biosynthetic pathway" or "functional omega-3/omega-6 fatty acid biosynthetic pathway" does not imply that all the PUFA biosynthetic pathway enzyme genes are required, as a number of fatty acid products will only require the expression of a subset of the genes of this pathway.

The term "delta-9 elongase/delta-8 desaturase pathway" refers to a biosynthetic pathway for production of long-chain PUFAs. This pathway, at a minimum, comprises a delta-9 elongase and a delta-8 desaturase, thereby enabling biosynthesis of DGLA and/or ETA from LA and ALA, respectively. With expression of other desaturases and elongases, ARA, EPA, DPA and DHA may also be synthesized. This pathway may be advantageous in some embodiments, as the biosynthesis of GLA and/or STA is excluded.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the delta-9 elongase/delta-8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the delta-9 elongase/delta-8 desaturase pathway, sciadonic acid (SCI) and juniperonic acid (JUP) also can be produced by the action of a delta-5 desaturase on either EDA or ETrA, respectively. They are considered to be "by-product fatty acids" since neither can be further converted to EPA by the action of other metabolic pathway enzymes.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long-chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

"Desaturase" is a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are delta-8 desaturases that will desaturate a fatty acid between the eighth and ninth carbon atom numbered from the carboxyl-terminal end of the molecule and that can, for example, catalyze the conversion of EDA to DGLA and/or ETrA to ETA. Other useful fatty acid desaturases include, for example: (1) delta-5 desaturases that catalyze the conversion of DGLA to ARA and/or ETA to EPA; (2) delta-6 desaturases that catalyze the conversion of LA to GLA and/or ALA to STA; (3) delta-4 desaturases that catalyze the conversion of DPA to DHA; (4) delta-12 desaturases that catalyze the conversion of oleic acid to LA; (5) delta-15 desaturases that catalyze the conversion of LA to ALA and/or GLA to STA; (6) delta-17 desaturases that catalyze the conversion of ARA to EPA and/or DGLA to ETA; and (7) delta-9 desaturases that catalyze the conversion of palmitic acid to palmitoleic acid (16:1) and/or stearic acid to oleic acid (18:1). In the art, delta-15 and delta-17 desaturases are also occasionally referred to as "omega-3 desaturases", "w-3 desaturases", and/or "ω-3 desaturases", based on their ability to convert omega-6 fatty acids into their omega-3 counterparts (e.g., conversion of LA into ALA and ARA into EPA, respectively). In some embodiments, it is most desirable to empirically determine the specificity of a particular fatty acid desaturase by transforming a suitable host with the gene for the fatty acid desaturase and determining its effect on the fatty acid profile of the host.

For the purposes herein, the term "TpomD8" refers to a delta-8 desaturase enzyme (SEQ ID NO:57) isolated from *Tetruetreptia pomquetensis* CCMP1491, encoded by SEQ ID NO:62 herein. The term "E389D8" refers to a delta-8 desaturase enzyme (SEQ ID NO:47) isolated from *Eutreptiella* sp. CCMP389, encoded by SEQ ID NO:92 herein. Likewise, the term "E1594D8" refers to a delta-8 desaturase enzyme (SEQ ID NO:49) isolated from *Eutreptiella* cf_*gymnastica* CCMP1594, encoded by SEQ ID NO:93 herein.

Similarly, the term "EgD8" refers to a delta-8 desaturase enzyme (SEQ ID NO:112) isolated from *Euglena gracilis*. EgD8 is 100% identical and functionally equivalent to "Eg5", as described in PCT Publication Nos. WO 2006/012325 and WO 2006/012326 (SEQ ID NO:2 of U.S. Publication No. 20050287652-A1).

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell* 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA, LA to EDA, ALA to ETRA and EPA to DPA.

For the purposes herein, an enzyme catalyzing the first condensation reaction (i.e., conversion of malonyl-CoA and long-chain acyl-CvoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). Similarly, a "delta-9 elongase" may be able to catalyze the conversion of LA to EDA and/or ALA to ETrA. It is important to note that some elongases have broad specificity and thus a single enzyme may be capable of catalyzing several elongase reactions. Thus, for example, a delta-9 elongase may also act as a $C_{16/18}$ elongase, $C_{18/20}$ elongase and/or $C_{20/22}$ elongase and may have alternate, but not preferred, specificities for delta-5 and delta-6 fatty acids such as EPA and/or GLA, respectively.

For the purposes herein, the term "IgD9e" refers to a delta-9 elongase (SEQ ID NO:76; NCBI Accession No. AAL37626 [GI 17226123], locus AAL37626, CDS AF390174; GenBank Accession No. AF390174) isolated from *Isochrysis galbana*, encoded by SEQ ID NO:70. In contrast, the term "IgD9eS" refers to a synthetic (codon-optimized) delta-9 elongase (SEQ ID NO:110) derived from the DNA sequence of the *Isochrysis galbana* delta-9 elongase (SEQ ID NO:70) which can be used for expression in *Yarrowia lipolytica*.

Similarly for the purposes herein, the term "EgD9e" refers to a delta-9 elongase (SEQ ID NO:75) isolated from *Euglena gracilis*, encoded by SEQ ID NO:74 (see Example 11 herein).

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., *Anal. Biochem.* 138:267-284 (1984): $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecu-*

*lar Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS.* 5:151-153 (1989); Higgins, D. G. et al. (1992) *Comput. Appl. Biosci.* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genome" as it applies to a plant cells encompasses not only chromosomal DNA found within the nucleus, but organelle DNA found within subcellular components (e.g., mitochondrial, plastid) of the cell.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or anti-sense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host (i.e., to a discrete nucleic acid fragment into which a nucleic acid sequence or fragment can be moved.)

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al.,

*Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into ac ell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., *Plant J.* 16:651-659 (1998); Gura, *Nature* 404:804-808 (2000)). The overall efficiency of this phenomenon is low, and the extent of the RNA reduction is widely variable. More recent work has described the use of "hairpin" structures that incorporate all, or part, of an mRNA encoding sequence in a complementary orientation that results in a potential "stem-loop" structure for the expressed RNA (PCT Publication No. WO 99/53050, published Oct. 21, 1999; PCT Publication No. WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, published Aug. 20, 1998). Both of these co-suppressing phenomena have not been elucidated mechanistically, although genetic evidence has begun to unravel this complex situation (Elmayan et al., *Plant Cell* 10:1747-1757 (1998)).

The term "oleaginous" refers to those organisms that tend to store their energy source in the form of lipid (Weete, In: Fungal Lipid Biochemistry, $2^{nd}$ Ed., Plenum, 1980). A class of plants identified as oleaginous are commonly referred to as "oilseed" plants. Examples of oilseed plants include, but are not limited to: soybean (*Glycine* and *Soja* sp.), flax (*Linum* sp.), rapeseed (*Brassica* sp.), maize, cotton, safflower (*Carthamus* sp.) and sunflower (*Helianthus* sp.). Within oleaginous microorganisms the cellular oil or TAG content generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "Euglenophyceae" refers to a group of unicellular colorless or photosynthetic flagellates ("euglenoids") found living in freshwater, marine, soil, and parasitic environments. The class is characterized by solitary unicells, wherein most are free-swimming and have two flagella (one of which may be nonemergent) arising from an anterior invagination known as a reservoir. Photosynthetic euglenoids contain one to many grass-green chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Eutreptiella* and *Tetruetreptia*.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

"Progeny" comprises any subsequent generation of a plant.

An Overview Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 6).

TAGs (the primary storage unit for fatty acids) are formed by a series of reactions that involve: (1) the esterification of one molecule of acyl-CoA to glycerol-3-phosphate via an acyltransferase to produce lysophosphatidic acid; (2) the esterification of a second molecule of acyl-CoA via an acyltransferase to yield 1,2-diacylglycerol phosphate (commonly identified as phosphatidic acid); (3) removal of a phosphate by phosphatidic acid phosphatase to yield 1,2-diacylglycerol (DAG); and (4) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to long chain omega-3/omega-6 fatty acids involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 6 and as described below, there are often multiple alternate pathways for production of a specific long chain omega-3/omega-6 fatty acid.

Specifically, all pathways require the initial conversion of oleic acid to LA, the first of the omega-6 fatty acids, by a delta-12 desaturase. Then, using the "delta-9 elongase/delta-8 desaturase pathway", long chain omega-6 fatty acids are formed as follows: (1) LA is converted to EDA by a delta-9 elongase; (2) EDA is converted to DGLA by a delta-8 desaturase; and (3) DGLA is converted to ARA by a delta-5 desaturase. Alternatively, the "delta-9 elongase/delta-8 desaturase pathway" can be utilized for formation of long chain omega-3 fatty acids as follows: (1) LA is converted to ALA, the first of the omega-3 fatty acids, by a delta-15 desaturase; (2) ALA is converted to ETrA by a delta-9 elongase; (3) ETrA is converted to ETA by a delta-8 desaturase; (4) ETA is converted to EPA by a delta-5 desaturase; (5) EPA is converted to DPA by a $C_{20/22}$ elongase; and (6) DPA is converted to DHA by a delta-4 desaturase. Optionally, omega-6 fatty acids may be converted to omega-3 fatty acids; for example, ETA and EPA are produced from DGLA and ARA, respectively, by delta-17 desaturase activity.

Alternate pathways for the biosynthesis of omega-3/omega-6 fatty acids utilize a delta-6 desaturase and $C_{18/20}$ elongase (also known as delta-6 elongase, the terms can be used interchangeably) (i.e., the "delta-6 desaturase/delta-6 elongase pathway"). More specifically, LA and ALA may be converted to GLA and STA, respectively, by a delta-6 desaturase; then, a $C_{18/20}$ elongase converts GLA to DGLA and/or STA to ETA.

It is contemplated that the particular functionalities required to be introduced into a specific host organism for production of omega-3/omega-6 fatty acids will depend on the host cell (and its native PUFA profile and/or desaturase/elongase profile), the availability of substrate, and the desired end product(s). For example, expression of the delta-9 elongase/delta-8 desaturase pathway may be preferred in some embodiments, as opposed to expression of the delta-6 desaturase/delta-6 elongase pathway, since PUFAs produced via the former pathway are devoid of GLA.

One skilled in the art will be able to identify various candidate genes encoding each of the enzymes desired for omega-3/omega-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: (1) the substrate specificity of the polypeptide; (2) whether the polypeptide or a component thereof is a rate-limiting enzyme; (3) whether the desaturase or elongase is essential for synthesis of a desired PUFA; and/or (4) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of unpurified oils produced in a host cell will typically be a mixture of various PUFAs consisting of the desired omega-3/omega-6 fatty acid, as well as various upstream intermediary PUFAs. Thus, consideration of each enzyme's conversion efficiency is also a variable when optimizing biosynthesis of a desired fatty acid that must be considered in light of the final desired lipid profile of the product.

With each of the considerations above in mind, candidate genes having the appropriate desaturase and elongase activities (e.g., delta-6 desaturases, $C_{18/20}$ elongases, delta-5 desaturases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of Novel Delta-8 Desaturases

In the present invention, nucleotide sequences encoding delta-8 desaturases have been isolated from *Tetruetreptia pomquetensis* CCMP1491 (designated herein as "TpomD8"), *Eutreptiella* sp. CCMP389 (designated herein as "E389D8") and *Eutreptiella* cf_*gymnastica* CCMP1594 (designated herein as "E1594D8").

Thus, the present invention concerns an isolated polynucleotide comprising:

(a) a nucleotide sequence encoding a polypeptide having delta-8 desaturase activity, wherein the polypeptide has at least 80% amino acid identity, based on the Clustal V method of alignment, when compared to an amino acid sequence as set forth in SEQ ID NO:47 [E389D8], SEQ ID NO:49 [E1594D8] or SEQ ID NO:57 [TpomD8];

(b) a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:92 [E389D8], SEQ ID NO:93 [E1594D8] or SEQ ID NO:62 [TpomD8]; or, (c) a complement of the nucleotide sequence of (a) or (b), wherein the complement and the nucleotide sequence consist of the same number of nucleotides and are 100% complementary.

In still another aspect, this invention concerns an isolated polynucleotide comprising a nucleotide sequence encoding a polypeptide having delta-8 desaturase activity, wherein the nucleotide sequence has at least 90% sequence identity, based on the BLASTN method of alignment, when compared to a nucleotide sequence as set forth in SEQ ID NO:92, SEQ ID NO:93 or SEQ ID NO:62.

In alternate embodiments, the instant E389D8, E1594D8 or TpomD8 desaturase sequences can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species.

In one embodiment of the invention herein, E389D8, E1594D8 and/or TpomD8 could be codon-optimized for expression in *Yarrowia lipolytica*, as taught in PCT Publication No. WO 04/101757. In alternate embodiments, it may be desirable to modify a portion of the codons encoding E389D8, E1594D8 and/or TpomD8 (as set forth in SEQ ID NOs:92, 93 and 62, respectively) to enhance expression of the gene in a host organism including, but not limited to, a plant or plant part.

One skilled in the art would be able to use the teachings herein to create various other codon-optimized delta-8 desaturase proteins suitable for optimal expression in alternate hosts, based on the wildtype E389D8, E1594D8 and/or TpomD8 sequences. Accordingly, the instant invention relates to any codon-optimized delta-8 desaturase protein that is derived from the wildtype E389D8 (i.e., encoded by SEQ ID NO:47), the wildtype E1594D8 (i.e., encoded by SEQ ID NO:49) or the wildtype TpomD8 (i.e., encoded by SEQ ID NO:57).

Identification and Isolation of Homologs

Any of the instant desaturase sequences (i.e., E389D8, E1594D8 or TpomD8) or portions thereof may be used to search for delta-8 desaturase homologs in the same or other bacterial, algal, fungal, euglenoid or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of delta-8 desaturase homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the delta-8 desaturase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor et al., *Proc. Acad. Sci. USA* 82:1074 (1985); or strand displacement amplification (SDA), Walker et al., *Proc. Natl. Acad. Sci. U.S.A.*, 89:392 (1992)]; and (3) methods of library construction and screening by complementation.

For example, genes encoding similar proteins or polypeptides to the delta-8 desaturases described herein could be isolated directly by using all or a portion of the instant nucleic acid fragments as DNA hybridization probes to screen libraries from e.g., any desired yeast or fungus using methodology well known to those skilled in the art (wherein those organisms producing DGLA and/or ETA would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA* 86:5673 (1989); Loh et al., *Science* 243:217 (1989)).

In other embodiments, any of the delta-8 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Alternatively, improved fatty acids may be synthesized by domain swapping, wherein a functional domain from any of the delta-8 desaturase nucleic acid fragments described herein are exchanged with a functional domain in an alternate desaturase gene to thereby result in a novel protein. As used herein, "domain" or "functional domain" refer to nucleic acid sequence(s) that are capable of eliciting a biological response in plants.

Methods for Production of Various Omega-3 and/or Omega-6 Fatty Acids

It is expected that introduction of chimeric genes encoding the delta-8 desaturases described herein (i.e., E389D8, E1594D8, TpomD8 or other mutant enzymes, codon-optimized enzymes or homologs thereof), under the control of the appropriate promoters will result in increased production of DGLA and/or ETA in the transformed host organism, respectively. As such, the present invention encompasses a method for the direct production of PUFAs comprising exposing a fatty acid substrate (i.e., EDA and/or ETrA) to the desaturase enzymes described herein (e.g., E389D8, E1594D8, TpomD8), such that the substrate is converted to the desired fatty acid product (i.e., DGLA and/or ETA).

More specifically, it is an object of the present invention to provide a method for the production of DGLA in a host cell (e.g., oleaginous yeast, soybean), wherein the host cell comprises:

(a) a recombinant construct encoding a delta-8 desaturase polypeptide selected from the group consisting of SEQ ID NO:47, SEQ ID NO:49 and SEQ ID NO:57; and, (b) a source of EDA;

wherein the host cell is grown under conditions such that the delta-8 desaturase is expressed and the EDA is converted to DGLA, and wherein the DGLA is optionally recovered.

In alternate embodiments of the present invention, the delta-8 desaturase may be used for the use of the enzyme for the conversion of ETrA to ETA. Accordingly the invention provides a method for the production of ETA, wherein the host cell comprises:

(a) a recombinant construct encoding a delta-8 desaturase polypeptide selected from the group consisting of SEQ ID NO:47, SEQ ID NO:49 and SEQ ID NO:57; and, (b) a source of ETrA;

wherein the host cell is grown under conditions such that the delta-8 desaturase is expressed and the ETrA is converted to ETA, and wherein the ETA is optionally recovered.

Alternatively, each delta-8 desaturase gene and its corresponding enzyme product described herein can be used indirectly for the production of various omega-6 and omega-3 PUFAs, including e.g., DGLA, ETA, ARA, EPA, DPA and/or DHA (FIG. 6; see PCT Publication No. WO 2004/101757). Indirect production of omega-3/omega-6 PUFAs occurs wherein the fatty acid substrate is converted indirectly into the desired fatty acid product, via means of an intermediate step(s) or pathway intermediate(s). Thus, it is contemplated that the delta-8 desaturases described herein (i.e., E389D8, E1594D8, TpomD8, or other mutant enzymes, codon-optimized enzymes or homologs thereof) may be expressed in conjunction with additional genes encoding enzymes of the PUFA biosynthetic pathway (e.g., delta-6 desaturases, $C_{18/20}$ elongases, delta-17 desaturases, delta-8 desaturases, delta-15 desaturases, delta-9 desaturases, delta-12 desaturases, $C_{14/16}$ elongases, $C_{16/18}$ elongases, delta-9 elongases, delta-5 desaturases, delta-4 desaturases, $C_{20/22}$ elongases) to result in higher levels of production of longer-chain omega-3/ omega-6 fatty acids (e.g., ARA, EPA, DPA and DHA).

In preferred embodiments, the delta-8 desaturases of the present invention will minimally be expressed in conjunction with a delta-9 elongase (e.g., a delta-9 elongase as set forth in SEQ ID NO:75 or a codon-optimized delta-9 elongase as set forth in SEQ ID NO:110). However, the particular genes included within a particular expression cassette will depend on the host cell (and its PUFA profile and/or desaturase/ elongase profile), the availability of substrate and the desired end product(s).

At times, it may be desirable to minimize by-product fatty acids. The relative abundance of by-product fatty acids could be decreased by increasing total delta-8 desaturase activity. One approach to minimize by-product fatty acids would be to express more than one delta-8 desaturase (i.e., the same or different delta-8 desaturase). For instance, the presence of sciadonic acid (SCI) and/or juniperonic acid (JUP) [commonly found in the seed lipids of gymnosperms (Wolff et al., Lipids 35(1):1-22 (2000)), such as those in the Pinaceae family (pine)] might be considered by-product fatty acids of a delta-6 desaturase/delta-6 elongase pathway or delta-9-elongase/delta-8 desaturase pathway. Although these fatty acids are considered to have various health-enhancing properties themselves (Nakane et al., Biol. Pharm. Bull. 23: 758-761 (2000)), their presence as by-product fatty acids in an engineered PUFA pathway, such as in an oilseed crop, may not be desirable depending on the application.

The term "delta-6 desaturase/delta-6 elongase pathway" also refers to a biosynthetic pathway for production of long-chain PUFAs. This pathway, at a minimum, comprises a delta-6 desaturase and a delta-6 elongase, thereby enabling biosynthesis of DGLA and/or ETA from LA and ALA, respectively. With expression of other desaturases and elongases, ARA, EPA, DPA and DHA may also be synthesized. Occasionally, a delta-6 elongase may elongate fatty acids other than the intended fatty acid. For instance, delta-6 elongases generally convert GLA to DGLA but some delta-6 elongases may also convert unintended substrates such as LA or ALA to EDA or ETrA, respectively. In a delta-6 desaturase/delta-6 elongase pathway, EDA and ETrA would be considered "by-product fatty acids" as defined below. Addition of a delta-8 desaturase to a delta-6 desaturase/delta-6 elongase pathway would provided a means to convert the "by-product fatty acids" EDA and ETrA back into the "intermediate fatty acids" (as defined below) DGLA and ETA, respectively.

Plant Expression Systems, Cassettes and Vectors, and Transformation

In one embodiment, this invention concerns a recombinant construct comprising any one of the delta-8 desaturase polynucleotides of the invention operably linked to at least one regulatory sequence suitable for expression in a plant. A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the delta-8 desaturase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, the Kunitz trypsin inhibitor 3 promoter, the annexin promoter, the glycinin Gy1 promoter, the beta subunit of beta conglycinin promoter, the P34/Gly Bd m 30K promoter, the albumin promoter, the Leg A1 promoter and the Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)); (2) the Arabidopsis oleosin promoters (Plant et al., Plant Mol. Biol. 25:193-205 (1994); Li, Texas A&M University Ph.D. dissertation, pp. 107-128 (1997)); (3) the Arabidopsis ubiquitin extension protein promoters (Callis et al., J Biol. Chem. 265(21):12486-93 (1990)); (4) a tomato ubiquitin gene promoter (Rollfinke et al., Gene. 211(2):267-76 (1998)); (5) a soybean heat shock protein promoter (Schoffl et al., Mol Gen Genet. 217(2-3): 246-53 (1989)); and, (6) a maize H3 histone gene promoter (Atanassova et al., Plant Mol. Biol. 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., Dev. Genet. 10:112-122 (1989); Ellerstrom et al., Plant Mol. Biol. 32:1019-1027 (1996); Keddie et al., Plant Mol. Biol. 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific delta-8 desaturase coding sequence, the promoter is then operably linked in a sense orientation using conventional means well known to those skilled in the art.

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or a group of tissues that constitute a morphologically and functionally distinct part of a plant. The term "genome" refers to the following: (1) the entire complement of genetic material (genes and non-coding sequences) that is present in each cell of an organism, or virus or organelle; and/or (2) a complete set of chromosomes inherited as a (haploid) unit from one parent.

Thus, this invention also concerns a method for transforming a cell, comprising transforming a cell with the recombinant construct of the invention and selecting those cells transformed with the recombinant construct of Claim 8.

Also of interest is a method for producing a transformed plant comprising transforming a plant cell with the delta-8 desaturase polynucleotides of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. Nos. 5,004,863; 5,159,135); soybean (U.S. Pat. Nos. 5,569,834; 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbiol. Sci.* 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci. U.S.A.* 84:3962-3966 (1987)), microinjection and particle bombardement (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: N.Y. (1989); Maliga et al., Methods in Plant Molecular Biology, Cold Spring Harbor: N.Y. (1995); Birren et al., Genome Analysis: Detecting Genes, Vol. 1, Cold Spring Harbor: N.Y. (1998); Birren et al., Genome Analysis: Analyzing DNA, Vol. 2, Cold Spring Harbor: N.Y. (1998); Plant Molecular Biology: A Laboratory Manual, eds. Clark, Springer: N.Y. (1997).

Examples of oilseed plants include, but are not limited to: soybean, *Brassica* species, sunflower, maize, cotton, flax and safflower.

Examples of PUFAs having at least twenty carbon atoms and five or more carbon-carbon double bonds include, but are not limited to, omega-3 fatty acids such as EPA, DPA and DHA. Seeds obtained from such plants are also within the scope of this invention as well as oil obtained from such seeds.

Thus, in one embodiment this invention concerns an oilseed plant comprising:
 (a) a first recombinant DNA construct comprising an isolated polynucleotide encoding a delta-8 desaturase polypeptide, operably linked to at least one regulatory sequence; and,
 (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase.

Such additional desaturases are discussed, for example, in U.S. Pat. Nos. 6,075,183, 5,968,809, 6,136,574, 5,972,664, 6,051,754, 6,410,288 and PCT Publication Nos. WO 98/46763, WO 98/46764, WO 00/12720 and WO 00/40705.

The choice of combination of cassettes used depends in part on the PUFA profile and/or desaturase/elongase profile of the oilseed plant cells to be transformed and the long-chain PUFA which is to be expressed.

In another aspect, this invention concerns a method for making long-chain PUFAs in a plant cell comprising:
 (a) transforming a cell with the recombinant construct of the invention; and,
 (b) selecting those transformed cells that make long-chain PUFAs.

In still another aspect, this invention concerns a method for producing at least one PUFA in a soybean cell comprising:
 (a) transforming a soybean cell with a first recombinant DNA construct comprising:
  (i) an isolated polynucleotide encoding a delta-8 desaturase polypeptide, operably linked to at least one regulatory sequence; and,
  (ii) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase;
 (b) regenerating a soybean plant from the transformed cell of step (a); and, (c) selecting those seeds obtained from the plants of step (b) having an altered level of PUFAs when compared to the level in seeds obtained from a nontransformed soybean plant.

In other preferred embodiments, the at least one additional recombinant DNA construct encodes a polypeptide having delta-9 elongase activity, e.g., the delta-9 elongase isolated or derived from *Isochrysis galbana* (GenBank Accession No. AF390174; IgD9e) as set forth in SEQ ID NO:76 or the delta-9 elongase isolated or derived from *Euglena gracilis* as set forth in SEQ ID NO:75.

Microbial Expression Systems, Cassettes and Vectors, and Transformation

The delta-8 elongase genes and gene products described herein (i.e., E389D8, E1594D8, TpomD8, or other mutant enzymes, codon-optimized enzymes or homologs thereof) may also be produced in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Initiation control regions or promoters which are useful to drive expression of the instant delta-8 desaturase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publication Nos. WO 2004/101757 and WO 2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, when the microbial host is a yeast cell, the termination region is derived from a yeast gene (particularly *Saccharomyces, Schizosaccharomyces, Candida, Yarrowia* or *Kluyveromyces*). The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Although not intended to be limiting, termination regions useful in the disclosure herein include: ~100 bp of the 3' region of the *Yarrowia lipolytica* extracellular protease (XPR; GenBank Accession No. M17741); the acyl-coA oxidase (Aco3: GenBank Accession No. AJ001301 and No. CAA04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: (1) the nature of the relevant transcriptional promoter and terminator sequences; (2) the number of copies of the cloned gene and whether the gene is plasmid-borne or integrated into the genome of the host cell; (3) the final cellular location of the synthesized foreign protein; (4) the efficiency of translation and correct folding of the protein in the host organism; (5) the intrinsic stability of the mRNA and protein of the cloned gene within the host cell; and (6) the codon usage within the cloned gene, such that its frequency approaches the frequency of preferred codon usage of the host cell. Each of these types of modifications are encompassed in the present invention, as means to further optimize expression of the delta-8 desaturases described herein.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

In the present invention, the preferred method of expressing genes in *Yarrowia lipolytica* is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus (PCT Publication No. WO2004/104167), the Lip1 gene locus (GenBank Accession No. Z50020) and/or the Lip2 gene locus (GenBank Accession No. AJ012632)].

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a microbial host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. Nos. 4,880,741 and 5,071,764 and Chen, D. C. et al. (*Appl. Microbiol. Biotechnol.*, 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication Nos. WO2004/101757 and WO 2006/052870. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura− mutants. The compound is toxic to yeast cells that possess a functioning URA3 gene encoding orotidine 5′-monophosphate decarboxylase (OMP decarboxylase); thus, based on this toxicity, 5-FOA is especially useful for the selection and identification of Ura− mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura− phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3− strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the instant delta-8 desaturases (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. Based on the needs of the Applicants' Assignee, the genes described in the instant invention will be expressed in an oleaginous yeast (and in particular *Yarrowia lipolytica*); however, it is contemplated that because transcription, translation and the protein biosynthetic apparatus is highly conserved, any bacteria, yeast, algae and/or fungus will be a suitable microbial host for expression of the present nucleic acid fragments.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia*, *Candida*, *Rhodotorula*, *Rhodosporidium*, *Cryptococcus*, *Trichosporon* and *Lipomyces*. More specifically, illustrative oil-synthesizing yeasts include: *Rhodosporidium toruloides*, *Lipomyces starkeyii*, *L. lipoferus*, *Candida revkaufi*, *C. pulcherrima*, *C. tropicalis*, *C. utilis*, *Trichosporon pullans*, *T. cutaneum*, *Rhodotorula glutinus*, *R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Historically, various strains of *Y. lipolytica* have been used for the manufacture and production of: isocitrate lyase; lipases; polyhydroxyalkanoates; citric acid; erythritol; 2-oxoglutaric acid; γ-decalactone; γ-dodecalatone; and pyruvic acid. Specific teachings applicable for engineering ARA, EPA and DHA production in *Y. lipolytica* are provided in U.S. patent application Ser. No. 11/264,784 (WO 2006/055322), U.S. patent application Ser. No. 11/265,761 (WO 2006/052870) and U.S. patent application Ser. No. 11/264,737 (WO 2006/052871), respectively.

Other preferred microbial hosts include oleaginous bacteria, algae and other fungi; and, within this broad group of microbial hosts, of particular interest are microorganisms that synthesize omega-3/omega-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present delta-8 desaturase genes under the control of inducible or regulated promoters could yield a transformant organism capable of synthesizing increased quantities of DGLA. The method of transformation of *M. alpina* is described by Mackenzie et al. (*Appl. Environ. Microbiol.*, 66:4655 (2000)). Similarly, methods for transformation of Thraustochytriales microorganisms are disclosed in U.S. Pat. No. 7,001,772.

Based on the teachings described above, in one embodiment this invention is drawn to a method of producing either DGLA or ETA, respectively, comprising:
 (a) providing an oleaginous yeast comprising:
  (i) a first recombinant DNA construct comprising an isolated polynucleotide encoding a delta-8 desaturase polypeptide, operably linked to at least one regulatory sequence; and,
  (ii) a source of desaturase substrate consisting of either EDA or ETrA, respectively; and,
 (b) growing the yeast of step (a) in the presence of a suitable fermentable carbon source wherein the gene encoding the delta-8 desaturase polypeptide is expressed and EDA is converted to DGLA or ETrA is converted to ETA, respectively; and,
 (c) optionally recovering the DGLA or ETA, respectively, of step (b).

Substrate feeding may be required.

Of course, since naturally produced PUFAs in oleaginous yeast are limited to 18:2 fatty acids (i.e., LA), and less commonly, 18:3 fatty acids (i.e., ALA), in more preferred embodiments of the present invention the oleaginous yeast will be genetically engineered to express multiple enzymes necessary for long-chain PUFA biosynthesis (thereby enabling production of e.g., ARA, EPA, DPA and DHA), in addition to the delta-8 desaturases described herein.

Specifically, in one embodiment this invention concerns an oleaginous yeast comprising:
 (a) a first recombinant DNA construct comprising an isolated polynucleotide encoding a delta-8 desaturase polypeptide, operably linked to at least one regulatory sequence; and,
 (b) at least one additional recombinant DNA construct comprising an isolated polynucleotide, operably linked to at least one regulatory sequence, encoding a polypeptide selected from the group consisting of: a delta-4 desaturase, a delta-5 desaturase, delta-6 desaturase, a delta-9 desaturase, a delta-12 desaturase, a delta-15 desaturase, a delta-17 desaturase, a delta-9 elongase, a $C_{14/16}$ elongase, a $C_{16/18}$ elongase, a $C_{18/20}$ elongase and a $C_{20/22}$ elongase.

In particularly preferred embodiments, the at least one additional recombinant DNA construct encodes a polypeptide having delta-9 elongase activity, e.g., the delta-9 elongase isolated or derived from *Isochrysis galbana* (GenBank Accession No. AF390174; IgD9e or IgD9eS) as set forth in SEQ ID NO:76 or the delta-9 elongase isolated or derived from *Euglena gracilis* as set forth in SEQ ID NO:75.

Metabolic Engineering of Omega-3 and/or Omega-6 Fatty Acid Biosynthesis in Microbes Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This manipulation may require metabolic engineering directly within the PUFA biosynthetic pathway or additional coordinated manipulation of various other metabolic pathways.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this. To maximize production of omega-6 unsaturated fatty acids, it is well known to one skilled in the art that production is favored in a host microorganism that is substantially free of ALA; thus, preferably, the host is selected or obtained by removing or inhibiting delta-15 or omega-3 type desaturase activity that permits conversion of LA to ALA. Alternatively, it may be desirable to maximize production of omega-3 fatty acids (and minimize synthesis of omega-6 fatty acids). In this example, one could utilize a host microorganism wherein the delta-12 desaturase activity that permits conversion of oleic acid to LA is removed or inhibited; subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

In alternate embodiments, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication Nos. WO 2006/055322, WO 2006/052870 and WO 2006/052871, respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the delta-9 elongase/delta-8 desaturase biosynthetic pathway are introduced into oleaginous yeasts for the production of omega-3 and/or omega-6 fatty acids. It will be particularly useful to express the present the delta-8 desaturase genes in oleaginous yeasts that do not naturally possess omega-3 and/or omega-6 fatty acid biosynthetic pathways and coordinate the expression of these genes, to maximize production of preferred PUFA products using various means for metabolic engineering of the host organism.

Microbial Fermentation Processes for PUFA Production

The transformed host cell is grown under conditions that optimize expression of chimeric desaturase genes and produce the greatest and the most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in PCT Publication No. WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(5/6): 463-491 (1992)). A brief review of downstream processing is also available by A. Singh and O. Ward (*Adv. Appl. Microbiol.*, 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details. Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in Table 3.

TABLE 3

Generalized Steps for Soybean Oil and Byproduct Production

| Process Step | Process | Impurities Removed and/or By-Products Obtained |
|---|---|---|
| # 1 | soybean seed | |
| # 2 | oil extraction | meal |
| # 3 | degumming | lecithin |
| # 4 | alkali or physical refining | gums, free fatty acids, pigments |
| # 5 | water washing | soap |
| # 6 | bleaching | color, soap, metal |
| # 7 | (hydrogenation) | |
| # 8 | (winterization) | stearine |
| # 9 | deodorization | free fatty acids, tocopherols, sterols, volatiles |
| # 10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel and cocoa butter.

Plant and microbial oils containing PUFAs that have been refined and/or purified can be hydrogenated, to thereby result in fats with various melting properties and textures. Many processed fats (including spreads, confectionery fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

PUFA-Containing Oils for Use in Foodstuffs

The market place currently supports a large variety of food and feed products, incorporating omega-3 and/or omega-6 fatty acids (particularly ARA, EPA and DHA). It is contemplated that the plant/seed oils, altered seeds and microbial oils of the invention comprising PUFAs will function in food and feed products to impart the health benefits of current formulations. Compared to other vegetable oils, the oils of the invention are believed to function similarly to other oils in food applications from a physical standpoint (for example, partially hydrogenated oils such as soybean oil are widely used as ingredients for soft spreads, margarine and shortenings for baking and frying).

Plant/seed oils, altered seeds and microbial oils containing omega-3 and/or omega-6 fatty acids as described herein will be suitable for use in a variety of food and feed products including, but not limited to: food analogs, meat products, cereal products, baked foods, snack foods and dairy products. Additionally, the present plant/seed oils, altered seeds and microbial oils may be used in formulations to impart health benefit in medical foods including medical nutritionals, dietary supplements, infant formula as well as pharmaceutical products. One of skill in the art of food processing and food formulation will understand how the amount and composition of the plant and microbial oils may be added to the food or feed product. Such an amount will be referred to herein as an "effective" amount and will depend on the food or feed product, the diet that the product is intended to supplement or the medical condition that the medical food or medical nutritional is intended to correct or treat.

Food analogs can be made using processes well known to those skilled in the art. There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milks and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processed meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking (i.e., to dry or harden by subjecting to heat). Examples of a baked good product include, but are not limited to: bread, cakes, doughnuts, bars, pastas, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

A beverage can be in a liquid or in a dry powdered form.

For example, there can be mentioned non-carbonated drinks such as fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aqueous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ (Mead Johnson & Company) and Similac Advance™ (Ross Products Division, Abbott Laboratories)). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yoghurt or sour milk, cream, butter, condensed milk, dehydrated milk, coffee whitener, coffee creamer, ice cream, cheese, etc.

Additional food products into which the PUFA-containing oils of the invention could be included are, for example, chewing gums, confections and frostings, gelatins and puddings, hard and soft candies, jams and jellies, white granulated sugar, sugar substitutes, sweet sauces, toppings and syrups, and dry-blended powder mixes.

PUFA-Containing Oils for Use in Health Food Products and Pharmaceuticals

A health food product is any food product that imparts a health benefit and include functional foods, medical foods, medical nutritionals and dietary supplements. Additionally, the plant/seed oils, altered seeds and microbial oils of the invention may be used in standard pharmaceutical compositions (e.g., the long-chain PUFA containing oils could readily be incorporated into the any of the above mentioned food products, to thereby produce a functional or medical food). More concentrated formulations comprising PUFAs include capsules, powders, tablets, softgels, gelcaps, liquid concentrates and emulsions which can be used as a dietary supplement in humans or animals other than humans.

PUFA-Containing Oils for Use in Animal Feeds

Animal feeds are generically defined herein as products intended for use as feed or for mixing in feed for animals other than humans. The plant/seed oils, altered seeds and microbial oils of the invention can be used as an ingredient in various animal feeds.

More specifically, although not limited therein, it is expected that the oils of the invention can be used within pet food products, ruminant and poultry food products and aquacultural food products. Pet food products are those products intended to be fed to a pet (e.g., dog, cat, bird, reptile, rodent). These products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to an animal (e.g., turkeys, chickens, cattle, swine). As with the pet foods above, these products can include cereal and health food products, soy protein products, meat and meat byproducts, and grass and hay products as listed above.

Aquacultural food products (or "aquafeeds") are those products intended to be used in aquafarming, i.e., which concerns the propagation, cultivation or farming of aquatic organisms and/or animals in fresh or marine waters.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

General Methods

Standard recombinant DNA and molecular cloning techniques used in the Examples are well known in the art and are described by: (1) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); (2) T. J. Silhavy, M. L. Bennan, and L. W. Enquist, Experiments with Gene Fusions; Cold Spring Harbor Laboratory: Cold Spring Harbor, N.Y. (1984); and (3) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNA Star, Inc.).

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*:

*Yarrowia lipolytica* strains with ATCC Accession Nos. were purchased from the American Type Culture Collection (Rockville, Md.). *Yarrowia lipolytica* strains were typically grown at 28° C. on YPD agar (1% yeast extract, 2% bactopeptone, 2% glucose, 2% agar).

Transformation of *Yarrowia lipolytica* was performed according to the method of Chen et al. (*Appl. Microbiol. Biotechnol.* 48(2):232-235 (1997)), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 µg sheared salmon sperm DNA. Then, approximately 500 ng of linearized plasmid DNA was incubated in 100 µL of resuspended cells, and maintained at 39° C. for 1 h with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (Difco Laboratories, Detroit, Mich.) without ammonium sulfate or amino acids, 2% glucose, 0.1% proline, pH 6.1). Supplements of leucine and/or uracil were added as appropriate to a final concentration of 0.01% (thereby producing "MMLe" and "MMU" selection media, each prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (Difco Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*:

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G. and Nishida, I., *Arch Biochem Biophys.* 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µL of 1%) was added to the sample, and then the sample was vortexed and rocked for 20 min. After adding 3 drops of 1 M NaCl and 400 µL hexane, the sample was vortexed and spun. The upper layer was removed and analyzed by GC as described above.

Example 1

Identification of Delta-8 Desaturase Enzyme Homologs from *Tetruetreptia pomquetensis* CCMP1491, *Eutreptiella* sp. CCMP389 and *Eutreptiella* cf_*gymnastica* CCMP1594

The present Example describes the identification of cDNA fragments (SEQ ID NOs:16, 17 and 18) encoding portions of delta-8 desaturases from *Tetruetreptia pomquetensis* CCMP1491, *Eutreptiella* sp. CCMP389 and *Eutreptiella* cf_*gymnastica* CCMP1594, respectively. This work included the generation of genomic DNA and RNA, synthesis of cDNA, and then the identification of portions of the genes encoding delta-8 desaturase, by use of primers derived from the *Euglena gracilis* delta-8 desaturase.

Preparation of Euglenoid RNA and Genomic DNA

*Tetruetreptia pomquetensis* CCMP1491, *Eutreptiella* sp. CCMP389 and *Eutreptiella* cf_*gymnastica* CCMP1594 cells (each from 1 liter of culture) were purchased from the Provasoli-Guillard National Center for Culture of Marine Phytoplakton (CCMP) (Bigelow Laboratory for Ocean Sciences, West Boothbay Harbor, Me.). Total RNA and genomic DNA were isolated from each strain using the trizol reagent (Invitrogen, Carlsbad, Calif.), according to the manufacturer's protocol. Cell pellet from each strain was individually resuspended in 0.75 mL of trizol reagent, mixed with 0.5 mL of 0.5 mm glass beads, and homogenized in a Biospec mini beadbeater (Bartlesville, Okla.) at the highest setting for 3 min. The mixtures were centrifuged in an Eppendorf centrifuge for 30 sec at 14,000 rpm to remove debris and glass beads. Supernatant from each sample was extracted with 150 µL of 24:1 chloroform:isoamy alcohol. The upper aqueous phase was used for RNA isolation and lower organic phase for DNA isolation.

For RNA isolation, the aqueous phase from each sample was mixed with 0.375 mL of isopropyl alcohol and allowed to incubate at room temperature for 5 min. Precipitated RNA was collected by centrifugation at 8,000 rpm and 4° C. for 5 min. The pellet was washed once with 0.7 mL of 80% ethanol and air dried. Thus, 360 µg of total RNA was obtained from *Eutreptiella* sp. CCMP389, 95 µg from *Tetruetreptia pomquetensis* CCMP1491 and 720 µg from *Eutreptiella* cf_*gymnastica* CCMP1594.

For genomic DNA isolation, the lower organic phase of each sample was mixed with 75 µL of ethanol and incubated at room temperature for 5 min. The samples were then centrifuged at 5,000 rpm for 2 min in an Eppendorf centrifuge. Each pellet was washed with 0.75 mL of 0.1 M sodium citrate:10% ethanol twice. Each time, samples were incubated for 15 min at room temperature in the wash solution, followed by centrifugation at 5,000 rpm for 5 min at 4° C. in an Eppendorf centrifuge. The pellet was air dried and redissolved in 300 µL of 8 mM NaOH. The pH of each sample was adjusted to 7.5 with 1 M HEPES. Each sample was then further purified with the Qiagen PCR purification kit according to the manufacturer's protocol. In this way, 40 µg of genomic DNA was isolated from *Eutreptiella* sp. CCMP389, 15 µg from *Tetruetreptia pomquetensis* CCMP1491 and 45 µg from *Eutreptiella* cf_*gymnastica* CCMP1594.

Preparation of Euglenoid cDNA

Total RNA (1.2 µg from *Eutreptiella* sp. CCMP389 and 2.4 µg from *Eutreptiella* cf_*gymnastica* CCMP1594) was used as template to synthesize double stranded cDNA. The Creator™ SMART™ cDNA Library Construction Kit from BD Bioscience Clontech (Palo Alto, Calif.) was used. Each total RNA sample (1 µL) was mixed individually with 1 µL of SMART IV oligonucleotide (SEQ ID NO:19), 1 µL CDSIII/3' PCR primer (SEQ ID NO:30) and 2 µL of water. The mixtures were heated to 75° C. for 5 min and then cooled on ice for 5 min. To each sample were added 2 µL of 5× first strand buffer, 1 µL 20 mM DTT, 1 µL of dNTP mix (10 mM each of dATP, dCTP, dGTP and dTTP) and 1 µL of PowerScript reverse transcriptase. The samples were incubated at 42° C. for 1 h. The resulting first strand cDNAs were then used as template for amplification. Each reaction mixture contained 2 µL of the above first strand cDNA sample, 80 µL of water, 10 µL of 10×

Advantage 2 PCR buffer, 2 µL 50×dNTP mix (10 mM each of dATP, dCTP, dGTP and dTTP), 2 µL of 5' PCR primer (SEQ ID NO:105), 2 µL CDSIII/3' PCR primer (SEQ ID NO:30) and 2 µL 50× Advantage 2 polymerase mix. PCR amplification was performed using the following conditions: 95° C. for 1 min, followed by 20 cycles of 95° C. for 10 sec and 68° C. for 6 min. Amplification products were purified with Qiagen PCR purification kits according to the manufacturer's protocol. Purified products were eluted with 50 µL of water.

For *Tetruetreptia pomquetensis* CCMP1491, 0.95 µg of total RNA in 1 µL was used as template. The procedure used to synthesize cDNA was the same as above except that CDSIII/3' PCR primer (SEQ ID NO:30) was replaced with the Adaptor Primer from Invitrogen 3'-RACE kit (SEQ ID NO:31).

Identification of cDNA Fragments Encoding Partial Putative Delta-8 Desaturases

Each of the above three cDNA samples were used as template for degenerate PCR using primers based on the amino acid sequence of the *Euglena gracilis* delta-8 fatty acid desaturase (EgD8; SEQ ID NO:112). The 9 forward and 2 reverse primers used are shown in Table 4:

TABLE 4

Degenerate Oligonucleotides Used to Amplify Portions of the Delta-8 Desaturase Genes From *Eutreptiella* sp. CCMP389, *Eutreptiella cf_gymnastica* CCMP1594 and *Tetruetreptia pomquetensis* CCMP1491

| Primer | Nucleotide Sequence | Amino Acid Sequence |
|---|---|---|
| D8F1 | GAYGCNACNGAYGCNTTCATG (SEQ ID NO: 1) | DATDAFM (SEQ ID NO: 12) |
| D8F2 | GAYGCNACNGAYGCNGTTATG (SEQ ID NO: 2) | DATDAVM (SEQ ID NO: 13) |
| D8F3 | GAYGCNACNGAYGCNGTGATG (SEQ ID NO: 3) | DATDAVM (SEQ ID NO: 13) |
| D8F4 | GAYGCNACNGAYGCNTTTATG (SEQ ID NO: 4) | DATDAFM (SEQ ID NO: 12) |
| D8F5 | GAYGCNACNGAYGCNGTAATG (SEQ ID NO: 5) | DATDAVM (SEQ ID NO: 13) |
| D8F6 | GAYGCNACNGAYGCNGTGATG (SEQ ID NO: 6) | DATDAVM (SEQ ID NO: 13) |
| D8F7 | TNGGNTGGTTRGGNGAYGA (SEQ ID NO: 7) | GWLGD(D/E) (SEQ ID NO: 14) |
| D8F8 | TNGGNTGGCTRGGNGAYGA (SEQ ID NO: 8) | GWLGD(D/E) (SEQ ID NO: 14) |
| D8F9 | TNGGNTGGCTYGGNGAYGA (SEQ ID NO: 9) | GWLGD(D/E) (SEQ ID NO: 14) |
| D8R1 | TGRTGYTCDATYTGRTARTT (SEQ ID NO: 10) | NYQIEH (SEQ ID NO: 15) |
| D8R2 | TGRTGYTCDATYTGCATRTT (SEQ ID NO: 11) | NYQIEH (SEQ ID NO: 15) |

A total of 18 reactions were set up for each cDNA sample, using all the possible combinations of the 9 forward and 2 reverse primers. The reaction mixture contained 1 µL of cDNA, 1 µL each of the forward and reverse primers (20 µM), 22 µL water and 25 µL of TaKaRa ExTaq 2× premix (TaKaRa Bio, Mountain View, Calif.). PCR amplification was performed using the following conditions: 94° C. for 1 min, 30 cycles of 94° C. for 30 sec, 55° C. for 30 sec, and 72° C. for 1 min, followed by 7 min at 72° C.

Agarose gel analysis of the PCR products showed that, with several primer combinations, a ~1 kb fragment was amplified from each cDNA sample. The fragments from the primer combination D8F4/D8R1 were cloned into pCR2.1-TOPO (SEQ ID NO:40) and sequenced to afford partial sequences of the putative delta-8 desaturases from *Tetruetreptia pomquetensis* CCMP1491 (SEQ ID NO:16; 977 bp), *Eutreptiella* sp. CCMP389 (SEQ ID NO:17; 968 bp) and *Eutreptiella* cf_*gymnastica* CCMP1594 (SEQ ID NO:18; 968 bp).

Example 2

Isolation of the Full-Length Delta-8 Desaturases from *Eutreptiella* sp. CCMP389 and *Eutreptiella cf_gymnastica* CCMP1594

Primers were designed (see Table 5), based on the partial sequences of the putative delta-8 desaturases from *Eutreptiella* sp. CCMP389 (SEQ ID NO:17) and *Eutreptiella* cf_*gymnastica* CCMP1594 (SEQ ID NO:18), to isolate the 5' and 3' ends of each gene from cDNA and genomic DNA samples.

TABLE 5

Primers Used to Clone the Full-Length Delta-8 Desaturase Genes From *Eutreptiella* sp. CCMP389 and *Eutreptiella cf_gymnastica* CCMP1594

| Organism | Primer Name | Primer Sequence | SEQ ID NO: |
|---|---|---|---|
| *Eutreptiella* sp. CCMP389 | 389D8-3-1 | CAACGCCAGTACGCAAAGGAG | 20 |
|  | 389D8-3-2 | CTCTGCATTGGATTCTGAAAGG | 21 |
|  | 389D8-5-1 | AATCATGTCCTTTCGAAGCTTG | 22 |
|  | 389D8-5-2 | GTCCTCAGCAACCTCGTCGTTG | 23 |
|  | 389D8-5-3 | CTTGGGGCTTCGTGGCGAAGTG | 24 |
| *Eutreptiella cf_gymnastica* CCMP1594 | 1594D8-3-1 | GAGCGTTTTCTTGTTCTGTTAC | 32 |
|  | 1594D8-3-2 | CGTTTTTCCTTATCTCGGAGTG | 33 |
|  | 1594D8-5-1 | GATTTGTACACATAAAACAGAG | 34 |
|  | 1594D8-5-2 | ACCCTTCTCAACCATACTGTTG | 35 |
|  | 1594D8-5-3 | CTTGGGAGTAAGTGGTGAAGAG | 36 |

Isolation of the 5'-End Sequences of the *Eutreptiella sp.* CCMP389 and *Eutreptiella cf_gymnastica* CCMP1594 Delta-8 Desaturase Genes The full 5'-end sequences of the putative delta-8 desaturases from *Eutreptiella* sp. CCMP389 and *Eutreptiella cf_gymnastica* CCMP1594 were obtained by genome walking using the Universal GenomeWalker™ kit (BD Biosciences Clonetech, Palo Alto, Calif.) following the manufacturer's protocol (Prot #PT3042-1). First, genomic DNA from *Eutreptiella* sp. CCMP389 and *Eutreptiella cf_gymnastica* CCMP1594 were digested with DraI, EcoRV, PvuII and StuI individually as described in the manufacturer's protocol. Genomic DNA (2 µg) was used for each digestion. Digested DNA samples were purified with a Qiagen enzyme reaction clean-up kit according to the manufacturer's protocol. Each sample was eluted with 20 µL of water.

The digested genomic DNA samples were ligated with the GenomeWalker adaptor (SEQ ID NO:37 and SEQ ID NO:111). Specifically, 4 µL each of the digested DNA was mixed with 1.9 µL of 25 µM GenomeWalker adaptor (SEQ ID NO:37 and SEQ ID NO:111), 1.6 µL of 10× ligation buffer and 0.5 µL of T4 DNA ligase. The reaction was carried out overnight at 16° C. After heating at 70° C. for 5 min, 72 μL of 10 mM Tris, 1 mM EDTA, pH 7.4 buffer was added to each reaction mixture. These reaction mixtures were then used as templates for PCR amplification.

For the first round of PCR, primers 389D8-5-1 (SEQ ID NO:22) and Universal GenomeWalker™ primer AP1 (SEQ ID NO:38) from the kit were used to amplify from *Eutreptiella* sp. CCMP389 samples, while primers 1594D8-5-1 (SEQ ID NO:34) and AP1 (SEQ ID NO:38) were used for *Eutreptiella* cf_*gymnastica* CCMP1594 samples. Each reaction mixture contained 1 μL of each primer at 10 μM, 2 μL of the purified ligation products as template, 21 μL water and 25 μL of TaKaRa ExTaq 2× premix. The PCR reaction conditions used were as follows: 94° C. for 30 sec, 30 cycles of 94° C. for 20 sec, 55° C. for 20 sec, and 72° C. for 2 min, followed by 5 min at 72° C.

The PCR products were diluted 1:100, and 1 μL of each diluted PCR product was used as template for a second round of PCR using primers 389D8-5-3 (SEQ ID NO:24) and Universal GenomeWalker™ primer AP2 (SEQ ID NO:39) for *Eutreptiella* sp. CCMP389 samples, and primers 1594D8-5-3 (SEQ ID NO:36) and Universal GenomeWalker™ primer AP2 (SEQ ID NO:39) for *Eutreptiella* cf_*gymnastica* CCMP1594 samples. Amplification was conducted as described above.

The second-round PCR products were purified by Qiagen PCR purification kit, cloned into pCR2.1-TOPO (SEQ ID NO:40) and sequenced. A 694 bp PCR fragment generated from *Eutreptiella* cf_*gymnastica* CCMP1594 samples and a 648 bp fragment generated from *Eutreptiella* sp. CCMP389 samples were shown to contain the 5' end of the putative delta-8 desaturase genes, including parts of the non-translated region (SEQ ID NO:41 and SEQ ID NO:42, respectively).

Isolation of the 3'-End Sequences of the *Eutreptiella* sp. CCMP389 and *Eutreptiella* cf_*gymnastica* CCMP1594 Delta-8 Desaturase Genes The full 3'-end sequences of the putative delta-8 desaturases from *Eutreptiella* sp. CCMP389 and *Eutreptiella* cf_*gymnastica* CCMP1594 were obtained by PCR amplification using cDNA samples as templates.

389D8-3-1 (SEQ ID NO:19) and CDSIII/3' PCR primer (SEQ ID NO:30; supplied with the Creator™ SMART™ cDNA Library Construction Kit of Example 1) were used as primers for first round amplification, using *Eutreptiella* sp. CCMP389 cDNA as template. 1594D8-3-1 (SEQ ID NO:32) and CDSIII/3' PCR primer (SEQ ID NO:30) were used as primers for amplification with *Eutreptiella* cf_*gymnastica* CCMP1594 cDNA as template. The reaction mixtures contained: 1 μL of each primer (10 μM), 1 μL of cDNA from Example 1, 22 μL water and 25 μL TaKaRa ExTaq 2× premix. The PCR reaction conditions used were as follows: 94° C. for 90 sec, 30 cycles of 94° C. for 30 sec, 55° C. for 30 sec, and 72° C. for 30 sec, followed by 5 min at 72° C.

The PCR product was diluted 1:50, and 1 μL of the diluted product was used as template for a second round of PCR using either 389D8-3-2 (SEQ ID NO:21) or 1594D8-3-2 (SEQ ID NO:33) with the CDSIII/3' PCR primer (SEQ ID NO:30) under the conditions described above. The second-round PCR products were purified with Qiagen PCR purification kit, cloned into pCR2.1-TOPO (SEQ ID NO:40) and sequenced. A fragment amplified from *Eutreptiella* sp. CCMP389 cDNA was shown to contain the 3'-end of the cDNA of putative delta-8 desaturase, including the polyA tail (SEQ ID NO:43; 717 bp).

Two different fragments were obtained and shown to contain the 3' end of the delta-8 desaturase from *Eutreptiella* cf_*gymnastica* CCMP1594. One of them, 1594D8-3'A (SEQ ID NO:44), was 1164 bp long and contained a long 3' untranslated region of 760 bp and a polyA tail. The other, 1594D8-3'B (SEQ ID NO:45), was 435 bp long and had a short 3' untranslated region of 30 bp. The sequences of the coding region of both fragments were the same.

Assembly of the Full-Length Sequences of the *Eutreptiella* sp. CCMP389 and *Eutreptiella* cf_*gymnastica* CCMP1594 Delta-8 Desaturase Genes Assembly of the 5' genomic region, the original partial cDNA sequence and the 3'-cDNA sequence resulted in the complete sequence of the delta-8 desaturases from *Eutreptiella* sp. CCMP389 and *Eutreptiella* cf_*gymnastica* CCMP1594 (SEQ ID NO:46 (1963 bp) and SEQ ID NO:48 (2063 bp), respectively; each sequence also contained untranslated 5' and 3' ends). Each coding region is 1254 bp long and each encodes a peptide of 417 amino acids (SEQ ID NO:47 and SEQ ID NO:49, respectively). SEQ ID NO:92 is the nucleotide sequence of the coding sequence of *Eutreptiella* sp. CCMP389 delta-8 desaturase (designated herein as "E389D8"), while SEQ ID NO:93 is the nucleotide sequence of the coding sequence of *Eutreptiella* cf_*gymnastica* CCMP1594 delta-8 desaturase (designated herein as "E1594D8").

Example 3

Isolation of the Full-Length Delta-8 Desaturase from *Tetruetreptia pomquetensis* CCMP1491

Primers were designed (see Table 6), based on the partial sequence of the putative delta-8 desaturase from *Tetruetreptia pomquetensis* CCMP1491 (SEQ ID NO:16), to isolate the 5' and 3' end of the gene from cDNA and genomic DNA samples.

TABLE 6

Primers Used to Clone the Full-Length Delta-8 Desaturase Gene From *Tetruetreptia pompuetensis* CCMP1491

| Primer Name | Primer Sequence | SEQ ID NO: |
|---|---|---|
| ED8-5-1 | CTCGAACATACCCTTGGAGATG | 25 |
| ED8-5-2 | CCCGCAACTTGCGGAAATCCTC | 26 |
| ED8-5-3 | GGGCTCATCACGCTTAGGCTTG | 27 |
| ED8-3-1 | CACTTTCTATTGCAGTGCCATG | 28 |
| ED8-3-2 | CTTTGCCACCGGTTTGGGATGC | 29 |

Isolation of the 5'-End Sequence of the *Tetruetreptia pomquetensis* CCMP1491 Delta-8 Desaturase Gene The Invitrogen TOPO walker kit was used for isolating the 5' end of the putative delta-8 desaturase gene from *Tetruetreptia pomquetensis* CCMP1491, following the manufacturer's protocol. Genomic DNA (0.3 μg) from *Tetruetreptia pomquetensis* CCMP1491 (see Example 1) was digested with ApaI. The reaction mixture contained 10 μL genomic DNA (~0.3 μg), 4 μL of 10× restriction buffer, 2 μL restriction enzyme (ApaI or KpnI) and 24 μL water. The reaction was carried out at 37° C. for 2 h. Then, 50 μL of water, 6 μL of dephosphorylation buffer and 4 μL of kit-supplied CIP were added to the mixture, and the reaction was allowed to continue for 1 h at 37° C. The reaction mixture was then purified with Qiagen reaction purification kit according to the manufacturer's protocol. DNA was eluted in 40 µL of water.

For primer extension, 15 µL of the purified DNA was mixed with 2 µL of 10×PCR buffer (Invitrogen Corporation), 1 µL of 2.5 mM each dNTPs, 1 µL of primer ED8-5-1 (SEQ ID NO:25) (20 µM) and 1 µL of Advantage 2 cDNA polymerase mix (BD Biosciences Clonetech, Palo Alto, Calif.). The PCR reaction conditions used were as follows: 94° C. for 4 min, 56° C. for 1 min, and 72° C. for 20 min. The primer extension reaction product (8 µL) was then used as substrate for TOPO linker in a mixture additionally comprising 1 µL TOPO linker (SEQ ID NO:50) and 1 µL 10×PCR buffer (Invitrogen Corporation). The mixture was incubated at 37° C. for 10 min and used directly as PCR template.

PCR amplification of the 5' end was carried out in a 50 µL reaction mix that contained 2 µL of TOPO linked genomic DNA, 1 µL of primer ED8-5-2 (SEQ ID NO:26) (10 µM), 1 µL of LinkAmp primer 1 (SEQ ID NO:51) (10 µM), 21 µL water and 25 µL TaKaRa ExTaq 2× premix. The PCR reaction conditions used were as follows: 94° C. for 90 sec, 30 cycles of 94° C. for 30 sec, 55° C. for 30 sec, and 72° C. for 2 min, followed by 7 min at 72° C. The PCR product was diluted 1:50, and 1 µL of the diluted product was used as template for a second round of PCR under the same conditions, except that primers ED8-5-3 (SEQ ID NO:27) and LinkAmp primer 2 (SEQ ID NO:52) replaced ED8-5-2 (SEQ ID NO:26) and LinkAmp primer 1 (SEQ ID NO:51).

A ~600 bp PCR product was purified with a Qiagen PCR purification kit, cloned into pCR2.1-TOPO (SEQ ID NO:40) and sequenced. Comparison of the partial delta-8 desaturase sequence of SEQ ID NO:16 with the 5' extension product (SEQ ID NO:53; 601 bp) showed that SEQ ID NO:53 extended upstream of the 'ATG' initiation codon of the delta-8 desaturase.

Isolation of the 3'-End Sequence of the *Tetruetreptia pomquetensis* CCMP1491 Delta-8 Desaturase Gene The full 3'-end sequence of the putative delta-8 desaturase from *Tetruetreptia pomquetensis* CCMP1491 was obtained by PCR amplification using a cDNA sample as template. Specifically, primers ED8-3-1 (SEQ ID NO:28) and AUAP (SEQ ID NO:54; supplied in Invitrogen's 3'-RACE kit) were used as primers. The reaction mixture contained 1 µL of each primer (10 µM), 1 µL of *Tetruetreptia pomquetensis* CCMP1491 cDNA from Example 1, 22 µL water and 25 µL TaKaRa ExTaq 2× premix. The PCR reaction conditions used were as follows: 94° C. for 90 sec, 30 cycles of 94° C. for 30 sec, 55° C. for 30 sec, and 72° C. for 30 sec, followed by 5 min at 72° C.

The PCR product was diluted 1:50, and 1 µL of the diluted product was used as template for a second round of PCR using ED8-3-2 (SEQ ID NO:29) and AUAP (SEQ ID NO:54) as primers under the same conditions as described above. The second round PCR generated a ~1 kb fragment, which was purified with Qiagen PCR purification kit, cloned into pCR2.1-TOPO (SEQ ID NO:40) and sequenced. The result of sequence analysis showed that this fragment (SEQ ID NO:55; 1028 bp) contained the 3' end of the putative delta-8 desaturase, including the polyA tail.

Assembly of the Full-Length Sequence of the *Tetruetreptia pomquetensis* CCMP1491 Delta-8 Desaturase Gene Assembly of the 5' genomic region, the original partial cDNA fragment and 3'-cDNA fragment resulted in the complete sequence of the delta-8 desaturase from *Tetruetreptia pomquetensis* CCMP1491, plus 358 bp of 5' untranslated region and 612 bp of 3' untranslated region (SEQ ID NO:56; 2233 bp). The coding region is 1263 bp long and encodes a protein of 420 amino acids (SEQ ID NO:57). SEQ ID NO:62 is the nucleotide sequence of the coding sequence of *Tetruetreptia pomquetensis* CCMP1491 delta-8 desaturase (designated herein as "TpomD8").

Example 4

Comparison of the Delta-8 Desaturase Sequences of *Tetruetreptia pomquetensis* CCMP1491. *Eutreptiella* sp. CCMP389 and *Eutreptiella* cf_*gymnastica* CCMP1594 to a Delta-8 Desaturase Sequence of *Euglena gracilis*

The delta-8 desaturase sequences of *Tetruetreptia pomquetensis* CCMP1491 (i.e., TpomD8), *Eutreptiella* sp. CCMP389 (i.e., E389D8) and *Eutreptiella* cf_*gymnastica* CCMP1594 (i.e., E1594D8) were analyzed for similarity to all publicly available protein sequences contained in the "nr" database provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins. TpomD8, E389D8 and E1594D8 each shared the greatest identity and similarity with the delta-8 desaturase of *Euglena gracilis* set forth as SEQ ID NO:98 (corresponding to NCBI Accession No. AAD45877 (GI 5639724)).

The delta-8 desaturase sequences of *Tetruetreptia pomquetensis* CCMP1491 (i.e., TpomD8), *Eutreptiella* sp. CCMP389 (i.e., E389D8) and *Eutreptiella* cf_*gymnastica* CCMP1594 (i.e., E1594D8) were also analyzed for similarity to the *Euglena gracilis* delta-8 desaturase (SEQ ID NO:112 of the instant application) in Applicants' Assignee's co-pending applications having U.S. application Ser. Nos. 11/166,003 and 11/166,993 filed Jun. 24, 2005 (Attorney Docket Nos. BB-1547 and CL-3150, respectively (PCT Publication Nos. WO 2006/012325 and WO 2006/012326; both published Feb. 2, 2006)).

FIGS. 7A and 7B show a Clustal V alignment of the delta-8 desaturases from *Tetruetreptia pomquetensis* CCMP1491 (SEQ ID NO:57), *Eutreptiella* sp. CCMP389 (SEQ ID NO:47), *Eutreptiella* cf_*gymnastica* CCMP1594 (SEQ ID NO:49), *Euglena gracilis* (SEQ ID NO:98; NCBI Accession No. AAD45877 (GI 5639724)) and *Euglena gracilis* (SEQ ID NO:112). SEQ ID NO:57 has 70.5%, 71.7%, 57.5% and 61.8% identity to SEQ ID NO:47, SEQ ID NO:49, SEQ ID NO:98 and SEQ ID NO:112, respectively. SEQ ID NO:47 has 83.0%, 58.3% and 63% identity to SEQ ID NO:49, SEQ ID NO:98 and SEQ ID NO:112, respectively. SEQ ID NO:49 has 58.0% and 62.7% identity to SEQ ID NO:98 and SEQ ID NO:112, respectively. SEQ ID NO:98 has 95% identity to SEQ ID NO:112.

More specifically, TpomD8, E389D8 and E1594D8 were evaluated by BLASTP, yielding a pLog value versus EgD8 (SEQ ID NO:112). Then, the % identity of TpomD8, E389D8 and E1594D8 was determined with respect to EgD8 using the Jotun Hein method. Sequence percent identity calculations performed by the Jotun Hein method (Hein, J. J., *Meth. Enz.* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2). As discussed above, the % identity of TpomD8, E389D8 and E1594D8 was determined with respect to EgD8 using the Clustal V method. Sequence percent identity calculations performed by the Clustal V method (Higgins, D. G. and Sharp, P. M., Comput. Appl. Biosci. 5:151-153 (1989); Higgins et al., Comput. Appl. Biosci. 8:189-191 (1992)) were done using the MegAlign™ v6.1 program of the LASER-GENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10). These results are summarized in Table 7.

TABLE 7

Sequence Comparison of TpomD8, E389D8 and E1594D8 to EgD8 (SEQ ID NO: 112)

| Desaturase | pLog value versus EgD8 by BLASTP | % Identity to EgD8 by the Jotun Hein Method | % Identity to EgD8 by the Clustal V Method |
|---|---|---|---|
| TpomD8 (SEQ ID NO: 57) | 155 (E value of 1e−155) | 63.5% | 61.8% |
| E389D8 (SEQ ID NO: 47) | 164 (E value of 1e−164) | 63.3% | 63.0% |
| E1594D8 (SEQ ID NO: 49) | 163 (E value of 1e−163) | 64.2% | 62.7% |

BLAST scores and probabilities indicate that the nucleic acid fragments set forth in SEQ ID NO:57, SEQ ID NO:47 and SEQ ID NO:49 each encode an entire delta-8 desaturase.

Example 5

Functional Analysis of the *Tetruetreptia pomquetensis* CCMP1491 Delta-8 Desaturase (TpomD8) in *Saccharomyces cerevisiae*

The present Example describes functional analysis of TpomD8 in *Saccharomyces cerevisiae*. This work included the following steps: (1) cloning of TpomD8 from a *Tetruetreptia pomquetensis* CCMP1491 cDNA library; (2) cloning of TpomD8 into yeast expression vector pY-75 to produce pY126; and, (3) comparison of lipid profiles within transformant organisms comprising pY-75 and pY126, after substrate feeding.

Cloning TpomD8 from a cDNA Library

*Tetruetreptia pomquetensis* CCMP1491 cDNA (1 µL; synthesized as described in Example 1) was combined with 50 pmol of TpomNot-5 (SEQ ID NO:58), 50 pmol of TpomNot-3 (SEQ ID NO:59), 1 µL of PCR nucleotide mix (10 mM, Promega, Madison, Wis.), 5 µL of 10×PCR buffer (Invitrogen Corporation), 1.5 µL of $MgCl_2$ (50 mM, Invitrogen Corporation), 0.5 µL of Taq polymerase (Invitrogen Corporation) and water to 50 µL. The reaction conditions were 94° C. for 3 min followed by 35 cycles of 94° C. for 45 sec, 55° C. for 45 sec and 72° C. for 1 min. The PCR was finished at 72° C. for 7 min and then held at 4° C. The PCR reaction was analyzed by agarose gel electrophoresis on 5 µL and a DNA band with molecular weight around 1.3 kb was observed.

The remaining 45 µL of product was separated by agarose gel electrophoresis and the DNA purified using the Zymoclean™ Gel DNA Recovery Kit (Zymo Research, Orange, Calif.) following the manufacturer's protocol. The resulting DNA was cloned into the PGEM®-T Easy Vector (Promega) following the manufacturer's protocol. Multiple clones were sequenced using the T7 (SEQ ID NO:60) and M13-28Rev (SEQ ID NO:61) oligonucleotides to verify that the TpomD8 sequence was identical to the previously deduced coding sequence of Example 3 (i.e., SEQ ID NOs:62 and 57). Clone pLF114-10 (SEQ ID NO:63) was chosen for further expression studies.

Construction of Plasmids pY-75 (Control) and pY126, Comprising TpomD8

The yeast episomal plasmid (YEp)-type vector pRS425 (Christianson et al., *Gene* 110:119-122 (1992)) contains sequences from the *Saccharomyces cerevisiae* 2µ endogenous plasmid, a LEU2 selectable marker and sequences based on the backbone of a multifunctional phagemid, pBluescript II SK(+). The *Saccharomyces cerevisiae* strong, constitutive glyceraldehyde-3-phosphate dehydrogenase (GPD) promoter was cloned between the SacII and SpeI sites of pRS425 in the same way as described by Jia et al. (*Physiol. Genom.* 3:83-92 (2000)) to produce pGPD-425. A NotI site was introduced into the BamHI site of pGPD-425, thus giving a NotI site flanked by BamHI sites, and this plasmid was called pY-75 (SEQ ID NO:64), which was previously described in PCT Publication No. WO 2006/012325 (published Feb. 2, 2006; the contents of which are hereby incorporated by reference).

TpomD8 was released from pLF114-10 (supra) by digestion with NotI and cloned into the NotI site of pY75 to produce pY126 (SEQ ID NO:65; FIG. 1).

Functional Analysis of TpomD8

Expression plasmids pY75 (control) and pY126 were transformed into *Saccharomyces cerevisiae* INVSC1 (Invitrogen Corporation) using standard lithium acetate transformation procedures. Transformants were selected on DOBA media supplemented with CSM-leu (Qbiogene, Carlsbad, Calif.). Transformants were evaluated for delta-8 desaturase activities in the following way. Transformants from each plate were inoculated into 2 mL of DOB medium supplemented with CSM-leu (Qbiogene) and 0.2% tergitol. Cells were grown for 1 day at 30° C. after which 0.1 mL was transferred to 3 mL of the same medium supplemented with either EDA [20:2(11,14)] or ETrA [20:3(11,14,17)] to 0.175 mM. These cells were incubated for 16 h at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.* 276(1):38-46 (1990)) with 500 µL of 1% sodium methoxide for 30 min at 50° C. after which 500 µL of 1 M sodium chloride and 100 µL of heptane were added. After thorough mixing and centrifugation, fatty acid methyl esters (FAMEs) were analyzed by GC as described in Example 10.

Results for 3 individual clones of pY126 (i.e., clones 6, 7 and 10) as well as the vector control are shown in Table 8. Fatty acid compositions are expressed as a weight percent of total fatty acids. The activity of the delta-8 desaturase is expressed as "percent desaturation", where % Desat. was calculated according to the following formula: ([product]/[substrate+product])*100.

TABLE 8

Comparison of Lipid Profiles of Yeast Expressing TpomD8

| Vector | Fatty Acid | 16:0 | 16:1 | 18:0 | 18:1 | EDA | DGLA | ETrA | ETA | % Desat. |
|---|---|---|---|---|---|---|---|---|---|---|
| pY75 | EDA | 13.3 | 37.4 | 4.0 | 34.2 | 11.1 | 0.0 | 0.0 | 0.0 | 0.0 |
| pY126-6 | EDA | 14.4 | 38.6 | 4.0 | 32.9 | 10.0 | 0.2 | 0.0 | 0.0 | 1.5 |
| pY126-7 | EDA | 13.6 | 36.3 | 4.4 | 34.3 | 11.2 | 0.2 | 0.0 | 0.0 | 1.9 |
| pY126-10 | EDA | 11.7 | 37.9 | 3.9 | 34.5 | 11.5 | 0.4 | 0.1 | 0.0 | 3.5 |
| pY75 | ETrA | 11.8 | 33.5 | 3.1 | 24.3 | 0.1 | 0.0 | 27.2 | 0.0 | 0.1 |
| pY126-6 | ETrA | 13.4 | 35.3 | 3.4 | 25.3 | 0.1 | 0.0 | 22.3 | 0.2 | 1.0 |
| pY126-7 | ETrA | 12.2 | 32.8 | 3.4 | 24.8 | 0.1 | 0.0 | 26.2 | 0.4 | 1.6 |
| pY126-10 | ETrA | 11.1 | 29.5 | 3.4 | 25.0 | 0.1 | 0.0 | 30.0 | 0.9 | 2.9 |

When feeding the cells EDA, the product of the TpomD8 delta-8 desaturation is DGLA; in contrast, substrate feeding with ETrA results in production of ETA by TpomD8 desaturation.

Example 6

Generation of *Yarrowia lipolytica* Strain Y4001 to Produce about 17% EDA of Total Lipids The present Example describes the construction of strain Y4001, derived from *Yarrowia lipolytica* ATCC #20362, capable of producing 17% EDA (C20:2) relative to the total lipids. The strain was engineered to test functional expression of TpomD8, E389D8 and E1594D8; specifically, it was necessary to construct a host strain capable of producing the delta-8 desaturase substrate, EDA.

The development of strain Y4001 required the construction of strain Y2224 (a FOA resistant mutant from an autonomous mutation of the Ura3 gene of wildtype *Yarrowia* strain ATCC #20362).

Generation of Strain Y2224

Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Generation of Strain Y4001 to Produce 17% EDA of Total Lipids

Strain Y4001 was created via integration of construct pZKLeuN-29E3 (FIG. 9; comprising four chimeric genes—a delta-12 desaturase, a $C_{16/18}$ elongase and two delta-9 elongases) into the Leu2 loci of Y2224 strain to thereby enable production of EDA.

Construct pZKLeuN-29E3 (FIG. 9) contained the components shown in Table 9.

TABLE 9

Description of Plasmid pZKLeuN-29E3 (SEQ ID NO: 106)

| RE Sites And Nucleotides Within SEQ ID NO: 106 | Description Of Fragment And Chimeric Gene Components |
|---|---|
| BsiW I/Asc I (7797-7002) | 795 bp 3' part of *Yarrowia* Leu2 gene (GenBank Accession No. AF260230) |
| Sph I/Pac I (4302-3591) | 703 bp 5' part of *Yarrowia* Leu2 gene (GenBank Accession No. AF260230) |
| Swa I/BsiW I (10500-7797) | GPD::F.D12::Pex20, comprising:<br>GPD: *Yarrowia lipolytica* GPD promoter (WO 2005/003310)<br>F.D12: *Fusarium moniliforme* delta-12 desaturase gene (WO 2005/047485)<br>Pex20: Pex20 terminator sequence from *Yarrowia* Pex20 gene (GenBank Accession No. AF054613) |
| Bgl II/Swa I (12526-10500) | Exp pro::EgD9E::Lip1, comprising:<br>Exp pro: *Yarrowia lipolytica* export protein (EXP1) promoter (WO 2006/052870 and U.S. Patent Application No. 11/265761)<br>EgD9E: (same as EgD9S, see infra): codon-optimized delta-9 elongase gene (SEQ ID NO: 107), derived from *Euglena gracilis* (SEQ ID NOs: 74 and 75 (see also U.S. Provisional Application No. 60/739989)<br>Lip1: Lip1 terminator sequence from *Yarrowia* Lip1 gene (GenBank Accession No. Z50020) |
| Pme I/Cla I (12544-1) | FBAINm::EgD9S::Lip2, comprising:<br>FBAINm: *Yarrowia lipolytica* FBAINm promoter (WO 2005/049805)<br>EgD9S: codon-optimized delta-9 elongase gene (SEQ ID NO: 107), derived from *Euglena gracilis* (SEQ ID NOs: 74 and 75 (see also U.S. Provisional Application No. 60/739989)<br>Lip2: Lip2 terminator sequence from *Yarrowia* Lip2 gene (GenBank Accession No. AJ012632) |
| Cla I/EcoR I (1-1736) | LoxP::Ura3::LoxP, comprising:<br>LoxP sequence (SEQ ID NO: 108)<br>*Yarrowia* Ura3 gene (GenBank Accession No. AJ306421)<br>LoxP sequence (SEQ ID NO: 108) |
| EcoR I/Pac I (1736-3591) | NT::ME3S::Pex16, comprising:<br>NT: *Yarrowia lipolytica* YAT1 promoter (Patent Publication No. U.S. 2006/0094102-A1)<br>ME3S: codon-optimized $C_{16/18}$ elongase gene (SEQ ID NO: 109), derived from *M. alpina* (see U.S. Patent Application No. 11/253882 and also WO 2006/052870)<br>Pex16: Pex16 terminator sequence of *Yarrowia* Pex 16 gene (GenBank Accession No. U75433) |

Plasmid pZKLeuN-29E3 was digested with Asc I/Sph I, and then used for transformation of *Y. lipolytica* strain Y2224 (i.e., ATCC #20362 Ura3−) according to the General Methods. The transformant cells were plated onto MMLeu media plates and maintained at 30° C. for 2 to 3 days. The colonies were picked and streaked onto MM and MMLeu selection plates. The colonies that could grow on MMLeu plates but not on MM plates were selected as Leu– strains. Single colonies of Leu– strains were then inoculated into liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EDA in the transformants containing the 4 chimeric genes of pZKLeuN-29E3, but not in the *Yarrowia* Y2224 control strain. Most of the selected 36 Leu– strains produced about 12 to 16.9% EDA of total lipids. There were 3 strains (i.e., strains #11, #30 and #34) that produced about 17.4%, 17% and 17.5% EDA of total lipids; they were designated as strains Y4001, Y4002 and Y4003, respectively.

Example 7

Functional Analysis of the *Tetruetreptia pomquetensis* CCMP1491 (TpomD8), *Eutreptiella* sp. CCMP389 (E389D8) and *Eutreptiella cf_gymnastica* CCMP1594 (E1594D8) Delta-8 Desaturases in *Yarrowia lipolytica* Strain Y4001

The present Example describes functional analysis of TpomD8, E389D8 and E1594D8 in *Yarrowia lipolytica* strain Y4001. This work included the following steps: (1) cloning of E389D8 from a *Eutreptiella* sp. CCMP389 cDNA library, E1594D8 from a *Eutreptiella cf_gymnastica* CCMP1594 cDNA library, and TpomD8 from a *Tetruetreptia pomquetensis* CCMP1491 cDNA library; (2) cloning of E389D8, E1594D8 and TpomD8 into yeast expression vector pFBAIn-MOD1 (SEQ ID NO:94); and, (3) comparison of lipid profiles within transformant organisms of *Yarrowia lipolytica* strain Y4001 that were additionally comprising each desaturase.

Cloning E389D8, E1594D8 and TpomD8 from cDNA Libraries

The Phusion polymerase from New England Biolab was used for amplification of E389D8 and E1594D8 cDNAs. Primers 389D8-F (SEQ ID NO:99) and 389D8-R (SEQ ID NO:100) were used for amplification of E389D8; in contrast, primers 1594D8-F (SEQ ID NO:103) and 1594D8-R (SEQ ID NO:104) were used for amplification of E1584D8. Each reaction mixture contained 1 μL each of 20 μM forward and reverse primers, 1 μL cDNA, 10 μL 5×PCR buffer, 1 μL dNTP mix (10 mM each), 35 μL water and 1 μL Phusion polymerase. The PCR reaction conditions used were as follows: 98° C. for 1 min, 30 cycles of 98° C. for 10 sec, 55° C. for 10 sec, and 72° C. for 40 sec, followed by 5 min at 72° C. The PCR product was digested with NcoI and NotI, and cloned into pFBAIn-MOD1 (SEQ ID NO:94) predigested with the same enzymes. The resulting plasmids were named pFBAIn-389D8 (SEQ ID NO:95) and pFBAIn-1594D8 (SEQ ID NO:96).

For amplification of TpomD8, the TaKaRa ExTaq 2× premix was used for PCR instead of the Phusion polymerase. The reaction mixture contained 1 μL of *Tetruetreptia pomquetensis* CCMP1491 cDNA, 1 μL each of 20 μM primers 1491 D8-F (SEQ ID NO:101) and 1491 D8-R (SEQ ID NO:102), 22 μL water and 25 μL ExTaq premix. The PCR reaction conditions used were as follows: 94° C. for 30 sec, 30 cycles of 94° C. for 20 sec, 55° C. for 20 sec, and 72° C. for 1 min 30 sec, followed by 7 min at 72° C. The PCR products were cloned into pCR2.1-TOPO (SEQ ID NO:40) and sequenced. One clone with the correct sequence was digested with NcoI and NotI, and the 1.3 kb fragment containing TpomD8 was excised from agarose gel and purified with Qiagen gel purification kit. The purified fragment was then cloned into pFBAIn-MOD1 (SEQ ID NO:94; see FIG. 8) pre-digested with NcoI and NotI. The resulting plasmid was named pFBAIn-1491D8 (SEQ ID NO:97). Construct pFBAIn-MOD1 (SEQ ID NO:94; FIG. 8) contained the components shown in Table 10.

TABLE 10

| Components of Plasmid pFBAIN-MOD1 (SEQ ID NO: 94) | |
|---|---|
| RE Sites and Nucleotides Within SEQ ID NO: 94 | Description of Fragment and Chimeric Gene Components |
| BglII-BsiWI (6278-539) | FBAIN promoter:: PEX20 terminator region, comprising: FBAIN: *Yarrowia lipolytica* FBAIN promoter (WO 2005/049805) Stuffer DNA fragment derived from pDNR-LIB _PEX20_terminator sequence of *Yarrowia* PEX20 gene (GenBank Accession No. AF054613.) |
| PacI-BglII (4768-6278) | *Y. lipolytica* URA3 (GenBank Accession No. AJ306421) |
| (3361-4725) | ARS18, (GenBank Accession No. A17608) |
| (2702-3102) | f1 origin |
| (1662-2522) | AmpR gene (for selection in media containing ampicilin) |
| (712-1592) | ColE1 *E. coli* origin of replication |

Functional Analysis of TpomD8, E389D8 and E1594D8

Plasmids pFBAIn-389D8 (SEQ ID NO:95), pFBAIn-1491D8 (SEQ ID NO:97), and pFBAIn-1594D8 (SEQ ID NO:96) were transformed into *Yarrowia lipolytica* strain Y4001 according to the General Methods.

The cells were plated onto MM plates (lacking uracil) and maintained at 30° C. for 2 to 3 days. Single colonies of transformants were then patched onto fresh MM plates (lacking uracil) and allowed to grow at 30° C. for 1 day. After this step, cells were scraped off the patches and transferred into 1.5 mL microfuge tubes. They were transesterified as described in the General Methods. FAMEs from cells containing each plasmid were analyzed by GC.

Lipid profiles of the transformant cells are shown below in Table 11. Fatty acids are identified as 16:0 (palmitic acid), 16:1 (palmitoleic acid), 18:0 (stearic acid), 18:1 (oleic acid), 18:2 (linoleic acid), 20:1 (eicosenoic acid), 20:2 (eicosadienoic acid) and DGLA (20:3; dihomo-γ-linolenic acid); and the composition of each is presented as a % of the total fatty acids.

The conversion efficiency was measured according to the following formula: ([product]/[substrate+product])*100, where 'product' includes the immediate product and all products in the pathway derived from it. As shown in Table 11, the results demonstrated that each delta-8 desaturase was able to convert EDA (20:2) to DGLA (20:3); this confirmed that TpomD8, E389D8 and E1594D8 indeed were delta-8 desaturases. The substrate conversion efficiency for E389D8 and E1594D8 was about 6%, and for that of TpomD8 was 2.89%. Although not included within the data herein, expression of PFBAIN-MOD (control) in strain Y4001 under comparable conditions resulted in c.a. 0% C20:2 (on average), wherein the conversion efficiency was c.a. 0% 9 on average).

TABLE 11

Comparison of Lipid Profiles of *Yarrowia lipolytica* Expressing TpomD8, E389D8 and E1594D8

| Plasmid (Desaturase) | C16:0 | C16:1 | C18:0 | C18:1 | C18:2 | C20:1 | C20:2 | DGLA | Conv. efficiency % |
|---|---|---|---|---|---|---|---|---|---|
| pFBAln-389D8 (E389D8) | 11.71 | 7.74 | 2.06 | 13.89 | 40.93 | 0.58 | 14.34 | 0.89 | 5.84 |
| pFBAln-389D8 (E389D8) | 11.64 | 7.74 | 2.06 | 14.57 | 39.95 | 0.57 | 14.69 | 0.98 | 6.25 |
| PFBAln-1491D8 (TpomD8) | 11.68 | 7.91 | 2.01 | 14.16 | 40.27 | 0.54 | 14.81 | 0.44 | 2.89 |
| PFBAln-1594D8 (E1594D8) | 12.03 | 7.71 | 2.3 | 15.18 | 38.95 | 0.57 | 14.97 | 0.9 | 5.67 |

Example 8

Construction of Soybean Expression Vector pKR1013 for Co-Expression of the *Tetruetreptia pomquetensis* CCMP1491 Delta-8 Desaturase (TpomD8) with a Delta-9 Elongase Derived from *Isochrysis galbana* (IgD9eS)

The present Example describes construction of a soybean vector for co-expression of TpomD8 with IgD9eS (a synthetic delta-9 elongase derived from *Isochrysis galbana* and codon-optimized for expression in *Yarrowia lipolytica*). As demonstrated in Examples 9 and 10 (infra), high concentrations of DGLA and/or ETA could readily be produced via expression of this vector in soybean.

Vector pKR123r (SEQ ID NO:66), which was previously described in PCT Publication No. WO 2004/071467 (published Aug. 26, 2004; the contents of which are hereby incorporated by reference), contains a NotI site flanked by the Kunitz soybean Trypsin Inhibitor (KTi3) promoter (Jofuku et al., *Plant Cell* 1:1079-1093 (1989)) and the KTi 3' termination region, the isolation of which is described in U.S. Pat. No. 6,372,965 (KTi3/NotI/KTi3' cassette). TpomD8 (SEQ ID NO:57) was released from pLF114-10 (SEQ ID NO:63; Example 5) by digestion with NotI and cloned into the NotI site of pKR123r to produce pKR1007 (SEQ ID NO:67).

Plasmid pKR607 (SEQ ID NO:68), previously described in PCT Publication No. WO 2006/012325 (the contents of which are hereby incorporated by reference), contained a chimeric construct comprising the α' subunit of β-conglycinin ("BCON Pro"; Beachy et al., *EMBO J.* 4:3047-3053 (1985)), IgD9eS (identified as "IG syel1" on FIG. 2 herein) and the 3' transcription termination region of the phaseolin gene (Doyle et al., *J. Biol. Chem.* 261:9228-9238 (1986)). The synthesis of IgDeS is similarly described in PCT Publication No. WO 2006/012325. Briefly, the codon usage of the delta-9 elongase gene of *Isochrysis galbana* was optimized for expression in *Yarrowia lipolytica*, in a manner similar to that described in PCT Publication No. WO 2004/101753. Thus, a codon-optimized delta-9 elongase gene (designated "IgD9eS", SEQ ID NO:110) was designed based on the coding sequence of IgD9e (SEQ ID NO:70) according to the *Yarrowia* codon usage pattern (PCT Publication No. WO 2004/101753), the consensus sequence around the ATG translation initiation codon, and the general rules of RNA stability (Guhaniyogi, G. and J. Brewer, *Gene* 265(1-2):11-23 (2001)). In addition to modification of the translation initiation site, 127 bp of the 792 bp coding region were modified (16.0%), and 122 codons were optimized. None of the modifications in the codon-optimized gene changed the amino acid sequence of the encoded protein (SEQ ID NO:76).

Plasmid pKR1007 (SEQ ID NO:67) was digested with PstI and the fragment containing TpomD8 was cloned into the SbfI site of plasmid pKR607 (SEQ ID NO:68) to produce pKR1013 (SEQ ID NO:69). In this way, TpomD8 is co-expressed with IgD9eS behind strong, seed-specific promoters. A schematic depiction of pKR1013 is shown in FIG. 2.

Example 9

Transformation of Somatic Soybean Embryo Cultures with Soybean Expression Vector pKR1013, for Co-Expression of TpomD8 and IgD9eS Culture Conditions:

Soybean embryogenic suspension cultures (cv. Jack) were maintained in 35 mL liquid medium SB196 (described infra) on a rotary shaker, 150 rpm, 26° C. with cool white fluorescent lights on 16:8 hr day/night photoperiod at light intensity of 60-85 µE/m2/s. Cultures were subcultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids by the method of particle gun bombardment (Klein et al., *Nature* 327:70 (1987)) using a DuPont Biolistic PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants 45-55 days after planting were picked, removed from their shells and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using 2 1-liter bottles of sterile distilled water and those less than 4 mm were placed on individual microscope slides. The small end of the seed was cut and the cotyledons pressed out of the seed coat. Cotyledons were transferred to plates containing SB199 medium (25-30 cotyledons per plate) for 2 weeks, then transferred to SB1 for 2-4 weeks. Plates were wrapped with fiber tape. After this time secondary embryos were cut and placed into SB196 liquid media for 7 days.

Preparation of DNA for Bombardment:

Either an intact plasmid or a DNA plasmid fragment containing the genes of interest and the selectable marker gene were used for bombardment. Fragments from soybean expression plasmids pKR1013 (see Example 8) were obtained by gel isolation of digested plasmids. In each case, 100 µg of plasmid DNA was used in 0.5 mL of the specific enzyme mix described below. Plasmids were digested with AscI (100 units) in NEBuffer 4 (20 mM Tris-acetate, 10 mM magnesium acetate, 50 mM potassium acetate, 1 mM dithiothreitol, pH 7.9), 100 µg/mL BSA, and 5 mM beta-mercaptoethanol at 37° C. for 1.5 hr. The resulting DNA fragments were separated by gel electrophoresis on 1% SeaPlaque GTG agarose (BioWhitaker Molecular Applications) and the DNA fragments containing gene cassettes were cut from the agarose gel. DNA was purified from the agarose using the GELase digesting enzyme following the manufacturer's protocol.

A 50 µL aliquot of sterile distilled water containing 1 mg of gold particles was added to 5 µL of a 1 µg/µL DNA solution (either intact plasmid or DNA fragment prepared as described above), 50 µL 2.5M $CaCl_2$ and 20 µL of 0.1 M spermidine. The mixture was pulsed 5 times on level 4 of a vortex shaker and spun for 5 sec in a bench microfuge. After a wash with 150 µL of 100% ethanol, the pellet was suspended by sonication in 85 µL of 100% ethanol. Five µL of DNA suspension was dispensed to each flying disk of the Biolistic PDS1000/HE instrument disk. Each 5 µL aliquot contained approximately 0.058 mg gold particles per bombardment (i.e., per disk).

Tissue Preparation and Bombardment with DNA:

Approximately 100-150 mg of 7 day old embryonic suspension cultures were placed in an empty, sterile 60×15 mm petri dish and the dish was placed inside of an empty 150×25 mm Petri dish. Tissue was bombarded 1 shot per plate with membrane rupture pressure set at 650 PSI and the chamber was evacuated to a vacuum of 27-28 inches of mercury. Tissue was placed approximately 2.5 inches from the retaining/stopping screen.

Selection of Transformed Embryos:

Transformed embryos were selected using hygromycin as the selectable marker. Specifically, following bombardment, the tissue was placed into fresh SB196 media and cultured as described above. Six to eight days post-bombardment, the SB196 is exchanged with fresh SB196 containing 30 mg/L hygromycin. The selection media was refreshed weekly. Four to six weeks post-selection, green, transformed tissue was observed growing from untransformed, necrotic embryogenic clusters. Isolated, green tissue was removed and inoculated into multiwell plates to generate new, clonally propagated, transformed embryogenic suspension cultures.

Embryo Maturation:

Transformed embryogenic clusters were cultured for one-three weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 µE/m²s. After this time embryo clusters were removed to a solid agar media, SB166, for 1 week and then subcultured to medium SB103 for 3 weeks. Alternatively, embryo clusters were removed from SB196 media to 35 mL of SB228 (described infra) (SHaM liquid media; Schmidt et al., *Cell Biology and Morphogenesis* 24:393 (2005)) in a 250 mL Erlenmeyer flask for 2-3 weeks. Tissue cultured in SB228 was maintained on a rotary shaker at 130 rpm and 26° C. with cool white fluorescent lights on a 16:8 hr day/night photoperiod at a light intensity of 60-85 µE/m2/s. After maturation on plates in SB103 or in flasks on SB228 media, individual embryos were removed from the clusters, dried and screened for alterations in their fatty acid compositions as described supra.

Media Recipes:

| SB 196 - FN Lite Liquid Proliferation Medium (per liter) | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

| FN Lite Stock Solutions | | | |
|---|---|---|---|
| Stock Number | | 1000 mL | 500 mL |
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| *Add first, dissolve in dark bottle while stirring | | | |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

SB1 Solid Medium (per liter)

1 package MS salts (Gibco/BRL - Cat. No. 11117-066)
1 mL B5 vitamins 1000X stock
31.5 g glucose
2 mL 2,4-D (20 mg/L final concentration)
pH 5.7
8 g TC agar SB199 Solid Medium (per liter)

1 package MS salts (Gibco/BRL - Cat. No. 11117-066)
1 mL B5 vitamins 1000X stock
30 g Sucrose
4 mL 2,4-D (40 mg/L final concentration)
pH 7.0
2 g Gelrite SB 166 Solid Medium (per liter)

1 package MS salts (Gibco/BRL - Cat. No. 11117-066)
1 mL B5 vitamins 1000X stock
60 g maltose
750 mg $MgCl_2$ hexahydrate
5 g activated charcoal
pH 5.7
2 g gelrite SB 103 Solid Medium (per liter)

1 package MS salts (Gibco/BRL - Cat. No. 11117-066)
1 mL B5 vitamins 1000X stock
60 g maltose
750 mg MgCl2 hexahydrate
pH 5.7
2 g gelrite SB 71-4 Solid Medium (per liter)

1 bottle Gamborg's B5 salts w/ sucrose (Gibco/BRL - Cat. No. 21153-036)
pH 5.7
5 g TC agar -continued 2,4-D Stock Obtain premade from Phytotech Cat. No. D 295 - concentration 1 mg/mL B5 Vitamins Stock (per 100 mL)

Store aliquots at −20° C.
10 g myo-inositol
100 mg nicotinic acid
100 mg pyridoxine HCl
1 g thiamine
If the solution does not dissolve quickly enough, apply a low level of heat via the hot stir plate.

SB 228 - Soybean Histodifferentiation & Maturation (SHaM) (per liter)

| | |
|---|---|
| DDI $H_2O$ | 600 mL |
| FN-Lite Macro Salts for SHaM 10X | 100 mL |
| MS Micro Salts 1000x | 1 mL |
| MS FeEDTA 100x | 10 mL |
| CaCl 100x | 6.82 mL |
| B5 Vitamins 1000x | 1 mL |
| L-Methionine | 0.149 g |
| Sucrose | 30 g |
| Sorbitol | 30 g |
| Adjust volume to 900 mL | |
| pH 5.8 | |
| Autoclave | |
| Add to cooled media (≦30° C.): | |
| *Glutamine (final concentration 30 mM) 4% | 110 mL |

*Note: Final volume will be 1010 mL after glutamine addition.
Since glutamine degrades relatively rapidly, it may be preferable to add immediately prior to using media. Expiration 2 weeks after glutamine is added; base media can be kept longer w/o glutamine.

FN-lite Macro for SHAM 10X - Stock #1 (per liter)

| | |
|---|---|
| $(NH_4)_2SO_4$ (ammonium sulfate) | 4.63 g |
| $KNO_3$ (potassium nitrate) | 28.3 g |
| $MgSO_4 \cdot 7H_2O$ (magnesium sulfate heptahydrate) | 3.7 g |
| $KH_2PO_4$ (potassium phosphate, monobasic) | 1.85 g |
| Bring to volume | |
| Autoclave | |

MS Micro 1000X - Stock #2 (per 1 liter)

| | |
|---|---|
| $H_3BO_3$ (boric acid) | 6.2 g |
| $MnSO_4 \cdot H_2O$ (manganese sulfate monohydrate) | 16.9 g |
| $ZnSO_4 \cdot 7H_2O$ (zinc sulfate heptahydrate) | 8.6 g |
| $Na_2MoO_4 \cdot 2H_2O$ (sodium molybdate dihydrate) | 0.25 g |
| $CuSO_4 \cdot 5H_2O$ (copper sulfate pentahydrate) | 0.025 g |
| $CoCl_2 \cdot 6H_2O$ (cobalt chloride hexahydrate) | 0.025 g |
| KI (potassium iodide) | 0.8300 g |
| Bring to volume | |
| Autoclave | |

FeEDTA 100X - Stock #3 (per liter)

| | |
|---|---|
| $Na_2EDTA^*$ (sodium EDTA) | 3.73 g |
| $FeSO_4 \cdot 7H_2O$ (iron sulfate heptahydrate) | 2.78 g |

*EDTA must be completely dissolved before adding iron.
Bring to Volume
Solution is photosensitive. Bottle(s) should be wrapped in foil to omit light.
Autoclave Ca 100X - Stock #4 (per liter)

| | |
|---|---|
| $CaCl_2 \cdot 2H_2O$ (calcium chloride dihydrate) | 44 g |
| Bring to Volume | |
| Autoclave | |

B5 Vitamin 1000X - Stock #5 (per liter)

| | |
|---|---|
| Thiamine*HCl | 10 g |
| Nicotinic Acid | 1 g |
| Pyridoxine*HCl | 1 g |
| Myo-Inositol | 100 g |
| Bring to Volume | |
| Store frozen | |

4% Glutamine - Stock #6 (per liter)

| | |
|---|---|
| DDI water heated to 30° C. | 900 mL |
| L-Glutamine | 40 g |

-continued

Gradually add while stirring and applying low heat.
Do not exceed 35° C.
Bring to Volume
Filter Sterilize
Store frozen*

*Note: Warm thawed stock in 31° C. bath to fully dissolve crystals.

Example 10

Functional Analysis of the *Tetruetreptia pomquetensis* CCMP1491 Delta-8 Desaturase (TpomD8) and the *Isochrysis galbana* Delta-9 Elongase (IgD9eS) in Somatic Soybean Embryos Transformed with Soybean Expression Vector pKR1013

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, Example 3). Most importantly, the model system is also predictive of the fatty acid composition of seeds from plants derived from transgenic embryos.

Fatty Acid Analysis of Transgenic Somatic Soybean Embryos Expressing pKR1013

Individual single, matured, somatic soybean embryos that had been transformed with pKR1013 (as described in Example 9 transformants were matured on SHaM liquid media) were picked into glass GC vials, frozen at minus 80° C., freeze dried overnight and fatty acid methyl esters were prepared by transesterification. For transesterification, 50 µL of trimethylsulfonium hydroxide (TMSH) and 0.5 mL of hexane were added to the embryos in glass vials and incubated for 30 min at room temperature while shaking. Fatty acid methyl esters (5 µL injected from hexane layer) were separated and quantified using a Hewlett-Packard 6890 Gas Chromatograph fitted with an Omegawax 320 fused silica capillary column (Catalog #24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.). Routinely, 5-10 embryos per event were analyzed by GC, using the methodology described above.

Embryo fatty acid profiles for each event (6 embryos each) containing pKR1013 were obtained and the lipid profiles of somatic soybean embryos expressing TpomD8 and IgD9eS for the top 5 events are shown in FIG. 5. Fatty acids are identified as 16:0 (palmitate), 18:0 (stearic acid), 18:1 (oleic acid), LA, GLA, ALA, EDA, DGLA, ERA and ETA; and, fatty acid compositions listed in FIG. 5 are expressed as a weight percent (wt. %) of total fatty acids. The activity of TpomD8 is expressed as percent desaturation (% desat), calculated according to the following formula: ([product]/[substrate+product])*100.

More specifically, the combined percent desaturation for EDA and ERA is shown as "C20% delta-8 desat", determined as: ([DGLA+ETA]/[DGLA+ETA+EDA+ERA])*100. This is also referred to as the overall % desaturation. The individual omega-6 delta-8 desaturation ("EDA % delta-8 desat.") was calculated as: ([DGLA]/[DGLA+EDA])*100. Similarly, the individual omega-3 delta-8 desaturation ("ERA % delta-8 desat.") was calculated as: ([ETA]/[ETA+ERA])*100. The ratio of delta-8 desaturation for omega-6 versus omega-3 substrates ("ratio [EDA/ERA] % desat.") was obtained by dividing the EDA % delta-8 desaturation by the ERA % delta-8 desaturation.

In summary of FIG. 5, TpomD8 worked in soybean to convert both EDA and ERA to DGLA and ETA, respectively. The line with the highest average DGLA content (i.e., 1974-5-6) had embryos with an average DGLA content of 12.9% and an average ETA content of 2.9%. The highest DGLA and ETA content for an individual embryo from this line was 14.6% and 3.4%, respectively. The highest average overall % desaturation was 50.7% with the highest overall % desaturation for an individual embryo being 55.5%. When broken down into % desaturation for the omega-6 and omega-3 substrates, the highest average % desaturation was 48.3% and 65.0% for EDA and ERA, respectively. The highest % desaturation for an individual embryo was 52.9% and 72.7% for EDA and ERA, respectively. In this example, TpomD8 had a preference for ERA over EDA, with the average desaturation ratio ranging from 0.6 to 0.8. No GLA was found to accumulate in the embryos.

Example 11 cDNA Synthesis and PCR of *Euglena gracilis* Delta-9 Elongase

The present Example, disclosed in U.S. Provisional Application No. 60/739,989 (filed Nov. 23, 2005), describes the isolation of a delta-9 elongase from *Euglena gracilis* ("EgD9e"; SEQ ID NOs:74 and 75). The isolation of this gene allowed co-expression of EgD9e and the delta-8 desaturases of the present invention, to thereby permit expression of the delta-9 elongase/delta-8 desaturase pathway leading to accumulation of DGLA and/or ETA from LA and/or ALA, respectively.

*Euglena gracilis* Growth Conditions, Lipid Profile and mRNA Isolation

*Euglena gracilis* was obtained from Dr. Richard Triemer's lab at Michigan State University (East Lansing, Mich.). From 10 mL of actively growing culture, a 1 mL aliquot was transferred into 250 mL of *Euglena gracilis* (Eg) Medium in a 500 mL glass bottle. Eg medium was made by combining 1 g of sodium acetate, 1 g of beef extract (U126-01, Difco Laboratories, Detroit, Mich.), 2 g of Bacto® tryptone (0123-17-3, Difco Laboratories), 2 g of Bacto® yeast extract (0127-17-9, Difco Laboratories) in 970 mL of water. After filter sterilizing, 30 mL of soil-water supernatant (15-3790, Carolina Biological Supply Company, Burlington, N.C.) was aseptically added to give the final Eg medium. *Euglena gracilis* cultures were grown at 23° C. with a 16 h light, 8 h dark cycle for 2 weeks with no agitation.

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 µL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 µL injected from hexane layer) were separated and quantified using a Hewlett-Packard 6890 Gas Chromatograph fitted with an Omegawax 320 fused silica capillary column (Supelco Inc., Catalog No. 24152). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Nu-Chek Prep, Inc. Catalog No. U-99-A).

The remaining 2 week culture (240 mL) was pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 µg of mRNA was obtained.

*Euglena gracilis* cDNA Synthesis, Library Construction and Sequencing

A cDNA library was generated using the Cloneminer™ cDNA Library Construction Kit (Catalog No. 18249-029, Invitrogen Corporation, Carlsbad, Calif.) and following the manufacturer's protocol provided (Version B, 25-0608). Using the non-radiolabeling method, cDNA was synthesized from 3.2 µg of mRNA (described above) using the Biotin-attB2-Oligo(dT) primer. After synthesis of the first and second strand, the attB1 adapter was added, ligated and the cDNA was size fractionated using column chromatography. DNA from fractions 7 and 8 (size ranging from ~800-1500 bp) were concentrated, recombined into pDONR™ 222 and transformed into *E. coli* ElectroMAX™ DH10B™ T1 Phage-Resistant cells (Invitrogen Corporation). The *Euglena gracilis* library was named eeg1c.

For sequencing, clones first were recovered from archived glycerol cultures grown/frozen in 384-well freezing media plates, and replicated with a sterile 384 pin replicator (Genetix, Boston, Mass.) in 384-well microtiter plates containing LB+75 µg/mL Kanamycin (replicated plates). Plasmids then were isolated, using the Templiphi DNA sequencing template amplification kit method (Amersham Biosciences) following the manufacturer's protocol. Briefly, the Templiphi method uses bacteriophage φ29 DNA polymerase to amplify circular single-stranded or double-stranded DNA by isothermal rolling circle amplification (Dean et al., *Genome Res.*, 11:1095-1099 (2001); Nelson et al., *Biotechniques*, 32:S44-S47 (2002)). After growing 20 h at 37° C., cells from the replicated plate were added to 5 µL of dilution buffer and denatured at 95° C. for 3 min to partially lyse cells and release the denatured template. Templiphi premix (5 µL) was then added to each sample and the resulting reaction mixture was incubated at 30° C. for 16 h, then at 65° C. for 10 min to inactivate the φ29 DNA polymerase activity. DNA quantification with the PicoGreen® dsDNA Quantitation Reagent (Molecular Probes) was performed after diluting the amplified samples 1:3 in distilled water.

The amplified products then were denatured at 95° C. for 10 min and end-sequenced in 384-well plates, using the M13F universal primer (SEQ ID NO:91), and the ABI Big-Dye version 3.1 Prism Sequencing Kit. For the sequencing reaction, 100-200 ng of templates and 6.4 pmol of primers were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3730xl automated sequencers.

Identification of Long-Chain Polyunsaturated Fatty Acid Elongation Enzyme Homologs from *Euglena gracilis* cDNA Library eeg1c cDNA clones encoding long-chain polyunsaturated fatty acid elongation enzyme homologs (i.e., LC-PUFA ELO homologs or delta-9 elongases) were identified by conducting BLAST (Basic Local Alignment Search Tool; Altschul et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The *Euglena gracilis* cDNA sequences obtained above were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States, *Nat. Genet.,* 3:266-272 (1993)) provided by the NCBI. For convenience, the P-value (probability) of observing a match of a cDNA sequence to a sequence contained in the searched databases merely by chance as calculated by BLAST are reported herein as "pLog" values (as described in Example 4).

The BLASTX search using the nucleotide sequences from clone eeg1c.pk001.n5.f revealed similarity of the protein encoded by the cDNA to the long-chain PUFA elongation enzyme from *Isochrysis galbana* (IgD9e; SEQ ID NO:76) (GenBank Accession No. AAL37626 (GI 17226123), locus AAL37626, CDS AF390174; Qi et al., *FEBS Lett.* 510(3): 159-165 (2002)). The sequence of a portion of the cDNA insert from clone eeg1c.pk001.n5.f is shown in SEQ ID NO:71 (5' end of cDNA insert).

Additional sequence was obtained from the 3' end of the cDNA insert of eeg1c.pk001.n5.1 as described above, but using the poly(A) tail-primed WobbleT oligonucleotides. Briefly, the WobbleT primer is an equimolar mix of 21 mer poly(T)A, poly(T)C, and poly(T)G, used to sequence the 3' end of cDNA clones. The 3' end sequence is shown in SEQ ID NO:72.

Both the 5' and 3' sequences were aligned using Sequencher™ (Version 4.2, Gene Codes Corporation, Ann Arbor, Mich.) and the resulting sequence for the cDNA is shown in SEQ ID NO:73 (1201 bp). Sequence for the coding sequence from the cDNA in eeg1c.pk001.n5.f and the corresponding deduced amino acid sequence is shown in SEQ ID NO:74 (777 bp) and SEQ ID NO:75 (258 amino acids), respectively.

The amino acid sequence set forth in SEQ ID NO:75 was evaluated by BLASTP, yielding a pLog value of 38.70 (E value of 2e-39) versus the *Isochrysis galbana* sequence (SEQ ID NO:76). The *Euglena gracilis* delta-9 elongase is 39.4% identical to IgD9e using the Jotun Hein method (as described in Example 4); similarly, the *Euglena gracilis* delta-9 elongase is 31.8% identical to IgD9e using the Clustal V method (as described in Example 4). BLAST scores and probabilities indicate that the nucleic acid fragment described herein as SEQ ID NO:75 encodes an entire *Euglena gracilis* delta-9 elongase (designated herein as "EgD9e").

Example 12

Construction of Soybean Expression Vector pKR1014 for Co-Expression of the *Tetruetreptia pomquetensis* CCMP1491 Delta-8 Desaturase (TpomD8) with the Delta-9 Elongase from *Euglena gracilis* (EgD9e)

The present Example describes construction of a soybean vector for co-expression of TpomD8 with EgD9e.

EgD9e (SEQ ID NOs:74 and 75; Example 11) was amplified with oligonucleotide primers oEugEL1-1 (SEQ ID NO:77) and oEugEL1-2 (SEQ ID NO:78) using the VentR® DNA Polymerase (Catalog No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906 (SEQ ID NO:79).

A starting plasmid pKR72 (ATCC Accession No. PTA-6019; SEQ ID NO:80, 7085 bp sequence), a derivative of pKS123 which was previously described in PCT Publication No. WO 02/008269 (the contents of which are hereby incorporated by reference), contains the hygromycin B phosphotransferase gene (HPT) (Gritz, L. and Davies, J., *Gene* 25:179-188 (1983)), flanked by the T7 promoter and transcription terminator (T7prom/HPT/T7term cassette), and a bacterial origin of replication (ori) for selection and replication in bacteria (e.g., *E. coli*). In addition, pKR72 also contains HPT, flanked by the 35S promoter (Odell et al., *Nature* 313:810-812 (1985)) and NOS 3' transcription terminator (Depicker et al., *J. Mol. Appl. Genet.* 1:561-570 (1982)) (35S/HPT/NOS3' cassette) for selection in plants such as soybean. pKR72 also contains a NotI restriction site, flanked by the promoter for the α' subunit of β-conglycinin (Beachy et al., *EMBO J.* 4:3047-3053 (1985)) and the 3' transcription termination region of the phaseolin gene (Doyle et al., *J. Biol. Chem.* 261:9228-9238 (1986)), thus allowing for strong tissue-specific expression in the seeds of soybean of genes cloned into the NotI site.

EgD9e was released from pKR906 by digestion with NotI and cloned into the NotI site of pKR72 to produce pKR912 (SEQ ID NO:81). In some instances, pKR912 is referred to as pKR1010 but they are identical.

Plasmid pKR1007 (in Example 8, SEQ ID NO:67) was digested with PstI and the fragment containing the *Tetruetreptia pomquetensis* delta-8 desaturase was cloned into the SbfI site of pKR912 (SEQ ID NO:81), to give pKR1014 (SEQ ID NO:82). In this way, the *Tetruetreptia pomquetensis* delta-8 desaturase is co-expressed with the *Isochrysis galbana* delta-9 elongase behind strong, seed-specific promoters. A schematic depiction of pKR1014 is shown in FIG. 3.

Plasmid pKR1014 was transformed into soybean embryogenic suspension cultures as described in Example 9 and embryos co-expressing of TpomD8 and EgD9e were analyzed as described in Example 10.

Embryo fatty acid profiles for each event (6 embryos each) containing pKR1014 were obtained and the lipid profiles of somatic soybean embryos expressing TpomD8 and EgD9e for the top 5 events are shown in FIG. 10. Fatty acids are identified as 16:0 (palmitate), 18:0 (stearic acid), 18:1 (oleic acid), LA, GLA, ALA, EDA, DGLA, ERA and ETA; and, fatty acid compositions listed in FIG. 10 are expressed as a weight percent (wt. %) of total fatty acids. The activity of TpomD8 is expressed as percent desaturation (% desat), calculated according to the following formula: ([product]/[substrate+product])*100.

More specifically, the combined percent desaturation for EDA and ERA is shown as "C20% delta-8 desat", determined as: ([DGLA+ETA]/[DGLA+ETA+EDA+ERA])*100. This is also referred to as the overall % desaturation. The individual omega-6 delta-8 desaturation ("EDA % delta-8 desat.") was calculated as: ([DGLA]/[DGLA+EDA])*100. Similarly, the individual omega-3 delta-8 desaturation ("ERA % delta-8 desat.") was calculated as: ([ETA]/[ETA+ERA])*100. The ratio of delta-8 desaturation for omega-6 versus omega-3 substrates ("ratio [EDA/ERA] % desat.") was obtained by dividing the EDA % delta-8 desaturation by the ERA % delta-8 desaturation.

In summary of FIG. 10, TpomD8 worked in soybean to convert both EDA and ERA to DGLA and ETA, respectively. The line with the highest average DGLA content (i.e., 2024-3-9) had embryos with an average DGLA content of 14.8% and an average ETA content of 3.8%. The highest DGLA and ETA content for an individual embryo from this line was 16.0% and 3.9%, respectively. The highest average overall % desaturation was 60.9% with the highest overall % desaturation for an individual embryo being 68.7%. When broken down into % desaturation for the omega-6 and omega-3 substrates, the highest average % desaturation was 59.1% and 73.9% for EDA and ERA, respectively. The highest % desaturation for an individual embryo was 66.7% and 80.9% for EDA and ERA, respectively. In this example, TpomD8 had a preference for ERA over EDA, with the average desaturation ratio ranging from 0.8 to 0.9. No GLA was found to accumulate in the embryos.

Example 13

Construction of Soybean Expression Vector pKR1005 for Co-Expression of the *Tetruetreptia pomquetensis* CCMP1491 Delta-8 Desaturase (TpomD8) with the Delta-17 Desaturase from *Saprolegnia diclina* (SdD17)

The present Example describes construction of a soybean vector for co-expression of TpomD8 with SdD17.

The PstI fragment, containing the Ann/Sdd17/BD30 cassette from pKR271 (SEQ ID NO:83; which is described in PCT Publication No. WO 2004/071467 and the contents of which are hereby incorporated by reference), was cloned into the SbfI site of pKR226 (SEQ ID NO:84, which is also described in PCT Publication No. WO 2004/071467) to produce vector pKR886r (SEQ ID NO:85). In this way, the *Saprolegnia diclina* delta-17 desaturase (SdD17) was cloned behind the annexin promoter which is strong and seed specific.

The βcon/NotI/Phas3' cassette in plasmid pKR72 (SEQ ID NO:80, having ATCC Accession No. PTA-6019) was amplified using oligonucleotide primers oCon-1 (SEQ ID NO:86) and oCon-2 (SEQ ID NO:87) using the VentR® DNA Polymerase (Catalog No. M0254S, New England Biolabs Inc., Beverly, Mass.) following the manufacturer's protocol. The resulting DNA fragment was digested with XbaI and cloned into the XbaI site of pUC19, to produce pKR179 (SEQ ID NO:88).

TpomD8 was released from plasmid pLF114-10 (SEQ ID NO:63, Example 5) by digestion with NotI and was cloned into the NotI site of plasmid pKR179 (SEQ ID NO:88) to produce pKR1002 (SEQ ID NO:89).

Vector pKR1002 was digested with PstI and the fragment containing TpomD8 was cloned into the SbfI site of pKR886r (SEQ ID NO:85) to produce pKR1005 (SEQ ID NO:90). A schematic depiction of pKR1005 is shown in FIG. 4.

One skilled in the art will recognize that pKR1005 could be readily transformed into soybean embryogenic suspension cultures (as described in Example 9) and co-expression of TpomD8 and SdD17 could analyzed (as described in Example 10).

Example 14

Construction of Alternate Soybean Expression Vectors for Expression of *Tetruetreptia pomquetensis* CCMP1491 (TpomD8), *Eutreptiella* sp. CCMP389 (E389D8) and/or *Eutreptiella* cf *gymnastica* CCMP1594 (E1594D8) Delta-8 Desaturases In addition to the genes, promoters, terminators and gene cassettes described herein, one skilled in the art can appreciate that other promoter/gene/terminator cassette combinations can be synthesized in a way similar to, but not limited to, that described herein for expression of TpomD8, E389D8 and/or E1594D8. Similarly, it may be desirable to express other PUFA genes (such as those described below in Table 14), for co-expression with any of the delta-8 desaturases of the present invention.

For instance, PCT Publication Nos. WO 2004/071467 and WO 2004/071178 describe the isolation of a number of promoter and transcription terminator sequences for use in embryo-specific expression in soybean. Furthermore, PCT Publication Nos. WO 2004/071467, WO 2005/047479 and WO 2006/012325 describe the synthesis of multiple promoter/gene/terminator cassette combinations by ligating individual promoters, genes and transcription terminators together in unique combinations. Generally, a NotI site flanked by the suitable promoter (such as those listed in, but not limited to, Table 12) and a transcription terminator (such as those listed in, but not limited to, Table 13) is used to clone the desired gene. NotI sites can be added to a gene of interest such as those listed in, but not limited to, Table 14 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publication Nos. WO 2004/071467, WO 2005/047479 and WO 2006/012325 describe the further linking together of individual gene cassettes in unique combinations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 12

Seed-specific Promoters

| Promoter | Organism | Promoter Reference |
| --- | --- | --- |
| β-conglycinin α'-subunit | soybean | Beachy et al., EMBO J. 4: 3047-3053 (1985) |
| kunitz trypsin inhibitor | soybean | Jofuku et al., Plant Cell 1: 1079-1093 (1989) |
| Annexin | soybean | WO 2004/071467 |
| glycinin Gy1 | soybean | WO 2004/071467 |
| albumin 2S | soybean | U.S. Pat. No. 6,177,613 |
| legumin A1 | pea | Rerie et al., Mol. Gen. Genet. 225: 148-157 (1991) |
| β-conglycinin β-subunit | soybean | WO 2004/071467 |
| BD30 (also called P34) | soybean | WO 2004/071467 |
| legumin A2 | pea | Rerie et al., Mol. Gen. Genet. 225: 148-157 (1991) |

TABLE 13

Transcription Terminators

| Transcription Terminator | Organism | Reference |
| --- | --- | --- |
| phaseolin 3' | bean | WO 2004/071467 |
| kunitz trypsin inhibitor 3' | soybean | WO 2004/071467 |
| BD30 (also called P34) 3' | soybean | WO 2004/071467 |
| legumin A2 3' | pea | WO 2004/071467 |
| albumin 2S 3' | soybean | WO 2004/071467 |

TABLE 14

PUFA Biosynthetic Pathway Genes

| Gene | Organism | Reference |
| --- | --- | --- |
| delta-6 desaturase | *Saprolegnia diclina* | WO 2002/081668 |
| delta-6 desaturase | *Mortierella alpina* | U.S. Pat. No. 5,968,809 |
| elongase | *Mortierella alpina* | WO 2000/12720 U.S. Pat. No. 6,403,349 |
| delta-5 desaturase | *Mortierella alpina* | U.S. Pat. No. 6,075,183 |
| delta-5 desaturase | *Saprolegnia diclina* | WO 2002/081668 |
| delta-15 desaturase | *Fusarium moniliforme* | WO 2005/047479 |
| delta-17 desaturase | *Saprolegnia diclina* | WO 2002/081668 |
| elongase | *Thraustochytrium aureum* | WO 2002/08401 U.S. Pat. No. 6,677,145 |
| elongase | *Pavlova* sp. | Pereira et al., Biochem. J. 384: 357-366 (2004) |
| delta-4 desaturase | *Schizochytrium aggregatum* | WO 2002/090493 |
| delta-9 elongase | *Isochrysis galbana* | WO 2002/077213 |
| delta-9 elongase | *Euglena gracilis* | U.S. Provisional Application No. 60/739,989 |
| delta-8 desaturase | *Euglena gracilis* | WO 2000/34439 U.S. Pat. No. 6,825,017 WO 2004/057001 WO 2006/012325 |
| delta-8 desaturase | *Acanthamoeba castellanii* | Sayanova et al., FEBS Lett. 580: 1946-1952 (2006) |
| delta-8 desaturase | *Pavlova salina* | WO 2005/103253 |
| delta-8 desaturase | *Pavlova lutheri* | U.S. Provisional Application No. 60/795,810 |

Example 15

Chlorsulfuron Selection (ALS) and Plant Regeneration

Chlorsulfuron (ALS) Selection:

Following bombardment, the tissue is divided between 2 flasks with fresh SB196 media and cultured as described in Example 9. Six to seven days post-bombardment, the SB196 is exchanged with fresh SB196 containing selection agent of 100 ng/mL chlorsulfuron (chlorsulfuron stock is 1 mg/mL in 0.01 N ammonium hydroxide). The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants:

In order to obtain whole plants from embryogenic suspension cultures, the tissue must be regenerated. Embryos are matured as described in Example 9. After subculturing on medium SB103 for 3 weeks, individual embryos can be removed from the clusters and screened for alterations in their fatty acid compositions as described in Example 10. It should be noted that any detectable phenotype, resulting from the expression of the genes of interest, could be screened at this stage. This would include, but not be limited to, alterations in fatty acid profile, protein profile and content, carbohydrate content, growth rate, viability, or the ability to develop normally into a soybean plant.

Matured individual embryos are desiccated by placing them into an empty, small petri dish (35×10 mm) for approximately 4 to 7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then are planted in Redi-Earth in 24-cell pack tray, covered with clear plastic dome. After 2 weeks the dome is removed and plants are hardened off for a further week. If plantlets looked hardy they are transplanted to 10" pot of Redi-Earth with up to 3 plantlets per pot. After 10 to 16 weeks, mature seeds are harvested, are chipped and are analyzed for fatty acids as described in Example 10 above.

Example 16

Construction of Soybean Expression Vector pKR973 for Co-Expression of the *Pavlova lutheri* Delta-8 Desaturase (PavD8) with the *Euglena gracilis* Delta-9 Elongase (EgD9e) and the *Mortierella alpina* Delta-5 Desaturase (MaD5)

*Euglena gracilis* Delta-9 Elongase (EgD9e):

Plasmid pKR906 (SEQ ID NO:79, Example 12) was digested with NotI and the fragment containing the *Euglena gracilis* delta-9 elongase was cloned into plasmid pKR132 (SEQ ID NO:113; which is described in PCT Publication No. WO 2004/071467) to produce pKR953 (SEQ ID NO:114).

*Mortierella alpina* Delta-5 Desaturase (MaD5):

Vector pKR287 (SEQ ID NO:115; which is described in PCT Publication No. WO 2004/071467, published Aug. 26, 2004; the contents of which are hereby incorporated by reference), contains the *Mortierella alpina* delta-5 desaturase (MaD5; SEQ ID NO:116, which is described in U.S. Pat. No. 6,075,183 and PCT Publication Nos. WO 2004/071467 and WO 2005/047479, the contents of which are hereby incorporated by reference), flanked by the soybean glycinin Gy1 promoter and the pea legumin A2 3' termination region (Gy1/MaD5/legA2 cassette). Vector pKR287 was digested with SbfI/BsiWI and the fragment containing the Gy1/MaD5/legA2 cassette was cloned into the SbfI/BsiWI fragment of pKR277 (SEQ ID NO:117; which is described in PCT Publication No. WO 2004/071467, the contents of which are hereby incorporated by reference) to produce pK952 (SEQ ID NO:118).

Vector pKR457 (SEQ ID NO:119), which was previously described in PCT Publication No. WO 2005/047479 (the contents of which are hereby incorporated by reference), contains a NotI site flanked by the Kunitz soybean Trypsin Inhibitor (KTi) promoter (Jofuku et al., *Plant Cell* 1:1079-1093 (1989)) and the KTi 3' termination region, the isolation of which is described in U.S. Pat. No. 6,372,965, followed by the soy albumin transcription terminator, which was previously described in PCT Publication No. WO 2004/071467 (Kti/NotI/Kti3'Salb3' cassette). Through a number of subcloning steps, sequences containing Asp718 restriction sites were added to the 5' and 3' ends of the Kti/NotI/Kti3'Salb3' cassette to produce SEQ ID NO:120.

*Pavlova lutheri* Delta-8 Desaturase (PavD8):

*Pavlova lutheri* (CCMP459) was obtained from the Culture of Marine Phytoplankton (CCMP, West Boothbay Harbor, Me.) and grown in 250 mL flasks containing 50 mL of F/2-Si medium (made using F/2 Family Medium Kit-KIT20F2 and Filtered Seqwater-SEA2 from CCMP) at 26° C. with shaking at 150 rpm. Cultures were transferred to new medium on a weekly basis using 1:4 (old culture:new medium) dilution.

Cultures from 28 flasks (1400 mL) were combined, cells were pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided. In this way, 2.6 mg of total RNA (2.6 mg/mL) was obtained from the pellet. The mRNA was isolated from 1.25 mg of total RNA using the mRNA Purification Kit (Amersham Biosciences, Piscataway, N.J.) following the manufacturer's protocol provided. In this way, 112 µg of mRNA was obtained.

cDNA was synthesized from 224 ng of mRNA using the SuperScript™ First-Strand Synthesis System for RT-PCR Kit (Invitrogen™ Life Technologies, Carlsbad, Calif.) with the provided oligo(dT) primer according to the manufacturer's protocol. After RNase H treatment as per the protocol, the *Pavlova lutheri* delta-8 desaturase (PavD8; SEQ ID NO:121; which is described in U.S. Provisional Application No. 60/795,810 (filed Apr. 28, 2006) and U.S. patent application Ser. No. 11/737,772 (filed Apr. 20, 2007) the contents of which are hereby incorporated by reference) was amplified from the resulting cDNA with oligonucleotide primers PvDES5'Not-1 (SEQ ID NO:122) and PvDES3'Not-1 (SEQ ID NO:123) using the conditions described below.

cDNA (2 µL) from the reaction described above was combined with 50 pmol of PvDES5'Not-1 (SEQ ID NO:122), 50 pmol of PvDES3'Not-1 (SEQ ID NO:123), 1 µL of PCR nucleotide mix (10 mM, Promega, Madison, Wis.), 5 µL of 10×PCR buffer (Invitrogen Corporation), 1.5 µL of MgCl₂ (50 mM, Invitrogen Corporation), 0.5 µL of Taq polymerase (Invitrogen Corporation) and water to 50 µL. The reaction conditions were 94° C. for 3 min followed by 35 cycles of 94° C. for 45 sec, 55° C. for 45 sec and 72° C. for 1 min. The PCR was finished at 72° C. for 7 min and then held at 4° C. The PCR reaction was analyzed by agarose gel electrophoresis on 5 µL and a DNA band with molecular weight around 1.3 kb was observed. The remaining 45 µL of product was separated by agarose gel electrophoresis and the DNA purified using the Zymoclean™ Gel DNA Recovery Kit (Zymo Research, Orange, Calif.) following the manufacturer's protocol.

The PavD8, flanked by NotI sites, was cloned into the NotI site of the modified Kti/NotI/Kti3'Salb3' cassette (SEQ ID NO:120), and then the DNA fragment was digested with Asp718 and cloned into the SbfI site of pKR952 (SEQ ID NO:118) to produce pKR970 (SEQ ID NO:124).

Plasmid pKR953 (SEQ ID NO:114) was digested with PstI and the fragment containing the *Euglena gracilis* delta-9 elongase was cloned into the SbfI site of pKR970 (SEQ ID NO:124) to produce pKR973 (SEQ ID NO:125, FIG. 11). In this way, the *Pavlova lutheri* delta-8 desaturase could be co-expressed with the *Mortierella alpina* delta-5 desaturase and the *Euglena gracilis* delta-9 elongase behind strong, seed-specific promoters.

Example 17

Construction of Soybean Expression Vector pKR1084 for Co-Expression of the *Euglena gracilis* Delta-9 Elongase (EgD9e) with the *Mortierella alpina* Delta-5 Desaturase (MaD5)

The NotI fragment of pKS129 (SEQ ID NO:126; which is described in PCT Publication No. WO 04/071467), containing the MaD5 (SEQ ID NO:116; Example 16) was cloned into the NotI site of pKR457 (SEQ ID NO:119; Example 16), to give pKR606 (SEQ ID NO:127).

Vector pKR606 (SEQ ID NO:127) was digested with BsiWI and after filling to blunt the ends, the fragment containing the Gy1/MaD5/legA2 cassette was cloned into the filled NgoMI site of pKR277 (SEQ ID NO:117; Example 16) to produce pKR804 (SEQ ID NO:128).

Plasmid pKR953 (SEQ ID NO:114; Example 16) was digested with PstI and the fragment containing the EgD9e was cloned into the SbfI site of pKR804 (SEQ ID NO:128) to give pKR1084 (SEQ ID NO:129; FIG. 12).

In this way, the *Mortierella alpina* delta-5 desaturase (MaD5) was expressed with the *Euglena gracilis* delta-9 elongase (EgD9e) behind strong, seed-specific promoters.

Example 18

Construction of Soybean Expression Vector pKR1123 for Co-Expression of the *Eutreptiella* cf *gymnastica* CCMP1594 Delta-8 Desaturase (E1594D8) with the Delta-9 Elongase from *Euglena gracilis* (EgD9e)

The present Example describes construction of a soybean vector for co-expression of E1594D8 with EgD9e and expression of these genes in somatic embryos.

An intermediate plasmid pKR908 (SEQ ID NO:130) allows the cloning of DNA fragments into an NcoI/XbaI site and thus add a flanking NotI site 5' to the NcoI site.

The NcoI/XbaI fragment of pFBAIn-1594D8 (SEQ ID NO:96; Example 7), containing E1594D8 and where a NotI site is already present just 5' to the XbaI site, was cloned into the NcoI/XbaI sites of pKR908 (SEQ ID NO:130) to produce pKR1118 (SEQ ID NO:131) and where E1594D8 is now flanked by NotI sites at the 5' and 3' ends.

E1594D8 was released from pKR1118 (SEQ ID NO:131) by digestion with NotI and cloned into the NotI site of pKR123r (SEQ ID NO:66; Example 8) to produce pKR1120 (SEQ ID NO:132).

Plasmid pKR1120 (SEQ ID NO:132) was digested with SbfI and the fragment containing E1594D8 was cloned into the SbfI site of pKR912 (SEQ ID NO:81; Example 12), to give pKR1123 (SEQ ID NO:133). In this way, the *Eutreptiella* cf *gymnastica* CCMP1594 delta-8 desaturase is co-expressed with the *Euglena gracilis* delta-9 elongase behind strong, seed-specific promoters. A schematic depiction of pKR1123 is shown in FIG. 13.

Plasmid pKR1123 was transformed into soybean embryogenic suspension cultures as described in Example 9 and embryos co-expressing E1594D8 and EgD9e were analyzed as described in Example 10.

Embryo fatty acid profiles for each event (6 embryos each) containing pKR1123 were obtained and the lipid profiles of somatic soybean embryos expressing E1594D8 and EgD9e for the top 5 events are shown in FIG. 14. Fatty acids are identified as 16:0 (palmitate), 18:0 (stearic acid), 18:1 (oleic acid), LA, GLA, ALA, EDA, DGLA, ERA and ETA; and, fatty acid compositions listed in FIG. 14 are expressed as a weight percent (wt. %) of total fatty acids. The activity of E1594D8 is expressed as percent desaturation (% desat), calculated according to the following formula: ([product]/[substrate+product])*100.

More specifically, the combined percent desaturation for EDA and ERA is shown as "C20% delta-8 desat", determined as: ([DGLA+ETA]/[DGLA+ETA+EDA+ERA])*100. This is also referred to as the overall % desaturation. The individual omega-6 delta-8 desaturation ("EDA % delta-8 desat.") was calculated as: ([DGLA]/[DGLA+EDA])*100. Similarly, the individual omega-3 delta-8 desaturation ("ERA % delta-8 desat.") was calculated as: ([ETA]/[ETA+ERA])*100. The ratio of delta-8 desaturation for omega-6 versus omega-3 substrates ("ratio [EDA/ERA] % desat.") was obtained by dividing the EDA % delta-8 desaturation by the ERA % delta-8 desaturation.

In summary of FIG. 14, E1594D8 worked in soybean to convert both EDA and ERA to DGLA and ETA, respectively. The line with the highest average DGLA content (i.e., 2108-6-6) had embryos with an average DGLA content of 13.6% and an average ETA content of 3.9%. The highest DGLA and ETA content for an individual embryo from this line was 17.7% and 4.7%, respectively. The highest average overall % desaturation was 66.4% (2108-5-2) with the highest overall % desaturation for an individual embryo being 71.3%. When broken down into % desaturation for the omega-6 and omega-3 substrates, the highest average % desaturation was 61.6% and 82.0% for EDA and ERA, respectively. The highest % desaturation for an individual embryo from this event was 62.5% and 82.2% for EDA and ERA, respectively. In this example, E1594D8 had a preference for ERA over EDA, with the average desaturation ratio ranging from 0.6-0.8. No GLA was found to accumulate in the embryos.

Example 19

Construction of Soybean Expression Vector pKR1122 for Co-Expression of the *Eutreptiella* sp. CCMP389 Delta-8 Desaturase (E389D8) with the Delta-9 Elongase from *Euglena gracilis* (EgD9e)

The present Example describes construction of a soybean vector for co-expression of E389D8 with EgD9e and expression of these genes in somatic embryos.

The NcoI/XbaI fragment of pFBAIn-389D8 (SEQ ID NO:95; Example 7), containing E389D8 and where a NotI site is already present just 5' to the XbaI site, was cloned into the NcoI/XbaI sites of pKR908 (SEQ ID NO:130) to produce pKR1117 (SEQ ID NO:134) and where E389D8 is now flanked by NotI sites at the 5' and 3' ends.

E389D8 was released from pKR1117 (SEQ ID NO:134) by digestion with NotI and cloned into the NotI site of pKR123r (SEQ ID NO:66; Example 8) to produce pKR1119 (SEQ ID NO:135).

Plasmid pKR1119 (SEQ ID NO:135) was digested with SbfI and the fragment containing E389D8 was cloned into the SbfI site of pKR912 (SEQ ID NO:81; Example 12), to give pKR1122 (SEQ ID NO:136). In this way, the *Eutreptiella* sp. CCMP389 delta-8 desaturase is co-expressed with the *Euglena gracilis* delta-9 elongase behind strong, seed-specific promoters. A schematic depiction of pKR1122 is shown in FIG. 15.

Plasmid pKR1122 was transformed into soybean embryogenic suspension cultures as described in Example 9 and embryos co-expressing E389D8 and EgD9e were analyzed as described in Example 10.

Embryo fatty acid profiles for each event (6 embryos each) containing pKR1122 were obtained and the lipid profiles of somatic soybean embryos expressing E389D8 and EgD9e for the top 5 events are shown in FIG. 16. Fatty acids are identified as 16:0 (palmitate), 18:0 (stearic acid), 18:1 (oleic acid), LA, GLA, ALA, EDA, DGLA, ERA and ETA; and, fatty acid compositions listed in FIG. 16 are expressed as a weight percent (wt. %) of total fatty acids. The activity of E389D8 is expressed as percent desaturation (% desat), calculated according to the following formula: ([product]/[substrate+product])*100.

More specifically, the combined percent desaturation for EDA and ERA is shown as "C20% delta-8 desat", determined as: ([DGLA+ETA]/[DGLA+ETA+EDA+ERA])*100. This is also referred to as the overall % desaturation. The individual omega-6 delta-8 desaturation ("EDA % delta-8 desat.") was calculated as: ([DGLA]/[DGLA+EDA])*100. Similarly, the individual omega-3 delta-8 desaturation ("ERA % delta-8 desat.") was calculated as: ([ETA]/[ETA+ERA])*100. The ratio of delta-8 desaturation for omega-6 versus omega-3 substrates ("ratio [EDA/ERA] % desat.") was obtained by dividing the EDA % delta-8 desaturation by the ERA % delta-8 desaturation.

In summary of FIG. 16, E389D8 worked in soybean to convert both EDA and ERA to DGLA and ETA, respectively. The line with the highest average DGLA content (i.e., 2107-4-14) had embryos with an average DGLA content of 16.1% and an average ETA content of 5.2%. The highest DGLA and ETA content for an individual embryo from this line was 16.1% and 6.0%, respectively. The highest average overall % desaturation was 68.5% (2107-4-14) with the highest overall % desaturation for an individual embryo being 68.6%. When broken down into % desaturation for the omega-6 and omega-3 substrates, the highest average % desaturation was 64.0% and 81.7% for EDA and ERA, respectively. The highest % desaturation for an individual embryo from this event was 68.6% and 83.4% for EDA and ERA, respectively. In this example, E389D8 had a preference for ERA over EDA, with the average desaturation ratio ranging from 0.6-0.8. No GLA was found to accumulate in the embryos.

Example 20

Construction of *Arabidopsis* Binary Expression Vector pKR1022R for Co-Expression of the *Tetruetreptia pomquetensis* CCMP1491 Delta-8 Desaturase (TpomD8) with the Delta-9 Elongase from *Euglena gracilis* (EgD9e)

The Gy1/Pavelo/legA2 cassette was released from plasmid pKR336 (described in PCT Publication Nos. WO 04/071467; the contents of which are hereby incorporated by reference) by digestion with PstI/BamHI and cloned into the PstI/BamHi site of pKR268 (described in PCT Publication Nos. WO 04/071467) to produce pKR393 (SEQ ID NO:137).

The Pavelo gene was released from pKR393 (SEQ ID NO:137) by digestion with NotI and the vector was re-ligated to from pKR407 (SEQ ID NO:138).

Vector pLF114-10 (SEQ ID NO:63; Example 5) was digested with NotI and the fragment containing TpomD8 was cloned into the NotI site of pKR407 (SEQ ID NO:138) to produce pKR1018 (SEQ ID NO:139).

The PstI fragment of pKR1018 (SEQ ID NO:139), containing the TpomD8 was cloned into the SbfI fragment of pKR911 (previously described in WO2007/061845 published on May 31, 2007 the contents of which are hereby incorporated by reference) to produce pKR1020R (SEQ ID NO:140).

The AscI fragment of pKR1020R (SEQ ID NO:140), containing EgD9e and TpomD8 was cloned into the AscI site of pKR92 (which was previously described in WO2007/061845 published on May 31, 2007 to give pKR1022R (SEQ ID NO:141). A schematic depiction of pKR1022R is shown in FIG. 17. In this way, EgD9e was expressed in *Arabidopsis* under control of the soybean beta-conglycinin promoter and TpomD8 was expressed under control of the soybean glycinin Gy1 promoter. The soybean beta-conglycinin promoter and Gy1 promoter function as a strong, seed-specific promoters in *Arabidopsis*.

Example 21

Transformation of *Arabidopsis*

Transformed *Arabidopsis* plants were created by whole plant *Agrobacterium* transformation. Binary vector pKR1022R (SEQ ID NO:141) was transformed into *Agrobacterium tumefaciens* NTL4 (Luo et al., *Molecular Plant-Microbe Interactions* 14(1):98-103 (2001)) by electroporation. Briefly, 1 µg plasmid DNA was mixed with 100 µL of electro-competent cells on ice. The cell suspension was transferred to a 100 µL electro oration curette (1 mm gap width) and electro orated using a BIORAD electro orator set to 1 kV, 400Ω and 25 µF. Cells were transferred to 1 mL LB medium and incubated for 2 h at 30° C. Cells were plated onto LB medium containing 50 µg/mL kanamycin. Plates were incubated at 30° C. for 60 h. Recombinant *agrobacterium* cultures (500 mL LB, 50 µg/mL kanamycin) were inoculated from single colonies of transformed *Agrobacterium* cells and grown at 30° C. for 60 h.

Cells were harvested by centrifugation (5000×g, 10 min) and resuspended in 1 L of 5% (W/V) sucrose containing 0.05% (V/V) Silwet L-77 (OSI Specialties, Inc). *Arabidopsis* plants were grown in soil at a density of 10 plants per 100 cm² pot in metromix 360 soil mixture for 4 weeks (22° C., 16 h light/8 h dark, 100 µE m$^{-2}$s$^{-1}$). At early bolting, *Arabidopsis* plants were dipped into the *Agrobacterium* suspension. Two days later, the same plants were dipped again with the same *Agrobacterium* strain in sucrose/Silwet. Plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% triton X-100, followed by 45 mL of 30% (V/V) household bleach in water, 0.01% triton X-100 and finally by repeated rinsing in sterile water. Aliquots of 20,000 seeds were transferred to square plates (20×20 cm) containing 150 mL of sterile plant growth medium comprised of 0.5×MS salts, 1.0% (W/V) sucrose, 0.05 MES/KOH (pH 5.8), 200 µg/mL timentin, and 50 µg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for fourteen days. Kanamycin-resistant seedlings were transferred to soil and grown to maturity as described above. T2 seed was obtained from these individual transformants.

Example 22

Functional Analysis of the *Tetruetreptia pomquetensis* CCMP1491 Delta-8 Desaturase (TpomD8) Co-Expressed with the Delta-9 Elongase from *Euglena gracilis* (EgD9e) in *Arabidopsis* Seed Transformed with *Arabidopsis* Expression Vector pKR1022R Wild-type *Arabidopsis thaliana* (Columbia ecotype) were transformed with pKR1022R (SEQ ID NO:141) as described in Example 21 and segregating T2 seed was obtained from a number of individual events for each. Bulk T2 seed lipid profiles for each event were obtained by transesterification with TMSH as described in Example 10 with the following modifications. For each event, a small scoopful of seeds (approximately 25-50 seed each scoopful) was crushed in 50 µL of TMSH in a 1.5 mL eppendorf tube. After shaking in TMSH for 15 min., 400 µL of heptane was added and the tubes were vortexed well, shaken for an additional 15 min and centrifuged at 13,000×g for 1 min. After shaking, the heptane layer was removed into glass GC vials and the fatty acid methyl esters were analyzed as described in Example 10.

Bulk T2 seed fatty acid profiles were obtained for 22 events where wild-type *Arabidopsis* was transformed with pKR1022R (SEQ ID NO:141). The lipid profiles of T2 bulk seed for the 22 wild-type-transformed events is shown in FIG. 18. Fatty acids are identified as 16:0 (palmitate), 18:0 (stearic acid), 18:1 (oleic acid), LA, ALA, 20:0 (arachidic acid), 20:1 (eicosenoic acid), EDA, DGLA, ERA and ETA; and, fatty acid compositions listed in FIG. 18 are expressed as a weight percent (wt. %) of total fatty acids.

Example 23

Functional Analysis of the *Tetruetreptia pomquetensis* CCMP1491 Delta-8 Desaturase (TpomD8) Co-Expressed with the *Saprolegnia diclina* Delta-17 Desaturase (SdD17), the *Euglena gracilis* Delta-9 Elongase (EgD9e), the *Pavlova lutheri* Delta-8 Desaturase (PavD8) and the *Mortierella alpina* Delta-5 Desaturase (MaD5) in Soybean Embryos and Seed Transformed with Soybean Expression Vectors pKR1005 and pKR973

The present Example describes the expression of an EPA biosynthetic pathway using a delta-9 elongase (EgD9e), a delta-5 desaturase (MaD5) and a delta-17 desaturase (SdD17) co-expressed with two delta-8 desaturases (TpomD8 & PavD8).

Soybean embryogenic suspension culture (cv. Jack) was transformed with the AscI fragments of pKR1005 (SEQ ID NO:90; FIG. 4) and pKR973 (SEQ ID NO:125; FIG. 11), as described in Example 9. Embryos were matured as described in Example 14 and a subset of soybean embryos generated from each event (ten embryos per event) were harvested, picked into glass GC vials, fatty acid methyl esters (FAMEs) were prepared by transesterification and analyzed by GC as described in Example 10. Retention times were compared to those for methyl esters of standards commercially available (Nu-Chek Prep, Inc.).

In this way, 373 events transformed with pKR1005 (SEQ ID NO:90; FIG. 4) and pKR973 (SEQ ID NO:125; FIG. 11) (experiment called Heal 17) were analyzed. From the 373 events analyzed, 319 were identified that produced delta-8 desaturation products (i.e. DGLA, ARA, ETA, EPA, DPA, DHA) in at least one embryo out of ten analyzed at a relative abundance greater than 1.0% of the total fatty acids. Of these, 140 were identified that produced delta-8 desaturation products at a relative abundance greater than 10.0% of the total fatty acids, 61 were identified that produced delta-8 desaturation products at a relative abundance greater than 20.0% of the total fatty acids and 20 were identified that produced delta-8 desaturation products at a relative abundance greater than 30.0% of the total fatty acids, in at least one embryo out of ten analyzed.

The average fatty acid profiles (average of 10 embryos per event) for the ten events having the highest amounts of delta-8 desaturation products are shown in FIG. 19. Fatty acids are identified as 16:0 (palmitate), 18:0 (stearic acid), 18:1 (oleic acid), LA, GLA, ALA, EDA, SCI, DGLA, ARA, ERA, JUP, ETA, EPA and DPA; and, fatty acid compositions listed in FIG. 19 are expressed as a weight percent (wt. %) of total fatty acids. For FIG. 19, fatty acids listed as "others" include: 18:2 (5,9), STA, 20:0, 20:1(11), 20:2 (7,11) or 20:2 (8,11), and DHA. Each of these fatty acids is present at a relative abundance of less than 1.6% of the total fatty acids. The total wt. % of fatty acids containing a delta-8 double bond is expressed as C20 delta-8 desat (DGLA+ARA+ETA+EPA+DPA) and the delta-8 desaturase activity is expressed as percent desaturation (C20% delta-8 desat), calculated according to the following formula: ([DGLA+ETA]/[DGLA+ETA+EDA+ERA])*100.

In summary of FIG. 19, TpomD8 and PavD8 functioned in soybean to convert both EDA and ERA to DGLA and ETA, respectively. Additionally, the activity of the delta-5 desaturase also functioned to convert the DGLA and ETA produced to ARA and EPA, respectively. In events such as AFS 4881-6-5 & 4881-4-5, delta-5 desaturase is somewhat limiting and DGLA and ETA are high while in others (e.g. AFS 4829-6-5 & AFS 4885-1-2), delta-5 desaturase activity is strong and the delta-8 desaturated products are further converted to ARA and EPA, respectively. Further, the presence of the delta-17 desaturase also functioned to convert DGLA and ARA to ETA and EPA, respectively. In events such as AFS 4880-8-8, the delta-17 desaturase is somewhat limiting while in others (e.g. AFS 4881-6-5 & AFS 4829-6-5), delta-17 desaturase activity is strong with DGLA and ARA being efficiently converted to ETA and EPA, respectively. The individual embryo with the highest total delta-8 desaturated products came from event AFS 4881-6-5, with as high as 43% of total fatty acids. The average concentration of delta-8 desaturated products from the top ten events was 27.7% of the total fatty acids.

The fatty acid profiles for ten individual T1 seeds from 2 plants from event AFS 4882-4-6 (plant #4882-4-6-1 & #4882-4-6-2) having some of the highest amounts of total delta-8 desaturation products are shown in FIG. 20. Fatty acids are identified as 16:0 (palmitate), 18:0 (stearic acid), 18:1 (oleic acid), 18:2 (5,9), LA, GLA, ALA, 20:1 (11), EDA, SCI, DGLA, ARA, ERA, JUP, ETA, EPA and DPA; and, fatty acid compositions listed in FIG. 20 are expressed as a weight percent (wt. %) of total fatty acids. For FIG. 20, fatty acids listed as "others" include: STA, 20:0, 20:2 (7,11) or 20:2 (8,11), and DHA. Each of these fatty acids is present at a relative abundance of less than 1.0% of the total fatty acids. The total wt. % of fatty acids containing a delta-8 double bond is expressed as C20 delta-8 desat (DGLA+ARA+ETA+EPA+DPA) and the delta-8 desaturase activity is expressed as percent desaturation (C20% delta-8 desat), calculated according to the following formula: ([DGLA+ETA]/[DGLA+ETA+EDA+ERA])*100.

In summary of FIG. 20, TpomD8 and PavD8 worked in soybean seed to convert both EDA and ERA to DGLA and ETA, respectively. Fatty acid compositions in T1 seed are similar to those in embryos. The T1 seed is segregating as expected with some wild-type present.

Example 24

Functional Analysis of the *Tetruetreptia pomquetensis* CCMP1491 Delta-8 Desaturase (TpomD8) Co-Expressed with the *Saprolegnia diclina* Delta-17 Desaturase (SdD17), the *Euglena gracilis* Delta-9 Elongase (EgD9e) and the *Mortierella alpina* Delta-5 Desaturase (MaD5) in Soybean Embryos and Seed Transformed with Soybean Expression Vectors pKR1005 and pKR1084

The present Example describes the expression of an EPA biosynthetic pathway using a delta-9 elongase (EgD9e), a delta-5 desaturase (MaD5) and a delta-17 desaturase (SdD17) co-expressed with one delta-8 desaturases (TpomD8).

Soybean embryogenic suspension culture (cv. Jack) was transformed with the AscI fragments of pKR1005 (SEQ ID NO:90; FIG. 4) and pKR1084 (SEQ ID NO:129; FIG. 12), as described in Example 9. Embryos were matured as described in Example 14 and a subset of soybean embryos generated from each event (ten embryos per event) were harvested, picked into glass GC vials, fatty acid methyl esters (FAMEs) were prepared by transesterification and analyzed by GC as described in Example 10. Retention times were compared to those for methyl esters of standards commercially available (Nu-Chek Prep, Inc.).

In this way, 182 events transformed with pKR1005 (SEQ ID NO:90; FIG. 4) and pKR1084 (SEQ ID NO: 129; FIG. 11) (experiment called Heal21) were analyzed. From the 182 events analyzed, 172 were identified that produced delta-8 desaturation products (i.e. DGLA, ARA, ETA, EPA, DPA, DHA) in at least one embryo out of ten analyzed at a relative abundance greater than 1.0% of the total fatty acids. Of these, 103 were identified that produced delta-8 desaturation products at a relative abundance greater than 10.0% of the total fatty acids, 59 were identified that produced delta-8 desaturation products at a relative abundance greater than 20.0% of the total fatty acids and 9 were identified that produced delta-8 desaturation products at a relative abundance greater than 30.0% of the total fatty acids, in at least one embryo out of ten analyzed.

The average fatty acid profiles (average of 10 embryos per event) for the ten events having the highest amounts of delta-8 desaturation products are shown in FIG. 21. Fatty acids are identified as 16:0 (palmitate), 18:0 (stearic acid), 18:1 (oleic acid), LA, GLA, ALA, EDA, SCI, DGLA, ARA, ERA, JUP, ETA, EPA and DPA; and, fatty acid compositions listed in FIG. 21 are expressed as a weight percent (wt. %) of total fatty acids. For FIG. 21, fatty acids listed as "others" include: 18:2 (5,9), STA, 20:0, 20:1(11), 20:2 (7,11) or 20:2 (8,11), and DHA. Each of these fatty acids is present at a relative abundance of less than 2.0% of the total fatty acids. The total wt. % of fatty acids containing a delta-8 double bond is expressed as C20 delta-8 desat (DGLA+ARA+ETA+EPA+DPA) and the delta-8 desaturase activity is expressed as percent desaturation (C20% delta-8 desat), calculated according to the following formula: ([DGLA+ETA]/[DGLA+ETA+EDA+ERA])*100.

As similar to that seen for the Heal17 embryos in Example 23, the Tpom delta-8 functioned alone to convert EDA and ERA to DGLA and ETA, respectively. Downstream products also varied depending on the expression of the delta-5 desaturase and delta-17 desaturase activities. But, while the range of delta-8 desaturated products for the Heal17 embryos, expressing 2 delta-8 desaturases, ranged from 25.5-33.7% of total fatty acids, those for the Heal21 embryos expressing only the single TpomD8 ranged from 18.4-22.7. The average delta-8 desaturated products for Heal17 and Heal21 embryos was 27.7% and 20.2%, respectively. With the decrease in overall delta-8 desaturase activity in Heal21 embryos compared to Heal17 embryos, EDA and ERA levels also increased from an average of 3.3% EDA and 1.2% ERA to 5.2% EDA and 2.0% ERA, respectively. An increase in the amounts of the fatty acid by-products, SCI and JUP, in Heal21 embryos compared to Heal17 embryos from 0% SCI and 0.6% JUP to 0.4% SCI and 2.3% JUP, respectively, was also observed.

The fatty acid profiles for individual T1 seeds from 2 plants from event AFS 5003-1-8 (plant #5003-1-8-1 & #5003-1-8-2) having some of the highest amounts of total delta-8 desaturation products are shown in FIG. 22. Fatty acids are identified as 16:0 (palmitate), 18:0 (stearic acid), 18:1 (oleic acid), 18:2 (5,9), LA, GLA, ALA, 20:1 (11), EDA, SCI, DGLA, ARA, ERA, JUP, ETA, EPA and DPA; and, fatty acid compositions listed in FIG. 22 are expressed as a weight percent (wt. %) of total fatty acids. For FIG. 22, fatty acids listed as "others" include: STA, 20:0, 20:2 (7,11) or 20:2 (8,11), and DHA. Each of these fatty acids is present at a relative abundance of less than 1.0% of the total fatty acids. The total wt. % of fatty acids containing a delta-8 double bond is expressed as C20 delta-8 desat (DGLA+ARA+ETA+EPA+DPA) and the delta-8 desaturase activity is expressed as percent desaturation (C20% delta-8 desat), calculated according to the following formula: ([DGLA+ETA]/[DGLA+ETA+EDA+ERA])*100.

In summary of FIG. 22, TpomD8 worked in soybean seed to convert both EDA and ERA to DGLA and ETA, respectively. Fatty acid compositions in T1 seed are similar to those in embryos. The T1 seed is segregating as expected with some wild-type present.

What is claimed is:

1. An isolated polynucleotide comprising:
   (a) a nucleotide sequence encoding a polypeptide having delta-8 desaturase activity, wherein the polypeptide has at least 80% amino acid identity, based on the Clustal V method of alignment, when compared to an amino acid sequence as set forth in SEQ ID NO:47, SEQ ID NO:49 or SEQ ID NO:57;
   (b) a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:92, SEQ ID NO:93 or SEQ ID NO:62;
   (c) a nucleotide sequence encoding a polypeptide having delta-8 desaturase activity, wherein the nucleotide sequence hybridizes under stringent conditions to a nucleotide sequence as set forth in SEQ ID NO:92, SEQ ID NO:93 or SEQ ID NO:62; or
   (d) a complement of the nucleotide sequence of (a), (b) or (c), wherein the complement and the nucleotide sequence consist of the same number of nucleotides and are 100% complementary.

2. The polynucleotide of claim 1 wherein the nucleotide sequence comprises SEQ ID NO:92, SEQ ID NO:93 or SEQ ID NO:62.

3. The polynucleotide of claim 1, wherein the amino acid sequence of the polypeptide comprises:
   (a) SEQ ID NO:47, SEQ ID NO:49 or SEQ ID NO:57; or
   (b) an amino acid sequence that differs from the amino acid sequences in (a) by at least one conservative amino acid substitution.

4. A recombinant DNA construct comprising the polynucleotide of claim 1 operably linked to at least one regulatory sequence.

5. A cell comprising in its genome the recombinant DNA construct of claim 4.

6. An oilseed plant comprising in its genome the recombinant construct of claim 4.

7. A transgenic seed comprising in its genome the recombinant construct of claim 4.

8. Progeny plants obtained from seed of claim 7.

9. A method for producing a transformed plant comprising transforming a plant cell with the polynucleotide of claim 1 and regenerating a plant from the transformed plant cell.

10. A transgenic seed obtained from the plant made by the method of claim 9.

11. Progeny plants obtained from seed of claim 10.

12. The oilseed plant of claim 6 further comprising
   at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

13. A transgenic seed obtained from the oilseed plant of claim 12.

14. Progeny plants obtained from the seed of claim 13.

15. The polynucleotide of claim 1 wherein the nucleotide sequence has at least 90% sequence identity, based on the BLASTN method of alignment, when compared to a nucleotide sequence as set forth in SEQ ID NO:92, SEQ ID NO:93 or SEQ ID NO:62.

16. The cell of claim 5 wherein wherein the nucleotide sequence has at least 90% sequence identity, based on the BLASTN method of alignment, when compared to a nucleotide sequence as set forth in SEQ ID NO:92, SEQ ID NO:93 or SEQ ID NO:62.

17. The oilseed plant of claim 6 wherein the nucleotide sequence has at least 90% sequence identity, based on the BLASTN method of alignment, when compared to a nucleotide sequence as set forth in SEQ ID NO:92, SEQ ID NO:93 or SEQ ID NO:62.

18. The transgenic seed of claim 7 wherein the nucleotide sequence has at least 90% sequence identity, based on the BLASTN method of alignment, when compared to a nucleotide sequence as set forth in SEQ ID NO:92, SEQ ID NO:93 or SEQ ID NO:62.

19. The method of claim 9 wherein the nucleotide sequence has at least 90% sequence identity, based on the BLASTN method of alignment, when compared to a nucleotide sequence as set forth in SEQ ID NO:92, SEQ ID NO:93 or SEQ ID NO:62.

20. The oilseed plant of claim 12 wherein the nucleotide sequence has at least 90% sequence identity, based on the BLASTN method of alignment, when compared to a nucleotide sequence as set forth in SEQ ID NO:92, SEQ ID NO:93 or SEQ ID NO:62.

* * * * *

SEQUENCE LISTING

<160> NUMBER OF SEQ ID NOS: 141

<210> SEQ ID NO 1
<211> LENGTH: 21
<212> TYPE: DNA
<213> ORGANISM: Artificial Sequence
<220> FEATURE:
<223> OTHER INFORMATION: primer D8F1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 1
gaygcnacng aygcnttcat g                        21

<210> SEQ ID NO 2
<211> LENGTH: 21
<212> TYPE: DNA
<213> ORGANISM: Artificial Sequence
<220> FEATURE:
<223> OTHER INFORMATION: primer D8F2
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)

```
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 2
gaygcnacng aygcngttat g                                              21

<210> SEQ ID NO 3
<211> LENGTH: 21
<212> TYPE: DNA
<213> ORGANISM: Artificial Sequence
<220> FEATURE:
<223> OTHER INFORMATION: primer D8F3
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 3
gaygcnacng aygcngtgat g                                              21

<210> SEQ ID NO 4
<211> LENGTH: 21
<212> TYPE: DNA
<213> ORGANISM: Artificial Sequence
<220> FEATURE:
<223> OTHER INFORMATION: primer D8F4
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 4
gaygcnacng aygcntttat g                                              21

<210> SEQ ID NO 5
<211> LENGTH: 21
<212> TYPE: DNA
<213> ORGANISM: Artificial Sequence
<220> FEATURE:
<223> OTHER INFORMATION: primer D8F5
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 5
```
gaygcnacng aygcngtaat g                                              21

<210> SEQ ID NO 6
<211> LENGTH: 21
<212> TYPE: DNA
<213> ORGANISM: Artificial Sequence
<220> FEATURE:
<223> OTHER INFORMATION: primer D8F6
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 6
gaygcnacng aygcngtgat g                                              21

<210> SEQ ID NO 7
<211> LENGTH: 19
<212> TYPE: DNA
<213> ORGANISM: Artificial Sequence
<220> FEATURE:
<223> OTHER INFORMATION: primer D8F7
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 7
tnggntggtt rggngayga                                                 19

<210> SEQ ID NO 8
<211> LENGTH: 19
<212> TYPE: DNA
<213> ORGANISM: Artificial Sequence
<220> FEATURE:
<223> OTHER INFORMATION: primer D8F8
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 8
tnggntggct rggngayga                                                 19

<210> SEQ ID NO 9
<211> LENGTH: 19
<212> TYPE: DNA

```
<213> ORGANISM: Artificial Sequence
<220> FEATURE:
<223> OTHER INFORMATION: primer D8F9
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 9
tnggntggct yggngayga                                                  19

<210> SEQ ID NO 10
<211> LENGTH: 20
<212> TYPE: DNA
<213> ORGANISM: Artificial Sequence
<220> FEATURE:
<223> OTHER INFORMATION: primer D8R1

<400> SEQUENCE: 10
tgrtgytcda tytgrtartt                                                 20

<210> SEQ ID NO 11
<211> LENGTH: 20
<212> TYPE: DNA
<213> ORGANISM: Artificial Sequence
<220> FEATURE:
<223> OTHER INFORMATION: primer D8R2

<400> SEQUENCE: 11
tgrtgytcda tytgcatrtt                                                 20

<210> SEQ ID NO 12
<211> LENGTH: 7
<212> TYPE: PRT
<213> ORGANISM: Artificial Sequence
<220> FEATURE:
<223> OTHER INFORMATION: primers D8F1 and D8F4

<400> SEQUENCE: 12

Asp Ala Thr Asp Ala Phe Met
1               5

<210> SEQ ID NO 13
<211> LENGTH: 7
<212> TYPE: PRT
<213> ORGANISM: Artificial Sequence
<220> FEATURE:
<223> OTHER INFORMATION: primers D8F2, D8F3, D8F5 and D8F6

<400> SEQUENCE: 13

Asp Ala Thr Asp Ala Val Met
1               5

<210> SEQ ID NO 14
<211> LENGTH: 6
<212> TYPE: PRT
<213> ORGANISM: Artificial Sequence
<220> FEATURE:
<223> OTHER INFORMATION: primers D8F7, D8F8 and D8F9
<220> FEATURE:
<221> NAME/KEY: MISC_FEATURE
```

<222> LOCATION: (6)..(6)
<223> OTHER INFORMATION: X = D or E

<400> SEQUENCE: 14

Gly Trp Leu Gly Asp Xaa
1               5

<210> SEQ ID NO 15
<211> LENGTH: 6
<212> TYPE: PRT
<213> ORGANISM: Artificial Sequence
<220> FEATURE:
<223> OTHER INFORMATION: primers D8R1 and D8R2

<400> SEQUENCE: 15

Asn Tyr Gln Ile Glu His
1               5

<210> SEQ ID NO 16
<211> LENGTH: 977
<212> TYPE: DNA
<213> ORGANISM: Tetruetreptia pomquetensis CCMP1491

<400> SEQUENCE: 16
gatgctacgg atgcgtttat ggtgatgcac tctcaagaag ccgtcgccaa gttgaagaga      60
atgcctgtta tggagccttc ctctcctgac acacctgttg cacccaagcc taagcgtgat     120
gagccccagg aggatttccg caagttgcgg aggaattca ctccaaggg tatgttcgag       180
acgagtttcc tttggtattt ttacaagact tcaactaccg tcggtttgat ggtcctttcc     240
atcttgatga ccgtgtacac gaattggtat tcaccgctg ctttggttct tggcgtgtgc      300
taccaacagc taggctggtt gtcccacgac tattgccatc accaggtttt cacgaaccgc     360
aagattaacg acgctttcgg tctctttttc ggtaacgtga tgcagggata ctcacagact     420
tggtggaagg ataggcacaa tggtcaccat gccgccacca atgtggtcgg ccatgaccca     480
gatactgata acctccccat cctggcttgg tctcccgaag atgtcaagag ggctactcct     540
tcgactcgga atctcatcaa gtaccagcag tactacttca ttcccaccat tgcatccctt     600
aggttcatct ggcgcctcca atccatcggc ggcgtcatgt cctacaagag cgaggagagg     660
aacctgtact acaagcgccg gtacactaag gaggcgattg gtctggccct cccttgggtg     720
ctcaaggcca cttctatg cagtgccatg cctagctttg ccaccggttt gggatgcttc       780
ttgatctccg agctgctcgg aggatttggc attgccatcg ttgtgtttct gaatcactat     840
cctttggaca aggttgagga gactgtctgg gatgagcacg ggttcagcgc cagccagatc     900
cacgagacgt tgaacattaa gcccggcctt ctcaccgatt gggtctttgg tggtctcaac     960
taccagatcg aacacca                                                    977

<210> SEQ ID NO 17
<211> LENGTH: 968
<212> TYPE: DNA
<213> ORGANISM: Eutreptiella sp. CCMP389

<400> SEQUENCE: 17
gacgctacsg aygcwtttat ggtcatgcac tcccacgatg cgttgaacaa gctgaagcgc      60
atgcctgtga tggagcccac ttcgccacga agccccaaga ctcccaacga cgaggttgct     120
gaggacttcc gcaagcttcg aaaggacatg attgcaaaag gcatgttcaa cgcatcccct     180
ctcttctacg tgtacaaaag tgcgaccaca gtagccctgg gcgccctggc tattctgatg     240

-continued

```
gtgatgcacc tgcagtggta ctacatccca gccatttgt tgggactttg ctaccagcag      300
ctggggtggt tggcacacga ttactgccac catcaggtgt tctctaaccg ggcgtacaac      360
aattttgctg gacttgtatt cggcaatgtg atgcaaggat actccgrgac ttggtggaag      420
gacaggcaca acggccatca cgccgccacg aacgtgcaag ggcacgatcc cgacatcgac      480
racctcccgg tgttggcctg gtccccggag gacgtcaaaa acgccggtcc cacgacgcgg      540
aagctcatca agtggcaaca atactatttc ctccccacca tcgcaaccct ccgattcatc      600
tggtgcttcc agagcattct ggcggttatg catacaaga cagatgcaag gaatatatat      660
taccaacgcc agtacgcaaa ggaggccgtg gggctggctc tgcattggat tctgaaaggg      720
gtrttcatgt tctgttacat gcccggcata ctgacgggct tggccttctt cctcatcycg      780
gagtgcctgg gcgggtttgg gattgccatt gtcgtgttct tgaatcacta cccattggag      840
aaggtggagg agtccgtgtg ggacagccac gggttttgcg cggggcagat ccacacgacg      900
atgaacatcc aacgcggggt catcgttgac tggttctttg gaggcctgaa ctaccaaatc      960
gaacacca                                                              968
```

<210> SEQ ID NO 18
<211> LENGTH: 968
<212> TYPE: DNA
<213> ORGANISM: Eutreptiella cf_gymnastica CCMP1594

<400> SEQUENCE: 18

```
gacgcyacsg acgcrttat ggtcatgcat tcacagcagg cgctcaacaa gttgaagcgg       60
atgcctgtta tggagccctc ttcaccactt actcccaaga gcccaagtga cgacatttcc     120
kaggatttcc gcaagctccg caacagtatg gttgagaagg gtatgttcaa cgcgtcccct     180
ctgttttatg tgtacaaatc actgaccact gtcgcccttg gcgccgtggg tgttctcatg     240
gttatgtacc tgcagtggta ctacgtttca gccatgtttt tgggactttg ctaccaacag     300
ctgggttggg tggcgcatga ctacgcgcat caccaggttt tcacgaaccg tgattatggc     360
aatcttggtg ggcttttctt tggcracgtt ctccaaggat attctttgac ttggtggaag     420
gacaggcaca acggccatca cgccgccaca aacgtgcaag gacatgaccc cgacattgat     480
aatctccccg ttttggcttg gtcgccagag gacgtcaaga atgccggacc tggaacccgc     540
aatatcatca agtaccagca gtattatttc ctccctacca tcgccatcct tcggttcatc     600
tggtgtttcc aaagcattct gggggtgatg tcatacaaga cagactccra gaatctctat     660
tacaaacggc agtaccggag agaggcagcc ggtctggcgc tgcactggat tctgaagagc     720
gttttcttgt tctgttacat gccaagtttc ctcactggcc tggcgttttt ccttatctcg     780
gagtgtctgg gcggctttgg gatcgcgatt gtggtgtttt tgaaccacta tccgctggat     840
aaggttgagg aatccgtttg ggatggtcac ggtttctgtg ctgggcagat cctcacaacc     900
atgaacatcc aacgcggact catcactgac tggttctttg gaggtttgaa ytaccaaatc     960
gaacacca                                                              968
```

<210> SEQ ID NO 19
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 19

```
aagcagtggt atcaacgcag agtggccatt acggccggg                             39
```

```
<210> SEQ ID NO 20
<211> LENGTH: 21
<212> TYPE: DNA
<213> ORGANISM: Artificial Sequence
<220> FEATURE:
<223> OTHER INFORMATION: primer 389D8-3-1

<400> SEQUENCE: 20
caacgccagt acgcaaagga g                                                21

<210> SEQ ID NO 21
<211> LENGTH: 22
<212> TYPE: DNA
<213> ORGANISM: Artificial Sequence
<220> FEATURE:
<223> OTHER INFORMATION: primer 389D8-3-2

<400> SEQUENCE: 21
ctctgcattg gattctgaaa gg                                               22

<210> SEQ ID NO 22
<211> LENGTH: 22
<212> TYPE: DNA
<213> ORGANISM: Artificial Sequence
<220> FEATURE:
<223> OTHER INFORMATION: primer 389D8-5-1

<400> SEQUENCE: 22
aatcatgtcc tttcgaagct tg                                               22

<210> SEQ ID NO 23
<211> LENGTH: 22
<212> TYPE: DNA
<213> ORGANISM: Artificial Sequence
<220> FEATURE:
<223> OTHER INFORMATION: primer 389D8-5-2

<400> SEQUENCE: 23
gtcctcagca acctcgtcgt tg                                               22

<210> SEQ ID NO 24
<211> LENGTH: 22
<212> TYPE: DNA
<213> ORGANISM: Artificial Sequence
<220> FEATURE:
<223> OTHER INFORMATION: primer 389D8-5-3

<400> SEQUENCE: 24
cttggggctt cgtggcgaag tg                                               22

<210> SEQ ID NO 25
<211> LENGTH: 22
<212> TYPE: DNA
<213> ORGANISM: Artificial Sequence
<220> FEATURE:
<223> OTHER INFORMATION: primer ED8-5-1

<400> SEQUENCE: 25
ctcgaacata cccttggaga tg                                               22

<210> SEQ ID NO 26
<211> LENGTH: 22
<212> TYPE: DNA
<213> ORGANISM: Artificial Sequence
<220> FEATURE:
```

```
<223> OTHER INFORMATION: primer ED8-5-2

<400> SEQUENCE: 26
cccgcaactt gcggaaatcc tc                                        22

<210> SEQ ID NO 27
<211> LENGTH: 22
<212> TYPE: DNA
<213> ORGANISM: Artificial Sequence
<220> FEATURE:
<223> OTHER INFORMATION: primer ED8-5-3

<400> SEQUENCE: 27
gggctcatca cgcttaggct tg                                        22

<210> SEQ ID NO 28
<211> LENGTH: 22
<212> TYPE: DNA
<213> ORGANISM: Artificial Sequence
<220> FEATURE:
<223> OTHER INFORMATION: primer ED8-3-1

<400> SEQUENCE: 28
cactttctat tgcagtgcca tg                                        22

<210> SEQ ID NO 29
<211> LENGTH: 22
<212> TYPE: DNA
<213> ORGANISM: Artificial Sequence
<220> FEATURE:
<223> OTHER INFORMATION: primer ED8-3-2

<400> SEQUENCE: 29
ctttgccacc ggtttgggat gc                                        22

<210> SEQ ID NO 30
<211> LENGTH: 59
<212> TYPE: DNA
<213> ORGANISM: Artificial Sequence
<220> FEATURE:
<223> OTHER INFORMATION: CDSIII/3' PCR primer
<220> FEATURE:
<221> NAME/KEY: misc_feature
<222> LOCATION: (59)..(59)
<223> OTHER INFORMATION: n is a, c, g, or t

<400> SEQUENCE: 30
attctagagg ccgaggcggc cgacatgttt ttttttttt ttttttttt tttttttvn   59

<210> SEQ ID NO 31
<211> LENGTH: 37
<212> TYPE: DNA
<213> ORGANISM: Artificial Sequence
<220> FEATURE:
<223> OTHER INFORMATION: Adaptor Primer from Invitrogen 3'-RACE kit

<400> SEQUENCE: 31
ggccacgcgt cgactagtac tttttttttt ttttttt                        37

<210> SEQ ID NO 32
<211> LENGTH: 22
<212> TYPE: DNA
<213> ORGANISM: Artificial Sequence
<220> FEATURE:
<223> OTHER INFORMATION: primer 1594D8-3-1

<400> SEQUENCE: 32
```

```
gagcgttttc ttgttctgtt ac                                          22
```

<210> SEQ ID NO 33
<211> LENGTH: 22
<212> TYPE: DNA
<213> ORGANISM: Artificial Sequence
<220> FEATURE:
<223> OTHER INFORMATION: primer 1594D8-3-2

<400> SEQUENCE: 33

```
cgttttcct tatctcggag tg                                           22
```

<210> SEQ ID NO 34
<211> LENGTH: 22
<212> TYPE: DNA
<213> ORGANISM: Artificial Sequence
<220> FEATURE:
<223> OTHER INFORMATION: primer 1594D8-5-1

<400> SEQUENCE: 34

```
gatttgtaca cataaaacag ag                                          22
```

<210> SEQ ID NO 35
<211> LENGTH: 22
<212> TYPE: DNA
<213> ORGANISM: Artificial Sequence
<220> FEATURE:
<223> OTHER INFORMATION: primer 1594D8-5-2

<400> SEQUENCE: 35

```
acccttctca accatactgt tg                                          22
```

<210> SEQ ID NO 36
<211> LENGTH: 22
<212> TYPE: DNA
<213> ORGANISM: Artificial Sequence
<220> FEATURE:
<223> OTHER INFORMATION: primer 1594D8-5-3

<400> SEQUENCE: 36

```
cttgggagta agtggtgaag ag                                          22
```

<210> SEQ ID NO 37
<211> LENGTH: 48
<212> TYPE: DNA
<213> ORGANISM: Artificial Sequence
<220> FEATURE:
<223> OTHER INFORMATION: GenomeWalker adaptor-1

<400> SEQUENCE: 37

```
gtaatacgac tcactatagg gcacgcgtgg tcgacggccc gggctggt              48
```

<210> SEQ ID NO 38
<211> LENGTH: 22
<212> TYPE: DNA
<213> ORGANISM: Artificial Sequence
<220> FEATURE:
<223> OTHER INFORMATION: primer AP1

<400> SEQUENCE: 38

```
gtaatacgac tcactatagg gc                                          22
```

<210> SEQ ID NO 39
<211> LENGTH: 19
<212> TYPE: DNA

<213> ORGANISM: Artificial Sequence
<220> FEATURE:
<223> OTHER INFORMATION: primer AP2

<400> SEQUENCE: 39
actatagggc acgcgtggt                                                    19

<210> SEQ ID NO 40
<211> LENGTH: 3931
<212> TYPE: DNA
<213> ORGANISM: Artificial Sequence
<220> FEATURE:
<223> OTHER INFORMATION: plasmid pCR2.1-TOPO

<400> SEQUENCE: 40

| | | | | | |
|---|---|---|---|---|---|
| aagggcgaat | tctgcagata | tccatcacac | tggcggccgc | tcgagcatgc | atctagaggg | 60 |
| cccaattcgc | cctatagtga | gtcgtattac | aattcactgg | ccgtcgtttt | acaacgtcgt | 120 |
| gactgggaaa | accctggcgt | tacccaactt | aatcgccttg | cagcacatcc | ccctttcgcc | 180 |
| agctggcgta | atagcgaaga | ggcccgcacc | gatcgccctt | cccaacagtt | gcgcagcctg | 240 |
| aatggcgaat | ggacgcgccc | tgtagcggcg | cattaagcgc | ggcgggtgtg | gtggttacgc | 300 |
| gcagcgtgac | cgctacactt | gccagcgccc | tagcgcccgc | tcctttcgct | ttcttccctt | 360 |
| cctttctcgc | cacgttcgcc | ggctttcccc | gtcaagctct | aaatcggggg | ctccctttag | 420 |
| ggttccgatt | tagtgcttta | cggcacctcg | accccaaaaa | acttgattag | ggtgatggtt | 480 |
| cacgtagtgg | gccatcgccc | tgatagacgg | ttttttcgccc | tttgacgttg | gagtccacgt | 540 |
| tctttaatag | tggactcttg | ttccaaactg | gaacaacact | caaccctatc | tcggtctatt | 600 |
| cttttgattt | ataagggatt | ttgccgattt | cggcctattg | gttaaaaaat | gagctgattt | 660 |
| aacaaaaatt | taacgcgaat | tttaacaaaa | tcagggcgc | aagggctgct | aaaggaagcg | 720 |
| gaacacgtag | aaagccagtc | cgcagaaacg | gtgctgaccc | cggatgaatg | tcagctactg | 780 |
| ggctatctgg | acaagggaaa | acgcaagcgc | aaagagaaag | caggtagctt | gcagtgggct | 840 |
| tacatggcga | tagctagact | gggcggtttt | atgacagca | agcgaaccgg | aattgccagc | 900 |
| tggggcgccc | tctggtaagg | ttgggaagcc | ctgcaaagta | aactggatgg | ctttcttgcc | 960 |
| gccaaggatc | tgatggcgca | ggggatcaag | atctgatcaa | gagacaggat | gaggatcgtt | 1020 |
| tcgcatgatt | gaacaagatg | gattgcacgc | aggttctccg | gccgcttggg | tggagaggct | 1080 |
| attcggctat | gactgggcac | aacagacaat | cggctgctct | gatgccgccg | tgttccggct | 1140 |
| gtcagcgcag | gggcgcccgg | ttcttttttgt | caagaccgac | ctgtccggtg | ccctgaatga | 1200 |
| actgcaggac | gaggcagcgc | ggctatcgtg | gctggccacg | acgggcgttc | cttgcgcagc | 1260 |
| tgtgctcgac | gttgtcactg | aagcgggaag | ggactggctg | ctattgggcg | aagtgccggg | 1320 |
| gcaggatctc | ctgtcatccc | accttgctcc | tgccgagaaa | gtatccatca | tggctgatgc | 1380 |
| aatgcggcgg | ctgcatacgc | ttgatccggc | tacctgccca | ttcgaccacc | aagcgaaaca | 1440 |
| tcgcatcgag | cgagcacgta | ctcggatgga | agccggtctt | gtcgatcagg | atgatctgga | 1500 |
| cgaagagcat | caggggctcg | cgccagccga | actgttcgcc | aggctcaagg | cgcgcatgcc | 1560 |
| cgacggcgag | gatctcgtcg | tgacccatgg | cgatgcctgc | ttgccgaata | tcatggtgga | 1620 |
| aaatggccgc | ttttctggat | tcatcgactg | tggccggctg | ggtgtggcgg | accgctatca | 1680 |
| ggacatagcg | ttggctaccc | gtgatattgc | tgaagagctt | ggcggcgaat | gggctgaccg | 1740 |
| cttcctcgtg | ctttacggta | tcgccgctcc | cgattcgcag | cgcatcgcct | tctatcgcct | 1800 |
| tcttgacgag | ttcttctgaa | ttgaaaaagg | aagagtatga | gtattcaaca | tttccgtgtc | 1860 |

```
gcccttattc cctttttgc ggcattttgc cttcctgttt ttgctcaccc agaaacgctg    1920
gtgaaagtaa aagatgctga agatcagttg ggtgcacgag tgggttacat cgaactggat    1980
ctcaacagcg gtaagatcct tgagagtttt cgccccgaag aacgttttcc aatgatgagc    2040
acttttaaag ttctgctatg tggcgcggta ttatcccgta ttgacgccgg gcaagagcaa    2100
ctcggtcgcc gcatacacta ttctcagaat gacttggttg agtactcacc agtcacagaa    2160
aagcatctta cggatggcat gacagtaaga gaattatgca gtgctgccat aaccatgagt    2220
gataacactg cggccaactt acttctgaca acgatcggag gaccgaagga gctaaccgct    2280
tttttgcaca acatggggga tcatgtaact cgccttgatc gttgggaacc ggagctgaat    2340
gaagccatac caaacgacga gcgtgacacc acgatgcctg tagcaatggc aacaacgttg    2400
cgcaaactat taactggcga actacttact ctagcttccc ggcaacaatt aatagactgg    2460
atggaggcgg ataaagttgc aggaccactt ctgcgctcgg cccttccggc tggctggttt    2520
attgctgata aatctggagc cggtgagcgt gggtctcgcg gtatcattgc agcactgggg    2580
ccagatggta agccctcccg tatcgtagtt atctacacga cggggagtca ggcaactatg    2640
gatgaacgaa atagacagat cgctgagata ggtgcctcac tgattaagca ttggtaactg    2700
tcagaccaag tttactcata tatactttag attgatttaa aacttcatt ttaatttaaa    2760 aggatctagg tgaagatcct ttttgataat ctcatgacca aaatccctta acgtgagttt    2820
tcgttccact gagcgtcaga ccccgtagaa aagatcaaag gatcttcttg agatcctttt    2880
tttctgcgcg taatctgctg cttgcaaaca aaaaaaccac cgctaccagc ggtggtttgt    2940
ttgccggatc aagagctacc aactcttttt ccgaaggtaa ctggcttcag cagagcgcag    3000
ataccaaata ctgttcttct agtgtagccg tagttaggcc accacttcaa gaactctgta    3060
gcaccgccta catacctcgc tctgctaatc ctgttaccag tggctgctgc cagtggcgat    3120
aagtcgtgtc ttaccgggtt ggactcaaga cgatagttac cggataaggc gcagcggtcg    3180
ggctgaacgg ggggttcgtg cacacagccc agcttggagc gaacgaccta caccgaactg    3240
agatacctac agcgtgagct atgagaaagc gccacgcttc ccgaagggag aaaggcggac    3300
aggtatccgg taagcggcag ggtcggaaca ggagagcgca cgagggagct ccaggggga    3360 aacgcctggt atctttatag tcctgtcggg tttcgccacc tctgacttga gcgtcgattt    3420
ttgtgatgct cgtcaggggg gcggagccta tggaaaaacg ccagcaacgc ggcctttta    3480 cggttcctgg ccttttgctg gccttttgct cacatgttct ttcctgcgtt atccctgat    3540 tctgtggata accgtattac cgcctttgag tgagctgata ccgctcgccg cagccgaacg    3600
accgagcgca gcgagtcagt gagcgaggaa gcggaagagc gcccaatacg caaaccgcct    3660
ctccccgcgc gttggccgat tcattaatgc agctggcacg acaggtttcc cgactggaaa    3720
gcgggcagtg agcgcaacgc aattaatgtg agttagctca ctcattaggc accccaggct    3780
ttacacttta tgcttccggc tcgtatgttg tgtggaattg tgagcggata acaatttcac    3840
acaggaaaca gctatgacca tgattacgcc aagcttggta ccgagctcgg atccactagt    3900
aacggccgcc agtgtgctgg aattcgccct t                                   3931
```

<210> SEQ ID NO 41
<211> LENGTH: 694
<212> TYPE: DNA
<213> ORGANISM: Eutreptiella cf_gymnastica CCMP1594

<400> SEQUENCE: 41

```
cttgttggta ttagtaatgg gacacagcag tatattttcc cattgagaaa aacgctgaaa      60
tactggttgg tgaaaacttg gtgagaacaa cggtccattt gaacacagct tcccaccgcc     120 tttcccccctt atctcatgtt gctggaccac actgcaagct gcatgagcga tagctgaacg    180
agacttcacg ctgtcatccc ttcacttcat atgcgttgtg caagggaaag ggtgccatca     240
ggtgtgactg tgcctccgtg ataaagtcga gggcacactc cgaattgggc agttctcgct     300
accgtgacca gatgcgtgtc aaaactagat cccgaagaaa cgcccgcgc ggagagcctt      360 gacacagttg tgttgaagaa aagtttgtgt ggcttcggag cgaaaaagac accgcaccat     420
agctgtggca gtgcaagacc ccagatccgc tggtccctgc acttgttgaa gcctcaaaat    480
gtcacctaaa cgggacgcat tgcctctgac aattgatggc accacgtacg acgtttccgc     540
ttgggtaaac catcaccctg aggggctca aatcattgaa aactaccgga accgagatgc       600
taccgacgtg ttcatggtca tgcattcaca gcaggcgctc aacaagttga agcggatgcc     660
tgttatggag ccctcttcac cacttactcc caag                                 694

<210> SEQ ID NO 42
<211> LENGTH: 648
<212> TYPE: DNA
<213> ORGANISM: Eutreptiella sp. CCMP389

<400> SEQUENCE: 42
cgtggcctga aattgcatct atgcaaatgg caactgccat gttgtgggac ttggcttgcc      60
actacccact aaaaaggcca acgctgccat aatcaaatat aaagaccact gcctgggcat    120
gaccactagt ggcgtatgca gcgccacatg ctccaacaca gcatgtcaag gcgctttgct    180
gagcgtctac ttcatgatgc atttgcctcc atttaaaagt cattaaaaga catactcatg    240
atgtaaccca acgcacgttg cactgcattt tgcgacctcc gcgtctacct ccattcaaaa    300
tgtgtgaatc atgattgctc caatttggga ggagggggta ataaactcag cccatccact    360
gcccttccct tgggacgtga cacgagtacc aacgcacttc tgcccgctgt ctttgctccg    420
cgtagtcttg gaatgtcacc caagcgagag gccttgccca tcacgattga tggcacaacc    480
tatgatgtgt ccgcatgggt gaaccatcac cccgggggcg cagacatcat ggagaattat    540
cggaaccgag atgccacgga tgtgttcatg gtcatgcact cccacgatgc gttgaacaag    600
ctgaagcgca tgcctgtgat ggagcccact tcgccacgaa gccccaag                648

<210> SEQ ID NO 43
<211> LENGTH: 717
<212> TYPE: DNA
<213> ORGANISM: Eutreptiella sp. CCMP389

<400> SEQUENCE: 43
ctctgcattg gattctgaaa ggggtattca tgttctgtta catgcccggc atactgacgg      60
gcttggcctt cttcctcatc tcggagtgcc tgggcgggtt tgggattgcc attgtcgtgt    120
tcttgaatca ctaccattg gagaaggtgg aggagtccgt gtgggacagc cacgggtttt      180
gcgcggggca gatccacacg acgatgaaca tccaacgcgg ggtcatcgtt gactggttct    240
ttggaggcct gaattatcag atcgaacacc atctgtggcc gacgctgccc cggcatcact    300
tgaaagctgc ttcttttgag gtggagaaaa tttgccagaa gcacaaattg ccatacagag    360 cacccccat gtccgatggt gttgctcaat tgcttggctt cttggggaag attgctaagc      420
tggcagctgt cccagtgtaa ccctaaacgt accacgcgcgt tgtcaagaca gtcagctggg    480
tttcggagtg gtagcagtgc gtgcagctgt gcagctgagg acgattgtgg ggtttgatca    540
```

| tgtctgtcag agttctttgt gcacgtagaa tgatgcacgg taccatcagg tcagcttggt | 600 |
| tggctctgca tgaggctgac ggtcttaatt tggggtgtct caaagatact caaggacgaa | 660 |
| gagtatgcac acgtgtttgg ccatttcmca gtgmmaaaaa aaaaaaaaaa aaaaaaa | 717 |

<210> SEQ ID NO 44
<211> LENGTH: 1164
<212> TYPE: DNA
<213> ORGANISM: Eutreptiella cf_gymnastica CCMP1594
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (707)..(708)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t

<400> SEQUENCE: 44

| gcccttcgtt tttccttatc tcggagtgtc tgggcggctt tgggatcgcg attgtggtgt | 60 |
| ttttgaacca ctatccgctg gataaggttg aggaatccgt ttgggatggt cacggtttct | 120 |
| gtgctgggca gatcctcaca accatgaaca tccaacgcgg actcatcact gactggttct | 180 |
| ttggaggttt gaattaccag attgagcatc atctgtggcc caaccttcca agacaccatt | 240 |
| tgaaagcagt ttcctttgag gttgagaaat tgtgccagaa gcacaacctg ccctacagag | 300 |
| ctccgccgat gcatactggt gttgcacaat tgcttggata tttggggaag attgctcagt | 360 |
| tggctgctgt cccagtataa ccctggatca ccttcatcga tcctattctg agtgttcagg | 420 |
| gtgcgactgc atccccgtt tttcttgcac agccgcgcat ttgcagggtg gtttctatta | 480 |
| caatttttt tctgcccaaa acaacacctg atgtggcgag cgaggttcac tcttgctgca | 540 |
| caccactcat tttgttctgg gttgagttat atgtgaatta atatgtaagc agtttncttg | 600 |
| cacagcccgg ggcattttt ntattcccaa gacagcgtga taacatttgg cgggcgaggt | 660 |
| tcactcttgc tgcacaccat catgttttgg gtgcccagcc ccccccnncc ccnctctatt | 720 |
| atgactgaat cgttgtagaa gcatggagtc caggtgtgg tttgcactgt aagcatgtcc | 780 |
| gctttggtga actggttatg gtgactcagg tctcgtgcct aggtttacta aatgcgtgac | 840 |
| atttgcagtc atcacatttc ttttttgatc acatgctgta acgttcacac tactgcctaa | 900 |
| ggttaggttg tgtgtttggg ccatttagct gtcaaaaccc tccctctttc agaagtgttt | 960 |
| gtcgaccaca aatattgcac caagttgtta catcattgtt tagttagttg cgttcagtgt | 1020 |
| ccaatttttc gacggccaaa ttttcttgct gggcttattc gttgggtggt gatgtggcat | 1080 |
| tgaaagatga tgcagtggtg cagatgagaa cagaaatggt ctgtgttgcg ttgatttgtt | 1140 |
| caaaaaaaaa aaaaaaaaaa aaaa | 1164 |

<210> SEQ ID NO 45
<211> LENGTH: 435
<212> TYPE: DNA
<213> ORGANISM: Eutreptiella cf_gymnastica CCMP1594

<400> SEQUENCE: 45

```
gcccttcgtt tttccttatc tcggagtgtc tgggcggctt tgggatcgcg attgtggtgt    60
ttttgaacca ctatccgctg gataaggttg aggaatccgt ttgggatggt cacggttttyt  120 gtgctgggca gatcctcaca accatgaaca tccaacgcgg actcatcact gactggttct   180
ttggaggttt gaattaccag attgagcatc atytgtggcc caaccttcca agacaccatt   240
tgaaagcagt ttcctttgag gttgagaaat tgtgccagaa gcacaacctg ccctgcagag   300
ctccgccgat gcatactggt gttgcacaat tgcttggata tttggggaag attgctcagt   360
tggctgctgt cccagtataa ccctggatca ccttcatcga tccttttttg aaaaaaaaa    420 aaaaaaaaaa aaaaa                                                    435
```

```
<210> SEQ ID NO 46
<211> LENGTH: 1963
<212> TYPE: DNA
<213> ORGANISM: Eutreptiella sp. CCMP389
<220> FEATURE:
<221> NAME/KEY: misc_feature
<222> LOCATION: (1934)..(1934)
<223> OTHER INFORMATION: n is a, c, g, or t
<220> FEATURE:
<221> NAME/KEY: misc_feature
<222> LOCATION: (1940)..(1941)
<223> OTHER INFORMATION: n is a, c, g, or t

<400> SEQUENCE: 46
```

```
cgtggcctga aattgcatct atgcaaatgg caactgccat gttgtgggac ttggcttgcc    60 actaccccact aaaaaggcca acgctgccat aatcaaatat aaagaccact gcctgggcat  120
gaccactagt ggcgtatgca gcgccacatg ctccaacaca gcatgtcaag gcgctttgct   180
gagcgtctac ttcatgatgc atttgcctcc atttaaaagt cattaaaaga catactcatg   240
atgtaaccca acgcacgttg cactgcattt tgcgacctcc gcgtctacct ccattcaaaa   300
tgtgtgaatc atgattgctc caatttggga ggagggggta ataaactcag cccatccact   360
gcccttccct tgggacgtga cacgagtacc aacgcacttc tgcccgctgt ctttgctccg   420
cgtagtcttg gaatgtcacc caagcgagag gccttgccca tcacgattga tggcacaacc   480
tatgatgtgt ccgcatgggt gaaccatcac cccggggggcg cagacatcat ggagaattat   540
cggaaccgag atgccacgga tgtgttcatg gtcatgcact cccacgatgc gttgaacaag   600
ctgaagcgca tgcctgtgat ggagcccact tcgccacgaa gccccaagac tcccaacgac   660
gaggttgctg aggacttccg caagcttcga aaggacatga ttgcaaaagg catgttcaac   720
gcatcccctc tcttctacgt gtacaaaagt gcgaccacag tagccctggg cgccctggct   780
attctgatgg tgatgcacct gcagtggtac tacatcccag ccattttgtt gggactttgc   840
taccagcagc tggggtggtt ggcacacgat tactgccacc atcaggtgtt ctctaaccgg   900
gcgtacaaca attttgctgg acttgtattc ggcaatgtga tgcaaggata ctccgggact   960
tggtggaagg acaggcacaa cggccatcac gccgccacga acgtgcaagg gcacgatccc  1020
gacatcgacg acctcccggt gttggcctgg tccccggagg acgtcaaaaa cgccggtccc  1080
acgacgcgga agctcatcaa gtggcaacaa tactatttcc tccccaccat cgcaaccctc  1140
cgattcatct ggtgcttcca gagcattctg gcggttatgg catacaagac agatgcaagg  1200
aatatatatt accaacgcca gtacgcaaag gaggccgtgg ggctggctct gcattggatt  1260
ctgaaagggg tattcatgtt ctgttacatg cccggcatac tgacgggctt ggccttcttc  1320
ctcatctcgg agtgcctggg cgggtttggg attgccattg tcgtgttctt gaatcactac  1380
ccattggaga aggtggagga gtccgtgtgg gacagccacg ggttttgcgc ggggcagatc  1440
```

-continued

```
cacacgacga tgaacatcca acgcggggtc atcgttgact ggttctttgg aggcctgaac    1500
taccaaatcg aacaccatct gtggccgacg ctgccccggc atcacttgaa agctgcttct    1560
tttgaggtgg agaaaatttg ccagaagcac aaattgccat acagagcacc cccatgtcc     1620 gatggtgttg ctcaattgct tggcttcttg gggaagattg ctaagctggc agctgtccca    1680
gtgtaaccct aaacgtacca cggcgttgtc aagacagtca gctgggtttc ggagtggtag    1740
cagtgcgtgc agctgtgcag ctgaggacga ttgtggggtt tgatcatgtc tgtcagagtt    1800
ctttgtgcac gtagaatgat gcacggtacc atcaggtcag cttggttggc tctgcatgag    1860
gctgacggtc ttaatttggg gtgtctcaaa gatactcaag gacgaagagt atgcacacgt    1920
gtttggccat ttcncagtgn naaaaaaaaa aaaaaaaaa aaa                       1963
```

<210> SEQ ID NO 47
<211> LENGTH: 417
<212> TYPE: PRT
<213> ORGANISM: Eutreptiella sp. CCMP389

<400> SEQUENCE: 47

```
Met Ser Pro Lys Arg Glu Ala Leu Pro Ile Thr Ile Asp Gly Thr Thr
1               5                   10                  15

Tyr Asp Val Ser Ala Trp Val Asn His His Pro Gly Gly Ala Asp Ile
            20                  25                  30

Met Glu Asn Tyr Arg Asn Arg Asp Ala Thr Asp Val Phe Met Val Met
        35                  40                  45

His Ser His Asp Ala Leu Asn Lys Leu Lys Arg Met Pro Val Met Glu
    50                  55                  60

Pro Thr Ser Pro Arg Ser Pro Lys Thr Pro Asn Asp Glu Val Ala Glu
65                  70                  75                  80

Asp Phe Arg Lys Leu Arg Lys Asp Met Ile Ala Lys Gly Met Phe Asn
                85                  90                  95

Ala Ser Pro Leu Phe Tyr Val Tyr Lys Ser Ala Thr Thr Val Ala Leu
            100                 105                 110

Gly Ala Leu Ala Ile Leu Met Val Met His Leu Gln Trp Tyr Tyr Ile
        115                 120                 125

Pro Ala Ile Leu Leu Gly Leu Cys Tyr Gln Gln Leu Gly Trp Leu Ala
    130                 135                 140

His Asp Tyr Cys His His Gln Val Phe Ser Asn Arg Ala Tyr Asn Asn
145                 150                 155                 160

Phe Ala Gly Leu Val Phe Gly Asn Val Met Gln Gly Tyr Ser Gly Thr
                165                 170                 175

Trp Trp Lys Asp Arg His Asn Gly His His Ala Ala Thr Asn Val Gln
            180                 185                 190

Gly His Asp Pro Asp Ile Asp Asp Leu Pro Val Leu Ala Trp Ser Pro
        195                 200                 205

Glu Asp Val Lys Asn Ala Gly Pro Thr Thr Arg Lys Leu Ile Lys Trp
    210                 215                 220

Gln Gln Tyr Tyr Phe Leu Pro Thr Ile Ala Thr Leu Arg Phe Ile Trp
225                 230                 235                 240

Cys Phe Gln Ser Ile Leu Ala Val Met Ala Tyr Lys Thr Asp Ala Arg
                245                 250                 255

Asn Ile Tyr Tyr Gln Arg Gln Tyr Ala Lys Glu Ala Val Gly Leu Ala
            260                 265                 270

Leu His Trp Ile Leu Lys Gly Val Phe Met Phe Cys Tyr Met Pro Gly
```

```
                275                  280                  285
Ile Leu Thr Gly Leu Ala Phe Phe Leu Ile Ser Glu Cys Leu Gly Gly
    290                  295                  300

Phe Gly Ile Ala Ile Val Val Phe Leu Asn His Tyr Pro Leu Glu Lys
305                  310                  315                  320

Val Glu Glu Ser Val Trp Asp Ser His Gly Phe Cys Ala Gly Gln Ile
                325                  330                  335

His Thr Thr Met Asn Ile Gln Arg Gly Val Ile Val Asp Trp Phe Phe
            340                  345                  350

Gly Gly Leu Asn Tyr Gln Ile Glu His His Leu Trp Pro Thr Leu Pro
        355                  360                  365

Arg His His Leu Lys Ala Ala Ser Phe Glu Val Glu Lys Ile Cys Gln
    370                  375                  380

Lys His Lys Leu Pro Tyr Arg Ala Pro Pro Met Ser Asp Gly Val Ala
385                  390                  395                  400

Gln Leu Leu Gly Phe Leu Gly Lys Ile Ala Lys Leu Ala Ala Val Pro
                405                  410                  415

Val

<210> SEQ ID NO 48
<211> LENGTH: 2063
<212> TYPE: DNA
<213> ORGANISM: Eutreptiella cf_gymnastica CCMP1594
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (980)..(980)
<223> OTHER INFORMATION: n is a, c, g, or t
<220> FEATURE:
<221> NAME/KEY: misc_feature
<222> LOCATION: (1244)..(1244)
<223> OTHER INFORMATION: n is a, c, g, or t
<220> FEATURE:
<221> NAME/KEY: misc_feature
<222> LOCATION: (1948)..(1948)
<223> OTHER INFORMATION: n is a, c, g, or t
<220> FEATURE:
<221> NAME/KEY: misc_feature
<222> LOCATION: (1973)..(1973)
<223> OTHER INFORMATION: n is a, c, g, or t

<400> SEQUENCE: 48
cttgttggta ttagtaatgg acacagcag tatattttcc cattgagaaa aacgctgaaa      60
tactggttgg tgaaaacttg gtgagaacaa cggtccattt gaacacagct tcccaccgcc    120
tttccccctt atctcatgtt gctggaccac actgcaagct gcatgagcga tagctgaacg    180
agacttcacg ctgtcatccc ttcacttcat atgcgttgtg caagggaaag ggtgccatca    240
ggtgtgactg tgcctccgtg ataaagtcga gggcacactc cgaattgggc agttctcgct    300
accgtgacca gatgcgtgtc aaaactagat cccgaagaaa acgcccgcgc ggagagcctt    360
gacacagttg tgttgaagaa aagtttgtgt ggcttcggag cgaaaaagac accgcaccat    420
agctgtggca gtgcaagacc ccagatccgc tggtccctgc acttgttgaa gcctcaaaat    480
gtcacctaaa cgggacgcat tgcctctgac aattgatggc accacgtacg acgtttccgc    540
ttgggtaaac catcaccctg gaggggctca atcattgaa aactaccgga accgagatgc     600
taccgacgtg ttcatggtca tgcattcaca gcaggcgctc aacaagttga agcggatgcc    660
tgttatggag ccctcttcac cacttactcc caagagccca agtgacgaca tttccnagga    720
```

```
tttccgcaag ctccgcaaca gtatggttga aagggtatg ttcaacgcgt ccctctgtt      780
ttatgtgtac aaatcactga ccactgtcgc ccttggcgcc gtgggtgttc tcatggttat     840
gtacctgcag tggtactacg tttcagccat gttttggga ctttgctacc aacagctggg      900
ttgggtggcg catgactacg cgcatcacca ggttttcacg aaccgtgatt atggcaatct     960
tggtgggctt ttctttggcn acgttctcca aggatattct ttgacttggt ggaaggacag    1020
gcacaacggc catcacgccg ccacaaacgt gcaaggacat gaccccgaca ttgataatct    1080
ccccgttttg gcttggtcgc cagaggacgt caagaatgcc ggacctggaa cccgcaatat    1140
catcaagtac cagcagtatt atttcctccc taccatcgcc atccttcggt tcatctggtg    1200
tttccaaagc attctggggg tgatgtcata caagacagac tccnagaatc tctattacaa    1260
acggcagtac cggagagagg cagccggtct ggcgctgcac tggattctga agagcgtttt    1320
cttgttctgt tacatgccaa gtttcctcac tggcctggcg ttttccctta tctcggagtg    1380
tctgggcggc tttgggatcg cgattgtggt gttttgaac cactatccgc tggataaggt    1440
tgaggaatcc gtttgggatg gtcacggttt ctgtgctggg cagatcctca caaccatgaa    1500
catccaacgc ggactcatca ctgactggtt ctttggaggt tgaattacc agattgagca    1560
tcatctgtgg cccaaccttc caagacacca tttgaaagca gtttcctttg aggttgagaa    1620
attgtgccag aagcacaacc tgccctacag agctccgccg atgcatactg gtgttgcaca    1680
attgcttgga tatttgggga agattgctca gttggctgct gtcccagtat aaccctggat    1740
caccttcatc gatcctattc tgagtgttca gggtgcgact gcatcccccg ttttctgc    1800
acagccgcgc atttgcaggg tggtttctat tacaattttt tttctgccca aaacaacacc    1860
tgatgtggcg agcgaggttc actcttgctg cacaccactc attttgttct gggttgagtt    1920
atatgtgaat taatatgtaa gcagtttnct tgcacagccc ggggcatttt ttntattccc    1980
aagacagcgt gataacattt ggcgggcgag gttcactctt gctgcacacc atcatgtttt    2040
gggtgcccag cccccccccc cct                                            2063
```

<210> SEQ ID NO 49
<211> LENGTH: 417
<212> TYPE: PRT
<213> ORGANISM: Eutreptiella cf_gymnastica CCMP1594
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (256)..(256)
<223> OTHER INFORMATION: Xaa can be any naturally occurring amino acid

<400> SEQUENCE: 49

```
Met Ser Pro Lys Arg Asp Ala Leu Pro Leu Thr Ile Asp Gly Thr Thr
 1               5                  10                  15

Tyr Asp Val Ser Ala Trp Val Asn His His Pro Gly Gly Ala Gln Ile
            20                  25                  30

Ile Glu Asn Tyr Arg Asn Arg Asp Ala Thr Asp Val Phe Met Val Met
        35                  40                  45

His Ser Gln Gln Ala Leu Asn Lys Leu Lys Arg Met Pro Val Met Glu
    50                  55                  60
```

```
Pro Ser Ser Pro Leu Thr Pro Lys Ser Pro Ser Asp Ile Ser Xaa
 65                  70                  75                  80

Asp Phe Arg Lys Leu Arg Asn Ser Met Val Glu Lys Gly Met Phe Asn
                 85                  90                  95

Ala Ser Pro Leu Phe Tyr Val Tyr Lys Ser Leu Thr Thr Val Ala Leu
            100                 105                 110

Gly Ala Val Gly Val Leu Met Val Met Tyr Leu Gln Trp Tyr Tyr Val
        115                 120                 125

Ser Ala Met Phe Leu Gly Leu Cys Tyr Gln Gln Leu Gly Trp Val Ala
    130                 135                 140

His Asp Tyr Ala His His Gln Val Phe Thr Asn Arg Asp Tyr Gly Asn
145                 150                 155                 160

Leu Gly Gly Leu Phe Phe Gly Xaa Val Leu Gln Gly Tyr Ser Leu Thr
                165                 170                 175

Trp Trp Lys Asp Arg His Asn Gly His His Ala Ala Thr Asn Val Gln
            180                 185                 190

Gly His Asp Pro Asp Ile Asp Asn Leu Pro Val Leu Ala Trp Ser Pro
        195                 200                 205

Glu Asp Val Lys Asn Ala Gly Pro Gly Thr Arg Asn Ile Ile Lys Tyr
    210                 215                 220

Gln Gln Tyr Tyr Phe Leu Pro Thr Ile Ala Ile Leu Arg Phe Ile Trp
225                 230                 235                 240

Cys Phe Gln Ser Ile Leu Gly Val Met Ser Tyr Lys Thr Asp Ser Xaa
                245                 250                 255

Asn Leu Tyr Tyr Lys Arg Gln Tyr Arg Arg Glu Ala Ala Gly Leu Ala
            260                 265                 270

Leu His Trp Ile Leu Lys Ser Val Phe Leu Phe Cys Tyr Met Pro Ser
        275                 280                 285

Phe Leu Thr Gly Leu Ala Phe Phe Leu Ile Ser Glu Cys Leu Gly Gly
    290                 295                 300

Phe Gly Ile Ala Ile Val Val Phe Leu Asn His Tyr Pro Leu Asp Lys
305                 310                 315                 320

Val Glu Glu Ser Val Trp Asp Gly His Gly Phe Cys Ala Gly Gln Ile
                325                 330                 335

Leu Thr Thr Met Asn Ile Gln Arg Gly Leu Ile Thr Asp Trp Phe Phe
            340                 345                 350

Gly Gly Leu Asn Tyr Gln Ile Glu His His Leu Trp Pro Asn Leu Pro
        355                 360                 365

Arg His His Leu Lys Ala Val Ser Phe Glu Val Glu Lys Leu Cys Gln
    370                 375                 380

Lys His Asn Leu Pro Tyr Arg Ala Pro Pro Met His Thr Gly Val Ala
385                 390                 395                 400

Gln Leu Leu Gly Tyr Leu Gly Lys Ile Ala Gln Leu Ala Ala Val Pro
                405                 410                 415

Val

<210> SEQ ID NO 50
<211> LENGTH: 60
<212> TYPE: DNA
<213> ORGANISM: Artificial Sequence
<220> FEATURE:
<223> OTHER INFORMATION: TOPO linker

<400> SEQUENCE: 50
tagaaggcac agtcgaggac ttatcctagc ctctgaatac tttcaacaag ttacaccctt    60
```

<210> SEQ ID NO 51
<211> LENGTH: 24
<212> TYPE: DNA
<213> ORGANISM: Artificial Sequence
<220> FEATURE:
<223> OTHER INFORMATION: LinkAmp primer 1

<400> SEQUENCE: 51
aggcacagtc gaggacttat ccta                                          24

<210> SEQ ID NO 52
<211> LENGTH: 26
<212> TYPE: DNA
<213> ORGANISM: Artificial Sequence
<220> FEATURE:
<223> OTHER INFORMATION: LinkAmp primer 2

<400> SEQUENCE: 52
gcctctgaat actttcaaca agttac                                        26

<210> SEQ ID NO 53
<211> LENGTH: 601
<212> TYPE: DNA
<213> ORGANISM: Tetruetreptia pomquetensis CCMP1491

<400> SEQUENCE: 53
gggctcatca cgcttaggct tgggtgcaac aggtgtgtca ggagaggaag gctccataac    60
aggcattctc ttcaacttgg cgacggcttc ttgagagtgc atcaccatga agacatcggt   120
cgcatcgcgg ttgcgatagt tctcgataat gtcagctcct ccagggtggt gattgaccca   180
agcagacaca tcataagttg cgccatcaat tgtgattggc agagcttgcc gcttaggaga   240
catcttagct gcagatgagt ttacacggtt ctagcattgg tcgaaagacg tttctacagc   300
cccaaagaat gtttgcatgt atttcataca tttcctactg agatagttcc tgtgcaaacg   360 ttttggata cattgtttct ggtgtgacag acaattttg ctgactgtaa gtaccgtgcc     420
ggtgtgcatg cgcttcagcg ggttgatgga gccttacaac tggaatgcaa ctgcaattgg   480
agtgcaagtt aatccgcgga ttggacagat gtggcactta gggaggggat gatttcgatt   540
tcatgccggg ataagccgaa acactccgga ccgagtcaag ccacacttca gcaatttgtg   600
t                                                                  601

<210> SEQ ID NO 54
<211> LENGTH: 20
<212> TYPE: DNA
<213> ORGANISM: Artificial Sequence
<220> FEATURE:
<223> OTHER INFORMATION: primer AUAP

<400> SEQUENCE: 54
ggccacgcgt cgactagtac                                               20

<210> SEQ ID NO 55
<211> LENGTH: 1028
<212> TYPE: DNA
<213> ORGANISM: Tetruetreptia pomquetensis CCMP1491
<220> FEATURE:
<221> NAME/KEY: misc_feature
<222> LOCATION: (793)..(794)
<223> OTHER INFORMATION: n is a, c, g, or t

<400> SEQUENCE: 55

```
gcccttcttt gccaccggtt tgggatgctt cttgatctcc gagctgctcg gaggatttgg      60
cattgccatc gttgtgtttc tgaatcacta tcctttggac aaggttgagg agactgtctg     120
ggatgagcac gggttcagcg ccagccagat ccacgagacg ttgaacatta agcccggcct     180
tctcaccgat tgggtctttg gtggtctcaa ctaccagatt gagcaccact tgtggcccaa     240
catgcccagg cacaacctca cggcagcttc cctggaggtg cagaagttgt gcgccaagca     300
caacctgccc tacagggccc cagccatcat ccccgggggtt cagaaattgg tcagcttctt     360
aggcgagatt gcccagctgg ctgctgtccc tgaatgattg gtgactaagc aagcgtcggc     420
atggcgtgcg tgtgtgggggc gggggttccc gcactgtaac ccgcggtgta acgcgcggtg     480
gccgttccac ccaatcaaat gacaccacct gcgccaacca tcgctccccc accaaaccaa     540
cccggaccaa aactaataaa catgtggttt tttccatcca ctggggccgc ctactccgcg     600
ccgtgtgccc atcgtgcggg ttgtaccccc tccccaccta tgtctaatgc gtgtgtgcgt     660
gcgtgtgtgc ctccttaatt gtacctattt atatctttcc tcctggggtg gcttttttac     720 accccttat catactctgg tcagcgcagt gcctgtgttg ccgctgagga tgaagaatgc     780
atggcagggc gcnnttttttt ttgcaccagt cacacatcca ccccttcgat aatgcccatg     840
ctacgcatgc aaccaggtgt tggccaccgg tgcctatgcg tagcggtgag cctcgcgagg     900
tgcatttggt caccaatccc caaggggcac ggccccagt ttggttgtac acttgcatac     960
agggactcaa tgggattttt gaattttgat catttataag catgactgct gaaaaaaaaa    1020
aaaaaaaa                                                              1028
```

<210> SEQ ID NO 56
<211> LENGTH: 2233
<212> TYPE: DNA
<213> ORGANISM: Tetruetreptia pomquetensis CCMP1491

<400> SEQUENCE: 56

```
acacaaattg ctgaagtgtg gcttgactcg gtccggagtg tttcggctta tcccggcatg      60
aaatcgaaat catcccctcc ctaagtgcca catctgtcca atccgcggat taacttgcac     120
tccaattgca gttgcattcc agttgtaagg ctccatcaac ccgctgaagc gcatgcacac     180
cggcacggta cttacagtca gcaaaattgt cctgtcacac cagaaacaat gtatccaaaa     240
acgtttgcac aggaactatc tcagtaggaa atgtatgaaa tacatgcaaa cattctttgg     300
ggctgtagaa acgtctttcg accaatgcta gaaccgtgta aactcatctg cagctaagat     360
gtctcctaag cggcaagctc tgccaatcac aattgatggc gcaacttatg atgtgtctgc     420
ttgggtcaat caccaccctg gaggagctga cattatcgag aactatcgca accgcgatgc     480
gaccgatgtc ttcatggtga tgcactctca agaagccgtc gccaagttga agagaatgcc     540
tgttatggag ccttcctctc ctgacacacc tgttgcaccc aagcctaagc gtgatgagcc     600
ccaggaggat ttccgcaagt tgcgggagga attcatctcc aagggtatgt cgagacgag      660 tttccttttgg tattttttaca agacttcaac taccgtcggt ttgatggtcc tttccatctt     720
gatgaccgtg tacgcgaatt ggtatttcac cgctgctttg gttcttggcg tgtgctacca     780
acagctaggc tggttgtccc acgactattg ccatcaccag gttttcacaa accgcaagat     840
taacgacgct ttcggtctct ttttcggtaa cgtgatgcag ggatactcac agacttggtg     900
gaaggatagg cacaatggtc accatgccgc caccaatgtg gtcggccatg acccagatat     960
tgataacctc cccatcctgg cttggtctcc gaagatgtcc aagagggcta ctccttcgac    1020
tcggaatctc atcaagtacc agcagtacta cttcattccc accattgcat cccttaggtt    1080
```

```
catctggtgc ctccaatcca tcggcggcgt catgtcctac aagagcgagg agaggaacct   1140
gtactacaag cgccagtaca ctaaggaggc gattggtctg gccctccatt gggtgctcaa   1200
ggccactttc tattgcagtg ccatgcctag ctttgccacc ggtttgggat gcttcttgat   1260
ctccgagctg ctcggaggat tggcattgc catcgttgtg tttctgaatc actatccttt    1320
ggacaaggtt gaggagactg tctgggatga gcacgggttc agcgccagcc agatccacga   1380
gacgttgaac attaagcccg ccttctcac cgattgggtc tttggtggtc tcaactacca    1440
gattgagcac cacttgtggc ccaacatgcc caggcacaac ctcacggcag cttccctgga   1500
ggtgcagaag ttgtgcgcca agcacaacct gccctacagg gccccagcca tcatccccgg   1560
ggttcagaaa ttggtcagct tcttaggcga gattgcccag ctggctgctg tccctgaatg   1620
attggtgact aagcaagcgt cggcatggcg tgcgtgtgtg gggcgggggt tcccgcactg   1680
taacccgcgg tgtaacgcgc ggtggccgtt ccacccaatc aaatgacacc acctgcgcca   1740
accatcgctc ccccaccaaa ccaacccgga ccaaaactaa taaacatgtg gttttttcca   1800
tccactgggg ccgcctactc cgcgccgtgt gcccatcgtg cggggttgtac cccctccccca  1860 cctatgtcta atgcgtgtgt gcgtgcgtgt gtgcctcctt aattgtacct atttatatct   1920
ttcctcctgg ggtggctttt ttacacccccc ttatcatact ctggtcagcg cagtgcctgt   1980
gttgccgctg aggatgaaga atgcatggca gggcgctttt ttttgcacca gtcacacatc   2040
caccccttcg ataatgccca tgctacgcat gcaaccaggt gttggccacc ggtgcctatg   2100
cgtagcggtg agcctcgcga ggtgcatttg gtcaccaatc cccaaggggc acggccccca   2160
gtttggttgt acacttgcat acagggactc aatgggattt ttgaattttg atcatttata   2220
agcatgactg ctg                                                      2233
```

<210> SEQ ID NO 57
<211> LENGTH: 420
<212> TYPE: PRT
<213> ORGANISM: Tetruetreptia pomquetensis CCMP1491

<400> SEQUENCE: 57

```
Met Ser Pro Lys Arg Gln Ala Leu Pro Ile Thr Ile Asp Gly Ala Thr
1               5                   10                  15

Tyr Asp Val Ser Ala Trp Val Asn His His Pro Gly Gly Ala Asp Ile
                20                  25                  30

Ile Glu Asn Tyr Arg Asn Arg Asp Ala Thr Asp Ala Phe Met Val Met
            35                  40                  45

His Ser Gln Glu Ala Val Ala Lys Leu Lys Arg Met Pro Val Met Glu
        50                  55                  60

Pro Ser Ser Pro Asp Thr Pro Val Ala Pro Lys Pro Lys Arg Asp Glu
65                  70                  75                  80

Pro Gln Glu Asp Phe Arg Lys Leu Arg Glu Glu Phe Ile Ser Lys Gly
                85                  90                  95

Met Phe Glu Thr Ser Phe Leu Trp Tyr Phe Lys Thr Ser Thr Thr
            100                 105                 110

Val Gly Leu Met Val Leu Ser Ile Leu Met Thr Val Tyr Thr Asn Trp
        115                 120                 125

Tyr Phe Thr Ala Ala Leu Val Leu Gly Val Cys Tyr Gln Gln Leu Gly
    130                 135                 140

Trp Leu Ser His Asp Tyr Cys His His Gln Val Phe Thr Asn Arg Lys
145                 150                 155                 160
```

```
Ile Asn Asp Ala Phe Gly Leu Phe Phe Gly Asn Val Met Gln Gly Tyr
                165                 170                 175
Ser Gln Thr Trp Trp Lys Asp Arg His Asn Gly His His Ala Ala Thr
            180                 185                 190
Asn Val Val Gly His Asp Pro Asp Ile Asp Asn Leu Pro Ile Leu Ala
        195                 200                 205
Trp Ser Pro Glu Asp Val Lys Arg Ala Thr Pro Ser Thr Arg Asn Leu
210                 215                 220
Ile Lys Tyr Gln Gln Tyr Tyr Phe Ile Pro Thr Ile Ala Ser Leu Arg
225                 230                 235                 240
Phe Ile Trp Cys Leu Gln Ser Ile Gly Gly Val Met Ser Tyr Lys Ser
                245                 250                 255
Glu Glu Arg Asn Leu Tyr Tyr Lys Arg Arg Tyr Thr Lys Glu Ala Ile
            260                 265                 270
Gly Leu Ala Leu Pro Trp Val Leu Lys Ala Thr Phe Tyr Cys Ser Ala
        275                 280                 285
Met Pro Ser Phe Ala Thr Gly Leu Gly Cys Phe Leu Ile Ser Glu Leu
290                 295                 300
Leu Gly Gly Phe Gly Ile Ala Ile Val Val Phe Leu Asn His Tyr Pro
305                 310                 315                 320
Leu Asp Lys Val Glu Glu Thr Val Trp Asp Glu His Gly Phe Ser Ala
                325                 330                 335
Ser Gln Ile His Glu Thr Leu Asn Ile Lys Pro Gly Leu Leu Thr Asp
            340                 345                 350
Trp Val Phe Gly Gly Leu Asn Tyr Gln Ile Glu His His Leu Trp Pro
        355                 360                 365
Asn Met Pro Arg His Asn Leu Thr Ala Ala Ser Leu Glu Val Gln Lys
370                 375                 380
Leu Cys Ala Lys His Asn Leu Pro Tyr Arg Ala Pro Ala Ile Ile Pro
385                 390                 395                 400
Gly Val Gln Lys Leu Val Ser Phe Leu Gly Glu Ile Ala Gln Leu Ala
                405                 410                 415
Ala Val Pro Glu
            420

<210> SEQ ID NO 58
<211> LENGTH: 31
<212> TYPE: DNA
<213> ORGANISM: Artificial Sequence
<220> FEATURE:
<223> OTHER INFORMATION: primer TpomNot-5

<400> SEQUENCE: 58
gcggccgcac catgtctcct aagcggcaag c                                    31

<210> SEQ ID NO 59
<211> LENGTH: 27
<212> TYPE: DNA
<213> ORGANISM: Artificial Sequence
<220> FEATURE:
<223> OTHER INFORMATION: primer TpomNot-3

<400> SEQUENCE: 59
gcggccgctc attcagggac agcagcc                                         27

<210> SEQ ID NO 60
<211> LENGTH: 19
<212> TYPE: DNA
```

<213> ORGANISM: Artificial Sequence
<220> FEATURE:
<223> OTHER INFORMATION: primer T7

<400> SEQUENCE: 60
ggaaacagct atgaccatg                                                  19

<210> SEQ ID NO 61
<211> LENGTH: 22
<212> TYPE: DNA
<213> ORGANISM: Artificial Sequence
<220> FEATURE:
<223> OTHER INFORMATION: primer M13-28Rev

<400> SEQUENCE: 61
gtaatacgac tcactatagg gc                                              22

<210> SEQ ID NO 62
<211> LENGTH: 1260
<212> TYPE: DNA
<213> ORGANISM: Tetruetreptia pomquetensis CCMP1491

<400> SEQUENCE: 62
atgtctccta agcggcaagc tctgccaatc acaattgatg gcgcaactta tgatgtgtct     60
gcttgggtca atcaccaccc tggaggagct gacattatcg agaactatcg caaccgcgat    120
gcgaccgatg tcttcatggt gatgcactct caagaagccg tcgccaagtt gaagagaatg    180
cctgttatgg agccttcctc tcctgacaca cctgttgcac ccaagcctaa gcgtgatgag    240
ccccaggagg atttccgcaa gttgcgggag gaattcatct ccaagggtat gttcgagacg    300
agtttccttt ggtatttta caagacttca actaccgtcg gtttgatggt cctttccatc    360
ttgatgaccg tgtacacgaa ttggtatttc accgctgctt tggttcttgg cgtgtgctac    420
caacagctag gctggttgtc ccacgactat tgccatcacc aggttttcac aaaccgcaag    480
attaacgacg ctttcggtct cttttttcggt aacgtgatgc agggatactc acagacttgg    540
tggaaggata ggcacaatgg tcaccatgcc gccaccaatg tggtcggcca tgacccagat    600
attgataacc tccccatcct ggcttggtct cccgaagatg tcaagagggc tactccttcg    660
actcggaatc tcatcaagta ccagcagtac tacttcattc ccaccattgc atcccttagg    720
ttcatctggt gcctccaatc catcggcggc gtcatgtcct acaagagcga ggagaggaac    780
ctgtactaca agcgccagta cactaaggag gcgattggtc tggccctcca ctgggtgctc    840
aaggccactt tctattgcag tgccatgcct agctttgcca ccggtttggg atgcttcttg    900
atctccgagc tgctcggagg atttggcatt gccatcgttg tgtttctgaa tcactatcct    960
ttggacaagg ttgaggagac tgtctgggat gagcacgggt tcagcgccag ccagatccac   1020
gagacgttga acattaagcc cggccttctc accgattggg tctttggtgg tctcaactac   1080
cagattgagc accacttgtg gcccaacatg cccaggcaca acctcacggc agcttccctg   1140
gaggtgcaga gttgtgcgc caagcacaac ctgccctaca gggccccagc catcatcccc   1200
ggggttcaga aattggtcag cttcttaggc gagattgccc agctggctgc tgtccctgaa   1260

<210> SEQ ID NO 63
<211> LENGTH: 4300
<212> TYPE: DNA
<213> ORGANISM: Artificial Sequence
<220> FEATURE:
<223> OTHER INFORMATION: plasmid pLF114-10

<400> SEQUENCE: 63

-continued

```
taatacgact cactataggg cgaattgggc ccgacgtcgc atgctcccgg ccgccatggc    60
ggccgcggga attcgattgg cggccgcacc atgtctccta agcggcaagc tctgccaatc   120
acaattgatg gcgcaactta tgatgtgtct gcttgggtca atcaccaccc tggaggagct   180
gacattatcg agaactatcg caaccgcgat gcgaccgatg tcttcatggt gatgcactct   240
caagaagccg tcgccaagtt gaagagaatg cctgttatgg agccttcctc tcctgacaca   300
cctgttgcac ccaagcctaa gcgtgatgag ccccaggagg atttccgcaa gttgcgggag   360
gaattcatct ccaagggtat gttcgagacg agtttccttt ggtattttta caagacttca   420
actaccgtcg gtttgatggt cctttccatc ttgatgaccg tgtacacgaa ttggtatttc   480
accgctgctt tggttcttgg cgtgtgctac aacagctag gctggttgtc ccacgactat    540
tgccatcacc aggttttcac aaaccgcaag attaacgacg ctttcggtct cttttcggt   600
aacgtgatgc agggatactc acagacttgg tggaaggata ggcacaatgg tcaccatgcc   660
gccaccaatg tggtcggcca tgacccagat attgataacc tccccatcct ggcttggtct   720
cccgaagatg tcaagagggc tactccttcg actcggaatc tcatcaagta ccagcagtac   780
tacttcattc ccaccattgc atcccttagg ttcatctggt gcctccaatc catcggcggc   840
gtcatgtcct acaagagcga ggagaggaac ctgtactaca agcgccagta cactaaggag   900
gcgattggtc tggccctcca ctgggtgctc aaggccactt tctattgcag tgccatgcct   960
agctttgcca ccggtttggg atgcttcttg atctccgagc tgctcggagg atttggcatt  1020
gccatcgttg tgtttctgaa tcactatcct ttggacaagg ttgaggagac tgtctgggat  1080
gagcacgggt tcagcgccag ccagatccac gagacgttga acattaagcc cggccttctc  1140
accgattggg tctttggtgg tctcaactac cagattgagc caccttgtg gcccaacatg  1200
cccaggcaca acctcacggc agcttccctg gaggtgcaga gttgtgcgc caagcacaac  1260
ctgccctaca gggccccagc catcatcccc ggggttcaga aattggtcag cttcttaggc  1320
gagattgccc agctggctgc tgtccctgaa tgagcggccg caatcactag tgaattcgcg  1380
gccgcctgca ggtcgaccat atgggagagc tcccaacgcg ttggatgcat agcttgagta  1440
ttctatagtg tcacctaaat agcttggcgt aatcatggtc atagctgttt cctgtgtgaa  1500
attgttatcc gctcacaatt ccacacaaca tacgagccgg aagcataaag tgtaaagcct  1560
ggggtgccta atgagtgagc taactcacat taattgcgtt gcgctcactg cccgctttcc  1620
agtcgggaaa cctgtcgtgc cagctgcatt aatgaatcgg ccaacgcgcg gggagaggcg  1680
gtttgcgtat tgggcgctct tccgcttcct cgctcactga ctcgctgcgc tcggtcgttc  1740
ggctgcggcg agcggtatca gctcactcaa aggcggtaat acggttatcc acagaatcag  1800
gggataacgc aggaaagaac atgtgagcaa aaggccagca aaaggccagg aaccgtaaaa  1860
aggccgcgtt gctggcgttt ttccataggc tccgcccccc tgacgagcat cacaaaaatc  1920
gacgctcaag tcagaggtgg cgaaacccga caggactata agataccag gcgtttcccc  1980
ctggaagctc cctcgtgcgc tctcctgttc cgaccctgcc gcttaccgga tacctgtccg  2040
cctttctccc ttcgggaagc gtggcgcttt ctcatagctc acgctgtagg tatctcagtt  2100
cggtgtaggt cgttcgctcc aagctgggct gtgtgcacga accccccgtt cagcccgacc  2160
gctgcgcctt atccggtaac tatcgtcttg agtccaaccc ggtaagacac gacttatcgc  2220
cactggcagc agccactggt aacaggatta gcagagcgag gtatgtaggc ggtgctacag  2280
agttcttgaa gtggtggcct aactacggct acactagaag aacagtattt ggtatctgcg  2340
```

```
ctctgctgaa gccagttacc ttcggaaaaa gagttggtag ctcttgatcc ggcaaacaaa    2400
ccaccgctgg tagcggtggt ttttttgttt gcaagcagca gattacgcgc agaaaaaaag    2460
gatctcaaga agatcctttg atctttttcta cggggtctga cgctcagtgg aacgaaaact    2520
cacgttaagg gattttggtc atgagattat caaaaaggat cttcacctag atccttttaa    2580
attaaaaatg aagttttaaa tcaatctaaa gtatatatga gtaaacttgg tctgacagtt    2640
accaatgctt aatcagtgag gcacctatct cagcgatctg tctatttcgt tcatccatag    2700
ttgcctgact ccccgtcgtg tagataacta cgatacggga gggcttacca tctggcccca    2760
gtgctgcaat gataccgcga gacccacgct caccggctcc agatttatca gcaataaacc    2820
agccagccgg aagggccgag cgcagaagtg gtcctgcaac tttatccgcc tccatccagt    2880
ctattaattg ttgccgggaa gctagagtaa gtagttcgcc agttaatagt ttgcgcaacg    2940
ttgttgccat tgctacaggc atcgtggtgt cacgctcgtc gtttggtatg gcttcattca    3000
gctccggttc ccaacgatca aggcgagtta catgatcccc catgttgtgc aaaaaagcgg    3060
ttagctcctt cggtcctccg atcgttgtca gaagtaagtt ggccgcagtg ttatcactca    3120
tggttatggc agcactgcat aattctctta ctgtcatgcc atccgtaaga tgcttttctg    3180
tgactggtga gtactcaacc aagtcattct gagaatagtg tatgcggcga ccgagttgct    3240
cttgcccggc gtcaatacgg gataataccg cgccacatag cagaacttta aaagtgctca    3300
tcattggaaa acgttcttcg gggcgaaaac tctcaaggat cttaccgctg ttgagatcca    3360
gttcgatgta acccactcgt gcacccaact gatcttcagc atcttttact ttcaccagcg    3420
tttctgggtg agcaaaaaca ggaaggcaaa atgccgcaaa aaagggaata agggcgacac    3480
ggaaatgttg aatactcata ctcttccttt ttcaatatta ttgaagcatt tatcagggtt    3540
attgtctcat gagcggatac atatttgaat gtatttagaa aaataaacaa ataggggttc    3600
cgcgcacatt tccccgaaaa gtgccacctg atgcggtgtg aaataccgca cagatgcgta    3660
aggagaaaat accgcatcag gaaattgtaa gcgttaatat tttgttaaaa ttcgcgttaa    3720 attttgtta aatcagctca ttttttaacc aataggccga atcggcaaa atcccttata     3780 aatcaaaga atagaccgag ataggttga gtgttgttcc agtttggaac aagagtccac     3840
tattaaagaa cgtggactcc aacgtcaaag ggcgaaaaac cgtctatcag ggcgatggcc    3900
cactacgtga accatcaccc taatcaagtt ttttggggtc gaggtgccgt aaagcactaa    3960
atcggaaccc taaagggagc ccccgattta gagcttgacg gggaaagccg gcgaacgtgg    4020
cgagaaagga agggaagaaa gcgaaaggag cgggcgctag gcgctggca agtgtagcgg     4080 tcacgctgcg cgtaaccacc acacccgccg cgcttaatgc gccgctacag ggcgcgtcca    4140
ttcgccattc aggctgcgca actgttggga agggcgatcg gtgcgggcct cttcgctatt    4200
acgccagctg gcgaaagggg gatgtgctgc aaggcgatta agttgggtaa cgccagggtt    4260
ttcccagtca cgacgttgta aaacgacggc cagtgaattg                         4300
```

<210> SEQ ID NO 64  
<211> LENGTH: 7518  
<212> TYPE: DNA  
<213> ORGANISM: Artificial Sequence  
<220> FEATURE:  
<223> OTHER INFORMATION: primer pY-75

<400> SEQUENCE: 64

```
ggccgcaggg cggatccccc gggctgcagg aattcgatat caagcttatc gataccgtcg      60
acctcgaggg ggggcccggt acccaattcg ccctatagtg agtcgtatta cgcgcgctca     120
```

```
ctggccgtcg ttttacaacg tcgtgactgg gaaaaccctg gcgttaccca acttaatcgc    180
cttgcagcac atcccccttt cgccagctgg cgtaatagcg aagaggcccg caccgatcgc    240
ccttcccaac agttgcgcag cctgaatggc gaatggcgcg acgcgccctg tagcggcgca    300
ttaagcgcgg cgggtgtggt ggttacgcgc agcgtgaccg ctacacttgc cagcgcccta    360
gcgcccgctc ctttcgcttt cttcccttcc tttctcgcca cgttcgccgg ctttccccgt    420
caagctctaa atcgggggct ccctttaggg ttccgattta gtgctttacg gcacctcgac    480
cccaaaaaac ttgattaggg tgatggttca cgtagtgggc catcgccctg atagacggtt    540
tttcgccctt tgacgttgga gtccacgttc tttaatagtg gactcttgtt ccaaactgga    600
acaacactca accctatctc ggtctattct tttgatttat aagggatttt gccgatttcg    660
gcctattggt taaaaaatga gctgatttaa caaaaattta cgcgaatttt aacaaaata    720 ttaacgttta caatttcctg atgcggtatt ttctccttac gcatctgtgc ggtatttcac    780
accgcatatc gacggtcgag gagaacttct agtatatcca catacctaat attattgcct    840
tattaaaaat ggaatcccaa caattacatc aaaatccaca ttctcttcaa aatcaattgt    900
cctgtacttc cttgttcatg tgtgttcaaa acgttatat ttataggata attatactct    960
atttctcaac aagtaattgg ttgtttggcc gagcggtcta aggcgcctga ttcaagaaat   1020
atcttgaccg cagttaactg tgggaatact caggtatcgt aagatgcaag agttcgaatc   1080
tcttagcaac cattattttt ttcctcaaca taacgagaac acacagggcc gctatcgcac   1140
agaatcaaat tcgatgactg gaaatttttt gttaatttca gaggtcgcct gacgcatata   1200
cctttttcaa ctgaaaaatt gggagaaaaa ggaaaggtga gaggccggaa ccggcttttc   1260
atatagaata gagaagcgtt catgactaaa tgcttgcatc acaatacttg aagttgacaa   1320
tattatttaa ggacctattg tttttttccaa taggtggtta gcaatcgtct tactttctaa   1380 ctttttcttac ctttttacatt tcagcaatat atatatatat ttcaaggata taccattcta   1440
atgtctgccc ctatgtctgc ccctaagaag atcgtcgttt tgccaggtga ccacgttggt   1500
caagaaatca cagccgaagc cattaaggtt cttaaagcta tttctgatgt tcgttccaat   1560
gtcaagttcg atttcgaaaa tcatttaatt ggtggtgctg ctatcgatgc tacaggtgtc   1620
ccacttccag atgaggcgct ggaagcctcc aagaaggttg atgccgtttt gttaggtgct   1680
gtggctggtc ctaaatgggg taccggtagt gttagacctg aacaaggttt actaaaaatc   1740
cgtaaagaac ttcaattgta cgccaactta agaccatgta actttgcatc cgactctctt   1800
ttagacttat ctccaatcaa gccacaattt gctaaaggta ctgacttcgt tgttgtcaga   1860
gaattagtgg gaggtattta ctttggtaag agaaaggaag acgatggtga tggtgtcgct   1920
tgggatagtg aacaatacac cgttccagaa gtgcaaagaa tcacaagaat ggccgctttc   1980
atggccctac aacatgagcc accattgcct atttggtcct tggataaagc taatctttg   2040 gcctcttcaa gattatggag aaaaactgtg gaggaaacca tcaagaacga attccctaca   2100
ttgaaggttc aacatcaatt gattgattct gccgccatga tcctagttaa gaacccaacc   2160
cacctaaatg gtattataat caccagcaac atgtttggtg atatcatctc cgatgaagcc   2220
tccgttatcc caggttcctt gggtttgttg ccatctgcgt ccttggcctc tttgccagac   2280
aagaacaccg catttggttt gtacgaacca tgccacggtt ctgctccaga tttgccaaag   2340
aataaggttg accctatcgc cactatcttg tctgctgcaa tgatgttgaa attgtcattg   2400
aacttgcctg aagaaggtaa ggccattgaa gatgcagtta aaaaggtttt ggatgcaggt   2460
```

```
atcagaactg gtgatttagg tggttccaac agtaccaccg aagtcggtga tgctgtcgcc    2520
gaagaagtta agaaaatcct tgcttaaaaa gattctcttt ttttatgata tttgtacata    2580
aactttataa atgaaattca aatagaaac gacacgaaat tacaaaatgg aatatgttca    2640
tagggtagac gaaactatat acgcaatcta catacattta tcaagaagga gaaaaaggag    2700
gatagtaaag gaatacaggt aagcaaattg atactaatgg ctcaacgtga taaggaaaaa    2760
gaattgcact ttaacattaa tattgacaag gaggagggca ccacacaaaa agttaggtgt    2820
aacagaaaat catgaaacta cgattcctaa tttgatattg gaggattttc tctaaaaaaa    2880
aaaaaataca acaaataaaa aacactcaat gacctgacca tttgatggag tttaagtcaa    2940
taccttcttg aagcatttcc cataatggtg aaagttccct caagaatttt actctgtcag    3000
aaacggcctt acgacgtagt cgatatgtg cactctcagt acaatctgct ctgatgccgc    3060
atagttaagc cagccccgac acccgccaac acccgctgac gcgccctgac gggcttgtct    3120
gctcccggca tccgcttaca gacaagctgt gaccgtctcc gggagctgca tgtgtcagag    3180
gttttcaccg tcatcaccga aacgcgcgag acgaaagggc ctcgtgatac gcctattttt    3240
ataggttaat gtcatgataa taatggtttc ttagtatgat ccaatatcaa aggaaatgat    3300
agcattgaag gatgagacta atccaattga ggagtggcag catatagaac agctaaaggg    3360
tagtgctgaa ggaagcatac gatacccgc atggaatggg ataatatcac aggaggtact    3420
agactacctt tcatcctaca taaatagacg catataagta cgcatttaag cataaacacg    3480
cactatgccg ttcttctcat gtatatatat atacaggcaa cacgcagata taggtgcgac    3540
gtgaacagtg agctgtatgt gcgcagctcg cgttgcattt tcggaagcgc tcgttttcgg    3600
aaacgctttg aagttcctat tccgaagttc ctattctcta gaaagtatag gaacttcaga    3660
gcgcttttga aaaccaaaag cgctctgaag acgcacttc aaaaaaccaa aaacgcaccg    3720
gactgtaacg agctactaaa atattgcgaa taccgcttcc acaaacattg ctcaaaagta    3780
tctctttgct atatatctct gtgctatatc cctatataac ctacccatcc acctttcgct    3840
ccttgaactt gcatctaaac tcgacctcta cattttttat gtttatctct agtattactc    3900
tttagacaaa aaaattgtag taagaactat tcatagagtg aatcgaaaac aatacgaaaa    3960
tgtaaacatt tcctatacgt agtatatag acaaaatag aagaaaccgt tcataatttt    4020
ctgaccaatg aagaatcatc aacgctatca ctttctgttc acaaagtatg cgcaatccac    4080
atcggtatag aatataatcg gggatgcctt tatcttgaaa aaatgcaccc gcagcttcgc    4140
tagtaatcag taaacgcggg aagtggagtc aggcttttt tatggaagag aaaatagaca    4200
ccaaagtagc cttcttctaa ccttaacgga cctacagtgc aaaaagttat caagagactg    4260
cattatagag cgcacaaagg agaaaaaaag taatctaaga tgctttgtta gaaaaatagc    4320
gctctcggga tgcattttg tagaacaaaa aagaagtata gattctttgt tggtaaaata    4380
gcgctctcgc gttgcatttc tgttctgtaa aaatgcagct cagattcttt gtttgaaaaa    4440
ttagcgctct cgcgttgcat ttttgtttta caaaaatgaa gcacagattc ttcgttggta    4500
aaatagcgct ttcgcgttgc atttctgttc tgtaaaatg cagctcagat tctttgtttg    4560
aaaaattagc gctctcgcgt tgcatttttg ttctacaaaa tgaagcacag atgcttcgtt    4620
caggtggcac ttttcgggga aatgtgcgcg gaacccctat ttgtttattt ttctaaatac    4680
attcaaatat gtatccgctc atgagacaat aaccctgata aatgcttcaa taatattgaa    4740
aaaggaagag tatgagtatt caacatttcc gtgtcgccct tattccctt tttgcggcat    4800 tttgccttcc tgttttttgct cacccagaaa cgctggtgaa agtaaaagat gctgaagatc    4860
```

```
agttgggtgc acgagtgggt tacatcgaac tggatctcaa cagcggtaag atccttgaga    4920
gttttcgccc cgaagaacgt tttccaatga tgagcacttt taaagttctg ctatgtggcg    4980
cggtattatc ccgtattgac gccgggcaag agcaactcgg tcgccgcata cactattctc    5040
agaatgactt ggttgagtac tcaccagtca cagaaaagca tcttacggat ggcatgacag    5100
taagagaatt atgcagtgct gccataacca tgagtgataa cactgcggcc aacttacttc    5160
tgacaacgat cggaggaccg aaggagctaa ccgcttttt gcacaacatg ggggatcatg    5220
taactcgcct tgatcgttgg gaaccggagc tgaatgaagc cataccaaac gacgagcgtg    5280
acaccacgat gcctgtagca atggcaacaa cgttgcgcaa actattaact ggcgaactac    5340
ttactctagc ttcccggcaa caattaatag actggatgga ggcggataaa gttgcaggac    5400
cacttctgcg ctcggccctt ccggctggct ggtttattgc tgataaatct ggagccggtg    5460
agcgtgggtc tcgcggtatc attgcagcac tggggccaga tggtaagccc tcccgtatcg    5520
tagttatcta cacgacgggg agtcaggcaa ctatggatga acgaaataga cagatcgctg    5580
agataggtgc ctcactgatt aagcattggt aactgtcaga ccaagtttac tcatatatac    5640
tttagattga tttaaaactt catttttaat ttaaaaggat ctaggtgaag atccttttg    5700
ataatctcat gaccaaaatc ccttaacgtg agttttcgtt ccactgagcg tcagaccccg    5760
tagaaaagat caaaggatct tcttgagatc cttttttct gcgcgtaatc tgctgcttgc    5820
aaacaaaaaa accaccgcta ccagcggtgg tttgtttgcc ggatcaagag ctaccaactc    5880
tttttccgaa ggtaactggc ttcagcagag cgcagatacc aaatactgtc cttctagtgt    5940
agccgtagtt aggccaccac ttcaagaact ctgtagcacc gcctacatac ctcgctctgc    6000
taatcctgtt accagtggct gctgccagtg gcgataagtc gtgtcttacc gggttggact    6060
caagacgata gttaccggat aaggcgcagc ggtcgggctg aacggggggt tcgtgcacac    6120
agcccagctt ggagcgaacg acctacaccg aactgagata cctacagcgt gagctatgag    6180
aaagcgccac gcttcccgaa gggagaaagg cggacaggta tccggtaagc ggcagggtcg    6240
gaacaggaga gcgcacgagg gagcttccag ggggaaacgc ctggtatctt tatagtcctg    6300
tcgggtttcg ccacctctga cttgagcgtc gatttttgtg atgctcgtca ggggggcgga    6360
gcctatggaa aaacgccagc aacgcggcct ttttacggtt cctggccttt tgctggcctt    6420
ttgctcacat gttctttcct gcgttatccc ctgattctgt ggataaccgt attaccgcct    6480
ttgagtgagc tgataccgct cgccgcagcc gaacgaccga gcgcagcgag tcagtgagcg    6540
aggaagcgga agagcgccca atacgcaaac cgcctctccc cgcgcgttgg ccgattcatt    6600
aatgcagctg gcacgacagg tttcccgact ggaaagcggg cagtgagcgc aacgcaatta    6660
atgtgagtta cctcactcat taggcacccc aggctttaca ctttatgctt ccggctccta    6720
tgttgtgtgg aattgtgagc ggataacaat ttcacacagg aaacagctat gaccatgatt    6780
acgccaagcg cgcaattaac cctcactaaa gggaacaaaa gctggagctc caccgcggga    6840
tttcgaaact aagttcttgg tgttttaaaa ctaaaaaaaa gactaactat aaaagtagaa    6900
tttaagaagt ttaagaaata gatttacaga attacaatca atacctaccg tctttatata    6960
cttattagtc aagtagggga ataatttcag ggaactggtt tcaaccttt ttttcagctt    7020
tttccaaatc agagagagca gaaggtaata gaaggtgtaa gaaaatgaga tagatacatg    7080
cgtgggtcaa ttgccttgtg tcatcatta ctccaggcag gttgcatcac tccattgagg    7140
ttgtgcccgt ttttgcctg tttgtgcccc tgttctctgt agttgcgcta agagaatgga    7200
```

```
cctatgaact gatggttggt gaagaaaaca atattttggt gctgggattc ttttttttc      7260 tggatgccag cttaaaaagc gggctccatt atatttagtg gatgccagga ataaactgtt      7320
cacccagaca cctacgatgt tatatattct gtgtaacccg ccccctattt tgggcatgta      7380
cgggttacag cagaattaaa aggctaattt tttgactaaa taaagttagg aaaatcacta      7440
ctattaatta tttacgtatt ctttgaaatg gcagtattga taatgataaa ctcgaaatca      7500
ctagtggatc cgcccagc                                                    7518

<210> SEQ ID NO 65
<211> LENGTH: 8792
<212> TYPE: DNA
<213> ORGANISM: Artificial Sequence
<220> FEATURE:
<223> OTHER INFORMATION: plasmid pY126

<400> SEQUENCE: 65
ggccgcaggg cggatccccc gggctgcagg aattcgatat caagcttatc gataccgtcg      60
acctcgaggg ggggcccggt acccaattcg ccctatagtg agtcgtatta cgcgcgctca     120
ctggccgtcg ttttacaacg tcgtgactgg gaaaaccctg gcgttaccca acttaatcgc     180
cttgcagcac atccccctttt cgccagctgg cgtaatagcg aagaggcccg caccgatcgc     240
ccttcccaac agttgcgcag cctgaatggc gaatggcgcg acgcgcctg tagcggcgca     300 ttaagcgcgg cgggtgtggt ggttacgcgc agcgtgaccg ctacacttgc cagcgcccta     360
gcgcccgctc ctttcgcttt cttcccttcc tttctcgcca cgttcgccgg ctttccccgt     420
caagctctaa atcgggggct ccctttaggg ttccgattta gtgctttacg gcacctcgac     480
cccaaaaaac ttgattaggg tgatggttca cgtagtgggc catcgccctg atagacggtt     540
tttcgccctt tgacgttgga gtccacgttc tttaatagtg gactcttgtt ccaaactgga     600
acaacactca accctatctc ggtctattct tttgatttat aagggatttt gccgatttcg     660
gcctattggt taaaaatga gctgatttaa caaaaattta cgcgaatttt taacaaaata     720
ttaacgttta caatttcctg atgcggtatt ttctccttac gcatctgtgc ggtatttcac     780
accgcatatc gacggtcgag gagaacttct agtatatcca cataccttaat attattgcct     840 tattaaaaat ggaatcccaa caattacatc aaaatccaca ttctcttcaa aatcaattgt     900
cctgtacttc cttgttcatg tgtgttcaaa acgttatat ttataggata attatactct     960
atttctcaac aagtaattgg ttgtttggcc gagcggtcta aggcgcctga ttcaagaaat    1020
atcttgaccg cagttaactg tgggaatact caggtatcgt aagatgcaag agttcgaatc    1080
tcttagcaac cattattttt ttcctcaaca taacgagaac acacaggggc gctatcgcac    1140
agaatcaaat tcgatgactg gaaatttttt gttaatttca gaggtcgcct gacgcatata    1200
cctttttcaa ctgaaaaatt gggagaaaaa ggaaaggtga gaggccggaa ccggcttttc    1260
atatagaata gagaagcgtt catgactaaa tgcttgcatc acaatacttg aagttgacaa    1320
tattatttaa ggacctattg ttttttccaa taggtggtta gcaatcgtct tactttctaa    1380 ctttttcttac ctttttacatt tcagcaatat atatatat ttcaaggata taccattcta    1440
atgtctgccc ctatgtctgc ccctaagaag atcgtcgttt tgccaggtga ccacgttggt    1500
caagaaatca cagccgaagc cattaaggtt cttaaagcta tttctgatgt tcgttccaat    1560
gtcaagttcg atttcgaaaa tcatttaatt ggtggtgctg ctatcgatgc tacaggtgtc    1620
ccacttccag atgaggcgct ggaagcctcc aagaaggttg atgccgtttt gttaggtgct    1680
gtggctggtc ctaaatgggg taccggtagt gttagacctg aacaaggttt actaaaaatc    1740
```

```
cgtaaagaac ttcaattgta cgccaactta agaccatgta actttgcatc cgactctctt   1800
ttagacttat ctccaatcaa gccacaattt gctaaaggta ctgacttcgt tgttgtcaga   1860
gaattagtgg gaggtattta ctttggtaag agaaaggaag acgatggtga tggtgtcgct   1920
tgggatagtg aacaatacac cgttccagaa gtgcaaagaa tcacaagaat ggccgctttc   1980
atggccctac aacatgagcc accattgcct atttggtcct tggataaagc taatcttttg   2040
gcctcttcaa gattatggag aaaaactgtg gaggaaacca tcaagaacga attccctaca   2100
ttgaaggttc aacatcaatt gattgattct gccgccatga tcctagttaa gaacccaacc   2160
cacctaaatg gtattataat caccagcaac atgtttggtg atatcatctc cgatgaagcc   2220
tccgttatcc caggttcctt gggtttgttg ccatctgcgt ccttggcctc tttgccagac   2280
aagaacaccg catttggttt gtacgaacca tgccacggtt ctgctccaga tttgccaaag   2340
aataaggttg accctatcgc cactatcttg tctgctgcaa tgatgttgaa attgtcattg   2400
aacttgcctg aagaaggtaa ggccattgaa gatgcagtta aaaaggtttt ggatgcaggt   2460
atcagaactg gtgatttagg tggttccaac agtaccaccg aagtcggtga tgctgtcgcc   2520
gaagaagtta agaaaatcct tgcttaaaaa gattctcttt ttttatgata tttgtacata   2580
aactttataa atgaaattca taatagaaac gacacgaaat tacaaaatgg aatatgttca   2640
tagggtagac gaaactatat acgcaatcta catacattta tcaagaagga gaaaaggag   2700 gatagtaaag gaatacaggt aagcaaattg atactaatgg ctcaacgtga taaggaaaaa   2760
gaattgcact ttaacattaa tattgacaag gaggagggca ccacacaaaa agttaggtgt   2820
aacagaaaat catgaaacta cgattcctaa tttgatattg gaggattttc tctaaaaaaa   2880
aaaaaataca caaataaaa aacactcaat gacctgacca tttgatggag tttaagtcaa   2940
taccttcttg aagcatttcc cataatggtg aaagttccct caagaatttt actctgtcag   3000
aaacggcctt acgacgtagt cgatatggtg cactctcagt acaatctgct ctgatgccgc   3060
atagttaagc cagccccgac acccgccaac acccgctgac gcgccctgac gggcttgtct   3120
gctcccggca tccgcttaca gacaagctgt gaccgtctcc gggagctgca tgtgtcagag   3180
gttttcaccg tcatcaccga aacgcgcgag acgaaagggc ctcgtgatac gcctattttt   3240
ataggttaat gtcatgataa taatggtttc ttagtatgat ccaatatcaa aggaaatgat   3300
agcattgaag gatgagacta atccaattga ggagtggcag catatagaac agctaaaggg   3360
tagtgctgaa ggaagcatac gatacccgc atggaatggg ataatatcac aggaggtact   3420
agactacctt tcatcctaca taaatagacg catataagta cgcatttaag cataaacacg   3480
cactatgccg ttcttctcat gtatatatat atacaggcaa cacgcagata taggtgcgac   3540
gtgaacagtg agctgtatgt gcgcagctcg cgttgcattt tcggaagcgc tcgttttcgg   3600
aaacgctttg aagttcctat tccgaagttc ctattctcta gaaagtatag gaacttcaga   3660
gcgcttttga aaaccaaaag cgctctgaag acgcactttc aaaaaaccaa aaacgcaccg   3720
gactgtaacg agctactaaa atattgcgaa taccgcttcc acaaacattg ctcaaaagta   3780
tctctttgct atatatctct gtgctatatc cctatataac ctacccatcc acctttcgct   3840
ccttgaactt gcatctaaac tcgacctcta cattttttat gtttatctct agtattactc   3900
tttagacaaa aaaattgtag taagaactat tcatagagtg aatcgaaaac aatacgaaaa   3960
tgtaaacatt tcctatacgt agtatataga gacaaaatag aagaaccgt tcataatttt   4020 ctgaccaatg aagaatcatc aacgctatca ctttctgttc acaaagtatg cgcaatccac   4080
```

```
atcggtatag aatataatcg gggatgcctt tatcttgaaa aaatgcaccc gcagcttcgc    4140
tagtaatcag taaacgcggg aagtggagtc aggcttttt tatggaagag aaaatagaca    4200
ccaaagtagc cttcttctaa ccttaacgga cctacagtgc aaaaagttat caagagactg    4260
cattatagag cgcacaaagg agaaaaaaag taatctaaga tgctttgtta gaaaaatagc    4320
gctctcggga tgcatttttg tagaacaaaa aagaagtata gattctttgt tggtaaaata    4380
gcgctctcgc gttgcatttc tgttctgtaa aaatgcagct cagattcttt gtttgaaaaa    4440
ttagcgctct cgcgttgcat ttttgtttta caaaaatgaa gcacagattc ttcgttggta    4500
aaatagcgct ttcgcgttgc atttctgttc tgtaaaaatg cagctcagat tctttgtttg    4560
aaaaattagc gctctcgcgt tgcatttttg ttctacaaaa tgaagcacag atgcttcgtt    4620
caggtggcac ttttcgggga aatgtgcgcg gaacccctat ttgtttattt ttctaaatac    4680
attcaaatat gtatccgctc atgagacaat aaccctgata aatgcttcaa taatattgaa    4740
aaaggaagag tatgagtatt caacatttcc gtgtcgccct tattcccttt tttgcggcat    4800
tttgccttcc tgttttgct cacccagaaa cgctggtgaa agtaaaagat gctgaagatc    4860
agttgggtgc acgagtgggt tacatcgaac tggatctcaa cagcggtaag atccttgaga    4920
gttttcgccc cgaagaacgt tttccaatga tgagcacttt taaagttctg ctatgtggcg    4980
cggtattatc ccgtattgac gccgggcaag agcaactcgg tcgccgcata cactattctc    5040
agaatgactt ggttgagtac tcaccagtca cagaaaagca tcttacggat ggcatgacag    5100
taagagaatt atgcagtgct gccataacca tgagtgataa cactgcggcc aacttacttc    5160
tgacaacgat cggaggaccg aaggagctaa ccgcttttt gcacaacatg ggggatcatg    5220
taactcgcct tgatcgttgg gaaccggagc tgaatgaagc cataccaaac gacgagcgtg    5280
acaccacgat gcctgtagca atggcaacaa cgttgcgcaa actattaact ggcgaactac    5340
ttactctagc ttcccggcaa caattaatag actggatgga ggcggataaa gttgcaggac    5400
cacttctgcg ctcggccctt ccggctggct ggtttattgc tgataaatct ggagccggtg    5460
agcgtgggtc tcgcggtatc attgcagcac tggggccaga tggtaagccc tcccgtatcg    5520
tagttatcta cacgacgggg agtcaggcaa ctatggatga acgaaataga cagatcgctg    5580
agataggtgc ctcactgatt aagcattggt aactgtcaga ccaagtttac tcatatatac    5640
tttagattga tttaaaactt catttttaat ttaaaaggat ctaggtgaag atcctttttg    5700
ataatctcat gaccaaaatc ccttaacgtg agttttcgtt ccactgagcg tcagaccccg    5760
tagaaaagat caaaggatct tcttgagatc ctttttttct gcgcgtaatc tgctgcttgc    5820
aaacaaaaaa accaccgcta ccagcggtgg tttgtttgcc ggatcaagag ctaccaactc    5880
tttttccgaa ggtaactggc ttcagcagag cgcagatacc aaatactgtc cttctagtgt    5940
agccgtagtt aggccaccac ttcaagaact ctgtagcacc gcctacatac ctcgctctgc    6000
taatcctgtt accagtggct gctgccagtg gcgataagtc gtgtcttacc gggttggact    6060
caagacgata gttaccggat aaggcgcagc ggtcgggctg aacggggggt tcgtgcacac    6120
agcccagctt ggagcgaacg acctacaccg aactgagata cctacagcgt gagctatgag    6180
aaagcgccac gcttcccgaa gggagaaagg cggacaggta tccggtaagc ggcagggtcg    6240
gaacaggaga gcgcacgagg gagcttccag ggggaaacgc ctggtatctt tatagtcctg    6300
tcgggtttcg ccacctctga cttgagcgtc gatttttgtg atgctcgtca ggggggcgga    6360
gcctatggaa aaacgccagc aacgcggcct ttttacggtt cctggccttt tgctggcctt    6420
ttgctcacat gttctttcct gcgttatccc ctgattctgt ggataaccgt attaccgcct    6480
```

```
ttgagtgagc tgataccgct cgccgcagcc gaacgaccga gcgcagcgag tcagtgagcg    6540
aggaagcgga agagcgccca atacgcaaac cgcctctccc cgcgcgttgg ccgattcatt    6600
aatgcagctg gcacgacagg tttcccgact ggaaagcggg cagtgagcgc aacgcaatta    6660
atgtgagtta cctcactcat taggcacccc aggctttaca ctttatgctt ccggctccta    6720
tgttgtgtgg aattgtgagc ggataacaat ttcacacagg aaacagctat gaccatgatt    6780
acgccaagcg cgcaattaac cctcactaaa gggaacaaaa gctggagctc caccgcggga    6840
tttcgaaact aagttcttgg tgttttaaaa ctaaaaaaaa gactaactat aaaagtagaa    6900
tttaagaagt ttaagaaata gatttacaga attacaatca atacctaccg tctttatata    6960
cttattagtc aagtagggga ataatttcag ggaactggtt tcaacctttt ttttcagctt    7020
tttccaaatc agagagagca aaggtaata gaaggtgtaa gaaaatgaga tagatacatg     7080
cgtgggtcaa ttgccttgtg tcatcattta ctccaggcag gttgcatcac tccattgagg    7140
ttgtgcccgt tttttgcctg tttgtgcccc tgttctctgt agttgcgcta agagaatgga    7200
cctatgaact gatggttggt gaagaaaaca atattttggt gctgggattc ttttttttc     7260 tggatgccag cttaaaaagc gggctccatt atatttagtg gatgccagga ataaactgtt    7320
cacccagaca cctacgatgt tatatattct gtgtaacccg cccccttatt tgggcatgta    7380
cgggttacag cagaattaaa aggctaattt tttgactaaa taaagttagg aaaatcacta    7440
ctattaatta tttacgtatt ctttgaaatg gcagtattga taatgataaa ctcgaaatca    7500
ctagtggatc cgcccagcgg ccgcaccatg tctcctaagc ggcaagctct gccaatcaca    7560
attgatggcg caacttatga tgtgtctgct tgggtcaatc accacctgg aggagctgac     7620 attatcgaga actatcgcaa ccgcgatgcg accgatgtct tcatggtgat gcactctcaa    7680
gaagccgtcg ccaagttgaa gagaatgcct gttatggagc cttcctctcc tgacacacct    7740
gttgcaccca gcctaagcg tgatgagccc caggaggatt ccgcaagtt gcgggaggaa      7800 ttcatctcca agggtatgtt cgagacgagt ttcctttggt attttttacaa gacttcaact    7860 accgtcggtt tgatggtcct ttccatcttg atgaccgtgt acacgaattg gtatttcacc    7920
gctgctttgg ttcttggcgt gtgctaccaa cagctaggct ggttgtccca cgactattgc    7980
catcaccagg ttttcacaaa ccgcaagatt aacgacgctt tcggtctctt tttcggtaac    8040
gtgatgcagg gatactcaca gacttggtgg aaggataggc acaatggtca ccatgccgcc    8100
accaatgtgg tcggccatga cccagatatt gataacctcc ccatcctggc ttggtctccc    8160
gaagatgtca agagggctac tccttcgact cggaatctca tcaagtacca gcagtactac    8220
ttcattccca ccattgcatc ccttaggttc atctggtgcc tccaatccat cggcggcgtc    8280
atgtcctaca agagcgagga gaggaacctg tactacaagc gccagtacac taaggaggcg    8340
attggtctgg ccctccactg ggtgctcaag gccactttct attgcagtgc catgcctagc    8400
tttgccaccg gtttgggatg cttcttgatc tccgagctgc tcggaggatt tggcattgcc    8460
atcgttgtgt ttctgaatca ctatccttg gacaaggttg aggagactgt ctgggatgag     8520
cacgggttca gcgccagcca gatccacgag acgttgaaca ttaagcccgg ccttctcacc    8580
gattgggtct tggtggtct caactaccag attgagcacc acttgtggcc caacatgccc    8640
aggcacaacc tcacggcagc ttccctggag gtgcagaagt tgtgcgccaa gcacaacctg    8700
ccctacaggg ccccagccat catccccggg gttcagaaat tggtcagctt cttaggcgag    8760
attgcccagc tggctgctgt ccctgaatga gc                                  8792
```

<210> SEQ ID NO 66
<211> LENGTH: 4993
<212> TYPE: DNA
<213> ORGANISM: Artificial Sequence
<220> FEATURE:
<223> OTHER INFORMATION: plasmid pKR123r
<220> FEATURE:
<221> NAME/KEY: misc_feature
<222> LOCATION: (1126)..(1126)
<223> OTHER INFORMATION: n is a, c, g, or t

<400> SEQUENCE: 66

| | | | | | |
|---|---|---|---|---|---|
| ctagacctgc | aggatataat | gagccgtaaa | caaagatgat | taagtagtaa | ttaatacgta | 60 |
| ctagtaaaag | tggcaaaaga | taacgagaaa | gaaccaattt | ctttgcattc | ggccttagcg | 120 |
| gaaggcatat | ataagctttg | attatttat | ttagtgtaat | gatttcgtac | aaccaaagca | 180 |
| tttatttagt | actctcacac | ttgtgtcgcg | gccgcttggg | gggctatgga | agactttctt | 240 |
| agttagttgt | gtgaataagc | aatgttggga | gaatcgggac | tacttatagg | ataggaataa | 300 |
| aacagaaaag | tattaagtgc | taatgaaata | tttagactga | taattaaaat | cttcacgtat | 360 |
| gtccacttga | tataaaaacg | tcaggaataa | aggaagtaca | gtagaattta | aaggtactct | 420 |
| ttttatatat | acccgtgttc | tcttttggc | tagctagttg | cataaaaaat | aatctatatt | 480 |
| tttatcatta | ttttaaatat | cttatgagat | ggtaaatatt | tatcataatt | tttttactta | 540 |
| ttatttatta | tttgtgtgtg | taatacatat | agaagttaat | tacaaatttt | atttactttt | 600 |
| tcattatttt | gatatgattc | accattaatt | tagtgttatt | attttataata | gttcatttta | 660 |
| atcttttgt | atatattatg | cgtgcagtac | tttttccta | catataacta | ctattacatt | 720 |
| ttatttatat | aatattttta | ttaatgaatt | ttcgtgataa | tatgtaatat | tgttcattat | 780 |
| tatttcagat | tttttaaaaa | tatttgtgtt | attatttatg | aaatatgtaa | ttttttagt | 840 |
| atttgatttt | atgatgataa | agtgttctaa | attcaaaaga | aggggaaag | cgtaaacatt | 900 |
| aaaaaacgtc | atcaaacaaa | aacaaaatct | tgttaataaa | gataaaactg | tttgttttga | 960 |
| tcactgttat | ttcgtaatat | aaaaacatta | tttatattta | tattgttgac | aaccaaattt | 1020 |
| gcctatcaaa | tctaaccaat | ataatgcatg | cgtggcaggt | aatgtactac | catgaactta | 1080 |
| agtcatgaca | taataaaccg | tgaatctgac | caatgcatgt | acctanctaa | attgtatttg | 1140 |
| tgacacgaag | caaatgattc | aattcacaat | ggagatggga | aacaaataat | gaagaaccca | 1200 |
| gaactaagaa | agcttttctg | aaaaataaaa | taaaggcaat | gtcaaaagta | tactgcatca | 1260 |
| tcagtccaga | aagcacatga | tatttttta | tcagtatcaa | tgcagctagt | tttattttac | 1320 |
| aatatcgata | tagctagttt | aaatatattg | cagctagatt | tataaatatt | tgtgttatta | 1380 |
| tttatcattt | gtgtaatcct | gttttagta | ttttagttta | tatatgatga | taatgtattc | 1440 |
| caaatttaaa | agaagggaaa | taaatttaaa | caagaaaaaa | agtcatcaaa | caaaaaacaa | 1500 |
| atgaaagggt | ggaaagatgt | taccatgtaa | tgtgaatgtt | acagtatttc | ttttattata | 1560 |
| gagttaacaa | attaactaat | atgatttgt | taataatgat | aaaatatttt | ttttattatt | 1620 |
| atttcataat | ataaaaatag | tttacttaat | ataaaaaaaa | ttctatcgtt | cacaacaaag | 1680 |
| ttggccacct | aatttaacca | tgcatgtacc | catggaccat | attaggtaac | catcaaacct | 1740 |
| gatgaagaga | taaagagatg | aagacttaag | tcataacaca | aaaccataaa | aaacaaaaat | 1800 |
| acaatcaacc | gtcaatctga | ccaatgcatg | aaaaagctgc | aatagtgagt | ggcgacacaa | 1860 |
| agcacatgat | tttcttacaa | cggagataaa | accaaaaaaa | tatttcatga | acaacctaga | 1920 |
| acaaataaag | cttttatata | ataaatatat | aaataaataa | aggctatgga | ataatatact | 1980 |

```
tcaatatatt tggattaaat aaattgttgg cggggttgat atatttatac acacctaaag   2040
tcacttcaat ctcattttca cttaactttt attttttttt tcttttatt tatcataaag    2100 agaatattga taatatactt tttaacatat ttttatgaca ttttttattg gtgaaaactt   2160
attaaaaatc ataaattttg taagttagat ttatttaaag agttcctctt cttattttaa   2220
attttttaat aaattttaa ataactaaaa tttgtgttaa aaatgttaaa aaatgtgtta    2280
ttaacccttc tcttcgagga cgtacgtcta gagtcgacct gcaggcatgc aagcttggcg   2340
taatcatggt catagctgtt tcctgtgtga aattgttatc cgctcacaat tccacacaac   2400
atacgagccg gaagcataaa gtgtaaagcc tggggtgcct aatgagtgag ctaactcaca   2460
ttaattgcgt tgcgctcact gcccgctttc cagtcgggaa acctgtcgtg ccagctgcat   2520
taatgaatcg gccaacgcgc ggggagaggc ggtttgcgta ttgggcgctc ttccgcttcc   2580
tcgctcactg actcgctgcg ctcggtcgtt cggctgcggc gagcggtatc agctcactca   2640
aaggcggtaa tacggttatc cacagaatca ggggataacg caggaaagaa catgtgagca   2700
aaaggccagc aaaaggccag gaaccgtaaa aaggccgcgt tgctggcgtt tttccatagg   2760
ctccgccccc ctgacgagca tcacaaaaat cgacgctcaa gtcagaggtg gcgaaacccg   2820
acaggactat aaagatacca ggcgtttccc cctggaagct ccctcgtgcg ctctcctgtt   2880
ccgaccctgc cgcttaccgg atacctgtcc gcctttctcc cttcgggaag cgtggcgctt   2940
tctcatagct cacgctgtag gtatctcagt tcggtgtagg tcgttcgctc caagctgggc   3000
tgtgtgcacg aaccccccgt tcagcccgac cgctgcgcct tatccggtaa ctatcgtctt   3060
gagtccaacc cggtaagaca cgacttatcg ccactggcag cagccactgg taacaggatt   3120
agcagagcga ggtatgtagg cggtgctaca gagttcttga agtggtggcc taactacggc   3180
tacactagaa ggacagtatt tggtatctgc gctctgctga agccagttac cttcggaaaa   3240
agagttggta gctcttgatc cggcaaacaa accaccgctg gtagcggtgg tttttttgtt   3300
tgcaagcagc agattacgcg cagaaaaaaa ggatctcaag aagatccttt gatcttttct   3360
acggggtctg acgctcagtg gaacgaaaac tcacgttaag ggattttggt catgagatta   3420
tcaaaaagga tcttcaccta gatcctttta aattaaaaat gaagttttaa atcaatctaa   3480
agtatatatg agtaaacttg gtctgacagt taccaatgct taatcagtga ggcacctatc   3540
tcagcgatct gtctatttcg ttcatccata gttgcctgac tccccgtcgt gtagataact   3600
acgatacggg agggcttacc atctggcccc agtgctgcaa tgataccgcg agacccacgc   3660
tcaccggctc cagatttatc agcaataaac cagccagccg aagggccga gcgcagaagt    3720 ggtcctgcaa ctttatccgc ctccatccag tctattaatt gttgccggga agctagagta   3780
agtagttcgc cagttaatag tttgcgcaac gttgttgcca ttgctacagg catcgtggtg   3840
tcacgctcgt cgtttggtat ggcttcattc agctccggtt cccaacgatc aaggcgagtt   3900
acatgatccc ccatgttgtg caaaaaagcg gttagctcct tcggtcctcc gatcgttgtc   3960
agaagtaagt tggccgcagt gttatcactc atggttatgg cagcactgca taattctctt   4020
actgtcatgc catccgtaag atgcttttct gtgactggtg agtactcaac caagtcattc   4080
tgagaatagt gtatgcggcg accgagttgc tcttgcccgg cgtcaatacg ggataatacc   4140
gcgccacata gcagaacttt aaaagtgctc atcattggaa aacgttcttc ggggcgaaaa   4200
ctctcaagga tcttaccgct gttgagatcc agttcgatgt aacccactcg tgcacccaac   4260
tgatcttcag catcttttac tttcaccagc gtttctgggt gagcaaaaac aggaaggcaa   4320
```

-continued

```
aatgccgcaa aaaagggaat aagggcgaca cggaaatgtt gaatactcat actcttcctt    4380
tttcaatatt attgaagcat ttatcagggt tattgtctca tgagcggata catatttgaa    4440
tgtatttaga aaaataaaca aatagggggtt ccgcgcacat ttccccgaaa agtgccacct    4500
gacgtctaag aaaccattat tatcatgaca ttaacctata aaaataggcg tatcacgagg    4560
ccctttcgtc tcgcgcgttt cggtgatgac ggtgaaaacc tctgacacat gcagctcccg    4620
gagacggtca cagcttgtct gtaagcggat gccgggagca gacaagcccg tcagggcgcg    4680
tcagcgggtg ttggcgggtg tcggggctgg cttaactatg cggcatcaga gcagattgta    4740
ctgagagtgc accatatgcg gtgtgaaata ccgcacagat gcgtaaggag aaaataccgc    4800
atcaggcgcc attcgccatt caggctgcgc aactgttggg aagggcgatc ggtgcgggcc    4860
tcttcgctat tacgccagct ggcgaaaggg ggatgtgctg caaggcgatt aagttgggta    4920
acgccagggt tttcccagtc acgacgttgt aaaacgacgg ccagtgaatt cgagctcggt    4980
acccggggat cct                                                      4993
```

<210> SEQ ID NO 67
<211> LENGTH: 6267
<212> TYPE: DNA
<213> ORGANISM: Artificial Sequence
<220> FEATURE:
<223> OTHER INFORMATION: plasmid pKR1007
<220> FEATURE:
<221> NAME/KEY: misc_feature
<222> LOCATION: (4081)..(4081)
<223> OTHER INFORMATION: n is a, c, g, or t

<400> SEQUENCE: 67

```
ggccgcgaca caagtgtgag agtactaaat aaatgctttg gttgtacgaa atcattacac      60
taaataaaat aatcaaagct tatatatgcc ttccgctaag gccgaatgca agaaattgg      120 ttctttctcg ttatcttttg ccacttttac tagtacgtat taattactac ttaatcatct     180
ttgtttacgg ctcattatat cctgcaggtc tagaggatcc ccgggtaccg agctcgaatt    240
cactggccgt cgttttacaa cgtcgtgact gggaaaaccc tggcgttacc caacttaatc    300
gccttgcagc acatccccct ttcgccagct ggcgtaatag cgaagaggcc cgcaccgatc    360
gcccttccca acagttgcgc agcctgaatg gcgaatggcg cctgatgcgg tattttctcc    420
ttacgcatct gtgcggtatt tcacaccgca tatggtgcac tctcagtaca atctgctctg    480
atgccgcata gttaagccag ccccgacacc cgccaacacc cgctgacgcg ccctgacggg    540
cttgtctgct cccggcatcc gcttacagac aagctgtgac cgtctccggg agctgcatgt    600
gtcagaggtt ttcaccgtca tcaccgaaac gcgcgagacg aaagggcctc gtgatacgcc    660
tatttttata ggttaatgtc atgataataa tggtttctta cgtcaggt ggcactttc     720 ggggaaatgt gcgcggaacc cctatttgtt tatttttcta aatacattca aatatgtatc    780
cgctcatgag acaataaccc tgataaatgc ttcaataata ttgaaaaagg aagagtatga    840
gtattcaaca tttccgtgtc gcccttattc cctttttttgc ggcattttgc cttcctgttt    900
ttgctcaccc agaaacgctg gtgaaagtaa aagatgctga agatcagttg ggtgcacgag    960
tgggttacat cgaactggat ctcaacagcg gtaagatcct tgagagtttt cgccccgaag    1020
aacgttttcc aatgatgagc acttttaaag ttctgctatg tggcgcggta ttatcccgta    1080
ttgacgccgg gcaagagcaa ctcggtcgcc gcatacacta ttctcagaat gacttggttg    1140
agtactcacc agtcacagaa aagcatctta cggatggcat gacagtaaga gaattatgca    1200
gtgctgccat aaccatgagt gataacactg cggccaactt acttctgaca acgatcggag    1260
```

```
gaccgaagga gctaaccgct tttttgcaca acatggggga tcatgtaact cgccttgatc   1320
gttgggaacc ggagctgaat gaagccatac caaacgacga gcgtgacacc acgatgcctg   1380
tagcaatggc aacaacgttg cgcaaactat taactggcga actacttact ctagcttccc   1440
ggcaacaatt aatagactgg atggaggcgg ataaagttgc aggaccactt ctgcgctcgg   1500
cccttccggc tggctggttt attgctgata atctggagc cggtgagcgt gggtctcgcg   1560
gtatcattgc agcactgggg ccagatggta agccctcccg tatcgtagtt atctacacga   1620
cggggagtca ggcaactatg gatgaacgaa atagacagat cgctgagata ggtgcctcac   1680
tgattaagca ttggtaactg tcagaccaag tttactcata tatactttag attgatttaa   1740
aacttcattt ttaatttaaa aggatctagg tgaagatcct ttttgataat ctcatgacca   1800
aaatccctta acgtgagttt tcgttccact gagcgtcaga ccccgtagaa aagatcaaag   1860
gatcttcttg agatcctttt tttctgcgcg taatctgctg cttgcaaaca aaaaaaccac   1920
cgctaccagc ggtggtttgt ttgccggatc aagagctacc aactcttttt ccgaaggtaa   1980
ctggcttcag cagagcgcag ataccaaata ctgtccttct agtgtagccg tagttaggcc   2040
accacttcaa gaactctgta gcaccgccta catacctcgc tctgctaatc ctgttaccag   2100
tggctgctgc cagtggcgat aagtcgtgtc ttaccgggtt ggactcaaga cgatagttac   2160
cggataaggc gcagcggtcg ggctgaacgg ggggttcgtg cacacagccc agcttggagc   2220
gaacgaccta caccgaactg agatacctac agcgtgagct atgagaaagc gccacgcttc   2280
ccgaagggag aaaggcggac aggtatccgg taagcggcag ggtcggaaca ggagagcgca   2340
cgagggagct ccaggggga aacgcctggt atctttatag tcctgtcggg tttcgccacc   2400
tctgacttga gcgtcgattt ttgtgatgct cgtcaggggg gcggagccta tggaaaaacg   2460
ccagcaacgc ggccttttta cggttcctgg ccttttgctg ccttttgct cacatgttct   2520 ttcctgcgtt atcccctgat tctgtggata accgtattac cgcctttgag tgagctgata   2580
ccgctcgccg cagccgaacg accgagcgca gcgagtcagt gagcgaggaa gcggaagagc   2640
gcccaatacg caaaccgcct ctccccgcgc gttggccgat tcattaatgc agctggcacg   2700
acaggtttcc cgactggaaa gcgggcagtg agcgcaacgc aattaatgtg agttagctca   2760
ctcattaggc accccaggct ttacacttta tgcttccggc tcgtatgttg tgtggaattg   2820
tgagcggata acaatttcac acaggaaaca gctatgacca tgattacgcc aagcttgcat   2880
gcctgcaggt cgactctaga cgtacgtcct cgaagagaag ggttaataac acattttta   2940 acatttttaa cacaaatttt agttatttaa aaatttatta aaaatttaa ataagaaga   3000 ggaactcttt aaataaatct aacttacaaa atttatgatt tttaataagt tttcaccaat   3060
aaaaaatgtc ataaaaatat gttaaaaagt atattatcaa tattctcttt atgataaata   3120 aaagaaaaa aaaataaaa gttaagtgaa aatgagattg aagtgacttt aggtgtgtat   3180
aaatatatca accccgccaa caatttattt aatccaaata tattgaagta tattattcca   3240
tagcctttat ttatttatat atttattata taaaagcttt atttgttcta ggttgttcat   3300
gaaatatttt tttggttta tctccgttgt aagaaaatca tgtgctttgt gtcgccactc   3360
actattgcag ctttttcatg cattggtcag attgacggtt gattgtattt ttgtttttta   3420
tggttttgtg ttatgactta agtcttcatc tctttatctc ttcatcaggt ttgatggtta   3480
cctaatatgg tccatgggta catgcatggt taaattaggt ggccaacttt gttgtgaacg   3540
atagaatttt ttttatatta agtaaactat ttttatatta tgaaataata ataaaaaaaa   3600
```

```
tattttatca ttattaacaa aatcatatta gttaatttgt taactctata ataaaagaaa    3660
tactgtaaca ttcacattac atggtaacat cttttccaccc tttcatttgt tttttgtttg    3720
atgacttttt ttcttgttta aatttatttc ccttcttta aatttggaat acattatcat    3780
catatataaa ctaaaatact aaaaacagga ttacacaaat gataaataat aacacaaata    3840
tttataaatc tagctgcaat atatttaaac tagctatatc gatattgtaa aataaaacta    3900
gctgcattga tactgataaa aaaatatcat gtgctttctg gactgatgat gcagtatact    3960
tttgacattg cctttatttt attttcaga aaagctttct tagttctggg ttcttcatta    4020
tttgtttccc atctccattg tgaattgaat catttgcttc gtgtcacaaa tacaatttag    4080
ntaggtacat gcattggtca gattcacggt ttattatgtc atgacttaag ttcatggtag    4140
tacattacct gccacgcatg cattatattg gttagatttg ataggcaaat ttggttgtca    4200
acaatataaa tataaataat gttttatat tacgaaataa cagtgatcaa acaaacagt    4260 tttatcttta ttaacaagat tttgttttg tttgatgacg ttttttaatg tttacgcttt    4320
cccccttctt ttgaatttag aacactttat catcataaaa tcaaatacta aaaaaattac    4380
atatttcata ataataaca caatatttt taaaaaatct gaaataataa tgaacaatat    4440
tacatattat cacgaaaatt cattaataaa aatattatat aaataaaatg taatagtagt    4500
tatatgtagg aaaaagtac tgcacgcata atatatacaa aagattaaa atgaactatt    4560 ataaataata acactaaatt aatggtgaat catatcaaaa taatgaaaaa gtaaataaaa    4620
tttgtaatta acttctatat gtattacaca cacaaataa aaataatagt aaaaaaaatt    4680
atgataaata tttaccatct cataagatat ttaaaataat gataaaaata tagattattt    4740
tttatgcaac tagctagcca aaaagagaac acgggtatat ataaaaagag tacctttaaa    4800
ttctactgta cttcctttat tcctgacgtt tttatatcaa gtggacatac gtgaagattt    4860
taattatcag tctaaatatt tcattagcac ttaaactttt tctgttttat tcctatccta    4920
taagtagtcc cgattctccc aacattgctt attcacacaa ctaactaaga aagtcttcca    4980
tagcccccca agcggccgca ccatgtctcc taagcggcaa gctctgccaa tcacaattga    5040
tggcgcaact tatgatgtgt ctgcttgggt caatcaccac cctggaggag ctgacattat    5100
cgagaactat cgcaaccgcg atgcgaccga tgtcttcatg gtgatgcact ctcaagaagc    5160
cgtcgccaag ttgaagagaa tgcctgttat ggagccttcc tctcctgaca cacctgttgc    5220
acccaagcct aagcgtgatg agccccagga ggatttccgc aagttgcggg aggaattcat    5280
ctccaagggt atgttcgaga cgagtttcct ttggtatttt tacaagactt caactaccgt    5340
cggtttgatg gtccttttcca tcttgatgac cgtgtacacg aattggtatt tcaccgctgc    5400
tttggttctt ggcgtgtgct accaacagct aggctggttg tcccacgact attgccatca    5460
ccaggttttc acaaaccgca agattaacga cgctttcggt ctcttttcg gtaacgtgat    5520 gcagggatac tcacagactt ggtggaagga taggcacaat ggtcaccatg ccgccaccaa    5580
tgtggtcggc catgacccag atattgataa cctccccatc ctggcttggt ctcccgaaga    5640
tgtcaagagg gctactcctt cgactcggaa tctcatcaag taccagcagt actacttcat    5700
tcccaccatt gcatccctta ggttcatctg gtgcctccaa tccatcggcg cgtcatgtc    5760 ctacaagagc gaggagagga acctgtacta caagcgccag tacactaagg aggcgattgg    5820
tctggccctc cactgggtgc tcaaggccac tttctattgc agtgccatgc ctagctttgc    5880
caccggtttg gatgcttct tgatctccga gctgctcgga ggatttggca ttgccatcgt    5940
tgtgtttctg aatcactatc ctttggacaa ggttgaggag actgtctggg atgagcacgg    6000
```

| | |
|---|---:|
| gttcagcgcc agccagatcc acgagacgtt gaacattaag cccggccttc tcaccgattg | 6060 |
| ggtctttggt ggtctcaact accagattga gcaccacttg tggcccaaca tgcccaggca | 6120 |
| caacctcacg gcagcttccc tggaggtgca gaagttgtgc gccaagcaca acctgcccta | 6180 |
| cagggcccca gccatcatcc ccggggttca gaaattggtc agcttcttag gcgagattgc | 6240 |
| ccagctggct gctgtccctg aatgagc | 6267 |

<210> SEQ ID NO 68
<211> LENGTH: 7887
<212> TYPE: DNA
<213> ORGANISM: Artificial Sequence
<220> FEATURE:
<223> OTHER INFORMATION: plasmid pKR607

<400> SEQUENCE: 68

| | |
|---|---:|
| ggccgcagta tatcttaaat tctttaatac ggtgtactag gatattgaac tggttcttga | 60 |
| tgatgaaaac ctgggccgag attgcagcta tttatagtca taggtcttgt taacatgcat | 120 |
| ggacatttgg ccacggggtg gcatgcagtt tgacgggtgt tgaaataaac aaaaatgagg | 180 |
| tggcggaaga gaatacgagt ttgaggttgg gttagaaaca acaaatgtga gggctcatga | 240 |
| tgggttgagt tggtgaatgt tttgggctgc tcgattgaca cctttgtgag tacgtgttgt | 300 |
| tgtgcatggc ttttggggtc cagttttttt ttcttgacgc ggcgatcctg atcagctagt | 360 |
| ggataagtga tgtccactgt gtgtgattgc gttttgtttt gaattttatg aacttagaca | 420 |
| ttgctatgca aaggatactc tcattgtgtt ttgtcttctt ttgttccttg cttttttctt | 480 |
| atgatccaag agactagtca gtgttgtggc attcgagact accaagatta attatgatgg | 540 |
| gggaaggata agtaactgat tagtacggac tgttaccaaa ttaattaata gcggcaaat | 600 |
| gaagggcatg gatcaaaagc ttggatctcc tgcaggatct ggccggccgg atctcgtacg | 660 |
| gatccgtcga cggcgcgccc gatcatccgg atatagttcc tcctttcagc aaaaaacccc | 720 |
| tcaagacccg tttagaggcc caaggggtt atgctagtta ttgctcagcg gtggcagcag | 780 |
| ccaactcagc ttcctttcgg gctttgttag cagccggatc gatccaagct gtacctcact | 840 |
| attcctttgc cctcggacga gtgctgggc gtcggtttcc actatcggcg agtacttcta | 900 |
| cacagccatc ggtccagacg gccgcgcttc tgcgggcgat ttgtgtacgc ccgacagtcc | 960 |
| cggctccgga tcggacgatt gcgtcgcatc gaccctgcgc ccaagctgca tcatcgaaat | 1020 |
| tgccgtcaac caagctctga tagagttggt caagaccaat gcggagcata tacgcccgga | 1080 |
| gccgcggcga tcctgcaagc tccggatgcc tccgctcgaa gtagcgcgtc tgctgctcca | 1140 |
| tacaagccaa ccacggcctc cagaagaaga tgttggcgac ctcgtattgg gaatccccga | 1200 |
| acatcgcctc gctccagtca atgaccgctg ttatgcggcc attgtccgtc aggacattgt | 1260 |
| tggagccgaa atccgcgtgc acgaggtgcc ggacttcggg gcagtcctcg gcccaaagca | 1320 |
| tcagctcatc gagagcctgc gcgacggacg cactgacggt gtcgtccatc acagtttgcc | 1380 |
| agtgatacac atggggatca gcaatcgcgc atatgaaatc acgccatgta gtgtattgac | 1440 |
| cgattccttg cggtccgaat gggccgaacc cgctcgtctg gctaagatcg gccgcagcga | 1500 |
| tcgcatccat agcctccgcg accggctgca gaacagcggg cagttcggtt tcaggcaggt | 1560 |
| cttgcaacgt gacaccctgt gcacggcggg agatgcaata ggtcaggctc tcgctgaatt | 1620 |
| ccccaatgtc aagcacttcc ggaatcggga gcgcggccga tgcaaagtgc cgataaacat | 1680 |
| aacgatcttt gtagaaacca tcggcgcagc tatttacccg caggacatat ccacgccctc | 1740 |

```
ctacatcgaa gctgaaagca cgagattctt cgccctccga gagctgcatc aggtcggaga   1800
cgctgtcgaa cttttcgatc agaaacttct cgacagacgc cgcggtgagt tcaggctttt   1860
ccatgggtat atctccttct taaagttaaa caaaattatt tctagaggga accgttgtg    1920
gtctccctat agtgagtcgt attaatttcg cgggatcgag atcgatccaa ttccaatccc   1980
acaaaaatct gagcttaaca gcacagttgc tcctctcaga gcagaatcgg gtattcaaca   2040
ccctcatatc aactactacg ttgtgtataa cggtccacat gccggtatat acgatgactg   2100
gggttgtaca aaggcggcaa caaacggcgt tcccggagtt gcacacaaga aatttgccac   2160
tattacagag gcaagagcag cagctgacgc gtacacaaca agtcagcaaa cagacaggtt   2220
gaacttcatc cccaaggag aagctcaact caagcccaag agctttgcta aggccctaac    2280
aagcccacca aagcaaaaag cccactggct cacgctagga accaaaaggc ccagcagtga   2340
tccagcccca aaagagatct cctttgcccc ggagattaca atggacgatt cctctatct    2400
ttacgatcta ggaaggaagt tcgaaggtga aggtgacgac actatgttca ccactgataa   2460
tgagaaggtt agcctcttca atttcagaaa gaatgctgac ccacagatgg ttagagaggc   2520
ctacgcagca ggtctcatca agacgatcta cccgagtaac aatctccagg agatcaaata   2580
ccttcccaag aaggttaaag atgcagtcaa aagattcagg actaattgca tcaagaacac   2640
agagaaagac atatttctca agatcagaag tactattcca gtatggacga ttcaaggctt   2700
gcttcataaa ccaaggcaag taatagagat tggagtctct aaaaaggtag ttcctactga   2760
atctaaggcc atgcatggag tctaagattc aaatcgagga tctaacagaa ctcgccgtga   2820
agactggcga acagttcata cagagtcttt tacgactcaa tgacaagaag aaaatcttcg   2880
tcaacatggt ggagcacgac actctggtct actccaaaaa tgtcaaagat acagtctcag   2940
aagaccaaag ggctattgag acttttcaac aaaggataat ttcgggaaac ctcctcggat   3000
tccattgccc agctatctgt cacttcatcg aaaggacagt agaaaaggaa ggtggctcct   3060
acaaatgcca tcattgcgat aaaggaaagg ctatcattca agatgcctct gccgacagtg   3120
gtcccaaaga tggacccca cccacgagga gcatcgtgga aaaagaagac gttccaacca   3180
cgtcttcaaa gcaagtggat tgatgtgaca tctccactga cgtaagggat gacgcacaat   3240
cccactatcc ttcgcaagac ccttcctcta tataaggaag ttcatttcat ttggagagga   3300
cacgctcgag ctcatttctc tattacttca gccataacaa aagaactctt ttctcttctt   3360
attaaaccat gaaaaagcct gaactcaccg cgacgtctgt cgagaagttt ctgatcgaaa   3420
agttcgacag cgtctccgac ctgatgcagc tctcggaggg cgaagaatct cgtgctttca   3480
gcttcgatgt aggagggcgt ggatatgtcc tgcgggtaaa tagctgcgcc gatggttttct  3540
acaaagatcg ttatgtttat cggcactttg catcggccgc gctcccgatt ccggaagtgc   3600
ttgacattgg ggaattcagc gagagcctga cctattgcat ctcccgccgt gcacagggtg   3660
tcacgttgca agacctgcct gaaaccgaac tgcccgctgt tctgcagccg gtcgcggagg   3720
ccatggatgc gatcgctgcg gccgatctta gccagacgag cgggttcggc ccattcggac   3780
cgcaaggaat cggtcaatac actacatggc gtgatttcat atgcgcgatt gctgatcccc   3840
atgtgtatca ctggcaaact gtgatggacg acaccgtcag tgcgtccgtc gcgcaggctc   3900
tcgatgagct gatgctttgg gccgaggact gccccgaagt ccggcacctc gtgcacgcgg   3960
atttcggctc caacaatgtc ctgacggaca atggccgcat aacagcggtc attgactgga   4020
gcgaggcgat gttcggggat tcccaatacg aggtcgccaa catcttcttc tggaggccgt   4080
ggttggcttg tatggagcag cagacgcgct acttcgagcg gaggcatccg gagcttgcag   4140
```

```
gatcgccgcg gctccgggcg tatatgctcc gcattggtct tgaccaactc tatcagagct    4200
tggttgacgg caatttcgat gatgcagctt gggcgcaggg tcgatgcgac gcaatcgtcc    4260
gatccggagc cgggactgtc gggcgtacac aaatcgcccg cagaagcgcg gccgtctgga    4320
ccgatggctg tgtagaagta ctcgccgata gtggaaaccg acgccccagc actcgtccga    4380
gggcaaagga atagtgaggt acctaaagaa ggagtgcgtc gaagcagatc gttcaaacat    4440
ttggcaataa agtttcttaa gattgaatcc tgttgccggt cttgcgatga ttatcatata    4500
atttctgttg aattacgtta agcatgtaat aattaacatg taatgcatga cgttatttat    4560
gagatgggtt tttatgatta gagtcccgca attatacatt taatacgcga tagaaaacaa    4620
aatatagcgc gcaaactagg ataaattatc gcgcgcggtg tcatctatgt tactagatcg    4680
atgtcgaatc gatcaacctg cattaatgaa tcggccaacg cgcggggaga ggcggtttgc    4740
gtattgggcg ctcttccgct tcctcgctca ctgactcgct gcgctcggtc gttcggctgc    4800
ggcgagcggt atcagctcac tcaaaggcgg taatacggtt atccacagaa tcaggggata    4860
acgcaggaaa gaacatgtga gcaaaaggcc agcaaaaggc caggaaccgt aaaaaggccg    4920
cgttgctggc gtttttccat aggctccgcc ccctgacga gcatcacaaa aatcgacgct     4980
caagtcagag gtggcgaaac ccgacaggac tataaagata ccaggcgttt ccccctggaa    5040
gctccctcgt gcgctctcct gttccgaccc tgccgcttac cggatacctg tccgcctttc    5100
tcccttcggg aagcgtggcg ctttctcaat gctcacgctg taggtatctc agttcggtgt    5160
aggtcgttcg ctccaagctg ggctgtgtgc acgaaccccc cgttcagccc gaccgctgcg    5220
ccttatccgg taactatcgt cttgagtcca acccggtaag acacgactta tcgccactgg    5280
cagcagccac tggtaacagg attagcagag cgaggtatgt aggcggtgct acagagttct    5340
tgaagtggtg gcctaactac ggctacacta aaggacagt atttggtatc tgcgctctgc     5400
tgaagccagt taccttcgga aaagagttg gtagctcttg atccggcaaa caaaccaccg     5460
ctggtagcgg tggttttttt gtttgcaagc agcagattac gcgcagaaaa aaaggatctc    5520
aagaagatcc tttgatcttt tctacggggt ctgacgctca gtggaacgaa aactcacgtt    5580
aagggatttt ggtcatgaca ttaacctata aaaataggcg tatcacgagg ccctttcgtc    5640
tcgcgcgttt cggtgatgac ggtgaaaacc tctgacacat gcagctcccg gagacggtca    5700
cagcttgtct gtaagcggat gccgggagca gacaagcccg tcagggcgcg tcagcgggtg    5760
ttggcgggtg tcggggctgg cttaactatg cggcatcaga gcagattgta ctgagagtgc    5820
accatatgga catattgtcg ttagaacgcg gctacaatta atacataacc ttatgtatca    5880
tacacatacg atttaggtga cactatagaa cggcgcgcca agcttgttga acatccctg     5940 aagtgtctca ttttatttta tttattcttt gctgataaaa aaataaaata aagaagcta     6000 agcacacggt caaccattgc tctactgcta aaagggttat gtgtagtgtt ttactgcata    6060
aattatgcag caaacaagac aactcaaatt aaaaaatttc ctttgcttgt ttttttgttg    6120
tctctgactt gactttcttg tggaagttgg ttgtataagg attgggacac cattgtcctt    6180
cttaatttaa ttttattctt tgctgataaa aaaaaaaatt tcatatagtg ttaaataata    6240
atttgttaaa taaccaaaaa gtcaaatatg tttactctcg tttaaataat tgagattcgt    6300
ccagcaaggc taaacgattg tatagattta tgacaatatt tacttttta tagataaatg     6360 ttatattata ataaatttat atacatatat tatatgttat ttattattat tttaaatcct    6420
tcaatatttt atcaaaccaa ctcataattt tttttttatc tgtaagaagc aataaaatta    6480
```

```
aatagaccca ctttaaggat gatccaacct ttatacagag taagagagtt caaatagtac    6540
cctttcatat acatatcaac taaaatatta gaaatatcat ggatcaaacc ttataaagac    6600
attaaataag tggataagta taatatataa atgggtagta tataatatat aaatggatac    6660
aaacttctct ctttataatt gttatgtctc cttaacatcc taatataata cataagtggg    6720
taatatataa tatataaatg gagacaaact tcttccatta taattgttat gtcttcttaa    6780
cacttatgtc tcgttcacaa tgctaaggtt agaattgttt agaaagtctt atagtacaca    6840 tttgttttg  tactatttga agcattccat aagccgtcac gattcagatg atttataata    6900
ataagaggaa atttatcata gaacaataag gtgcatagat agagtgttaa tatatcataa    6960
catcctttgt ttattcatag aagaagtgag atggagctca gttattatac tgttacatgg    7020
tcggatacaa tattccatgc tctccatgag ctcttacacc tacatgcatt ttagttcata    7080
cttgcggccg ctaaagctgc ttaccagcct tagcggattt cttggtggcc aggttgtcct    7140
ggtaaaagaa gtgacagaac aggagaaaga cagatccgac gtaggcgtag ttgaaagccc    7200
aggagaacag cttgcccttg tcagagttga agcagggaac gttgatgtag tcccagacca    7260
ggagaaagcc accgacgaac tggcaaatct gcatggcagt gatcagaggc ttggccttga    7320
acttgtagcc agcggcagtc agtccatagt aggtgtacat gatggtgtga atgaacgagt    7380
taaagaacat gaagatccac acaccctcgt tgtgcagtcg aatgccgagg tagacgtccc    7440
agggagctcc aaagtgatgg aaggcctgca gaaaggacac tcgcttgccc ttgaggacca    7500
gccaagcggt gtcgaggtac tccacgtact tagaatagta gaaggccttg gcagtccagg    7560
tgaacagctt ggagtcccag acaggagagg gacactgaaa gagaggctgg ggagtatcac    7620
cggtctgtct tcgcagccag gctccagtac cgtagtccca gccgagagcg gtggcagtca    7680
cgtagaagga cagggcagag aagagagcca ggaggacgtt gtaccagatc atggaggttc    7740
ggtaggctcc tttcttctcg tccacgagac cagagtttcg caggagaggc ttcaggagca    7800
ggtaggagaa ggtgccaatg aggatttcgg gatcggtgac ggcagcccag attcgctcgc    7860
cagcgtcgtt ggccagagcc atggtgc                                        7887
```

<210> SEQ ID NO 69
<211> LENGTH: 11473
<212> TYPE: DNA
<213> ORGANISM: Artificial Sequence
<220> FEATURE:
<223> OTHER INFORMATION: plasmid pKR1013
<220> FEATURE:
<221> NAME/KEY: misc_feature
<222> LOCATION: (10276)..(10276)
<223> OTHER INFORMATION: n is a, c, g, or t

<400> SEQUENCE: 69

```
ggagatccaa gcttttgatc catgcccttc atttgccgct tattaattaa tttggtaaca     60
gtccgtacta atcagttact tatccttccc ccatcataat taatcttggt agtctcgaat    120
gccacaacac tgactagtct cttggatcat aagaaaagc  caaggaacaa agaagacaa     180 aacacaatga gagtatcctt tgcatagcaa tgtctaagtt cataaaattc aaacaaaaac    240
gcaatcacac acagtggaca tcacttatcc actagctgat caggatcgcc gcgtcaagaa    300
aaaaaaactg accccaaaa  gccatgcaca acaacacgta ctcacaaagg tgtcaatcga    360
gcagcccaaa acattcacca actcaaccca tcatgagccc tcacatttgt tgtttctaac    420
ccaacctcaa actcgtattc tcttccgcca cctcattttt gtttatttca acacccgtca    480
aactgcatgc caccccgtgg ccaaatgtcc atgcatgtta acaagaccta tgactataaa    540
```

```
tagctgcaat ctcggcccag gttttcatca tcaagaacca gttcaatatc ctagtacacc    600
gtattaaaga atttaagata tactgcggcc gcaccatggc tctggccaac gacgctggcg    660
agcgaatctg ggctgccgtc accgatcccg aaatcctcat tggcaccttc tcctacctgc    720
tcctgaagcc tctcctgcga aactctggtc tcgtggacga agaaaagga gcctaccgaa    780
cctccatgat ctggtacaac gtcctcctgg ctctcttctc tgccctgtcc ttctacgtga    840
ctgccaccgc tctcggctgg gactacggta ctggagcctg gctgcgaaga cagaccggtg    900
atactcccca gcctctcttt cagtgtccct ctcctgtctg ggactccaag ctgttcacct    960
ggactgccaa ggccttctac tattctaagt acgtggagta cctcgacacc gcttggctgg   1020
tcctcaaggg caagcgagtg tcctttctgc aggccttcca tcactttgga gctccctggg   1080
acgtctacct cggcattcga ctgcacaacg agggtgtgtg gatcttcatg ttctttaact   1140
cgttcattca caccatcatg tacacctact atggactgac tgccgctggc tacaagttca   1200
aggccaagcc tctgatcact gccatgcaga tttgccagtt cgtcggtggc tttctcctgg   1260
tctgggacta catcaacgtt ccctgcttca actctgacaa gggcaagctg ttctcctggg   1320
cttcaacta cgcctacgtc ggatctgtct ttctcctgtt ctgtcacttc ttttaccagg   1380
acaacctggc caccaagaaa tccgctaagg ctggtaagca gctttagcgg ccgcaagtat   1440
gaactaaaat gcatgtaggt gtaagagctc atggagagca tggaatattg tatccgacca   1500
tgtaacagta taataactga gctccatctc acttcttcta tgaataaaca aaggatgtta   1560
tgatatatta acactctatc tatgcacctt attgttctat gataaatttc ctcttattat   1620
tataaatcat ctgaatcgtg acggcttatg gaatgcttca aatagtacaa aaacaaatgt   1680
gtactataag actttctaaa caattctaac cttagcattg tgaacgagac ataagtgtta   1740
agaagacata acaattataa tggaagaagt ttgtctccat ttatatatta tatattaccc   1800
acttatgtat tatattagga tgttaaggag acataacaat tataaagaga gaagtttgta   1860
tccattttata tattatatac tacccatttta tatattatac ttatccactt atttaatgtc   1920
tttataaggt ttgatccatg atatttctaa tattttagtt gatatgtata tgaaagggta   1980
ctatttgaac tctcttactc tgtataaagg ttggatcatc cttaaagtgg gtctatttaa   2040
ttttattgct tcttacagat aaaaaaaaaa ttatgagttg gtttgataaa atattgaagg   2100
atttaaaata ataataaata acatataata tatgtatata aatttattat aatataacat   2160
ttatctataa aaaagtaaat attgtcataa atctatacaa tcgtttagcc ttgctggacg   2220
aatctcaatt atttaaacga gagtaaacat atttgacttt ttggttattt aacaaattat   2280
tatttaacac tatatgaaat ttttttttttt atcagcaaag aataaaatta aattaagaag   2340
gacaatggtg tcccaatcct tatacaacca acttccacaa gaaagtcaag tcagagacaa   2400
caaaaaaaca agcaaaggaa attttttaat ttgagttgtc ttgtttgctg cataatttat   2460
gcagtaaaac actacacata acccttttag cagtagagca atggttgacc gtgtgcttag   2520
cttctttttat tttattttttt tatcagcaaa gaataaataa aataaaatga gacacttcag   2580
ggatgtttca acaagcttgg cgcgccgttc tatagtgtca cctaaatcgt atgtgtatga   2640
tacataaggt tatgtattaa ttgtagccgc gttctaacga caatatgtcc atatggtgca   2700
ctctcagtac aatctgctct gatgccgcat agttaagcca gccccgacac cgccaacac   2760
ccgctgacgc gccctgacgg gcttgtctgc tcccggcatc cgcttacaga caagctgtga   2820
ccgtctccgg gagctgcatg tgtcagaggt tttcaccgtc atcaccgaaa cgcgcgagac   2880
```

```
gaaagggcct cgtgatacgc ctattttat aggttaatgt catgaccaaa atcccttaac    2940
gtgagttttc gttccactga gcgtcagacc ccgtagaaaa gatcaaagga tcttcttgag   3000
atccttttt tctgcgcgta atctgctgct tgcaaacaaa aaaaccaccg ctaccagcgg    3060
tggtttgttt gccggatcaa gagctaccaa ctcttttcc gaaggtaact ggcttcagca    3120
gagcgcagat accaaatact gtccttctag tgtagccgta gttaggccac cacttcaaga   3180
actctgtagc accgcctaca tacctcgctc tgctaatcct gttaccagtg ctgctgcca    3240
gtggcgataa gtcgtgtctt accgggttgg actcaagacg atagttaccg gataaggcgc   3300
agcggtcggg ctgaacgggg ggttcgtgca cacagcccag cttggagcga acgacctaca   3360
ccgaactgag atacctacag cgtgagcatt gagaaagcgc cacgcttccc gaagggagaa   3420
aggcggacag gtatccggta agcggcaggg tcggaacagg agagcgcacg agggagcttc   3480
caggggggaaa cgcctggtat ctttatagtc ctgtcgggtt tcgccacctc tgacttgagc  3540
gtcgattttt gtgatgctcg tcaggggggc ggagcctatg gaaaaacgcc agcaacgcgg   3600
ccttttttacg gttcctggcc ttttgctggc cttttgctca catgttcttt cctgcgttat   3660
cccctgattc tgtggataac cgtattaccg cctttgagtg agctgatacc gctcgccgca   3720
gccgaacgac cgagcgcagc gagtcagtga gcgaggaagc ggaagagcgc ccaatacgca   3780
aaccgcctct ccccgcgcgt tggccgattc attaatgcag gttgatcgat tcgacatcga   3840
tctagtaaca tagatgacac cgcgcgcgat aatttatcct agtttgcgcg ctatattttg   3900
ttttctatcg cgtattaaat gtataattgc gggactctaa tcataaaac ccatctcata   3960
aataacgtca tgcattacat gttaattatt acatgcttaa cgtaattcaa cagaaattat   4020
atgataatca tcgcaagacc ggcaacagga ttcaatctta agaaacttta ttgccaaatg   4080
tttgaacgat ctgcttcgac gcactccttc tttaggtacc tcactattcc tttgccctcg   4140
gacgagtgct ggggcgtcgg tttccactat cggcgagtac ttctacacag ccatcggtcc   4200
agacggccgc gcttctgcgg gcgatttgtg tacgcccgac agtcccggct ccggatcgga   4260
cgattgcgtc gcatcgaccc tgcgcccaag ctgcatcatc gaaattgccg tcaaccaagc   4320
tctgatagag ttggtcaaga ccaatgcgga gcatatacgc ccggagccgc ggcgatcctg   4380
caagctccgg atgcctccgc tcgaagtagc gcgtctgctg ctccatacaa gccaaccacg   4440
gcctccagaa gaagatgttg gcgacctcgt attgggaatc cccgaacatc gcctcgctcc   4500
agtcaatgac cgctgttatg cggccattgt ccgtcaggac attgttggag ccgaaatccg   4560
cgtgcacgag gtgccggact tcggggcagt cctcggccca agcatcagc tcatcgagag    4620
cctgcgcgac ggacgcactg acggtgtcgt ccatcacagt ttgccagtga tacacatggg   4680
gatcagcaat cgcgcatatg aaatcacgcc atgtagtgta ttgaccgatt ccttgcggtc   4740
cgaatgggcc gaacccgctc gtctggctaa gatcggccgc agcgatcgca tccatggcct   4800
ccgcgaccgg ctgcagaaca gcgggcagtt cggtttcagg caggtcttgc aacgtgacac   4860
cctgtgcacg gcgggagatg caataggtca ggctctcgct gaattcccca atgtcaagca   4920
cttccggaat cgggagcgcg gccgatgcaa agtgccgata aacataacga tctttgtaga   4980
aaccatcggc gcagctattt acccgcagga catatccacg ccctcctaca tcgaagctga   5040
aagcacgaga ttcttcgccc tccgagagct gcatcaggtc ggagacgctg tcgaactttt   5100
cgatcagaaa cttctcgaca gacgtcgcgg tgagttcagg ctttttcatg gtttaataag   5160
aagagaaaag agttctttg ttatggctga agtaatagag aaatgagctc gagcgtgtcc    5220
tctccaaatg aaatgaactt ccttatatag aggaagggtc ttgcgaagga tagtgggatt   5280
```

```
gtgcgtcatc ccttacgtca gtggagatgt cacatcaatc cacttgcttt gaagacgtgg    5340
ttggaacgtc ttcttttttcc acgatgctcc tcgtgggtgg gggtccatct ttgggaccac    5400
tgtcggcaga ggcatcttga atgatagcct ttcctttatc gcaatgatgg catttgtagg    5460
agccaccttc cttttctact gtcctttcga tgaagtgaca gatagctggg caatggaatc    5520
cgaggaggtt tcccgaaatt atcctttgtt gaaaagtctc aatagccctt tggtcttctg    5580
agactgtatc tttgacattt ttggagtaga ccagagtgtc gtgctccacc atgttgacga    5640
agattttctt cttgtcattg agtcgtaaaa gactctgtat gaactgttcg ccagtcttca    5700
cggcgagttc tgttagatcc tcgatttgaa tcttagactc catgcatggc cttagattca    5760
gtaggaacta cctttttaga gactccaatc tctattactt gccttggttt atgaagcaag    5820
ccttgaatcg tccatactgg aatagtactt ctgatcttga gaaatatgtc tttctctgtg    5880
ttcttgatgc aattagtcct gaatcttttg actgcatctt taaccttctt gggaaggtat    5940
ttgatctcct ggagattgtt actcgggtag atcgtcttga tgagacctgc tgcgtaggcc    6000
tctctaacca tctgtgggtc agcattcttt ctgaaattga agaggctaac cttctcatta    6060
tcagtggtga acatagtgtc gtcaccttca ccttcgaact tccttcctag atcgtaaaga    6120
tagaggaaat cgtccattgt aatctccggg gcaaaggaga tctcttttgg ggctggatca    6180
ctgctgggcc ttttggttcc tagcgtgagc cagtgggctt tttgctttgg tgggcttgtt    6240
agggccttag caaagctctt gggcttgagt tgagcttctc ctttggggat gaagttcaac    6300
ctgtctgttt gctgacttgt tgtgtacgcg tcagctgctg ctcttgcctc tgtaatagtg    6360
gcaaatttct tgtgtgcaac tccgggaacg ccgtttgttg ccgcctttgt acaaccccag    6420
tcatcgtata taccggcatg tggaccgtta tacacaacgt agtagttgat atgagggtgt    6480
tgaatacccg attctgctct gagaggagca actgtgctgt taagctcaga ttttttgtggg    6540 attggaattg gatcgatctc gatcccgcga aattaatacg actcactata gggagaccac    6600
aacggtttcc ctctagaaat aattttgttt aactttaaga aggagatata cccatggaaa    6660
agcctgaact caccgcgacg tctgtcgaga gttttctgat cgaaaagttc gacagcgtct    6720
ccgacctgat gcagctctcg gagggcgaag aatctcgtgc tttcagcttc gatgtaggag    6780
ggcgtggata tgtcctgcgg gtaaatagct gcgccgatgg tttctacaaa gatcgttatg    6840
tttatcggca cttgcatcg gccgcgctcc cgattccgga agtgcttgac attggggaat    6900
tcagcgagag cctgacctat tgcatctccc gccgtgcaca gggtgtcacg ttgcaagacc    6960
tgcctgaaac cgaactgccc gctgttctgc agccggtcgc ggaggctatg gatgcgatcg    7020
ctgcggccga tcttagccag acgagcgggt tcggcccatt cggaccgcaa ggaatcggtc    7080
aatacactac atggcgtgat ttcatatgcg cgattgctga tccccatgtg tatcactggc    7140
aaactgtgat ggacgacacc gtcagtgcgt ccgtcgcgca ggctctcgat gagctgatgc    7200
tttgggccga ggactgcccc gaagtccggc acctcgtgca cgcggatttc ggctccaaca    7260
atgtcctgac ggacaatggc cgcataacag cggtcattga ctggagcgag gcgatgttcg    7320
gggattccca atacgaggtc gccaacatct tcttctggag gccgtggttg gcttgtatgg    7380
agcagcagac gcgctacttc gagcggaggc atccggagct tgcaggatcg ccgcggctcc    7440
gggcgtatat gctccgcatt ggtcttgacc aactctatca gagcttggtt gacggcaatt    7500
tcgatgatgc agcttgggcg cagggtcgat gcgacgcaat cgtccgatcc ggagccggga    7560
ctgtcgggcg tacacaaatc gcccgcagaa gcgcggccgt ctggaccgat ggctgtgtag    7620
```

```
aagtactcgc cgatagtgga aaccgacgcc ccagcactcg tccgaggca  aaggaatagt    7680 gaggtacagc ttggatcgat ccggctgcta acaaagcccg aaaggaagct gagttggctg    7740
ctgccaccgc tgagcaataa ctagcataac cccttgggc  ctctaaacgg gtcttgaggg    7800
gttttttgct gaaaggagga actatatccg gatgatcggg cgcgccgtcg acggatccgt    7860
acgagatccg gccggccaga tcctgcagga tataatgagc cgtaaacaaa gatgattaag    7920
tagtaattaa tacgtactag taaaagtggc aaaagataac gagaaagaac caatttcttt    7980
gcattcggcc ttagcggaag gcatatataa gctttgatta ttttatttag tgtaatgatt    8040
tcgtacaacc aaagcattta tttagtactc tcacacttgt gtcgcggccg ctcattcagg    8100
gacagcagcc agctgggcaa tctcgcctaa gaagctgacc aatttctgaa ccccggggat    8160
gatggctggg gccctgtagg gcaggttgtg cttggcgcac aacttctgca cctccaggga    8220
agctgccgtg aggttgtgcc tgggcatgtt gggccacaag tggtgctcaa tctggtagtt    8280
gagaccacca aagacccaat cggtgagaag gccgggctta atgttcaacg tctcgtggat    8340
ctggctggcg ctgaacccgt gctcatccca gacagtctcc tcaaccttgt ccaaaggata    8400
gtgattcaga acacaacga  tggcaatgcc aaatcctccg agcagctcgg agatcaagaa    8460
gcatcccaaa ccggtggcaa agctaggcat ggcactgcaa tagaaagtgg ccttgagcac    8520
ccagtggagg gccagaccaa tcgcctcctt agtgtactgg cgcttgtagt acaggttcct    8580
ctcctcgctc ttgtaggaca tgacgccgcc gatggattgg aggcaccaga tgaacctaag    8640
ggatgcaatg gtgggaatga agtagtactg ctggtacttg atgagattcc gagtcgaagg    8700
agtagccctc ttgacatctt cgggagacca agccaggatg gggaggttat caatatctgg    8760
gtcatggccg accacattgg tggcggcatg gtgaccattg tgcctatcct tccaccaagt    8820
ctgtgagtat ccctgcatca cgttaccgaa aaagagaccg aaagcgtcgt taatcttgcg    8880
gtttgtgaaa acctggtgat ggcaatagtc gtgggacaac cagccagctt gttggtagca    8940
cacgccaaga accaaagcag cggtgaaata ccaattcgtg tacacggtca tcaagatgga    9000
aaggaccatc aaaccgacgg tagttgaagt cttgtaaaaa taccaaagga aactcgtctc    9060
gaacataccc ttggagatga attcctcccg caacttgcgg aaatcctcct ggggctcatc    9120
acgcttaggc ttgggtgcaa caggtgtgtc aggagaggaa ggctccataa caggcattct    9180
cttcaacttg gcgacggctt cttgagagtg catcaccatg aagacatcgg tcgcatcgcg    9240
gttgcgatag ttctcgataa tgtcagctcc tccagggtgg tgattgaccc aagcagacac    9300
atcataagtt gcgccatcaa ttgtgattgg cagagcttgc cgcttaggag acatggtgcg    9360
gccgcttggg gggctatgga agactttctt agttagttgt gtgaataagc aatgttggga    9420
gaatcgggac tacttatagg ataggaataa aacagaaaag tattaagtgc taatgaaata    9480
tttagactga taattaaaat cttcacgtat gtccacttga tataaaaacg tcaggaataa    9540
aggaagtaca gtagaattta aaggtactct ttttatatat acccgtgttc tcttttggc    9600 tagctagttg cataaaaaat aatctatatt tttatcatta ttttaaatat cttatgagat    9660
ggtaaatatt tatcataatt ttttttacta ttatttatta tttgtgtgtg taatacatat    9720
agaagttaat tacaaatttt atttactttt tcattatttt gatatgattc accattaatt    9780
tagtgttatt atttataata gttcatttta atctttttgt atatattatg cgtgcagtac    9840
ttttttccta catataacta ctattacatt ttatttatat aatattttta ttaatgaatt    9900
ttcgtgataa tatgtaatat tgttcattat tatttcagat ttttttaaaaa tatttgtgtt    9960 attatttatg aaatatgtaa ttttttttagt atttgatttt atgatgataa agtgttctaa   10020
```

```
attcaaaaga agggggaaag cgtaaacatt aaaaaacgtc atcaaacaaa aacaaaatct    10080
tgttaataaa gataaaactg tttgttttga tcactgttat ttcgtaatat aaaaacatta    10140
tttatattta tattgttgac aaccaaattt gcctatcaaa tctaaccaat ataatgcatg    10200
cgtggcaggt aatgtactac catgaactta agtcatgaca taataaaccg tgaatctgac    10260
caatgcatgt acctanctaa attgtatttg tgacacgaag caaatgattc aattcacaat    10320
ggagatggga aacaaataat gaagaaccca gaactaagaa agcttttctg aaaaataaaa    10380
taaaggcaat gtcaaaagta tactgcatca tcagtccaga aagcacatga tatttttta    10440
tcagtatcaa tgcagctagt tttattttac aatatcgata tagctagttt aaatatattg    10500
cagctagatt tataaatatt tgtgttatta tttatcattt gtgtaatcct gtttttagta    10560
ttttagttta tatgatga taatgtattc caaatttaaa agaagggaaa taaatttaaa    10620
caagaaaaaa agtcatcaaa caaaaaacaa atgaaagggt ggaaagatgt taccatgtaa    10680
tgtgaatgtt acagtatttc ttttattata gagttaacaa attaactaat atgattttgt    10740
taataatgat aaaatatttt ttttattatt atttcataat ataaaaatag tttacttaat    10800
ataaaaaaaa ttctatcgtt cacaacaaag ttggccacct aatttaacca tgcatgtacc    10860
catggaccat attaggtaac catcaaacct gatgaagaga taaagagatg aagacttaag    10920
tcataacaca aaaccataaa aaacaaaaat acaatcaacc gtcaatctga ccaatgcatg    10980
aaaaagctgc aatagtgagt ggcgacacaa agcacatgat tttcttacaa cggagataaa    11040
accaaaaaaa tatttcatga acaacctaga acaaataaag cttttatata ataaatatat    11100
aaataaataa aggctatgga ataatatact tcaatatatt tggattaaat aaattgttgg    11160
cggggttgat atatttatac acacctaaag tcacttcaat ctcattttca cttaactttt    11220
attttttttt tcttttttatt tatcataaag agaatattga taatatactt tttaacatat    11280
ttttatgaca ttttttattg gtgaaaactt attaaaaatc ataaattttg taagttagat    11340
ttatttaaag agttcctctt cttattttaa attttttaat aaattttaa ataactaaaa    11400
tttgtgttaa aaatgttaaa aaatgtgtta ttaacccttc tcttcgagga cgtacgtcta    11460
gagtcgacct gca                                                      11473
```

<210> SEQ ID NO 70
<211> LENGTH: 792
<212> TYPE: DNA
<213> ORGANISM: Isochrysis galbana

<400> SEQUENCE: 70

```
atggccctcg caaacgacgc gggagagcgc atctgggcgg ctgtgaccga cccggaaatc      60
ctcattggca ccttctcgta cttgctactc aaaccgctgc tccgcaattc cgggctggtg     120
gatgagaaga agggcgcata caggacgtcc atgatctggt acaacgttct gctgcgctc     180
ttctctgcgc tgagcttcta cgtgacggcg accgccctcg gctgggacta tggtacgggc     240
gcgtggctgc gcaggcaaac cggcgacaca ccgcagccgc tcttccagtg cccgtccccg     300
gtttgggact cgaagctctt cacatggacc gccaaggcat tctattactc caagtacgtg     360
gagtacctcg acacggcctg gctggtgctc aagggcaaga gggtctcctt tctccaggcc     420
ttccaccact ttggcgcgcc gtgggatgtg tacctcggca ttcggctgca caacgagggc     480
gtatggatct tcatgttttt caactcgttc attcacacca tcatgtacac ctactacggc     540
ctcaccgccg ccgggtataa gttcaaggcc aagccgctca tcaccgcgat gcagatctgc     600
```

```
cagttcgtgg gcggcttcct gttggtctgg gactacatca acgtcccctg cttcaactcg     660
gacaaaggga agttgttcag ctgggctttc aactatgcat acgtcggctc ggtcttcttg     720
ctcttctgcc acttttctta ccaggacaac ttggcaacga agaaatcggc caaggcgggc     780
aagcagctct ag                                                         792

<210> SEQ ID NO 71
<211> LENGTH: 757
<212> TYPE: DNA
<213> ORGANISM: Euglena gracilis
<220> FEATURE:
<221> NAME/KEY: misc_feature
<222> LOCATION: (677)..(677)
<223> OTHER INFORMATION: n is a, c, g, or t

<400> SEQUENCE: 71
ttttttttcg aacacttaat ggaggtggtg aatgaaatag tctcaattgg gcaggaagtt     60
ttacccaaag ttgattatgc ccaactctgg agtgatgcca gtcactgtga ggtgctttac     120
ttgtccatcg catttgtcat cttgaagttc actcttggcc cccttggtcc aaaaggtcag     180
tctcgtatga agtttgtttt caccaattac aaccttctca tgtccattta ttcgttggga     240
tcattcctct caatggcata tgccatgtac accatcggtg ttatgtctga caactgcgag     300
aaggcttttg acaacaacgt cttcaggatc accacgcagt tgttctattt gagcaagttc     360
ctggagtata ttgactcctt ctatttgcca ctgatgggca agcctctgac ctggttgcaa     420
ttcttccatc atttggggc accgatggat atgtggctgt tctataatta ccgaaatgaa      480
gctgtttgga tttttgtgct gttgaatggt tcatccact ggatcatgta cggttattat      540
tggaccagat tgatcaagct gaagttcccc atgccaaaat ccctgattac atcaatgcag    600
atcattcaat tcaatgttgg tttctacatt gtctggaagt acaggaacat tccctgttat    660
cgccaagatg ggatgangat gtttggctgg ttcttcaatt acttttatgt tggcacagtc    720
ttgtgtttgt tcttgaattt ctatgtgcaa acgtata                             757

<210> SEQ ID NO 72
<211> LENGTH: 774
<212> TYPE: DNA
<213> ORGANISM: Euglena gracilis
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (218)..(220)
<223> OTHER INFORMATION: n is a, c, g, or t
<220> FEATURE:
<221> NAME/KEY: misc_feature
<222> LOCATION: (707)..(709)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
```

<400> SEQUENCE: 72

```
tcaggatcac cacgcagttg ttctatttga gcangttcct ggagtatatt gactccttct        60
atttgccant gatgggcaag cntctgacct ggttgcaatt cttccatcat tnggggcac        120
cgatggatat gtggctgttc tataattacc gaaatgaagc tgtttggatt tttgtgctgt       180
tgaatggttt catccactgg atcatgtacg gttattannn gaccagattg atcaagctga       240
agttccccat gccaaaatcc ctgattacat caatgcagat cattcaattc aatgttggtt       300
tctacattgt ctggaagtac aggaacattc cctgttatcg ccaagatggg atgaggatgt       360
ttggctggtt cttcaattac ttttatgttg gcacagtctt gtgtttgttc ttgaatttct       420
atgtgcaaac gtatatcgtc aggaagcaca agggagccaa aaagattcag tgatatttcc       480
tcctctgcgg tggcctcttt tgacctcccc ttgacaccta atgtggag gtgtcgggct         540
ctctccgtct caccagcact tgactctgca ggtgctcact tttatttttt acccatcttt       600
gcttgttgac cattcacctc tcccacttcc acatagtcca ttctaactgt tgcagactgc       660
ggtccatttt ttccagagct cccaatgacc atacgcgaca ccttgtnnnc ncccagccca       720
ttgtgcacaa ttcatagtgg catcgttttg ccttgatacg tgtgcatcca gcgg            774
```

```
<210> SEQ ID NO 73
<211> LENGTH: 1201
<212> TYPE: DNA
<213> ORGANISM: Euglena gracilis
<220> FEATURE:
<221> NAME/KEY: misc_feature
<222> LOCATION: (1134)..(1136)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t
```

<400> SEQUENCE: 73

```
gacatggcaa ctatgatttt attttgactg atagtgacct gttcgttgca acaaattgat        60
gagcaatgct tttttataat gccaactttg tacaaaaaag ttggattttt tttcgaacac       120
ttaatggagg tggtgaatga aatagtctca attgggcagg aagttttacc caaagttgat       180
tatgcccaac tctggagtga tgccagtcac tgtgaggtgc tttacttgtc catcgcattt       240
gtcatcttga agttcactct tggcccccctt ggtccaaaag gtcagtctcg tatgaagttt       300
gttttcacca attacaacct tctcatgtcc atttattcgt tgggatcatt cctctcaatg       360
gcatatgcca tgtacaccat cggtgttatg tctgacaact gcgagaaggc ttttgacaac       420
aacgtcttca ggatcaccac gcagttgttc tatttgagca agttcctgga gtatattgac       480
tccttctatt tgccactgat gggcaagcct ctgacctggt tgcaattctt ccatcatttg       540
ggggcaccga tggatatgtg gctgttctat aattaccgaa atgaagctgt ttggattttt       600
gtgctgttga atggtttcat ccactggatc atgtacggtt attattggac cagattgatc       660
aagctgaagt tccccatgcc aaaatccctg attacatcaa tgcagatcat tcaattcaat       720
gttggtttct acattgtctg gaagtacagg aacattccct gttatcgcca agatgggatg       780
aggatgtttg gctggttctt caattacttt tatgttggca cagtcttgtg tttgttcttg       840
aatttctatg tgcaaacgta tatcgtcagg aagcacaagg gagccaaaaa gattcagtga       900
tatttcctcc tctgcggtgg cctcttttga cctccccttg acacctataa tgtggaggtg       960
tcgggctctc tccgtctcac cagcacttga ctctgcaggt gctcactttt atttttacc      1020
```

```
catctttgct tgttgaccat tcacctctcc cacttccaca tagtccattc taactgttgc   1080
agactgcggt ccattttttc cagagctccc aatgaccata cgcgacacct tgtnnncncc   1140
cagcccattg tgcacaattc atagtggcat cgttttgcct tgatacgtgt gcatccagcg   1200
g                                                                  1201
```

<210> SEQ ID NO 74
<211> LENGTH: 777
<212> TYPE: DNA
<213> ORGANISM: Euglena gracilis

<400> SEQUENCE: 74

```
atggaggtgg tgaatgaaat agtctcaatt gggcaggaag ttttacccaa agttgattat    60
gcccaactct ggagtgatgc cagtcactgt gaggtgcttt acttgtccat cgcatttgtc   120
atcttgaagt tcactcttgg cccccttggt ccaaaaggtc agtctcgtat gaagtttgtt   180
ttcaccaatt acaaccttct catgtccatt tattcgttgg gatcattcct ctcaatggca   240
tatgccatgt acaccatcgg tgttatgtct gacaactgcg agaaggcttt tgacaacaac   300
gtcttcagga tcaccacgca gttgttctat ttgagcaagt tcctggagta tattgactcc   360
ttctatttgc cactgatggg caagcctctg acctggttgc aattcttcca tcatttgggg   420
gcaccgatgg atatgtggct gttctataat taccgaaatg aagctgtttg gattttgtg    480 ctgttgaatg gtttcatcca ctggatcatg tacggttatt attggaccag attgatcaag   540
ctgaagttcc ccatgccaaa atccctgatt acatcaatgc agatcattca attcaatgtt   600
ggtttctaca ttgtctggaa gtacaggaac attccctgtt atcgccaaga tgggatgagg   660
atgtttggct ggttcttcaa ttacttttat gttggcacag tcttgtgttt gttcttgaat   720
ttctatgtgc aaacgtatat cgtcaggaag cacaagggag ccaaaaagat tcagtga      777
```

<210> SEQ ID NO 75
<211> LENGTH: 258
<212> TYPE: PRT
<213> ORGANISM: Euglena gracilis

<400> SEQUENCE: 75

```
Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160
```

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
                180                 185                 190

Met Gln Ile Ile Gln Phe Asn Val Gly Phe Tyr Ile Val Trp Lys Tyr
                195                 200                 205

Arg Asn Ile Pro Cys Tyr Arg Gln Asp Gly Met Arg Met Phe Gly Trp
                210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 76
<211> LENGTH: 263
<212> TYPE: PRT
<213> ORGANISM: Isochrysis galbana

<400> SEQUENCE: 76

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
                20                  25                  30

Leu Leu Arg Asn Ser Gly Leu Val Asp Glu Lys Lys Gly Ala Tyr Arg
                35                  40                  45

Thr Ser Met Ile Trp Tyr Asn Val Leu Leu Ala Leu Phe Ser Ala Leu
        50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
                100                 105                 110

Ala Phe Tyr Tyr Ser Lys Tyr Val Glu Tyr Leu Asp Thr Ala Trp Leu
                115                 120                 125

Val Leu Lys Gly Lys Arg Val Ser Phe Leu Gln Ala Phe His His Phe
                130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
                180                 185                 190

Leu Ile Thr Ala Met Gln Ile Cys Gln Phe Val Gly Gly Phe Leu Leu
                195                 200                 205

Val Trp Asp Tyr Ile Asn Val Pro Cys Phe Asn Ser Asp Lys Gly Lys
                210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
                260

<210> SEQ ID NO 77
<211> LENGTH: 30
<212> TYPE: DNA
<213> ORGANISM: Artificial Sequence
<220> FEATURE:
<223> OTHER INFORMATION: primer sense oligonucleotide oEugEL1-1

<400> SEQUENCE: 77
agcggccgca ccatggaggt ggtgaatgaa                                30

<210> SEQ ID NO 78
<211> LENGTH: 30
<212> TYPE: DNA
<213> ORGANISM: Artificial Sequence
<220> FEATURE:
<223> OTHER INFORMATION: primer sense oligonucleotide oEugEL1-2

<400> SEQUENCE: 78
tgcggccgct cactgaatct ttttggctcc                                30

<210> SEQ ID NO 79
<211> LENGTH: 4311
<212> TYPE: DNA
<213> ORGANISM: Artificial Sequence
<220> FEATURE:
<223> OTHER INFORMATION: plasmid pKR906

<400> SEQUENCE: 79

| | |
|---|---|
| agcggccgca ccatggaggt ggtgaatgaa atagtctcaa ttgggcagga agttttaccc | 60 |
| aaagttgatt atgcccaact ctggagtgat gccagtcact gtgaggtgct ttacttgtcc | 120 |
| atcgcatttg tcatcttgaa gttcactctt ggccccttg gtccaaaagg tcagtctcgt | 180 |
| atgaagtttg ttttcaccaa ttacaacctt ctcatgtcca tttattcgtt gggatcattc | 240 |
| ctctcaatgg catatgccat gtacaccatc ggtgttatgt ctgacaactg cgagaaggct | 300 |
| tttgacaaca acgtcttcag gatcaccacg cagttgttct atttgagcaa gttcctggag | 360 |
| tatattgact ccttctattt gccactgatg ggcaagcctc tgacctggtt gcaattcttc | 420 |
| catcatttgg gggcaccgat ggatatgtgg ctgttctata attaccgaaa tgaagctgtt | 480 |
| tggattttg tgctgttgaa tggtttcatc cactggatca tgtacggtta ttattggacc | 540 |
| agattgatca agctgaagtt ccccatgcca aaatccctga ttacatcaat gcagatcatt | 600 |
| caattcaatg ttggtttcta cattgtctgg aagtacagga acattccctg ttatcgccaa | 660 |
| gatgggatga ggatgtttgg ctggttcttc aattactttt atgttggcac agtcttgtgt | 720 |
| ttgttcttga atttctatgt gcaaacgtat atcgtcagga agcacaaggg agccaaaaag | 780 |
| attcagtgag cggccgcacc tgaattccag cacactggcg gccgttacta gtggatccga | 840 |
| gctcggtacc aagcttgatg catagcttga gtattctaac gcgtcaccta atagcttgg | 900 |
| cgtaatcatg gtcatagctg tttcctgtgt gaaattgtta tccgctcaca attccacaca | 960 |
| acatacgagc cggaagcata aagtgtaaag cctggggtgc ctaatgagtg agctaactca | 1020 |
| cattaattgc gttgcgctca ctgcccgctt tccagtcggg aaacctgtcg tgccagctgc | 1080 |
| attaatgaat cggccaacgc gcggggagag gcggtttgcg tattgggcgc tcttccgctt | 1140 |
| cctcgctcac tgactcgctg cgctcggtcg ttcggctgcg gcgagcggta tcagctcact | 1200 |
| caaaggcggt aatacggtta tccacagaat caggggataa cgcaggaaag aacatgtgag | 1260 |
| caaaaggcca gcaaaagccc aggaaccgta aaaaggccgc gttgctggcg ttttccata | 1320 |

-continued

```
ggctccgccc ccctgacgag catcacaaaa atcgacgctc aagtcagagg tggcgaaacc    1380
cgacaggact ataaagatac caggcgtttc ccctggaag ctccctcgtg cgctctcctg    1440
ttccgaccct gccgcttacc ggatacctgt ccgcctttct cccttcggga agcgtggcgc    1500
tttctcatag ctcacgctgt aggtatctca gttcggtgta ggtcgttcgc tccaagctgg    1560
gctgtgtgca cgaaccccc gttcagcccg accgctgcgc cttatccggt aactatcgtc    1620
ttgagtccaa cccggtaaga cacgacttat cgccactggc agcagccact ggtaacagga    1680
ttagcagagc gaggtatgta ggcggtgcta cagagttctt gaagtggtgg cctaactacg    1740
gctacactag aaggacagta tttggtatct gcgctctgct gaagccagtt accttcggaa    1800
aaagagttgg tagctcttga tccggcaaac aaaccaccgc tggtagcggt ggtttttttg    1860
tttgcaagca gcagattacg cgcagaaaaa aaggatctca agaagatcct ttgatctttt    1920
ctacggggtc tgacgctcag tggaacgaaa actcacgtta agggattttg gtcatgagat    1980
tatcaaaaag gatcttcacc tagatccttt taaattaaaa atgaagtttt agcacgtgtc    2040
agtcctgctc ctcggccacg aagtgcacgc agttgccggc cgggtcgcgc agggcgaact    2100
cccgccccca cggctgctcg ccgatctcgg tcatggccgg cccggaggcg tcccggaagt    2160
tcgtggacac gacctccgac cactcggcgt acagctcgtc caggccgcgc acccacaccc    2220
aggccagggt gttgtccggc accacctggt cctggaccgc gctgatgaac agggtcacgt    2280
cgtcccggac cacaccggcg aagtcgtcct ccacgaagtc ccgggagaac ccgagccggt    2340
cggtccagaa ctcgaccgct ccggcgacgt cgcgcgcggt gagcaccgga acggcactgg    2400
tcaacttggc catggtggcc ctcctcacgt gctattattg aagcatttat cagggttatt    2460
gtctcatgag cggatacata tttgaatgta tttagaaaaa taaacaaata ggggttccgc    2520
gcacatttcc ccgaaaagtg ccacctgtat gcggtgtgaa ataccgcaca gatgcgtaag    2580
gagaaaatac cgcatcagga aattgtaagc gttaataatt cagaagaact cgtcaagaag    2640
gcgatagaag gcgatgcgct gcgaatcggg agcggcgata ccgtaaagca cgaggaagcg    2700
gtcagcccat tcgccgccaa gctcttcagc aatatcacgg gtagccaacg ctatgtcctg    2760
atagcggtcc gccacaccca gccggccaca gtcgatgaat ccagaaaagc ggccattttc    2820
caccatgata ttcggcaagc aggcatcgcc atgggtcacg acgagatcct cgccgtcggg    2880
catgctcgcc ttgagcctgg cgaacagttc ggctggcgcg agccctgat gctcttcgtc    2940
cagatcatcc tgatcgacaa gaccggcttc catccgagta cgtgctcgct cgatgcgatg    3000
tttcgcttgg tggtcgaatg ggcaggtagc cggatcaagc gtatgcagcc gccgcattgc    3060
atcagccatg atggatactt tctcggcagg agcaaggtga gatgacagga gatcctgccc    3120
cggcacttcg cccaatagca gccagtccct tcccgcttca gtgacaacgt cgagcacagc    3180
tgcgcaagga acgcccgtcg tggccagcca cgatagccgc gctgcctcgt cttgcagttc    3240
attcagggca ccggacaggt cggtcttgac aaaaagaacc gggcgcccct gcgctgacag    3300
ccggaacacg gcggcatcag agcagccgat tgtctgttgt gcccagtcat agccgaatag    3360
cctctccacc caagcggccg gagaacctgc gtgcaatcca tcttgttcaa tcatgcgaaa    3420
cgatcctcat cctgtctctt gatcagagct tgatccctg cgccatcaga tccttggcgg    3480
cgagaaagcc atccagttta ctttgcaggg cttcccaacc ttaccagagg cgcccagc    3540
tggcaattcc ggttcgcttg ctgtccataa aaccgcccag tctagctatc gccatgtaag    3600
cccactgcaa gctacctgct ttctctttgc gcttgcgttt tcccttgtcc agatagccca    3660
gtagctgaca ttcatccggg gtcagcaccg tttctgcgga ctggctttct acgtgaaaag    3720
```

-continued

```
gatctaggtg aagatccttt ttgataatct catgcctgac atttatattc cccagaacat    3780
caggttaatg gcgttttgga tgtcattttc gcggtggctg agatcagcca cttcttcccc    3840
gataacggag accggcacac tggccatatc ggtggtcatc atgcgccagc tttcatcccc    3900
gatatgcacc accgggtaaa gttcacggga gactttatct gacagcagac gtgcactggc    3960 caggggatc accatccgtc gccccggcgt gtcaataata tcactctgta catccacaaa    4020
cagacgataa cggctctctc ttttataggt gtaaaccttaa aactgccgta cgtataggct    4080
gcgcaactgt tgggaagggc gatcggtgcg ggcctcttcg ctattacgcc agctggcgaa    4140 aggggatgt gctgcaaggc gattaagttg gtaacgcca gggttttccc agtcacgacg    4200
ttgtaaaacg acggccagtg aattgtaata cgactcacta tagggcgaat tgggccctct    4260
agatgcatgc tcgagcggcc gccagtgtga tggatatctg cagaattcag g    4311
```

<210> SEQ ID NO 80
<211> LENGTH: 7085
<212> TYPE: DNA
<213> ORGANISM: Artificial Sequence
<220> FEATURE:
<223> OTHER INFORMATION: plasmid pKR72 (ATCC Accession No. PTA-6019)

<400> SEQUENCE: 80

```
gtacggatcc gtcgacggcg cgcccgatca tccggatata gttcctcctt tcagcaaaaa      60 accctcaag acccgtttag aggccccaag gggttatgct agttattgct cagcggtggc     120
agcagccaac tcagcttcct ttcgggcttt gttagcagcc ggatcgatcc aagctgtacc     180
tcactattcc tttgccctcg gacgagtgct ggggcgtcgg tttccactat cggcgagtac     240
ttctacacag ccatcggtcc agacggccgc gcttctgcgg gcgatttgtg tacgcccgac     300
agtcccggct ccggatcgga cgattgcgtc gcatcgaccc tgcgcccaag ctgcatcatc     360
gaaattgccg tcaaccaagc tctgatagag ttggtcaaga ccaatgcgga gcatatacgc     420
ccggagccgc ggcgatcctg caagctccgg atgcctccgc tcgaagtagc gcgtctgctg     480
ctccatacaa gccaaccacg gcctccagaa gaagatgttg gcgacctcgt attgggaatc     540
cccgaacatc gcctcgctcc agtcaatgac cgctgttatg cggccattgt ccgtcaggac     600
attgttggag ccgaaatccg cgtgcacgag gtgccggact cggggcagt cctcggccca     660 aagcatcagc tcatcgagag cctgcgcgac ggacgcactg acggtgtcgt ccatcacagt     720
ttgccagtga tacacatggg gatcagcaat cgcgcatatg aaatcacgcc atgtagtgta     780
ttgaccgatt ccttgcggtc cgaatgggcc gaacccgctc gtctggctaa gatcggccgc     840
agcgatcgca tccatagcct ccgcgaccgg ctgcagaaca gcgggcagtt cggtttcagg     900
caggtcttgc aacgtgacac cctgtgcacg gcgggagatg caataggtca ggctctcgct     960
gaattcccca atgtcaagca cttccggaat cgggagcgcg gccgatgcaa agtgccgata    1020
aacataacga tctttgtaga aaccatcggc gcagctattt acccgcagga catatccacg    1080
ccctcctaca tcgaagctga aagcacgaga ttcttcgccc tccgagagct gcatcaggtc    1140
ggagacgctg tcgaactttt cgatcagaaa cttctcgaca gacgtcgcgg tgagttcagg    1200 ctttccatg gtatatctc cttcttaaag ttaaacaaaa ttatttctag agggaaaccg    1260
ttgtggtctc cctatagtga gtcgtattaa tttcgcggga tcgagatcga tccaattcca    1320
atcccacaaa aatctgagct taacagcaca gttgctcctc tcagagcaga atcgggtatt    1380 caacacccte atatcaacta ctacgttgtg tataacggtc cacatgccgg tatatacgat    1440
```

```
gactggggtt gtacaaaggc ggcaacaaac ggcgttcccg gagttgcaca caagaaattt    1500
gccactatta cagaggcaag agcagcagct gacgcgtaca caacaagtca gcaaacagac    1560
aggttgaact tcatcccaa aggagaagct caactcaagc ccaagagctt tgctaaggcc     1620
ctaacaagcc caccaaagca aaaagcccac tggctcacgc taggaaccaa aaggcccagc    1680
agtgatccag ccccaaaaga gatctccttt gccccggaga ttacaatgga cgatttcctc    1740
tatctttacg atctaggaag gaagttcgaa ggtgaaggtg acgacactat gttcaccact    1800
gataatgaga aggttagcct cttcaatttc agaaagaatg ctgacccaca gatggttaga    1860
gaggcctaca cagcaggtct catcaagacg atctacccga gtaacaatct ccaggagatc    1920
aaataccttc caagaaggt taaagatgca gtcaaaagat tcaggactaa ttgcatcaag     1980
aacacagaga aagacatatt tctcaagatc agaagtacta ttccagtatg gacgattcaa    2040
ggcttgcttc ataaaccaag gcaagtaata gagattggag tctctaaaaa ggtagttcct    2100
actgaatcta aggccatgca tggagtctaa gattcaaatc gaggatctaa cagaactcgc    2160
cgtgaagact ggcgaacagt tcatacagag tcttttacga ctcaatgaca agaagaaaat    2220
cttcgtcaac atggtggagc acgacactct ggtctactcc aaaaatgtca agatacagt     2280 ctcagaagac caaagggcta ttgagacttt tcaacaaagg ataatttcgg gaaacctcct    2340
cggattccat tgcccagcta tctgtcactt catcgaaagg acagtagaaa aggaaggtgg    2400
ctcctacaaa tgccatcatt gcgataaagg aaaggctatc attcaagatg cctctgccga    2460
cagtggtccc aaagatggac ccccacccac gaggagcatc gtggaaaaag aagacgttcc    2520
aaccacgtct tcaaagcaag tggattgatg tgacatctcc actgacgtaa gggatgacgc    2580
acaatcccac tatccttcgc aagacccttc ctctatataa ggaagttcat ttcatttgga    2640
gaggacacgc tcgagctcat ttctctatta cttcagccat aacaaaagaa ctcttttctc    2700
ttcttattaa accatgaaaa agcctgaact caccgcgacg tctgtcgaga gtttctgat     2760 cgaaaagttc gacagcgtct ccgacctgat gcagctctcg gagggcgaag aatctcgtgc    2820
tttcagcttc gatgtaggag ggcgtggata tgtcctgcgg gtaaatagct gcgccgatgg    2880
tttctacaaa gatcgttatg tttatcggca cttttgcatcg gccgcgctcc cgattccgga   2940
agtgcttgac attggggaat tcagcgagag cctgacctat tgcatctccc gccgtgcaca    3000
gggtgtcacg ttgcaagacc tgcctgaaac cgaactgccc gctgttctgc agccggtcgc    3060
ggaggccatg gatgcgatcg ctgcggccga tcttagccag acgagcgggt tcggcccatt    3120
cggaccgcaa ggaatcggtc aatacactac atggcgtgat ttcatatgcg cgattgctga    3180
tccccatgtg tatcactggc aaactgtgat ggacgacacc gtcagtgcgt ccgtcgcgca    3240
ggctctcgat gagctgatgc tttgggccga ggactgcccc gaagtccggc acctcgtgca    3300
cgcggatttc ggctccaaca atgtcctgac ggacaatggc cgcataacag cggtcattga    3360
ctggagcgag gcgatgttcg gggattccca atacgaggtc gccaacatct tcttctggag    3420
gccgtggttg gcttgtatgg agcagcagac gcgctacttc gagcggaggc atccggagct    3480
tgcaggatcg ccgcggctcc gggcgtatat gctccgcatt ggtcttgacc aactctatca    3540
gagcttggtt gacggcaatt tcgatgatgc agcttgggcg cagggtcgat gcgacgcaat    3600
cgtccgatcc ggagccggga ctgtcggcgc tacacaaatc gcccgcagaa gcgcggccgt    3660
ctggaccgat ggctgtgtag aagtactcgc cgatagtgga aaccgacgcc ccagcactcg    3720
tccgagggca aaggaatagt gaggtaccta aagaaggagt gcgtcgaagc agatcgttca    3780
aacatttggc aataaagttt cttaagattg aatcctgttg ccggtcttgc gatgattatc    3840
```

```
atataatttc tgttgaatta cgttaagcat gtaataatta acatgtaatg catgacgtta    3900
tttatgagat gggtttttat gattagagtc ccgcaattat acatttaata cgcgatagaa    3960
aacaaaatat agcgcgcaaa ctaggataaa ttatcgcgcg cggtgtcatc tatgttacta    4020
gatcgatgtc gaatcgatca acctgcatta atgaatcggc caacgcgcgg ggagaggcgg    4080
tttgcgtatt gggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
ctttctccct tcgggaagcg tggcgctttc tcaatgctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt tttttgtttg caagcagcag attacgcgca gaaaaaaagg    4860
atctcaagaa gatcctttga tcttttctac ggggtctgac gctcagtgga acgaaaactc    4920
acgttaaggg attttggtca tgacattaac ctataaaaat aggcgtatca cgaggccctt    4980
tcgtctcgcg cgtttcggtg atgacggtga aaacctctga cacatgcagc tcccggagac    5040
ggtcacagct tgtctgtaag cggatgccgg gagcagacaa gcccgtcagg gcgcgtcagc    5100
gggtgttggc gggtgtcggg gctggcttaa ctatgcggca tcagagcaga ttgtactgag    5160
agtgcaccat atggacatat tgtcgttaga acgcggctac aattaataca taaccttatg    5220
tatcatacac atacgattta ggtgacacta tagaacggcg cgccaagctt gttgaaacat    5280
ccctgaagtg tctcatttta ttttatttat tctttgctga taaaaaaata aaataaaaga    5340
agctaagcac acgtcaacc attgctctac tgctaaaagg gttatgtgta gtgttttact    5400
gcataaatta tgcagcaaac aagacaactc aaattaaaaa atttcctttg cttgtttttt    5460
tgttgtctct gacttgactt tcttgtggaa gttggttgta taaggattgg gacaccattg    5520
tccttcttaa tttaattta ttctttgctg ataaaaaaaa aaatttcata tagtgttaaa    5580
taataatttg ttaaataacc aaaaagtcaa atatgtttac tctcgtttaa ataattgaga    5640
ttcgtccagc aaggctaaac gattgtatag atttatgaca atatttactt ttttatagat    5700
aaatgttata ttataataaa tttatataca tatattatat gttatttatt attattttaa    5760
atccttcaat attttatcaa accaactcat aatttttttt ttatctgtaa gaagcaataa    5820
aattaaatag acccacttta aggatgatcc aaccttata cagagtaaga gagttcaaat    5880
agtacccttt catatacata tcaactaaaa tattagaaat atcatggatc aaaccttata    5940 aagcacattaa ataagtggat aagtataata tataaatggg tagtatataa tatataaatg    6000
gatacaaact tctctctttta taattgttat gtctccttaa catcctaata taatacataa    6060
gtgggtaata tataatatat aaatggagac aaacttcttc cattataatt gttatgtctt    6120
cttaacactt atgtctcgtt cacaatgcta aggttagaat tgtttagaaa gtcttatagt    6180
```

```
acacatttgt ttttgtacta tttgaagcat tccataagcc gtcacgattc agatgattta    6240
taataataag aggaaattta tcatagaaca ataaggtgca tagatagagt gttaatatat    6300
cataacatcc tttgtttatt catagaagaa gtgagatgga gctcagttat tatactgtta    6360
catggtcgga tacaatattc catgctctcc atgagctctt acacctacat gcattttagt    6420
tcatacttgc ggccgcagta tatcttaaat tctttaatac ggtgtactag gatattgaac    6480
tggttcttga tgatgaaaac ctgggccgag attgcagcta tttatagtca taggtcttgt    6540
taacatgcat ggacatttgg ccacggggtg gcatgcagtt tgacgggtgt gaaataaac     6600 aaaaatgagg tggcggaaga gaatacgagt ttgaggttgg gttagaaaca acaaatgtga    6660
gggctcatga tgggttgagt tggtgaatgt tttgggctgc tcgattgaca cctttgtgag    6720
tacgtgttgt tgtgcatggc ttttggggtc cagttttttt ttcttgacgc ggcgatcctg    6780
atcagctagt ggataagtga tgtccactgt gtgtgattgc gttttgtttt gaattttatg    6840
aacttagaca ttgctatgca aaggatactc tcattgtgtt ttgtcttctt ttgttccttg    6900 gcttttctt atgatccaag agactagtca gtgttgtggc attcgagact accaagatta     6960
attatgatgg gggaaggata agtaactgat tagtacggac tgttaccaaa ttaattaata    7020
agcggcaaat gaagggcatg gatcaaaagc ttggatctcc tgcaggatct ggccggccgg    7080
atctc                                                                7085

<210> SEQ ID NO 81
<211> LENGTH: 7873
<212> TYPE: DNA
<213> ORGANISM: Artificial Sequence
<220> FEATURE:
<223> OTHER INFORMATION: plasmid pKR912

<400> SEQUENCE: 81
ggccgcaagt atgaactaaa atgcatgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta aacaattcta accttagcat tgtgaacgag     300
acataagtgt taagaagaca taacaattat aatggaagaa gtttgtctcc atttatatat     360
tatatattac ccacttatgt attatattag gatgttaagg agacataaca attataaaga     420
gagaagtttg tatccattta tatattatat actacccatt tatatattat acttatccac     480
ttatttaatg tctttataag gtttgatcca tgatatttct aatattttag ttgatatgta    540
tatgaaaggg tactatttga actctcttac tctgtataaa ggttggatca tccttaaagt     600
gggtctattt aatttattg cttcttacag ataaaaaaaa aattatgagt tggtttgata     660
aaatattgaa ggatttaaaa taataataaa taacatataa tatatgtata taaatttatt     720
ataatataac atttatctat aaaaaagtaa atattgtcat aaatctatac aatcgtttag    780
ccttgctgga cgaatctcaa ttatttaaac gagagtaaac atatttgact ttttggttat    840
ttaacaaatt attatttaac actatatgaa attttttttt ttatcagcaa agaataaaat    900
taaattaaga aggacaatgg tgtcccaatc cttatacaac caacttccac aagaaagtca    960
agtcagagac aacaaaaaaa caagcaaagg aaatttttta atttgagttg tcttgtttgc   1020
tgcataattt atgcagtaaa acactacaca taacccttt agcagtagag caatggttga    1080
ccgtgtgctt agcttctttt atttttattttt tttatcagca aagaataaat aaaataaat    1140
```

```
gagacacttc agggatgttt caacaagctt ggcgcgccgt tctatagtgt cacctaaatc   1200
gtatgtgtat gatacataag gttatgtatt aattgtagcc gcgttctaac gacaatatgt   1260
ccatatggtg cactctcagt acaatctgct ctgatgccgc atagttaagc cagccccgac   1320
acccgccaac acccgctgac gcgccctgac gggcttgtct gctcccggca tccgcttaca   1380
gacaagctgt gaccgtctcc gggagctgca tgtgtcagag gttttcaccg tcatcaccga   1440
aacgcgcgag acgaaagggc ctcgtgatac gcctattttt ataggttaat gtcatgacca   1500
aaatccctta acgtgagttt tcgttccact gagcgtcaga ccccgtagaa aagatcaaag   1560
gatcttcttg agatcctttt tttctgcgcg taatctgctg cttgcaaaca aaaaaaccac   1620
cgctaccagc ggtggtttgt ttgccggatc aagagctacc aactcttttt ccgaaggtaa   1680
ctggcttcag cagagcgcag ataccaaata ctgtccttct agtgtagccg tagttaggcc   1740
accacttcaa gaactctgta gcaccgccta catacctcgc tctgctaatc ctgttaccag   1800
tggctgctgc cagtggcgat aagtcgtgtc ttaccgggtt ggactcaaga cgatagttac   1860
cggataaggc gcagcggtcg ggctgaacgg ggggttcgtg cacacagccc agcttggagc   1920
gaacgaccta caccgaactg agatacctac agcgtgagca ttgagaaagc gccacgcttc   1980
ccgaagggag aaaggcggac aggtatccgg taagcggcag ggtcggaaca ggagagcgca   2040
cgagggagct tccaggggga aacgcctggt atctttatag tcctgtcggg tttcgccacc   2100
tctgacttga gcgtcgattt ttgtgatgct cgtcaggggg gcggagccta tggaaaaacg   2160
ccagcaacgc ggccttttta cggttcctgg ccttttgctg gccttttgct cacatgttct   2220
ttcctgcgtt atcccctgat tctgtggata accgtattac cgcctttgag tgagctgata   2280
ccgctcgccg cagccgaacg accgagcgca gcgagtcagt gagcgaggaa gcggaagagc   2340
gcccaatacg caaaccgcct ctccccgcgc gttggccgat tcattaatgc aggttgatcg   2400
attcgacatc gatctagtaa catagatgac accgcgcgcg ataatttatc ctagtttgcg   2460
cgctatattt tgttttctat cgcgtattaa atgtataatt gcgggactct aatcataaaa   2520
acccatctca taaataacgt catgcattac atgttaatta ttacatgctt aacgtaattc   2580
aacagaaatt atatgataat catcgcaaga ccggcaacag gattcaatct taagaaactt   2640
tattgccaaa tgtttgaacg atctgcttcg acgcactcct tctttaggta cctcactatt   2700
cctttgccct cggacgagtg ctggggcgtc ggtttccact atcggcgagt acttctacac   2760
agccatcggt ccagacggcc gcgcttctgc gggcgatttg tgtacgcccg acagtcccgg   2820
ctccggatcg gacgattgcg tcgcatcgac cctgcgccca agctgcatca tcgaaattgc   2880
cgtcaaccaa gctctgatag agttggtcaa gaccaatgcg gagcatatac gcccggagcc   2940
gcggcgatcc tgcaagctcc ggatgcctcc gctcgaagta gcgcgtctgc tgctccatac   3000
aagccaacca cggcctccag aagaagatgt tggcgacctc gtattgggaa tccccgaaca   3060
tcgcctcgct ccagtcaatg accgctgtta tgcggccatt gtccgtcagg acattgttgg   3120
agccgaaatc cgcgtgcacg aggtgccgga cttcggggca gtcctcggcc caaagcatca   3180
gctcatcgag agcctgcgcg acggacgcac tgacggtgtc gtccatcaca gtttgccagt   3240
gatacacatg gggatcagca atcgcgcata tgaaatcacg ccatgtagtg tattgaccga   3300
ttccttgcgg tccgaatggg ccgaacccgc tcgtctggct aagatcggcc gcagcgatcg   3360
catccatggc ctccgcgacc ggctgcagaa cagcgggcag ttcggtttca ggcaggtctt   3420
gcaacgtgac accctgtgca cggcgggaga tgcaataggt caggctctcg ctgaattccc   3480
```

```
caatgtcaag cacttccgga atcgggagcg cggccgatgc aaagtgccga taaacataac    3540
gatctttgta gaaaccatcg gcgcagctat ttacccgcag acatatcca cgccctccta    3600
catcgaagct gaaagcacga gattcttcgc cctccgagag ctgcatcagg tcggagacgc    3660
tgtcgaactt ttcgatcaga aacttctcga cagacgtcgc ggtgagttca ggcttttca    3720
tggtttaata agaagagaaa agagttcttt tgttatggct gaagtaatag agaaatgagc    3780
tcgagcgtgt cctctccaaa tgaaatgaac ttccttatat agaggaaggg tcttgcgaag    3840
gatagtggga ttgtgcgtca tcccttacgt cagtggagat gtcacatcaa tccacttgct    3900
ttgaagacgt ggttggaacg tcttcttttt ccacgatgcc cctcgtgggt gggggtccat    3960
ctttgggacc actgtcggca gaggcatctt gaatgatagc ctttcctta tcgcaatgat    4020
ggcatttgta ggagccacct tcctttcta ctgtcctttc gatgaagtga cagatagctg    4080
ggcaatggaa tccgaggagg tttcccgaaa ttatcctttg ttgaaaagtc tcaatagccc    4140
tttggtcttc tgagactgta tctttgacat ttttggagta gaccagagtg tcgtgctcca    4200
ccatgttgac gaagattttc ttcttgtcat tgagtcgtaa aagactctgt atgaactgtt    4260
cgccagtctt cacggcgagt tctgttagat cctcgatttg aatcttagac tccatgcatg    4320
gccttagatt cagtaggaac tacctttta gagactccaa tctctattac ttgccttggt    4380
ttatgaagca agcctgaat cgtccatact ggaatagtac ttctgatctt gagaaatatg    4440
tctttctctg tgttcttgat gcaattagtc ctgaatcttt tgactgcatc tttaaccttc    4500
ttgggaaggt atttgatctc ctggagattg ttactcgggt agatcgtctt gatgagacct    4560
gctgcgtagg cctctctaac catctgtggg tcagcattct ttctgaaatt gaagaggcta    4620
accttctcat tatcagtggt gaacatagtg tcgtcacctt caccttcgaa cttccttcct    4680
agatcgtaaa gatagaggaa atcgtccatt gtaatctccg gggcaaagga gatctctttt    4740
ggggctggat cactgctggg ccttttggtt cctagcgtga gccagtgggc ttttgctttt    4800
ggtgggcttg ttagggcctt agcaaagctc ttgggcttga gttgagcttc tcctttgggg    4860
atgaagttca acctgtctgt ttgctgactt gttgtgtacg cgtcagctgc tgctcttgcc    4920
tctgtaatag tggcaaattt cttgtgtgca actccgggaa cgccgtttgt tgccgccttt    4980
gtacaacccc agtcatcgta tataccggca tgtggaccgt tatacacaac gtagtagttg    5040
atatgagggt gttgaatacc cgattctgct ctgagaggag caactgtgct gttaagctca    5100
gattttgtg ggattggaat tggatcgatc tcgatcccgc gaaattaata cgactcacta    5160
tagggagacc acaacggttt ccctctagaa ataattttgt ttaactttaa gaaggagata    5220
tacccatgga aaagcctgaa ctcaccgcga cgtctgtcga agtttctg atcgaaaagt    5280
tcgacagcgt ctccgacctg atgcagctct cggagggcga gaatctcgt gctttcagct    5340
tcgatgtagg agggcgtgga tatgtcctgc gggtaaatag ctgcgccgat ggtttctaca    5400
aagatcgtta tgtttatcgg cactttgcat cggccgcgct cccgattccg gaagtgcttg    5460
acattgggga attcagcgag agcctgacct attgcatctc ccgccgtgca cagggtgtca    5520
cgttgcaaga cctgcctgaa accgaactgc ccgctgttct gcagccggtc gcggaggcta    5580
tggatgcgat cgctgcggcc gatcttagcc agacgagcgg ttcggccca ttcggaccgc    5640
aaggaatcgg tcaatacact acatggcgtg atttcatatg cgcgattgct gatccccatg    5700
tgtatcactg gcaaactgtg atggacgaca ccgtcagtgc gtccgtcgcg caggctctcg    5760
atgagctgat gctttgggcc gaggactgcc ccgaagtccg gcacctcgtg cacgcggatt    5820
tcggctccaa caatgtcctg acggacaatg gccgcataac agcggtcatt gactggagcg    5880
```

```
aggcgatgtt cggggattcc caatacgagg tcgccaacat cttcttctgg aggccgtggt  5940
tggcttgtat ggagcagcag acgcgctact tcgagcggag gcatccggag cttgcaggat  6000
cgccgcggct ccgggcgtat atgctccgca ttggtcttga ccaactctat cagagcttgg  6060
ttgacggcaa tttcgatgat gcagcttggg cgcagggtcg atgcgacgca atcgtccgat  6120
ccggagccgg gactgtcggg cgtacacaaa tcgcccgcag aagcgcggcc gtctggaccg  6180
atggctgtgt agaagtactc gccgatagtg gaaaccgacg ccccagcact cgtccgaggg  6240
caaaggaata gtgaggtaca gcttggatcg atccggctgc taacaaagcc cgaaaggaag  6300
ctgagttggc tgctgccacc gctgagcaat aactagcata accccttggg gcctctaaac  6360
gggtcttgag gggttttttg ctgaaaggag gaactatatc cggatgatcg ggcgcgccgt  6420
cgacggatcc gtacgagatc cggccggcca gatcctgcag gagatccaag cttttgatcc  6480
atgcccttca tttgccgctt attaattaat ttggtaacag tccgtactaa tcagttactt  6540
atccttcccc catcataatt aatcttggta gtctcgaatg ccacaacact gactagtctc  6600
ttggatcata agaaaaagcc aaggaacaaa agaagacaaa acacaatgag agtatccttt  6660
gcatagcaat gtctaagttc ataaaattca acaaaaacg caatcacaca cagtggacat  6720
cacttatcca ctagctgatc aggatcgccg cgtcaagaaa aaaaaactgg accccaaaag  6780
ccatgcacaa caacacgtac tcacaaaggt gtcaatcgag cagcccaaaa cattcaccaa  6840
ctcaacccat catgagccct cacatttgtt gtttctaacc caacctcaaa ctcgtattct  6900
cttccgccac ctcatttttg tttatttcaa cacccgtcaa actgcatgcc accccgtggc  6960
caaatgtcca tgcatgttaa caagacctat gactataaat agctgcaatc tcggcccagg  7020
ttttcatcat caagaaccag ttcaatatcc tagtacaccg tattaaagaa tttaagatat  7080
actgcggccg caccatggag gtggtgaatg aaatagtctc aattgggcag gaagttttac  7140
ccaaagttga ttatgcccaa ctctggagtg atgccagtca ctgtgaggtg ctttacttgt  7200
ccatcgcatt tgtcatcttg aagttcactc ttggcccct tggtccaaaa ggtcagtctc  7260
gtatgaagtt tgttttcacc aattacaacc ttctcatgtc catttattcg ttgggatcat  7320
tcctctcaat ggcatatgcc atgtacacca tcggtgttat gtctgacaac tgcgagaagg  7380
cttttgacaa caacgtcttc aggatcacca cgcagttgtt ctatttgagc aagttcctgg  7440
agtatattga ctccttctat ttgccactga tgggcaagcc tctgacctgg ttgcaattct  7500
tccatcattt gggggcaccg atggatatgt ggctgttcta taattaccga aatgaagctg  7560
tttggatttt tgtgctgttg aatggtttca tccactggat catgtacggt tattattgga  7620
ccagattgat caagctgaag ttccccatgc caaaatccct gattacatca atgcagatca  7680
ttcaattcaa tgttggttc tacattgtct ggaagtacag gaacattccc tgttatcgcc  7740
aagatgggat gaggatgttt ggctggttct tcaattactt ttatgttggc acagtcttgt  7800
gtttgttctt gaatttctat gtgcaaacgt atatcgtcag gaagcacaag ggagccaaaa  7860
agattcagtg agc                                                    7873
```

<210> SEQ ID NO 82
<211> LENGTH: 11459
<212> TYPE: DNA
<213> ORGANISM: Artificial Sequence
<220> FEATURE:
<223> OTHER INFORMATION: plasmid pKR1014
<220> FEATURE:
<221> NAME/KEY: misc_feature
<222> LOCATION: (10262)..(10262)

<223> OTHER INFORMATION: n is a, c, g, or t

<400> SEQUENCE: 82

| | | | | | |
|---|---|---|---|---|---:|
| ggagatccaa | gcttttgatc | catgcccttc | atttgccgct | tattaattaa | tttggtaaca | 60 |
| gtccgtacta | atcagttact | tatccttccc | ccatcataat | taatcttggt | agtctcgaat | 120 |
| gccacaacac | tgactagtct | cttggatcat | aagaaaaagc | caaggaacaa | agaagacaa | 180 |
| aacacaatga | gagtatcctt | tgcatagcaa | tgtctaagtt | cataaaattc | aaacaaaaac | 240 |
| gcaatcacac | acagtggaca | tcacttatcc | actagctgat | caggatcgcc | gcgtcaagaa | 300 |
| aaaaaaactg | gaccccaaaa | gccatgcaca | acaacacgta | ctcacaaagg | tgtcaatcga | 360 |
| gcagcccaaa | acattcacca | actcaaccca | tcatgagccc | tcacatttgt | tgtttctaac | 420 |
| ccaacctcaa | actcgtattc | tcttccgcca | cctcattttt | gtttatttca | acacccgtca | 480 |
| aactgcatgc | caccccgtgg | ccaaatgtcc | atgcatgtta | acaagaccta | tgactataaa | 540 |
| tagctgcaat | ctcggcccag | ttttcatca | tcaagaacca | gttcaatatc | ctagtacacc | 600 |
| gtattaaaga | atttaagata | tactgcggcc | gcaccatgga | ggtggtgaat | gaaatagtct | 660 |
| caattgggca | ggaagtttta | cccaaagttg | attatgccca | actctggagt | gatgccagtc | 720 |
| actgtgaggt | gctttacttg | tccatcgcat | ttgtcatctt | gaagttcact | cttggccccc | 780 |
| ttggtccaaa | aggtcagtct | cgtatgaagt | ttgttttcac | caattacaac | cttctcatgt | 840 |
| ccatttattc | gttgggatca | ttcctctcaa | tggcatatgc | catgtacacc | atcggtgtta | 900 |
| tgtctgacaa | ctgcgagaag | gcttttgaca | acaacgtctt | caggatcacc | acgcagttgt | 960 |
| tctatttgag | caagttcctg | gagtatattg | actccttcta | tttgccactg | atgggcaagc | 1020 |
| ctctgacctg | gttgcaattc | ttccatcatt | tgggggcacc | gatggatatg | tggctgttct | 1080 |
| ataattaccg | aaatgaagct | gttttggattt | ttgtgctgtt | gaatggtttc | atccactgga | 1140 |
| tcatgtacgg | ttattattgg | accagattga | tcaagctgaa | gttccccatg | ccaaaatccc | 1200 |
| tgattacatc | aatgcagatc | attcaattca | atgttggttt | ctacattgtc | tggaagtaca | 1260 |
| ggaacattcc | ctgttatcgc | caagatggga | tgaggatgtt | tggctggttc | ttcaattact | 1320 |
| tttatgttgg | cacagtcttg | tgtttgttct | tgaatttcta | tgtgcaaacg | tatatcgtca | 1380 |
| ggaagcacaa | gggagccaaa | aagattcagt | gagcggccgc | aagtatgaac | taaaatgcat | 1440 |
| gtaggtgtaa | gagctcatgg | agagcatgga | atattgtatc | cgaccatgta | acagtataat | 1500 |
| aactgagctc | catctcactt | cttctatgaa | taaacaaagg | atgttatgat | atattaacac | 1560 |
| tctatctatg | caccttattg | ttctatgata | aatttcctct | tattattata | aatcatctga | 1620 |
| atcgtgacgg | cttatggaat | gcttcaaata | gtacaaaaac | aaatgtgtac | tataagactt | 1680 |
| tctaaacaat | tctaaccttta | gcattgtgaa | cgagacataa | gtgttaagaa | gacataacaa | 1740 |
| ttataatgga | agaagtttgt | ctccatttat | atattatata | ttacccactt | atgtattata | 1800 |
| ttaggatgtt | aaggagacat | aacaattata | agagagaag | tttgtatcca | tttatatatt | 1860 |
| atatactacc | catttatata | ttatacttat | ccacttattt | aatgtcttta | taaggtttga | 1920 |
| tccatgatat | ttctaatatt | ttagttgata | tgtatatgaa | agggtactat | ttgaactctc | 1980 |
| ttactctgta | taaaggttgg | atcatcctta | aagtgggtct | attaattttt | attgcttctt | 2040 |
| acagataaaa | aaaaaattat | gagttggttt | gataaaaatat | tgaaggattt | aaaataataa | 2100 |
| taaataacat | ataatatatg | tatataaatt | tattataata | taacatttat | ctataaaaaa | 2160 |
| gtaaatattg | tcataaatct | atacaatcgt | ttagccttgc | tggacgaatc | tcaattattt | 2220 |
| aaacgagagt | aaacatattt | gacttttttgg | ttatttaaca | aattattatt | taacactata | 2280 |

-continued

```
tgaaattttt ttttttatca gcaaagaata aaattaaatt aagaaggaca atggtgtccc      2340
aatccttata caaccaactt ccacaagaaa gtcaagtcag agacaacaaa aaaacaagca      2400
aaggaaattt tttaatttga gttgtcttgt ttgctgcata atttatgcag taaaacacta      2460
cacataaccc ttttagcagt agagcaatgg ttgaccgtgt gcttagcttc ttttatttta      2520
tttttttatc agcaaagaat aaataaaata aaatgagaca cttcagggat gtttcaacaa      2580
gcttggcgcg ccgttctata gtgtcaccta atcgtatgt gtatgataca taaggttatg      2640
tattaattgt agccgcgttc taacgacaat atgtccatat ggtgcactct cagtacaatc      2700
tgctctgatg ccgcatagtt aagccagccc cgacacccgc caacacccgc tgacgcgccc      2760
tgacgggctt gtctgctccc ggcatccgct tacagacaag ctgtgaccgt ctccgggagc      2820
tgcatgtgtc agaggttttc accgtcatca ccgaaacgcg cgagacgaaa gggcctcgtg      2880
atacgcctat ttttataggt taatgtcatg accaaaatcc cttaacgtga gttttcgttc      2940
cactgagcgt cagaccccgt agaaaagatc aaaggatctt cttgagatcc ttttttttctg      3000 cgcgtaatct gctgcttgca acaaaaaaaa ccaccgctac cagcggtggt ttgtttgccg      3060
gatcaagagc taccaactct ttttccgaag gtaactggct tcagcagagc gcagatacca      3120
aatactgtcc ttctagtgta gccgtagtta ggccaccact tcaagaactc tgtagcaccg      3180
cctacatacc tcgctctgct aatcctgtta ccagtgctg ctgccagtgg cgataagtcg      3240
tgtcttaccg ggttggactc aagacgatag ttaccggata aggcgcagcg gtcgggctga      3300 acgggggggtt cgtgcacaca gcccagcttg gagcgaacga cctacaccga actgagatac      3360
ctacagcgtg agcattgaga aagcgccacg cttcccgaag ggagaaaggc ggacaggtat      3420
ccggtaagcg gcagggtcgg aacaggagag cgcacgaggg agcttccagg gggaaacgcc      3480
tggtatcttt atagtcctgt cgggtttcgc cacctctgac ttgagcgtcg attttttgtga      3540 tgctcgtcag gggggcggag cctatggaaa aacgccagca acgcggcctt tttacggttc      3600
ctggcctttt gctggccttt tgctcacatg ttctttcctg cgttatcccc tgattctgtg      3660
gataaccgta ttaccgcctt tgagtgagct gataccgctc gccgcagccg aacgaccgag      3720
cgcagcgagt cagtgagcga ggaagcggaa gagcgcccaa tacgcaaacc gcctctcccc      3780
gcgcgttggc cgattcatta atgcaggttg atcgattcga catcgatcta gtaacataga      3840
tgacaccgcg cgcgataatt tatcctagtt tgcgcgctat attttgtttt ctatcgcgta      3900
ttaaatgtat aattgcggga ctctaatcat aaaaacccat ctcataaata acgtcatgca      3960
ttacatgtta attattacat gcttaacgta attcaacaga aattatatga taatcatcgc      4020
aagaccggca acaggattca atcttaagaa actttattgc caaatgtttg aacgatctgc      4080
ttcgacgcac tccttcttta ggtacctcac tattcctttg ccctcggacg agtgctgggg      4140
cgtcggtttc cactatcggc gagtacttct acacagccat cggtccagac ggccgcgctt      4200
ctgcgggcga tttgtgtacg cccgacagtc ccggctccgg atcggacgat tgcgtcgcat      4260
cgaccctgcg cccaagctgc atcatcgaaa ttgccgtcaa ccaagctctg atagagttgg      4320
tcaagaccaa tgcggagcat atacgcccgg agccgcggcg atcctgcaag ctccggatgc      4380
ctccgctcga agtagcgcgt ctgctgcctc atacaagcca accacggcct ccagaagaag      4440
atgttggcga cctcgtattg ggaatccccg aacatcgcct cgctccagtc aatgaccgct      4500
gttatgcggc cattgtccgt caggacattg ttggagccga atccgcgtg cacgaggtgc      4560 cggacttcgg ggcagtcctc ggcccaaagc atcagctcat cgagagcctg cgcgacggac      4620
```

```
gcactgacgg tgtcgtccat cacagtttgc cagtgataca catggggatc agcaatcgcg    4680
catatgaaat cacgccatgt agtgtattga ccgattcctt gcggtccgaa tgggccgaac    4740
ccgctcgtct ggctaagatc ggccgcagcg atcgcatcca tggcctccgc gaccggctgc    4800
agaacagcgg gcagttcggt ttcaggcagg tcttgcaacg tgacaccctg tgcacggcgg    4860
gagatgcaat aggtcaggct ctcgctgaat tccccaatgt caagcacttc cggaatcggg    4920
agcgcggccg atgcaaagtg ccgataaaca taacgatctt tgtagaaacc atcggcgcag    4980
ctatttaccc gcaggacata tccacgccct cctacatcga agctgaaagc acgagattct    5040
tcgccctccg agagctgcat caggtcggag acgctgtcga acttttcgat cagaaacttc    5100
tcgacagacg tcgcggtgag ttcaggcttt ttcatggttt aataagaaga gaaaagagtt    5160
cttttgttat ggctgaagta atagagaaat gagctcgagc gtgtcctctc caaatgaaat    5220
gaacttcctt atatagagga agggtcttgc gaaggatagt gggattgtgc gtcatccctt    5280
acgtcagtgg agatgtcaca tcaatccact tgctttgaag acgtggttgg aacgtcttct    5340
ttttccacga tgctcctcgt gggtgggggt ccatctttgg gaccactgtc ggcagaggca    5400
tcttgaatga tagcctttcc tttatcgcaa tgatggcatt tgtaggagcc accttccttt    5460
tctactgtcc tttcgatgaa gtgacagata gctgggcaat ggaatccgag gaggtttccc    5520
gaaattatcc tttgttgaaa agtctcaata gcccttggt cttctgagac tgtatctttg    5580
acatttttgg agtagaccag agtgtcgtgc tccaccatgt tgacgaagat tttcttcttg    5640
tcattgagtc gtaaaagact ctgtatgaac tgttcgccag tcttcacggc gagttctgtt    5700
agatcctcga tttgaatctt agactccatg catggcctta gattcagtag gaactacctt    5760
tttagagact ccaatctcta ttacttgcct tggtttatga agcaagcctt gaatcgtcca    5820
tactggaata gtacttctga tcttgagaaa tatgtctttc tctgtgttct tgatgcaatt    5880
agtcctgaat cttttgactg catctttaac cttcttggga aggtatttga tctcctggag    5940
attgttactc gggtagatcg tcttgatgag acctgctgcg taggcctctc taaccatctg    6000
tgggtcagca ttcttttctga aattgaagag gctaaccttc tcattatcag tggtgaacat    6060
agtgtcgtca ccttcacctt cgaacttcct tcctagatcg taaagataga ggaaatcgtc    6120
cattgtaatc tccggggcaa aggagatctc ttttggggct ggatcactgc tgggcctttt    6180
ggttcctagc gtgagccagt gggcttttg cttggtggg cttgttaggg ccttagcaaa    6240
gctcttgggc ttgagttgag cttctccttt ggggatgaag ttcaacctgt ctgtttgctg    6300
acttgttgtg tacgcgtcag ctgctgctct tgcctctgta atagtggcaa atttcttgtg    6360
tgcaactccg ggaacgccgt tgttgccgc cttttgtacaa ccccagtcat cgtatatacc    6420
ggcatgtgga ccgttataca caacgtagta gttgatatga gggtgttgaa tacccgattc    6480
tgctctgaga ggagcaactg tgctgttaag ctcagatttt tgtgggattg gaattggatc    6540
gatctcgatc ccgcgaaatt aatacgactc actatagga gaccacaacg gtttccctct    6600
agaaataatt tgtttaact ttaagaagga gatataccca tggaaagcc tgaactcacc    6660
gcgacgtctg tcgagaagtt tctgatcgaa aagttcgaca gcgtctccga cctgatgcag    6720
ctctcggagg gcgaagaatc tcgtgctttc agcttcgatg taggagggcg tggatatgtc    6780
ctgcgggtaa atagctgcgc cgatggtttc tacaaagatc gttatgttta tcggcacttt    6840
gcatcggccg cgctcccgat tccggaagtg cttgacattg gggaattcag cgagagcctg    6900
acctattgca tctcccgccg tgcacagggt gtcacgttgc aagacctgcc tgaaaccgaa    6960
ctgcccgctg ttctgcagcc ggtcgcggag gctatggatg cgatcgctgc ggccgatctt    7020
```

```
agccagacga gcgggttcgg cccattcgga ccgcaaggaa tcggtcaata cactacatgg   7080
cgtgatttca tatgcgcgat tgctgatccc catgtgtatc actggcaaac tgtgatggac   7140
gacaccgtca gtgcgtccgt cgcgcaggct ctcgatgagc tgatgctttg ggccgaggac   7200
tgccccgaag tccggcacct cgtgcacgcg gatttcggct ccaacaatgt cctgacggac   7260
aatggccgca taacagcggt cattgactgg agcgaggcga tgttcgggga ttcccaatac   7320
gaggtcgcca acatcttctt ctggaggccg tggttggctt gtatggagca gcagacgcgc   7380
tacttcgagc ggaggcatcc ggagcttgca ggatcgccgc ggctccgggc gtatatgctc   7440
cgcattggtc ttgaccaact ctatcagagc ttggttgacg gcaatttcga tgatgcagct   7500
tgggcgcagg tcgatgcgca cgcaatcgtc cgatccggag ccgggactgt cgggcgtaca   7560
caaatcgccc gcagaagcgc ggccgtctgg accgatggct gtgtagaagt actcgccgat   7620
agtggaaacc gacgcccag cactcgtccg agggcaaagg aatagtgagg tacagcttgg   7680
atcgatccgg ctgctaacaa agcccgaaag gaagctgagt tggctgctgc caccgctgag   7740
caataactag cataacccct tggggcctct aaacgggtct tgaggggttt tttgctgaaa   7800
ggaggaacta tatccggatg atcgggcgcg ccgtcgacgg atccgtacga gatccggccg   7860
gccagatcct gcaggatata atgagccgta aacaaagatg attaagtagt aattaatacg   7920
tactagtaaa agtggcaaaa gataacgaga aagaaccaat ttctttgcat tcggccttag   7980
cggaaggcat atataagctt tgattatttt atttagtgta atgatttcgt acaaccaaag   8040
catttattta gtactctcac acttgtgtcg cggccgctca ttcagggaca gcagccagct   8100
gggcaatctc gcctaagaag ctgaccaatt tctgaacccc ggggatgatg gctggggccc   8160
tgtagggcag gttgtgcttg gcgcacaact tctgcacctc cagggaagct gccgtgaggt   8220
tgtgcctggg catgttgggc cacaagtggt gctcaatctg gtagttgaga ccaccaaaga   8280
cccaatcggt gagaaggccg ggcttaatgt tcaacgtctc gtggatctgg ctggcgctga   8340
acccgtgctc atcccagaca gtctcctcaa ccttgtccaa aggatagtga ttcagaaaca   8400
caacgatggc aatgccaaat cctccgagca gctcggagat caagaagcat cccaaaccgg   8460
tggcaaagct aggcatggca ctgcaataga aagtggcctt gagcacccag tggagggcca   8520
gaccaatcgc ctccttagtg tactggcgct tgtagtacag gttcctctcc tcgctcttgt   8580
aggacatgac gccgccgatg gattggaggc accagatgaa cctaagggat gcaatggtgg   8640
gaatgaagta gtactgctgg tacttgatga gattccgagt cgaaggagta gccctcttga   8700
catcttcggg agaccaagcc aggatgggga ggttatcaat atctgggtca tggccgacca   8760
cattggtggc ggcatggtga ccattgtgcc tatccttcca ccaagtctgt gagtatccct   8820
gcatcacgtt accgaaaaag agaccgaaag cgtcgttaat cttgcggttt gtgaaaacct   8880
ggtgatggca atagtcgtgg gacaaccagc ctagctgttg gtagcacacg ccaagaacca   8940
aagcagcggt gaaataccaa ttcgtgtaca cggtcatcaa gatggaaagg accatcaaac   9000
cgacggtagt tgaagtcttg taaaaatacc aaaggaaact cgtctcgaac ataccttgg    9060
agatgaattc ctcccgcaac ttgcggaaat cctcctgggg ctcatcacgc ttaggcttgg   9120
gtgcaacagg tgtgtcagga gaggaaggct ccataacagg cattctcttc aacttggcga   9180
cggcttcttg agagtgcatc accatgaaga catcggtcgc atcgcggttg cgatagttct   9240
cgataatgtc agctcctcca gggtggtgat tgacccaagc agacacatca taagttgcgc   9300
catcaattgt gattggcaga gcttgccgct taggagacat ggtgcggccg cttgggggc    9360
```

```
tatggaagac tttcttagtt agttgtgtga ataagcaatg ttgggagaat cgggactact    9420
tataggatag gaataaaaca gaaaagtatt aagtgctaat gaaatattta gactgataat    9480
taaaatcttc acgtatgtcc acttgatata aaaacgtcag gaataaagga agtacagtag    9540
aatttaaagg tactctttt atatataccc gtgttctctt tttggctagc tagttgcata    9600
aaaaataatc tatatttta tcattatttt aaatatctta tgagatggta aatatttatc    9660
ataatttttt ttactattat ttattatttg tgtgtgtaat acatatagaa gttaattaca    9720
aattttattt acttttcat tattttgata tgattcacca ttaatttagt gttattattt    9780
ataatagttc attttaatct ttttgtatat attatgcgtg cagtactttt ttcctacata    9840
taactactat tacattttat ttatataata ttttattaa tgaattttcg tgataatatg    9900
taatattgtt cattattatt tcagatttt taaaaatatt tgtgttatta tttatgaaat    9960
atgtaatttt tttagtattt gattttatga tgataaagtg ttctaaattc aaagaaggg   10020 ggaaagcgta acattaaaa aacgtcatca aacaaaaaca aaatcttgtt aataaagata   10080
aaactgtttg ttttgatcac tgttatttcg taatataaaa acattattta tatttatatt   10140
gttgacaacc aaatttgcct atcaaatcta accaatataa tgcatgcgtg gcaggtaatg   10200
tactaccatg aacttaagtc atgacataat aaaccgtgaa tctgaccaat gcatgtacct   10260
anctaaattg tatttgtgac acgaagcaaa tgattcaatt cacaatggag atgggaaaca   10320
aataatgaag aacccagaac taagaaagct tttctgaaaa ataaaataaa ggcaatgtca   10380
aaagtatact gcatcatcag tccagaaagc acatgatatt ttttttatcag tatcaatgca   10440 gctagttta ttttacaata tcgatatagc tagtttaaat atattgcagc tagatttata   10500
aatatttgtg ttattattta tcatttgtgt aatcctgttt ttagtatttt agtttatata   10560
tgatgataat gtattccaaa tttaaaagaa gggaaataaa tttaaacaag aaaaaaagtc   10620
atcaaacaaa aaacaaatga aagggtggaa agatgttacc atgtaatgtg aatgttacag   10680
tatttctttt attatagagt taacaaatta actaatatga ttttgttaat aatgataaaa   10740 tattttttt attattattt cataatataa aaatagttta cttaatataa aaaaaattct   10800
atcgttcaca acaaagttgg ccacctaatt taaccatgca tgtacccatg gaccatatta   10860
ggtaaccatc aaacctgatg aagagataaa gagatgaaga cttaagtcat aacacaaaac   10920
cataaaaaac aaaaatacaa tcaaccgtca atctgaccaa tgcatgaaaa agctgcaata   10980
gtgagtggcg acacaaagca catgattttc ttacaacgga gataaaacca aaaaatatt   11040 tcatgaacaa cctagaacaa ataaagcttt tatataataa atatataaat aaataaaggc   11100
tatggaataa tatacttcaa tatatttgga ttaaataaat tgttggcggg gttgatatat   11160
ttatacacac ctaaagtcac ttcaatctca ttttcacttA acttttattt ttttttctt    11220 tttatttatc ataagagaa tattgataat atacttttta acatatttt atgacatttt    11280 ttattggtga aaacttatta aaaatcataa attttgtaag ttagatttat ttaaagagtt   11340
cctcttctta ttttaaattt tttaataat tttaaataa ctaaaatttg tgttaaaaat    11400
gttaaaaaat gtgttattaa cccttctctt cgaggacgta cgtctagagt cgacctgca   11459
```

<210> SEQ ID NO 83
<211> LENGTH: 6021
<212> TYPE: DNA
<213> ORGANISM: Artificial Sequence
<220> FEATURE:
<223> OTHER INFORMATION: plasmid pKR271

<400> SEQUENCE: 83

```
ggccgcgaat tcaatcacta gtgaattcgc ggccgcatga gccgtaaagg ttcaatacaa      60
cgagtgcttg ttttcttagg gacaagcatt gtacttatgt atgattctgt gtaaccatga     120
gtcttccacg ttgtactaat gtgaagggca aaaataaaac acagaacaag ttcgtttttc     180
tcaaataatg tgaaggtaga aaatggaacc atgcctcctc tcttgcatgt gatttaaaat     240
attagcagat ggtaccgtac gtgggcggat cccccgggct gcaggaattc actggccgtc     300
gttttacaac gtcgtgactg ggaaaaccct ggcgttaccc aacttaatcg ccttgcagca     360
catccccctt tcgccagctg gcgtaatagc gaagaggccc gcaccgatcg cccttcccaa     420
cagttgcgca gcctgaatgg cgaatggcgc ctgatgcggt attttctcct tacgcatctg     480
tgcggtattt cacaccgcat atggtgcact ctcagtacaa tctgctctga tgccgcatag     540
ttaagccagc cccgacaccc gccaacaccc gctgacgcgc cctgacgggc ttgtctgctc     600
ccggcatccg cttacagaca agctgtgacc gtctccggga gctgcatgtg tcagaggttt     660
tcaccgtcat caccgaaacg cgcgagacga agggcctcg tgatacgcct attttatag      720
gttaatgtca tgataataat ggtttcttag acgtcaggtg gcacttttcg gggaaatgtg     780
cgcggaaccc ctatttgttt atttttctaa atacattcaa atatgtatcc gctcatgaga     840
caataaccct gataaatgct tcaataatat tgaaaaagga agagtatgag tattcaacat     900
ttccgtgtcg cccttattcc cttttttgcg gcattttgcc ttcctgtttt tgctcaccca     960
gaaacgctgg tgaaagtaaa agatgctgaa gatcagttgg gtgcacgagt gggttacatc    1020
gaactggatc tcaacagcgg taagatcctt gagagttttc gccccgaaga acgttttcca    1080
atgatgagca cttttaaagt tctgctatgt ggcgcggtat tatcccgtat tgacgccggg    1140
caagagcaac tcggtcgccg catacactat tctcagaatg acttggttga gtactcacca    1200
gtcacagaaa agcatcttac ggatggcatg acagtaagag aattatgcag tgctgccata    1260
accatgagtg ataacactgc ggccaactta cttctgacaa cgatcggagg accgaaggag    1320
ctaaccgctt ttttgcacaa catgggggat catgtaactc gccttgatcg ttgggaaccg    1380
gagctgaatg aagccatacc aaacgacgag cgtgacacca cgatgcctgt agcaatggca    1440
acaacgttgc gcaaactatt aactggcgaa ctacttactc tagcttcccg gcaacaatta    1500
atagactgga tggaggcgga taaagttgca ggaccacttc tgcgctcggc ccttccggct    1560
ggctggttta ttgctgataa atctggagcc ggtgagcgtg ggtctcgcgg tatcattgca    1620
gcactggggc cagatggtaa gccctcccgt atcgtagtta tctacacgac ggggagtcag    1680
gcaactatgg atgaacgaaa tagacagatc gctgagatag gtgcctcact gattaagcat    1740
tggtaactgt cagaccaagt ttactcatat atactttaga ttgatttaaa acttcatttt    1800
taatttaaaa ggatctaggt gaagatcctt tttgataatc tcatgaccaa aatcccttaa    1860
cgtgagtttt cgttccactg agcgtcagac cccgtagaaa agatcaaagg atcttcttga    1920
gatcctttt ttctgcgcgt aatctgctgc ttgcaaacaa aaaaaccacc gctaccagcg    1980
gtggtttgtt tgccggatca agagctacca actctttttc cgaaggtaac tggcttcagc    2040
agagcgcaga taccaaatac tgtccttcta gtgtagccgt agttaggcca ccacttcaag    2100
aactctgtag caccgcctac atacctcgct ctgctaatcc tgttaccagt ggctgctgcc    2160
agtggcgata agtcgtgtct taccgggttg gactcaagac gatagttacc ggataaggcg    2220
cagcggtcgg gctgaacggg gggttcgtgc acacagccca gcttggagcg aacgacctac    2280
accgaactga gatacctaca gcgtgagcta tgagaaagcg ccacgcttcc cgaagggaga    2340
```

```
aaggcggaca ggtatccggt aagcggcagg gtcggaacag gagagcgcac gagggagctt    2400 ccaggggaa  acgcctggta tctttatagt cctgtcgggt ttcgccacct ctgacttgag    2460
cgtcgatttt tgtgatgctc gtcagggggg cggagcctat ggaaaaacgc cagcaacgcg    2520 gccttttac  ggttcctggc cttttgctgg ccttttgctc acatgttctt tcctgcgtta    2580 tccctgatt  ctgtggataa ccgtattacc gcctttgagt gagctgatac cgctcgccgc    2640
agccgaacga ccgagcgcag cgagtcagtg agcgaggaag cggaagagcg cccaatacgc    2700
aaaccgcctc tccccgcgcg ttggccgatt cattaatgca gctggcacga caggtttccc    2760
gactggaaag cgggcagtga gcgcaacgca attaatgtga gttagctcac tcattaggca    2820
ccccaggctt tacactttat gcttccggct cgtatgttgt gtggaattgt gagcggataa    2880
caatttcaca caggaaacag ctatgaccat gattacgcca agcttgcatg cctgcaggtc    2940
gactcgacgt acgatcccac atgcaagttt ttatttcaat ccctttcct  ttgaataact    3000 gaccaagaac aacaagaaaa aaaaaaaaa  agaaaaggat cattttgaaa ggatattttt    3060
cgctcctatt caaatactgt attttacca  aaaaaactgt attttccta  cactctcaag    3120 ctttgttttt cgcttcgact ctcatgcatt ccttcatatg ccaatcactc tatttataaa    3180
tggcataagg tagtgtgaac aattgcaaag cttgtcatca aaagcttgca atgtacaaat    3240
taatgttttt catgccttc  aaaattatct gcacccccta gctattaatc taacatctaa    3300
gtaaggctag tgaattttt  cgaatagtca tgcagtgcat taatttcccc gtgactattt    3360 tggcttgac  tccaacactg gccccgtaca tccgtccctc attacatgaa agaaatatt    3420 gtttatattc ttaattaaaa atattgtccc ttctaaattt tcatatagtt aattattata    3480 ttacttttt  ctctattcta ttagttctat tttcaaatta ttatttatgc atatgtaaag    3540
tacattatat ttttgctata tacttaaata tttctaaatt attaaaaaaa gactgatatg    3600
aaaaatttat tcttttaaa  gctatatcat tttatatata ctttttcttt tcttttcttt    3660
cattttctat tcaatttaat aagaaataaa ttttgtaaat ttttatttat caatttataa    3720
aaatatttta cttatatgt  ttttttcacat ttttgttaaa caaatcatat cattatgatt    3780
gaaagagagg aaattgacag tgagtaataa gtgatgagaa aaaaatgtgt tatttcctaa    3840
aaaaaaccta acaaacatg  tatctactct ctatttcatc tatctctcat ttcattttc    3900 tctttatctc tttctttatt tttttatcat atcatttcac attaattatt tttactctct    3960
ttattttttc tctctatccc tctcttattt ccactcatat atacactcca aaattggggc    4020
atgcctttat cactactcta tctcctccac taaatcattt aaatgaaact gaaaagcatt    4080
ggcaagtctc ctccctcct  caagtgattt ccaactcagc attggcatct aattgattca    4140
gtatatctat tgcatgtgta aaagtctttc cacaatacat aactattaat taatcttaaa    4200
taaataaagg ataaaatatt ttttttttctt cataaaatta aaatatgtta ttttttgttt    4260
agatgtatat tcgaataaat ctaaatatat gataatgatt tttatattg  attaaacata    4320 taatcaatat taaatatgat attttttat  ataggttgta cacataattt tataaggata    4380
aaaaatatga taaaaataaa ttttaaatat tttatattt  acgagaaaaa aaatatttt    4440 agccataaat aaatgaccag catatttac  aaccttagta attcataaat tcctatatgt    4500
atatttgaaa ttaaaacag  ataatcgtta agggaaggaa tcctacgtca tctcttgcca    4560 tttgttttc  atgcaaacag aaagggacga aaaaccacct caccatgaat cactcttcac    4620
accattttta ctagcaaaca agtctcaaca actgaagcca gctctctttc cgttctttt    4680 tacaacactt tctttgaaat agtagtattt ttttttcaca tgatttatta acgtgccaaa    4740
```

| | |
|---|---|
| agatgcttat tgaatagagt gcacatttgt aatgtactac taattagaac atgaaaaagc | 4800 |
| attgttctaa cacgataatc ctgtgaaggc gttaactcca aagatccaat ttcactatat | 4860 |
| aaattgtgac gaaagcaaaa tgaattcaca tagctgagag agaaaggaaa ggttaactaa | 4920 |
| gaagcaatac ttcagcggcc gcatgactga ggataagacg aaggtcgagt tcccgacgct | 4980 |
| cacggagctc aagcactcga tcccgaacgc gtgctttgag tcgaacctcg gcctctcgct | 5040 |
| ctactacacg gcccgcgcga tcttcaacgc gtcggcctcg gcggcgctgc tctacgcggc | 5100 |
| gcgctcgacg ccgttcattg ccgataacgt tctgctccac gcgctcgttt gcgccaccta | 5160 |
| catctacgtg cagggcgtca tcttctgggg cttcttcacg gtcggccacg actgcggcca | 5220 |
| ctcggccttc tcgcgctacc acagcgtcaa ctttatcatc ggctgcatca tgcactctgc | 5280 |
| gattttgacg ccgttcgaga gctggcgcgt gacgcaccgc caccaccaca agaacacggg | 5340 |
| caacattgat aaggacgaga tcttttaccc gcaccggtcg gtcaaggacc tccaggacgt | 5400 |
| gcgccaatgg gtctacacgc tcggcggtgc gtggtttgtc tacttgaagg tcgggtatgc | 5460 |
| cccgcgcacg atgagccact ttgacccgtg ggacccgctc ctccttcgcc gcgcgtcggc | 5520 |
| cgtcatcgtg tcgctcggcg tctgggccgc cttcttcgcc gcgtacgcgt acctcacata | 5580 |
| ctcgctcggc tttgccgtca tgggcctcta ctactatgcg ccgctctttg tctttgcttc | 5640 |
| gttcctcgtc attacgacct tcttgcacca caacgacgaa gcgacgccgt ggtacggcga | 5700 |
| ctcggagtgg acgtacgtca agggcaacct ctcgagcgtc gaccgctcgt acggcgcgtt | 5760 |
| cgtggacaac ctgagccacc acattggcac gcaccaggtc caccacttgt tcccgatcat | 5820 |
| tccgcactac aagctcaacg aagccaccaa gcactttgcg gccgcgtacc cgcacctcgt | 5880 |
| gcgcaggaac gacgagccca tcatcacggc cttcttcaag accgcgcacc tctttgtcaa | 5940 |
| ctacggcgct gtgcccgaga cggcgcagat cttcacgctc aaagagtcgg ccgcggccgc | 6000 |
| caaggccaag tcggactaag c | 6021 |

<210> SEQ ID NO 84
<211> LENGTH: 6524
<212> TYPE: DNA
<213> ORGANISM: Artificial Sequence
<220> FEATURE:
<223> OTHER INFORMATION: plasmid pKR226

<400> SEQUENCE: 84

| | |
|---|---|
| gtacgtctag aggatccgtc gacggcgcgc ccgatcatcc ggatatagtt cctcctttca | 60 |
| gcaaaaaacc cctcaagacc cgtttagagg ccccaagggg ttatgctagt tattgctcag | 120 |
| cggtggcagc agccaactca gcttcctttc gggctttgtt agcagccgga tcgatccaag | 180 |
| ctgtacctca ctattccttt gccctcggac gagtgctggg gcgtcggttt ccactatcgg | 240 |
| cgagtacttc tacacagcca tcggtccaga cggccgcgct tctgcgggcg atttgtgtac | 300 |
| gcccgacagt cccggctccg gatcggacga ttgcgtcgca tcgaccctgc gcccaagctg | 360 |
| catcatcgaa attgccgtca accaagctct gatagagttg gtcaagacca atgcggagca | 420 |
| tatacgcccg gagccgcggc gatcctgcaa gctccggatg cctccgctcg aagtagcgcg | 480 |
| tctgctgctc catacaagcc aaccacggcc tccagaagaa gatgttggcg acctcgtatt | 540 |
| gggaatcccc gaacatcgcc tcgctccagt caatgaccgc tgttatgcgg ccattgtccg | 600 |
| tcaggacatt gttggagccg aaatccgcgt gcacgaggtg ccggacttcg ggcagtcct | 660 |
| cggcccaaag catcagctca tcgagagcct gcgcgacgga cgcactgacg gtgtcgtcca | 720 |

-continued

| | | | | |
|---|---|---|---|---|
| tcacagtttg | ccagtgatac | acatgggat | cagcaatcgc | gcatatgaaa | tcacgccatg | 780 |
| tagtgtattg | accgattcct | tgcggtccga | atgggccgaa | cccgctcgtc | tggctaagat | 840 |
| cggccgcagc | gatcgcatcc | atagcctccg | cgaccggctg | cagaacagcg | ggcagttcgg | 900 |
| tttcaggcag | gtcttgcaac | gtgacaccct | gtgcacggcg | ggagatgcaa | taggtcaggc | 960 |
| tctcgctgaa | ttccccaatg | tcaagcactt | ccggaatcgg | gagcgcggcc | gatgcaaagt | 1020 |
| gccgataaac | ataacgatct | ttgtagaaac | catcggcgca | gctatttacc | cgcaggacat | 1080 |
| atccacgccc | tcctacatcg | aagctgaaag | cacgagattc | ttcgccctcc | gagagctgca | 1140 |
| tcaggtcgga | gacgctgtcg | aacttttcga | tcagaaactt | ctcgacagac | gtcgcggtga | 1200 |
| gttcaggctt | ttccatgggt | atatctcctt | cttaaagtta | aacaaaatta | tttctagagg | 1260 |
| gaaaccgttg | tggtctccct | atagtgagtc | gtattaattt | cgcgggatcg | agatctgatc | 1320 |
| aacctgcatt | aatgaatcgg | ccaacgcgcg | gggagaggcg | gtttgcgtat | tgggcgctct | 1380 |
| tccgcttcct | cgctcactga | ctcgctgcgc | tcggtcgttc | ggctgcggcg | agcggtatca | 1440 |
| gctcactcaa | aggcggtaat | acggttatcc | acagaatcag | gggataacgc | aggaaagaac | 1500 |
| atgtgagcaa | aaggccagca | aaaggccagg | aaccgtaaaa | aggccgcgtt | gctggcgttt | 1560 |
| ttccataggc | tccgcccccc | tgacgagcat | cacaaaaatc | gacgctcaag | tcagaggtgg | 1620 |
| cgaaacccga | caggactata | aagataccag | gcgtttcccc | ctggaagctc | cctcgtgcgc | 1680 |
| tctcctgttc | cgaccctgcc | gcttaccgga | tacctgtccg | cctttctccc | ttcgggaagc | 1740 |
| gtggcgcttt | ctcaatgctc | acgctgtagg | tatctcagtt | cggtgtaggt | cgttcgctcc | 1800 |
| aagctgggct | gtgtgcacga | accccccgtt | cagcccgacc | gctgcgcctt | atccggtaac | 1860 |
| tatcgtcttg | agtccaaccc | ggtaagacac | gacttatcgc | cactggcagc | agccactggt | 1920 |
| aacaggatta | gcagagcgag | gtatgtaggc | ggtgctacag | agttcttgaa | gtggtggcct | 1980 |
| aactacggct | acactagaag | gacagtattt | ggtatctgcg | ctctgctgaa | gccagttacc | 2040 |
| ttcggaaaaa | gagttggtag | ctcttgatcc | ggcaaacaaa | ccaccgctgg | tagcggtggt | 2100 |
| ttttttgttt | gcaagcagca | gattacgcgc | agaaaaaaag | gatctcaaga | agatcctttg | 2160 |
| atcttttcta | cggggtctga | cgctcagtgg | aacgaaaact | cacgttaagg | gattttggtc | 2220 |
| atgacattaa | cctataaaaa | taggcgtatc | acgaggccct | ttcgtctcgc | gcgtttcggt | 2280 |
| gatgacggtg | aaaacctctg | acacatgcag | ctcccggaga | cggtcacagc | ttgtctgtaa | 2340 |
| gcggatgccg | ggagcagaca | agcccgtcag | ggcgcgtcag | cgggtgttgg | cgggtgtcgg | 2400 |
| ggctggctta | actatgcggc | atcagagcag | attgtactga | gagtgcacca | tatggacata | 2460 |
| ttgtcgttag | aacgcggcta | caattaatac | ataaccttat | gtatcataca | catacgattt | 2520 |
| aggtgacact | atagaacggc | gcgccaagct | gggtctagaa | ctagaaacgt | gatgccactt | 2580 |
| gttattgaag | tcgattacag | catctattct | gttttactat | ttataacttt | gccatttctg | 2640 |
| acttttgaaa | actatctctg | gatttcggta | tcgctttgtg | aagatcgagc | aaaagagacg | 2700 |
| ttttgtggac | gcaatggtcc | aaatccgttc | tacatgaaca | aattggtcac | aatttccact | 2760 |
| aaaagtaaat | aaatgcaag | ttaaaaaagg | aatatgcatt | ttactgattg | cctaggtgag | 2820 |
| ctccaagaga | agttgaatct | acacgtctac | caaccgctaa | aaaagaaaa | acattgatat | 2880 |
| gtaacctgat | tccattagct | tttgacttct | tcaacagatt | ctctacttag | atttctaaca | 2940 |
| gaaatattat | tactagcaca | tcattttcag | tctcactaca | gcaaaaaatc | caacggcaca | 3000 |
| atacagacaa | caggagatat | cagactacag | agatagatag | atgctactgc | atgtagtaag | 3060 |
| ttaaataaaa | ggaaaataaa | atgtcttgct | accaaaacta | ctacagacta | tgatgctcac | 3120 |

```
cacaggccaa atcctgcaac taggacagca ttatcttata tatattgtac aaaacaagca    3180
tcaaggaaca tttggtctag gcaatcagta cctcgttcta ccatcaccct cagttatcac    3240
atccttgaag gatccattac tgggaatcat cggcaacaca tgctcctgat ggggcacaat    3300
gacatcaaga aggtaggggc caggggtgtc caacattctc tgaattgccg ctctaagctc    3360
ttccttcttc gtcactcgcg ctgccggtat cccacaagca tcagcaaact tgagcatgtt    3420
tgggaatatc tcgctctcgc tagacggatc tccaagatag gtgtgagctc tattggactt    3480
gtagaaccta cctccaact gaaccaccat acccaaatgc tgattgttca acaacaatat     3540
cttaactggg agattctcca ctcttatagt ggccaactcc tgaacattca tgatgaaact    3600
accatcccca tcaatgtcaa ccacaacagc cccagggtta gcaacagcag caccaatagc    3660
cgcaggcaat ccaaaaccca tggctccaag accccctgag gtcaaccact gcctcggtct    3720
cttgtacttg taaaactgcg cagcccacat ttgatgctgc caacccag tactaacaat      3780
agcatctcca ttagtcaact catcaagaac ctcgatagca tgctgcggag aaatcgcgtc    3840
ctggaatgtc ttgtaaccca atggaaactt gtgtttctgc acattaatct cttctctcca    3900
acctccaaga tcaaacttac cctccactcc tttctcctcc aaaatcatat taattcccctt   3960
caaggccaac ttcaaatccg cgcaaaccga cacgtgcgcc tgcttgttct tcccaatctc    4020
ggcagaatca atatcaatgt gaacaatctt agccctacta gcaaaagcct caagcttccc    4080
agtaacacgg tcatcaaacc ttaccccaaa ggcaagcaac aaatcactat tgtcaacagc    4140
atagttagca taaacagtac catgcatacc cagcatctga agggaatatt catcaccaat    4200
aggaaaagtt ccaagaccca ttaaagtgct agcaacggga ataccagtga gttcaacaaa    4260
gcgcctcaat tcagcactgg aattcaaact gccaccgccg acgtagagaa cgggcttttg    4320
ggcctccatg atgagtctga caatgtgttc caattgggcc tcggcggggg gcctgggcag    4380
cctggcgagg taaccgggga ggttaacggg ctcgtcccaa ttaggcacgg cgagttgctg    4440
ctgaacgtct ttgggaatgt cgatgaggac cggaccgggg cggccggagg tggcgacgaa    4500
gaaagcctcg gcgacgacgc gggggatgtc gtcgacgtcg aggatgaggt agttgtgctt    4560
cgtgatggat ctgctcacct ccacgatcgg ggtttcttgg aaggcgtcgg tgccgatcat    4620
ccggcgggcg acctgccggg tgatggcgac gactgggacg ctgtccatta aagcgtcggc    4680
gaggccgctc acgaggttgg tggcgccggg gccggaggtg gcaatgcaga cgccggggag    4740
gccggaggaa cgcgcgtagc cttcggcggc gaagacgccg ccctgctcgt ggcgcggag    4800
cacgttgcgg atggcggcgg agcgcgtgag cgcctggtgg atctccatcg acgcaccgcc    4860
ggggtacgcg aacaccgtcg tcacgccctg cctctccagc gcctccacaa ggatgtccgc    4920
gcccttgcga ggttcgccgg aggcgaaccg tgacacgaag ggctccgtgg tcggcgcttc    4980
cttggtgaag ggcgccgccg tggggggttt ggagatggaa catttgattt tgagagcgtg    5040
gttgggtttg gtgagggttt gatgagagag agggagggtg gatctagtaa tgcgtttggg    5100
gaaggtgggg tgtgaagagg aagaagagaa tcgggtggtt ctggaagcgg tggccgccat    5160
tgtgttgtgt ggcatggtta tacttcaaaa actgcacaac aagcctagag ttagtaccta    5220
aacagtaaat ttacaacaga gagcaaagac acatgcaaaa atttcagcca taaaaaaagt    5280
tataatagaa tttaaagcaa aagtttcatt ttttaaacat atatacaaac aaactggatt    5340
tgaaggaagg gattaattcc cctgctcaaa gtttgaattc ctattgtgac ctatactcga    5400
ataaaattga agcctaagga atgtatgaga aacaagaaaa caaaacaaaa ctacagacaa    5460
```

-continued

```
acaagtacaa ttacaaaatt cgctaaaatt ctgtaatcac caaacccat ctcagtcagc      5520 acaaggccca aggtttattt tgaaataaaa aaaaagtgat tttatttctc ataagctaaa      5580
agaaagaaag gcaattatga aatgatttcg actagatctg aaagtccaac gcgtattccg      5640
cagatattaa agaaagagta gagtttcaca tggatcctag atggacccag ttgaggaaaa      5700
agcaaggcaa agcaaaccag aagtgcaaga tccgaaattg aaccacggaa tctaggattt      5760
ggtagaggga gaagaaaagt accttgagag gtagaagaga agagaagagc agagagatat      5820
atgaacgagt gtgtcttggt ctcaactctg aagcgatacg agtttagagg ggagcattga      5880
gttccaattt atagggaaac cgggtggcag gggtgagtta atgacggaaa agcccctaag      5940
taacgagatt ggattgtggg ttagattcaa ccgtttgcat ccgcggctta gattggggaa      6000
gtcagagtga atctcaaccg ttgactgagt tgaaaattga atgtagcaac caattgagcc      6060
aaccccagcc tttgcccttt gattttgatt tgtttgttgc atacttttta tttgtcttct      6120
ggttctgact ctctttctct cgtttcaatg ccaggttgcc tactcccaca ccactcacaa      6180
gaagattcta ctgttagtat taaatatttt ttaatgtatt aaatgatgaa tgcttttgta      6240
aacagaacaa gactatgtct aataagtgtc ttgcaacatt ttttaagaaa ttaaaaaaaa      6300
tatatttatt atcaaaatca aatgtatgaa aaatcatgaa taatataatt ttatacatttt     6360 ttttaaaaaa tcttttaatt tcttaattaa tatcttaaaa ataatgatta atatttaacc      6420
caaaataatt agtatgattg gtaaggaaga tatccatgtt atgtttggat gtgagtttga      6480
tctagagcaa agcttactag agtcgacctg caggtcgact cgac                       6524
```

<210> SEQ ID NO 85
<211> LENGTH: 9892
<212> TYPE: DNA
<213> ORGANISM: Artificial Sequence
<220> FEATURE:
<223> OTHER INFORMATION: plasmid pKR886r

<400> SEQUENCE: 85

```
ggtcgactcg acgtacgtct agaggatccg tcgacggcgc gcccgatcat ccggatatag        60
ttcctccttt cagcaaaaaa ccccctcaaga cccgtttaga ggccccaagg ggttatgcta      120
gttattgctc agcggtggca gcagccaact cagcttcctt tcgggctttg ttagcagccg      180
gatcgatcca agctgtacct cactattcct ttgccctcgg acgagtgctg gggcgtcggt      240
ttccactatc ggcgagtact tctacacagc catcggtcca gacggccgcg cttctgcggg      300
cgatttgtgt acgcccgaca gtcccggctc cggatcggac gattgcgtcg catcgaccct      360
gcgcccaagc tgcatcatcg aaattgccgt caaccaagct ctgatagagt tggtcaagac      420
caatgcggag catatacgcc cggagccgcg gcgatcctgc aagctccgga tgcctccgct      480
cgaagtagcg cgtctgctgc tccatacaag ccaaccacgg cctccagaag aagatgttgg      540
cgacctcgta ttgggaatcc ccgaacatcg cctcgctcca gtcaatgacc gctgttatgc      600
ggccattgtc cgtcaggaca ttgttggagc cgaaatccgc gtgcacgagg tgccggactt      660
cggggcagtc ctcggcccaa agcatcagct catcgagagc ctgcgcgacg acgcactga      720 cggtgtcgtc catcacagtt tgccagtgat acacatgggg atcagcaatc gcgcatatga      780
aatcacgcca tgtagtgtat tgaccgattc cttgcggtcc gaatgggccg aacccgctcg      840
tctggctaag atcggccgca gcgatcgcat ccatagcctc cgcgaccggc tgcagaacag      900
cgggcagttc ggtttcaggc aggtcttgca acgtgacacc ctgtgcacgg cgggagatgc      960
aataggtcag gctctcgctg aattccccaa tgtcaagcac ttccggaatc gggagcgcgg     1020
```

```
ccgatgcaaa gtgccgataa acataacgat ctttgtagaa accatcggcg cagctattta    1080
cccgcaggac atatccacgc cctcctacat cgaagctgaa agcacgagat tcttcgccct    1140
ccgagagctg catcaggtcg gagacgctgt cgaacttttc gatcagaaac ttctcgacag    1200
acgtcgcggt gagttcaggc ttttccatgg gtatatctcc ttcttaaagt taaacaaaat    1260
tatttctaga gggaaaccgt tgtggtctcc ctatagtgag tcgtattaat ttcgcgggat    1320
cgagatctga tcaacctgca ttaatgaatc ggccaacgcg cggggagagg cggtttgcgt    1380
attgggcgct cttccgcttc ctcgctcact gactcgctgc gctcggtcgt tcggctgcgg    1440
cgagcggtat cagctcactc aaaggcggta atacggttat ccacagaatc aggggataac    1500
gcaggaaaga acatgtgagc aaaaggccag caaaaggcca ggaaccgtaa aaaggccgcg    1560
ttgctggcgt ttttccatag gctccgcccc cctgacgagc atcacaaaaa tcgacgctca    1620
agtcagaggt ggcgaaaccc gacaggacta taaagatacc aggcgtttcc ccctggaagc    1680
tccctcgtgc gctctcctgt tccgaccctg ccgcttaccg gatacctgtc cgcctttctc    1740
ccttcgggaa gcgtggcgct ttctcaatgc tcacgctgta ggtatctcag ttcggtgtag    1800
gtcgttcgct ccaagctggg ctgtgtgcac gaaccccccg ttcagcccga ccgctgcgcc    1860
ttatccggta actatcgtct tgagtccaac ccggtaagac acgacttatc gccactggca    1920
gcagccactg gtaacaggat tagcagagcg aggtatgtag gcggtgctac agagttcttg    1980
aagtggtggc ctaactacgg ctacactaga aggacagtat ttggtatctg cgctctgctg    2040
aagccagtta ccttcggaaa aagagttggt agctcttgat ccggcaaaca aaccaccgct    2100
ggtagcggtg gttttttttgt ttgcaagcag cagattacgc gcagaaaaaa aggatctcaa    2160
gaagatcctt tgatctttttc tacggggtct gacgctcagt ggaacgaaaa ctcacgttaa    2220
gggattttgg tcatgacatt aacctataaa aataggcgta tcacgaggcc ctttcgtctc    2280
gcgcgtttcg gtgatgacgg tgaaaacctc tgacacatgc agctcccgga cacggtcaca    2340
gcttgtctgt aagcggatgc cgggagcaga caagcccgtc agggcgcgtc agcgggtgtt    2400
ggcgggtgtc ggggctggct taactatgcg gcatcagagc agattgtact gagagtgcac    2460
catatggaca tattgtcgtt agaacgcggc tacaattaat acataacctt atgtatcata    2520
cacatacgat ttaggtgaca ctatagaacg gcgcgccaag ctgggtctag aactagaaac    2580
gtgatgccac ttgttattga agtcgattac agcatctatt ctgttttact atttataact    2640
ttgccatttc tgacttttga aaactatctc tggatttcgg tatcgctttg tgaagatcga    2700
gcaaaagaga cgttttgtgg acgcaatggt ccaaatccgt tctacatgaa caaattggtc    2760
acaatttcca ctaaaagtaa ataaatggca agttaaaaaa ggaatatgca ttttactgat    2820
tgcctaggtg agctccaaga gaagttgaat ctacacgtct accaaccgct aaaaaaagaa    2880
aaacattgat atgtaacctg attccattag cttttgactt cttcaacaga ttctctactt    2940
agatttctaa cagaaatatt attactagca catcattttc agtctcacta cagcaaaaaa    3000
tccaacggca caatacagac aacaggagat atcagactac agagatagat agatgctact    3060
gcatgtagta agttaaataa aaggaaaata aaatgtcttg ctaccaaaac tactacagac    3120
tatgatgctc accacaggcc aaatcctgca actaggacag cattatctta tatatattgt    3180
acaaaacaag catcaaggaa catttggtct aggcaatcag tacctcgttc taccatcacc    3240
ctcagttatc acatccttga aggatccatt actgggaatc atcggcaaca catgctcctg    3300
atggggcaca atgacatcaa gaaggtaggg gccagggggtg tccaacattc tctgaattgc    3360
```

```
cgctctaagc tcttccttct cgtcactcg cgctgccggt atcccacaag catcagcaaa    3420
cttgagcatg tttgggaata tctcgctctc gctagacgga tctccaagat aggtgtgagc    3480
tctattggac ttgtagaacc tatcctccaa ctgaaccacc atacccaaat gctgattgtt    3540
caacaacaat atcttaactg ggagattctc cactcttata gtggccaact cctgaacatt    3600
catgatgaaa ctaccatccc catcaatgtc aaccacaaca gccccagggt tagcaacagc    3660
agcaccaata gccgcaggca atccaaaacc catggctcca agaccccctg aggtcaacca    3720
ctgcctcggt ctcttgtact tgtaaaactg cgcagcccac atttgatgct gcccaacccc    3780
agtactaaca atagcatctc cattagtcaa ctcatcaaga acctcgatag catgctgcgg    3840
agaaatcgcg tcctggaatg tcttgtaacc caatggaaac ttgtgtttct gcacattaat    3900
ctcttctctc caacctccaa gatcaaactt accctccact cctttctcct ccaaaatcat    3960
attaattccc ttcaaggcca acttcaaatc cgcgcaaacc gacacgtgcg cctgcttgtt    4020
cttcccaatc tcggcagaat caatatcaat gtgaacaatc ttagccctac tagcaaaagc    4080
ctcaagcttc ccagtaacac ggtcatcaaa ccttacccca aaggcaagca acaaatcact    4140
attgtcaaca gcatagttag cataaacagt accatgcata cccagcatct gaagggaata    4200
ttcatcacca ataggaaaag ttccaagacc cattaaagtg ctagcaacgg gaataccagt    4260
gagttcaaca aagcgcctca attcagcact ggaattcaaa ctgccaccgc cgacgtagag    4320
aacgggcttt tgggcctcca tgatgagtct gacaatgtgt tccaattggg cctcggcggg    4380
gggcctgggc agcctggcga ggtaaccggg gaggttaacg ggctcgtccc aattaggcac    4440
ggcgagttgc tgctgaacgt cttggggaat gtcgatgagg accggaccgg ggcggccgga    4500
ggtggcgacg aagaaagcct cggcgacgac gcggggatg tcgtcgacgt cgaggatgag    4560
gtagttgtgc ttcgtgatgg atctgctcac ctccacgatc ggggttctt ggaaggcgtc    4620 ggtgccgatc atccggcggg cgacctggcc ggtgatggcg acgactggga cgctgtccat    4680
taaagcgtcg gcgaggccgc tcacgaggtt ggtggcgccg gggccggagg tggcaatgca    4740
gacgccgggg aggccggagg aacgcgcgta gccttcggcg gcgaagacgc cgccctgctc    4800
gtggcgcggg agcacgttgc ggatggcggc ggagcgcgtg agcgcctggt ggatctccat    4860
cgacgcaccg ccggggtacg cgaacaccgt cgtcacgccc tgcctctcca gcgcctccac    4920
aaggatgtcc gcgcccttgc gaggttcgcc ggaggcgaac cgtgacacga agggctccgt    4980
ggtcggcgct tccttggtga agggcgccgc cgtgggggt ttggagatgg aacatttgat    5040
tttgagagcg tggttgggtt tggtgagggt ttgatgagag agagggaggg tggatctagt    5100
aatgcgtttg gggaaggtgg ggtgtgaaga ggaagaagag aatcgggtgg ttctggaagc    5160
ggtggccgcc attgtgttgt gtggcatggt tatacttcaa aaactgcaca acaagcctag    5220
agttagtacc taaacagtaa atttacaaca gagagcaaag acacatgcaa aaatttcagc    5280
cataaaaaaa gttataatag aatttaaagc aaaagtttca ttttttaaac atatatacaa    5340
acaaactgga tttgaaggaa gggattaatt cccctgctca agtttgaat tcctattgtg    5400 acctatactc gaataaaatt gaagcctaag gaatgtatga gaaacaagaa acaaaacaa    5460 aactacagac aaacaagtac aattacaaaa ttcgctaaaa ttctgtaatc accaaacccc    5520
atctcagtca gcacaaggcc caaggtttat tttgaaataa aaaaaagtg atttatttc    5580 tcataagcta aagaaagaa aggcaattat gaaatgattt cgactagatc tgaaagtcca    5640
acgcgtattc cgcagatatt aaagaaagag tagagttca catggatcct agatggaccc    5700
agttgaggaa aaagcaaggc aaagcaaacc agaagtgcaa gatccgaaat tgaaccacgg    5760
```

```
aatctaggat tggtagagg gagaagaaaa gtaccttgag aggtagaaga gaagagaaga   5820
gcagagagat atatgaacga gtgtgtcttg gtctcaactc tgaagcgata cgagtttaga   5880
ggggagcatt gagttccaat ttatagggaa accgggtggc aggggtgagt taatgacgga   5940
aaagccccta agtaacgaga ttggattgtg ggttagattc aaccgtttgc atccgcggct   6000
tagattgggg aagtcagagt gaatctcaac cgttgactga gttgaaaatt gaatgtagca   6060
accaattgag ccaaccccag cctttgccct ttgattttga tttgtttgtt gcatactttt   6120
tatttgtctt ctggttctga ctctctttct ctcgtttcaa tgccaggttg cctactccca   6180
caccactcac aagaagattc tactgttagt attaaatatt ttttaatgta ttaaatgatg   6240
aatgcttttg taaacagaac aagactatgt ctaataagtg tcttgcaaca tttttttaaga  6300
aattaaaaaa aatatattta ttatcaaaat caaatgtatg aaaaatcatg aataatataa   6360
ttttatacat ttttttaaaa aatcttttaa tttcttaatt aatatcttaa aaataatgat   6420
taatatttaa cccaaaataa ttagtatgat tggtaaggaa gatatccatg ttatgtttgg   6480
atgtgagttt gatctagagc aaagcttact agagtcgacc tgcagcccgg ggatccgcc    6540
cacgtacggt accatctgct aatatttaa atcacatgca agagaggagg catggttcca    6600
ttttctacct tcacattatt tgagaaaaac gaacttgttc tgtgttttat ttttgccctt   6660
cacattagta caacgtggaa gactcatggt tacacagaat catacataag tacaatgctt   6720
gtccctaaga aaacaagcac tcgttgtatt gaacctttac ggctcatgcg ccgcgaatt    6780
cactagtgat tgaattcgcg gccgcttagt ccgacttggc cttggcggcc gcggccgact   6840
ctttgagcgt gaagatctgc gccgtctcgg gcacagcgcc gtagttgaca aagaggtgcg   6900
cggtcttgaa gaaggccgtg atgatgggct cgtcgttcct gcgcacgagg tgcgggtacg   6960
cggccgcaaa gtgcttggtg gcttcgttga gcttgtagtg cggaatgatc gggaacaagt   7020
ggtggacctg gtgcgtgcca atgtggtggc tcaggttgtc cacgaacgcg ccgtacgagc   7080
ggtcgacgct cgagaggttg cccttgacgt acgtccactc cgagtcgccg taccacggcg   7140
tcgcttcgtc gttgtggtgc aagaaggtcg taatgacgag gaacgaagca agacaaaga    7200
gcggcgcata gtagtagagg cccatgacgg caaagccgag cgagtatgtg aggtacgcgt   7260
acgcggcgaa gaaggcggcc cagacgccga gcgacacgat gacggccgac gcgcggcgaa   7320
ggaggagcgg gtcccacggg tcaaagtggc tcatcgtgcg cggggcatac ccgaccttca   7380
agtagacaaa ccacgcaccg ccgagcgtgt agacccattg gcgcacgtcc tggaggtcct   7440
tgaccgaccg gtgcgggtaa aagatctcgt ccttatcaat gttgcccgtg ttcttgtggt   7500
ggtggcggtg cgtcacgcgc cagctctcga acggcgtcaa aatcgcagag tgcatgatgc   7560
agccgatgat aaagttgacg ctgtggtagc gcgagaaggc cgagtggccg cagtcgtggc   7620
cgaccgtgaa gaagcccag aagatgacgc cctgcacgta gatgtaggtg gcgcaaacga    7680
gcgcgtggag cagaacgtta tcggcaatga acggcgtcga gcgcgccgcg tagagcagcg   7740
ccgccgaggc cgacgcgttg aagatcgcgc gggccgtgta gtagagcgag aggccgaggt   7800
tcgactcaaa gcacgcgttc gggatcgagt gcttgagctc cgtgagcgtc gggaactcga   7860
ccttcgtctt atcctcagtc atgcggccgc tgaagtattg cttcttagtt aaccttttcct  7920
ttctctctca gctatgtgaa ttcattttgc tttcgtcaca atttatatag tgaaattgga   7980
tctttggagt taacgccttc acaggattat cgtgttagaa caatgctttt tcatgttcta   8040
attagtagta cattacaaat gtgcactcta ttcaataagc atcttttggc acgttaataa   8100
```

```
atcatgtgaa aaaaaaatac tactatttca agaaagtgt tgtaaaaaga acggaaaga     8160
gagctggctt cagttgttga gacttgtttg ctagtaaaaa tggtgtgaag agtgattcat   8220
ggtgaggtgg tttttcgtcc ctttctgttt gcatgaaaaa caaatggcaa gagatgacgt   8280
aggattcctt cccttaacga ttatctgttt ttaatttcaa atatacatat aggaatttat   8340
gaattactaa ggttgtaaaa tatgctggtc atttatttat ggctaaaata ttttttttc    8400
tcgtaaatat aaaatatttt aaatttatt tttatcatat tttttatcct tataaaatta   8460
tgtgtacaac ctatataaaa aaatatcata tttaatattg attatatgtt taatcaatat   8520
aaaaaatcat tatcatatat ttagatttat tcgaatatac atctaaacaa aaaataacat   8580
attttaattt tatgaagaaa aaaaaatatt ttatccttta tttatttaag attaattaat   8640
agttatgtat tgtggaaaga cttttacaca tgcaatagat atactgaatc aattagatgc   8700
caatgctgag ttggaaaatca cttgaggagg ggaggagact tgccaatgct tttcagtttc   8760
atttaaatga tttagtggag gagatagagt agtgataaag gcatgcccca atttggagt   8820
gtatatatga gtggaaataa gagagggata gagagaaaaa ataagagag taaaaataat   8880
taatgtgaaa tgatatgata aaaaaataaa gaaagagata aagagaaaaa tgaaatgaga   8940
gatagatgaa atagagagta gatacatgtt tgtttaggtt ttttttagga aataacacat   9000
tttttctca tcacttatta ctcactgtca atttcctctc tttcaatcat aatgatatga    9060
tttgtttaac aaaaatgtga aaaacatat aaagtaaaat attttataa attgataaat    9120
aaaaatttac aaaattttatt tcttattaaa ttgaatagaa aatgaaagaa agaaaagaa   9180
aaagtatata taaaatgata tagctttaaa aagaataaat ttttcatatc agtctttttt   9240
taataattta gaaatatta agtatatagc aaaaatataa tgtactttac atatgcataa    9300
ataataattt gaaatagaa ctaatagaat agagaaaaaa gtaatataat aattaactat   9360
atgaaaattt agaagggaca atattttaa ttaagaatat aaacaatatt tcttttcatg   9420
taatgaggga cggatgtacg gggccagtgt tggagtcaaa gccaaaatag tcacggggaa   9480
attaatgcac tgcatgacta ttcgaaaaaa ttcactagcc ttacttagat gttagattaa   9540
tagctagggg gtgcagataa ttttgaaagg catgaaaaac attaatttgt acattgcaag   9600
cttttgatga caagctttgc aattgttcac actaccttat gccattata aatagagtga   9660
ttggcatatg aaggaaatca tgagagtcga agcgaaaaac aaagcttgag agtgtaggaa   9720
aaatacagtt ttttggtaa aaatacagta tttgaatagg agcgaaaaat atcctttcaa   9780
aatgatcctt ttctttttt ttttttttct tgttgttctt ggtcagttat tcaaaggaaa   9840
agggattgaa ataaaaactt gcatgtggga tcgtacgtcg agtcgacctg ca           9892
```

<210> SEQ ID NO 86
<211> LENGTH: 32
<212> TYPE: DNA
<213> ORGANISM: Artificial Sequence
<220> FEATURE:
<223> OTHER INFORMATION: primer oCon1

<400> SEQUENCE: 86
aatctagacc tgcaggatcc atgcccttca tt                                 32

<210> SEQ ID NO 87
<211> LENGTH: 33
<212> TYPE: DNA
<213> ORGANISM: Artificial Sequence
<220> FEATURE:
<223> OTHER INFORMATION: primer oCon2

<400> SEQUENCE: 87
tttctagacc tgcaggttga aacatccctg aag    33

<210> SEQ ID NO 88
<211> LENGTH: 4480
<212> TYPE: DNA
<213> ORGANISM: Artificial Sequence
<220> FEATURE:
<223> OTHER INFORMATION: plasmid pKR179

<400> SEQUENCE: 88

| ctagacctgc aggatccatg cccttcattt gccgcttatt aattaatttg gtaacagtcc | 60 |
|---|---|
| gtactaatca gttacttatc cttcccccat cataattaat cttggtagtc tcgaatgcca | 120 |
| caacactgac tagtctcttg gatcataaga aaaagccaag gaacaaaaga agacaaaaca | 180 |
| caatgagagt atcctttgca tagcaatgtc taagttcata aaattcaaac aaaaacgcaa | 240 |
| tcacacacag tggacatcac ttatccacta gctgatcagg atcgccgcgt caagaaaaaa | 300 |
| aaactggacc ccaaaagcca tgcacaacaa cacgtactca caaggtgtc aatcgagcag | 360 |
| cccaaaacat tcaccaactc aacccatcat gagccctcac atttgttgtt tctaacccaa | 420 |
| cctcaaactc gtattctctt ccgccacctc attttgttt atttcaacac ccgtcaaact | 480 |
| gcatgccacc ccgtggccaa atgtccatgc atgttaacaa gacctatgac tataaatagc | 540 |
| tgcaatctcg gcccaggttt tcatcatcaa gaaccagttc aatatcctag tacaccgtat | 600 |
| taaagaattt aagatatact gcggccgcaa gtatgaacta aatgcatgt aggtgtaaga | 660 |
| gctcatggag agcatggaat attgtatccg accatgtaac agtataataa ctgagctcca | 720 |
| tctcacttct tctatgaata acaaaggat gttatgatat attaacactc tatctatgca | 780 |
| ccttattgtt ctatgataaa tttcctctta ttattataaa tcatctgaat cgtgacggct | 840 |
| tatgaatgc ttcaaatagt acaaaaacaa atgtgtacta aagactttc taaacaattc | 900 |
| taaccttagc attgtgaacg agacataagt gttaagaaga cataacaatt ataatggaag | 960 |
| aagtttgtct ccatttatat attatatatt acccacttat gtattatatt aggatgttaa | 1020 |
| ggagacataa caattataaa gagagaagtt tgtatccatt tatatattat atactaccca | 1080 |
| tttatatatt atacttatcc acttatttaa tgtctttata aggtttgatc catgatattt | 1140 |
| ctaatatttt agttgatatg tatatgaaag ggtactattt gaactctctt actctgtata | 1200 |
| aaggttggat catccttaaa gtgggtctat ttaatttat tgcttcttac agataaaaaa | 1260 |
| aaaattatga gttggtttga taaaatattg aaggatttaa aataataata ataacatat | 1320 |
| aatatatgta tataaattta ttataatata acatttatct ataaaaaagt aaatattgtc | 1380 |
| ataaatctat acaatcgttt agccttgctg gacgaatctc aattatttaa acgagagtaa | 1440 |
| acatatttga cttttggtt atttaacaaa ttattattta acactatatg aaattttttt | 1500 |
| ttttatcagc aaagaataaa attaaattaa gaaggacaat ggtgtcccaa tccttataca | 1560 |
| accaacttcc acaagaaagt caagtcagag acaacaaaaa aacaagcaaa ggaaattttt | 1620 |
| taattttgagt tgtcttgttt gctgcataat ttatgcagta aaacactaca cataacccct | 1680 |
| ttagcagtag agcaatggtt gaccgtgtgc ttagcttctt ttattttatt tttttatcag | 1740 |
| caaagaataa ataaaataaa atgagacact tcagggatgt tcaacctgc aggtctagag | 1800 |
| gatccccggg taccgagctc gaattcactg ccgtcgtttt acaacgtcg tgactgggaa | 1860 |
| aaccctggcg ttacccaact taatcgcctt gcagcacatc ccccttcgc cagctggcgt | 1920 |

```
aatagcgaag aggcccgcac cgatcgccct tcccaacagt tgcgcagcct gaatggcgaa      1980
tggcgcctga tgcggtattt tctccttacg catctgtgcg gtatttcaca ccgcatatgg      2040
tgcactctca gtacaatctg ctctgatgcc gcatagttaa gccagccccg acacccgcca      2100 acaccgctg  acgcgccctg acgggcttgt ctgctcccgg catccgctta cagacaagct      2160
gtgaccgtct ccgggagctg catgtgtcag aggttttcac cgtcatcacc gaaacgcgcg      2220
agacgaaagg gcctcgtgat acgcctattt ttataggtta atgtcatgat aataatggtt      2280
tcttagacgt caggtggcac ttttcgggga atgtgcgcg  gaaccccta  ttgtttattt      2340 ttctaaatac attcaaatat gtatccgctc atgagacaat aaccctgata aatgcttcaa      2400
taatattgaa aaaggaagag tatgagtatt caacatttcc gtgtcgccct tattccctt       2460 tttgcggcat tttgccttcc tgttttgct  cacccagaaa cgctggtgaa agtaaaagat      2520
gctgaagatc agttgggtgc acgagtgggt tacatcgaac tggatctcaa cagcggtaag      2580
atccttgaga gttttcgccc cgaagaacgt tttccaatga tgagcacttt taaagttctg      2640
ctatgtggcg cggtattatc cgtattgac  gccgggcaag agcaactcgg tcgccgcata      2700
cactattctc agaatgactt ggttgagtac tcaccagtca cagaaaagca tcttacggat      2760
ggcatgacag taagagaatt atgcagtgct gccataacca tgagtgataa cactgcggcc      2820
aacttacttc tgacaacgat cggaggaccg aaggagctaa ccgcttttt  gcacaacatg      2880 ggggatcatg taactcgcct tgatcgttgg gaaccggagc tgaatgaagc cataccaaac      2940
gacgagcgtg acaccacgat gcctgtagca atggcaacaa cgttgcgcaa actattaact      3000
ggcgaactac ttactctagc ttcccggcaa caattaatag actggatgga ggcggataaa      3060
gttgcaggac cacttctgcg ctcggccctt ccggctggct ggtttattgc tgataaatct      3120
ggagccggtg agcgtgggtc tcgcggtatc attgcagcac tggggccaga tggtaagccc      3180
tcccgtatcg tagttatcta cacgacgggg agtcaggcaa ctatggatga acgaaataga      3240
cagatcgctg agataggtgc ctcactgatt aagcattggt aactgtcaga ccaagtttac      3300
tcatatatac tttagattga tttaaaactt cattttaat  ttaaaaggat ctaggtgaag      3360
atcctttttg ataatctcat gaccaaaatc ccttaacgtg agttttcgtt ccactgagcg      3420
tcagaccccg tagaaaagat caaaggatct tcttgagatc cttttttct  gcgcgtaatc      3480 tgctgcttgc aaacaaaaaa accaccgcta ccagcggtgg tttgtttgcc ggatcaagag      3540
ctaccaactc tttttccgaa ggtaactggc ttcagcagag cgcagatacc aaatactgtc      3600
cttctagtgt agccgtagtt aggccaccac ttcaagaact ctgtagcacc gcctacatac      3660
ctcgctctgc taatcctgtt accagtggct gctgccagtg gcgataagtc gtgtcttacc      3720
gggttggact caagacgata gttaccggat aaggcgcagc ggtcgggctg aacggggggt      3780
tcgtgcacac agcccagctt ggagcgaacg acctacaccg aactgagata cctacagcgt      3840
gagctatgag aaagcgccac gcttcccgaa gggagaaagg cggacaggta tccggtaagc      3900
ggcagggtcg gaacaggaga gcgcacgagg gagcttccag ggggaaacgc ctggtatctt      3960
tatagtcctg tcgggtttcg ccacctctga cttgagcgtc gatttttgtg atgctcgtca      4020
ggggggcgga gcctatggaa aaacgccagc aacgcggcct ttttacggtt cctggccttt      4080
tgctggcctt tgctcacat  gttctttcct gcgttatccc ctgattctgt ggataaccgt      4140
attaccgcct ttgagtgagc tgataccgct cgccgcagcc gaacgaccga gcgcagcgag      4200
tcagtgagcg aggaagcgga agagcgccca atacgcaaac cgcctctccc cgcgcgttgg      4260
ccgattcatt aatgcagctg gcacgacagg tttcccgact ggaaagcggg cagtgagcgc      4320
```

-continued

| | |
|---|---|
| aacgcaatta atgtgagtta gctcactcat taggcacccc aggctttaca ctttatgctt | 4380 |
| ccggctcgta tgttgtgtgg aattgtgagc ggataacaat ttcacacagg aaacagctat | 4440 |
| gaccatgatt acgccaagct tgcatgcctg caggtcgact | 4480 |

<210> SEQ ID NO 89
<211> LENGTH: 5754
<212> TYPE: DNA
<213> ORGANISM: Artificial Sequence
<220> FEATURE:
<223> OTHER INFORMATION: plasmid pKR1002

<400> SEQUENCE: 89

| | |
|---|---|
| ggccgcaagt atgaactaaa atgcatgtag gtgtaagagc tcatggagag catggaatat | 60 |
| tgtatccgac catgtaacag tataataact gagctccatc tcacttcttc tatgaataaa | 120 |
| caaaggatgt tatgatatat taacactcta tctatgcacc ttattgttct atgataaatt | 180 |
| tcctcttatt attataaatc atctgaatcg tgacggctta tggaatgctt caaatagtac | 240 |
| aaaaacaaat gtgtactata agactttcta aacaattcta accttagcat tgtgaacgag | 300 |
| acataagtgt taagaagaca taacaattat aatggaagaa gtttgtctcc atttatatat | 360 |
| tatatattac ccacttatgt attatattag gatgttaagg agacataaca attataaaga | 420 |
| gagaagtttg tatccattta tatattatat actacccatt tatatattat acttatccac | 480 |
| ttatttaatg tctttataag gtttgatcca tgatatttct aatattttag ttgatatgta | 540 |
| tatgaaaggg tactatttga actctcttac tctgtataaa ggttggatca tccttaaagt | 600 |
| gggtctattt aattttattg cttcttacag ataaaaaaaa aattatgagt tggtttgata | 660 |
| aaatattgaa ggatttaaaa taataataaa taacatataa tatatgtata taaatttatt | 720 |
| ataaatataac atttatctat aaaaaagtaa atattgtcat aaatctatac aatcgtttag | 780 |
| ccttgctgga cgaatctcaa ttatttaaac gagagtaaac atatttgact ttttggttat | 840 |
| ttaacaaatt attatttaac actatatgaa atttttttt ttatcagcaa agaataaaat | 900 |
| taaattaaga aggacaatgg tgtcccaatc cttatacaac caacttccac aagaaagtca | 960 |
| agtcagagac aacaaaaaaa caagcaaagg aaatttttta atttgagttg tcttgtttgc | 1020 |
| tgcataattt atgcagtaaa acactacaca taacccttt agcagtagag caatggttga | 1080 |
| ccgtgtgctt agcttctttt attttatttt tttatcagca aagaataaat aaaataaaat | 1140 |
| gagacacttc agggatgttt caacctgcag gtctagagga tccccgggta ccgagctcga | 1200 |
| attcactggc cgtcgtttta caacgtcgtg actgggaaaa ccctggcgtt acccaactta | 1260 |
| atcgccttgc agcacatccc cctttcgcca gctggcgtaa tagcgaagag gcccgcaccg | 1320 |
| atcgccctc ccaacagttg cgcagcctga atggcgaatg gcgcctgatg cggtattttc | 1380 |
| tccttacgca tctgtgcggt atttcacacc gcatatggtg cactctcagt acaatctgct | 1440 |
| ctgatgccgc atagttaagc cagccccgac acccgccaac acccgctgac gcgccctgac | 1500 |
| gggcttgtct gctcccggca tccgcttaca gacaagctgt gaccgtctcc gggagctgca | 1560 |
| tgtgtcagag gttttcaccg tcatcaccga aacgcgcgag acgaaagggc ctcgtgatac | 1620 |
| gcctattttt ataggttaat gtcatgataa taatggtttc ttagacgtca ggtggcactt | 1680 |
| ttcggggaaa tgtgcgcgga acccctattt gtttattttt ctaaatacat tcaaatatgt | 1740 |
| atccgctcat gagacaataa ccctgataaa tgcttcaata atattgaaaa aggaagagta | 1800 |
| tgagtattca acatttccgt gtcgccctta ttcccttttt tgcggcattt tgccttcctg | 1860 |

```
tttttgctca cccagaaacg ctggtgaaag taaaagatgc tgaagatcag ttgggtgcac    1920
gagtgggtta catcgaactg gatctcaaca gcggtaagat ccttgagagt tttcgccccg    1980
aagaacgttt tccaatgatg agcactttta aagttctgct atgtggcgcg gtattatccc    2040
gtattgacgc cgggcaagag caactcggtc gccgcataca ctattctcag aatgacttgg    2100
ttgagtactc accagtcaca gaaaagcatc ttacggatgg catgacagta agagaattat    2160
gcagtgctgc cataaccatg agtgataaca ctgcggccaa cttacttctg acaacgatcg    2220
gaggaccgaa ggagctaacc gcttttttgc acaacatggg gatcatgta actcgccttg    2280
atcgttggga accggagctg aatgaagcca taccaaacga cgagcgtgac accacgatgc    2340
ctgtagcaat ggcaacaacg ttgcgcaaac tattaactgg cgaactactt actctagctt    2400
cccgcaaca attaatagac tggatggagg cggataaagt tgcaggacca cttctgcgct    2460
cggcccttcc ggctggctgg tttattgctg ataaatctgg agccggtgag cgtgggtctc    2520
gcggtatcat tgcagcactg gggccagatg gtaagccctc ccgtatcgta gttatctaca    2580
cgacggggag tcaggcaact atggatgaac gaaatagaca gatcgctgag ataggtgcct    2640
cactgattaa gcattggtaa ctgtcagacc aagtttactc atatatactt tagattgatt    2700
taaaacttca ttttttaattt aaaaggatct aggtgaagat cctttttgat aatctcatga    2760
ccaaaatccc ttaacgtgag ttttcgttcc actgagcgtc agaccccgta gaaaagatca    2820
aaggatcttc ttgagatcct ttttttctgc gcgtaatctg ctgcttgcaa acaaaaaaac    2880
caccgctacc agcggtggtt tgtttgccgg atcaagagct accaactctt tttccgaagg    2940
taactggctt cagcagagcg cagataccaa atactgtcct tctagtgtag ccgtagttag    3000
gccaccactt caagaactct gtagcaccgc ctacatacct cgctctgcta atcctgttac    3060
cagtggctgc tgccagtggc gataagtcgt gtcttaccgg gttggactca agacgatagt    3120
taccggataa ggcgcagcgg tcgggctgaa cggggggttc gtgcacacag cccagcttgg    3180
agcgaacgac ctacaccgaa ctgagatacc tacagcgtga gctatgagaa agcgccacgc    3240
ttcccgaagg gagaaaggcg gacaggtatc cggtaagcgg cagggtcgga acaggagagc    3300
gcacgaggga gcttccaggg ggaaacgcct ggtatcttta tagtcctgtc gggtttcgcc    3360
acctctgact tgagcgtcga ttttgtgat gctcgtcagg gggcggagc ctatggaaaa    3420
acgccagcaa cgcggccttt ttacggttcc tggccttttg ctggccttttt gctcacatgt    3480
tctttcctgc gttatcccct gattctgtgg ataaccgtat taccgccttt gagtgagctg    3540
ataccgctcg ccgcagccga acgaccgagc gcagcgagtc agtgagcgag gaagcggaag    3600
agcgcccaat acgcaaaccg cctctccccg cgcgttggcc gattcattaa tgcagctggc    3660
acgacaggtt tcccgactgg aaagcgggca gtgagcgcaa cgcaattaat gtgagttagc    3720
tcactcatta ggcaccccag gctttacact ttatgcttcc ggctcgtatg ttgtgtggaa    3780
ttgtgagcgg ataacaattt cacacaggaa acagctatga ccatgattac gccaagcttg    3840
catgcctgca ggtcgactct agacctgcag gatccatgcc cttcatttgc cgcttattaa    3900
ttaatttggt aacagtccgt actaatcagt tacttatcct tcccccatca taattaatct    3960
tggtagtctc gaatgccaca acactgacta gtctcttgga tcataagaaa agccaagga    4020
acaaagaag acaaaacaca atgagagtat cctttgcata gcaatgtcta agttcataaa    4080
attcaaacaa aaacgcaatc acacacagtg gacatcactt atccactagc tgatcaggat    4140
cgccgcgtca agaaaaaaaa actggacccc aaaagccatg cacaacaaca cgtactcaca    4200
aaggtgtcaa tcgagcagcc caaaacattc accaactcaa cccatcatga gccctcacat    4260
```

-continued

```
ttgttgtttc taacccaacc tcaaactcgt attctcttcc gccacctcat ttttgtttat      4320
ttcaacaccc gtcaaactgc atgccacccc gtggccaaat gtccatgcat gttaacaaga      4380
cctatgacta taaatagctg caatctcggc ccaggttttc atcatcaaga accagttcaa      4440
tatcctagta caccgtatta aagaatttaa gatatactgc ggccgcacca tgtctcctaa      4500
gcggcaagct ctgccaatca caattgatgg cgcaacttat gatgtgtctg cttgggtcaa      4560
tcaccaccct ggaggagctg acattatcga gaactatcgc aaccgcgatg cgaccgatgt      4620
cttcatggtg atgcactctc aagaagccgt cgccaagttg aagagaatgc tgttatggga      4680
gccttcctct cctgacacac ctgttgcacc caagcctaag cgtgatgagc cccaggagga      4740
tttccgcaag ttgcgggagg aattcatctc caagggtatg ttcgagacga gtttcctttg      4800
gtattttac aagacttcaa ctaccgtcgg tttgatggtc ctttccatct tgatgaccgt      4860
gtacacgaat tggtatttca ccgctgcttt ggttcttggc gtgtgctacc aacagctagg      4920
ctggttgtcc cacgactatt gccatcacca ggttttcaca aaccgcaaga ttaacgacgc      4980
tttcggtctc tttttcggta acgtgatgca gggatactca cagacttggt ggaaggatag      5040
gcacaatggt caccatgccg ccaccaatgt ggtcggccat gacccagata ttgataaacct      5100
ccccatcctg gcttggtctc ccgaagatgt caagagggct actccttcga ctcggaatct      5160
catcaagtac cagcagtact acttcattcc caccattgca tcccttaggt tcatctggtg      5220
cctccaatcc atcggcggcg tcatgtccta caagagcgag gagaggaacc tgtactacaa      5280
gcgccagtac actaaggagg cgattggtct ggccctccac tgggtgctca aggccacttt      5340
ctattgcagt gccatgccta gctttgccac cggtttggga tgcttcttga tctccgagct      5400
gctcggagga tttggcattg ccatcgttgt gtttctgaat cactatcctt tggacaaggt      5460
tgaggagact gtctgggatg agcacggggtt cagcgccagc cagatccacg agacgttgaa      5520
cattaagccc ggccttctca ccgattgggt ctttggtggt ctcaactacc agattgagca      5580
ccacttgtgg cccaacatgc ccaggcacaa cctcacggca gcttccctgg aggtgcagaa      5640
gttgtgcgcc aagcacaacc tgccctacag ggccccagcc atcatcccg gggttcgaaa      5700
attggtcagc ttcttaggcg agattgccca gctggctgct gtccctgaat gagc            5754
```

<210> SEQ ID NO 90
<211> LENGTH: 12947
<212> TYPE: DNA
<213> ORGANISM: Artificial Sequence
<220> FEATURE:
<223> OTHER INFORMATION: plasmid pKR1005

<400> SEQUENCE: 90

```
ggtcgactcg acgtacgtct agaggatccg tcgacggcgc gcccgatcat ccggatatag       60
ttcctccttt cagcaaaaaa cccctcaaga cccgtttaga ggccccaagg ggttatgcta      120
gttattgctc agcggtggca gcagccaact cagcttcctt tcgggctttg ttagcagccg      180
gatcgatcca agctgtacct cactattcct ttgccctcgg acgagtgctg gggcgtcggt      240
ttccactatc ggcgagtact tctacacagc catcggtcca gacggccgcg cttctgcggg      300
cgatttgtgt acgcccgaca gtcccggctc cggatcggac gattgcgtcg catcgaccct      360
gcgcccaagc tgcatcatcg aaattgccgt caaccaagct ctgatagagt tggtcaagac      420
caatgcggag catatacgcc cggagccgcg gcgatcctgc aagctccgga tgcctccgct      480
cgaagtagcg cgtctgctgc tccatacaag ccaaccacgg cctccagaag aagatgttgg      540
```

```
cgacctcgta ttgggaatcc ccgaacatcg cctcgctcca gtcaatgacc gctgttatgc    600
ggccattgtc cgtcaggaca ttgttggagc cgaaatccgc gtgcacgagg tgccggactt    660
cggggcagtc ctcggcccaa agcatcagct catcgagagc ctgcgcgacg gacgcactga    720
cggtgtcgtc catcacagtt tgccagtgat acacatgggg atcagcaatc gcgcatatga    780
aatcacgcca tgtagtgtat tgaccgattc cttgcggtcc gaatgggccg aacccgctcg    840
tctggctaag atcggccgca gcgatcgcat ccatagcctc cgcgaccggc tgcagaacag    900
cgggcagttc ggtttcaggc aggtcttgca acgtgacacc ctgtgcacgg cgggagatgc    960
aataggtcag gctctcgctg aattccccaa tgtcaagcac ttccggaatc gggagcgcgg   1020
ccgatgcaaa gtgccgataa acataacgat ctttgtagaa accatcggcg cagctattta   1080
cccgcaggac atatccacgc cctcctacat cgaagctgaa agcacgagat tcttcgccct   1140
ccgagagctg catcaggtcg gagacgctgt cgaacttttc gatcagaaac ttctcgacag   1200
acgtcgcggt gagttcaggc ttttccatgg gtatatctcc ttcttaaagt taaacaaaat   1260
tatttctaga gggaaaccgt tgtggtctcc ctatagtgag tcgtattaat ttcgcgggat   1320
cgagatctga tcaacctgca ttaatgaatc ggccaacgcg cggggagagg cggtttgcgt   1380
attgggcgct cttccgcttc ctcgctcact gactcgctgc gctcggtcgt tcggctgcgg   1440
cgagcggtat cagctcactc aaaggcggta atacggttat ccacagaatc aggggataac   1500
gcaggaaaga acatgtgagc aaaaggccag caaaaggcca ggaaccgtaa aaaggccgcg   1560
ttgctggcgt ttttccatag gctccgcccc cctgacgagc atcacaaaaa tcgacgctca   1620
agtcagaggt ggcgaaaccc gacaggacta taaagatacc aggcgtttcc ccctggaagc   1680
tccctcgtgc gctctcctgt tccgaccctg ccgcttaccg gatacctgtc cgcctttctc   1740
ccttcgggaa gcgtggcgct ttctcaatgc tcacgctgta ggtatctcag ttcggtgtag   1800
gtcgttcgct ccaagctggg ctgtgtgcac gaaccccccg ttcagcccga ccgctgcgcc   1860
ttatccggta actatcgtct tgagtccaac ccggtaagac acgacttatc gccactggca   1920
gcagccactg gtaacaggat tagcagagcg aggtatgtag cggtgctac agagttcttg    1980
aagtggtggc ctaactacgg ctacactaga aggacagtat ttggtatctg cgctctgctg   2040
aagccagtta ccttcggaaa aagagttggt agctcttgat ccggcaaaca aaccaccgct   2100
ggtagcggtg gttttttgt ttgcaagcag cagattacgc gcagaaaaaa aggatctcaa   2160
gaagatcctt tgatcttttc tacggggtct gacgctcagt ggaacgaaaa ctcacgttaa   2220
gggattttgg tcatgacatt aacctataaa aataggcgta tcacgaggcc ctttcgtctc   2280
gcgcgtttcg gtgatgacgg tgaaaacctc tgacacatgc agctcccgga gacggtcaca   2340
gcttgtctgt aagcggatgc cgggagcaga caagcccgtc agggcgcgtc agcgggtgtt   2400
ggcgggtgtc ggggctggct taactatgcg gcatcagagc agattgtact gagagtgcac   2460
catatggaca tattgtcgtt agaacgcggc tacaattaat acataacctt atgtatcata   2520
cacatacgat ttaggtgaca ctatagaacg gcgcgccaag ctgggtctag aactagaaac   2580
gtgatgccac ttgttattga agtcgattac agcatctatt ctgttttact atttataact   2640
ttgccatttc tgacttttga aaactatctc tggatttcgg tatcgctttg tgaagatcga   2700
gcaaaagaga cgttttgtgg acgcaatggt ccaaatccgt tctacatgaa caaattggtc   2760
acaatttcca ctaaaagtaa ataaatggca agttaaaaaa ggaatatgca ttttactgat   2820
tgcctaggtg agctccaaga gaagttgaat ctacacgtct accaaccgct aaaaaaagaa   2880
aaacattgaa tatgtaacct gattccatta gcttttgact tcttcaacag attctctact   2940
```

```
tagatttcta acagaaatat tattactagc acatcatttt cagtctcact acagcaaaaa    3000
atccaacggc acaatacaga caacaggaga tatcagacta cagagataga tagatgctac    3060
tgcatgtagt aagttaaata aaaggaaaat aaaatgtctt gctaccaaaa ctactacaga    3120
ctatgatgct caccacaggc caaatcctgc aactaggaca gcattatctt atatatattg    3180
tacaaaacaa gcatcaagga acatttggtc taggcaatca gtacctcgtt ctaccatcac    3240
cctcagttat cacatccttg aaggatccat tactgggaat catcggcaac acatgctcct    3300
gatgggcac aatgacatca agaaggtagg ggccaggggt gtccaacatt ctctgaattg    3360
ccgctctaag ctcttccttc ttcgtcactc gcgctgccgg tatcccacaa gcatcagcaa    3420
acttgagcat gtttgggaat atctcgctct cgctagacgg atctccaaga taggtgtgag    3480
ctctattgga cttgtagaac ctatcctcca actgaaccac catacccaaa tgctgattgt    3540
tcaacaacaa tatcttaact gggagattct ccactcttat agtggccaac tcctgaacat    3600
tcatgatgaa actaccatcc ccatcaatgt caaccacaac agcccagggg ttagcaacag    3660
cagcaccaat agccgcaggc aatccaaaac ccatggctcc aagaccccct gaggtcaacc    3720
actgcctcgg tctcttgtac ttgtaaaact gcgcagccca catttgatgc tgcccaaccc    3780
cagtactaac aatagcatct ccattagtca actcatcaag aacctcgata gcatgctgcg    3840
gagaaatcgc gtcctggaat gtcttgtaac ccaatggaaa cttgtgtttc tgcacattaa    3900
tctcttctct ccaacctcca agatcaaact taccctccac tcctttctcc tccaaaatca    3960
tattaattcc cttcaaggcc aacttcaaat ccgcgcaaac cgacacgtgc gcctgcttgt    4020
tcttcccaat ctcggcagaa tcaatatcaa tgtgaacaat cttagcccta ctagcaaaag    4080
cctcaagctt cccagtaaca cggtcatcaa accttacccc aaaggcaagc aacaaatcac    4140
tattgtcaac agcatagtta gcataaacag taccatgcat acccagcatc tgaagggaat    4200
attcatcacc aataggaaaa gttccaagac ccattaaagt gctagcaacg ggaataccag    4260
tgagttcaac aaagcgcctc aattcagcac tggaattcaa actgccaccg ccgacgtaga    4320
gaacgggctt ttgggcctcc atgatgagtc tgacaatgtg ttccaattgg gcctcggcgg    4380
ggggcctggg cagcctggcg aggtaaccgg ggaggttaac gggctcgtcc caattaggca    4440
cggcgagttg ctgctgaacg tctttgggaa tgtcgatgag gaccggaccg gggcggccgg    4500
aggtggcgac gaagaaagcc tcggcgacga cgcgggggat gtcgtcgacg tcgaggatga    4560
ggtagttgtg cttcgtgatg gatctgctca cctccacgat cggggtttct tggaaggcgt    4620
cggtgccgat catccggcgg gcgacctggc cggtgatggc gacgactggg acgctgtcca    4680
ttaaagcgtc ggcgaggccg ctcacgaggt tggtggcgcc ggggccggag gtggcaatgc    4740
agacgccggg gaggccggag gaacgcgcgt agccttcggc ggcgaagacg ccgccctgct    4800
cgtggcgcgg gagcacgttg cggatggcgg cggagcgcgt gagcgcctgg tggatctcca    4860
tcgacgcacc gccggggtac gcgaacaccg tcgtcacgcc ctgcctctcc agcgcctcca    4920
caaggatgtc cgcgcccttg cgaggttcgc cggaggcgaa ccgtgacacg aagggctccg    4980
tggtcggcgc ttccttggtg aagggcgccg ccgtgggggg tttggagatg aacatttga    5040
ttttgagagc gtggttgggt ttggtgaggg tttgatgaga gagagggagg gtggatctag    5100
taatgcgttt ggggaaggtg gggtgtgaag aggaagaaga gaatcgggtg gttctggaag    5160
cggtggccgc cattgtgttg tgtggcatgg ttatacttca aaaactgcac aacaagccta    5220
gagttagtac ctaaacagta aatttacaac agagagcaaa gacacatgca aaaatttcag    5280
```

```
ccataaaaaa agttataata gaatttaaag caaaagtttc attttttaaa catatataca    5340
aacaaactgg atttgaagga agggattaat tcccctgctc aaagtttgaa ttcctattgt    5400
gacctatact cgaataaaat tgaagcctaa ggaatgtatg agaaacaaga aaacaaaaca    5460
aaactacaga caaacaagta caattacaaa attcgctaaa attctgtaat caccaaaccc    5520
catctcagtc agcacaaggc ccaaggttta ttttgaaata aaaaaaaagt gattttattt    5580
ctcataagct aaaagaaaga aaggcaatta tgaaatgatt tcgactagat ctgaaagtca    5640
aacgcgtatt ccgcagatat taaagaaaga gtagagtttc acatggatcc tagatggacc    5700
cagttgagga aaaagcaagg caaagcaaac cagaagtgca agatccgaaa ttgaaccacg    5760
gaatctagga tttggtagag ggagaagaaa agtaccttga gaggtagaag agaagagaag    5820
agcagagaga tatatgaacg agtgtgtctt ggtctcaact ctgaagcgat acgagtttag    5880
aggggagcat tgagttccaa tttatagggg aaccgggtgg caggggtgag ttaatgacgg    5940
aaaagcccct aagtaacgag attggattgt gggttagatt caaccgtttg catccgcggc    6000
ttagattggg gaagtcagag tgaatctcaa ccgttgactg agttgaaaat tgaatgtagc    6060
aaccaattga gccaaccccca gcctttgccc tttgattttg atttgtttgt tgcatacttt    6120
ttatttgtct tctggttctg actctctttc tctcgtttca atgccaggtt gcctactccc    6180
acaccactca caagaagatt ctactgttag tattaaatat tttttaatgt attaaatgat    6240
gaatgctttt gtaaacagaa caagactatg tctaataagt gtcttgcaac attttttaag    6300
aaattaaaaa aaatatattt attatcaaaa tcaaatgtat gaaaaatcat gaataatata    6360
atttttataca tttttttaaa aaatcttttt atttcttaat taatatctta aaaataatga    6420
ttaatattta acccaaaata attagtatga ttggtaagga agatatccat gttatgtttg    6480
gatgtgagtt tgatctagag caaagcttac tagagtcgac ctgcagcccg ggggatccgc    6540
ccacgtacgg taccatctgc taatatttta aatcacatgc aagagaggag gcatggttcc    6600
attttctacc ttcacattat ttgagaaaaa cgaacttgtt ctgtgtttta tttttgccct    6660
tcacattagt acaacgtgga agactcatgg ttacacagaa tcatacataa gtacaatgct    6720
tgtccctaag aaaacaagca ctcgttgtat tgaacccttta cggctcatgc ggccgcgaat    6780
tcactagtga ttgaattcgc ggccgcttag tccgacttgg ccttggcggc gcggccgac    6840
tctttgagcg tgaagatctg cgccgtctcg ggcacagcgc cgtagttgac aaagaggtgc    6900
gcggtcttga agaaggccgt gatgatgggc tcgtcgttcc tgcgcacgag gtgcgggtac    6960
gcggccgcaa agtgcttggt ggcttcgttg agcttgtagt gcggaatgat cgggaacaag    7020
tggtggacct ggtgcgtgcc aatgtggtgg ctcaggttgt ccacgaacgc gccgtacgag    7080
cggtcgacgc tcgagaggtt gcccttgacg tacgtccact ccgagtcgcc gtaccacggc    7140
gtcgcttcgt cgttgtggtg caagaaggtc gtaatgacga ggaacgaagc aaagacaaag    7200
agcggcgcat agtagtagag gcccatgacg gcaaagccga gcgagtatgt gaggtacgcg    7260
tacgcggcga agaaggcggc ccagacgccg agcgacacga tgacggccga cgcgcggcga    7320
aggaggagcg ggtccacggg tcaaagtggc tcatcgtgcc gcggggcata cccgaccttc    7380
aagtagacaa accacgcacc gccgagcgtg tagacccatt ggcgcacgtc ctggaggtcc    7440
ttgaccgacc ggtgcgggta aaagatctcg tccttatcaa tgttgcccgt gttcttgtgg    7500
tggtggcggt gcgtcacgcg ccagctctcg aacggcgtca aaatcgcaga gtgcatgatg    7560
cagccgatga taaagttgac gctgtggtag cgcgagaagg ccgagtggcc gcagtcgtgg    7620
ccgaccgtga agaagcccca gaagatgacg ccctgcacgt agatgtaggt ggcgcaaacg    7680
```

```
agcgcgtgga gcagaacgtt atcggcaatg aacggcgtcg agcgcgccgc gtagagcagc    7740
gccgccgagg ccgacgcgtt gaagatcgcg cgggccgtgt agtagagcga gaggccgagg    7800
ttcgactcaa agcacgcgtt cgggatcgag tgcttgagct ccgtgagcgt cgggaactcg    7860
accttcgtct tatcctcagt catgcggccg ctgaagtatt gcttcttagt taacctttcc    7920
tttctctctc agctatgtga attcattttg ctttcgtcac aatttatata gtgaaattgg    7980
atctttggag ttaacgcctt cacaggatta tcgtgttaga acaatgcttt ttcatgttct    8040
aattagtagt acattacaaa tgtgcactct attcaataag catcttttgg cacgttaata    8100
aatcatgtga aaaaaaaata ctactatttc aaagaaagtg ttgtaaaaag aaacggaaag    8160
agagctggct tcagttgttg agacttgttt gctagtaaaa atggtgtgaa gagtgattca    8220
tggtgaggtg gttttttcgtc cctttctgtt tgcatgaaaa acaaatggca agagatgacg    8280
taggattcct tcccttaacg attatctgtt tttaatttca aatatacata taggaattta    8340
tgaattacta aggttgtaaa atatgctggt catttattta tggctaaaat attttttttt    8400
ctcgtaaata taaaaatatt taaaatttat ttttatcata ttttttatcc ttataaaatt    8460
atgtgtacaa cctatataaa aaaatatcat atttaatatt gattatatgt ttaatcaata    8520
taaaaaatca ttatcatata tttagattta ttcgaatata catctaaaca aaaaataaca    8580
tattttaatt ttatgaagaa aaaaaaatat tttatccttt atttatttaa gattaattaa    8640
tagttatgta ttgtggaaag acttttacac atgcaataga tatactgaat caattagatg    8700
ccaatgctga gttggaaatc acttgaggag gggaggagac ttgccaatgc ttttcagttt    8760
catttaaatg atttagtgga ggagatagag tagtgataaa ggcatgcccc aattttggag    8820
tgtatatatg agtggaaata agagagggat agagagaaaa aataagaga gtaaaaataa    8880 ttaatgtgaa atgatatgat aaaaaaataa agaaagagat aaagagaaaa atgaaatgag    8940
agatagatga aatagagagt agatacatgt ttgtttaggt ttttttttagg aaataacaca    9000 tttttttctc atcacttatt actcactgtc aatttcctct ctttcaatca taatgatatg    9060
atttgtttaa caaaaatgtg aaaaaacata taaagtaaaa tatttttata aattgataaa    9120
taaaaattta caaatttat ttcttattaa attgaataga aaatgaaaga aagaaaaga    9180 aaagtatat ataaaatgat atagctttaa aaagaataaa ttttttcatat cagtcttttt    9240 ttaataattt agaaatattt aagtatatag caaaaatata atgtacttta catatgcata    9300
aataataatt tgaaaataga actaatgaaa tagagaaaaa agtaatataa taattaacta    9360
tatgaaaatt tagaagggac aatattttta attaagaata taaacaatat ttcttttcat    9420
gtaatgaggg acggatgtac ggggccagtg ttggagtcaa agccaaaata gtcacgggga    9480
aattaatgca ctgcatgact attcgaaaaa attcactagc cttacttaga tgttagatta    9540
atagctaggg ggtgcagata attttgaaag gcatgaaaaa cattaatttg tacattgcaa    9600
gcttttgatg acaagctttg caattgttca cactaccta tgccatttat aaatagagtg    9660
attggcatat gaaggaaatc atgagagtcg aagcgaaaaa caaagcttga gagtgtagga    9720
aaaatacagt tttttggta aaaatacagt atttgaatag gagcgaaaaa tatcctttca    9780
aaatgatcct tttctttttt tttttttttc ttgttgttct tggtcagtta ttcaaaggaa    9840
aagggattga aataaaaact tgcatgtggg atcgtacgtc gagtcgacct gcaggatcca    9900
tgcccttcat ttgccgctta ttaattaatt tggtaacagt ccgtactaat cagttactta    9960
tccttccccc atcataatta atcttggtag tctcgaatgc cacaacactg actagtctct   10020
```

-continued

```
tggatcataa gaaaaagcca aggaacaaaa gaagacaaaa cacaatgaga gtatcctttg   10080
catagcaatg tctaagttca taaaattcaa acaaaaacgc aatcacacac agtggacatc   10140
acttatccac tagctgatca ggatcgccgc gtcaagaaaa aaaaactgga ccccaaaagc   10200
catgcacaac aacacgtact cacaaaggtg tcaatcgagc agcccaaaac attccaac    10260 tcaacccatc atgagccctc acatttgttg tttctaaccc aacctcaaac tcgtattctc   10320
ttccgccacc tcattttgt ttatttcaac acccgtcaaa ctgcatgcca ccccgtggcc    10380
aaatgtccat gcatgttaac aagacctatg actataaata gctgcaatct cggcccaggt   10440
tttcatcatc aagaaccagt tcaatatcct agtacaccgt attaaagaat ttaagatata   10500
ctgcggccgc accatgtctc ctaagcggca agctctgcca atcacaattg atggcgcaac   10560
ttatgatgtg tctgcttggg tcaatcacca ccctggagga gctgacatta tcgagaacta   10620
tcgcaaccgc gatgcgaccg atgtcttcat ggtgatgcac tctcaagaag ccgtcgccaa   10680
gttgaagaga atgcctgtta tggagccttc ctctcctgac acacctgttg cacccaagcc   10740
taagcgtgat gagccccagg aggatttccg caagttgcgg gaggaattca tctccaaggg   10800
tatgttcgag acgagtttcc tttggtattt ttacaagact tcaactaccg tcggtttgat   10860
ggtcctttcc atcttgatga ccgtgtacac gaattggtat ttcaccgctg ctttggttct   10920
tggcgtgtgc taccaacagc taggctggtt gtcccacgac tattgccatc accaggtttt   10980
cacaaaccgc aagattaacg acgctttcgg tctcttttc ggtaacgtga tgcagggata   11040
ctcacagact tggtggaagg ataggcacaa tggtcaccat gccgccacca atgtggtcgg   11100
ccatgaccca gatattgata acctccccat cctggcttgg tctcccgaag atgtcaagag   11160
ggctactcct tcgactcgga atctcatcaa gtaccagcag tactacttca ttcccaccat   11220
tgcatccctt aggttcatct ggtgcctcca atccatcggc ggcgtcatgt cctacaagag   11280
cgaggagagg aacctgtact acaagcgcca gtacactaag gaggcgattg gtctggccct   11340
ccactgggtg ctcaaggcca ctttctattg cagtgccatg cctagctttg ccaccggttt   11400
gggatgcttc ttgatctccg agctgctcgg aggatttggc attgccatcg ttgtgtttct   11460
gaatcactat cctttggaca aggttgagga gactgtctgg gatgagcacg ggttcagcgc   11520
cagccagatc cacgagacgt tgaacattaa gcccggcctt ctcaccgatt gggtctttgg   11580
tggtctcaac taccagattg agcaccactt gtggcccaac atgcccaggc acaacctcac   11640
ggcagcttcc ctggaggtgc agaagttgtg cgccaagcac aacctgccct acagggcccc   11700
agccatcatc cccggggttc agaaattggt cagcttctta ggcgagattg cccagctggc   11760
tgctgtccct gaatgagcgg ccgcaagtat gaactaaaat gcatgtaggt gtaagagctc   11820
atggagagca tggaatattg tatccgacca tgtaacagta taataactga gctccatctc   11880
acttcttcta tgaataaaca aaggatgtta tgatatatta acactctatc tatgcacctt   11940
attgttctat gataaatttc ctcttattat tataaatcat ctgaatcgtg acggcttatg   12000
gaatgcttca aatagtacaa aaacaaatgt gtactataag actttctaaa caattctaac   12060
cttagcattg tgaacgagac ataagtgtta agaagacata caattataa tggaagaagt   12120 ttgtctccat ttatatatta tatattaccc acttatgtat tatattagga tgttaaggag   12180
acataacaat tataaagaga gaagtttgta tccatttata tattatatac tacccattta   12240
tatattatac ttatccactt atttaatgtc tttataaggt ttgatccatg atatttctaa   12300
tattttagtt gatatgtata tgaaagggta ctatttgaac tctcttactc tgtataaagg   12360
ttggatcatc cttaaagtgg gtctatttaa ttttattgct tcttacagat aaaaaaaaaa   12420
```

```
ttatgagttg gtttgataaa atattgaagg atttaaaata ataataaata acatataata    12480
tatgtatata aatttattat aatataacat ttatctataa aaaagtaaat attgtcataa    12540
atctatacaa tcgtttagcc ttgctggacg aatctcaatt atttaaacga gagtaaacat    12600
atttgacttt ttggttattt aacaaattat tatttaacac tatatgaaat ttttttttt     12660 atcagcaaag aataaaatta aattaagaag gacaatggtg tcccaatcct tatacaacca    12720
acttccacaa gaaagtcaag tcagagacaa caaaaaaaca agcaaaggaa attttttaat    12780
ttgagttgtc ttgtttgctg cataatttat gcagtaaaac actacacata acccttttag    12840
cagtagagca atggttgacc gtgtgcttag cttcttttat tttatttttt tatcagcaaa    12900
gaataaataa aataaaatga gacacttcag ggatgtttca acctgca                  12947

<210> SEQ ID NO 91
<211> LENGTH: 18
<212> TYPE: DNA
<213> ORGANISM: Artificial Sequence
<220> FEATURE:
<223> OTHER INFORMATION: universal primer M13F

<400> SEQUENCE: 91
tgtaaaacga cggccagt                                                  18

<210> SEQ ID NO 92
<211> LENGTH: 1254
<212> TYPE: DNA
<213> ORGANISM: Eutreptiella sp. CCMP389

<400> SEQUENCE: 92
atgtcaccca agcgagaggc cttgcccatc acgattgatg gcacaaccta tgatgtgtcc    60
gcatgggtga accatcaccc cgggggcgca gacatcatgg agaattatcg gaaccgagat    120
gccacggatg tgttcatggt catgcactcc cacgatgcgt tgaacaagct gaagcgcatg    180
cctgtgatgg agcccacttc gccacgaagc cccaagactc ccaacgacga ggttgctgag    240
gacttccgca agcttcgaaa ggacatgatt gcaaaaggca tgttcaacgc atccctctc    300 ttctacgtgt acaaaagtgc gaccacagta gccctgggcg ccctggctat tctgatggtg    360
atgcacctgc agtggtacta catcccagcc attttgttgg gactttgcta ccagcagctg    420
gggtggttgg cacacgatta ctgccaccat caggtgttct ctaaccgggc gtacaacaat    480
tttgctggac ttgtattcgg caatgtgatg caaggatact ccgggacttg gtggaaggac    540
aggcacaacg gccatcacgc cgccacgaac gtgcaagggc acgatcccga catcgacgac    600
ctcccggtgt tggcctggtc cccggaggac gtcaaaaacg ccggtcccac gacgcggaag    660
ctcatcaagt ggcaacaata ctatttcctc cccaccatcg caaccctccg attcatctgg    720
tgcttccaga gcattctggc ggttatggca tacaagacag atgcaaggaa tatatattac    780
caacgccagt acgcaaagga ggccgtgggg ctggctctgc attggattct gaaagggta    840 ttcatgttct gttacatgcc cggcatactg acgggcttgg ccttcttcct catctcggag    900
tgcctgggcg ggtttgggat tgccattgtc gtgttcttga atcactaccc attggagaag    960
gtggaggagt ccgtgtggga cagccacggg ttttgcgcgg ggcagatcca cacgacgatg    1020
aacatccaac gcggggtcat cgttgactgg ttctttggag gcctgaacta ccaaatcgaa    1080
caccatctgt ggccgacgct gccccggcat cacttgaaag ctgcttcttt tgaggtggag    1140
aaaatttgcc agaagcacaa attgccatac agagcacccc ccatgtccga tggtgttgct    1200
```

```
caattgcttg gcttcttggg gaagattgct aagctggcag ctgtcccagt gtaa        1254
```

<210> SEQ ID NO 93
<211> LENGTH: 1254
<212> TYPE: DNA
<213> ORGANISM: Eutreptiella cf_gymnastica CCMP1594
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (766)..(766)
<223> OTHER INFORMATION: n is a, c, g, or t

<400> SEQUENCE: 93

```
atgtcaccta aacgggacgc attgcctctg acaattgatg gcaccacgta cgacgtttcc    60
gcttgggtaa accatcaccc tggaggggct caaatcattg aaaactaccg gaaccgagat   120
gctaccgacg tgttcatggt catgcattca cagcaggcgc tcaacaagtt gaagcggatg   180
cctgttatgg agccctcttc accacttact cccaagagcc caagtgacga catttccnag   240
gatttccgca agctccgcaa cagtatggtt gagaagggta tgttcaacgc gtcccctctg   300
tttatgtgt acaaatcact gaccactgtc gcccttggcg ccgtgggtgt tctcatggtt   360
atgtacctgc agtggtacta cgtttcagcc atgttttttgg gactttgcta ccaacagctg   420
ggttgggtgg cgcatgacta cgcgcatcac caggttttca cgaaccgtga ttatggcaat   480
cttggtgggc ttttctttgg cnacgttctc caaggatatt ctttgacttg gtggaaggac   540
aggcacaacg gccatcacgc cgccacaaac gtgcaaggac atgaccccga cattgataat   600
ctccccgttt tggcttggtc gccagaggac gtcaagaatg ccggacctgg aacccgcaat   660
atcatcaagt accagcagta ttatttcctc cctaccatcg ccatccttcg gttcatctgg   720
tgtttccaaa gcattctggg ggtgatgtca tacaagacag actccnagaa tctctattac   780
aaacggcagt accggagaga ggcagccggt ctggcgctgc actggattct gaagagcgtt   840
ttcttgttct gttacatgcc aagtttcctc actggcctgg cgttttttcct tatctcggag   900
tgtctgggcg gctttgggat cgcgattgtg gtgttttga accactatcc gctggataag   960
gttgaggaat ccgttgggga tggtcacggt ttctgtgctg ggcagatcct cacaaccatg  1020
aacatccaac gcggactcat cactgactgg ttctttggag gtttgaatta ccagattgag  1080
catcatctgt ggcccaacct tccaagacac catttgaaag cagtttcctt tgaggttgag  1140
aaattgtgcc agaagcacaa cctgccctac agagctccgc cgatgcatac tggtgttgca  1200
caattgcttg gatatttggg gaagattgct cagttggctg ctgtcccagt ataa        1254
```

<210> SEQ ID NO 94
<211> LENGTH: 7222
<212> TYPE: DNA
<213> ORGANISM: Artificial Sequence
<220> FEATURE:
<223> OTHER INFORMATION: Yarrowia lipolytica expression vector
     pFBAIn-MOD-1

<400> SEQUENCE: 94

```
catggatcca ggcctgttaa cggccattac ggcctgcagg atccgaaaaa acctcccaca    60
cctcccctg aacctgaaac ataaaatgaa tgcaattgtt gttgttaact tgtttattgc   120
```

```
agcttataat ggttacaaat aaagcaatag catcacaaat ttcacaaata aagcattttt    180
ttcactgcat tctagttgtg gtttgtccaa actcatcaat gtatcttatc atgtctgcgg    240
ccgcaagtgt ggatggggaa gtgagtgccc ggttctgtgt gcacaattgg caatccaaga    300
tggatggatt caacacaggg atatagcgag ctacgtggtg gtgcgaggat atagcaacgg    360
atatttatgt ttgacacttg agaatgtacg atacaagcac tgtccaagta caatactaaa    420
catactgtac atactcatac tcgtacccgg gcaacggttt cacttgagtg cagtggctag    480
tgctcttact cgtacagtgt gcaatactgc gtatcatagt ctttgatgta tatcgtattc    540
attcatgtta gttgcgtacg agccggaagc ataaagtgta aagcctgggg tgcctaatga    600
gtgagctaac tcacattaat tgcgttgcgc tcactgcccg ctttccagtc gggaaacctg    660
tcgtgccagc tgcattaatg aatcggccaa cgcgcgggga gaggcggttt gcgtattggg    720
cgctcttccg cttcctcgct cactgactcg ctgcgctcgg tcgttcggct gcggcgagcg    780
gtatcagctc actcaaaggc ggtaatacgg ttatccacag aatcagggga taacgcagga    840
aagaacatgt gagcaaaagg ccagcaaaag gccaggaacc gtaaaaaggc cgcgttgctg    900
gcgtttttcc ataggctccg ccccctgac gagcatcaca aaaatcgacg ctcaagtcag    960
aggtggcgaa acccgacagg actataaaga taccaggcgt ttccccctgg aagctccctc   1020
gtgcgctctc ctgttccgac cctgccgctt accggatacc tgtccgcctt ctcccttcg   1080
ggaagcgtgg cgctttctca tagctcacgc tgtaggtatc tcagttcggt gtaggtcgtt   1140
cgctccaagc tgggctgtgt gcacgaaccc ccgttcagc ccgaccgctg cgccttatcc    1200
ggtaactatc gtcttgagtc caacccggta agacacgact tatcgccact ggcagcagcc   1260
actggtaaca ggattagcag agcgaggtat gtaggcggtg ctacagagtt cttgaagtgg   1320
tggcctaact acggctacac tagaaggaca gtatttggta tctgcgctct gctgaagcca   1380
gttaccttcg gaaaaagagt tggtagctct tgatccggca acaaaccac cgctggtagc    1440
ggtggttttt ttgtttgcaa gcagcagatt acgcgcagaa aaaaaggatc tcaagaagat   1500
cctttgatct tttctacggg gtctgacgct cagtggaacg aaaactcacg ttaagggatt   1560
ttggtcatga gattatcaaa aaggatcttc acctagatcc ttttaaatta aaatgaagt    1620
tttaaatcaa tctaaagtat atatgagtaa acttggtctg acagttacca atgcttaatc   1680
agtgaggcac ctatctcagc gatctgtcta tttcgttcat ccatagttgc ctgactcccc   1740
gtcgtgtaga taactacgat acgggagggc ttaccatctg gccccagtgc tgcaatgata   1800
ccgcgagacc cacgctcacc ggctccagat ttatcagcaa taaaccagcc agccggaagg   1860
gccgagcgca gaagtggtcc tgcaacttta tccgcctcca tccagtctat taattgttgc   1920
cgggaagcta gagtaagtag ttcgccagtt aatagtttgc gcaacgttgt tgccattgct   1980
acaggcatcg tggtgtcacg ctcgtcgttt ggtatggctt cattcagctc cggttcccaa   2040
cgatcaaggc gagttacatg atcccccatg ttgtgcaaaa aagcggttag ctccttcggt   2100
cctccgatcg ttgtcagaag taagttggcc gcagtgttat cactcatggt tatggcagca   2160
ctgcataatt ctcttactgt catgccatcc gtaagatgct tttctgtgac tggtgagtac   2220
tcaaccaagt cattctgaga atagtgtatg cggcgaccga gttgctcttg cccggcgtca   2280
atacgggata taccgcgcc acatagcaga actttaaaag tgctcatcat tggaaaacgt    2340
tcttcggggc gaaaactctc aaggatctta ccgctgttga gatccagttc gatgtaaccc   2400
actcgtgcac ccaactgatc ttcagcatct tttactttca ccagcgtttc tgggtgagca   2460
aaaacaggaa ggcaaaatgc cgcaaaaaag ggaataaggg cgacacggaa atgttgaata   2520
```

```
ctcatactct tccttttca atattattga agcatttatc agggttattg tctcatgagc    2580
ggatacatat ttgaatgtat ttagaaaaat aaacaaatag gggttccgcg cacatttccc    2640
cgaaaagtgc cacctgacgc gccctgtagc ggcgcattaa gcgcggcggg tgtggtggtt    2700
acgcgcagcg tgaccgctac acttgccagc gccctagcgc ccgctccttt cgctttcttc    2760
ccttcctttc tcgccacgtt cgccggcttt ccccgtcaag ctctaaatcg ggggctccct    2820
ttagggttcc gatttagtgc tttacggcac ctcgacccca aaaaacttga ttagggtgat    2880
ggttcacgta gtgggccatc gccctgatag acggttttc gcccttgac gttggagtcc    2940 acgttcttta atagtggact cttgttccaa actggaacaa cactcaaccc tatctcggtc    3000
tattcttttg atttataagg gattttgccg atttcggcct attggttaaa aaatgagctg    3060
atttaacaaa aatttaacgc gaattttaac aaaatattaa cgcttacaat tccattcgc     3120 cattcaggct gcgcaactgt tgggaagggc gatcggtgcg ggcctcttcg ctattacgcc    3180
agctggcgaa aggggggatgt gctgcaaggc gattaagttg ggtaacgcca gggttttccc    3240
agtcacgacg ttgtaaaacg acggccagtg aattgtaata cgactcacta tagggcgaat    3300
tgggtaccgg gccccccctc gaggtcgatg tgtcgataa gcttgatatc gaattcatgt    3360
cacacaaacc gatcttcgcc tcaaggaaac ctaattctac atccgagaga ctgccgagat    3420
ccagtctaca ctgattaatt ttcgggccaa taatttaaaa aaatcgtgtt atataatatt    3480
atatgtatta tatatataca tcatgatgat actgacagtc atgtcccatt gctaaataga    3540
cagactccat ctgccgcctc caactgatgt tctcaatatt taaggggtca tctcgcattg    3600
tttaataata aacagactcc atctaccgcc tccaaatgat gttctcaaaa tatattgtat    3660
gaacttattt ttattactta gtattattag acaacttact tgctttatga aaacacttc     3720 ctatttagga aacaatttat aatggcagtt cgttcattta acaatttatg tagaataaat    3780
gttataaatg cgtatgggaa atcttaaata tggatagcat aaatgatatc tgcattgcct    3840
aattcgaaat caacagcaac gaaaaaaatc ccttgtacaa cataaatagt catcgagaaa    3900
tatcaactat caaagaacag ctattcacac gttactattg agattattat tggacgagaa    3960
tcacacactc aactgtcttt ctctcttcta gaaatacagg tacaagtatg tactattctc    4020
attgttcata cttctagtca tttcatccca catattcctt ggatttctct ccaatgaatg    4080
acattctatc ttgcaaattc aacaattata ataagatata ccaaagtagc ggtatagtgg    4140
caatcaaaaa gcttctctgg tgtgcttctc gtatttattt ttattctaat gatccattaa    4200
aggtatatat ttatttcttg ttatataatc cttttgttta ttacatgggc tggatacata    4260
aaggtatttt gatttaattt tttgcttaaa ttcaatcccc cctcgttcag tgtcaactgt    4320
aatggtagga aattaccata cttttgaaga agcaaaaaaa atgaaagaaa aaaaaaatcg    4380
tatttccagg ttagacgttc cgcagaatct agaatgcggt atgcggtaca ttgttcttcg    4440
aacgtaaaag ttgcgctccc tgagatattg tacattttg ctttacaag tacaagtaca     4500 tcgtacaact atgtactact gttgatgcat ccacaacagt ttgttttgtt ttttttgtt     4560 tttttttt ctaatgattc attaccgcta tgtatacta cttgtacttg tagtaagccg       4620
ggttattggc gttcaattaa tcatagactt atgaatctgc acggtgtgcg ctgcgagtta    4680
cttttagctt atgcatgcta cttgggtgta atattgggat ctgttcggaa atcaacggat    4740
gctcaatcga tttcgacagt aattaattaa gtcatacaca agtcagcttt cttcgagcct    4800
catataagta taagtagttc aacgtattag cactgtaccc agcatctccg tatcgagaaa    4860
```

-continued

```
cacaacaaca tgccccattg gacagatcat gcggatacac aggttgtgca gtatcataca    4920
tactcgatca gacaggtcgt ctgaccatca tacaagctga acaagcgctc catacttgca    4980
cgctctctat atacacagtt aaattacata tccatagtct aacctctaac agttaatctt    5040
ctggtaagcc tcccagccag ccttctggta tcgcttggcc tcctcaatag gatctcggtt    5100
ctggccgtac agacctcggc cgacaattat gatatccgtt ccggtagaca tgacatcctc    5160
aacagttcgg tactgctgtc cgagagcgtc tcccttgtcg tcaagaccca ccccggggt    5220
cagaataagc cagtcctcag agtcgccctt aggtcggttc tgggcaatga agccaaccac    5280
aaactcgggg tcggatcggg caagctcaat ggtctgcttg gagtactcgc cagtggccag    5340
agagcccttg caagacagct cggccagcat gagcagacct ctggccagct tctcgttggg    5400
agaggggact aggaactcct tgtactggga gttctcgtag tcagagacgt cctccttctt    5460
ctgttcagag acagtttcct cggcaccagc tcgcaggcca gcaatgattc cggttccggg    5520
tacaccgtgg gcgttggtga tatcggacca ctcggcgatt cggtgacacc ggtactggtg    5580
cttgacagtg ttgccaatat ctgcgaactt tctgtcctcg aacaggaaga aaccgtgctt    5640
aagagcaagt tccttgaggg ggagcacagt gccggcgtag gtgaagtcgt caatgatgtc    5700
gatatgggtt ttgatcatgc acacataagg tccgacctta tcggcaagct caatgagctc    5760
cttggtggtg gtaacatcca gagaagcaca caggttggtt ttcttggctg ccacgagctt    5820
gagcactcga gcggcaaagg cggacttgtg gacgttagct cgagcttcgt aggagggcat    5880
tttggtggtg aagaggagac tgaaataaat ttagtctgca gaacttttta tcggaacctt    5940
atctggggca gtgaagtata tgttatggta atagttacga gttagttgaa cttatagata    6000
gactggacta tacggctatc ggtccaaatt agaaagaacg tcaatggctc tctgggcgtc    6060
gcctttgccg acaaaaatgt gatcatgatg aaagccagca atgacgttgc agctgatatt    6120
gttgtcggcc aaccgcgccg aaaacgcagc tgtcagaccc acagcctcca acgaagaatg    6180
tatcgtcaaa gtgatccaag cacactcata gttggagtcg tactccaaag gcggcaatga    6240
cgagtcagac agatactcgt cgaaaacagt gtacgcagat ctactataga ggaacattta    6300
aattgccccg gagaagacgg ccaggccgcc tagatgacaa attcaacaac tcacagctga    6360
ctttctgcca ttgccactag gggggggcct ttttatatgg ccaagccaag ctctccacgt    6420
cggttgggct gcacccaaca ataaatgggt agggttgcac caacaaaggg atgggatggg    6480
gggtagaaga tacgaggata acggggctca atggcacaaa taagaacgaa tactgccatt    6540
aagactcgtg atccagcgac tgacaccatt gcatcatcta agggcctcaa aactacctcg    6600
gaactgctgc gctgatctgg acaccacaga ggttccgagc actttaggtt gcaccaaatg    6660
tcccaccagg tgcaggcaga aaacgctgga acagcgtgta cagtttgtct taacaaaaag    6720
tgagggcgct gaggtcgagc agggtggtgt gacttgttat agcctttaga gctgcgaaag    6780
cgcgtatgga tttggctcat caggccagat tgagggtctg tggacacatg tcatgttagt    6840
gtacttcaat cgcccctgg atatagcccc gacaataggc cgtggcctca ttttttttgcc    6900
ttccgcacat ttccattgct cggtacccac accttgcttc tcctgcactt gccaaccta    6960
atactggttt acattgacca acatcttaca agcgggggc ttgtctaggg tatatataaa    7020
cagtggctct cccaatcgt tgccagtctc tttttttctt tctttcccca cagattcgaa    7080
atctaaacta cacatcacag aattccgagc cgtgagtatc cacgacaaga tcagtgtcga    7140
gacgacgcgt tttgtgtaat gacacaatcc gaaagtcgct agcaacacac actctctaca    7200
caaactaacc cagctctggt ac                                            7222
```

<210> SEQ ID NO 95
<211> LENGTH: 8256
<212> TYPE: DNA
<213> ORGANISM: Artificial Sequence
<220> FEATURE:
<223> OTHER INFORMATION: Yarrowia lipolytica expression vector
      pFBAIn-389D8

<400> SEQUENCE: 95

| | | | | | |
|---|---|---|---|---|---|
| ggccgcaagt | gtggatgggg | aagtgagtgc | ccggttctgt | gtgcacaatt | ggcaatccaa | 60 |
| gatggatgga | ttcaacacag | ggatatagcg | agctacgtgg | tggtgcgagg | atatagcaac | 120 |
| ggatatttat | gtttgacact | tgagaatgta | cgatacaagc | actgtccaag | tacaatacta | 180 |
| aacatactgt | acatactcat | actcgtaccc | gggcaacggt | ttcacttgag | tgcagtggct | 240 |
| agtgctctta | ctcgtacagt | gtgcaatact | gcgtatcata | gtctttgatg | tatatcgtat | 300 |
| tcattcatgt | tagttgcgta | cgagccgaaa | gcataaagtg | taaagcctgg | ggtgcctaat | 360 |
| gagtgagcta | actcacatta | attgcgttgc | gctcactgcc | cgctttccag | tcgggaaacc | 420 |
| tgtcgtgcca | gctgcattaa | tgaatcggcc | aacgcgcggg | gagaggcggt | ttgcgtattg | 480 |
| ggcgctcttc | cgcttcctcg | ctcactgact | cgctgcgctc | ggtcgttcgg | ctgcggcgag | 540 |
| cggtatcagc | tcactcaaag | gcggtaatac | ggttatccac | agaatcaggg | gataacgcag | 600 |
| gaaagaacat | gtgagcaaaa | ggccagcaaa | aggccaggaa | ccgtaaaaag | gccgcgttgc | 660 |
| tggcgttttt | ccataggctc | cgcccccctg | acgagcatca | caaaaatcga | cgctcaagtc | 720 |
| agaggtggcg | aaacccgaca | ggactataaa | gataccaggc | gtttccccct | ggaagctccc | 780 |
| tcgtgcgctc | tcctgttccg | accctgccgc | ttaccggata | cctgtccgcc | tttctccctt | 840 |
| cgggaagcgt | ggcgctttct | catagctcac | gctgtaggta | tctcagttcg | gtgtaggtcg | 900 |
| ttcgctccaa | gctgggctgt | gtgcacgaac | cccccgttca | gcccgaccgc | tgcgccttat | 960 |
| ccggtaacta | tcgtcttgag | tccaacccgg | taagacacga | cttatcgcca | ctggcagcag | 1020 |
| ccactggtaa | caggattagc | agagcgaggt | atgtaggcgg | tgctacagag | ttcttgaagt | 1080 |
| ggtggcctaa | ctacggctac | actagaagga | cagtatttgg | tatctgcgct | ctgctgaagc | 1140 |
| cagttacctt | cggaaaaaga | gttggtagct | cttgatccgg | caaacaaacc | accgctggta | 1200 |
| gcggtggttt | ttttgtttgc | aagcagcaga | ttacgcgcag | aaaaaaagga | tctcaagaag | 1260 |
| atcctttgat | cttttctacg | gggtctgacg | ctcagtggaa | cgaaaactca | cgttaaggga | 1320 |
| ttttggtcat | gagattatca | aaaaggatct | tcacctagat | ccttttaaat | taaaaatgaa | 1380 |
| gttttaaatc | aatctaaagt | atatatgagt | aaacttggtc | tgacagttac | caatgcttaa | 1440 |
| tcagtgaggc | acctatctca | gcgatctgtc | tatttcgttc | atccatagtt | gcctgactcc | 1500 |
| ccgtcgtgta | gataactacg | atacgggagg | gcttaccatc | tggccccagt | gctgcaatga | 1560 |
| taccgcgaga | cccacgctca | ccggctccag | atttatcagc | aataaaccag | ccagccggaa | 1620 |
| gggccgagcg | cagaagtggt | cctgcaactt | tatccgcctc | catccagtct | attaattgtt | 1680 |
| gccgggaagc | tagagtaagt | agttcgccag | ttaatagttt | gcgcaacgtt | gttgccattg | 1740 |
| ctacaggcat | cgtggtgtca | cgctcgtcgt | ttggtatggc | ttcattcagc | tccggttccc | 1800 |
| aacgatcaag | gcgagttaca | tgatccccca | tgttgtgcaa | aaaagcggtt | agctccttcg | 1860 |
| gtcctccgat | cgttgtcaga | agtaagttgg | ccgcagtgtt | atcactcatg | gttatggcag | 1920 |
| cactgcataa | ttctcttact | gtcatgccat | ccgtaagatg | cttttctgtg | actggtgagt | 1980 |
| actcaaccaa | gtcattctga | gaatagtgta | tgcggcgacc | gagttgctct | tgcccggcgt | 2040 |

```
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttcctttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct tccccgtca agctctaaat cggggctcc    2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataattaa aaaaatcgtg ttatataata    3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaacttc cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt tgatttaat ttttgctta aattcaatcc cccctcgttc agtgtcaact     4080
gtaatggtag gaaattacca tacttttgaa gaagcaaaaa aaatgaaaga aaaaaaaat    4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg ttttttttg    4320
tttttttttt ttctaatgat tcattaccgc tatgtatacc tacttgtact tgtagtaagc   4380
```

```
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccgcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgaaaaca gtgtacgcag atctactata gaggaacatt    6060
taaattgccc cggagaagac ggccaggccg cctagatgac aaattcaaca actcacagct    6120
gactttctgc cattgccact aggggggggc ctttttatat ggccaagcca agctctccac    6180
gtcggttggg ctgcacccaa caataaatgg gtagggttgc accaacaaag ggatgggatg    6240
gggggtagaa gatacgagga taacggggct caatggcaca ataagaacg aatactgcca    6300 ttaagactcg tgatccagcg actgacacca ttgcatcatc taagggcctc aaaactacct    6360
cggaactgct gcgctgatct ggacaccaca gaggttccga gcactttagg ttgcaccaaa    6420
tgtcccacca ggtgcaggca gaaaacgctg aacagcgtg tacagtttgt cttaacaaaa    6480
agtgagggcg ctgaggtcga gcagggtggt gtgacttgtt atagccttta gagctgcgaa    6540
agcgcgtatg gatttggctc atcaggccag attgagggtc tgtggacaca tgtcatgtta    6600
gtgtacttca atcgccccct ggatatagcc ccgacaatag gccgtggcct catttttttg    6660
ccttccgcac atttccattg ctcggtaccc acaccttgct tctcctgcac ttgccaacct    6720
taatactggt ttacattgac caacatctta caagcggggg gcttgtctag ggtatatata    6780
```

```
aacagtggct ctcccaatcg gttgccagtc tcttttttcc tttctttccc cacagattcg    6840
aaatctaaac tacacatcac agaattccga gccgtgagta tccacgacaa gatcagtgtc    6900
gagacgacgc gttttgtgta atgacacaat ccgaaagtcg ctagcaacac acactctcta    6960
cacaaactaa cccagctctg gtaccatggc acccaagcga gaggccttgc ccatcacgat    7020
tgatggcaca acctatgatg tgtccgcatg ggtgaaccat caccccgggg cgcagacat    7080 catggagaat tatcggaacc gagatgccac ggatgtgttc atggtcatgc actcccacga    7140
tgcgttgaac aagctgaagc gcatgcctgt gatggagccc acttcgccac gaagccccaa    7200
gactcccaac gacgaggttg ctgaggactt ccgcaagctt cgaaaggaca tgattgcaaa    7260
aggcatgttc aacgcatccc ctctcttcta cgtgtacaaa agtgcgacca cagtagccct    7320
gggcgccctg gctattctga tggtgatgca cctgcagtgg tactacatcc cagccatttt    7380
gttgggactt tgctaccagc agctggggtg gttggcacac gattactgcc accatcaggt    7440
gttctctaac cgggcgtaca acaattttgc tggacttgta ttcggcaatg tgatgcaagg    7500
atactccggg acttggtgga aggacaggca caacggccat cacgccgcca cgaacgtgca    7560
agggcacgat cccgacatcg acgacctccc ggtgttggcc tggtccccgg aggacgtcaa    7620
aaacgccggt cccacgacgc ggaagctcat caagtggcaa caatactatt tcctccccac    7680
catcgcaacc ctccgattca tctggtgctt ccagagcatt ctggcggtta tggcatacaa    7740
gacagatgca aggaatatat attaccaacg ccagtacgca aaggaggccg tggggctggc    7800
tctgcattgg attctgaaag gggtattcat gttctgttac atgcccggca tactgacggg    7860
cttggccttc ttcctcatct cggagtgcct gggcgggttt gggattgcca ttgtcgtgtt    7920
cttgaatcac tacccattgg agaaggtgga ggagtccgtg tgggacagcc acgggttttg    7980
cgcggggcag atccacacga cgatgaacat ccaacgcggg gtcatcgttg actggttctt    8040
tggaggcctg aactaccaaa tcgaacacca tctgtggccg acgctgcccc ggcatcactt    8100
gaaagctgct tcttttgagg tggagaaaat ttgccagaag cacaaattgc catacagagc    8160 acccccccatg tccgatggtg ttgctcaatt gcttggcttc ttggggaaga ttgctaagct    8220
ggcagctgtc ccagtgtaac cctaaacgta ccacgc                              8256
```

<210> SEQ ID NO 96
<211> LENGTH: 8262
<212> TYPE: DNA
<213> ORGANISM: Artificial Sequence
<220> FEATURE:
<223> OTHER INFORMATION: Yarrowia lipolytica expression vector
      pFBAIn-1594D8
<220> FEATURE:
<221> NAME/KEY: misc_feature
<222> LOCATION: (7223)..(7223)
<223> OTHER INFORMATION: n is a, c, g, or t
<220> FEATURE:
<221> NAME/KEY: misc_feature
<222> LOCATION: (7487)..(7487)
<223> OTHER INFORMATION: n is a, c, g, or t
<220> FEATURE:
<221> NAME/KEY: misc_feature
<222> LOCATION: (7751)..(7751)
<223> OTHER INFORMATION: n is a, c, g, or t

<400> SEQUENCE: 96

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac    120
ggatatttat gtttgacact tgagaatgta cgatacaagc actgtccaag tacaatacta    180
```

-continued

```
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag ccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacgacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttcctttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgcctgta gcggcgcatt aagcgcggcg ggtgtggtgg   2460
ttacgcgcag cgtgaccgct acacttgcca gcgccctagc gcccgctcct ttcgctttct   2520
```

```
tcccttcctt tctcgccacg ttcgccggct ttccccgtca agctctaaat cggggctcc   2580
ctttagggtt ccgatttagt gctttacggc acctcgaccc caaaaaactt gattagggtg  2640
atggttcacg tagtgggcca tcgccctgat agacggtttt tcgcccttg acgttggagt   2700
ccacgttctt taatagtgga ctcttgttcc aaactggaac aacactcaac cctatctcgg  2760
tctattcttt tgatttataa gggattttgc cgatttcggc ctattggtta aaaaatgagc  2820
tgatttaaca aaaatttaac gcgaatttta acaaaatatt aacgcttaca atttccattc  2880
gccattcagg ctgcgcaact gttgggaagg gcgatcggtg cgggcctctt cgctattacg  2940
ccagctggcg aaagggggat gtgctgcaag gcgattaagt tgggtaacgc cagggttttc  3000
ccagtcacga cgttgtaaaa cgacggccag tgaattgtaa tacgactcac tatagggcga  3060
attgggtacc gggccccccc tcgaggtcga tggtgtcgat aagcttgata tcgaattcat  3120
gtcacacaaa ccgatcttcg cctcaaggaa acctaattct acatccgaga gactgccgag  3180
atccagtcta cactgattaa ttttcgggcc aataatttaa aaaaatcgtg ttatataata  3240
ttatatgtat tatatatata catcatgatg atactgacag tcatgtccca ttgctaaata  3300
gacagactcc atctgccgcc tccaactgat gttctcaata tttaaggggt catctcgcat  3360
tgtttaataa taaacagact ccatctaccg cctccaaatg atgttctcaa aatatattgt  3420
atgaacttat ttttattact tagtattatt agacaactta cttgctttat gaaaaacact  3480
tcctatttag gaaacaattt ataatggcag ttcgttcatt taacaattta tgtagaataa  3540
atgttataaa tgcgtatggg aaatcttaaa tatggatagc ataaatgata tctgcattgc  3600
ctaattcgaa atcaacagca acgaaaaaaa tcccttgtac aacataaata gtcatcgaga  3660
aatatcaact atcaaagaac agctattcac acgttactat tgagattatt attggacgag  3720
aatcacacac tcaactgtct ttctctcttc tagaaataca ggtacaagta tgtactattc  3780
tcattgttca tacttctagt catttcatcc cacatattcc ttggatttct ctccaatgaa  3840
tgacattcta tcttgcaaat tcaacaatta taataagata taccaaagta gcggtatagt  3900
ggcaatcaaa aagcttctct ggtgtgcttc tcgtatttat ttttattcta atgatccatt  3960
aaaggtatat atttatttct tgttatataa tccttttgtt tattacatgg gctggataca  4020
taaaggtatt ttgatttaat ttttttgctta aattcaatcc cccctcgttc agtgtcaact  4080
gtaatggtag gaaattacca tacttttgaa gaagcaaaaa aaatgaaaga aaaaaaaaat  4140
cgtatttcca ggttagacgt tccgcagaat ctagaatgcg gtatgcggta cattgttctt  4200
cgaacgtaaa agttgcgctc cctgagatat tgtacatttt tgcttttaca agtacaagta  4260
catcgtacaa ctatgtacta ctgttgatgc atccacaaca gtttgttttg tttttttttg  4320
tttttttttt ttctaatgat tcattaccgc tatgtatacc tacttgtact tgtagtaagc  4380
cgggttattg gcgttcaatt aatcatagac ttatgaatct gcacggtgtg cgctgcgagt  4440
tactttagc ttatgcatgc tacttgggtg taatattggg atctgttcgg aaatcaacgg   4500
atgctcaatc gatttcgaca gtaattaatt aagtcataca caagtcagct ttcttcgagc  4560
ctcatataag tataagtagt tcaacgtatt agcactgtac ccagcatctc cgtatcgaga  4620
aacacaacaa catgccccat tggacagatc atgcggatac acaggttgtg cagtatcata  4680
catactcgat cagacaggtc gtctgaccat catacaagct gaacaagcgc tccatacttg  4740
cacgctctct atatacacag ttaaattaca tatccatagt ctaacctcta acagttaatc  4800
ttctggtaag cctcccagcc agccttctgg tatcgcttgg cctcctcaat aggatctcgg  4860
ttctggccgt acagacctcg gccgacaatt atgatatccg ttccggtaga catgacatcc  4920
```

```
tcaacagttc ggtactgctg tccgagagcg tctcccttgt cgtcaagacc cacccegggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcag aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgaaaaca gtgtacgcag atctactata gaggaacatt    6060
taaattgccc cggagaagac ggccaggccg cctagatgac aaaattcaaca actcacagct    6120
gactttctgc cattgccact aggggggggc cttttatat ggccaagcca agctctccac    6180
gtcggttggg ctgcacccaa caataaatgg gtagggttgc accaacaaag ggatgggatg    6240
gggggtagaa gatacgagga taacgggggct caatggcaca ataagaacg aatactgcca    6300
ttaagactcg tgatccagcg actgacacca ttgcatcatc taagggcctc aaaactacct    6360
cggaactgct gcgctgatct ggacaccaca gaggttccga gcactttagg ttgcaccaaa    6420
tgtcccacca ggtgcaggca gaaaacgctg aacagcgtg tacagttttgt cttaacaaaa    6480
agtgagggcg ctgaggtcga gcagggtggt gtgacttgtt atagccttta gagctgcgaa    6540
agcgcgtatg gatttggctc atcaggccag attgagggtc tgtggacaca tgtcatgtta    6600
gtgtacttca atcgccccct ggatatagcc ccgacaatag gccgtggcct cattttttg    6660
ccttccgcac atttccattg ctcggtaccc acaccttgct tctcctgcac ttgccaacct    6720
taatactggt ttacattgac caacatctta caagcggggg gcttgtctag ggtatatata    6780
aacagtggct ctcccaatcg gttgccagtc tcttttttcc tttctttccc cacagattcg    6840
aaatctaaac tacacatcac agaattccga gccgtgagta tccacgacaa gatcagtgtc    6900
gagacgacgc gttttgtgta atgacacaat ccgaaagtcg ctagcaacac acactctcta    6960
cacaaactaa cccagctctg gtaccatggc acctaaacgg gacgcattgc ctctgacaat    7020
tgatggcacc acgtacgacg tttccgcttg ggtaaaccat cacctggag gggctcaaat    7080
cattgaaaac taccggaacc gagatgctac cgacgtgttc atggtcatgc attcacagca    7140
ggcgctcaac aagttgaagc ggatgcctgt tatggagccc tcttcaccac ttactcccaa    7200
gagcccaagt gacgacattt ccnaggattt ccgcaagctc cgcaacagta tggttgagaa    7260
```

```
gggtatgttc aacgcgtccc ctctgtttta tgtgtacaaa tcactgacca ctgtcgccct    7320
tggcgccgtg ggtgttctca tggttatgta cctgcagtgg tactacgttt cagccatgtt    7380
tttgggactt tgctaccaac agctggggttg ggtggcgcat gactacgcgc atcaccaggt   7440
tttcacgaac cgtgattatg gcaatcttgg tgggcttttc tttggcnacg ttctccaagg    7500
atattctttg acttggtgga aggacaggca caacggccat cacgccgcca caaacgtgca    7560
aggacatgac cccgacattg ataatctccc cgttttggct tggtcgccag aggacgtcaa    7620
gaatgccgga cctggaaccc gcaatatcat caagtaccag cagtattatt tcctccctac    7680
catcgccatc cttcggttca tctggtgttt ccaaagcatt ctgggggtga tgtcatacaa    7740
gacagactcc nagaatctct attacaaacg gcagtaccgg agagaggcag ccggtctggc    7800
gctgcactgg attctgaaga gcgttttctt gttctgttac atgccaagtt tcctcactgg    7860
cctggcgttt ttccttatct cggagtgtct gggcggcttt gggatcgcga ttgtggtgtt    7920
tttgaaccac tatccgctgg ataaggttga ggaatccgtt tgggatggtc acggtttctg    7980
tgctgggcag atcctcacaa ccatgaacat ccaacgcgga ctcatcactg actggttctt    8040
tggaggtttg aattaccaga ttgagcatca tctgtggccc aaccttccaa gacaccattt    8100
gaaagcagtt tcctttgagg ttgagaaatt gtgccagaag cacaacctgc cctacagagc    8160
tccgccgatg catactggtg ttgcacaatt gcttggatat ttggggaaga ttgctcagtt    8220
ggctgctgtc ccagtataac cctggatcac cttcatcgat gc                        8262
```

<210> SEQ ID NO 97
<211> LENGTH: 8363
<212> TYPE: DNA
<213> ORGANISM: Artificial Sequence
<220> FEATURE:
<223> OTHER INFORMATION: Yarrowia lipolytica expression vector
      pFBAIn-1491D8

<400> SEQUENCE: 97

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
```

```
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg gggtctgacg ctcagtggaa cgaaaactca cgttaaggga    1320
ttttggtcat gagattatca aaaaggatct tcacctagat ccttttaaat taaaaatgaa    1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt gcgcaacgtt gttgccattg    1740
ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga atagtgtata gcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttcctttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgcctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cggggggctcc    2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt taatagtgga ctcttgttcc aaactggaac aacactcaac cctatctcgg    2760
tctattcttt tgatttataa gggatttttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaatcgtg ttatataata    3240 ttatatgtat tatatatata catcatgatg atactgacag tcatgtccca ttgctaaata    3300
gacagactcc atctgccgcc tccaactgat gttctcaata tttaagggt catctcgcat    3360 tgtttaataa taaacagact ccatctaccg cctccaaatg atgttctcaa aatatattgt    3420
```

```
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat tttttgctta aattcaatcc ccctcgttc agtgtcaact     4080
gtaatggtag gaaattacca tacttttgaa gaagcaaaaa aatgaaaga aaaaaaaat      4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg ttttttttg     4320
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tactttagc ttatgcatgc tacttgggtg taatattggg atctgttcgg aaatcaacgg     4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc cacccegggg   4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaacttt tatcggaacc     5700
ttatctgggg cagtgaagta tatgttatgg taatagttac gagttagttg aacttataga    5760
```

```
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgaaaaca gtgtacgcag atctactata gaggaacatt   6060
taaattgccc cggagaagac ggccaggccg cctagatgac aaattcaaca actcacagct   6120
gactttctgc cattgccact agggggggc cttttatat ggccaagcca agctctccac   6180
gtcggttggg ctgcacccaa caataaatgg gtagggttgc accaacaaag ggatgggatg   6240
gggggtagaa gatacgagga taacggggct caatggcaca ataagaacg aatactgcca   6300 ttaagactcg tgatccagcg actgacacca ttgcatcatc taagggcctc aaaactacct   6360
cggaactgct gcgctgatct ggacaccaca gaggttccga gcactttagg ttgcaccaaa   6420
tgtcccacca ggtgcaggca gaaaacgctg aacagcgtg tacagtttgt cttaacaaaa   6480
agtgagggcg ctgaggtcga gcagggtggt gtgacttgtt atagccttta gagctgcgaa   6540
agcgcgtatg gatttggctc atcaggccag attgagggtc tgtggacaca tgtcatgtta   6600
gtgtacttca atcgcccct ggatatagcc ccgacaatag gccgtggcct cattttttg   6660 ccttccgcac atttccattg ctcggtaccc acaccttgct tctcctgcac ttgccaacct   6720
taatactggt ttacattgac caacatctta caagcgggg gcttgtctag ggtatatata   6780
aacagtggct ctcccaatcg gttgccagtc tctttttcc tttctttccc cacagattcg   6840
aaatctaaac tacacatcac agaattccga gccgtgagta tccacgacaa gatcagtgtc   6900
gagacgacgc gttttgtgta atgacacaat ccgaaagtcg ctagcaacac acactctcta   6960
cacaaactaa cccagctctg gtaccatggc tcctaagcgg caagctctgc caatcacaat   7020
tgatggcgca acttatgatg tgtctgcttg ggtcaatcac caccctggag gagctgacat   7080
tatcgagaac tatcgcaacc gcgatgcgac cgatgtcttc atggtgatgc actctcaaga   7140
agccgtcgcc aagttgaaga gaatgcctgt tatggagcct tcctctcctg acacacctgt   7200
tgcacccaag cctaagcgtg atgagcccca ggaggatttc cgcaagttgc gggaggaatt   7260
catctccaag ggtatgttcg agacgagttt cctttggtat ttttacaaga cttcaactac   7320
cgtcggtttg atggtccttt ccatcttgat gaccgtgtac acgaattggt atttcaccgc   7380
tgctttggtt cttggcgtgt gctaccaaca gctaggctgg ttgtcccacg actattgcca   7440
tcaccaggtt ttcacaaacc gcaagattaa cgacgctttc ggtctctttt tcggtaacgt   7500
gatgcaggga tactcacaga cttggtggaa ggataggcac aatggtcacc atgccgccac   7560
caatgtggtc ggccatgacc cagatattga taacctcccc atcctggctt ggtctcccga   7620
agatgtcaag agggctactc cttcgactcg gaatctcatc aagtaccagc agtactactt   7680
cattcccacc attgcatccc ttaggttcat ctggtgcctc caatccatcg gcggcgtcat   7740
gtcctacaag agcgaggaga ggaacctgta ctacaagcgc cagtacacta aggaggcgat   7800
tggtctggcc ctccattggg tgctcaaggc cactttctat tgcagtgcca tgcctagctt   7860
tgccaccggt ttgggatgct tcttgatctc cgagctgctc ggaggatttg gcattgccat   7920
cgttgtgttt ctgaatcact atcctttgga caaggttgag gagactgtct gggatgagca   7980
cgggttcagc gccagccaga tccacgagac gttgaacatt aagcccggcc ttctcaccga   8040 ttgggtctttt ggtggtctca actaccagat tgagcaccac ttgtgcccca acatgccag   8100 gcacaaccctc acggcagctt ccctggaggt gcagaagttg tgcgccaagc acaacctgcc   8160
```

```
ctacagggcc ccagccatca tccccgggggt tcagaaattg gtcagcttct taggcgagat    8220
tgcccagctg gctgctgtcc ctgaatgatt ggtgactaag caagcgtcgg catggcgtgc    8280
gtgtgtgggg cggggttcc cgcactgtaa cccgcggtgt aacgcgcggt ggccgttcca    8340
cccaatcaaa tgacaccacc tgc                                             8363
```

<210> SEQ ID NO 98
<211> LENGTH: 419
<212> TYPE: PRT
<213> ORGANISM: Euglena gracilis

<400> SEQUENCE: 98

```
Met Lys Ser Lys Arg Gln Ala Leu Ser Pro Leu Gln Leu Met Glu Gln
 1               5                  10                  15

Thr Tyr Asp Val Val Asn Phe His Pro Gly Gly Ala Glu Ile Ile Glu
             20                  25                  30

Asn Tyr Gln Gly Arg Asp Ala Thr Asp Ala Phe Met Val Met His Phe
         35                  40                  45

Gln Glu Ala Phe Asp Lys Leu Lys Arg Met Pro Lys Ile Asn Pro Ser
 50                  55                  60

Phe Glu Leu Pro Pro Gln Ala Ala Val Asn Glu Ala Gln Glu Asp Phe
 65                  70                  75                  80

Arg Lys Leu Arg Glu Glu Leu Ile Ala Thr Gly Met Phe Asp Ala Ser
                 85                  90                  95

Pro Leu Trp Tyr Ser Tyr Lys Ile Ser Thr Thr Leu Gly Leu Gly Val
            100                 105                 110

Leu Gly Tyr Phe Leu Met Val Gln Tyr Gln Met Tyr Phe Ile Gly Ala
        115                 120                 125

Val Leu Leu Gly Met His Tyr Gln Gln Met Gly Trp Leu Ser His Asp
130                 135                 140

Ile Cys His His Gln Thr Phe Lys Asn Arg Asn Trp Asn Asn Leu Val
145                 150                 155                 160

Gly Leu Val Phe Gly Asn Gly Leu Gln Gly Phe Ser Val Thr Cys Trp
                165                 170                 175

Lys Asp Arg His Asn Ala His His Ser Ala Thr Asn Val Gln Gly His
            180                 185                 190

Asp Pro Asp Ile Asp Asn Leu Pro Pro Leu Ala Trp Ser Glu Asp Asp
        195                 200                 205

Val Thr Arg Ala Ser Pro Ile Ser Arg Lys Leu Ile Gln Phe Gln Gln
    210                 215                 220

Tyr Tyr Phe Leu Val Ile Cys Ile Leu Leu Arg Phe Ile Trp Cys Phe
225                 230                 235                 240

Gln Cys Val Leu Thr Val Arg Ser Leu Lys Asp Arg Asp Asn Gln Phe
                245                 250                 255

Tyr Arg Ser Gln Tyr Lys Lys Glu Ala Ile Gly Leu Ala Leu His Trp
            260                 265                 270

Thr Leu Lys Ala Leu Phe His Leu Phe Phe Met Pro Ser Ile Leu Thr
        275                 280                 285

Ser Leu Leu Val Phe Phe Val Ser Glu Leu Val Gly Gly Phe Gly Ile
    290                 295                 300

Ala Ile Val Val Phe Met Asn His Tyr Pro Leu Glu Lys Ile Gly Asp
305                 310                 315                 320

Pro Val Trp Asp Gly His Gly Phe Ser Val Gly Gln Ile His Glu Thr
                325                 330                 335
```

```
Met Asn Ile Arg Arg Gly Ile Ile Thr Asp Trp Phe Phe Gly Gly Leu
            340                 345                 350

Asn Tyr Gln Ile Glu His His Leu Trp Pro Thr Leu Pro Arg His Asn
        355                 360                 365

Leu Thr Ala Val Ser Tyr Gln Val Glu Gln Leu Cys Gln Lys His Asn
    370                 375                 380

Leu Pro Tyr Arg Asn Pro Leu Pro His Glu Gly Leu Val Ile Leu Leu
385                 390                 395                 400

Arg Tyr Leu Ala Val Phe Ala Arg Met Ala Glu Lys Gln Pro Ala Gly
            405                 410                 415

Lys Ala Leu

<210> SEQ ID NO 99
<211> LENGTH: 32
<212> TYPE: DNA
<213> ORGANISM: Artificial Sequence
<220> FEATURE:
<223> OTHER INFORMATION: primer 389D8-F

<400> SEQUENCE: 99
cggatcccat ggcacccaag cgagaggcct tg                               32

<210> SEQ ID NO 100
<211> LENGTH: 37
<212> TYPE: DNA
<213> ORGANISM: Artificial Sequence
<220> FEATURE:
<223> OTHER INFORMATION: primer 389D8-R

<400> SEQUENCE: 100
aagatcgcgg ccgcgtggta cgtttagggt tacactg                          37

<210> SEQ ID NO 101
<211> LENGTH: 35
<212> TYPE: DNA
<213> ORGANISM: Artificial Sequence
<220> FEATURE:
<223> OTHER INFORMATION: primer 1491D8-F

<400> SEQUENCE: 101
ggaactgcac catggctcct aagcggcaag ctctg                            35

<210> SEQ ID NO 102
<211> LENGTH: 37
<212> TYPE: DNA
<213> ORGANISM: Artificial Sequence
<220> FEATURE:
<223> OTHER INFORMATION: primer 1491D8-R

<400> SEQUENCE: 102
gcttagcgcg gccgccgcag gtggtgtcat ttgattg                          37

<210> SEQ ID NO 103
<211> LENGTH: 33
<212> TYPE: DNA
<213> ORGANISM: Artificial Sequence
<220> FEATURE:
<223> OTHER INFORMATION: primer 1594D8-F

<400> SEQUENCE: 103
cggatcccat ggcacctaaa cgggacgcat tgc                              33
```

<210> SEQ ID NO 104
<211> LENGTH: 35
<212> TYPE: DNA
<213> ORGANISM: Artificial Sequence
<220> FEATURE:
<223> OTHER INFORMATION: primer 1594D8-R

<400> SEQUENCE: 104

```
aagatcgcgg ccgcggatcg atgaaggtga tccag                                35
```

<210> SEQ ID NO 105
<211> LENGTH: 23
<212> TYPE: DNA
<213> ORGANISM: Artificial Sequence
<220> FEATURE:
<223> OTHER INFORMATION: 5' PCR primer

<400> SEQUENCE: 105

```
aagcagtggt atcaacgcag agt                                             23
```

<210> SEQ ID NO 106
<211> LENGTH: 14655
<212> TYPE: DNA
<213> ORGANISM: Artificial Sequence
<220> FEATURE:
<223> OTHER INFORMATION: plasmid pZKLeuN-29E3
<220> FEATURE:
<221> NAME/KEY: misc_feature
<222> LOCATION: (8822)..(8822)
<223> OTHER INFORMATION: n is a, c, g, or t
<220> FEATURE:
<221> NAME/KEY: misc_feature
<222> LOCATION: (8827)..(8830)
<223> OTHER INFORMATION: n is a, c, g, or t

<400> SEQUENCE: 106

```
cgattgttgt ctactaacta tcgtacgata acttcgtata gcatacatta tacgaagtta     60
tcgcgtcgac gagtatctgt ctgactcgtc attgccgcct ttggagtacg actccaacta    120
tgagtgtgct tggatcactt tgacgataca ttcttcgttg gaggctgtgg gtctgacagc    180
tgcgttttcg gcgcggttgg ccgacaacaa tatcagctgc aacgtcattg ctggctttca    240
tcatgatcac attttttgtcg gcaaaggcga cgcccagaga gccattgacg ttctttctaa    300
tttggaccga tagccgtata gtccagtcta tctataagtt caactaactc gtaactatta    360
ccataacata tacttcactg ccccagataa ggttccgata aaaagttctg cagactaaat    420
ttatttcagt ctcctcttca ccaccaaaat gccctcctac gaagctcgag ctaacgtcca    480
caagtccgcc tttgccgctc gagtgctcaa gctcgtggca gccaagaaaa ccaacctgtg    540
tgcttctctg gatgttacca ccaccaagga gctcattgag cttgccgata aggtcggacc    600
ttatgtgtgc atgatcaaaa cccatatcga catcattgac gacttcacct acgccggcac    660
tgtgctcccc ctcaaggaac ttgctcttaa gcacggtttc ttcctgttcg aggacagaaa    720
gttcgcagat attggcaaca ctgtcaagca ccagtaccgg tgtcaccgaa tcgccgagtg    780
gtccgatatc accaacgccc acggtgtacc cggaaccgga atcattgctg gcctgcgagc    840
tggtgccgag gaaactgtct ctgaacagaa gaaggaggac gtctctgact acgagaactc    900
ccagtacaag gagttcctag tcccctctcc caacgagaag ctggccagag gtctgctcat    960
gctggccgag ctgtcttgca agggctctct ggccactggc gagtactcca agcagaccat   1020
tgagcttgcc cgatccgacc ccgagtttgt ggttggcttc attgcccaga accgacctaa   1080
gggcgactct gaggactggc ttattctgac ccccggggtg ggtcttgacg acaagggaga   1140
```

```
cgctctcgga cagcagtacc gaactgttga ggatgtcatg tctaccgaa  cggatatcat   1200 aattgtcggc cgaggtctgt acggccagaa ccgagatcct attgaggagg ccaagcgata   1260
ccagaaggct ggctgggagg cttaccagaa gattaactgt tagaggttag actatggata   1320
tgtaatttaa ctgtgtatat agagagcgtg caagtatgga gcgcttgttc agcttgtatg   1380
atggtcagac gacctgtctg atcgagtatg tatgatactg cacaacctgt gtatccgcat   1440
gatctgtcca atggggcatg ttgttgtgtt tctcgatacg gagatgctgg gtacagtgct   1500
aatacgttga actacttata cttatatgag gctcgaagaa agctgacttg tgtatgactt   1560
attctcaact acatccccag tcacaatacc accactgcac taccactaca ccaaaaccat   1620
gatcaaacca cccatggact tcctggaggc agaagaactt gttatggaaa agctcaagag   1680
agagatcata acttcgtata gcatacatta tacgaagtta tcctgcaggt aaaggaattc   1740
tggagtttct gagagaaaaa ggcaagatac gtatgtaaca aagcgacgca tggtacaata   1800
ataccggagg catgtatcat agagagttag tggttcgatg atggcactgg tgcctggtat   1860
gactttatac ggctgactac atatttgtcc tcagacatac aattacagtc aagcacttac   1920
ccttggacat ctgtaggtac cccccggcca agacgatctc agcgtgtcgt atgtcggatt   1980
ggcgtagctc cctcgctcgt caattggctc ccatctactt tcttctgctt ggctacaccc   2040
agcatgtctg ctatggctcg ttttcgtgcc ttatctatcc tcccagtatt accaactcta   2100
aatgacatga tgtgattggg tctacacttt catatcagag ataaggagta gcacagttgc   2160
ataaaaagcc caactctaat cagcttcttc ctttcttgta attagtacaa aggtgattag   2220
cgaaatctgg aagcttagtt ggccctaaaa aaatcaaaaa aagcaaaaaa cgaaaaacga   2280
aaaaccacag ttttgagaac agggaggtaa cgaaggatcg tatatatata tatatatata   2340
tatacccacg atcccgagac cggcctttg  attcttccct acaaccaacc attctcacca   2400
ccctaattca caaccatgga gtctggaccc atgcctgctg gcattccctt ccctgagtac   2460
tatgacttct ttatggactg gaagactccc ctggccatcg ctgccaccta cactgctgcc   2520
gtcggtctct tcaaccccaa ggttggcaag gtctcccgag tggttgccaa gtcggctaac   2580
gcaaagcctg ccgagcgaac ccagtccgga gctgccatga ctgccttcgt ctttgtgcac   2640
aacctcattc tgtgtgtcta ctctggcatc accttctact acatgtttcc tgctatggtc   2700
aagaacttcc gaacccacac actgcacgaa gcctactgcg acacggatca gtccctctgg   2760
aacaacgcac ttggctactg gggttacctc ttctacctgt ccaagttcta cgaggtcatt   2820
gacaccatca tcatcatcct gaagggacga cggtcctcgc tgcttcagac ctaccaccat   2880
gctggagcca tgattaccat gtggtctggc atcaactacc aagccactcc catttggatc   2940
tttgtggtct tcaactcctt cattcacacc atcatgtact gttactatgc cttcacctct   3000
atcggattcc atcctcctgg caaaaagtac ctgacttcga tgcagattac tcagtttctg   3060
gtcggtatca ccattgccgt gtcctacctc ttcgttcctg ctgcatccg  aacacccggt   3120 gctcagatgg ctgtctggat caacgtcggc tacctgtttc ccttgaccta tctgttcgtg   3180
gactttgcca agcgaaccta ctccaagcga tctgccattg ccgctcagaa aaaggctcag   3240
taagcggccg cattgatgat tggaaacaca cacatgggtt atatctaggt gagagttagt   3300
tggacagtta tatattaaat cagctatgcc aacggtaact tcattcatgt caacgaggaa   3360
ccagtgactg caagtaatat agaatttgac caccttgcca ttctcttgca ctcctttact   3420
atatctcatt tatttcttat atacaaatca cttcttcttc ccagcatcga gctcggaaac   3480
ctcatgagca ataacatcgt ggatctcgtc aatagagggc tttttggact ccttgctgtt   3540
```

```
ggccaccttg tccttgctgt ctggctcatt ctgtttcaac gccttttaat taacggagta   3600
ggtctcggtg tcggaagcga cgccagatcc gtcatcctcc tttcgctctc caaagtagat   3660
acctccgacg agctctcgga caatgatgaa gtcggtgccc tcaacgtttc ggatggggga   3720
gagatcggcg agcttgggcg acagcagctg gcagggtcgc aggttggcgt acaggttcag   3780
gtcctttcgc agcttgagga gaccctgctc gggtcgcacg tcggttcgtc cgtcgggagt   3840
ggtccatacg gtgttggcag cgcctccgac agcaccgagc ataatagagt cagcctttcg   3900
gcagatgtcg agagtagcgt cggtgatggg ctcgccctcc ttctcaatgg cagctcctcc   3960
aatgagtcgg tcctcaaaca caaactcggt gccggaggcc tcagcaacag acttgagcac   4020
cttgacggcc tcgcaatca cctcggggcc acagaagtcg ccgccgagaa gaacaatctt   4080
cttggagtca gtcttggtct tcttagtttc gggttccatt gtggatgtgt gtggttgtat   4140
gtgtgatgtg gtgtgtggag tgaaaatctg tggctggcaa acgctcttgt atatatacgc   4200
acttttgccc gtgctatgtg gaagactaaa cctccgaaga ttgtgactca ggtagtgcgg   4260
tatcggctag ggacccaaac cttgtcgatg ccgatagcat gcgacgtcgg gcccaattcg   4320
ccctatagtg agtcgtatta caattcactg gccgtcgttt tacaacgtcg tgactgggaa   4380
aaccctggcg ttacccaact taatcgcctt gcagcacatc cccctttcgc cagctggcgt   4440
aatagcgaag aggcccgcac cgatcgccct tcccaacagt tgcgcagcct gaatggcgaa   4500
tggacgcgcc ctgtagcggc gcattaagcg cggcgggtgt ggtggttacg cgcagcgtga   4560
ccgctacact tgccagcgcc ctagcgcccg ctcctttcgc tttcttccct tcctttctcg   4620
ccacgttcgc cggctttccc cgtcaagctc taaatcgggg gctcccttta gggttccgat   4680
ttagtgcttt acggcacctc gaccccaaaa aacttgatta gggtgatggt tcacgtagtg   4740
ggccatcgcc ctgatagacg gttttccgcc ctttgacgtt ggagtccacg ttctttaata   4800
gtggactctt gttccaaact ggaacaacac tcaaccctat ctcggtctat tcttttgatt   4860
tataagggat tttgccgatt tcggcctatt ggttaaaaaa tgagctgatt taacaaaaat   4920
ttaacgcgaa ttttaacaaa atattaacgc ttacaatttc ctgatgcggt attttctcct   4980
tacgcatctg tgcggtattt cacaccgcat caggtggcac ttttcgggga atgtgcgcg   5040
gaacccctat ttgtttattt ttctaaatac attcaaatat gtatccgctc atgagacaat   5100
aaccctgata aatgcttcaa taatattgaa aaggaagag tatgagtatt caacatttcc   5160
gtgtcgccct tattcccttt tttgcggcat tttgccttcc tgtttttgct cacccagaaa   5220
cgctggtgaa agtaaaagat gctgaagatc agttgggtgc acgagtgggt tacatcgaac   5280
tggatctcaa cagcggtaag atccttgaga gttttcgccc cgaagaacgt tttccaatga   5340
tgagcacttt taaagttctg ctatgtggcg cggtattatc ccgtattgac gccgggcaag   5400
agcaactcgg tcgccgcata cactattctc agaatgactt ggttgagtac tcaccagtca   5460
cagaaaagca tcttacggat ggcatgacag taagagaatt atgcagtgct gccataacca   5520
tgagtgataa cactgcggcc aacttacttc tgacaacgat cggaggaccg aaggagctaa   5580
ccgcttttt gcacaacatg gggatcatg taactcgcct gatcgttgg gaaccggagc   5640
tgaatgaagc cataccaaac gacgagcgtg acaccacgat gcctgtagca atggcaacaa   5700
cgttgcgcaa actattaact ggcgaactac ttactctagc ttcccggcaa caattaatag   5760
actggatgga ggcggataaa gttgcaggac cacttctgcg ctcggccctt ccggctggct   5820
ggtttattgc tgataaatct ggagccggtg agcgtgggtc tcgcggtatc attgcagcac   5880
```

```
tggggccaga tggtaagccc tcccgtatcg tagttatcta cacgacgggg agtcaggcaa  5940
ctatggatga acgaaataga cagatcgctg agataggtgc ctcactgatt aagcattggt  6000
aactgtcaga ccaagtttac tcatatatac tttagattga tttaaaactt cattttaat   6060 ttaaaaggat ctaggtgaag atccttttg ataatctcat gaccaaaatc ccttaacgtg    6120
agttttcgtt ccactgagcg tcagaccccg tagaaaagat caaggatct tcttgagatc    6180 cttttttct gcgcgtaatc tgctgcttgc aaacaaaaaa accaccgcta ccagcggtgg    6240
tttgtttgcc ggatcaagag ctaccaactc ttttccgaa ggtaactggc ttcagcagag    6300
cgcagatacc aaatactgtt cttctagtgt agccgtagtt aggccaccac ttcaagaact   6360
ctgtagcacc gcctacatac ctcgctctgc taatcctgtt accagtggct gctgccagtg   6420
gcgataagtc gtgtcttacc gggttggact caagacgata gttaccggat aaggcgcagc   6480
ggtcgggctg aacggggggt tcgtgcacac agcccagctt ggagcgaacg acctacaccg   6540
aactgagata cctacagcgt gagctatgag aaagcgccac gcttcccgaa gggagaaagg   6600
cggacaggta tccggtaagc ggcagggtcg gaacaggaga gcgcacgagg gagcttccag   6660
ggggaaacgc ctggtatctt tatagtcctg tcgggtttcg ccacctctga cttgagcgtc   6720
gatttttgtg atgctcgtca gggggggga gcctatggaa aaacgccagc aacgcggcct   6780
ttttacggtt cctggccttt tgctggcctt ttgctcacat gttctttcct gcgttatccc   6840
ctgattctgt ggataaccgt attaccgcct ttgagtgagc tgataccgct cgccgcagcc   6900
gaacgaccga gcgcagcgag tcagtgagcg aggaagcgga agagcgccca atacgcaaac   6960
cgcctctccc cgcgcgttgg ccgattcatt aatgcagctg gcgcgcccac tgagctcgtc   7020
taacggactt gatatacaac caattaaaac aaatgaaaag aaatacagtt ctttgtatca   7080
tttgtaacaa ttaccctgta caaactaagg tattgaaatc ccacaatatt cccaaagtcc   7140
acccctttcc aaattgtcat gcctacaact catataccaa gcactaacct accaaacacc   7200
actaaaaccc cacaaaatat atcttaccga atatacagta acaagctacc accacactcg   7260
ttgggtgcag tcgccagctt aaagatatct atccacatca gccacaactc ccttccttta   7320
ataaaccgac tacacccttg gctattgagg ttatgagtga atatactgta gacaagacac   7380
tttcaagaag actgtttcca aaacgtacca ctgtcctcca ctacaaacac acccaatctg   7440
cttcttctag tcaaggttgc tacaccggta aattataaat catcatttca ttagcagggc   7500
agggcccttt ttatagagtc ttatacacta gcggaccctg ccggtagacc aacccgcagg   7560
cgcgtcagtt tgctccttcc atcaatgcgt cgtagaaacg acttactcct tcttgagcag   7620
ctccttgacc ttgttggcaa caagtctccg acctcggagg tggaggaaga gcctccgata   7680
tcggcggtag tgataccagc ctcgacggac tccttgacgg cagcctcaac agcgtcaccg   7740
gcgggcttca tgttaagaga gaacttgagc atcatggcgg cagacagaat ggtggcgtac   7800
gcaactaaca tgaatgaata cgatatacat caaagactat gatacgcagt attgcacact   7860
gtacgagtaa gagcactagc cactgcactc aagtgaaacc gttgcccggg tacgagtatg   7920
agtatgtaca gtatgtttag tattgtactt ggacagtgct tgtatcgtac attctcaagt   7980
gtcaaacata aatatccgtt gctatatcct cgcaccacca cgtagctcgc tatatccctg   8040
tgttgaatcc atccatcttg gattgccaat tgtgcacaca gaaccgggca ctcacttccc   8100
catccacact tgcggccgcg cctacttaag caacgggctt gataacagcg ggggggtgc    8160 ccacgttgtt gcggttgcgg aagaacagaa caccccttacc agcaccctcg gcaccagcgc  8220
tgggctcaac ccactggcac atacgcgcac tgcggtacat ggcgcggatg aagccacgag   8280
```

```
gaccatcctg gacatcagcc cggtagtgct tgcccatgat gggcttaatg gcctcggtgg   8340
cctcgtccgc gttgtagaag gggatgctgc tgacgtagtg gtggaggaca tgagtctcga   8400
tgatgccgtg gagaaggtgg cggccgatga agcccatctc acggtcaatg gtagcagcgg   8460
caccacggac gaagttccac tcgtcgttgg tgtagtgggg aagggtaggg tcggtgtgct   8520
ggaggaaggt gatggcaacg agccagtggt taacccagag gtagggaaca aagtaccaga   8580
tggccatgtt gtagaaaccg aacttctgaa cgaggaagta cagagcagtg gccatcagac   8640
cgataccaat atcgctgagg acgatgagct tagcgtcact gttctcgtac agagggctgc   8700
ggggatcgaa gtggttaaca ccaccgccga ggccgttatg cttgcccttg ccgcgaccct   8760
cacgctggcg ctcgtggtag ttgtggccgg taacattggt gatgaggtag ttgggccagc   8820
cnacgannnn ctcagtaaga tgagcgagct cgtgggtcat ctttccgaga cgagtagcct   8880
gctgctcgcg ggttcgggga acgaagacca tgtcacgctc catgttgcca gtggccttgt   8940
ggtgctttcg gtgggagatt tgccagctga agtaggggac aaggagggaa gagtgaagaa   9000
cccagccagt aatgtcgttg atgatgcgag aatcggagaa agcaccgtga ccgcactcat   9060
gggcaataac ccagagacca gtaccgaaaa gaccctgaag aacggtgtac acggcccaca   9120
gaccagcgcg ggcgggggtg gaggggatat attcggggt cacaaagttg taccagatgc    9180
tgaaagtggt agtcaggagg acaatgtcgc ggaggatata accgtatccc ttgagagcgg   9240
agcgcttgaa gcagtgctta gggatggcat tgtagatgtc cttgatggta aagtcgggaa   9300
cctcgaactg gttgccgtag gtgtcgagca tgacaccata ctcggacttg ggcttggcga   9360
tatcaacctc ggacatggac gagagcgatg tggaagaggc cgagtggcgg ggagagtctg   9420
aaggagagac ggcggcagac tcagaatccg tcacagtagt tgaggtgacg gtgcgtctaa   9480
gcgcagggtt ctgcttgggc agagccgaag tggacgccat ggttgatgtg tgtttaattc   9540
aagaatgaat atagaagaa gaagaagaaa aaagattcaa ttgagccggc gatgcagacc    9600
cttatataaa tgttgccttg gacagacgga gcaagcccgc ccaaacctac gttcggtata   9660
atatgttaag ctttttaaca caaaggtttg gcttgggta acctgatgtg gtgcaaaaga    9720
ccgggcgttg gcgagccatt gcgcgggcga atggggccgt gactcgtctc aaattcgagg   9780
gcgtgcctca attcgtgccc ccgtggcttt ttcccgccgt ttccgccccg tttgcaccac   9840
tgcagccgct tctttggttc ggacaccttg ctgcgagcta ggtgccttgt gctacttaaa   9900
aagtggcctc caacaccaa catgacatga gtgcgtgggc caagacacgt tggcggggtc     9960
gcagtcggct caatggcccg gaaaaaacgc tgctggagct ggttcggacg cagtccgccg  10020
cggcgtatgg atatccgcaa ggttccatag cgccattgcc ctccgtcggc gtctatcccg  10080
caacctctaa atagagcggg aatataaccc aagcttcttt ttttccttt aacacgcaca   10140
cccccaacta tcatgttgct gctgctgttt gactctactc tgtggagggg tgctcccacc  10200
caacccaacc tacaggtgga tccggcgctg tgattggctg ataagtctcc tatccggact  10260
aattctgacc aatgggacat gcgcgcagga cccaaatgcc gcaattacgt aaccccaacg  10320
aaatgcctac ccctctttgg agcccagcgg ccccaaatcc ccccaagcag cccggttcta  10380
ccggcttcca tctccaagca caagcagccc ggttctaccg gcttccatct ccaagcaccc  10440
ctttctccac accccacaaa aagacccgtg caggacatcc tactgcgtcg acatcattta  10500
aattccttca cttcaagttc attcttcatc tgcttctgtt ttactttgac aggcaaatga  10560
agacatggta cgacttgatg gaggccaaga acgccatttc accccgagac accgaagtgc  10620
```

```
ctgaaatcct ggctgccccc attgataaca tcggaaacta cggtattccg gaaagtgtat   10680
atagaacctt tccccagctt gtgtctgtgg atatggatgg tgtaatcccc tttgagtact   10740
cgtcttggct tctctccgag cagtatgagg ctctctaatc tagcgcattt aatatctcaa   10800
tgtatttata tatttatctt ctcatgcggc cgctcactga atcttttggg ctcccttgtg   10860
cttcctgacg atatacgttt gcacatagaa attcaagaac aaacacaaga ctgtgccaac   10920
ataaaagtaa ttgaagaacc agccaaacat cctcatccca tcttggcgat aacagggaat   10980
gttcctgtac ttccagacaa tgtagaaacc aacattgaat tgaatgatct gcattgatgt   11040
aatcagggat tttggcatgg ggaacttcag cttgatcaat ctggtccaat aataaccgta   11100
catgatccag tggatgaaac cattcaacag cacaaaaatc caaacagctt catttcggta   11160
attatagaac agccacatat ccatcggtgc ccccaaatga tggaagaatt gcaaccaggt   11220
cagaggcttg cccatcagtg gcaaatagaa ggagtcaata tactccagga acttgctcaa   11280
atagaacaac tgcgtggtga tcctgaagac gttgttgtca aaagccttct cgcagttgtc   11340
agacataaca ccgatggtgt acatggcata tgccattgag aggaatgatc ccaacgaata   11400
aatggacatg agaaggttgt aattggtgaa aacaaacttc atacgagact gaccttttgg   11460
accaaggggg ccaagagtga acttcaagat gacaaatgcg atggacaagt aaagcacctc   11520
acagtgactg gcatcactcc agagttgggc ataatcaact ggttgggtaa aacttcctgc   11580
ccaattgaga ctatttcatt caccacctcc atggccattg ctgtagatat gtcttgtgtg   11640
taagggggtt ggggtggttg tttgtgttct tgacttttgt gttagcaagg gaagacgggc   11700
aaaaaagtga gtgtggttgg gagggagaga cgagccttat atataatgct tgtttgtgtt   11760
tgtgcaagtg gacgccgaaa cgggcaggag ccaaactaaa caaggcagac aatgcgagct   11820
taattggatt gcctgatggg caggggttag ggctcgatca atgggggtgc gaagtgacaa   11880
aattgggaat taggttcgca agcaaggctg acaagacttt ggcccaaaca tttgtacgcg   11940
gtggacaaca ggagccaccc atcgtctgtc acgggctagc cggtcgtgcg tcctgtcagg   12000
ctccacctag gctccatgcc actccataca atcccactag tgtaccgcta ggccgctttt   12060
agctcccatc taagacccccc ccaaaacctc cactgtacag tgcactgtac tgtgtggcga   12120
tcaagggcaa gggaaaaaag cgcaaacat gcacgcatgg aatgacgtag gtaaggcgtt   12180
actagactga aaagtggcac atttcggcgt gccaaagggt cctaggtgcg tttcgcgagc   12240
tgggcgccag gccaagccgc tccaaaacgc ctctccgact ccctccagcg gcctccatat   12300
ccccatccct ctccacagca atgttgttaa gccttgcaaa cgaaaaaata gaaaggctaa   12360
taagcttcca atattgtggt gtacgctgca taacgcaaca atgagcgcca aacaacacac   12420
acacacagca cacagcagca ttaaccacga tgaacagcat gacattacag gtgggtgtgt   12480
aatcagggcc ctgattgctg gtggtgggag ccccatcat gggcagatct gcgtacactg   12540
tttaaacagt gtacgcagat ctactataga ggaacattta aattgccccg gagaagacgg   12600
ccaggccgcc tagatgacaa attcaacaac tcacagctga ctttctgcca ttgccactag   12660
gggggggcct ttttatatgg ccaagccaag ctctccacgt cggttgggct gcacccaaca   12720
ataaatgggt agggttgcac caacaaaggg atgggatggg gggtagaaga tacgaggata   12780
acggggctca atggcacaaa taagaacgaa tactgccatt aagactcgtg atccagcgac   12840
tgacaccatt gcatcatcta agggcctcaa aactacctcg gaactgctgc gctgatctgg   12900
acaccacaga ggttccgagc actttaggtt gcaccaaatg tcccaccagg tgcaggcaga   12960
aaacgctgga acagcgtgta cagtttgtct taacaaaaag tgagggcgct gaggtcgagc   13020
```

```
agggtggtgt gacttgttat agcctttaga gctgcgaaag cgcgtatgga tttggctcat    13080
caggccagat tgagggtctg tggacacatg tcatgttagt gtacttcaat cgcccctgg     13140 atatagcccc gacaataggc cgtggcctca ttttttgcc ttccgcacat ttccattgct     13200
cgatacccac accttgcttc tcctgcactt gccaacctta atactggttt acattgacca    13260
acatcttaca agcgggggc ttgtctaggg tatatataaa cagtggctct cccaatcggt     13320
tgccagtctc ttttttcctt tctttcccca cagattcgaa atctaaacta cacatcacag    13380
aattccgagc cgtgagtatc cacgacaaga tcagtgtcga gacgacgcgt tttgtgtaat    13440
gacacaatcc gaaagtcgct agcaacacac actctctaca caaactaacc cagctctggt    13500
accatggagg tcgtgaacga aatcgtctcc attggccagg aggttcttcc caaggtcgac    13560
tatgctcagc tctggtctga tgcctcgcac tgcgaggtgc tgtacctctc catcgccttc    13620
gtcatcctga agttcaccct tggtcctctc ggacccaagg gtcagtctcg aatgaagttt    13680
gtgttcacca actacaacct gctcatgtcc atctactcgc tgggctcctt cctctctatg    13740
gcctacgcca tgtacaccat tggtgtcatg tccgacaact gcgagaaggc tttcgacaac    13800
aatgtcttcc gaatcaccac tcagctgttc tacctcagca agttcctcga gtacattgac    13860
tccttctatc tgcccctcat gggcaagcct ctgacctggt tgcagttctt tcaccatctc    13920
ggagctccta tggacatgtg gctgttctac aactaccgaa cgaagccgt ttggatcttt     13980 gtgctgctca acggcttcat tcactggatc atgtacggct actattggac ccgactgatc    14040
aagctcaagt tccctatgcc caagtcctg attacttcta tgcagatcat tcagttcaac     14100
gttggcttct acatcgtctg gaagtaccgg aacattccct gctaccgaca agatggaatg    14160
agaatgtttg gctggttttt caactacttc tacgttggta ctgtcctgtg tctgttcctc    14220
aacttctacg tgcagaccta catcgtccga aagcacaagg gagccaaaaa gattcagtga    14280
gcggccgcat gtacatacaa gattatttat agaaatgaat cgcgatcgaa caaagagtac    14340
gagtgtacga gtagggatg atgataaaag tggaagaagt tccgcatctt tggatttatc    14400
aacgtgtagg acgatacttc ctgtaaaaat gcaatgtctt taccataggt tctgctgtag    14460
atgttattaa ctaccattaa catgtctact tgtacagttg cagaccagtt ggagtataga    14520
atggtacact taccaaaaag tgttgatggt tgtaactacg atatataaaa ctgttgacgg    14580
gatccccgct gatatgccta aggaacaatc aaagaggaag atattaattc agaatgctag    14640
tatacagtta gggat                                                     14655
```

<210> SEQ ID NO 107
<211> LENGTH: 777
<212> TYPE: DNA
<213> ORGANISM: Artificial Sequence
<220> FEATURE:
<223> OTHER INFORMATION: synthetic delta-9 elongase (initially from
      Euglena gracilis) codon-optimized for Yarrowia lipolytica; U.S.
      Patent Application No. 60/739989, filed 11/23/2005

<400> SEQUENCE: 107

```
atggaggtcg tgaacgaaat cgtctccatt ggccaggagg ttcttcccaa ggtcgactat      60
gctcagctct ggtctgatgc ctcgcactgc gaggtgctgt acctctccat cgccttcgtc     120
atcctgaagt tcacccttgg tcctctcgga cccaagggtc agtctcgaat gaagtttgtg     180
ttcaccaact acaacctgct catgtccatc tactcgctgg gctccttcct ctctatggcc     240
tacgccatgt acaccattgg tgtcatgtcc gacaactgcg agaaggcttt cgacaacaat     300
```

```
gtcttccgaa tcaccactca gctgttctac ctcagcaagt tcctcgagta cattgactcc    360
ttctatctgc ccctcatggg caagcctctg acctggttgc agttctttca ccatctcgga    420
gctcctatgg acatgtggct gttctacaac taccgaaacg aagccgtttg gatctttgtg    480
ctgctcaacg gcttcattca ctggatcatg tacggctact attggacccg actgatcaag    540
ctcaagttcc ctatgcccaa gtccctgatt acttctatgc agatcattca gttcaacgtt    600
ggcttctaca tcgtctggaa gtaccggaac attcctgct accgacaaga tggaatgaga     660
atgtttggct ggttttcaa ctacttctac gttggtactg tcctgtgtct gttcctcaac     720
ttctacgtgc agacctacat cgtccgaaag cacaagggag ccaaaaagat tcagtga       777
```

<210> SEQ ID NO 108
<211> LENGTH: 34
<212> TYPE: DNA
<213> ORGANISM: Escherichia coli

<400> SEQUENCE: 108

```
ataacttcgt ataatgtatg ctatacgaag ttat                                34
```

<210> SEQ ID NO 109
<211> LENGTH: 828
<212> TYPE: DNA
<213> ORGANISM: Artificial Sequence
<220> FEATURE:
<223> OTHER INFORMATION: synthetic C16/18 elongase (initally from M.
      alpina) codon-optimized for Yarrowia lipolytica; see also U.S.
      Patent Application No. 11/253882, filed October 19, 2005

<400> SEQUENCE: 109

```
atggagtctg gacccatgcc tgctggcatt cccttccctg agtactatga cttctttatg    60
gactggaaga ctcccctggc catcgctgcc acctacactg ctgccgtcgg tctcttcaac    120
cccaaggttg gcaaggtctc ccgagtggtt gccaagtcgg ctaacgcaaa gcctgccgag    180
cgaacccagt ccggagctgc catgactgcc ttcgtctttg tgcacaacct cattctgtgt    240
gtctactctg gcatcacctt ctactacatg tttcctgcta tggtcaagaa cttccgaacc    300
cacacactgc acgaagccta ctgcgacacg gatcagtccc tctggaacaa cgcacttggc    360
tactggggtt acctcttcta cctgtccaag ttctacgagg tcattgacac catcatcatc    420
atcctgaagg gacgacggtc ctcgctgctt cagacctacc accatgctgg agccatgatt    480
accatgtggt ctggcatcaa ctaccaagcc actcccattt ggatctttgt ggtcttcaac    540
tccttcattc acaccatcat gtactgttac tatgccttca cctctatcgg attccatcct    600
cctggcaaaa agtacctgac ttcgatgcag attactcagt ttctggtcgg tatcaccatt    660
gccgtgtcct acctcttcgt tcctggctgc atccgaacac ccggtgctca gatggctgtc    720
tggatcaacg tcggctacct gttttcccttg acctatctgt tcgtggactt gccaagcga    780 acctactcca agcgatctgc cattgccgct cagaaaaagg tcagtaa                   828
```

<210> SEQ ID NO 110
<211> LENGTH: 792
<212> TYPE: DNA
<213> ORGANISM: Artificial Sequence
<220> FEATURE:
<223> OTHER INFORMATION: IgD9e: synthetic delta-9 elongase (initally
      from Isochrysis galbana) codon-optimized for Yarrowia lipolytica

<400> SEQUENCE: 110

```
atggctctgg ccaacgacgc tggcgagcga atctgggctg ccgtcaccga tcccgaaatc    60
```

```
ctcattggca ccttctccta cctgctcctg aagcctctcc tgcgaaactc tggtctcgtg    120
gacgagaaga aaggagccta ccgaacctcc atgatctggt acaacgtcct cctggctctc    180
ttctctgccc tgtccttcta cgtgactgcc accgctctcg gctgggacta cggtactgga    240
gcctggctgc gaagacagac cggtgatact ccccagcctc tctttcagtg tccctctcct    300
gtctgggact ccaagctgtt cacctggact gccaaggcct tctactattc taagtacgtg    360
gagtacctcg acaccgcttg gctggtcctc aagggcaagc gagtgtcctt tctgcaggcc    420
ttccatcact ttggagctcc ctgggacgtc tacctcggca ttcgactgca caacgagggt    480
gtgtggatct tcatgttctt taactcgttc attcacacca tcatgtacac ctactatgga    540
ctgactgccg ctggctacaa gttcaaggcc aagcctctga tcactgccat gcagatttgc    600
cagttcgtcg gtggctttct cctggtctgg gactacatca cgttccctg cttcaactct    660 gacaagggca gctgttctc ctgggctttc aactacgcct acgtcggatc tgtctttctc    720
ctgttctgtc acttctttta ccaggacaac ctggccacca gaaatccgc taaggctggt    780 aagcagcttt ag                                                         792

<210> SEQ ID NO 111
<211> LENGTH: 8
<212> TYPE: DNA
<213> ORGANISM: Artificial Sequence
<220> FEATURE:
<223> OTHER INFORMATION: GenomeWalker adaptor-2
<220> FEATURE:
<221> NAME/KEY: misc_feature
<222> LOCATION: (1)..(1)
<223> OTHER INFORMATION: 5' end is associated with a -PO4 group
<220> FEATURE:
<221> NAME/KEY: misc_feature
<222> LOCATION: (8)..(8)
<223> OTHER INFORMATION: 3' end is associated with a -NH2 group

<400> SEQUENCE: 111 accagccc                                                              8

<210> SEQ ID NO 112
<211> LENGTH: 416
<212> TYPE: PRT
<213> ORGANISM: Euglena gracilis

<400> SEQUENCE: 112

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
                20                  25                  30

Ile Glu Asn Tyr Gln Gly Arg Asp Ala Thr Asp Ala Phe Met Val Met
            35                  40                  45

His Ser Gln Glu Ala Phe Asp Lys Leu Lys Arg Met Pro Lys Ile Asn
        50                  55                  60

Pro Ser Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
```

|     |     |     |     |     |     |     |     |     |     |     |     |     |     |     |     |
|-----|-----|-----|-----|-----|-----|-----|-----|-----|-----|-----|-----|-----|-----|-----|-----|
|     |     |     |     | 130 |     |     |     |     | 135 |     |     |     |     | 140 |     |
| His | Asp | Ile | Cys | His | His | Gln | Thr | Phe | Lys | Asn | Arg | Asn | Trp | Asn | Asn |
| 145 |     |     |     |     | 150 |     |     |     |     | 155 |     |     |     |     | 160 |
| Leu | Val | Gly | Leu | Val | Phe | Gly | Asn | Gly | Leu | Gln | Gly | Phe | Ser | Val | Thr |
|     |     |     |     | 165 |     |     |     |     | 170 |     |     |     |     | 175 |     |
| Trp | Trp | Lys | Asp | Arg | His | Asn | Ala | His | His | Ser | Ala | Thr | Asn | Val | Gln |
|     |     |     | 180 |     |     |     |     | 185 |     |     |     |     | 190 |     |     |
| Gly | His | Asp | Pro | Asp | Ile | Asp | Asn | Leu | Pro | Leu | Leu | Ala | Trp | Ser | Glu |
|     |     | 195 |     |     |     |     | 200 |     |     |     |     | 205 |     |     |     |
| Asp | Asp | Val | Thr | Arg | Ala | Ser | Pro | Ile | Ser | Arg | Lys | Leu | Ile | Gln | Phe |
| 210 |     |     |     |     | 215 |     |     |     |     | 220 |     |     |     |     |     |
| Gln | Gln | Tyr | Tyr | Phe | Leu | Val | Ile | Cys | Ile | Leu | Leu | Arg | Phe | Ile | Trp |
| 225 |     |     |     |     | 230 |     |     |     |     | 235 |     |     |     |     | 240 |
| Cys | Phe | Gln | Ser | Val | Leu | Thr | Val | Arg | Ser | Leu | Lys | Asp | Arg | Asp | Asn |
|     |     |     |     | 245 |     |     |     |     | 250 |     |     |     |     | 255 |     |
| Gln | Phe | Tyr | Arg | Ser | Gln | Tyr | Lys | Lys | Glu | Ala | Ile | Gly | Leu | Ala | Leu |
|     |     |     | 260 |     |     |     |     | 265 |     |     |     |     | 270 |     |     |
| His | Trp | Thr | Leu | Lys | Thr | Leu | Phe | His | Leu | Phe | Phe | Met | Pro | Ser | Ile |
|     |     | 275 |     |     |     |     | 280 |     |     |     |     | 285 |     |     |     |
| Leu | Thr | Ser | Leu | Leu | Val | Phe | Phe | Val | Ser | Glu | Leu | Val | Gly | Gly | Phe |
|     | 290 |     |     |     |     | 295 |     |     |     |     | 300 |     |     |     |     |
| Gly | Ile | Ala | Ile | Val | Val | Phe | Met | Asn | His | Tyr | Pro | Leu | Glu | Lys | Ile |
| 305 |     |     |     |     | 310 |     |     |     |     | 315 |     |     |     |     | 320 |
| Gly | Asp | Ser | Val | Trp | Asp | Gly | His | Gly | Phe | Ser | Val | Gly | Gln | Ile | His |
|     |     |     |     | 325 |     |     |     |     | 330 |     |     |     |     | 335 |     |
| Glu | Thr | Met | Asn | Ile | Arg | Arg | Gly | Ile | Ile | Thr | Asp | Trp | Phe | Phe | Gly |
|     |     |     | 340 |     |     |     |     | 345 |     |     |     |     | 350 |     |     |
| Gly | Leu | Asn | Tyr | Gln | Ile | Glu | His | His | Leu | Trp | Pro | Thr | Leu | Pro | Arg |
|     |     | 355 |     |     |     |     | 360 |     |     |     |     | 365 |     |     |     |
| His | Asn | Leu | Thr | Ala | Val | Ser | Tyr | Gln | Val | Glu | Gln | Leu | Cys | Gln | Lys |
|     | 370 |     |     |     |     | 375 |     |     |     |     | 380 |     |     |     |     |
| His | Asn | Leu | Pro | Tyr | Arg | Asn | Pro | Leu | Pro | His | Glu | Gly | Leu | Val | Ile |
| 385 |     |     |     |     | 390 |     |     |     |     | 395 |     |     |     |     | 400 |
| Leu | Leu | Arg | Tyr | Leu | Ala | Val | Phe | Ala | Arg | Met | Ala | Glu | Lys | Gln | Pro |
|     |     |     |     | 405 |     |     |     |     | 410 |     |     |     |     | 415 |     |

<210> SEQ ID NO 113
<211> LENGTH: 3983
<212> TYPE: DNA
<213> ORGANISM: Artificial Sequence
<220> FEATURE:
<223> OTHER INFORMATION: pKR132

<400> SEQUENCE: 113

| ctagagtcga cctgcaggca tgcaagcttg gcgtaatcat ggtcatagct gtttcctgtg | 60 |
| tgaaattgtt atccgctcac aattccacac aacatacgag ccggaagcat aaagtgtaaa | 120 |
| gcctggggtg cctaatgagt gagctaactc acattaattg cgttgcgctc actgcccgct | 180 |
| ttccagtcgg gaaacctgtc gtgccagctg cattaatgaa tcggccaacg cgcggggaga | 240 |
| ggcggtttgc gtattgggcg ctcttccgct tcctcgctca ctgactcgct gcgctcggtc | 300 |
| gttcggctgc ggcgagcggt atcagctcac tcaaaggcgg taatacggtt atccacagaa | 360 |
| tcagggggata acgcaggaaa gaacatgtga gcaaaaggcc agcaaaaggc caggaaccgt | 420 |
| aaaaaggccg cgttgctggc gttttttccat aggctccgcc cccctgacga gcatcacaaa | 480 |

```
aatcgacgct caagtcagag gtggcgaaac ccgacaggac tataaagata ccaggcgttt    540 cccccctggaa gctccctcgt gcgctctcct gttccgaccc tgccgcttac cggatacctg    600
tccgcctttc tcccttcggg aagcgtggcg ctttctcata gctcacgctg taggtatctc    660
agttcggtgt aggtcgttcg ctccaagctg ggctgtgtgc acgaaccccc cgttcagccc    720
gaccgctgcg ccttatccgg taactatcgt cttgagtcca acccgtaag acacgactta     780 tcgccactgg cagcagccac tggtaacagg attagcagag cgaggtatgt aggcggtgct    840
acagagttct tgaagtggtg gcctaactac ggctacacta aaggacagt atttggtatc     900 tgcgctctgc tgaagccagt taccttcgga aaaagagttg gtagctcttg atccggcaaa    960
caaaccaccg ctggtagcgg tggttttttt gtttgcaagc agcagattac gcgcagaaaa   1020
aaaggatctc aagaagatcc tttgatcttt tctacgggt ctgacgctca gtggaacgaa    1080
aactcacgtt aagggatttt ggtcatgaga ttatcaaaaa ggatcttcac ctagatcctt   1140
ttaaattaaa aatgaagttt taaatcaatc taaagtatat atgagtaaac ttggtctgac   1200
agttaccaat gcttaatcag tgaggcacct atctcagcga tctgtctatt tcgttcatcc   1260
atagttgcct gactccccgt cgtgtagata actacgatac ggggggcttt accatctggc   1320
cccagtgctg caatgatacc gcgagaccca cgctcaccgg ctccagattt atcagcaata   1380
aaccagccag ccggaagggc cgagcgcaga agtggtcctg caactttatc cgcctccatc   1440
cagtctatta attgttgccg ggaagctaga gtaagtagtt cgccagttaa tagtttgcgc   1500
aacgttgttg ccattgctac aggcatcgtg gtgtcacgct cgtcgtttgg tatggcttca   1560
ttcagctccg gttcccaacg atcaaggcga gttacatgat cccccatgtt gtgcaaaaaa   1620
gcggttagct ccttcggtcc tccgatcgtt gtcagaagta agttggccgc agtgttatca   1680
ctcatggtta tggcagcact gcataattct cttactgtca tgccatccgt aagatgcttt   1740
tctgtgactg gtgagtactc aaccaagtca ttctgagaat agtgtatgcg gcgaccgagt   1800
tgctcttgcc cggcgtcaat acgggataat accgcgccac atagcagaac tttaaaagtg   1860
ctcatcattg gaaaacgttc ttcggggcga aaactctcaa ggatcttacc gctgttgaga   1920
tccagttcga tgtaacccac tcgtgcaccc aactgatctt cagcatcttt tactttcacc   1980
agcgtttctg ggtgagcaaa aacaggaagg caaaatgccg caaaaaaggg aataagggcg   2040
acacggaaat gttgaatact catactcttc cttttcaat attattgaag catttatcag   2100
ggttattgtc tcatgagcgg atacatattt gaatgtattt agaaaaataa acaaataggg   2160
gttccgcgca catttccccg aaaagtgcca cctgacgtct aagaaaccat tattatcatg   2220
acattaacct ataaaaatag gcgtatcacg aggccctttc gtctcgcgcg tttcggtgat   2280
gacggtgaaa acctctgaca catgcagctc ccggagacgg tcacagcttg tctgtaagcg   2340
gatgccggga gcagacaagc ccgtcagggc gcgtcagcgg gtgttggcgg gtgtcggggc   2400
tggcttaact atgcggcatc agagcagatt gtactgagag tgcaccatat gcggtgtgaa   2460
ataccgcaca gatgcgtaag gagaaaatac cgcatcaggc gccattcgcc attcaggctg   2520
cgcaactgtt gggaagggcg atcggtgcgg gcctcttcgc tattacgcca gctggcgaaa   2580
gggggatgtg ctgcaaggcg attaagttgg gtaacgccag gttttccca gtcacgacgt    2640 tgtaaaacga cggccagtga attcgagctc ggtacccggg gatcctctag acctgcaggc   2700
caactgcgtt tggggctcca gattaaacga cgccgtttcg ttcctttcgc ttcacggctt   2760
aacgatgtcg tttctgtctg tgcccaaaaa ataaaggcat tgttatttg caccagatat    2820 ttactaagtg caccctagtt tgacaagtag gcgataatta caaatagatg cggtgcaaat   2880
```

```
aataaattttt gaaggaaata attacaaaag aacagaactt atatttactt tattttaaaa    2940
aactaaaatg aaagaacaaa aaaagtaaaa aatacaaaaa atgtgcttta accactttca    3000
ttatttgtta cagaaagtat gattctactc aaattgatct gttgtatctg gtgctgcctt    3060
gtcacactgg cgatttcaat cccctaaaga tatggtgcaa actgcgaagt gatcaatatc    3120
tgctcggtta atttagatta attaataata ttcaacgtga tgtaccaaaa aaagacaatt    3180
ttttgctcca ttgacaaatt aaacctcatc aaggtaattt ccaaacctat aagcaaaaaa    3240
atttcacatt aattggcccg caatcctatt agtcttatta tactagagta ggaaaaaaaa    3300
caattacaca acttgtctta ttattctcta tgctaatgaa tattttccc ttttgttaga    3360 aatcagtgtt tcctaattta ttgagtatta attccactca ccgcatatat ttaccgttga    3420
ataagaaaat tttacacata attctttta agataaataa ttttttata ctagatctta    3480 tatgattacg tgaagccaag tgggttatac taatgatata taatgtttga tagtaatcag    3540
tttataaacc aaatgcatgg aaatgttacg tggaagcacg taaattaaca agcattgaag    3600
caaatgcagc caccgcacca aaaccacccc acttcacttc cacgtaccat attccatgca    3660
actacaacac cctaaaactt caataaatgc ccccaccttc acttcacttc acccatcaat    3720
agcaagcggc cgcgaagtta aaagcaatgt tgtcacttgt cgtactaaca catgatgtga    3780
tagtttatgc tagctagcta aacataagc tgtctctgag tgtgttgtat attaataaag    3840
atcatcactg gtgaatggtg atcgtgtacg taccctactt agtaggcaat ggaagcactt    3900
agagtgtgct ttgtgcatgg ccttgcctct gttttgagac ttttgtaatg ttttcgagtt    3960
taaatctttg cctttgcgta cgt                                           3983

<210> SEQ ID NO 114
<211> LENGTH: 4771
<212> TYPE: DNA
<213> ORGANISM: Artificial Sequence
<220> FEATURE:
<223> OTHER INFORMATION: pKR953

<400> SEQUENCE: 114
ggccgcgaag ttaaaagcaa tgttgtcact tgtcgtacta acacatgatg tgatagttta     60
tgctagctag ctataacata agctgtctct gagtgtgttg tatattaata agatcatca    120 ctggtgaatg gtgatcgtgt acgtacccta cttagtaggc aatggaagca cttagagtgt    180
gctttgtgca tggccttgcc tctgttttga gacttttgta atgttttcga gtttaaatct    240
ttgcctttgc gtacgtctag agtcgacctg caggcatgca agcttggcgt aatcatggtc    300
atagctgttt cctgtgtgaa attgttatcc gctcacaatt ccacacaaca tacgagccgg    360
aagcataaag tgtaaagcct ggggtgccta atgagtgagc taactcacat taattgcgtt    420
gcgctcactg cccgctttcc agtcgggaaa cctgtcgtgc cagctgcatt aatgaatcgg    480
ccaacgcgcg gggagaggcg gtttgcgtat tgggcgctct tccgcttcct cgctcactga    540
ctcgctgcgc tcggtcgttc ggctgcggcg agcggtatca gctcactcaa aggcggtaat    600
acggttatcc acagaatcag gggataacgc aggaaagaac atgtgagcaa aaggccagca    660
aaaggccagg aaccgtaaaa aggccgcgtt gctggcgttt ttccataggc tccgcccccc    720
tgacgagcat cacaaaaatc gacgctcaag tcagaggtgg cgaaacccga caggactata    780
aagataccag gcgtttcccc ctggaagctc cctcgtgcgc tctcctgttc cgaccctgcc    840
gcttaccgga tacctgtccg cctttctccc ttcgggaagc gtggcgcttt ctcatagctc    900
```

```
acgctgtagg tatctcagtt cggtgtaggt cgttcgctcc aagctgggct gtgtgcacga    960
accccccgtt cagcccgacc gctgcgcctt atccggtaac tatcgtcttg agtccaaccc   1020
ggtaagacac gacttatcgc cactggcagc agccactggt aacaggatta gcagagcgag   1080
gtatgtaggc ggtgctacag agttcttgaa gtggtggcct aactacggct acactagaag   1140
gacagtattt ggtatctgcg ctctgctgaa gccagttacc ttcggaaaaa gagttggtag   1200
ctcttgatcc ggcaaacaaa ccaccgctgg tagcggtggt ttttttgttt gcaagcagca   1260
gattacgcgc agaaaaaaag gatctcaaga agatcctttg atctttccta cggggtctga   1320
cgctcagtgg aacgaaaact cacgttaagg gattttggtc atgagattat caaaaaggat   1380
cttcacctag atcctttttaa attaaaaatg aagttttaaa tcaatctaaa gtatatatga   1440
gtaaacttgg tctgacagtt accaatgctt aatcagtgag gcacctatct cagcgatctg   1500
tctatttcgt tcatccatag ttgcctgact ccccgtcgtg tagataacta cgatacggga   1560
gggcttacca tctggcccca gtgctgcaat gataccgcga acccacgct caccggctcc   1620
agatttatca gcaataaacc agccagccgg aagggccgag cgcagaagtg gtcctgcaac   1680
tttatccgcc tccatccagt ctattaattg ttgccgggaa gctagagtaa gtagttcgcc   1740
agttaatagt ttgcgcaacg ttgttgccat tgctacaggc atcgtggtgt cacgctcgtc   1800
gtttggtatg gcttcattca gctccggttc ccaacgatca aggcgagtta catgatcccc   1860
catgttgtgc aaaaaagcgg ttagctcctt cggtcctccg atcgttgtca gaagtaagtt   1920
ggccgcagtg ttatcactca tggttatggc agcactgcat aattctctta ctgtcatgcc   1980
atccgtaaga tgcttttctg tgactggtga gtactcaacc aagtcattct gagaatagtg   2040
tatgcggcga ccgagttgct cttgcccggc gtcaatacgg gataataccg cgccacatag   2100
cagaacttta aaagtgctca tcattggaaa acgttcttcg gggcgaaaac tctcaaggat   2160
cttaccgctg ttgagatcca gttcgatgta acccactcgt gcacccaact gatcttcagc   2220
atcttttact ttcaccagcg tttctgggtg agcaaaaaca ggaaggcaaa atgccgcaaa   2280
aaagggaata agggcgacac ggaaatgttg aatactcata ctcttccttt ttcaatatta   2340
ttgaagcatt tatcagggtt attgtctcat gagcggatac atatttgaat gtatttagaa   2400
aaataaacaa ataggggttc gcgcacatt tccccgaaaa gtgccacctg acgtctaaga   2460
aaccattatt atcatgacat taacctataa aaataggcgt atcacgaggc cctttcgtct   2520
cgcgcgtttc ggtgatgacg gtgaaaacct ctgacacatg cagctcccgg agacggtcac   2580
agcttgtctg taagcggatg ccgggagcag acaagcccgt cagggcgcgt cagcgggtgt   2640
tggcgggtgt cggggctggc ttaactatgc ggcatcagag cagattgtac tgagagtgca   2700
ccatatgcgg tgtgaaatac cgcacagatg cgtaaggaga aaataccgca tcaggcgcca   2760
ttcgccattc aggctgcgca actgttggga agggcgatcg gtgcgggcct cttcgctatt   2820
acgccagctg gcgaaagggg gatgtgctgc aaggcgatta agttgggtaa cgccaggggt   2880
ttcccagtca cgacgttgta aaacgacggc cagtgaattc gagctcggta cccggggatc   2940
ctctagacct gcaggccaac tgcgtttggg gctccagatt aaacgacgcc gtttcgttcc   3000
tttcgcttca cggcttaacg atgtcgtttc tgtctgtgcc caaaaaataa aggcatttgt   3060
tatttgcacc agatatttac taagtgcacc ctagtttgac aagtaggcga taattacaaa   3120
tagatgcggt gcaaataata aattttgaag gaaataatta caaagaacaa gaacttatat   3180
ttactttatt ttaaaaaact aaaatgaaag aacaaaaaaa gtaaaaaata caaaaaatgt   3240
gctttaaccca ctttcattat ttgttacaga aagtatgatt ctactcaaat tgatctgttg   3300
```

```
tatctggtgc tgccttgtca cactggcgat ttcaatcccc taaagatatg gtgcaaactg    3360
cgaagtgatc aatatctgct cggttaattt agattaatta ataatattca acgtgatgta    3420
ccaaaaaaag acaattttt gctccattga caaattaaac ctcatcaagg taatttccaa     3480
acctataagc aaaaaaattt cacattaatt ggcccgcaat cctattagtc ttattatact    3540
agagtaggaa aaaaacaat tacacaactt gtcttattat tctctatgct aatgaatatt     3600 tttcccttt gttagaaatc agtgtttcct aatttattga gtattaattc cactcaccgc     3660
atatatttac cgttgaataa gaaaatttta cacataattc tttttaagat aaataatttt    3720
tttatactag atcttatatg attacgtgaa gccaagtggg ttatactaat gatatataat    3780
gtttgatagt aatcagttta taaccaaat gcatggaaat gttacgtgga agcacgtaaa     3840
ttaacaagca ttgaagcaaa tgcagccacc gcaccaaaac caccccactt cacttccacg    3900
taccatattc catgcaacta caacaccta aaacttcaat aaatgccccc accttcactt     3960
cacttcaccc atcaatagca agcggccgca ccatggaggt ggtgaatgaa atagtctcaa    4020
ttgggcagga agttttaccc aaagttgatt atgcccaact ctggagtgat gccagtcact    4080
gtgaggtgct ttacttgtcc atcgcatttg tcatcttgaa gttcactctt ggccccttg     4140 gtccaaaagg tcagtctcgt atgaagtttg ttttcaccaa ttacaacctt ctcatgtcca    4200
tttattcgtt gggatcattc ctctcaatgg catatgccat gtacaccatc ggtgttatgt    4260
ctgacaactg cgagaaggct tttgacaaca acgtcttcag gatcaccacg cagttgttct    4320
atttgagcaa gttcctggag tatattgact ccttctattt gccactgatg ggcaagcctc    4380
tgacctggtt gcaattcttc catcatttgg gggcaccgat ggatatgtgg ctgttctata    4440
attaccgaaa tgaagctgtt tggattttg tgctgttgaa tggtttcatc cactggatca    4500
tgtacggtta ttattggacc agattgatca agctgaagtt ccccatgcca aaatccctga    4560
ttacatcaat gcagatcatt caattcaatg ttggtttcta cattgtctgg aagtacagga    4620
acattccctg ttatcgccaa gatgggatga ggatgtttgg ctggttcttc aattactttt    4680
atgttggcac agtcttgtgt ttgttcttga atttctatgt gcaaacgtat atcgtcagga    4740
agcacaaggg agccaaaaag attcagtgag c                                   4771
```

<210> SEQ ID NO 115
<211> LENGTH: 5492
<212> TYPE: DNA
<213> ORGANISM: Artificial Sequence
<220> FEATURE:
<223> OTHER INFORMATION: pKR287

<400> SEQUENCE: 115

```
ggccgcattt cgcaccaaat caatgaaagt aataatgaaa agtctgaata agaatactta      60
ggcttagatg cctttgttac ttgtgtaaaa taacttgagt catgtacctt tggcggaaac     120
agaataaata aaaggtgaaa ttccaatgct ctatgtataa gttagtaata cttaatgtgt     180
tctacggttg tttcaatatc atcaaactct aattgaaact ttagaaccac aaatctcaat    240 ctttttcttaa tgaaatgaaa atcttaatt gtaccatgtt tatgttaaac accttacaat     300
tggttggaga ggaggaccaa ccgatgggac aacattggga gaaagagatt caatggagat    360
ttggatagga gaacaacatt ctttttcact tcaatacaag atgagtgcaa cactaaggat    420
atgtatgaga ctttcagaag ctacgacaac atagatgagt gaggtggtga ttcctagcaa     480
gaaagacatt agaggaagcc aaaatcgaac aaggaagaca tcaagggcaa gagacaggac    540
```

```
catccatctc aggaaaagga gctttgggat agtccgagaa gttgtacaag aaattttttg    600
gagggtgagt gatgcattgc tggtgacttt aactcaatca aaattgagaa agaaagaaaa    660
gggaggggc tcacatgtga atagaaggga acgggagaa ttttacagtt ttgatctaat     720
gggcatccca gctagtggta acatattcac catgtttaac cttcacgtac gtctagagga    780
tccccgggta ccgagctcga attcactggc cgtcgtttta caacgtcgtg actgggaaaa    840
ccctggcgtt acccaactta atcgccttgc agcacatccc cctttcgcca gctggcgtaa    900
tagcgaagag gcccgcaccg atcgcccttc ccaacagttg cgcagcctga atggcgaatg    960
gcgcctgatg cggtattttc tccttacgca tctgtgcggt atttcacacc gcatatggtg    1020
cactctcagt acaatctgct ctgatgccgc atagttaagc cagccccgac acccgccaac    1080
acccgctgac gcgccctgac gggcttgtct gctcccggca tccgcttaca gacaagctgt    1140
gaccgtctcc gggagctgca tgtgtcagag gttttcaccg tcatcaccga aacgcgcgag    1200
acgaaagggc ctcgtgatac gcctattttt ataggttaat gtcatgataa taatggtttc    1260
ttagacgtca ggtggcactt ttcggggaaa tgtgcgcgga acccctattt gtttattttt    1320
ctaaatacat tcaaatatgt atccgctcat gagacaataa ccctgataaa tgcttcaata    1380
atattgaaaa aggaagagta tgagtattca acatttccgt gtcgccctta ttccctttt     1440
tgcggcattt tgccttcctg tttttgctca cccagaaacg ctggtgaaag taaaagatgc    1500
tgaagatcag ttgggtgcac gagtgggtta catcgaactg gatctcaaca gcggtaagat    1560
ccttgagagt tttcgccccg aagaacgttt tccaatgatg agcacttta aagttctgct     1620
atgtggcgcg gtattatccc gtattgacgc cgggcaagag caactcggtc gccgcataca    1680
ctattctcag aatgacttgg ttgagtactc accagtcaca gaaaagcatc ttacggatgg    1740
catgacagta agagaattat gcagtgctgc cataaccatg agtgataaca ctgcggccaa    1800
cttacttctg acaacgatcg gaggaccgaa ggagctaacc gcttttttgc acaacatggg    1860
ggatcatgta actcgccttg atcgttggga accggagctg aatgaagcca taccaaacga    1920
cgagcgtgac accacgatgc ctgtagcaat ggcaacaacg ttgcgcaaac tattaactgg    1980
cgaactactt actctagctt cccggcaaca attaatagac tggatggagg cggataaagt    2040
tgcaggacca cttctgcgct cggcccttcc ggctggctgg tttattgctg ataaatctgg    2100
agccggtgag cgtgggtctc gcggtatcat tgcagcactg gggccagatg gtaagccctc    2160
ccgtatcgta gttatctaca cgacggggag tcaggcaact atggatgaac gaaatagaca    2220
gatcgctgag ataggtgcct cactgattaa gcattggtaa ctgtcagacc aagtttactc    2280
atatatactt tagattgatt taaaacttca ttttaattt aaaaggatct aggtgaagat     2340
ccttttgat aatctcatga ccaaaatccc ttaacgtgag ttttcgttcc actgagcgtc      2400
agaccccgta gaaagatca aaggatcttc ttgagatcct ttttttctgc gcgtaatctg     2460
ctgcttgcaa acaaaaaaac caccgctacc agcggtggtt tgtttgccgg atcaagagct    2520
accaactctt tttccgaagg taactggctt cagcagagcg cagataccaa atactgtcct    2580
tctagtgtag ccgtagttag gccaccactt caagaactct gtagcaccgc ctacatacct    2640
cgctctgcta atcctgttac cagtggctgc tgccagtggc gataagtcgt gtcttaccgg    2700
gttggactca agacgatagt taccggataa ggcgcagcgg tcgggctgaa cggggggttc    2760
gtgcacacag cccagcttgg agcgaacgac ctacaccgaa ctgagatacc tacagcgtga    2820
gctatgagaa agcgccacgc ttcccgaagg gagaaaggcg gacaggtatc cggtaagcgg    2880
cagggtcgga acaggagagc gcacgaggga gcttccaggg ggaaacgcct ggtatcttta    2940
```

-continued

```
tagtcctgtc gggtttcgcc acctctgact tgagcgtcga ttttgtgat gctcgtcagg      3000
ggggcggagc ctatggaaaa acgccagcaa cgcggccttt ttacggttcc tggccttttg      3060
ctggcctttt gctcacatgt tctttcctgc gttatcccct gattctgtgg ataaccgtat      3120
taccgccttt gagtgagctg ataccgctcg ccgcagccga acgaccgagc gcagcgagtc      3180
agtgagcgag gaagcggaag agcgcccaat acgcaaaccg cctctccccg cgcgttggcc      3240
gattcattaa tgcagctggc acgacaggtt cccgactgg aaagcgggca gtgagcgcaa      3300
cgcaattaat gtgagttagc tcactcatta ggcaccccag ctttacact ttatgcttcc      3360
ggctcgtatg ttgtgtggaa ttgtgagcgg ataacaattt cacacaggaa acagctatga      3420
ccatgattac gccaagcttg catgcctgca ggctagccta agtacgtact caaaatgcca      3480
acaaataaaa aaaagttgc tttaataatg ccaaaacaaa ttaataaaac acttacaaca      3540
ccggattttt tttaattaaa atgtgccatt taggataaat agttaatatt tttaataatt      3600
atttaaaaag ccgtatctac taaaatgatt tttatttggt tgaaaatatt aatatgttta      3660
aatcaacaca atctatcaaa attaaactaa aaaaaaaata agtgtacgtg gttaacatta      3720
gtacagtaat ataagaggaa aatgagaaat taagaaattg aaagcgagtc taattttaa      3780
attatgaacc tgcatatata aaaggaaaga aagaatccag gaagaaaaga aatgaaacca      3840
tgcatggtcc cctcgtcatc acgagtttct gccatttgca atagaaacac tgaaacacct      3900
ttctctttgt cacttaattg agatgccgaa gccacctcac accatgaact tcatgaggtg      3960
tagcacccaa ggcttccata gccatgcata ctgaagaatg tctcaagctc agcaccctac      4020
ttctgtgacg tgtccctcat tcaccttcct ctcttcccta taaataacca cgcctcaggt      4080
tctccgcttc acaactcaaa cattctctcc attggtcctt aaacactcat cagtcatcac      4140
cgcggccgca tgggaacgga ccaaggaaaa accttcacct gggaagagct ggcggcccat      4200
aacaccaagg acgacctact cttggccatc cgcggcaggg tgtacgatgt cacaaagttc      4260
ttgagccgcc atcctggtgg agtggacact ctcctgctcg gagctggccg agatgttact      4320
ccggtctttg agatgtatca cgcgtttggg gctgcagatg ccattatgaa gaagtactat      4380
gtcggtacac tggtctcgaa tgagctgccc atcttcccgg agccaacggt gttccacaaa      4440
accatcaaga cgagagtcga gggctacttt acggatcgga acattgatcc caagaataga      4500
ccagagatct ggggacgata cgctcttatc tttggatcct tgatcgcttc ctactacgcg      4560
cagctctttg tgcctttcgt tgtcgaacgc acatggcttc aggtggtgtt tgcaatcatc      4620
atgggatttg cgtgcgcaca agtcggactc aaccctcttc atgatgcgtc tcacttttca      4680
gtgacccaca accccactgt ctggaagatt ctggagccca cgcacgactt tttcaacgga      4740
gcatcgtacc tggtgtggat gtaccaacat atgctcggcc atcacccta caccaacatt      4800
gctggagcag atcccgacgt gtcgacgtct gagcccgatg ttcgtcgtat caagcccaac      4860
caaaagtggt ttgtcaacca catcaaccag cacatgtttg ttcctttcct gtacggactg      4920
ctggcgttca aggtgcgcat tcaggacatc aacatttgt actttgtcaa gaccaatgac      4980
gctattcgtg tcaatcccat ctcgacatgg cacactgtga tgttctgggg cggcaaggct      5040
ttctttgtct ggtatcgcct gattgttccc ctgcagtatc tgcccctggg caaggtgctg      5100
ctcttgttca cggtcgcgga catggtgtcg tcttactggc tggcgctgac cttccaggcg      5160
aaccacgttg ttgaggaagt tcagtggccg ttgcctgacg agaacgggat catccaaaag      5220
gactgggcag ctatgcaggt cgagactacg caggattacg cacacgattc gcacctctgg      5280
```

-continued

```
accagcatca ctggcagctt gaactaccag gctgtgcacc atctgttccc caacgtgtcg   5340
cagcaccatt atcccgatat tctggccatc atcaagaaca cctgcagcga gtacaaggtt   5400
ccataccttg tcaaggatac gttttggcaa gcatttgctt cacatttgga gcacttgcgt   5460
gttcttggac tccgtcccaa ggaagagtag gc                                 5492
```

<210> SEQ ID NO 116
<211> LENGTH: 1338
<212> TYPE: DNA
<213> ORGANISM: Mortierella alpina

<400> SEQUENCE: 116

```
atgggaacgg accaaggaaa aaccttcacc tgggaagagc tggcggccca taacaccaag     60
gacgacctac tcttggccat ccgcggcagg gtgtacgatg tcacaaagtt cttgagccgc    120
catcctggtg gagtggacac tctcctgctc ggagctggcc gagatgttac tccggtcttt    180
gagatgtatc acgcgtttgg ggctgcagat gccattatga agaagtacta tgtcggtaca    240
ctggtctcga atgagctgcc catcttcccg gagccaacgg tgttccacaa aaccatcaag    300
acgagagtcg agggctactt tacgatcgg aacattgatc ccaagaatag accagagatc    360
tggggacgat acgctcttat cttgatcc ttgatcgctt cctactacgc gcagctcttt    420
gtgcctttcg ttgtcgaacg cacatggctt caggtggtgt ttgcaatcat catgggattt    480
gcgtgcgcac aagtcggact caaccctctt catgatgcgt ctcactttc agtgacccac    540 aaccccactg tctggaagat tctgggagcc acgcacgact ttttcaacgg agcatcgtac    600
ctggtgtgga tgtaccaaca tatgctcggc catcacccct acaccaacat gctggagca    660 gatcccgacg tgtcgacgtc tgagcccgat gttcgtcgta tcaagcccaa ccaaaagtgg    720
tttgtcaacc acatcaacca gcacatgttt gttccttcc tgtacggact gctggcgttc    780
aaggtgcgca ttcaggacat caacattttg tactttgtca agaccaatga cgctattcgt    840
gtcaatccca tctcgacatg gcacactgtg atgttctggg gcggcaaggc tttcttttgtc    900 tggtatcgcc tgattgttcc cctgcagtat ctgcccctgg gcaaggtgct gctcttgttc    960
acggtcgcgg acatggtgtc gtcttactgg ctggcgctga ccttccaggc gaaccacgtt   1020
gttgaggaag ttcagtggcc gttgcctgac gagaacggga tcatccaaaa ggactgggca   1080
gctatgcagg tcgagactac gcaggattac gcacacgatt cgcacctctg gaccagcatc   1140
actggcagct tgaactacca ggctgtgcac atctgttcc ccaacgtgtc gcagcaccat   1200
tatcccgata ttctggccat catcaagaac acctgcagcg agtacaaggt tccataccttt   1260 gtcaaggata cgttttggca agcatttgct tcacatttgg agcacttgcg tgttcttgga   1320
ctccgtccca aggaagag                                                 1338
```

<210> SEQ ID NO 117
<211> LENGTH: 2577
<212> TYPE: DNA
<213> ORGANISM: Artificial Sequence
<220> FEATURE:
<223> OTHER INFORMATION: pKR277

<400> SEQUENCE: 117

```
agcttggatc tcctgcagga tctgccggc cggatctcgt acggatccgt cgacggcgcg     60
cccgatcatc cggatatagt tcctcctttc agcaaaaaac ccctcaagac ccgtttagag    120
gccccaaggg gttatgctag ttattgctca gcggtggcag cagccaactc agcttccttt    180
cgggctttgt tagcagccgg atcgatccaa gctgtacctc actattcctt tgccctcgga    240
```

```
cgagtgctgg ggcgtcggtt tccactatcg gcgagtactt ctacacagcc atcggtccag    300
acggccgcgc ttctgcgggc gatttgtgta cgcccgacag tcccggctcc ggatcggacg    360
attgcgtcgc atcgaccctg cgcccaagct gcatcatcga aattgccgtc aaccaagctc    420
tgatagagtt ggtcaagacc aatgcggagc atatacgccc ggagccgcgg cgatcctgca    480
agctccggat gcctccgctc gaagtagcgc gtctgctgct ccatacaagc caaccacggc    540
ctccagaaga agatgttggc gacctcgtat tgggaatccc cgaacatcgc ctcgctccag    600
tcaatgaccg ctgttatgcg gccattgtcc gtcaggacat tgttggagcc gaaatccgcg    660
tgcacgaggt gccggacttc ggggcagtcc tcggcccaaa gcatcagctc atcgagagcc    720
tgcgcgacgg acgcactgac ggtgtcgtcc atcacagttt gccagtgata cacatgggga    780
tcagcaatcg cgcatatgaa atcacgccat gtagtgtatt gaccgattcc ttgcggtccg    840
aatgggccga acccgctcgt ctggctaaga tcggccgcag cgatcgcatc catagcctcc    900
gcgaccggct gcagaacagc gggcagttcg gtttcaggca ggtcttgcaa cgtgacaccc    960
tgtgcacggc gggagatgca ataggtcagg ctctcgctga attccccaat gtcaagcact   1020
tccggaatcg ggagcgcggc cgatgcaaag tgccgataaa cataacgatc tttgtagaaa   1080
ccatcggcgc agctatttac ccgcaggaca tatccacgcc ctcctacatc gaagctgaaa   1140
gcacgagatt cttcgccctc cgagagctgc atcaggtcgg agacgctgtc gaacttttcg   1200
atcagaaact tctcgacaga cgtcgcggtg agttcaggct tttccatggg tatatctcct   1260
tcttaaagtt aaacaaaatt atttctagag ggaaaccgtt gtggtctccc tatagtgagt   1320
cgtattaatt tcgcgggatc gagatctgat caacctgcat taatgaatcg gccaacgcgc   1380
ggggagaggc ggtttgcgta ttgggcgctc ttccgcttcc tcgctcactg actcgctgcg   1440
ctcggtcgtt cggctgcggc gagcggtatc agctcactca aaggcggtaa tacggttatc   1500
cacagaatca ggggataacg caggaaagaa catgtgagca aaaggccagc aaaaggccag   1560
gaaccgtaaa aaggccgcgt tgctggcgtt tttccatagg ctccgccccc ctgacgagca   1620
tcacaaaaat cgacgctcaa gtcagaggtg gcgaaacccg acaggactat aaagatacca   1680
ggcgtttccc cctggaagct ccctcgtgcg ctctcctgtt ccgaccctgc cgcttaccgg   1740
atacctgtcc gcctttctcc cttcgggaag cgtggcgctt tctcaatgct cacgctgtag   1800
gtatctcagt tcggtgtagg tcgttcgctc caagctgggc tgtgtgcacg aaccccccgt   1860
tcagcccgac cgctgcgcct tatccggtaa ctatcgtctt gagtccaacc cggtaagaca   1920
cgacttatcg ccactggcag cagccactgg taacaggatt agcagagcga ggtatgtagg   1980
cggtgctaca gagttcttga agtggtggcc taactacggc tacactagaa ggacagtatt   2040
tggtatctgc gctctgctga agccagttac cttcggaaaa agagttggta gctcttgatc   2100
cggcaaacaa accaccgctg gtagcggtgg tttttttgtt tgcaagcagc agattacgcg   2160
cagaaaaaaa ggatctcaag aagatccttt gatcttttct acggggtctg acgctcagtg   2220
gaacgaaaac tcacgttaag ggattttggt catgacatta acctataaaa ataggcgtat   2280
cacgaggccc tttcgtctcg cgcgtttcgg tgatgacggt gaaaacctct gacacatgca   2340
gctcccggag acggtcacag cttgtctgta agcggatgcc gggagcagac aagcccgtca   2400
gggcgcgtca gcgggtgttg gcgggtgtcg ggctggctt aactatgcgg catcagagca   2460
gattgtactg agagtgcacc atatggacat attgtcgtta gaacgcggct acaattaata   2520
cataacctta tgtatcatac acatacgatt taggtgacac tatagaacgg cgcgcca     2577
```

```
<210> SEQ ID NO 118
<211> LENGTH: 5364
<212> TYPE: DNA
<213> ORGANISM: Artificial Sequence
<220> FEATURE:
<223> OTHER INFORMATION: pKR952

<400> SEQUENCE: 118
ggctagccta agtacgtact caaaatgcca acaaataaaa aaaagttgc tttaataatg      60 ccaaaacaaa ttaataaaac acttacaaca ccggattttt tttaattaaa atgtgccatt    120
taggataaat agttaatatt tttaataatt atttaaaaag ccgtatctac taaaatgatt    180
tttatttggt tgaaaatatt aatatgttta aatcaacaca atctatcaaa attaaactaa    240
aaaaaaaata gtgtacgtg gttaacatta gtacagtaat ataagaggaa aatgagaaat    300
taagaaattg aaagcgagtc taatttttaa attatgaacc tgcatatata aaaggaaaga    360
aagaatccag gaagaaaaga aatgaaacca tgcatggtcc cctcgtcatc acgagtttct    420
gccatttgca atagaaacac tgaaacacct ttctctttgt cacttaattg agatgccgaa    480
gccacctcac accatgaact tcatgaggtg tagcacccaa ggcttccata gccatgcata    540
ctgaagaatg tctcaagctc agcaccctac ttctgtgacg tgtccctcat tcaccttcct    600
ctcttcccta taataaccca cgcctcaggt tctccgcttc acaatcaaaa cattctctcc    660
attggtcctt aaacactcat cagtcatcac cgcggccgca tgggaacgga ccaaggaaaa    720
accttcacct gggaagagct ggcggcccat aacaccaagg acgacctact cttggccatc    780
cgcggcaggg tgtacgatgt cacaaagttc ttgagccgcc atcctggtgg agtggacact    840
ctcctgctcg gagctggccg agatgttact ccggtctttg agatgtatca cgcgtttggg    900
gctgcagatg ccattatgaa gaagtactat gtcggtacac tggtctcgaa tgagctgccc    960
atcttcccgg agccaacggt gttccacaaa accatcaaga cgagagtcga gggctacttt   1020
acggatcgga acattgatcc caagaataga ccagagatct ggggacgata cgctcttatc   1080
tttggatcct tgatcgcttc ctactacgcg cagctctttg tgcctttcgt tgtcgaacgc   1140
acatggcttc aggtggtgtt tgcaatcatc atgggatttg cgtgcgcaca agtcggactc   1200
aaccctcttc atgatgcgtc tcacttttca gtgacccaca accccactgt ctggaagatt   1260
ctgggagcca cgcacgactt tttcaacgga gcatcgtacc tggtgtggat gtaccaacat   1320
atgctcggcc atcacccta caccaacatt gctggagcag atcccgacgt gtcgacgtct   1380
gagcccgatg ttcgtcgtat caagcccaac caaaagtggt tgtcaaccca catcaaccag   1440
cacatgtttg ttccttttcct gtacggactg ctggcgttca aggtgcgcat tcaggacatc   1500 aacatttttgt actttgtcaa gaccaatgac gctattcgtg tcaatccat ctcgacatgg   1560 cacactgtga tgttctgggg cggcaaggct ttctttgtct ggtatcgcct gattgttccc   1620
ctgcagtatc tgccctggg caaggtgctg ctcttgttca cggtcgcgga catggtgtcg   1680
tcttactggc tggcgctgac cttccaggcg aaccacgttg ttgaggaagt tcagtggccg   1740
ttgcctgacg agaacgggat catccaaaag gactgggcag ctatgcaggt cgagactacg   1800
caggattacg cacacgattc gcacctctgg accagcatca ctggcagctt gaactaccag   1860
gctgtgcacc atctgttccc caacgtgtcg cagcaccatt atcccgatat tctggccatc   1920
atcaagaaca cctgcagcga gtacaaggtt ccataccttg tcaaggatac gttttggcaa   1980
gcatttgctt cacatttgga gcacttgcgt gttcttggac tccgtcccaa ggaagagtag   2040
gcggccgcat ttcgcaccaa atcaatgaaa gtaataatga aaagtctgaa taagaatact   2100
```

```
taggcttaga tgcctttgtt acttgtgtaa aataacttga gtcatgtacc tttggcggaa    2160
acagaataaa taaaggtga aattccaatg ctctatgtat aagttagtaa tacttaatgt    2220
gttctacggt tgtttcaata tcatcaaact ctaattgaaa ctttagaacc acaaatctca    2280 atctttctt aatgaaatga aaaatcttaa ttgtaccatg tttatgttaa acaccttaca    2340
attggttgga gaggaggacc aaccgatggg acaacattgg agaaagaga ttcaatggag    2400 atttggatag gagaacaaca ttcttttca cttcaataca agatgagtgc aacactaagg    2460
atatgtatga gactttcaga agctacgaca acatagatga gtgaggtggt gattcctagc    2520
aagaaagaca ttagaggaag ccaaaatcga acaaggaaga catcaagggc aagagacagg    2580
accatccatc tcaggaaaag gagctttggg atagtccgag aagttgtaca agaaattttt    2640
tggagggtga gtgatgcatt gctggtgact ttaactcaat caaaattgag aaagaaagaa    2700
aagggagggg gctcacatgt gaatagaagg gaaacgggag aattttacag ttttgatcta    2760
atgggcatcc cagctagtgg taacatattc accatgttta accttcacgt acggatccgt    2820
cgacggcgcg cccgatcatc cggatatagt tcctcctttc agcaaaaaac ccctcaagac    2880
ccgtttagag gccccaaggg gttatgctag ttattgctca gcggtggcag cagccaactc    2940
agcttccttt cgggctttgt tagcagccgg atcgatccaa gctgtacctc actattcctt    3000
tgccctcgga cgagtgctgg ggcgtcggtt tccactatcg gcgagtactt ctacacagcc    3060
atcggtccag acggccgcgc ttctgcgggc gatttgtgta cgcccgacag tcccggctcc    3120
ggatcggacg attgcgtcgc atcgaccctg cgcccaagct gcatcatcga aattgccgtc    3180
aaccaagctc tgatagagtt ggtcaagacc aatgcggagc atatacgccc ggagccgcgg    3240
cgatcctgca agctccggat gcctccgctc gaagtagcgc gtctgctgct ccatacaagc    3300
caaccacggc ctccagaaga agatgttggc gacctcgtat tgggaatccc cgaacatcgc    3360
ctcgctccag tcaatgaccg ctgttatgcg gccattgtcc gtcaggacat gttggagcc    3420 gaaatccgcg tgcacgaggt gccggacttc ggggcagtcc tcggcccaaa gcatcagctc    3480
atcgagagcc tgcgcgacgg acgcactgac ggtgtcgtcc atcacagttt gccagtgata    3540
cacatgggga tcagcaatcg cgcatatgaa atcacgccat gtagtgtatt gaccgattcc    3600
ttgcggtccg aatgggccga acccgctcgt ctggctaaga tcggccgcag cgatcgcatc    3660
catagcctcc gcgaccggct gcagaacagc gggcagttcg gtttcaggca ggtcttgcaa    3720
cgtgacaccc tgtgcacggc gggagatgca ataggtcagg ctctcgctga attccccaat    3780
gtcaagcact tccggaatcg ggagcgcggc cgatgcaaag tgccgataaa cataacgatc    3840
tttgtagaaa ccatcggcgc agctatttac ccgcaggaca tatccacgcc ctcctacatc    3900
gaagctgaaa gcacgagatt cttcgccctc cgagagctgc atcaggtcgg agacgctgtc    3960 gaactttttcg atcagaaact tctcgacaga cgtcgcggtg agttcaggct tttccatggg    4020
tatatctcct tcttaaagtt aaacaaaatt atttctagag ggaaaccgtt gtggtctccc    4080
tatagtgagt cgtattaatt tcgcgggatc gagatctgat caacctgcat taatgaatcg    4140
gccaacgcgc ggggagaggc ggtttgcgta ttgggcgctc ttccgcttcc tcgctcactg    4200
actcgctgcg ctcggtcgtt cggctgcggc gagcggtatc agctcactca aaggcggtaa    4260
tacggttatc cacagaatca ggggataacg caggaaagaa catgtgagca aaaggccagc    4320
aaaaggccag gaaccgtaaa aaggccgcgt tgctggcgtt tttccatagg ctccgccccc    4380
ctgacgagca tcacaaaaat cgacgctcaa gtcagaggtg cgaaacccg acaggactat    4440
```

| | |
|---|---|
| aaagatacca ggcgtttccc cctggaagct ccctcgtgcg ctctcctgtt ccgaccctgc | 4500 |
| cgcttaccgg atacctgtcc gcctttctcc cttcgggaag cgtggcgctt tctcaatgct | 4560 |
| cacgctgtag gtatctcagt tcggtgtagg tcgttcgctc caagctgggc tgtgtgcacg | 4620 |
| aaccccccgt tcagcccgac cgctgcgcct tatccggtaa ctatcgtctt gagtccaacc | 4680 |
| cggtaagaca cgacttatcg ccactggcag cagccactgg taacaggatt agcagagcga | 4740 |
| ggtatgtagg cggtgctaca gagttcttga agtggtggcc taactacggc tacactagaa | 4800 |
| ggacagtatt tggtatctgc gctctgctga agccagttac cttcggaaaa agagttggta | 4860 |
| gctcttgatc cggcaaacaa accaccgctg gtagcggtgg ttttttttgtt tgcaagcagc | 4920 |
| agattacgcg cagaaaaaaa ggatctcaag aagatccttt gatcttttct acggggtctg | 4980 |
| acgctcagtg gaacgaaaac tcacgttaag ggattttggt catgacatta acctataaaa | 5040 |
| ataggcgtat cacgaggccc tttcgtctcg cgcgtttcgg tgatgacggt gaaaacctct | 5100 |
| gacacatgca gctcccggag acggtcacag cttgtctgta agcggatgcc gggagcagac | 5160 |
| aagcccgtca gggcgcgtca gcgggtgttg gcgggtgtcg gggctggctt aactatgcgg | 5220 |
| catcagagca gattgtactg agagtgcacc atatggacat attgtcgtta gaacgcggct | 5280 |
| acaattaata cataaccta tgtatcatac acatacgatt taggtgacac tatagaacgg | 5340 |
| cgcgccaagc ttggatctcc tgca | 5364 |

<210> SEQ ID NO 119
<211> LENGTH: 5252
<212> TYPE: DNA
<213> ORGANISM: Artificial Sequence
<220> FEATURE:
<223> OTHER INFORMATION: pKR457
<220> FEATURE:
<221> NAME/KEY: misc_feature
<222> LOCATION: (3872)..(3872)
<223> OTHER INFORMATION: n is a, c, g, or t

<400> SEQUENCE: 119

| | |
|---|---|
| gtacgtgggc ggatccccg ggctgcagga attcactggc cgtcgtttta caacgtcgtg | 60 |
| actgggaaaa ccctggcgtt acccaactta atcgccttgc agcacatccc ctttcgcca | 120 |
| gctggcgtaa tagcgaagag gcccgcaccg atcgcccttc ccaacagttg cgcagcctga | 180 |
| atggcgaatg gcgcctgatg cggtattttc tccttacgca tctgtgcggt atttcacacc | 240 |
| gcatatggtg cactctcagt acaatctgct ctgatgccgc atagttaagc cagccccgac | 300 |
| acccgccaac acccgctgac gcgccctgac gggcttgtct gctcccggca tccgcttaca | 360 |
| gacaagctgt gaccgtctcc gggagctgca tgtgtcagag gttttcaccg tcatcaccga | 420 |
| aacgcgcgag acgaaagggc ctcgtgatac gcctattttt ataggttaat gtcatgataa | 480 |
| taatggtttc ttagacgtca ggtggcactt ttcggggaaa tgtgcgcgga acccctattt | 540 |
| gtttattttt ctaaatacat tcaaatatgt atccgctcat gagacaataa ccctgataaa | 600 |
| tgcttcaata atattgaaaa aggaagagta tgagtattca acatttccgt gtcgccctta | 660 |
| ttcccttttt tgcggcattt tgccttcctg ttttgctca cccagaaacg ctggtgaaag | 720 |
| taaaagatgc tgaagatcag ttgggtgcac gagtgggtta catcgaactg gatctcaaca | 780 |
| gcggtaagat ccttgagagt tttcgccccg aagaacgttt tccaatgatg agcacttta | 840 |
| aagttctgct atgtggcgcg gtattatccc gtattgacgc cgggcaagag caactcggtc | 900 |
| gccgcataca ctattctcag aatgacttgg ttgagtactc accagtcaca gaaaagcatc | 960 |
| ttacggatgg catgacagta agagaattat gcagtgctgc cataaccatg agtgataaca | 1020 |

```
ctgcggccaa cttacttctg acaacgatcg gaggaccgaa ggagctaacc gcttttttgc    1080
acaacatggg ggatcatgta actcgccttg atcgttggga accggagctg aatgaagcca    1140
taccaaacga cgagcgtgac accacgatgc ctgtagcaat ggcaacaacg ttgcgcaaac    1200
tattaactgg cgaactactt actctagctt cccggcaaca attaatagac tggatggagg    1260
cggataaagt tgcaggacca cttctgcgct cggcccttcc ggctggctgg tttattgctg    1320
ataaatctgg agccggtgag cgtgggtctc gcggtatcat tgcagcactg gggccagatg    1380
gtaagccctc ccgtatcgta gttatctaca cgacggggag tcaggcaact atggatgaac    1440
gaaatagaca gatcgctgag ataggtgcct cactgattaa gcattggtaa ctgtcagacc    1500
aagtttactc atatatactt tagattgatt taaaacttca ttttaatttt aaaaggatct    1560
aggtgaagat cctttttgat aatctcatga ccaaaatccc ttaacgtgag ttttcgttcc    1620
actgagcgtc agaccccgta gaaaagatca aaggatcttc ttgagatcct ttttttctgc    1680
gcgtaatctg ctgcttgcaa acaaaaaaac caccgctacc agcggtggtt tgtttgccgg    1740
atcaagagct accaactctt tttccgaagg taactggctt cagcagagcg cagataccaa    1800
atactgtcct tctagtgtag ccgtagttag gccaccactt caagaactct gtagcaccgc    1860
ctacatacct cgctctgcta atcctgttac cagtggctgc tgccagtggc gataagtcgt    1920
gtcttaccgg gttggactca agacgatagt taccggataa ggcgcagcgg tcgggctgaa    1980
cggggggttc gtgcacacag cccagcttgg agcgaacgac ctacaccgaa ctgagatacc    2040
tacagcgtga gctatgagaa agcgccacgc ttcccgaagg gagaaaggcg gacaggtatc    2100
cggtaagcgg cagggtcgga acaggagagc gcacgaggga gcttccaggg ggaaacgcct    2160
ggtatcttta tagtcctgtc gggtttcgcc acctctgact tgagcgtcga ttttgtgat    2220 gctcgtcagg gggcggagc ctatggaaaa acgccagcaa cgcggccttt ttacggttcc    2280
tggccttttg ctggcctttt gctcacatgt tctttcctgc gttatcccct gattctgtgg    2340
ataaccgtat taccgccttt gagtgagctg ataccgctcg ccgcagccga acgaccgagc    2400
gcagcgagtc agtgagcgag gaagcggaag agcgcccaat acgcaaaccg cctctccccg    2460
cgcgttggcc gattcattaa tgcagctggc acgacaggtt cccgactgg aaagcgggca    2520 gtgagcgcaa cgcaattaat gtgagttagc tcactcatta ggcaccccag gctttacact    2580
ttatgcttcc ggctcgtatg ttgtgtggaa ttgtgagcgg ataacaattt cacacaggaa    2640
acagctatga ccatgattac gccaagcttg catgcctgca ggtcgactcg acgtacgtcc    2700
tcgaagagaa gggttaataa cacatttttt aacattttta acacaaattt tagttattta    2760
aaaatttatt aaaaaattta aaataagaag aggaactctt taaataaatc taacttacaa    2820
aatttatgat tttaataag ttttcaccaa taaaaaatgt cataaaaata tgttaaaaag    2880
tatattatca atattctctt tatgataaat aaaaagaaaa aaaaaataaa agttaagtga    2940
aaatgagatt gaagtgactt taggtgtgta taaatatatc aaccccgcca acaatttatt    3000
taatccaaat atattgaagt atattattcc atagccttta tttatttata tatttattat    3060
ataaaagctt tatttgttct aggttgttca tgaaatattt ttttggtttt atctccgttg    3120
taagaaaatc atgtgctttg tgtcgccact cactattgca gcttttttcat gcattggtca    3180 gattgacggt tgattgtatt tttgtttttt atggttttgt gttatgactt aagtcttcat    3240
ctctttatct cttcatcagg tttgatggtt acctaatatg gtccatgggt acatgcatgg    3300
ttaaattagg tggccaactt tgttgtgaac gatagaattt ttttatatt aagtaaacta    3360
```

```
ttttatatt atgaaataat aataaaaaaa atattttatc attattaaca aaatcatatt    3420
agttaatttg ttaactctat aataaaagaa atactgtaac attcacatta catggtaaca    3480
tctttccacc ctttcatttg tttttttgttt gatgactttt tttcttgttt aaatttattt    3540 cccttcttt aaatttggaa tacattatca tcatatataa actaaaatac taaaaacagg    3600
attacacaaa tgataaataa taacacaaat atttataaat ctagctgcaa tatatttaaa    3660
ctagctatat cgatattgta aaataaaact agctgcattg atactgataa aaaaatatca    3720
tgtgctttct ggactgatga tgcagtatac ttttgacatt gcctttattt tattttttcag   3780 aaaagctttc ttagttctgg gttcttcatt atttgtttcc catctccatt gtgaattgaa    3840
tcatttgctt cgtgtcacaa atacaattta gntaggtaca tgcattggtc agattcacgg    3900
tttattatgt catgacttaa gttcatggta gtacattacc tgccacgcat gcattatatt    3960
ggttagattt gataggcaaa tttggttgtc aacaatataa atataaataa tgttttata    4020 ttacgaaata acagtgatca aaacaaacag ttttatctttt attaacaaga ttttgttttt   4080
gtttgatgac gttttttaat gtttacgctt tcccccttct tttgaattta gaacacttta    4140
tcatcataaa atcaaatact aaaaaaatta catatttcat aaataataac acaaatattt    4200
ttaaaaaatc tgaaataata atgaacaata ttacatatta tcacgaaaat tcattaataa    4260
aaatattata taaataaaat gtaatagtag ttatatgtag gaaaaaagta ctgcacgcat    4320
aatatataca aaaagattaa aatgaactat tataaataat aacactaaat taatggtgaa    4380
tcatatcaaa ataatgaaaa agtaaataaa atttgtaatt aacttctata tgtattacac    4440
acacaaataa taaataatag taaaaaaaat tatgataaat atttaccatc tcataagata    4500 tttaaaaataa tgataaaaat atagattatt ttttatgcaa ctagctagcc aaaaagagaa    4560
cacgggtata tataaaaga gtacctttaa attctactgt acttcctta ttcctgacgt    4620 tttttatatca agtggacata cgtgaagatt ttaattatca gtctaaatat ttcattagca    4680
cttaatactt ttctgttta ttcctatcct ataagtagtc ccgattctcc caacattgct    4740
tattcacaca actaactaag aaagtcttcc atagccccc aagcggccgc gacacaagtg    4800
tgagagtact aaataaatgc tttggttgta cgaaatcatt acactaaata aaataatcaa    4860
agcttatata tgccttccgc taaggccgaa tgcaaagaaa ttggttcttt ctcgttatct    4920
tttgccactt ttactagtac gtattaatta ctacttaatc atctttgttt acggctcatt    4980
atatccggtc tagaggatcc aaggccgcga agtaaaagc aatgttgtca cttgtcgtac    5040
taacacatga tgtgatagtt tatgctagct agctataaca taagctgtct ctgagtgtgt    5100
tgtatattaa taaagatcat cactggtgaa tggtgatcgt gtacgtaccc tacttagtag    5160
gcaatggaag cacttagagt gtgctttgtg catggccttg cctctgtttt gagacttttg    5220
taatgttttc gagtttaaat ctttgccttt gc                                 5252
```

<210> SEQ ID NO 120
<211> LENGTH: 2635
<212> TYPE: DNA
<213> ORGANISM: Artificial Sequence
<220> FEATURE:
<223> OTHER INFORMATION: modified Kti-NotI-Kti3'Salb3'cassette
<220> FEATURE:
<221> NAME/KEY: misc_feature
<222> LOCATION: (1229)..(1229)
<223> OTHER INFORMATION: n is a, c, g, or t

<400> SEQUENCE: 120

```
ggtaccgggc cccccctcga ggtcgcccgg gggatccgcc ctaagcttcg tacgtcctcg    60
```

```
aagagaaggg ttaataacac attttttaac attttttaaca caaatttttag ttatttaaaa      120
atttattaaa aaatttaaaa taagaagagg aactctttaa ataaatctaa cttacaaaat      180
ttatgatttt taataagttt tcaccaataa aaaatgtcat aaaaatatgt taaaaagtat      240
attatcaata ttctctttat gataaataaa aagaaaaaaa aaataaaagt taagtgaaaa      300
tgagattgaa gtgactttag gtgtgtataa atatatcaac cccgccaaca atttatttaa      360
tccaaatata ttgaagtata ttattccata gcctttattt atttatatat ttattatata      420
aaagctttat ttgttctagg ttgttcatga aatattttttt tggttttatc tccgttgtaa      480
gaaaatcatg tgctttgtgt cgccactcac tattgcagct ttttcatgca ttggtcagat      540
tgacggttga ttgtattttt gttttttatg gttttgtgtt atgacttaag tcttcatctc      600
tttatctctt catcaggttt gatggttacc taatatggtc catgggtaca tgcatggtta      660
aattaggtgg ccaactttgt tgtgaacgat agaattttttt ttatattaag taaactatttt      720
ttatattatg aaataataat aaaaaaaata ttttatcatt attaacaaaa tcatattagt      780
taatttgtta actctataat aaaagaaata ctgtaacatt cacattacat ggtaacatct      840
ttccacccctt tcatttgttt tttgtttgat gacttttttt cttgtttaaa tttatttccc      900
ttcttttaaa tttggaatac attatcatca tatataaact aaaatactaa aaacaggatt      960
acacaaatga taaataataa cacaaatatt tataaatcta gctgcaatat atttaaacta     1020
gctatatcga tattgtaaaa taaaactagc tgcattgata ctgataaaaa aatatcatgt     1080
gctttctgga ctgatgatgc agtatacttt tgacattgcc tttatttttat ttttcagaaa     1140
agctttctta gttctgggtt cttcattatt tgtttcccat ctccattgtg aattgaatca     1200
tttgcttcgt gtcacaaata caatttagnt aggtacatgc attggtcaga ttcacggttt     1260
attatgtcat gacttaagtt catggtagta cattacctgc cacgcatgca ttatattggt     1320
tagatttgat aggcaaattt ggttgtcaac aatataaata taaataatgt ttttatatta     1380
cgaaataaca gtgatcaaaa caaacagttt tatctttatt aacaagatttt gttttttgtt      1440
tgatgacgtt ttttaatgtt tacgctttcc cccttctttt gaatttagaa cactttatca     1500
tcataaaatc aaatactaaa aaaattacat atttcataaa taataacaca aatattttta     1560
aaaaatctga aataataatg aacaatatta catattatca cgaaaattca ttaataaaaa     1620
tattatataa ataaaatgta atagtagtta tatgtaggaa aaaagtactg cacgcataat     1680
atatacaaaa agattaaaat gaactattat aaataataac actaaattaa tggtgaatca     1740
tatcaaaata atgaaaaagt aaataaaatt tgtaattaac ttctatatgt attacacaca     1800
caaataataa ataatagtaa aaaaaattat gataaatatt taccatctca taagatatttt     1860
aaaataatga taaaaatata gattattttttt tatgcaacta gctagccaaa aagagaacac     1920
gggtatatat aaaaagagta ccttttaaatt ctactgtact tcctttattc ctgacgtttt     1980
tatatcaagt ggacatacgt gaagatttta attatcagtc taaatatttc attagcactt     2040
aatactttttc tgttttattc ctatcctata agtagtcccg attctcccaa cattgcttat     2100
tcacacaact aactaagaaa gtcttccata gcccccccaag cggccgcgac acaagtgtga     2160
gagtactaaa taaatgctttt ggttgtacga aatcattaca ctaaataaaa taatcaaagc     2220
ttatatatgc cttccgctaa ggcgaatgc aaagaaattg gttctttctc gttatctttt     2280
gccactttta ctagtacgta ttaattacta cttaatcatc tttgtttacg gctcattata     2340
tccggtctag aggatccaag gccgcgaagt taaaagcaat gttgtcactt gtcgtactaa     2400
```

-continued

```
cacatgatgt gatagtttat gctagctagc tataacataa gctgtctctg agtgtgttgt    2460
atattaataa agatcatcac tggtgaatgg tgatcgtgta cgtaccctac ttagtaggca    2520
atggaagcac ttagagtgtg ctttgtgcat ggccttgcct ctgttttgag acttttgtaa    2580
tgttttcgag tttaaatctt tgcctttgcg tacgtctaga ggatcccggg tacc          2635
```

<210> SEQ ID NO 121
<211> LENGTH: 1269
<212> TYPE: DNA
<213> ORGANISM: Pavlova lutheri

<400> SEQUENCE: 121

```
atgggcaagg gtggagacgg cggcgcgcag gcggtgagcg ggaccgacgc gtctctcgct     60
gaggtgagct ccgtcgatag caagagcgtg cacgtcgtgc tctacggcaa gcgcgtggat    120
gtcacaaagt tccagaaggc acacccgggc gggagcaagg tgttccgcat cttccaggag    180
cgcgacgcga cggagcagtt cgagtcttac cactcgccca aggccatcaa gatgatggag    240
ggcatgctca agaagtcgga ggatgcgccc gcttccgtgc ccctgccctc gcggtccacc    300
atgggcacgg agttcaagga gatgattgag cgccacaaga gggctggtct ctacgaccct    360
tgcccgttgg acgagctgtt caagctcacc atcgtccttg cgcccatctt cgtgggcgcc    420
tatctcgtgc ggagcggcgt ctcgcccctc gcgggcgcgc tctccatggg ctttggcttc    480
tacctcgacg gctggcttgc tcacgactac ctgcatcacg cagtcttcaa gggctcggtc    540
aacacgctcg tcaaggcgaa caacgccatg ggatacgccc tcggcttcct ccagggctac    600
gacgtggcct ggtggcgcgc gcgccataac acgcaccacg tgtgcaccaa cgaggatggt    660
tcggacccgg acatcaagac ggcgcccctg ctcatctacg tgcgagagaa cccgtccatt    720
gccaagcggc tcaacttctt ccagcgctgg cagcagtact actatgtgcc gaccatggcc    780
atcctcgacc tctactggcg cctggagtcc atcgcgtacg tggctgtgcg cctgcctaag    840
atgtggatgc aggccgccgc tcttgccgct cactacgcgc tcctgtgctg ggtcttcgca    900
gcgcatctca acctcatccc tctcatgatg gttgcacgcg gcttcgcgac gggcatcgtt    960
gtctttgcaa cccactatgg tgaggacatc ctcgaccgcg agcacgtcga gggcatgacg   1020
ctcgtcgagc agaccgccaa gacctcccgt aacatcacgg gcggctggct agtgaacgtg   1080
ctcacgggct tcatctccct gcagaccgag catcacctct tccccatgat gcccaccggc   1140
aacctaatga ctatccagcc cgaggtacgc gacttcttca agaagcatgg cctcgagtac   1200
cgcgagggca acctcttcca gtgcgtgcac cagaacatca aggctctcgc cttcgagcac   1260
ctcctccac                                                            1269
```

<210> SEQ ID NO 122
<211> LENGTH: 30
<212> TYPE: DNA
<213> ORGANISM: Artificial
<220> FEATURE:
<223> OTHER INFORMATION: primer PvDES5'Not-1

<400> SEQUENCE: 122

```
gcggccgcac catgggcaag ggtggagacg                                       30
```

<210> SEQ ID NO 123
<211> LENGTH: 27
<212> TYPE: DNA
<213> ORGANISM: Artificial
<220> FEATURE:
<223> OTHER INFORMATION: primer PvDES3'Not-1

<400> SEQUENCE: 123
gcggccgctc agtggaggag gtgctcg    27

<210> SEQ ID NO 124
<211> LENGTH: 9276
<212> TYPE: DNA
<213> ORGANISM: Artificial Sequence
<220> FEATURE:
<223> OTHER INFORMATION: pKR970
<220> FEATURE:
<221> NAME/KEY: misc_feature
<222> LOCATION: (6592)..(6592)
<223> OTHER INFORMATION: n is a, c, g, or t

<400> SEQUENCE: 124

| | |
|---|---|
| gtacggatcc gtcgacggcg cgcccgatca tccggatata gttcctcctt tcagcaaaaa | 60 |
| acccctcaag acccgtttag aggccccaag gggttatgct agttattgct cagcggtggc | 120 |
| agcagccaac tcagcttcct ttcgggcttt gttagcagcc ggatcgatcc aagctgtacc | 180 |
| tcactattcc tttgccctcg acgagtgct ggggcgtcgg tttccactat cggcgagtac | 240 |
| ttctacacag ccatcggtcc agacggccgc gcttctgcgg gcgatttgtg tacgcccgac | 300 |
| agtcccggct ccggatcgga cgattgcgtc gcatcgaccc tgcgcccaag ctgcatcatc | 360 |
| gaaattgccg tcaaccaagc tctgatagag ttggtcaaga ccaatgcgga gcatatacgc | 420 |
| ccggagccgc ggcgatcctg caagctccgg atgcctccgc tcgaagtagc gcgtctgctg | 480 |
| ctccatacaa gccaaccacg gcctccagaa gaagatgttg gcgacctcgt attgggaatc | 540 |
| cccgaacatc gcctcgctcc agtcaatgac cgctgttatg cggccattgt ccgtcaggac | 600 |
| attgttggag ccgaaatccg cgtgcacgag gtgccggact tcggggcagt cctcggccca | 660 |
| aagcatcagc tcatcgagag cctgcgcgac ggacgcactg acggtgtcgt ccatcacagt | 720 |
| ttgccagtga tacacatggg gatcagcaat cgcgcatatg aaatcacgcc atgtagtgta | 780 |
| ttgaccgatt ccttgcggtc cgaatgggcc gaacccgctc gtctggctaa gatcggccgc | 840 |
| agcgatcgca tccatagcct ccgcgaccgg ctgcagaaca gcgggcagtt cggtttcagg | 900 |
| caggtcttgc aacgtgacac cctgtgcacg gcgggagatg caataggtca ggctctcgct | 960 |
| gaattccca atgtcaagca cttccggaat cgggagcgcg gccgatgcaa agtgccgata | 1020 |
| aacataacga tctttgtaga aaccatcggc gcagctattt acccgcagga catatccacg | 1080 |
| ccctcctaca tcgaagctga agcacgaga ttcttcgccc tccgagagct gcatcaggtc | 1140 |
| ggagacgctg tcgaactttt cgatcagaaa cttctcgaca gacgtcgcgg tgagttcagg | 1200 |
| cttttccatg gtatatctc cttcttaaag ttaaacaaaa ttatttctag agggaaaccg | 1260 |
| ttgtggtctc cctatagtga gtcgtattaa tttcgcggga tcgagatctg atcaacctgc | 1320 |
| attaatgaat cggccaacgc gcggggagag gcggtttgcg tattgggcgc tcttccgctt | 1380 |
| cctcgctcac tgactcgctg cgctcggtcg ttcggctgcg gcgagcggta tcagctcact | 1440 |
| caaaggcggt aatacggtta tccacagaat caggggataa cgcaggaaag aacatgtgag | 1500 |
| caaaaggcca gcaaaaggcc aggaaccgta aaaaggccgc gttgctggcg ttttccata | 1560 |
| ggctccgccc cctgacgag catcacaaaa atcgacgctc aagtcagagg tggcgaaacc | 1620 |
| cgacaggact ataaagatac caggcgtttc ccctggaag ctccctcgtg cgctctcctg | 1680 |
| ttccgaccct gccgcttacc ggatacctgt ccgcctttct cccttcggga agcgtggcgc | 1740 |
| tttctcaatg ctcacgctgt aggtatctca gttcggtgta ggtcgttcgc tccaagctgg | 1800 |

```
gctgtgtgca cgaacccccc gttcagcccg accgctgcgc cttatccggt aactatcgtc    1860
ttgagtccaa cccggtaaga cacgacttat cgccactggc agcagccact ggtaacagga    1920
ttagcagagc gaggtatgta ggcggtgcta cagagttctt gaagtggtgg cctaactacg    1980
gctacactag aaggacagta tttggtatct gcgctctgct gaagccagtt accttcggaa    2040
aaagagttgg tagctcttga tccggcaaac aaaccaccgc tggtagcggt ggttttttg     2100
tttgcaagca gcagattacg cgcagaaaaa aaggatctca agaagatcct ttgatctttt    2160
ctacggggtc tgacgctcag tggaacgaaa actcacgtta agggattttg gtcatgacat    2220
taacctataa aaataggcgt atcacgaggc cctttcgtct cgcgcgtttc ggtgatgacg    2280
gtgaaaacct ctgacacatg cagctcccgg agacggtcac agcttgtctg taagcggatg    2340
ccgggagcag acaagcccgt cagggcgcgt cagcgggtgt tggcgggtgt cggggctggc    2400
ttaactatgc ggcatcagag cagattgtac tgagagtgca ccatatggac atattgtcgt    2460
tagaacgcgg ctacaattaa tacataacct tatgtatcat acacatacga tttaggtgac    2520
actatagaac ggcgcgccaa gcttggatct cctgcaggct agcctaagta cgtactcaaa    2580
atgccaacaa ataaaaaaaa agttgcttta ataatgccaa aacaaattaa taaaacactt    2640
acaacaccgg attttttta attaaaatgt gccatttagg ataaatagtt aatattttta    2700
ataattattt aaaaagccgt atctactaaa atgattttta tttggttgaa aatattaata    2760
tgtttaaatc aacacaatct atcaaaatta aactaaaaaa aaaataagtg tacgtggtta    2820
acattagtac agtaatataa gaggaaaatg agaaattaag aaattgaaag cgagtctaat    2880
ttttaaatta tgaacctgca tatataaaag gaaagaaaga atccaggaag aaaagaaatg    2940
aaaccatgca tggtcccctc gtcatcacga gtttctgcca tttgcaatag aaacactgaa    3000
acacctttct ctttgtcact taattgagat gccgaagcca cctcacacca tgaacttcat    3060
gaggtgtagc acccaaggct tccatagcca tgcatactga agaatgtctc aagctcagca    3120
ccctacttct gtgacgtgtc cctcattcac cttcctctct tccctataaa taaccacgcc    3180
tcaggttctc cgcttcacaa ctcaaacatt ctctccattg gtccttaaac actcatcagt    3240
catcaccgcg gccgcatggg aacggaccaa ggaaaaacct tcacctggga agagctggcg    3300
gcccataaca ccaaggacga cctactcttg gccatccgcg gcagggtgta cgatgtcaca    3360
aagttcttga gccgccatcc tggtggagtg gacactctcc tgctcggagc tggccgagat    3420
gttactccgg tctttgagat gtatcacgcg tttgggggctg cagatgccat tatgaagaag    3480
tactatgtcg gtacactggt ctcgaatgag ctgcccatct tcccggagcc aacggtgttc    3540
cacaaaacca tcaagacgag agtcgagggc tactttacgg atcggaacat tgatcccaag    3600
aatagaccag agatctgggg acgatacgct cttatctttg gatccttgat cgcttcctac    3660
tacgcgcagc tctttgtgcc tttcgttgtc gaacgcacat ggcttcaggt ggtgtttgca    3720
atcatcatgg gatttgcgtg cgcacaagtc ggactcaacc ctcttcatga tgcgtctcac    3780
ttttcagtga cccacaaccc cactgtctgg aagattctgg gagccacgca cgactttttc    3840
aacggagcat cgtacctggt gtggatgtac caacatatgc tcggccatca ccctacacc     3900
aacattgctg gagcagatcc cgacgtgtcg acgtctgagc ccgatgttcg tcgtatcaag    3960
cccaaccaaa agtggtttgt caaccacatc aaccagcaca tgtttgttcc tttcctgtac    4020
ggactgctgg cgttcaaggt gcgcattcag gacatcaaca ttttgtactt tgtcaagacc    4080
aatgacgcta ttcgtgtcaa tcccatctcg acatggcaca ctgtgatgtt ctggggcggc    4140
aaggctttct ttgtctggta tcgcctgatt gttccctgc agtatctgcc cctgggcaag    4200
```

```
gtgctgctct tgttcacggt cgcggacatg gtgtcgtctt actggctggc gctgaccttc    4260
caggcgaacc acgttgttga ggaagttcag tggccgttgc ctgacgagaa cgggatcatc    4320
caaaaggact gggcagctat gcaggtcgag actacgcagg attacgcaca cgattcgcac    4380
ctctggacca gcatcactgg cagcttgaac taccaggctg tgcaccatct gttccccaac    4440
gtgtcgcagc accattatcc cgatattctg gccatcatca gaacacctg cagcgagtac     4500 aaggttccat accttgtcaa ggatacgttt tggcaagcat ttgcttcaca tttggagcac    4560
ttgcgtgttc ttggactccg tcccaaggaa gagtaggcgg ccgcatttcg caccaaatca    4620
atgaaagtaa taatgaaaag tctgaataag aatacttagg cttagatgcc tttgttactt    4680
gtgtaaaata acttgagtca tgtacctttg gcggaaacag aataaataaa aggtgaaatt    4740
ccaatgctct atgtataagt tagtaatact taatgtgttc tacggttgtt tcaatatcat    4800
caaactctaa ttgaaacttt agaaccacaa atctcaatct tttcttaatg aaatgaaaaa    4860
tcttaattgt accatgttta tgttaaacac cttacaattg gttggagagg aggaccaacc    4920
gatgggacaa cattgggaga aagagattca atggagattt ggataggaga acaacattct    4980
ttttcacttc aatacaagat gagtgcaaca ctaaggatat gtatgagact ttcagaagct    5040
acgacaacat agatgagtga ggtggtgatt cctagcaaga aagacattag aggaagccaa    5100
aatcgaacaa ggaagacatc aagggcaaga gacaggacca tccatctcag gaaaaggagc    5160
tttgggatag tccgagaagt tgtacaagaa atttttttgga gggtgagtga tgcattgctg    5220
gtgactttaa ctcaatcaaa attgagaaag aaagaaaagg gaggggctc acatgtgaat     5280 agaagggaaa cggagagaatt ttacagtttt gatctaatgg gcatcccagc tagtggtaac   5340
atattcacca tgtttaacct tcacgtaccg ggccccccct cgaggtcgcc cgggggatcc    5400
gccctaagct tcgtacgtcc tcgaagagaa gggttaataa cacatttttt aacatttta    5460 acacaaattt tagttatttta aaaatttatt aaaaaattta aaataagaag aggaactctt   5520
taaataaatc taacttacaa aatttatgat ttttaataag ttttcaccaa taaaaaatgt    5580
cataaaaata tgttaaaaag tatattatca atattctctt tatgataaat aaaaagaaaa    5640
aaaaaataaa agttaagtga aaatgagatt gaagtgactt taggtgtgta taaatatatc    5700
aaccccgcca acaatttatt taatccaaat atattgaagt atattattcc atagccttta    5760
tttatttata tatttattat ataaaagctt tatttgttct aggttgttca tgaaatattt    5820
ttttggtttt atctccgttg taagaaaatc atgtgctttg tgtcgccact cactattgca    5880 gcttttttcat gcattggtca gattgacggt tgattgtatt tttgtttttt atggttttgt   5940
gttatgactt aagtcttcat ctctttatct cttcatcagg tttgatggtt acctaatatg    6000
gtccatgggt acatgcatgg ttaaattagg tggccaactt tgttgtgaac gatagaattt    6060
tttttatatt aagtaaacta ttttttatatt atgaaataat aataaaaaaa atattttatc   6120
attattaaca aaatcatatt agttaatttg ttaactctat aataaaagaa atactgtaac    6180
attcacatta catggtaaca tctttccacc ctttcatttg ttttttgttt gatgactttt    6240
tttcttgttt aaatttattt cccttctttt aaatttggaa tacattatca tcatatataa    6300
actaaaatac taaaaacagg attacacaaa tgataaataa taacacaaat atttataaat    6360
ctagctgcaa tatatttaaa ctagctatat cgatattgta aaataaaact agctgcattg    6420
atactgataa aaaaatatca tgtgcttttct ggactgatga tgcagtatac ttttgacatt   6480
gcctttattt tatttttcag aaaagctttc ttagttctgg gttcttcatt atttgtttcc    6540
```

```
catctccatt gtgaattgaa tcatttgctt cgtgtcacaa atacaattta gntaggtaca   6600
tgcattggtc agattcacgg tttattatgt catgacttaa gttcatggta gtacattacc   6660
tgccacgcat gcattatatt ggttagattt gataggcaaa tttggttgtc aacaatataa   6720
atataaataa tgttttata ttacgaaata acagtgatca aaacaaacag ttttatcttt    6780
attaacaaga ttttgttttt gtttgatgac gttttttaat gtttacgctt tcccccttct   6840
tttgaattta gaacacttta tcatcataaa atcaaatact aaaaaaatta catatttcat   6900
aaataataac acaaatattt ttaaaaaatc tgaaataata atgaacaata ttacatatta   6960
tcacgaaaat tcattaataa aaatattata taaataaaat gtaatagtag ttatatgtag   7020
gaaaaaagta ctgcacgcat aatatataca aaaagattaa aatgaactat tataaataat   7080
aacactaaat taatggtgaa tcatatcaaa ataatgaaaa agtaaataaa atttgtaatt   7140
aacttctata tgtattacac acacaaataa taaataatag taaaaaaaat tatgataaat   7200
atttaccatc tcataagata tttaaaataa tgataaaaat atagattatt ttttatgcaa   7260
ctagctagcc aaaaagagaa cacgggtata tataaaaaga gtacctttaa attctactgt   7320
acttccttta ttcctgacgt ttttatatca agtggacata cgtgaagatt ttaattatca   7380
gtctaaatat ttcattagca cttaatactt ttctgtttta ttcctatcct ataagtagtc   7440
ccgattctcc caacattgct tattcacaca actaactaag aaagtcttcc atagcccccc   7500
aagcggccgc accatgggca agggtggaga cggcggcgcg caggcggtga gcgggaccga   7560
cgcgtctctc gctgaggtga gctccgtcga tagcaagagc gtgcacgtcg tgctctacgg   7620
caagcgcgtg gatgtcacaa agttccagaa ggcacacccg ggcgggagca aggtgttccg   7680
catcttccag gagcgcgacg cgacggagca gttcgagtct taccactcgc ccaaggccat   7740
caagatgatg gagggcatgc tcaagaagtc ggaggatgcg cccgcttccg tgcccctgcc   7800
ctcgcggtcc accatgggca cggagttcaa ggagatgatt gagcgccaca agagggctgg   7860
tctctacgac ccttgcccgt tggacgagct gttcaagctc accatcgtcc ttgcgcccat   7920
cttcgtgggc gcctatctcg tgcggagcgg cgtctcgccc ctcgcgggcg cgctctccat   7980
gggctttggc ttctacctcg acggctggct tgctcacgac tacctgcatc acgcagtctt   8040
caagggctcg gtcaacacgc tcgtcaaggc gaacaacgcc atgggatacg ccctcggctt   8100
cctccagggc tacgacgtgg cctggtggcg cgcgcgccat aacacgcacc acgtgtgcac   8160
caacgaggat ggttcggacc cggacatcaa gacggcgccc ctgctcatct acgtgcgaga   8220
gaacccgtcc attgccaagc ggctcaactt cttccagcgc tggcagcagt actactatgt   8280
gccgaccatg gccatcctcg acctctactg gcgcctggag tccatcgcgt acgtggctgt   8340
gcgcctgcct aagatgtgga tgcaggccgc cgctcttgcc gctcactacg cgctcctgtg   8400
ctgggtcttc gcagcgcatc tcaacctcat ccctctcatg atggttgcac gcggcttcgc   8460
gacgggcatc gttgtctttg caacccacta tggtgaggac atcctcgacc gcgagcacgt   8520
cgagggcatg acgctcgtcg agcagaccgc caagacctcc cgtaacatca cgggcggctg   8580
gctagtgaac gtgctcacgg gcttcatctc cctgcagacc gagcatcacc tcttccccat   8640
gatgcccacc ggcaacctaa tgactatcca gcccgaggta cgcgacttct tcaagaagca   8700
tggcctcgag taccgcgagg gcaacctctt ccagtgcgtg caccagaaca tcaaggctct   8760
cgccttcgag cacctcctcc actgagcggc cgcgacacaa gtgtgagagt actaaataaa   8820
tgctttggtt gtacgaaatc attacactaa ataaaataat caaagcttat atatgccttc   8880
cgctaaggcc gaatgcaaag aaattggttc tttctcgtta tcttttgcca cttttactag   8940
```

```
tacgtattaa ttactactta atcatctttg tttacggctc attatatccg gtctagagga   9000
tccaaggccg cgaagttaaa agcaatgttg tcacttgtcg tactaacaca tgatgtgata   9060
gtttatgcta gctagctata acataagctg tctctgagtg tgttgtatat taataaagat   9120
catcactggt gaatggtgat cgtgtacgta ccctacttag taggcaatgg aagcacttag   9180
agtgtgcttt gtgcatggcc ttgcctctgt tttgagactt ttgtaatgtt ttcgagttta   9240
aatctttgcc tttgcgtacg tctagaggat ccccgg                              9276
```

<210> SEQ ID NO 125
<211> LENGTH: 11366
<212> TYPE: DNA
<213> ORGANISM: Artificial Sequence
<220> FEATURE:
<223> OTHER INFORMATION: pKR973
<220> FEATURE:
<221> NAME/KEY: misc_feature
<222> LOCATION: (5237)..(5237)
<223> OTHER INFORMATION: n is a, c, g, or t

<400> SEQUENCE: 125

```
ggagatccaa gcttggcgcg ccgttctata gtgtcaccta aatcgtatgt gtatgataca     60
taaggttatg tattaattgt agccgcgttc taacgacaat atgtccatat ggtgcactct    120
cagtacaatc tgctctgatg ccgcatagtt aagccagccc cgacacccgc caacacccgc    180
tgacgcgccc tgacgggctt gtctgctccc ggcatccgct tacagacaag ctgtgaccgt    240
ctccgggagc tgcatgtgtc agaggttttc accgtcatca ccgaaacgcg cgagacgaaa    300
gggcctcgtg atacgcctat ttttataggt taatgtcatg accaaaatcc cttaacgtga    360
gttttcgttc cactgagcgt cagaccccgt agaaaagatc aaaggatctt cttgagatcc    420 ttttttttctg cgcgtaatct gctgcttgca acaaaaaaa ccaccgctac cagcggtggt    480
ttgtttgccg gatcaagagc taccaactct ttttccgaag gtaactggct tcagcagagc    540
gcagatacca aatactgtcc ttctagtgta gccgtagtta ggccaccact tcaagaactc    600
tgtagcaccg cctacatacc tcgctctgct aatcctgtta ccagtggctg ctgccagtgg    660
cgataagtcg tgtcttaccg ggttggactc aagacgatag ttaccggata aggcgcagcg    720
gtcgggctga acggggggtt cgtgcacaca gcccagcttg gagcgaacga cctacaccga    780
actgagatac ctacagcgtg agcattgaga aagcgccacg cttcccgaag ggagaaaggc    840
ggacaggtat ccggtaagcg gcagggtcgg aacaggagag cgcacgaggg agcttccagg    900
gggaaacgcc tggtatcttt atagtcctgt cgggtttcgc cacctctgac ttgagcgtcg    960
atttttgtga tgctcgtcag ggggcggag cctatggaaa aacgccagca acgcggcctt   1020
tttacggttc ctggcctttt gctggccttt tgctcacatg ttctttcctg cgttatcccc   1080
tgattctgtg gataaccgta ttaccgcctt tgagtgagct gataccgctc gccgcagccg   1140
aacgaccgag cgcagcgagt cagtgagcga ggaagcggaa gagcgcccaa tacgcaaacc   1200
gcctctcccc gcgcgttggc cgattcatta atgcaggttg atcagatctc gatcccgcga   1260
aattaatacg actcactata gggagaccac aacggtttcc ctctagaaat aattttgttt   1320
aactttaaga aggagatata cccatggaaa agcctgaact caccgcgacg tctgtcgaga   1380
agtttctgat cgaaaagttc gacagcgtct ccgacctgat gcagctctcg gagggcgaag   1440
aatctcgtgc tttcagcttc gatgtaggag ggcgtggata tgtcctgcgg gtaaatagct   1500
gcgccgatgg tttctacaaa gatcgttatg tttatcggca ctttgcatcg gccgcgctcc   1560
```

```
cgattccgga agtgcttgac attggggaat tcagcgagag cctgacctat tgcatctccc    1620
gccgtgcaca gggtgtcacg ttgcaagacc tgcctgaaac cgaactgccc gctgttctgc    1680
agccggtcgc ggaggctatg gatgcgatcg ctgcggccga tcttagccag acgagcgggt    1740
tcggcccatt cggaccgcaa ggaatcggtc aatacactac atggcgtgat ttcatatgcg    1800
cgattgctga tccccatgtg tatcactggc aaactgtgat ggacgacacc gtcagtgcgt    1860
ccgtcgcgca ggctctcgat gagctgatgc tttgggccga ggactgcccc gaagtccggc    1920
acctcgtgca cgcggatttc ggctccaaca atgtcctgac ggacaatggc cgcataacag    1980
cggtcattga ctggagcgag gcgatgttcg gggattccca atacgaggtc gccaacatct    2040
tcttctggag gccgtggttg gcttgtatgg agcagcagac gcgctacttc gagcggaggc    2100
atccggagct tgcaggatcg ccgcggctcc gggcgtatat gctccgcatt ggtcttgacc    2160
aactctatca gagcttggtt gacggcaatt cgatgatgc agcttgggcg cagggtcgat    2220
gcgacgcaat cgtccgatcc ggagccggga ctgtcgggcg tacacaaatc gcccgcagaa    2280
gcgcggccgt ctggaccgat ggctgtgtag aagtactcgc cgatagtgga aaccgacgcc    2340
ccagcactcg tccgagggca aaggaatagt gaggtacagc ttggatcgat ccggctgcta    2400
acaaagcccg aaaggaagct gagttggctg ctgccaccgc tgagcaataa ctagcataac    2460
cccttggggc tctaaacgg gtcttgaggg gttttttgct gaaaggagga actatatccg    2520
gatgatcggg cgcgccgtcg acggatccgt acccggggat cctctagacg tacgcaaagg    2580
caaagattta aactcgaaaa cattacaaaa gtctcaaaac agaggcaagg ccatgcacaa    2640
agcacactct aagtgcttcc attgcctact aagtagggta cgtacacgat caccattcac    2700
cagtgatgat cttattaat atacaacaca ctcagagaca gcttatgtta tagctagcta    2760
gcataaacta tcacatcatg tgttagtacg acaagtgaca acattgcttt taacttcgcg    2820
gccttggatc ctctagaccg gatataatga gccgtaaaca aagatgatta agtagtaatt    2880
aatacgtact agtaaaagtg gcaaaagata acgagaaaga accaatttct ttgcattcgg    2940
ccttagcgga aggcatatat aagctttgat tattttattt agtgtaatga tttcgtacaa    3000
ccaaagcatt tatttagtac tctcacactt gtgtcgcggc cgctcagtgg aggaggtgct    3060
cgaaggcgag agccttgatg ttctggtgca cgcactggaa gaggttgccc tcgcggtact    3120
cgaggccatg cttcttgaag aagtcgcgta cctcgggctg gatagtcatt aggttgccgg    3180
tgggcatcat ggggaagagg tgatgctcgg tctgcaggga gatgaagccc gtgagcacgt    3240
tcactagcca gccgcccgtg atgttacggg aggtcttggc ggtctgctcg acgagcgtca    3300
tgccctcgac gtgctcgcgg tcgaggatgt cctcaccata gtgggttgca agacaacga    3360 tgcccgtcgc gaagccgcgt gcaaccatca tgagagggat gaggttgaga tgcgctgcga    3420
agacccagca caggagcgcg tagtgagcgg caagagcggc ggcctgcatc cacatcttag    3480
gcaggcgcac agccacgtac gcgatggact ccaggcgcca gtagaggtcg aggatggcca    3540
tggtcggcac atagtagtac tgctgccagc gctggaagaa gttgagccgc ttggcaatgg    3600
acgggttctc tcgcacgtag atgagcaggg gcgccgtctt gatgtccggg tccgaaccat    3660
cctcgttggt gcacacgtgg tgcgtgttat ggcgcgcgcg ccaccaggcc acgtcgtagc    3720
cctggaggaa gccgagggcg tatcccatgc cgttgttcgc cttgacgagc gtgttgaccg    3780
agcccttgaa gactgcgtga tgcaggtagt cgtgagcaag ccagccgtcg aggtagaagc    3840
caaagcccat ggagagcgcg cccgcgaggg gcgagacgcc gctccgcacg agataggcgc    3900
ccacgaagat gggcgcaagg acgatggtga gcttgaacag ctcgtccaac gggcaagggt    3960
```

```
cgtagagacc agccctcttg tggcgctcaa tcatctcctt gaactccgtg cccatggtgg    4020
accgcgaggg caggggcacg gaagcgggcg catcctccga cttcttgagc atgccctcca    4080
tcatcttgat ggccttgggc gagtggtaag actcgaactg ctccgtcgcg tcgcgctcct    4140
ggaagatgcg gaacaccttg ctcccgcccg ggtgtgcctt ctggaacttt gtgacatcca    4200
cgcgcttgcc gtagagcacg acgtgcacgc tcttgctatc gacggagctc acctcagcga    4260
gagacgcgtc ggtcccgctc accgcctgcg cgccgccgtc tccacccttg cccatggtgc    4320
ggccgcttgg ggggctatgg aagactttct tagttagttg tgtgaataag caatgttggg    4380
agaatcggga ctacttatag gataggaata aaacagaaaa gtattaagtg ctaatgaaat    4440
atttagactg ataattaaaa tcttcacgta tgtccacttg atataaaaac gtcaggaata    4500
aaggaagtac agtagaattt aaaggtactc ttttttatata tacccgtgtt ctcttttttgg    4560 ctagctagtt gcataaaaaa taatctatat ttttatcatt attttaaata tcttatgaga    4620
tggtaaatat ttatcataat ttttttttact attatttatt atttgtgtgt gtaatacata    4680
tagaagttaa ttacaaattt tatttacttt tcattatttt tgatatgatt caccattaat    4740
ttagtgttat tatttataat agttcatttt aatctttttg tatatattat gcgtgcagta    4800 ctttttttcct acatataact actattcat tttatttata taatattttt attaatgaat    4860
tttcgtgata atatgtaata ttgttcatta ttatttcaga ttttttaaaa atatttgtgt    4920
tattatttat gaaatatgta attttttttag tatttgattt tatgatgata aagtgttcta    4980
aattcaaaag aagggggaaa gcgtaaacat taaaaaacgt catcaaacaa aaacaaaatc    5040
ttgttaataa agataaaact gtttgttttg atcactgtta tttcgtaata taaaaacatt    5100
atttatattt atattgttga caaccaaatt tgcctatcaa atctaaccaa tataatgcat    5160
gcgtggcagg taatgtacta ccatgaactt aagtcatgac ataataaacc gtgaatctga    5220
ccaatgcatg tacctancta aattgtattt gtgacacgaa gcaaatgatt caattcacaa    5280
tggagatggg aaacaaataa tgaagaaccc agaactaaga aagcttttct gaaaaataaa    5340
ataaaggcaa tgtcaaaagt atactgcatc atcagtccag aaagcacatg atatttttt    5400 atcagtatca atgcagctag ttttattta caatatcgat atagctagtt taaatatatt    5460
gcagctagat ttataaatat ttgtgttatt atttatcatt tgtgtaatcc tgtttttagt    5520 atttagttt atatatgatg ataatgtatt ccaaatttaa aagaagggaa ataaatttaa    5580
acaagaaaaa aagtcatcaa acaaaaaaca aatgaaaggg tggaaagatg ttaccatgta    5640
atgtgaatgt tacagtattt cttttattat agagttaaca aattaactaa tatgattttg    5700
ttaataatga taaaatattt tttttattat tatttcataa tataaaaata gtttacttaa    5760
tataaaaaaa attctatcgt tcacaacaaa gttggccacc taatttaacc atgcatgtac    5820
ccatggacca tattaggtaa ccatcaaacc tgatgaagag ataaagagat gaagacttaa    5880
gtcataacac aaaaccataa aaaacaaaaa tacaatcaac cgtcaatctg accaatgcat    5940
gaaaaagctg caatagtgag tggcgacaca aagcacatga ttttcttaca acggagataa    6000
aaccaaaaaa atatttcatg aacaacctag aacaaataaa gcttttatat aataaatata    6060
taaataaata aaggctatgg aataatatac ttcaatatat ttggattaaa taaattgttg    6120
gcggggttga tatatttata cacacctaaa gtcacttcaa tctcatttttc acttaacttt    6180 tattttttt ttctttttat ttatcataaa gagaatattg ataatatact ttttaacata    6240
tttttatgac attttttatt ggtgaaaact tattaaaaat cataaatttt gtaagttaga    6300
```

```
tttatttaaa gagttcctct tcttatttta aattttttaa taaattttta aataactaaa  6360
atttgtgtta aaaatgttaa aaaatgtgtt attaaccctt ctcttcgagg acgtacgaag  6420
cttagggcgg atccccgggg cgacctcgag gggggggcccg gtacgtgaag gttaaacatg  6480
gtgaatatgt taccactagc tgggatgccc attagatcaa aactgtaaaa ttctcccgtt  6540
tcccttctat tcacatgtga gccccctccc ttttctttct ttctcaattt tgattgagtt  6600
aaagtcacca gcaatgcatc actcaccctc caaaaaattt cttgtacaac ttctcggact  6660
atcccaaagc tccttttcct gagatggatg gtcctgtctc ttgcccttga tgtcttcctt  6720
gttcgatttt ggcttcctct aatgtctttc ttgctaggaa tcaccacctc actcatctat  6780
gttgtcgtag cttctgaaag tctcatacat atccttagtg ttgcactcat cttgtattga  6840
agtgaaaaag aatgttgttc tcctatccaa atctccattg aatctctttc tcccaatgtt  6900
gtcccatcgg ttggtcctcc tctccaacca attgtaaggt gtttaacata aacatggtac  6960
aattaagatt tttcatttca ttaagaaaag attgagattt gtggttctaa agtttcaatt  7020
agagtttgat gatattgaaa caaccgtaga acacattaag tattactaac ttatacatag  7080
agcattggaa tttcacctt tatttattct gtttccgcca aaggtacatg actcaagtta   7140
ttttacacaa gtaacaaagg catctaagcc taagtattct tattcagact tttcattatt  7200
actttcattg atttggtgcg aaatgcggcc gcctactctt ccttgggacg gagtccaaga  7260
acacgcaagt gctccaaatg tgaagcaaat gcttgccaaa acgtatcctt gacaaggtat  7320
ggaaccttgt actcgctgca ggtgttcttg atgatggcca gaatatcggg ataatggtgc  7380
tgcgacacgt tggggaacag atggtgcaca gcctggtagt tcaagctgcc agtgatgctg  7440
gtccagaggt gcgaatcgtg tgcgtaatcc tgcgtagtct cgacctgcat agctgcccag  7500
tccttttgga tgatcccgtt ctcgtcaggc aacggccact gaacttcctc aacaacgtgg  7560
ttcgcctgga aggtcagcgc cagccagtaa gacgacacca tgtccgcgac cgtgaacaag  7620
agcagcacct tgcccagggg cagatactgc aggggaacaa tcaggcgata ccagacaaag  7680
aaagccttgc cgccccagaa catcacagtg tgccatgtcg agatgggatt gacacgaata  7740
gcgtcattgg tcttgacaaa gtacaaaatg ttgatgtcct gaatgcgcac cttgaacgcc  7800
agcagtccgt acaggaaagg aacaaacatg tgctggttga tgtggttgac aaaccacttt  7860
tggttgggct tgatacgacg aacatcgggc tcagacgtcg acacgtcggg atctgctcca  7920
gcaatgttgg tgtaggggtg atggccgagc atatgttggt acatccacac caggtacgat  7980
gctccgttga aaaagtcgtg cgtggctccc agaatcttcc agacagtggg gttgtgggtc  8040
actgaaaagt gagacgcatc atgaagaggg ttgagtccga cttgtgcgca cgcaaatccc  8100
atgatgattg caaacaccac ctgaagccat gtgcgttcga caacgaaagg cacaaagagc  8160
tgcgcgtagt aggaagcgat caaggatcca aagataagag cgtatcgtcc ccagatctct  8220
ggtctattct tgggatcaat gttccgatcc gtaaagtagc cctcgactct cgtcttgatg  8280
gttttgtgga acaccgttgg ctccgggaag atgggcagct cattcgagac cagtgtaccg  8340
acatagtact tcttcataat ggcatctgca gccccaaacg cgtgatacat ctcaaagacc  8400
ggagtaacat ctcggccagc tccgagcagg agagtgtcca ctccaccagg atggcggctc  8460
aagaactttg tgacatcgta caccctgccg cggatggcca agagtaggtc gtccttggtg  8520
ttatgggccg ccagctcttc ccaggtgaag gttttccctt ggtccgttcc catgcggccg  8580
cggtgatgac tgatgagtgt ttaaggacca atggagagaa tgtttgagtt gtgaagcgga  8640
gaacctgagg cgtggttatt tatagggaag agaggaaggt gaatgaggga cacgtcacag  8700
```

```
aagtagggtg ctgagcttga gacattcttc agtatgcatg gctatggaag ccttgggtgc   8760
tacacctcat gaagttcatg gtgtgaggtg gcttcggcat ctcaattaag tgacaaagag   8820
aaaggtgttt cagtgtttct attgcaaatg gcagaaactc gtgatgacga ggggaccatg   8880
catggtttca tttcttttct tcctggattc tttctttcct tttatatatg caggttcata   8940
atttaaaaat tagactcgct ttcaatttct taatttctca ttttcctctt atattactgt   9000
actaatgtta accacgtaca cttattttt ttttagttta attttgatag attgtgttga   9060
tttaaacata ttaatatttt caaccaaata aaaatcattt tagtagatac ggcttttaa    9120 ataattatta aaatattaa ctatttatcc taaatggcac attttaatta aaaaaaatcc    9180
ggtgttgtaa gtgttttatt aatttgtttt ggcattatta aagcaacttt ttttttattt   9240
gttggcattt tgagtacgta cttaggctag cctgcaggcc aactgcgttt ggggctccag   9300
attaaacgac gccgtttcgt tcctttcgct tcacggctta acgatgtcgt ttctgtctgt   9360
gcccaaaaaa taaaggcatt tgttatttgc accagatatt tactaagtgc accctagttt   9420
gacaagtagg cgataattac aaatagatgc ggtgcaaata ataaattttg aaggaaataa   9480
ttacaaagaa acagaactta tatttacttt attttaaaaa actaaaatga aagaacaaaa   9540
aaagtaaaaa atacaaaaaa tgtgcttaaa ccactttcat tatttgttac agaaagtatg   9600
attctactca aattgatctg ttgtatctgg tgctgccttg tcacactggc gatttcaatc   9660
ccctaaagat atggtgcaaa ctgcgaagtg atcaatatct gctcggttaa tttagattaa   9720
ttaataatat tcaacgtgat gtaccaaaaa aagacaattt tttgctccat tgacaaatta   9780
aacctcatca aggtaatttc caaacctata agcaaaaaaa tttcacatta attggcccgc   9840
aatcctatta gtcttattat actagagtag gaaaaaaaac aattacacaa cttgtcttat   9900
tattctctat gctaatgaat attttttccct tttgttagaa atcagtgttt cctaatttat   9960
tgagtattaa ttccactcac cgcatatatt taccgttgaa taagaaaatt ttacacataa   10020 ttcttttaa gataaataat tttttatac tagatcttat atgattacgt gaagccaagt    10080
gggttatact aatgatatat aatgtttgat agtaatcagt ttataaacca aatgcatgga   10140
aatgttacgt ggaagcacgt aaattaacaa gcattgaagc aaatgcagcc accgcaccaa   10200
aaccacccca cttcacttcc acgtaccata ttccatgcaa ctacaacacc ctaaaacttc   10260
aataaatgcc cccaccttca cttcacttca cccatcaata gcaagcggcc gcaccatgga   10320
ggtggtgaat gaaatagtct caattgggca ggaagtttta cccaaagttg attatgccca   10380
actctggagt gatgccagtc actgtgaggt gcttacttg tccatcgcat ttgtcatctt    10440
gaagttcact cttggccccc ttggtccaaa aggtcagtct cgtatgaagt ttgttttcac   10500
caattacaac cttctcatgt ccatttattc gttgggatca ttcctctcaa tggcatatgc   10560
catgtacacc atcggtgtta tgtctgacaa ctgcgagaag gcttttgaca acaacgtctt   10620
caggatcacc acgcagttgt tctatttgag caagttcctg gagtatattg actccttcta   10680
tttgccactg atgggcaagc ctctgacctg gttgcaattc ttccatcatt tgggggcacc   10740
gatggatatg tggctgttct ataattaccg aaatgaagct gtttggattt ttgtgctgtt   10800
gaatggtttc atccactgga tcatgtacgg ttattattgg accagattga tcaagctgaa   10860
gttccccatg ccaaaatccc tgattacatc aatgcagatc attcaattca atgttggttt   10920
ctacattgtc tggaagtaca ggaacattcc ctgttatcgc caagatggga tgaggatgtt   10980
tggctggttc ttcaattact tttatgttgg cacagtcttg tgtttgttct tgaatttcta   11040
```

```
tgtgcaaacg tatatcgtca ggaagcacaa gggagccaaa aagattcagt gagcggccgc  11100
gaagttaaaa gcaatgttgt cacttgtcgt actaacacat gatgtgatag tttatgctag  11160
ctagctataa cataagctgt ctctgagtgt gttgtatatt aataaagatc atcactggtg  11220
aatggtgatc gtgtacgtac cctacttagt aggcaatgga agcacttaga gtgtgctttg  11280
tgcatggcct tgcctctgtt ttgagacttt tgtaatgttt tcgagtttaa atctttgcct  11340
ttgcgtacgt ctagagtcga cctgca                                       11366

<210> SEQ ID NO 126
<211> LENGTH: 5671
<212> TYPE: DNA
<213> ORGANISM: Artificial Sequence
<220> FEATURE:
<223> OTHER INFORMATION: pKS129

<400> SEQUENCE: 126
ggccgcaagt atgaactaaa atgcatgtag gtgtaagagc tcatggagag catggaatat    60
tgtatccgac catgtaacag tataataact gagctccatc tcacttcttc tatgaataaa   120
caaaggatgt tatgatatat taacactcta tctatgcacc ttattgttct atgataaatt   180
tcctcttatt attataaatc atctgaatcg tgacggctta tggaatgctt caaatagtac   240
aaaaacaaat gtgtactata agactttcta aacaattcta accttagcat gtgaacgag    300 acataagtgt taagaagaca taacaattat aatggaagaa gtttgtctcc atttatatat   360
tatatattac ccacttatgt attatattag gatgttaagg agacataaca attataaaga   420
gagaagtttg tatccattta tatattatat actacccatt tatatattat acttatccac   480
ttatttaatg tctttataag gtttgatcca tgatatttct aatatttag ttgatatgta   540 tatgaaaggg tactatttga actctcttac tctgtataaa ggttggatca tccttaaagt   600
gggtctattt aattttattg cttcttacag ataaaaaaaa aattatgagt tggtttgata   660
aaatattgaa ggatttaaaa taataataaa taacatataa tatatgtata taaatttatt   720
ataatataac atttatctat aaaaaagtaa atattgtcat aaatctatac aatcgtttag   780
ccttgctgga cgaatctcaa ttatttaaac gagagtaaac atatttgact ttttggttat   840
ttaacaaatt attatttaac actatatgaa attttttttt ttatcagcaa agaataaaat   900
taaattaaga aggacaatgg tgtcccaatc cttatacaac caacttccac aagaaagtca   960
agtcagagac aacaaaaaaa caagcaaagg aaatttttta atttgagttg tcttgtttgc  1020
tgcataattt atgcagtaaa acactacaca taaccctttt agcagtagag caatggttga  1080
ccgtgtgctt agcttctttt attttatttt tttatcagca aagaataaat aaaataaaat  1140
gagacacttc agggatgttt caacaagctt ggatccgtcg acggcgcgcc cgatcatccg  1200
gatatagttc ctcctttcag caaaaaaccc ctcaagaccc gtttagaggc cccaaggggt  1260
tatgctagtt attgctcagc ggtggcagca gccaactcag cttcctttcg ggctttgtta  1320
gcagccggat cgatccaagc tgtacctcac tattcctttg ccctcggacg agtgctgggg  1380
cgtcggtttc cactatcggc gagtacttct acacagccat cggtccagac ggccgcgctt  1440
ctgcgggcga tttgtgtacg cccgacagtc ccggctccgg atcggacgat tgcgtcgcat  1500
cgaccctgcg cccaagctgc atcatcgaaa ttgccgtcaa ccaagctctg atagagttgg  1560
tcaagaccaa tgcggagcat atacgcccgg agccgcggcg atcctgcaag ctccggatgc  1620
ctccgctcga gtagcgcgt ctgctgctcc atacaagcca accacggcct ccagaagaag  1680
atgttggcga cctcgtattg ggaatccccg aacatcgcct cgctccagtc aatgaccgct  1740
```

```
gttatgcggc cattgtccgt caggacattg ttggagccga atccgcgtg cacgaggtgc    1800 cggacttcgg ggcagtcctc ggcccaaagc atcagctcat cgagagcctg cgcgacggac    1860
gcactgacgg tgtcgtccat cacagtttgc cagtgataca catggggatc agcaatcgcg    1920
catatgaaat cacgccatgt agtgtattga ccgattcctt gcggtccgaa tgggccgaac    1980
ccgctcgtct ggctaagatc ggccgcagcg atcgcatcca tagcctccgc gaccggctgc    2040
agaacagcgg gcagttcggt ttcaggcagg tcttgcaacg tgacaccctg tgcacggcgg    2100
gagatgcaat aggtcaggct ctcgctgaat tccccaatgt caagcacttc cggaatcggg    2160
agcgcggccg atgcaaagtg ccgataaaca taacgatctt tgtagaaacc atcggcgcag    2220
ctatttaccc gcaggacata tccacgcccct cctacatcga agctgaaagc acgagattct    2280
tcgccctccg agagctgcat caggtcggag acgctgtcga acttttcgat cagaaacttc    2340
tcgacagacg tcgcggtgag ttcaggcttt tccatgggta tatctccttc ttaaagttaa    2400
acaaaattat ttctagaggg aaaccgttgt ggtctcccta tagtgagtcg tattaatttc    2460 gcggatcga gatctgatca acctgcatta atgaatcggc caacgcgcgg ggagaggcgg    2520
tttgcgtatt gggcgctctt ccgcttcctc gctcactgac tcgctgcgct cggtcgttcg    2580
gctgcggcga gcggtatcag ctcactcaaa ggcggtaata cggttatcca cagaatcagg    2640
ggataacgca ggaaagaaca tgtgagcaaa aggccagcaa aaggccagga accgtaaaaa    2700
ggccgcgttg ctggcgtttt tccataggct ccgcccccct gacgagcatc acaaaaatcg    2760
acgctcaagt cagaggtggc gaaacccgac aggactataa agataccagg cgtttccccc    2820
tggaagctcc ctcgtgcgct ctcctgttcc gaccctgccg cttaccggat acctgtccgc    2880
ctttctccct tcgggaagcg tggcgctttc tcaatgctca cgctgtaggt atctcagttc    2940
ggtgtaggtc gttcgctcca agctgggctg tgtgcacgaa ccccccgttc agcccgaccg    3000
ctgcgcctta tccggtaact atcgtcttga gtccaacccg gtaagacacg acttatcgcc    3060
actggcagca gccactggta acaggattag cagagcgagg tatgtaggcg gtgctacaga    3120
gttcttgaag tggtggccta actacggcta cactagaagg acagtatttg gtatctgcgc    3180
tctgctgaag ccagttacct tcggaaaaag agttggtagc tcttgatccg gcaaacaaac    3240
caccgctggt agcggtggtt tttttgtttg caagcagcag attacgcgca gaaaaaaagg    3300
atctcaagaa gatcctttga tcttttctac ggggtctgac gctcagtgga acgaaaactc    3360
acgttaaggg attttggtca tgacattaac ctataaaaat aggcgtatca cgaggccctt    3420
tcgtctcgcg cgtttcggtg atgacggtga aaacctctga cacatgcagc tcccggagac    3480
ggtcacagct tgtctgtaag cggatgccgg gagcagacaa gcccgtcagg gcgcgtcagc    3540
gggtgttggc gggtgtcggg gctggcttaa ctatgcggca tcagagcaga ttgtactgag    3600
agtgcaccat atggacatat tgtcgttaga acgcggctac aattaataca taaccttatg    3660
tatcatacac atacgattta ggtgacacta tagaacggcg cgccaagctt tgatccatg    3720 cccttcattt gccgcttatt aattaattg gtaacagtcc gtactaatca gttacttatc    3780
cttcccccat cataattaat cttggtagtc tcgaatgcca caacactgac tagtctcttg    3840
gatcataaga aaaagccaag gaacaaaaga agacaaaaca caatgagagt atcctttgca    3900
tagcaatgtc taagttcata aaattcaaac aaaaacgcaa tcacacacag tggacatcac    3960
ttatccacta gctgatcagg atcgccgcgt caagaaaaaa aaactggacc ccaaaagcca    4020
tgcacaacaa cacgtactca caaaggtgtc aatcgagcag cccaaaacat tcaccaactc    4080
```

```
aacccatcat gagccctcac atttgttgtt tctaacccaa cctcaaactc gtattctctt    4140
ccgccacctc atttttgttt atttcaacac ccgtcaaact gcatgccacc ccgtggccaa    4200
atgtccatgc atgttaacaa gacctatgac tataaatagc tgcaatctcg gcccaggttt    4260
tcatcatcaa gaaccagttc aatatcctag tacaccgtat taaagaattt aagatatact    4320
gcggccgcat gggaacggac caaggaaaaa ccttcacctg gaagagctg gcggcccata     4380 acaccaagga cgacctactc ttggccatcc gcggcagggt gtacgatgtc acaaagttct    4440
tgagccgcca tcctggtgga gtggacactc tcctgctcgg agctggccga tgttactc      4500 cggtctttga gatgtatcac gcgtttgggg ctgcagatgc cattatgaag aagtactatg    4560
tcggtacact ggtctcgaat gagctgccca tcttcccgga ccaacggtg ttccacaaaa    4620 ccatcaagac gagagtcgag ggctacttta cggatcggaa cattgatccc aagaatagac    4680
cagagatctg gggacgatac gctcttatct ttggatcctt gatcgcttcc tactacgcgc    4740
agctctttgt gcctttcgtt gtcgaacgca catggcttca ggtggtgttt gcaatcatca    4800
tgggatttgc gtgcgcacaa gtcggactca accctcttca tgatgcgtct cacttttcag    4860
tgacccacaa ccccactgtc tggaagattc tgggagccac gcacgacttt tcaacggag    4920 catcgtacct ggtgtggatg taccaacata tgctcggcca tcaccctac accaacattg     4980 ctggagcaga tccgacgtg tcgacgtctg agccgatgt tcgtcgtatc aagcccaacc      5040
aaaagtggtt tgtcaaccac atcaaccagc acatgtttgt tccttcctg tacggactgc     5100 tggcgttcaa ggtgcgcatt caggacatca acattttgta ctttgtcaag accaatgacg    5160
ctattcgtgt caatcccatc tcgacatggc acactgtgat gttctggggc ggcaaggctt    5220
tctttgtctg gtatcgcctg attgttcccc tgcagtatct gcccctgggc aaggtgctgc    5280
tcttgttcac ggtcgcggac atggtgtcgt cttactggct ggcgctgacc ttccaggcga    5340
accacgttgt tgaggaagtt cagtggccgt tgcctgacga aacgggatc atccaaaagg     5400 actgggcagc tatgcaggtc gagactacgc aggattacgc acacgattcg cacctctgga    5460
ccagcatcac tggcagcttg aactaccagg ctgtgcacca tctgttcccc aacgtgtcgc    5520
agcaccatta tcccgatatt ctggccatca tcaagaacac ctgcagcgag tacaaggttc    5580 catacttgt caaggatacg tttttggcaag catttgcttc acatttggag cacttgcgtg    5640
ttcttggact ccgtcccaag gaagagtagg c                                    5671
```

<210> SEQ ID NO 127
<211> LENGTH: 6601
<212> TYPE: DNA
<213> ORGANISM: Artificial Sequence
<220> FEATURE:
<223> OTHER INFORMATION: pKR606
<220> FEATURE:
<221> NAME/KEY: misc_feature
<222> LOCATION: (5689)..(5689)
<223> OTHER INFORMATION: n is a, c, g, or t

<400> SEQUENCE: 127

```
ggccgcatgg gaacggacca aggaaaaacc ttcacctggg aagagctggc ggcccataac      60
accaaggacg acctactctt ggccatccgc ggcagggtgt acgatgtcac aaagttcttg    120
agccgccatc ctggtggagt ggacactctc ctgctcggag ctggccgaga tgttactccg    180
gtctttgaga tgtatcacgc gtttgggct gcagatgcca ttatgaagaa gtactatgtc     240
ggtacactgg tctcgaatga gctgcccatc ttcccggagc aacggtgtt ccacaaaacc    300 atcaagacga gagtcgaggg ctactttacg gatcggaaca ttgatcccaa gaatagacca    360
```

-continued

```
gagatctggg gacgatacgc tcttatcttt ggatccttga tcgcttccta ctacgcgcag    420
ctctttgtgc ctttcgttgt cgaacgcaca tggcttcagg tggtgtttgc aatcatcatg    480
ggatttgcgt gcgcacaagt cggactcaac cctcttcatg atgcgtctca cttttcagtg    540
acccacaacc ccactgtctg gaagattctg ggagccacgc acgactttt caacggagca    600
tcgtacctgg tgtggatgta ccaacatatg ctccggccatc accccctacac caacattgct    660
ggagcagatc ccgacgtgtc gacgtctgag cccgatgttc gtcgtatcaa gcccaaccaa    720
aagtggtttg tcaaccacat caaccagcac atgtttgttc ctttcctgta cggactgctg    780
gcgttcaagg tgcgcattca ggacatcaac attttgtact ttgtcaagac caatgacgct    840
attcgtgtca atcccatctc gacatggcac actgtgatgt tctggggcgg caaggctttc    900
tttgtctggt atcgcctgat tgttcccctg cagtatctgc ccctgggcaa ggtgctgctc    960
ttgttcacgg tcgcggacat ggtgtcgtct tactggctgg cgctgacctt ccaggcgaac    1020
cacgttgttg aggaagttca gtggccgttg cctgacgaga acgggatcat ccaaaaggac    1080
tgggcagcta tgcaggtcga gactacgcag gattacgcac acgattcgca cctctggacc    1140
agcatcactg gcagcttgaa ctaccaggct gtgcaccatc tgttccccaa cgtgtcgcag    1200
caccattatc ccgatattct ggccatcatc aagaacacct gcagcgagta caaggttcca    1260
taccttgtca aggatacgtt tggcaagca tttgcttcac atttggagca cttgcgtgtt    1320
cttggactcc gtcccaagga gagtaggcg gccgcgacac aagtgtgaga gtactaaata    1380
aatgctttgg ttgtacgaaa tcattacact aaataaaata atcaaagctt atatatgcct    1440
tccgctaagg ccgaatgcaa agaaattggt tcttttctcgt tatctttgc cacttttact    1500
agtacgtatt aattactact taatcatctt tgtttacggc tcattatatc cggtctagag    1560
gatccaaggc cgcgaagtta aaagcaatgt tgtcacttgt cgtactaaca catgatgtga    1620
tagtttatgc tagctagcta aacataagc tgtctctgag tgtgttgtat attaataaag    1680
atcatcactg gtgaatggtg atcgtgtacg taccctactt agtaggcaat ggaagcactt    1740
agagtgtgct ttgtgcatgg ccttgcctct gttttgagac ttttgtaatg ttttcgagtt    1800
taaatctttg cctttgcgta cgtgggcgga tcccccgggc tgcaggaatt cactggccgt    1860
cgttttacaa cgtcgtgact gggaaaaccc tggcgttacc caacttaatc gccttgcagc    1920
acatcccct ttcgccagct ggcgtaatag cgaagaggcc cgcaccgatc gcccttccca    1980
acagttgcgc agcctgaatg gcgaatggcg cctgatgcgg tatttctcc ttacgcatct    2040
gtgcggtatt tcacaccgca tatggtgcac tctcagtaca atctgctctg atgccgcata    2100
gttaagccag ccccgacacc cgccaacacc cgctgacgcg ccctgacggg cttgtctgct    2160
cccggcatcc gcttacagac aagctgtgac cgtctccggg agctgcatgt gtcagaggtt    2220
ttcaccgtca tcaccgaaac gcgcgagacg aaagggcctc gtgatacgcc tatttttata    2280
ggttaatgtc atgataataa tggtttctta gacgtcaggt ggcacttttc ggggaaatgt    2340
gcgcggaacc cctatttgtt tatttttcta aatacattca aatatgtatc cgctcatgag    2400
acaataaccc tgataaatgc ttcaataata ttgaaaaagg aagagtatga gtattcaaca    2460
tttccgtgtc gcccttattc cctttttgc ggcattttgc cttcctgttt ttgctcaccc    2520
agaaacgctg gtgaaagtaa aagatgctga agatcagttg ggtgcacgag tgggttacat    2580
cgaactggat ctcaacagcg gtaagatcct tgagagtttt cgccccgaag aacgttttcc    2640
aatgatgagc acttttaaag ttctgctatg tggcgcggta ttatcccgta ttgacgccgg    2700
```

```
gcaagagcaa ctcggtcgcc gcatacacta ttctcagaat gacttggttg agtactcacc    2760
agtcacagaa aagcatctta cggatggcat gacagtaaga gaattatgca gtgctgccat    2820
aaccatgagt gataacactg cggccaactt acttctgaca acgatcggag gaccgaagga    2880
gctaaccgct tttttgcaca acatggggga tcatgtaact cgccttgatc gttgggaacc    2940
ggagctgaat gaagccatac caaacgacga gcgtgacacc acgatgcctg tagcaatggc    3000
aacaacgttg cgcaaactat taactggcga actacttact ctagcttccc ggcaacaatt    3060
aatagactgg atggaggcgg ataaagttgc aggaccactt ctgcgctcgg cccttccggc    3120
tggctggttt attgctgata atctggagc cggtgagcgt gggtctcgcg gtatcattgc    3180
agcactgggg ccagatggta agccctcccg tatcgtagtt atctacacga cggggagtca    3240
ggcaactatg gatgaacgaa atagacagat cgctgagata ggtgcctcac tgattaagca    3300
ttggtaactg tcagaccaag tttactcata tatactttag attgatttaa aacttcattt    3360
ttaatttaaa aggatctagg tgaagatcct ttttgataat ctcatgacca aaatccctta    3420
acgtgagttt tcgttccact gagcgtcaga ccccgtagaa aagatcaaag gatcttcttg    3480
agatcctttt tttctgcgcg taatctgctg cttgcaaaca aaaaaaccac cgctaccagc    3540
ggtggtttgt ttgccggatc aagagctacc aactcttttt ccgaaggtaa ctggcttcag    3600
cagagcgcag ataccaaata ctgtccttct agtgtagccg tagttaggcc accacttcaa    3660
gaactctgta gcaccgccta catacctcgc tctgctaatc ctgttaccag tggctgctgc    3720
cagtggcgat aagtcgtgtc ttaccgggtt ggactcaaga cgatagttac cggataaggc    3780
gcagcggtcg ggctgaacgg ggggttcgtg cacacagccc agcttggagc gaacgaccta    3840
caccgaactg agatacctac agcgtgagct atgagaaagc gccacgcttc ccgaagggag    3900
aaaggcggac aggtatccgg taagcggcag ggtcggaaca ggagagcgca cgagggagct    3960
tccaggggga aacgcctggt atctttatag tcctgtcggg tttcgccacc tctgacttga    4020
gcgtcgattt ttgtgatgct cgtcaggggg gcggagccta tggaaaaacg ccagcaacgc    4080
ggccttttta cggttcctgg ccttttgctg gccttttgct cacatgttct ttcctgcgtt    4140
atcccctgat tctgtggata accgtattac cgcctttgag tgagctgata ccgctcgccg    4200
cagccgaacg accgagcgca gcgagtcagt gagcgaggaa gcggaagagc gcccaatacg    4260
caaaccgcct ctccccgcgc gttggccgat tcattaatgc agctggcacg acaggtttcc    4320
cgactggaaa gcgggcagtg agcgcaacgc aattaatgtg agttagctca ctcattaggc    4380
accccaggct ttacacttta tgcttccggc tcgtatgttg tgtggaattg tgagcggata    4440
acaatttcac acaggaaaca gctatgacca tgattacgcc aagcttgcat gcctgcaggt    4500
cgactcgacg tacgtcctcg aagagaaggg ttaataacac atttttttaac attttttaaca    4560 caaattttag ttatttaaaa atttattaaa aatttaaaa taagaagagg aactctttaa    4620
ataaatctaa cttacaaaat ttatgatttt taataagttt tcaccaataa aaaatgtcat    4680
aaaaatatgt taaaaagtat attatcaata ttctctttat gataaataaa aagaaaaaaa    4740
aaataaaagt taagtgaaaa tgagattgaa gtgactttag gtgtgtataa atatatcaac    4800
cccgccaaca atttatttaa tccaaatata ttgaagtata ttattccata gcctttattt    4860
atttatatat ttattatata aaagctttat ttgttctagg ttgttcatga atatttttt     4920 tggttttatc tccgttgtaa gaaaatcatg tgctttgtgt cgccactcac tattgcagct    4980
ttttcatgca ttggtcagat tgacggttga ttgtattttt gtttttatg gttttgtgtt     5040 atgacttaag tcttcatctc tttatctctt catcaggttt gatggttacc taatatggtc    5100
```

```
catgggtaca tgcatggtta aattaggtgg ccaactttgt tgtgaacgat agaattttt    5160 ttatattaag taaactattt ttatattatg aaataataat aaaaaaaata ttttatcatt    5220
attaacaaaa tcatattagt taatttgtta actctataat aaaagaaata ctgtaacatt    5280
cacattacat ggtaacatct ttccaccctt tcatttgttt tttgtttgat gactttttt    5340 cttgtttaaa tttatttccc ttcttttaaa tttggaatac attatcatca tatataaact    5400
aaaatactaa aaacaggatt acacaaatga taaataataa cacaaatatt tataaatcta    5460
gctgcaatat atttaaacta gctatatcga tattgtaaaa taaaactagc tgcattgata    5520
ctgataaaaa aatatcatgt gctttctgga ctgatgatgc agtatacttt tgacattgcc    5580
tttattttat ttttcagaaa agctttctta gttctgggtt cttcattatt tgtttcccat    5640
ctccattgtg aattgaatca tttgcttcgt gtcacaaata caatttagnt aggtacatgc    5700
attggtcaga ttcacggttt attatgtcat gacttaagtt catggtagta cattacctgc    5760
cacgcatgca ttatattggt tagatttgat aggcaaattt ggttgtcaac aatataaata    5820
taaataatgt ttttatatta cgaaataaca gtgatcaaaa caaacagttt tatctttatt    5880
aacaagattt tgttttgtt tgatgacgtt ttttaatgtt tacgctttcc cccttcttt    5940 gaatttagaa cactttatca tcataaaatc aaatactaaa aaaattacat atttcataaa    6000
taataacaca aatattttta aaaaatctga aataataatg aacaatatta catattatca    6060
cgaaaattca ttaataaaaa tattatataa ataaaatgta atagtagtta tatgtaggaa    6120
aaaagtactg cacgcataat atatacaaaa agattaaaat gaactattat aaataataac    6180
actaaattaa tggtgaatca tatcaaaata atgaaaagt aaataaaatt tgtaattaac    6240
ttctatatgt attacacaca caaataataa ataatagtaa aaaaaattat gataaatatt    6300
taccatctca taagatattt aaaataatga taaaaatata gattattttt tatgcaacta    6360
gctagccaaa aagagaacac gggtatatat aaaaagagta cctttaaatt ctactgtact    6420
tcctttattc ctgacgtttt tatatcaagt ggacatacgt gaagatttta attatcagtc    6480 taaaatttc attagcactt aatacttttc tgttttattc ctatcctata agtagtcccg    6540
attctcccaa cattgcttat tcacacaact aactaagaaa gtcttccata gccccccaag    6600
c                                                                   6601
```

<210> SEQ ID NO 128
<211> LENGTH: 6494
<212> TYPE: DNA
<213> ORGANISM: Artificial Sequence
<220> FEATURE:
<223> OTHER INFORMATION: pKR804
<220> FEATURE:
<221> NAME/KEY: misc_feature
<222> LOCATION: (3761)..(3761)
<223> OTHER INFORMATION: n is a, c, g, or t

<400> SEQUENCE: 128

```
ccggccggat ctcgtacgga tccgtcgacg gcgcgcccga tcatccggat atagttcctc      60
ctttcagcaa aaaacccctc aagacccgtt tagaggcccc aaggggttat gctagttatt     120
gctcagcggt ggcagcagcc aactcagctt cctttcgggc tttgttagca gccggatcga     180
tccaagctgt acctcactat tcctttgccc tcggacgagt gctggggcgt cggtttccac     240
tatcggcgag tacttctaca cagccatcgg tccagacggc cgcgcttctg cgggcgattt     300
gtgtacgccc gacagtcccg gctccggatc ggacgattgc gtcgcatcga ccctgcgccc     360
```

```
aagctgcatc atcgaaattg ccgtcaacca agctctgata gagttggtca agaccaatgc    420
ggagcatata cgcccggagc cgcggcgatc ctgcaagctc cggatgcctc cgctcgaagt    480
agcgcgtctg ctgctccata caagccaacc acggcctcca gaagaagatg ttggcgacct    540
cgtattggga atccccgaac atcgcctcgc tccagtcaat gaccgctgtt atgcggccat    600
tgtccgtcag gacattgttg gagccgaaat ccgcgtgcac gaggtgccgg acttcggggc    660
agtcctcggc ccaaagcatc agctcatcga gagcctgcgc gacggacgca ctgacggtgt    720
cgtccatcac agtttgccag tgatacacat ggggatcagc aatcgcgcat atgaaatcac    780
gccatgtagt gtattgaccg attccttgcg gtccgaatgg gccgaacccg ctcgtctggc    840
taagatcggc cgcagcgatc gcatccatag cctccgcgac cggctgcaga acagcgggca    900
gttcggtttc aggcaggtct tgcaacgtga caccctgtgc acggcgggag atgcaatagg    960
tcaggctctc gctgaattcc ccaatgtcaa gcacttccgg aatcgggagc gcggccgatg   1020
caaagtgccg ataaacataa cgatctttgt agaaaccatc ggcgcagcta tttacccgca   1080
ggacatatcc acgccctcct acatcgaagc tgaaagcacg agattcttcg ccctccgaga   1140
gctgcatcag gtcggagacg ctgtcgaact tttcgatcag aaacttctcg acagacgtcg   1200
cggtgagttc aggcttttcc atgggtatat ctccttctta aagttaaaca aaattatttc   1260
tagagggaaa ccgttgtggt ctccctatag tgagtcgtat taatttcgcg ggatcgagat   1320
ctgatcaacc tgcattaatg aatcggccaa cgcgcgggga gaggcggttt gcgtattggg   1380
cgctcttccg cttcctcgct cactgactcg ctgcgctcgg tcgttcggct gcggcgagcg   1440
gtatcagctc actcaaaggc ggtaatacgg ttatccacag aatcagggga taacgcagga   1500
aagaacatgt gagcaaaagg ccagcaaaag gccaggaacc gtaaaaaggc cgcgttgctg   1560
gcgttttttcc ataggctccg cccccctgac gagcatcaca aaaatcgacg ctcaagtcag   1620
aggtggcgaa acccgacagg actataaaga taccaggcgt ttccccctgg aagctccctc   1680
gtgcgctctc ctgttccgac cctgccgctt accggatacc tgtccgcctt tctcccttcg   1740
ggaagcgtgg cgctttctca atgctcacgc tgtaggtatc tcagttcggt gtaggtcgtt   1800
cgctccaagc tgggctgtgt gcacgaaccc cccgttcagc ccgaccgctg cgccttatcc   1860
ggtaactatc gtcttgagtc aacccggta agacacgact tatcgccact ggcagcagcc   1920
actggtaaca ggattagcag agcgaggtat gtaggcggtg ctacagagtt cttgaagtgg   1980
tggcctaact acggctacac tagaaggaca gtatttggta tctgcgctct gctgaagcca   2040
gttaccttcg gaaaaagagt tggtagctct tgatccggca acaaaccac cgctggtagc   2100
ggtggttttt tgtttgcaa gcagcagatt acgcgcagaa aaaaggatc tcaagaagat   2160
cctttgatct tttctacggg gtctgacgct cagtggaacg aaaactcacg ttaagggatt   2220
ttggtcatga cattaaccta aaaaatagg cgtatcacga ggccctttcg tctcgcgcgt   2280
ttcggtgatg acggtgaaaa cctctgacac atgcagctcc cggagacggt cacagcttgt   2340
ctgtaagcgg atgccgggag cagacaagcc cgtcagggcg cgtcagcggg tgttggcggg   2400
tgtcggggct ggcttaacta tgcggcatca gagcagattg tactgagagt gcaccatatg   2460
gacatattgt cgttagaacg cggctacaat taatacataa ccttatgtat catacacata   2520
cgatttaggt gacactatag aacgcgcgcg caagcttgga tctcctgcag gatctggccg   2580
ggtacgtcct cgaagagaag ggttaataac acatttttta acattttaa cacaaatttt   2640
agttatttaa aaatttatta aaaaatttaa aataagaaga ggaactcttt aaataaatct   2700
aacttacaaa atttatgatt tttaataagt tttcaccaat aaaaaatgtc ataaaaatat   2760
```

```
gttaaaaagt atattatcaa tattctcttt atgataaata aaaagaaaaa aaaaataaaa    2820
gttaagtgaa aatgagattg aagtgacttt aggtgtgtat aaatatatca accccgccaa    2880
caatttattt aatccaaata tattgaagta tattattcca tagcctttat ttatttatat    2940
atttattata taaaagcttt atttgttcta ggttgttcat gaaatatttt tttggtttta    3000
tctccgttgt aagaaaatca tgtgctttgt gtcgccactc actattgcag cttttttcatg   3060 cattggtcag attgacggtt gattgtattt ttgtttttta tggttttgtg ttatgactta    3120
agtcttcatc tctttatctc ttcatcaggt ttgatggtta cctaatatgg tccatgggta    3180
catgcatggt taaattaggt ggccaacttt gttgtgaacg atagaatttt ttttatatta    3240
agtaaactat ttttatatta tgaaataata ataaaaaaaa tattttatca ttattaacaa    3300
aatcatatta gttaatttgt taactctata ataaagaaa tactgtaaca ttcacattac     3360
atggtaacat ctttccaccc tttcattgt tttttgtttg atgactttt ttcttgttta      3420 aatttatttc ccttcttta aatttggaat acattatcat catatataaa ctaaaatact    3480
aaaaacagga ttacacaaat gataaataat aacacaaata tttataaatc tagctgcaat   3540
atatttaaac tagctatatc gatattgtaa aataaaacta gctgcattga tactgataaa   3600
aaaatatcat gtgctttctg gactgatgat gcagtatact tttgacattg cctttatttt   3660 attttcaga aaagctttct tagttctggg ttcttcatta tttgtttccc atctccattg    3720
tgaattgaat catttgcttc gtgtcacaaa tacaatttag ntaggtacat gcattggtca   3780
gattcacggt ttattatgtc atgacttaag ttcatggtag tacattacct gccacgcatg   3840
cattatattg gttagatttg ataggcaaat ttggttgtca acaatataaa tataaataat   3900 gttttatat tacgaaataa cagtgatcaa acaaacagt tttatctta ttaacaagat      3960 tttgtttttg tttgatgacg ttttttaatg tttacgcttt ccccttctt ttgaatttag    4020 aacactttat catcataaaa tcaaatacta aaaaaattac atatttcata ataataaca    4080 caaatatttt taaaaaatct gaaataataa tgaacaatat tacatattat cacgaaaatt   4140
cattaataaa aatattatat aaataaaatg taatagtagt tatatgtagg aaaaaagtac   4200
tgcacgcata atatatacaa aaagattaaa atgaactatt ataaataata acactaaatt   4260
aatggtgaat catatcaaaa taatgaaaaa gtaaataaaa tttgtaatta acttctatat   4320
gtattacaca cacaaataat aaataatagt aaaaaaaatt atgataaata tttaccatct   4380
cataagatat ttaaaataat gataaaaata tagattattt tttatgcaac tagctagcca   4440
aaaagagaac acgggtatat ataaaaagag tacctttaaa ttctactgta cttcctttat   4500
tcctgacgtt tttatatcaa gtggacatac gtgaagattt taattatcag tctaaatatt   4560
tcattagcac ttaatacttt tctgttttat tcctatccta taagtagtcc cgattctccc   4620
aacattgctt attcacacaa ctaactaaga aagtcttcca tagcccccca agcggccgca   4680
tgggaacgga ccaaggaaaa accttcacct gggaagagct ggcggcccat aacaccaagg   4740
acgacctact cttggccatc cgcggcaggg tgtacgatgt cacaaagttc ttgagccgcc   4800
atcctggtgg agtggacact ctcctgctcg gagctggccg agatgttact ccggtctttg   4860
agatgtatca cgcgtttggg gctgcagatg ccattatgaa gaagtactat gtcggtacac   4920
tggtctcgaa tgagctgccc atcttcccgg agccaacggt gttccacaaa accatcaaga   4980
cgagagtcga gggctacttt acggatcgga acattgatcc caagaataga ccagagatct   5040
ggggacgata cgctcttatc tttggatcct tgatcgcttc ctactacgcg cagctctttg   5100
```

```
tgcctttcgt tgtcgaacgc acatggcttc aggtggtgtt tgcaatcatc atgggatttg    5160
cgtgcgcaca agtcggactc aaccctcttc atgatgcgtc tcacttttca gtgacccaca    5220
accccactgt ctggaagatt ctgggagcca cgcacgactt tttcaacgga gcatcgtacc    5280
tggtgtggat gtaccaacat atgctcggcc atcacccta caccaacatt gctggagcag    5340
atcccgacgt gtcgacgtct gagcccgatg ttcgtcgtat caagcccaac caaaagtggt    5400
ttgtcaacca catcaaccag cacatgtttg ttcctttcct gtacggactg ctggcgttca    5460
aggtgcgcat tcaggacatc aacattttgt actttgtcaa gaccaatgac gctattcgtg    5520
tcaatcccat ctcgacatgg cacactgtga tgttctgggg cggcaaggct ttctttgtct    5580
ggtatcgcct gattgttccc ctgcagtatc tgcccctggg caaggtgctg ctcttgttca    5640
cggtcgcgga catggtgtcg tcttactggc tggcgctgac cttccaggcg aaccacgttg    5700
ttgaggaagt tcagtggccg ttgcctgacg agaacgggat catccaaaag gactgggcag    5760
ctatgcaggt cgagactacg caggattacg cacacgattc gcacctctgg accagcatca    5820
ctggcagctt gaactaccag gctgtgcacc atctgttccc caacgtgtcg cagcaccatt    5880
atcccgatat tctggccatc atcaagaaca cctgcagcga gtacaaggtt ccataccttg    5940
tcaaggatac gttttggcaa gcatttgctt cacatttgga gcacttgcgt gttcttggac    6000
tccgtcccaa ggaagagtag gcggccgcga cacaagtgtg agagtactaa ataaatgctt    6060
tggttgtacg aaatcattac actaaataaa ataatcaaag cttatatatg ccttccgcta    6120
aggccgaatg caaagaaatt ggttctttct cgttatcttt tgccactttt actagtacgt    6180
attaattact acttaatcat ctttgtttac ggctcattat atccggtcta gaggatccaa    6240
ggccgcgaag ttaaaagcaa tgttgtcact tgtcgtacta acacatgatg tgatagttta    6300
tgctagctag ctataacata agctgtctct gagtgtgttg tatattaata aagatcatca    6360
ctggtgaatg gtgatcgtgt acgtacccta cttagtaggc aatggaagca cttagagtgt    6420
gctttgtgca tggccttgcc tctgttttga gacttttgta atgttttcga gtttaaatct    6480
ttgcctttgc gtac                                                      6494
```

<210> SEQ ID NO 129
<211> LENGTH: 8584
<212> TYPE: DNA
<213> ORGANISM: Artificial Sequence
<220> FEATURE:
<223> OTHER INFORMATION: pKR1084
<220> FEATURE:
<221> NAME/KEY: misc_feature
<222> LOCATION: (5299)..(5299)
<223> OTHER INFORMATION: n is a, c, g, or t

<400> SEQUENCE: 129

```
ggagatccaa gcttggcgcg ccgttctata gtgtcaccta aatcgtatgt gtatgataca      60
taaggttatg tattaattgt agccgcgttc taacgacaat atgtccatat ggtgcactct     120
cagtacaatc tgctctgatg ccgcatagtt aagccagccc cgacacccgc caacacccgc     180
tgacgcgccc tgacgggctt gtctgctccc ggcatccgct tacagacaag ctgtgaccgt     240
ctccgggagc tgcatgtgtc agaggttttc accgtcatca ccgaaacgcg cgagacgaaa     300
gggcctcgtg atacgcctat ttttataggt taatgtcatg accaaaatcc cttaacgtga     360
gttttcgttc cactgagcgt cagaccccgt agaaaagatc aaaggatctt cttgagatcc     420 ttttttttctg cgcgtaatct gctgcttgca acaaaaaaa ccaccgctac cagcggtggt     480
ttgtttgccg gatcaagagc taccaactct ttttccgaag gtaactggct tcagcagagc     540
```

```
gcagatacca aatactgtcc ttctagtgta gccgtagtta ggccaccact tcaagaactc    600
tgtagcaccg cctacatacc tcgctctgct aatcctgtta ccagtggctg ctgccagtgg    660
cgataagtcg tgtcttaccg ggttggactc aagacgatag ttaccggata aggcgcagcg    720
gtcgggctga acgggggggtt cgtgcacaca gcccagcttg gagcgaacga cctacaccga    780
actgagatac ctacagcgtg agcattgaga aagcgccacg cttcccgaag ggagaaaggc    840
ggacaggtat ccggtaagcg gcagggtcgg aacaggagag cgcacgaggg agcttccagg    900
gggaaacgcc tggtatcttt atagtcctgt cgggtttcgc cacctctgac ttgagcgtcg    960
atttttgtga tgctcgtcag gggggcggag cctatggaaa aacgccagca acgcggcctt   1020
tttacggttc ctggccttt  gctggccttt tgctcacatg ttctttcctg cgttatcccc   1080
tgattctgtg gataaccgta ttaccgcctt tgagtgagct gataccgctc gccgcagccg   1140
aacgaccgag cgcagcgagt cagtgagcga ggaagcggaa gagcgcccaa tacgcaaacc   1200
gcctctcccc gcgcgttggc cgattcatta atgcaggttg atcagatctc gatcccgcga   1260
aattaatacg actcactata gggagaccac aacggtttcc ctctagaaat aattttgttt   1320
aactttaaga aggagatata cccatggaaa agcctgaact caccgcgacg tctgtcgaga   1380
agtttctgat cgaaaagttc gacagcgtct ccgacctgat gcagctctcg gagggcgaag   1440
aatctcgtgc tttcagcttc gatgtaggag ggcgtggata tgtcctgcgg gtaaatagct   1500
gcgccgatgg tttctacaaa gatcgttatg tttatcggca ctttgcatcg gccgcgctcc   1560
cgattccgga agtgcttgac attggggaat tcagcgagag cctgacctat tgcatctccc   1620
gccgtgcaca gggtgtcacg ttgcaagacc tgcctgaaac cgaactgccc gctgttctgc   1680
agccggtcgc ggaggctatg gatgcgatcg ctgcggccga tcttagccag acgagcgggt   1740
tcggcccatt cggaccgcaa ggaatcggtc aatacactac atggcgtgat ttcatatgcg   1800
cgattgctga tccccatgtg tatcactggc aaactgtgat ggacgacacc gtcagtgcgt   1860
ccgtcgcgca ggctctcgat gagctgatgc tttgggccga ggactgcccc gaagtccggc   1920
acctcgtgca cgcggatttc ggctccaaca atgtcctgac ggacaatggc cgcataacag   1980
cggtcattga ctggagcgag gcgatgttcg gggattccca atacgaggtc gccaacatct   2040
tcttctggag gccgtggttg gcttgtatgg agcagcagac gcgctacttc gagcggaggc   2100
atccggagct tgcaggatcg ccgcggctcc gggcgtatat gctccgcatt ggtcttgacc   2160
aactctatca gagcttggtt gacggcaatt tcgatgatgc agcttgggcg cagggtcgat   2220
gcgacgcaat cgtccgatcc ggagccggga ctgtcgggcg tacacaaatc gcccgcagaa   2280
gcgcggccgt ctggaccgat ggctgtgtag aagtactcgc cgatagtgga aaccgacgcc   2340
ccagcactcg tccgagggca aaggaatagt gaggtacagc ttggatcgat ccggctgcta   2400
acaaagcccg aaaggaagct gagttggctg ctgccaccgc tgagcaataa ctagcataac   2460
cccttggggc ctctaaacgg gtcttgaggg gttttttgct gaaaggagga actatatccg   2520
gatgatcggg cgcgccgtcg acggatccgt acgagatccg gccgggtacg caaaggcaaa   2580
gatttaaact cgaaaacatt acaaaagtct caaaacagag gcaaggccat gcacaaagca   2640
cactctaagt gcttccattg cctactaagt agggtacgta cacgatcacc attcaccagt   2700
gatgatcttt attaatatac aacacactca gagacagctt atgttatagc tagctagcat   2760
aaactatcac atcatgtgtt agtacgacaa gtgacaacat tgcttttaac ttcgcggcct   2820
tggatcctct agaccggata taatgagccg taaacaaaga tgattaagta gtaattaata   2880
```

```
cgtactagta aaagtggcaa aagataacga gaaagaacca atttctttgc attcggcctt    2940
agcggaaggc atatataagc tttgattatt ttatttagtg taatgatttc gtacaaccaa    3000
agcatttatt tagtactctc acacttgtgt cgcggccgcc tactcttcct tgggacggag    3060
tccaagaaca cgcaagtgct ccaaatgtga agcaaatgct tgccaaaacg tatccttgac    3120
aaggtatgga accttgtact cgctgcaggt gttcttgatg atggccagaa tatcgggata    3180
atggtgctgc gacacgttgg ggaacagatg gtgcacagcc tggtagttca agctgccagt    3240
gatgctggtc cagaggtgcg aatcgtgtgc gtaatcctgc gtagtctcga cctgcatagc    3300
tgcccagtcc ttttggatga tcccgttctc gtcaggcaac ggccactgaa cttcctcaac    3360
aacgtggttc gcctggaagg tcagcgccag ccagtaagac gacaccatgt ccgcgaccgt    3420
gaacaagagc agcaccttgc ccaggggcag atactgcagg ggaacaatca ggcgatacca    3480
gacaaagaaa gccttgccgc cccagaacat cacagtgtgc catgtcgaga tgggattgac    3540
acgaatagcg tcattggtct tgacaaagta caaaatgttg atgtcctgaa tgcgcacctt    3600
gaacgccagc agtccgtaca ggaaaggaac aaacatgtgc tggttgatgt ggttgacaaa    3660
ccacttttgg ttgggcttga tacgacgaac atcgggctca gacgtcgaca cgtcgggatc    3720
tgctccagca atgttggtgt agggggtgatg gccgagcata tgttggtaca tccacaccag    3780
gtacgatgct ccgttgaaaa agtcgtgcgt ggctcccaga atcttccaga cagtggggtt    3840
gtgggtcact gaaaagtgag acgcatcatg aagagggttg agtccgactt gtgcgcacgc    3900
aaatcccatg atgattgcaa acaccacctg aagccatgtg cgttcgacaa cgaaaggcac    3960
aaagagctgc gcgtagtagg aagcgatcaa ggatccaaag ataagagcgt atcgtcccca    4020
gatctctggt ctattcttgg gatcaatgtt ccgatccgta aagtagccct cgactctcgt    4080
cttgatggtt ttgtggaaca ccgttggctc cgggaagatg ggcagctcat tcgagaccag    4140
tgtaccgaca tagtacttct tcataatggc atctgcagcc ccaaacgcgt gatacatctc    4200
aaagaccgga gtaacatctc ggccagctcc gagcaggaga gtgtccactc caccaggatg    4260
gcggctcaag aactttgtga catcgtacac cctgccgcgg atggccaaga gtaggtcgtc    4320
cttggtgtta tgggccgcca gctcttccca ggtgaaggtt tttccttggt ccgttcccat    4380
gcggccgctt gggggggctat ggaagacttt cttagttagt tgtgtgaata agcaatgttg    4440
ggagaatcgg gactacttat aggataggaa taaaacagaa aagtattaag tgctaatgaa    4500
atatttagac tgataattaa aatcttcacg tatgtccact tgatataaaa acgtcaggaa    4560
taaaggaagt acagtagaat ttaaaggtac tcttttata tatacccgtg ttctcttttt    4620
ggctagctag ttgcataaaa aataatctat atttttatca ttattttaaa tatcttatga    4680
gatggtaaat atttatcata attttttta ctattattta ttatttgtgt gtgtaataca    4740
tatagaagtt aattacaaat ttatttact ttttcattat tttgatatga ttcaccatta    4800
atttagtgtt attatttata atagttcatt ttaatctttt tgtatatatt atgcgtgcag    4860 tactttttc ctacatataa ctactattac attttattta tataatattt ttattaatga    4920
attttcgtga taatatgtaa tattgttcat tattatttca gattttttaa aaatatttgt    4980
gttattattt atgaaatatg taatttttt agtatttgat tttatgatga taaagtgttc    5040
taaattcaaa agaaggggga aagcgtaaac attaaaaaac gtcatcaaac aaaaacaaaa    5100
tcttgttaat aaagataaaa ctgtttgttt tgatcactgt tatttcgtaa tataaaaaca    5160
ttatttatat ttatattgtt gacaaccaaa tttgcctatc aaatctaacc aatataatgc    5220
atgcgtggca ggtaatgtac taccatgaac ttaagtcatg acataataaa ccgtgaatct    5280
```

```
gaccaatgca tgtacctanc taaattgtat ttgtgacacg aagcaaatga ttcaattcac   5340
aatggagatg ggaaacaaat aatgaagaac ccagaactaa gaaagctttt ctgaaaaata   5400
aaataaaggc aatgtcaaaa gtatactgca tcatcagtcc agaaagcaca tgatatttt    5460 ttatcagtat caatgcagct agttttattt tacaatatcg atatagctag tttaaatata   5520
ttgcagctag atttataaat atttgtgtta ttatttatca tttgtgtaat cctgttttta   5580 gtatttagt ttatatatga tgataatgta ttccaaattt aaaagaaggg aaataaattt    5640
aaacaagaaa aaagtcatc aaacaaaaaa caaatgaaag ggtggaaaga tgttaccatg    5700
taatgtgaat gttacagtat ttcttttatt atagagttaa caaattaact aatatgattt   5760
tgttaataat gataaaatat tttttttatt attatttcat aatataaaaa tagtttactt   5820
aatataaaaa aaattctatc gttcacaaca aagttggcca cctaatttaa ccatgcatgt   5880
acccatggac catattaggt aaccatcaaa cctgatgaag agataaagag atgaagactt   5940
aagtcataac acaaaaccat aaaaaacaaa aatacaatca accgtcaatc tgaccaatgc   6000
atgaaaaagc tgcaatagtg agtggcgaca caaagcacat gattttctta caacggagat   6060
aaaaccaaaa aaatatttca tgaacaacct agaacaaata aagcttttat ataataaata   6120
tataaataaa taaaggctat ggaataatat acttcaatat atttggatta aataaattgt   6180
tggcggggtt gatatattta tacacaccta aagtcacttc aatctcattt tcacttaact   6240
tttatttttt ttttcttttt atttatcata aagagaatat tgataatata cttttttaaca  6300 tattttatg acatttttta ttggtgaaaa cttattaaaa atcataaatt ttgtaagtta    6360
gatttattta aagagttcct cttcttattt taaatttttt aataaatttt taaataacta   6420
aaatttgtgt taaaaatgtt aaaaaatgtg ttattaaccc ttctcttcga ggacgtaccc   6480
ggccagatcc tgcaggccaa ctgcgtttgg ggctccagat taaacgacgc cgtttcgttc   6540
ctttcgcttc acggcttaac gatgtcgttt ctgtctgtgc ccaaaaaata aaggcatttg   6600
ttatttgcac cagatattta ctaagtgcac cctagtttga caagtaggcg ataattacaa   6660
atagatgcgg tgcaaataat aaattttgaa ggaaataatt acaaagaac agaacttata    6720 tttactttat tttaaaaac taaaatgaaa gaacaaaaaa agtaaaaat acaaaaaatg     6780 tgctttaacc actttcatta tttgttacag aaagtatgat tctactcaaa ttgatctgtt   6840
gtatctggtg ctgccttgtc acactggcga tttcaatccc ctaaagatat ggtgcaaact   6900
gcgaagtgat caatatctgc tcggttaatt tagattaatt aataatattc aacgtgatgt   6960
accaaaaaaa gacaattttt tgctccattg acaaattaaa cctcatcaag gtaatttcca   7020
aacctataag caaaaaaatt tcacattaat tggcccgcaa tcctattagt cttattatac   7080
tagagtagga aaaaaacaa ttacacaact tgtcttatta ttctctatgc taatgaatat    7140
ttttcccttt tgttagaaat cagtgttttcc taatttattg agtattaatt ccactcaccg  7200
catatattta ccgttgaata agaaaatttt acacataatt ctttttaaga taaataattt   7260
ttttatacta gatcttatat gattacgtga agccaagtgg gttatactaa tgatatataa   7320
tgtttgatag taatcagttt ataaaccaaa tgcatggaaa tgttacgtgg aagcacgtaa   7380
attaacaagc attgaagcaa atgcagccac cgcaccaaaa ccaccccact tcacttccac   7440
gtaccatatt ccatgcaact acaacaccct aaaacttcaa taaatgcccc caccttcact   7500
tcacttcacc catcaatagc aagcggccgc accatggagg tggtgaatga atagtctca    7560 attgggcagg aagttttacc caaagttgat tatgcccaac tctggagtga tgccagtcac   7620
```

```
tgtgaggtgc tttacttgtc catcgcattt gtcatcttga agttcactct tggccccctt      7680
ggtccaaaag gtcagtctcg tatgaagttt gttttcacca attacaacct tctcatgtcc      7740
atttattcgt tgggatcatt cctctcaatg gcatatgcca tgtacaccat cggtgttatg      7800
tctgacaact gcgagaaggc ttttgacaac aacgtcttca ggatcaccac gcagttgttc      7860
tatttgagca agttcctgga gtatattgac tccttctatt tgccactgat gggcaagcct      7920
ctgacctggt tgcaattctt ccatcatttg ggggcaccga tggatatgtg gctgttctat      7980
aattaccgaa atgaagctgt ttggattttt gtgctgttga atggtttcat ccactggatc      8040
atgtacggtt attattggac cagattgatc aagctgaagt tccccatgcc aaaatccctg      8100
attacatcaa tgcagatcat tcaattcaat gttggtttct acattgtctg gaagtacagg      8160
aacattccct gttatcgcca agatgggatg aggatgtttg gctggttctt caattacttt      8220
tatgttggca cagtcttgtg tttgttcttg aatttctatg tgcaaacgta tatcgtcagg      8280
aagcacaagg gagccaaaaa gattcagtga gcggccgcga agttaaaagc aatgttgtca      8340
cttgtcgtac taacacatga tgtgatagtt tatgctagct agctataaca taagctgtct      8400
ctgagtgtgt tgtatattaa taaagatcat cactggtgaa tggtgatcgt gtacgtaccc      8460
tacttagtag gcaatggaag cacttagagt gtgctttgtg catggccttg cctctgtttt      8520
gagacttttg taatgttttc gagtttaaat ctttgccttt cgtacgtct agagtcgacc       8580 tgca                                                                    8584

<210> SEQ ID NO 130
<211> LENGTH: 5095
<212> TYPE: DNA
<213> ORGANISM: Artificial Seqeunce
<220> FEATURE:
<223> OTHER INFORMATION: pKR908

<400> SEQUENCE: 130
catggttggg tctatttgcc aactggttca cgggtggatt gaactatcag atcgagcacc        60
acttgttccc ttcgatgcct cgccacaact tttcaaagat ccagcctgct gtcgagaccc       120
tgtgcaaaaa gtacaatgtc cgataccaca ccaccggtat gatcgaggga actgcagagg       180
tctttagccg tctgaacgag gtctccaagg ctacctccaa gatgggtaag gcgcagtaag       240
cggccgcatt tcgcaccaaa tcaatgaaag taataatgaa aagtctgaat aagaatactt       300
aggcttagat gcctttgtta cttgtgtaaa ataacttgag tcatgtacct ttggcggaaa       360
cagaataaat aaaaggtgaa attccaatgc tctatgtata agttagtaat acttaatgtg       420
ttctacggtt gtttcaatat catcaaactc taattgaaac tttagaacca caaatctcaa       480
tcttttctta atgaaatgaa aaatcttaat tgtaccatgt ttatgttaaa caccttacaa       540
ttggttggag aggaggacca accgatggga caacattggg agaaagagat tcaatggaga       600 tttgatagg agaacaacat tcttttttcac ttcaatacaa gatgagtgca acactaagga       660
tatgtatgag actttcagaa gctacgacaa catagatgag tgaggtggtg attcctagca       720
agaaagacat tagaggaagc caaaatcgaa caaggaagac atcaagggca agagacagga       780
ccatccatct caggaaaagg agctttggga tagtccgaga agttgtacaa gaaattttt       840 ggagggtgag tgatgcattg ctggtgactt taactcaatc aaaattgaga agaaagaaa       900 agggagggg ctcacatgtg aatagaaggg aaacgggaga attttacagt tttgatctaa       960
tgggcatccc agctagtggt aacatattca ccatgtttaa ccttcacgta cgtctagagg      1020
atcccccggg ctgcaggaat tcactggccg tcgttttaca acgtcgtgac tgggaaaacc      1080
```

```
ctggcgttac ccaacttaat cgccttgcag cacatccccc tttcgccagc tggcgtaata   1140
gcgaagaggc ccgcaccgat cgcccttccc aacagttgcg cagcctgaat ggcgaatggc   1200
gcctgatgcg gtattttctc cttacgcatc tgtgcggtat ttcacaccgc atatggtgca   1260
ctctcagtac aatctgctct gatgccgcat agttaagcca gccccgacac ccgccaacac   1320
ccgctgacgc gccctgacgg gcttgtctgc tcccggcatc cgcttacaga caagctgtga   1380
ccgtctccgg gagctgcatg tgtcagaggt tttcaccgtc atccgaaa cgcgcgagac   1440
gaaagggcct cgtgatacgc ctatttttat aggttaatgt catgataata atggtttctt   1500
agacgtcagg tggcacttt cggggaaatg tgcgcggaac ccctatttgt ttatttttct   1560
aaatacattc aaatatgtat ccgctcatga gacaataacc ctgataaatg cttcaataat   1620
attgaaaaag gaagagtatg agtattcaac atttccgtgt cgcccttatt cccttttttg   1680
cggcattttg ccttcctgtt tttgctcacc cagaaacgct ggtgaaagta aaagatgctg   1740
aagatcagtt gggtgcacga gtgggttaca tcgaactgga tctcaacagc ggtaagatcc   1800
ttgagagttt tcgccccgaa gaacgttttc caatgatgag cacttttaaa gttctgctat   1860
gtggcgcggt attatcccgt attgacgccg ggcaagagca actcggtcgc cgcatacact   1920
attctcagaa tgacttggtt gagtactcac cagtcacaga aaagcatctt acggatggca   1980
tgacagtaag agaattatgc agtgctgcca taaccatgag tgataacact gcggccaact   2040
tacttctgac aacgatcgga ggaccgaagg agctaaccgc ttttttgcac aacatggggg   2100
atcatgtaac tcgccttgat cgttgggaac cggagctgaa tgaagccata ccaaacgacg   2160
agcgtgacac cacgatgcct gtagcaatgg caacaacgtt gcgcaaacta ttaactggcg   2220
aactacttac tctagcttcc cggcaacaat taatagactg gatggaggcg gataaagttg   2280
caggaccact tctgcgctcg gcccttccgg ctggctggtt tattgctgat aaatctggag   2340
ccggtgagcg tgggtctcgc ggtatcattg cagcactggg gccagatggt aagccctccc   2400
gtatcgtagt tatctacacg acggggagtc aggcaactat ggatgaacga aatagacaga   2460
tcgctgagat aggtgcctca ctgattaagc attggtaact gtcagaccaa gtttactcat   2520
atatacttta gattgattta aaacttcatt tttaatttaa aaggatctag gtgaagatcc   2580
tttttgataa tctcatgacc aaaatccctt aacgtgagtt ttcgttccac tgagcgtcag   2640
accccgtaga aaagatcaaa ggatcttctt gagatccttt ttttctgcgc gtaatctgct   2700
gcttgcaaac aaaaaaacca ccgctaccag cggtggtttg tttgccggat caagagctac   2760
caactctttt tccgaaggta actggcttca gcagagcgca gataccaaat actgtccttc   2820
tagtgtagcc gtagttaggc caccacttca agaactctgt agcaccgcct acatacctcg   2880
ctctgctaat cctgttacca gtggctgctg ccagtggcga taagtcgtgt cttaccgggt   2940
tggactcaag acgatagtta ccggataagg cgcagcggtc gggctgaacg gggggttcgt   3000
gcacacagcc cagcttggag cgaacgacct acaccgaact gagatacta cagcgtgagc   3060
tatgagaaag cgccacgctt cccgaaggga gaaaggcgga caggtatccg gtaagcggca   3120
gggtcggaac aggagagcgc acgagggagc ttccagggg aaacgcctgg tatctttata   3180
gtcctgtcgg gtttcgccac ctctgacttg agcgtcgatt tttgtgatgc tcgtcagggg   3240
ggcggagcct atggaaaaac gccagcaacg cggcctttt acggttcctg gccttttgct   3300
ggccttttgc tcacatgttc tttcctgcgt tatcccctga ttctgtggat aaccgtatta   3360
ccgcctttga gtgagctgat accgctcgcc gcagccgaac gaccgagcgc agcgagtcag   3420
```

-continued

```
tgagcgagga agcggaagag cgcccaatac gcaaaccgcc tctccccgcg cgttggccga    3480
ttcattaatg cagctggcac gacaggtttc ccgactggaa agcgggcagt gagcgcaacg    3540
caattaatgt gagttagctc actcattagg caccccaggc tttacactt atgcttccgg     3600 ctcgtatgtt gtgtggaatt gtgagcggat aacaatttca cacaggaaac agctatgacc    3660
atgattacgc caagcttgca tgcctgcagg ctagcctaag tacgtactca aaatgccaac    3720
aaataaaaaa aaagttgctt taataatgcc aaaacaaatt aataaaacac ttacaacacc    3780
ggattttttt taattaaaat gtgccattta ggataaatag ttaatatttt taataattat    3840
ttaaaaagcc gtatctacta aatgattttt tatttggttg aaaatattaa tatgtttaaa    3900
tcaacacaat ctatcaaaat taaactaaaa aaaaaataag tgtacgtggt taacattagt    3960
acagtaatat aagaggaaaa tgagaaatta agaaattgaa agcgagtcta atttttaaat    4020
tatgaacctg catatataaa aggaaagaaa gaatccagga agaaaagaaa tgaaaccatg    4080
catggtcccc tcgtcatcac gagtttctgc catttgcaat agaaacactg aaacacctt     4140 ctctttgtca cttaattgag atgccgaagc cacctcacac catgaacttc atgaggtgta    4200
gcacccaagg cttccatagc catgcatact gaagaatgtc tcaagctcag caccctactt    4260
ctgtgacgtg tccctcattc accttcctct cttccctata aataaccacg cctcaggttc    4320
tccgcttcac aactcaaaca ttctctccat tggtccttaa acactcatca gtcatcaccg    4380
cggccgcaaa ccatggccca cagcaagcac ggcctgaagg aggagatgac catgaagtac    4440
cacatggagg gctgcgtgaa cggccacaag ttcgtgatca ccggcgaggg catcggctac    4500
cccttcaagg gcaagcagac catcaacctg tgcgtgatcg agggcggccc cctgcccttc    4560
agcgaggaca tcctgagcgc cggcttcaag tacggcgacc ggatcttcac cgagtacccc    4620
caggacatcg tggactactt caagaacagc tgccccgccg gctacacctg gggccggagc    4680
ttcctgttcg aggacggcgc cgtgtgcatc tgtaacgtgg acatcaccgt gagcgtgaag    4740
gagaactgca tctaccacaa gagcatcttc aacggcgtga acttccccgc cgacggcccc    4800
gtgatgaaga agatgaccac caactgggag gccagctgcg agaagatcat gcccgtgcct    4860
aagcagggca tcctgaaggg cgacgtgagc atgtacctgc tgctgaagga cggcggccgg    4920
taccggtgcc agttcgacac cgtgtacaag gccaagagcg tgcccagcaa gatgcccgag    4980
tggcacttca tccagcacaa gctgctgcgg gaggaccgga gcgacgccaa gaaccagaag    5040
tggcagctga ccgagcacgc catcgccttc cccagcgccc tggcctgaag cggcc         5095
```

<210> SEQ ID NO 131
<211> LENGTH: 4716
<212> TYPE: DNA
<213> ORGANISM: Artificial Seqeunce
<220> FEATURE:
<223> OTHER INFORMATION: pKR1118
<220> FEATURE:
<221> NAME/KEY: misc_feature
<222> LOCATION: (3617)..(3617)
<223> OTHER INFORMATION: n is a, c, g, or t
<220> FEATURE:
<221> NAME/KEY: misc_feature
<222> LOCATION: (3881)..(3881)
<223> OTHER INFORMATION: n is a, c, g, or t
<220> FEATURE:
<221> NAME/KEY: misc_feature
<222> LOCATION: (4145)..(4145)
<223> OTHER INFORMATION: n is a, c, g, or t

<400> SEQUENCE: 131

```
ctagaggatc ccccgggctg caggaattca ctggccgtcg ttttacaacg tcgtgactgg    60
```

```
gaaaaccctg gcgttaccca acttaatcgc cttgcagcac atccccsctt cgccagctgg    120
cgtaatagcg aagaggcccg caccgatcgc ccttcccaac agttgcgcag cctgaatggc    180
gaatggcgcc tgatgcggta ttttctcctt acgcatctgt gcggtatttc acaccgcata    240
tggtgcactc tcagtacaat ctgctctgat gccgcatagt taagccagcc ccgacacccg    300
ccaacacccg ctgacgcgcc ctgacgggct tgtctgctcc cggcatccgc ttacagacaa    360
gctgtgaccg tctccgggag ctgcatgtgt cagaggtttt caccgtcatc accgaaacgc    420
gcgagacgaa agggcctcgt gatacgccta ttttatagg ttaatgtcat gataataatg    480
gtttcttaga cgtcaggtgg cacttttcgg ggaaatgtgc gcggaacccc tatttgttta    540
tttttctaaa tacattcaaa tatgtatccg ctcatgagac aataaccctg ataaatgctt    600
caataatatt gaaaaggaa gagtatgagt attcaacatt tccgtgtcgc ccttattccc    660
ttttttgcgg cattttgcct tcctgttttt gctcacccag aaacgctggt gaaagtaaaa    720
gatgctgaag atcagttggg tgcacgagtg ggttacatcg aactggatct caacagcggt    780
aagatccttg agagttttcg ccccgaagaa cgttttccaa tgatgagcac ttttaaagtt    840
ctgctatgtg gcgcggtatt atcccgtatt gacgccgggc aagagcaact cggtcgccgc    900
atacactatt ctcagaatga cttggttgag tactcaccag tcacagaaaa gcatcttacg    960
gatggcatga cagtaagaga attatgcagt gctgccataa ccatgagtga taacactgcg    1020
gccaacttac ttctgacaac gatcggagga ccgaaggagc taaccgcttt tttgcacaac    1080
atggggggatc atgtaactcg ccttgatcgt tgggaaccgg agctgaatga agccatacca    1140
aacgacgagc gtgacaccac gatgcctgta gcaatggcaa caacgttgcg caaactatta    1200
actggcgaac tacttactct agcttcccgg caacaattaa tagactggat ggaggcggat    1260
aaagttgcag gaccacttct gcgctcggcc cttccggctg gctggtttat tgctgataaa    1320
tctggagccg gtgagcgtgg gtctcgcggt atcattgcag cactggggcc agatggtaag    1380
ccctcccgta tcgtagttat ctacacgacg gggagtcagg caactatgga tgaacgaaat    1440
agacagatcg ctgagatagg tgcctcactg attaagcatt ggtaactgtc agaccaagtt    1500
tactcatata ctttagat tgatttaaaa cttcattttt aatttaaaag gatctaggtg    1560
aagatccttt ttgataatct catgaccaaa atcccttaac gtgagttttc gttccactga    1620
gcgtcagacc ccgtagaaaa gatcaaagga tcttcttgag atcctttttt tctgcgcgta    1680
atctgctgct tgcaaacaaa aaaccaccg ctaccagcgg tggtttgttt gccggatcaa    1740
gagctaccaa ctcttttcc gaaggtaact ggcttcagca gagcgcagat accaaatact    1800
gtccttctag tgtagccgta gttaggccac cacttcaaga actctgtagc accgcctaca    1860
tacctcgctc tgctaatcct gttaccagtg gctgctgcca gtggcgataa gtcgtgtctt    1920
accgggttgg actcaagacg atagttaccg gataaggcgc agcggtcggg ctgaacgggg    1980
ggttcgtgca cacagcccag cttggagcga acgacctaca ccgaactgag atacctacag    2040
cgtgagctat gagaaagcgc cacgcttccc gaagggagaa aggcggacag gtatccggta    2100
agcggcaggg tcggaacagg agagcgcacg agggagcttc caggggggaaa cgcctggtat    2160
ctttatagtc ctgtcgggtt tcgccacctc tgacttgagc gtcgatttt gtgatgctcg    2220
tcagggggc ggagcctatg gaaaaacgcc agcaacgcgg ccttttacg gttcctggcc    2280
ttttgctggc ctttgctca catgttcttt cctgcgttat cccctgattc tgtggataac    2340
cgtattaccg cctttgagtg agctgatacc gctcgccgca gccgaacgac cgagcgcagc    2400
```

```
gagtcagtga gcgaggaagc ggaagagcgc ccaatacgca aaccgcctct ccccgcgcgt    2460
tggccgattc attaatgcag ctggcacgac aggtttcccg actggaaagc gggcagtgag    2520
cgcaacgcaa ttaatgtgag ttagctcact cattaggcac cccaggcttt acactttatg    2580
cttccggctc gtatgttgtg tggaattgtg agcggataac aatttcacac aggaaacagc    2640
tatgaccatg attacgccaa gcttgcatgc ctgcaggcta gcctaagtac gtactcaaaa    2700
tgccaacaaa taaaaaaaaa gttgctttaa taatgccaaa acaaattaat aaaacactta    2760
caacaccgga ttttttttaa ttaaaatgtg ccatttagga taaatagtta atattttttaa   2820
taattattta aaaagccgta tctactaaaa tgattttat ttggttgaaa atattaatat     2880
gtttaaatca acacaatcta tcaaaattaa actaaaaaaa aataagtgt acgtggttaa     2940
cattagtaca gtaatataag aggaaaatga gaaattaaga aattgaaagc gagtctaatt    3000
tttaaattat gaacctgcat atataaaagg aaagaaagaa tccaggaaga aagaaatga    3060
aaccatgcat ggtcccctcg tcatcacgag tttctgccat ttgcaataga aacactgaaa    3120
cacctttctc tttgtcactt aattgagatg ccgaagccac ctcacaccat gaacttcatg    3180
aggtgtagca cccaaggctt ccatagccat gcatactgaa gaatgtctca agctcagcac    3240
cctacttctg tgacgtgtcc ctcattcacc ttcctctctt ccctataaat aaccacgcct    3300
caggttctcc gcttcacaac tcaaacattc tctccattgg tccttaaaca ctcatcagtc    3360
atcaccgcgg ccgcaaacca tggcacctaa acgggacgca ttgcctctga caattgatgg    3420
caccacgtac gacgtttccg cttgggtaaa ccatcaccct ggaggggctc aaatcattga    3480
aaactaccgg aaccgagatg ctaccgacgt gttcatggtc atgcattcac agcaggcgct    3540
caacaagttg aagcggatgc ctgttatgga gccctcttca ccacttactc caagagccc    3600
aagtgacgac atttccnagg atttccgcaa gctccgcaac agtatggttg agaagggtat    3660
gttcaacgcg tcccctctgt tttatgtgta caaatcactg accactgtcg cccttggcgc    3720
cgtgggtgtt ctcatggtta tgtacctgca gtggtactac gtttcagcca tgttttggg    3780
actttgctac caacagctgg gttgggtggc gcatgactac gcgcatcacc aggttttcac    3840
gaaccgtgat tatggcaatc ttggtgggct tttctttggc nacgttctcc aaggatattc    3900
tttgacttgg tggaaggaca ggcacaacgg ccatcacgcc gccacaaacg tgcaaggaca    3960
tgaccccgac attgataatc tccccgtttt ggcttggtcg ccagaggacg tcaagaatgc    4020
cggacctgga acccgcaata tcatcaagta ccagcagtat tatttcctcc ctaccatcgc    4080
catccttcgg ttcatctggt gtttccaaag cattctgggg gtgatgtcat acaagacaga    4140
ctccnagaat ctctattaca aacggcagta ccggagagag gcagccggtc tggcgctgca    4200
ctggattctg aagagcgttt tcttgttctg ttacatgcca agtttcctca ctggcctggc    4260
gtttttcctt atctcggagt gtctgggcgg ctttgggatc gcgattgtgg tgttttgaa     4320
ccactatccg ctggataagg ttgaggaatc cgtttggat ggtcacggtt tctgtgctgg     4380
gcagatcctc acaaccatga acatccaacg cggactcatc actgactggt tctttggagg    4440
tttgaattac cagattgagc atcatctgtg gcccaacctt ccaagacacc atttgaaagc    4500
agtttccttt gaggttgaga aattgtgcca gaagcacaac ctgccctaca gagctccgcc    4560
gatgcatact ggtgttgcac aattgcttgg atatttgggg aagattgctc agttggctgc    4620
tgtcccagta taaccctgga tcaccttcat cgatgcggcc gccaccgcgg cccgagattc    4680
cggcctcttc ggccgccaag cgacccgggt ggacgt                              4716
```

```
<210> SEQ ID NO 132
<211> LENGTH: 6281
<212> TYPE: DNA
<213> ORGANISM: Artificial Sequence
<220> FEATURE:
<223> OTHER INFORMATION: pKR1120
<220> FEATURE:
<221> NAME/KEY: misc_feature
<222> LOCATION: (4081)..(4081)
<223> OTHER INFORMATION: n is a, c, g, or t
<220> FEATURE:
<221> NAME/KEY: misc_feature
<222> LOCATION: (5242)..(5242)
<223> OTHER INFORMATION: n is a, c, g, or t
<220> FEATURE:
<221> NAME/KEY: misc_feature
<222> LOCATION: (5506)..(5506)
<223> OTHER INFORMATION: n is a, c, g, or t
<220> FEATURE:
<221> NAME/KEY: misc_feature
<222> LOCATION: (5770)..(5770)
<223> OTHER INFORMATION: n is a, c, g, or t

<400> SEQUENCE: 132
```

| | | | | | |
|---|---|---|---|---|---|
| ggccgcgaca | caagtgtgag | agtactaaat | aaatgctttg | gttgtacgaa | atcattacac | 60 |
| taaataaaat | aatcaaagct | tatatatgcc | ttccgctaag | gccgaatgca | aagaaattgg | 120 |
| ttctttctcg | ttatcttttg | ccacttttac | tagtacgtat | taattactac | ttaatcatct | 180 |
| ttgtttacgg | ctcattatat | cctgcaggtc | tagaggatcc | ccgggtaccg | agctcgaatt | 240 |
| cactggccgt | cgttttacaa | cgtcgtgact | gggaaaaccc | tggcgttacc | caacttaatc | 300 |
| gccttgcagc | acatcccccct | ttcgccagct | ggcgtaatag | cgaagaggcc | cgcaccgatc | 360 |
| gcccttccca | acagttgcgc | agcctgaatg | gcgaatggcg | cctgatgcgg | tattttctcc | 420 |
| ttacgcatct | gtgcggtatt | tcacaccgca | tatggtgcac | tctcagtaca | atctgctctg | 480 |
| atgccgcata | gttaagccag | ccccgacacc | cgccaacacc | cgctgacgcg | ccctgacggg | 540 |
| cttgtctgct | cccggcatcc | gcttacagac | aagctgtgac | cgtctccggg | agctgcatgt | 600 |
| gtcagaggtt | ttcaccgtca | tcaccgaaac | gcgcgagacg | aaagggcctc | gtgatacgcc | 660 |
| tatttttata | ggttaatgtc | atgataataa | tggtttctta | gacgtcaggt | ggcacttttc | 720 |
| ggggaaatgt | gcgcggaacc | cctatttgtt | tatttttcta | aatacattca | aatatgtatc | 780 |
| cgctcatgag | acaataaccc | tgataaatgc | ttcaataata | ttgaaaaagg | aagagtatga | 840 |
| gtattcaaca | tttccgtgtc | gcccttattc | cctttttgc | ggcattttgc | cttcctgttt | 900 |
| ttgctcaccc | agaaacgctg | gtgaaagtaa | aagatgctga | agatcagttg | ggtgcacgag | 960 |
| tgggttacat | cgaactggat | ctcaacagcg | gtaagatcct | tgagagtttt | cgccccgaag | 1020 |
| aacgttttcc | aatgatgagc | acttttaaag | ttctgctatg | tggcgcggta | ttatcccgta | 1080 |
| ttgacgccgg | gcaagagcaa | ctcggtcgcc | gcatacacta | ttctcagaat | gacttggttg | 1140 |
| agtactcacc | agtcacagaa | aagcatctta | cggatggcat | gacagtaaga | gaattatgca | 1200 |
| gtgctgccat | aaccatgagt | gataacactg | cggccaactt | acttctgaca | acgatcggag | 1260 |
| gaccgaagga | gctaaccgct | tttttgcaca | acatggggga | tcatgtaact | cgccttgatc | 1320 |
| gttgggaacc | ggagctgaat | gaagccatac | caaacgacga | gcgtgacacc | acgatgcctg | 1380 |
| tagcaatggc | aacaacgttg | cgcaaactat | taactggcga | actacttact | ctagcttccc | 1440 |
| ggcaacaatt | aatagactgg | atggaggcgg | ataaagttgc | aggaccactt | ctgcgctcgg | 1500 |
| cccttccggc | tggctggttt | attgctgata | aatctggagc | cggtgagcgt | gggtctcgcg | 1560 |
| gtatcattgc | agcactgggg | ccagatggta | agccctcccg | tatcgtagtt | atctacacga | 1620 |

```
cggggagtca ggcaactatg gatgaacgaa atagacagat cgctgagata ggtgcctcac    1680
tgattaagca ttggtaactg tcagaccaag tttactcata tatactttag attgatttaa    1740
aacttcattt ttaatttaaa aggatctagg tgaagatcct ttttgataat ctcatgacca    1800
aaatccctta acgtgagttt tcgttccact gagcgtcaga ccccgtagaa aagatcaaag    1860
gatcttcttg agatcctttt tttctgcgcg taatctgctg cttgcaaaca aaaaaaccac    1920
cgctaccagc ggtggtttgt ttgccggatc aagagctacc aactcttttt ccgaaggtaa    1980
ctggcttcag cagagcgcag ataccaaata ctgtccttct agtgtagccg tagttaggcc    2040
accacttcaa gaactctgta gcaccgccta catacctcgc tctgctaatc ctgttaccag    2100
tggctgctgc cagtggcgat aagtcgtgtc ttaccgggtt ggactcaaga cgatagttac    2160
cggataaggc gcagcggtcg ggctgaacgg ggggttcgtg cacacagccc agcttggagc    2220
gaacgaccta caccgaactg agatacctac agcgtgagct atgagaaagc gccacgcttc    2280
ccgaagggag aaaggcggac aggtatccgg taagcggcag ggtcggaaca ggagagcgca    2340
cgagggagct ccaggggga aacgcctggt atctttatag tcctgtcggg tttcgccacc    2400
tctgacttga gcgtcgattt ttgtgatgct cgtcaggggg gcggagccta tggaaaaacg    2460
ccagcaacgc ggcctttta cggttcctgg ccttttgctg gccttttgct cacatgttct    2520
ttcctgcgtt atcccctgat tctgtggata accgtattac cgcctttgag tgagctgata    2580
ccgctcgccg cagccgaacg accgagcgca gcgagtcagt gagcgaggaa gcggaagagc    2640
gcccaatacg caaaccgcct ctccccgcgc gttggccgat tcattaatgc agctggcacg    2700
acaggtttcc cgactggaaa gcgggcagtg agcgcaacgc aattaatgtg agttagctca    2760
ctcattaggc accccaggct ttacacttta tgcttccggc tcgtatgttg tgtggaattg    2820
tgagcggata acaatttcac acaggaaaca gctatgacca tgattacgcc aagcttgcat    2880
gcctgcaggt cgactctaga cgtacgtcct cgaagagaag ggttaataac acattttta    2940
acatttttaa cacaaatttt agttatttaa aaatttatta aaaaatttaa ataagaaga    3000
ggaactcttt aaataaatct aacttacaaa atttatgatt tttaataagt tttcaccaat    3060
aaaaaatgtc ataaaaatat gttaaaaagt atattatcaa tattctcttt atgataaata    3120
aaaagaaaaa aaaataaaa gttaagtgaa aatgagattg aagtgacttt aggtgtgtat    3180
aaatatatca accccgccaa caatttattt aatccaaata tattgaagta tattattcca    3240
tagcctttat ttatttatat atttattata taaaagcttt atttgttcta ggttgttcat    3300
gaaatatttt tttggtttta tctccgttgt aagaaaatca tgtgctttgt gtcgccactc    3360
actattgcag cttttttcatg cattggtcag attgacggtt gattgtattt ttgttttta    3420
tggttttgtg ttatgactta agtcttcatc tctttatctc ttcatcaggt ttgatggtta    3480
cctaatatgg tccatgggta catgcatggt taaattaggt ggccaacttt gttgtgaacg    3540
atagaatttt tttatatta agtaaactat ttttatatta tgaaataata ataaaaaaa    3600
tattttatca ttattaacaa aatcatatta gttaatttgt taactctata ataaagaaa    3660
tactgtaaca ttcacattac atggtaacat cttttccaccc tttcatttgt ttttgtttg    3720
atgacttttt ttcttgtttta aatttatttc ccttctttta aatttggaat acattatcat    3780
catatataaa ctaaaatact aaaaacagga ttacacaaat gataaataat aacacaaata    3840
tttataaatc tagctgcaat atatttaaac tagctatatc gatattgtaa aataaaacta    3900
gctgcattga tactgataaa aaaatatcat gtgcttctg gactgatgat gcagtatact    3960
tttgacattg cctttatttt attttcaga aaagctttct tagttctggg ttcttcatta    4020
```

```
tttgtttccc atctccattg tgaattgaat catttgcttc gtgtcacaaa tacaatttag    4080
ntaggtacat gcattggtca gattcacggt ttattatgtc atgacttaag ttcatggtag    4140
tacattacct gccacgcatg cattatattg gttagatttg ataggcaaat ttggttgtca    4200
acaatataaa tataaataat gtttttatat tacgaaataa cagtgatcaa acaaacagt     4260
tttatcttta ttaacaagat tttgttttg tttgatgacg ttttttaatg tttacgcttt     4320
ccccttctt ttgaatttag aacactttat catcataaaa tcaaatacta aaaaattac      4380
atatttcata ataataaca caaatatttt taaaaaatct gaataataa tgaacaatat      4440
tacatattat cacgaaaatt cattaataaa aatattatat aaataaaatg taatagtagt    4500
tatatgtagg aaaaaagtac tgcacgcata atatatacaa aaagattaaa atgaactatt    4560
ataaataata acactaaatt aatggtgaat catatcaaaa taatgaaaaa gtaaataaaa    4620
tttgtaatta acttctatat gtattacaca cacaaataat aaataatagt aaaaaaaatt   4680
atgataaata tttaccatct cataagatat ttaaaataat gataaaaata tagattattt   4740
tttatgcaac tagctagcca aaaagagaac acgggtatat ataaaaagag tacctttaaa    4800
ttctactgta cttcctttat tcctgacgtt tttatatcaa gtggacatac gtgaagattt   4860
taattatcag tctaaatatt tcattagcac ttaatacttt tctgttttat tcctatccta   4920
taagtagtcc cgattctccc aacattgctt attcacacaa ctaactaaga aagtcttcca   4980
tagccccca agcggccgca aaccatggcc cctaaacggg acgcattgcc tctgacaatt    5040
gatggcacca cgtacgacgt ttccgcttgg gtaaaccatc accctggagg ggctcaaatc   5100
attgaaaact accggaaccg agatgctacc gacgtgttca tggtcatgca ttcacagcag   5160
gcgctcaaca agttgaagcg gatgcctgtt atggagccct cttcaccact tactcccaag   5220
agcccaagtg acgacatttc cnaggatttc cgcaagctcc gcaacagtat ggttgagaag   5280
ggtatgttca acgcgtcccc tctgttttat gtgtacaaat cactgaccac tgtcgccctt   5340
ggcgccgtgg gtgttctcat ggttatgtac ctgcagtggt actacgtttc agccatgttt   5400
ttgggactt gctaccaaca gctgggttgg gtggcgcatg actacgcgca tcaccaggtt    5460
ttcacgaacc gtgattatgg caatcttggt gggcttttct ttggcnacgt tctccaagga   5520
tattctttga cttggtggaa ggacaggcac aacggccatc acgccgccac aaacgtgcaa   5580
ggacatgacc ccgacattga taatctcccc gttttggctt ggtcgccaga ggacgtcaag   5640
aatgccggac ctggaacccg caatatcatc aagtaccagc agtattattt cctccctacc   5700
atcgccatcc ttcggttcat ctggtgtttc caaagcattc tggggtgat gtcatacaag    5760
acagactccn agaatctcta ttacaaacgg cagtaccgga gagaggcagc cggtctggcg   5820
ctgcactgga ttctgaagag cgttttcttg ttctgttaca tgccaagttt cctcactggc   5880
ctggcgtttt tccttatctc ggagtgtctg ggcggctttg ggatcgcgat tgtggtgttt   5940
ttgaaccact atccgctgga taaggttgag gaatccgttt gggatggtca cggtttctgt   6000
gctgggcaga tcctcacaac catgaacatc aacgcggac tcatcactga ctggttcttt    6060
ggaggtttga attaccagat tgagcatcat ctgtggccca accttccaag acaccatttg   6120
aaagcagttt cctttgaggt tgagaaattg tgccagaagc acaacctgcc ctacagagct   6180
ccgccgatgc atactggtgt tgcacaattg cttggatatt tggggaagat tgctcagttg   6240
gctgctgtcc cagtataacc ctggatcacc ttcatcgatg c                       6281
```

<210> SEQ ID NO 133

```
<211> LENGTH: 11473
<212> TYPE: DNA
<213> ORGANISM: Artificial Sequence
<220> FEATURE:
<223> OTHER INFORMATION: pKR1123
<220> FEATURE:
<221> NAME/KEY: misc_feature
<222> LOCATION: (8587)..(8587)
<223> OTHER INFORMATION: n is a, c, g, or t
<220> FEATURE:
<221> NAME/KEY: misc_feature
<222> LOCATION: (8851)..(8851)
<223> OTHER INFORMATION: n is a, c, g, or t
<220> FEATURE:
<221> NAME/KEY: misc_feature
<222> LOCATION: (9115)..(9115)
<223> OTHER INFORMATION: n is a, c, g, or t
<220> FEATURE:
<221> NAME/KEY: misc_feature
<222> LOCATION: (10276)..(10276)
<223> OTHER INFORMATION: n is a, c, g, or t

<400> SEQUENCE: 133
ggagatccaa gcttttgatc catgcccttc atttgccgct tattaattaa tttggtaaca      60
gtccgtacta atcagttact tatccttccc ccatcataat taatcttggt agtctcgaat    120
gccacaacac tgactagtct cttggatcat aagaaaaagc caaggaacaa agaagacaa     180
aacacaatga gagtatcctt tgcatagcaa tgtctaagtt cataaaattc aaacaaaaac    240
gcaatcacac acagtggaca tcacttatcc actagctgat caggatcgcc gcgtcaagaa    300
aaaaaaactg accccaaaa gccatgcaca acaacacgta ctcacaaagg tgtcaatcga     360
gcagcccaaa acattcacca actcaaccca tcatgagccc tcacatttgt tgtttctaac    420
ccaacctcaa actcgtattc tcttccgcca cctcattttt gtttatttca acacccgtca    480
aactgcatgc caccccgtgg ccaaatgtcc atgcatgtta acaagaccta tgactataaa    540
tagctgcaat ctcggcccag ttttcatca tcaagaacca gttcaatatc ctagtacacc     600
gtattaaaga atttaagata tactgcggcc gcaccatgga ggtggtgaat gaaatagtct    660
caattgggca ggaagtttta cccaaagttg attatgccca actctggagt gatgccagtc    720
actgtgaggt gctttacttg tccatcgcat tgtcatctt gaagttcact cttggccccc     780
ttggtccaaa aggtcagtct cgtatgaagt ttgttttcac caattacaac cttctcatgt    840
ccatttattc gttgggatca ttcctctcaa tggcatatgc catgtacacc atcggtgtta    900
tgtctgacaa ctgcgagaag cttttgaca caacgtctt caggatcacc acgcagttgt      960
tctatttgag caagttcctg gagtatattg actccttcta tttgccactg atgggcaagc   1020
ctctgacctg gttgcaattc ttccatcatt tggggcacc gatggatatg tggctgttct    1080
ataattaccg aaatgaagct gttttggattt ttgtgctgtt gaatggtttc atccactgga   1140
tcatgtacgg ttattattgg accagattga tcaagctgaa gttccccatg ccaaaatccc   1200
tgattacatc aatgcagatc attcaattca atgttggttt ctacattgtc tggaagtaca   1260
ggaacattcc ctgttatcgc caagatggga tgaggatgtt tggctggttc ttcaattact   1320
tttatgttgg cacagtcttg tgtttgttct tgaatttcta tgtgcaaacg tatatcgtca   1380
ggaagcacaa gggagccaaa aagattcagt gagcggccgc aagtatgaac taaaatgcat   1440
gtaggtgtaa gagctcatgg agagcatgga atattgtatc cgaccatgta acagtataat   1500
aactgagctc catctcactt cttctatgaa taaacaaagg atgttatgat atattaacac   1560
tctatctatg caccttattg ttctatgata aatttcctct tattattata aatcatctga   1620
atcgtgacgg cttatggaat gcttcaaata gtacaaaaac aaatgtgtac tataagactt   1680
```

```
tctaaacaat tctaaccttta gcattgtgaa cgagacataa gtgttaagaa gacataacaa    1740
ttataatgga agaagtttgt ctccatttat atattatata ttacccactt atgtattata    1800
ttaggatgtt aaggagacat aacaattata aagagagaag tttgtatcca tttatatatt    1860
atatactacc catttatata ttatacttat ccacttattt aatgtcttta taaggtttga    1920
tccatgatat ttctaatatt ttagttgata tgtatatgaa agggtactat ttgaactctc    1980
ttactctgta taaaggttgg atcatcctta aagtgggtct atttaatttt attgcttctt    2040
acagataaaa aaaaaattat gagttggttt gataaaatat tgaaggattt aaaataataa    2100
taaataacat ataatatatg tatataaatt tattataata taacatttat ctataaaaaa    2160
gtaaatattg tcataaatct atacaatcgt ttagccttgc tggacgaatc tcaattattt    2220
aaacgagagt aaacatattt gactttttgg ttatttaaca aattattatt taacactata    2280
tgaaattttt ttttttatca gcaaagaata aaattaaatt aagaaggaca atggtgtccc    2340
aatccttata caaccaactt ccacaagaaa gtcaagtcag agacaacaaa aaacaagca    2400 aaggaaattt tttaatttga gttgtcttgt ttgctgcata attatgcag taaaacacta    2460 cacataaccc ttttagcagt agagcaatgg ttgaccgtgt gcttagcttc ttttatttta    2520
tttttttatc agcaaagaat aaataaaata aatgagaca cttcagggat gtttcaacaa    2580
gcttggcgcg ccgttctata gtgtcaccta aatcgtatgt gtatgataca taaggttatg    2640
tattaattgt agccgcgttc taacgacaat atgtccatat ggtgcactct cagtacaatc    2700
tgctctgatg ccgcatagtt aagccagccc cgacacccgc caacccgc tgacgcgccc    2760 tgacgggctt gtctgctccc ggcatccgct tacagacaag ctgtgaccgt ctccgggagc    2820
tgcatgtgtc agaggttttc accgtcatca ccgaaacgcg cgagacgaaa gggcctcgtg    2880
atacgcctat ttttataggt taatgtcatg accaaaatcc cttaacgtga gttttcgttc    2940
cactgagcgt cagacccgt agaaaagatc aaaggatctt cttgagatcc ttttttctg    3000 cgcgtaatct gctgcttgca acaaaaaaa ccaccgctac cagcggtggt ttgtttgccg    3060
gatcaagagc taccaactct ttttccgaag gtaactggct tcagcagagc gcagatacca    3120
aatactgtcc ttctagtgta gccgtagtta ggccaccact tcaagaactc tgtagcaccg    3180
cctacatacc tcgctctgct aatcctgtta ccagtggctg ctgccagtgg cgataagtcg    3240
tgtcttaccg ggttggactc aagacgatag ttaccggata aggcgcagcg gtcgggctga    3300
acggggggtt cgtgcacaca gcccagcttg gagcgaacga cctacaccga actgagatac    3360
ctacagcgtg agcattgaga aagcgccacg cttcccgaag ggagaaaggc ggacaggtat    3420
ccggtaagcg gcagggtcgg aacaggagag cgcacgaggg agcttccagg gggaaacgcc    3480
tggtatcttt atagtcctgt cgggtttcgc cacctctgac ttgagcgtcg attttgtga    3540 tgctcgtcag gggggcggag cctatggaaa aacgccagca acgcggcctt tttacggttc    3600
ctggcctttt gctggccttt tgctcacatg ttctttcctg cgttatcccc tgattctgtg    3660
gataaccgta ttaccgcctt tgagtgagct gataccgctc gccgcagccg aacgaccgag    3720
cgcagcgagt cagtgagcga ggaagcggaa gagcgcccaa tacgcaaacc gcctctcccc    3780
gcgcgttggc cgattcatta atgcaggttg atcgattcga catcgatcta gtaacataga    3840
tgacaccgcg cgcgataatt tatcctagtt tgcgcgctat atttttgtttt ctatcgcgta    3900 ttaaatgtat aattgcggga ctctaatcat aaaaacccat ctcataaata acgtcatgca    3960
ttacatgtta attattacat gcttaacgta attcaacaga aattatatga taatcatcgc    4020
```

```
aagaccggca acaggattca atcttaagaa actttattgc caaatgtttg aacgatctgc    4080
ttcgacgcac tccttcttta ggtacctcac tattcctttg ccctcggacg agtgctgggg    4140
cgtcggtttc cactatcggc gagtacttct acacagccat cggtccagac ggccgcgctt    4200
ctgcgggcga tttgtgtacg cccgacagtc ccggctccgg atcggacgat tgcgtcgcat    4260
cgaccctgcg cccaagctgc atcatcgaaa ttgccgtcaa ccaagctctg atagagttgg    4320
tcaagaccaa tgcggagcat atacgcccgg agccgcggcg atcctgcaag ctccggatgc    4380
ctccgctcga agtagcgcgt ctgctgctcc atacaagcca accacggcct ccagaagaag    4440
atgttggcga cctcgtattg ggaatccccg aacatcgcct cgctccagtc aatgaccgct    4500
gttatgcggc cattgtccgt caggacattg ttggagccga atccgcgtg cacgaggtgc    4560 cggacttcgg ggcagtcctc ggcccaaagc atcagctcat cgagagcctg cgcgacggac    4620
gcactgacgg tgtcgtccat cacagtttgc cagtgataca catgggatc agcaatcgcg    4680 catatgaaat cacgccatgt agtgtattga ccgattcctt gcggtccgaa tgggccgaac    4740
ccgctcgtct ggctaagatc ggccgcagcg atcgcatcca tggcctccgc gaccggctgc    4800
agaacagcgg gcagttcggt ttcaggcagg tcttgcaacg tgacaccctg tgcacggcgg    4860
gagatgcaat aggtcaggct ctcgctgaat tccccaatgt caagcacttc cggaatcggg    4920 agcgcggcc atgcaaagtg ccgataaaca taacgatctt tgtagaaacc atcggcgcag    4980
ctatttaccc gcaggacata tccacgccct cctacatcga agctgaaagc acgagattct    5040
tcgccctccg agagctgcat caggtcggag acgctgtcga acttttcgat cagaaacttc    5100
tcgacagacg tcgcggtgag ttcaggcttt ttcatggttt aataagaaga gaaaagagtt    5160
cttttgttat ggctgaagta atagagaaat gagctcgagc gtgtcctctc caaatgaaat    5220
gaacttcctt atatagagga agggtcttgc gaaggatagt gggattgtgc gtcatccctt    5280
acgtcagtgg agatgtcaca tcaatccact tgctttgaag acgtggttgg aacgtcttct    5340 tttttccacga tgctcctcgt gggtgggggt ccatctttgg gaccactgtc ggcagaggca    5400
tcttgaatga tagcctttcc tttatcgcaa tgatggcatt tgtaggagcc accttccttt    5460
tctactgtcc tttcgatgaa gtgacagata gctgggcaat ggaatccgag gaggtttccc    5520
gaaattatcc tttgttgaaa agtctcaata gcccttttggt cttctgagac tgtatctttg    5580
acatttttgg agtagaccag agtgtcgtgc tccaccatgt tgacgaagat tttcttcttg    5640
tcattgagtc gtaaaagact ctgtatgaac tgttcgccag tcttcacggc gagttctgtt    5700
agatcctcga tttgaatctt agactccatg catggcctta gattcagtag gaactacctt    5760
tttagagact ccaatctcta ttacttgcct tggtttatga agcaagcctt gaatcgtcca    5820
tactggaata gtacttctga tcttgagaaa tatgtctttc tctgtgttct tgatgcaatt    5880
agtcctgaat cttttgactg catctttaac cttcttggga aggtatttga tctcctggag    5940
attgttactc gggtagatcg tcttgatgag acctgctgcg taggcctctc taaccatctg    6000
tgggtcagca ttctttctga aattgaagag gctaaccttc tcattatcag tggtgaacat    6060
agtgtcgtca ccttcacctt cgaacttcct tcctagatcg taaagataga ggaaatcgtc    6120
cattgtaatc tccggggcaa aggagatctc ttttggggct ggatcactgc tgggcctttt    6180
ggttcctagc gtgagccagt gggctttttg ctttggtggg cttgttaggg ccttagcaaa    6240
gctcttgggc ttgagttgag cttctccttt ggggatgaag ttcaacctgt ctgtttgctg    6300
acttgttgtg tacgcgtcag ctgctgctct tgcctctgta atagtggcaa atttcttgtg    6360
tgcaactccg ggaacgccgt ttgttgccgc ctttgtacaa ccccagtcat cgtatatacc    6420
```

```
ggcatgtgga ccgttataca caacgtagta gttgatatga gggtgttgaa tacccgattc   6480
tgctctgaga ggagcaactg tgctgttaag ctcagatttt tgtgggattg gaattggatc   6540
gatctcgatc ccgcgaaatt aatacgactc actataggga gaccacaacg gtttccctct   6600
agaaataatt ttgtttaact ttaagaagga gatataccca tggaaaagcc tgaactcacc   6660
gcgacgtctg tcgagaagtt tctgatcgaa aagttcgaca gcgtctccga cctgatgcag   6720
ctctcggagg gcgaagaatc tcgtgctttc agcttcgatg taggagggcg tggatatgtc   6780
ctgcgggtaa atagctgcgc cgatggtttc tacaaagatc gttatgttta tcggcacttt   6840
gcatcggccg cgctcccgat tccggaagtg cttgacattg gggaattcag cgagagcctg   6900
acctattgca tctcccgccg tgcacagggt gtcacgttgc aagacctgcc tgaaaccgaa   6960
ctgcccgctg ttctgcagcc ggtcgcggag gctatggatg cgatcgctgc ggccgatctt   7020
agccagacga gcgggttcgg cccattcgga ccgcaaggaa tcggtcaata cactacatgg   7080
cgtgatttca tatgcgcgat tgctgatccc catgtgtatc actggcaaac tgtgatggac   7140
gacaccgtca gtgcgtccgt cgcgcaggct ctcgatgagc tgatgctttg gccgaggac   7200 tgccccgaag tccggcacct cgtgcacgcg gatttcggct ccaacaatgt cctgacggac   7260
aatggccgca taacagcggt cattgactgg agcgaggcga tgttcgggga ttcccaatac   7320
gaggtcgcca acatcttctt ctggaggccg tggttggctt gtatggagca gcagacgcgc   7380
tacttcgagc ggaggcatcc ggagcttgca ggatcgccgc ggctccgggc gtatatgctc   7440
cgcattggtc ttgaccaact ctatcagagc ttggttgacg gcaatttcga tgatgcagct   7500
tgggcgcagg gtcgatgcga cgcaatcgtc cgatccggag ccgggactgt cgggcgtaca   7560
caaatcgccc gcagaagcgc ggccgtctgg accgatggct gtgtagaagt actcgccgat   7620
agtggaaacc gacgcccag cactcgtccg agggcaaagg aatagtgagg tacagcttgg   7680
atcgatccgg ctgctaacaa agcccgaaag gaagctgagt tggctgctgc caccgctgag   7740
caataactag cataaccccct tggggcctct aaacgggtct tgagggggttt tttgctgaaa   7800 ggaggaacta tatccggatg atcgggcgcg ccgtcgacgg atccgtacga gatccggccg   7860
gccagatcct gcaggatata atgagccgta acaaagatg attaagtagt aattaatacg   7920
tactagtaaa agtggcaaaa gataacgaga agaaccaat ttctttgcat tcggccttag   7980
cggaaggcat atataagctt tgattatttt atttagtgta atgatttcgt acaaccaaag   8040 catttatta gtactctcac acttgtgtcg cggccgcatc gatgaaggtg atccaggggtt   8100 atactgggac agcagccaac tgagcaatct tccccaaata tccaagcaat gtgcaacac   8160 cagtatgcat cggcggagct ctgtagggca ggttgtgctt ctggcacaat ttctcaacct   8220
caaaggaaac tgctttcaaa tggtgtcttg gaaggttggg ccacagatga tgctcaatct   8280
ggtaattcaa acctccaaag aaccagtcag tgatgagtcc gcgttggatg ttcatggttg   8340
tgaggatctg cccagcacag aaaccgtgac catcccaaac ggattcctca accttatcca   8400
gcggatagtg gttcaaaaac accacaatcg cgatcccaaa gccgcccaga cactccgaga   8460
taaggaaaaa cgccaggcca gtgaggaaac ttggcatgta acagaacaag aaaacgctct   8520
tcagaatcca gtgcagcgcc agaccggctg cctctctccg gtactgccgt ttgtaataga   8580
gattctngga gtctgtcttg tatgacatca cccccagaat gctttggaaa caccagatga   8640
accgaaggat ggcgatggta gggaggaaat aatactgctg gtacttgatg atattgcggg   8700
ttccaggtcc ggcattcttg acgtcctctg gcgaccaagc caaaacgggg agattatcaa   8760
```

```
tgtcgggtc atgtccttgc acgtttgtgg cggcgtgatg gccgttgtgc ctgtccttcc    8820
accaagtcaa agaatatcct tggagaacgt ngccaaagaa aagcccacca agattgccat    8880
aatcacggtt cgtgaaaacc tggtgatgcg cgtagtcatg cgccacccaa cccagctgtt    8940
ggtagcaaag tcccaaaaac atggctgaaa cgtagtacca ctgcaggtac ataaccatga    9000
gaacacccac ggcgccaagg gcgacagtgg tcagtgattt gtacacataa acagagggg     9060
acgcgttgaa catacccttc tcaaccatac tgttgcggag cttgcggaaa tcctnggaaa    9120
tgtcgtcact tgggctcttg ggagtaagtg gtgaagaggg ctccataaca ggcatccgct    9180
tcaacttgtt gagcgcctgc tgtgaatgca tgaccatgaa cacgtcggta gcatctcggt    9240
tccggtagtt ttcaatgatt tgagcccctc cagggtgatg gtttacccaa gcggaaacgt    9300
cgtacgtggt gccatcaatt gtcagaggca atgcgtcccg tttaggtgcc atggtttgcg    9360
gccgcttggg gggctatgga agactttctt agttagttgt gtgaataagc aatgttggga    9420
gaatcgggac tacttatagg ataggaataa aacagaaaag tattaagtgc taatgaaata    9480
tttagactga taattaaaat cttcacgtat gtccacttga tataaaaacg tcaggaataa    9540
aggaagtaca gtagaattta aaggtactct ttttatatat acccgtgttc tcttttttggc   9600
tagctagttg cataaaaaat aatctatatt tttatcatta ttttaaatat cttatgagat    9660
ggtaaatatt tatcataatt ttttttacta ttatttatta tttgtgtgtg taatacatat    9720
agaagttaat tacaaatttt atttactttt tcattatttt gatatgattc accattaatt    9780
tagtgttatt atttataata gttcatttta atcttttgt atatattatg cgtgcagtac      9840
tttttttccta catataacta ctattacatt ttatttatat aatattttta ttaatgaatt   9900
ttcgtgataa tatgtaatat tgttcattat tatttcagat ttttttaaaaa tatttgtgtt   9960
attatttatg aaatatgtaa ttttttttagt atttgatttt atgatgataa agtgttctaa   10020
attcaaaaga aggggaaag cgtaaacatt aaaaaacgtc atcaaacaaa aacaaaatct     10080
tgttaataaa gataaaactg tttgttttga tcactgttat ttcgtaatat aaaaacatta    10140
tttatattta tattgttgac aaccaaattt gcctatcaaa tctaaccaat ataatgcatg    10200
cgtggcaggt aatgtactac catgaactta agtcatgaca taataaaccg tgaatctgac    10260
caatgcatgt acctanctaa attgtatttg tgacacgaag caaatgattc aattcacaat    10320
ggagatggga aacaaataat gaagaaccca gaactaagaa agcttttctg aaaaataaaa    10380
taaaggcaat gtcaaaagta tactgcatca tcagtccaga aagcacatga tattttttta   10440
tcagtatcaa tgcagctagt tttatttac aatatcgata tagctagttt aaatatattg    10500
cagctagatt tataaatatt tgtgttatta tttatcattt gtgtaatcct gttttagta    10560
ttttagttta tatgatga taatgtattc caaatttaaa agaagggaaa taaatttaaa      10620
caagaaaaaa agtcatcaaa caaaaaacaa atgaaagggt ggaaagatgt taccatgtaa    10680
tgtgaatgtt acagtatttc ttttattata gagttaacaa attaactaat atgatttgt    10740
taataatgat aaaatatttt ttttattatt atttcataat ataaaaatag tttacttaat   10800
ataaaaaaaa ttctatcgtt cacaacaaag ttggccacct aatttaacca tgcatgtacc    10860
catggaccat attaggtaac catcaaacct gatgaagaga taaagagatg aagacttaag   10920
tcataacaca aaaccataaa aaacaaaaat acaatcaacc gtcaatctga ccaatgcatg    10980
aaaaagctgc aatagtgagt ggcgacacaa agcacatgat tttcttacaa cggagataaa    11040
accaaaaaaa tatttcatga acaacctaga acaaataaag cttttatata ataaatatat   11100
aaataaataa aggctatgga ataatatact tcaatatatt tggattaaat aaattgttgg   11160
```

```
cggggttgat atatttatac acacctaaag tcacttcaat ctcattttca cttaactttt    11220 atttttttt tcttttatt tatcataaag agaatattga taatatactt tttaacatat    11280
ttttatgaca tttttattg gtgaaaactt attaaaaatc ataaatttg taagttagat    11340 ttatttaaag agttcctctt cttattttaa attttttaat aaatttttaa ataactaaaa   11400
tttgtgttaa aaatgttaaa aaatgtgtta ttaacccttc tcttcgagga cgtacgtcta   11460
gagtcgacct gca                                                     11473
```

<210> SEQ ID NO 134
<211> LENGTH: 4710
<212> TYPE: DNA
<213> ORGANISM: Artificial Sequence
<220> FEATURE:
<223> OTHER INFORMATION: pKR1117

<400> SEQUENCE: 134

```
ctagaggatc cccgggctg caggaattca ctggccgtcg ttttacaacg tcgtgactgg     60
gaaaaccctg gcgttaccca acttaatcgc cttgcagcac atccccctt cgccagctgg   120 cgtaatagcg aagaggcccg caccgatcgc ccttcccaac agttgcgcag cctgaatggc   180
gaatggcgcc tgatgcggta ttttctcctt acgcatctgt gcggtattc acaccgcata   240 tggtgcactc tcagtacaat ctgctctgat gccgcatagt taagccagcc ccgacacccg   300
ccaacacccg ctgacgcgcc ctgacgggct tgtctgctcc cggcatccgc ttacagacaa   360
gctgtgaccg tctccgggag ctgcatgtgt cagaggtttt caccgtcatc accgaaacgc   420
gcgagacgaa agggcctcgt gatacgccta ttttataggt taatgtcat gataataatg   480 gtttcttaga cgtcaggtgg cacttttcgg ggaaatgtgc gcggaacccc tatttgttta   540
tttttctaaa tacattcaaa tatgtatccg ctcatgagac aataaccctg ataaatgctt   600
caataatatt gaaaaaggaa gagtatgagt attcaacatt tccgtgtcgc ccttattccc   660 tttttgcgg cattttgcct tcctgttttt gctcacccag aaacgctggt gaaagtaaaa   720
gatgctgaag atcagttggg tgcacgagtg ggttacatcg aactggatct caacagcggt   780
aagatccttg agagttttcg ccccgaagaa cgttttccaa tgatgagcac ttttaaagtt   840
ctgctatgtg gcgcggtatt atcccgtatt gacgccggc aagagcaact cggtcgccgc   900
atacactatt ctcagaatga cttggttgag tactcaccag tcacagaaaa gcatcttacg   960
gatggcatga cagtaagaga attatgcagt gctgccataa ccatgagtga taacactgcg  1020
gccaacttac ttctgacaac gatcggagga ccgaaggagc taaccgcttt tttgcacaac  1080 atggggatc atgtaactcg ccttgatcgt tgggaaccgg agctgaatga agccatacca  1140
aacgacgagc gtgacaccac gatgcctgta gcaatggcaa caacgttgcg caaactatta  1200
actggcgaac tacttactct agcttcccgg caacaattaa tagactggat ggaggcggat  1260
aaagttgcag gaccacttct gcgctcggcc cttccggctg gctggtttat tgctgataaa  1320
tctggagccg gtgagcgtgg gtctcgcggt atcattgcag cactgggcc agatggtaag  1380 ccctcccgta tcgtagttat ctacacgacg gggagtcagg caactatgga tgaacgaaat  1440
agacagatcg ctgagatagg tgcctcactg attaagcatt ggtaactgtc agaccaagtt  1500
tactcatata tactttagat tgatttaaaa cttcattttt aatttaaaag gatctaggtg  1560
aagatccttt ttgataatct catgaccaaa atcccttaac gtgagttttc gttccactga  1620
gcgtcagacc ccgtagaaaa gatcaaagga tcttcttgag atcctttttt tctgcgcgta  1680
```

```
atctgctgct tgcaaacaaa aaaaccaccg ctaccagcgg tggtttgttt gccggatcaa    1740
gagctaccaa ctcttttttcc gaaggtaact ggcttcagca gagcgcagat accaaatact   1800
gtccttctag tgtagccgta gttaggccac cacttcaaga actctgtagc accgcctaca    1860
tacctcgctc tgctaatcct gttaccagtg gctgctgcca gtggcgataa gtcgtgtctt    1920
accgggttgg actcaagacg atagttaccg gataaggcgc agcggtcggg ctgaacgggg    1980
ggttcgtgca cacagcccag cttggagcga acgacctaca ccgaactgag atacctacag    2040
cgtgagctat gagaaagcgc cacgcttccc gaagggagaa aggcggacag gtatccggta    2100
agcggcaggg tcggaacagg agagcgcacg agggagcttc caggggggaaa cgcctggtat   2160
ctttatagtc ctgtcgggtt tcgccacctc tgacttgagc gtcgattttt gtgatgctcg    2220
tcagggggc ggagcctatg gaaaaacgcc agcaacgcgg cctttttacg gttcctggcc     2280
ttttgctggc cttttgctca catgttcttt cctgcgttat ccctgattc tgtggataac     2340
cgtattaccg cctttgagtg agctgatacc gctcgccgca gccgaacgac cgagcgcagc    2400
gagtcagtga gcgaggaagc ggaagagcgc ccaatacgca aaccgcctct ccccgcgcgt    2460
tggccgattc attaatgcag ctggcacgac aggtttcccg actggaaagc gggcagtgag    2520
cgcaacgcaa ttaatgtgag ttagctcact cattaggcac cccaggcttt acactttatg    2580
cttccggctc gtatgttgtg tggaattgtg agcggataac aatttcacac aggaaacagc    2640
tatgaccatg attacgccaa gcttgcatgc ctgcaggcta gcctaagtac gtactcaaaa    2700
tgccaacaaa taaaaaaaaa gttgctttaa taatgccaaa acaaattaat aaaacactta    2760
caacaccgga tttttttttaa ttaaaatgtg ccatttagga taaatagtta atattttttaa  2820
taattattta aaagccgta tctactaaaa tgatttttat ttggttgaaa atattaatat     2880
gtttaaatca acacaatcta tcaaaattaa actaaaaaaa aaataagtgt acgtggttaa    2940
cattagtaca gtaatataag aggaaaatga gaaattaaga aattgaaagc gagtctaatt    3000
tttaaattat gaacctgcat atataaaagg aaagaaagaa tccaggaaga aagaaatga    3060
aaccatgcat ggtcccctcg tcatcacgag tttctgccat ttgcaataga aacactgaaa    3120
cacctttctc tttgtcactt aattgagatg ccgaagccac ctcacaccat gaacttcatg    3180
aggtgtagca cccaaggctt ccatagccat gcatactgaa gaatgtctca agctcagcac    3240
cctacttctg tgacgtgtcc ctcattcacc ttcctctctt ccctataaat aaccacgcct    3300
caggttctcc gcttcacaac tcaaacattc tctccattgg tccttaaaca ctcatcagtc    3360
atcaccgcgg ccgcaaacca tggcacccaa gcgagaggcc ttgcccatca cgattgatgg   3420
cacaacctat gatgtgtccg catgggtgaa ccatcacccc ggggcgcag acatcatgga    3480
gaattatcgg aaccgagatg ccacggatgt gttcatggtc atgcactccc acgatgcgtt   3540
gaacaagctg aagcgcatgc ctgtgatgga gcccacttcg ccacgaagcc ccaagactcc    3600
caacgacgag gttgctgagg acttccgcaa gcttcgaaag gacatgattg caaaggcat    3660
gttcaacgca tcccctctct tctacgtgta caaaagtgcg accacagtag ccctgggcgc    3720
cctggctatt ctgatggtga tgcacctgca gtggtactac atcccagcca ttttgttggg   3780
actttgctac cagcagctgg ggtggttggc acacgattac tgccaccatc aggtgttctc    3840
taaccgggcg tacaacaatt ttgctggact tgtattcggc aatgtgatgc aaggatactc    3900
cgggacttgg tggaaggaca ggcacaacgg ccatcacgcc gccacgaacg tgcaagggca   3960
cgatcccgac atcgacgacc tcccggtgtt ggcctggtcc ccggaggacg tcaaaaacgc    4020
cggtcccacg acgcgggaagc tcatcaagtg gcaacaatac tatttcctcc ccaccatcgc   4080
```

```
aaccctccga ttcatctggt gcttccagag cattctggcg gttatggcat acaagacaga    4140
tgcaaggaat atatattacc aacgccagta cgcaaaggag gccgtggggc tggctctgca    4200
ttggattctg aaaggggtat tcatgttctg ttacatgccc ggcatactga cgggcttggc    4260
cttcttcctc atctcggagt gcctgggcgg gtttgggatt gccattgtcg tgttcttgaa    4320
tcactaccca ttggagaagg tggaggagtc cgtgtgggac agccacgggt tttgcgcggg    4380
gcagatccac acgacgatga acatccaacg cggggtcatc gttgactggt tctttggagg    4440
cctgaactac caaatcgaac accatctgtg gccgacgctg ccccggcatc acttgaaagc    4500
tgcttctttt gaggtggaga aaatttgcca gaagcacaaa ttgccataca gagcaccccc    4560
catgtccgat ggtgttgctc aattgcttgg cttcttgggg aagattgcta agctggcagc    4620
tgtcccagtg taaccctaaa cgtaccacgc ggccgccacc gcggcccgag attccggcct    4680
cttcggccgc caagcgaccc gggtggacgt                                     4710
```

<210> SEQ ID NO 135
<211> LENGTH: 6275
<212> TYPE: DNA
<213> ORGANISM: Artificial Sequence
<220> FEATURE:
<223> OTHER INFORMATION: pKR1119
<220> FEATURE:
<221> NAME/KEY: misc_feature
<222> LOCATION: (4081)..(4081)
<223> OTHER INFORMATION: n is a, c, g, or t

<400> SEQUENCE: 135

```
ggccgcgaca caagtgtgag agtactaaat aaatgctttg gttgtacgaa atcattacac      60
taaataaaat aatcaaagct tatatatgcc ttccgctaag gccgaatgca agaaattgg     120 ttctttctcg ttatctttg ccactttttac tagtacgtat taattactac ttaatcatct    180
ttgtttacgg ctcattatat cctgcaggtc tagaggatcc ccgggtaccg agctcgaatt    240
cactggccgt cgttttacaa cgtcgtgact gggaaaaccc tggcgttacc caacttaatc    300
gccttgcagc acatccccct ttcgccagct ggcgtaatag cgaagaggcc cgcaccgatc    360
gcccttccca acagttgcgc agcctgaatg gcgaatggcg cctgatgcgg tattttctcc    420
ttacgcatct gtgcggtatt tcacaccgca tatggtgcac tctcagtaca atctgctctg    480
atgccgcata gttaagccag ccccgacacc cgccaacacc cgctgacgcg ccctgacggg    540
cttgtctgct cccggcatcc gcttacagac aagctgtgac cgtctccggg agctgcatgt    600
gtcagaggtt ttcaccgtca tcaccgaaac gcgcgagacg aaagggcctc gtgatacgcc    660
tatttttata ggttaatgtc atgataataa tggtttctta cgtcaggt ggcacttttc     720 ggggaaatgt gcgcggaacc cctatttgtt tatttttcta aatacattca aatatgtatc    780
cgctcatgag acaataaccc tgataaatgc ttcaataata ttgaaaaagg aagagtatga    840
gtattcaaca tttccgtgtc gcccttattc ccttttttgc ggcattttgc cttcctgttt    900
ttgctcaccc agaaacgctg gtgaaagtaa aagatgctga agatcagttg ggtgcacgag    960
tgggttacat cgaactggat ctcaacagcg gtaagatcct tgagagtttt cgccccgaag   1020
aacgttttcc aatgatgagc acttttaaag ttctgctatg tggcgcggta ttatcccgta   1080
ttgacgccgg gcaagagcaa ctcggtcgcc gcatacacta ttctcagaat gacttggttg   1140
agtactcacc agtcacagaa aagcatctta cggatggcat gacagtaaga gaattatgca   1200
gtgctgccat aaccatgagt gataacactg cggccaactt acttctgaca acgatcggag   1260
```

```
gaccgaagga gctaaccgct tttttgcaca acatggggga tcatgtaact cgccttgatc    1320
gttgggaacc ggagctgaat gaagccatac caaacgacga gcgtgacacc acgatgcctg    1380
tagcaatggc aacaacgttg cgcaaactat taactggcga actacttact ctagcttccc    1440
ggcaacaatt aatagactgg atggaggcgg ataaagttgc aggaccactt ctgcgctcgg    1500
cccttccggc tggctggttt attgctgata atctggagc cggtgagcgt gggtctcgcg    1560
gtatcattgc agcactgggg ccagatggta agccctcccg tatcgtagtt atctacacga    1620
cggggagtca ggcaactatg gatgaacgaa atagacagat cgctgagata ggtgcctcac    1680
tgattaagca ttggtaactg tcagaccaag tttactcata tatactttag attgatttaa    1740
aacttcattt ttaatttaaa aggatctagg tgaagatcct ttttgataat ctcatgacca    1800
aaatccctta acgtgagttt tcgttccact gagcgtcaga ccccgtagaa aagatcaaag    1860
gatcttcttg agatcctttt tttctgcgcg taatctgctg cttgcaaaca aaaaaaccac    1920
cgctaccagc ggtggtttgt ttgccggatc aagagctacc aactcttttt ccgaaggtaa    1980
ctggcttcag cagagcgcag ataccaaata ctgtccttct agtgtagccg tagttaggcc    2040
accacttcaa gaactctgta gcaccgccta catacctcgc tctgctaatc ctgttaccag    2100
tggctgctgc cagtggcgat aagtcgtgtc ttaccgggtt ggactcaaga cgatagttac    2160
cggataaggc gcagcggtcg ggctgaacgg ggggttcgtg cacacagccc agcttggagc    2220
gaacgaccta caccgaactg agatacctac agcgtgagct atgagaaagc gccacgcttc    2280
ccgaagggag aaaggcggac aggtatccgg taagcggcag ggtcggaaca ggagagcgca    2340
cgagggagct ccaggggga acgcctggt atctttatag tcctgtcggg tttcgccacc    2400
tctgacttga gcgtcgattt tgtgatgct cgtcaggggg gcggagccta tggaaaaacg    2460
ccagcaacgc ggcctttta cggttcctgg ccttttgctg gccttttgct cacatgttct    2520
ttcctgcgtt atcccctgat tctgtggata accgtattac cgcctttgag tgagctgata    2580
ccgctcgccg cagccgaacg accgagcgca gcgagtcagt gagcgaggaa gcggaagagc    2640
gcccaatacg caaaccgcct ctccccgcgc gttggccgat tcattaatgc agctggcacg    2700
acaggtttcc cgactggaaa gcgggcagtg agcgcaacgc aattaatgtg agttagctca    2760
ctcattaggc accccaggct ttacacttta tgcttccggc tcgtatgttg tgtggaattg    2820
tgagcggata acaatttcac acaggaaaca gctatgacca tgattacgcc aagcttgcat    2880
gcctgcaggt cgactctaga cgtacgtcct cgaagagaag ggttaataac acatttttta    2940
acatttttaa cacaaatttt agttatttaa aaatttatta aaaatttaa ataagaaga     3000 ggaactcttt aaataaatct aacttacaaa atttatgatt tttaataagt tttcaccaat    3060
aaaaaatgtc ataaaaatat gttaaaaagt atattatcaa tattctcttt atgataaata    3120 aaagaaaaa aaaaataaaa gttaagtgaa aatgagattg aagtgacttt aggtgtgtat     3180
aaatatatca accccgccaa caatttattt aatccaaata tattgaagta tattattcca    3240
tagcctttat ttatttatat atttattata taaaagcttt atttgttcta ggttgttcat    3300
gaaatatttt tttggtttta tctccgttgt aagaaaatca tgtgctttgt gtcgccactc    3360
actattgcag cttttttcatg cattggtcag attgacggtt gattgtattt tgtttttta    3420 tggttttgtg ttatgactta agtcttcatc tctttatctc ttcatcaggt ttgatggtta    3480
cctaatatgg tccatgggta catgcatggt taaattaggt ggccaacttt gttgtgaacg    3540
atagaatttt tttatatta agtaaactat ttttatatta tgaaataata ataaaaaaa     3600 tattttatca ttattaacaa aatcatatta gttaatttgt taactctata ataaagaaa    3660
```

```
tactgtaaca ttcacattac atggtaacat ctttccaccc tttcatttgt tttttgtttg    3720 atgactttt ttcttgttta aatttatttc ccttcttta aatttggaat acattatcat    3780
catatataaa ctaaaatact aaaaacagga ttacacaaat gataaataat aacacaaata    3840
tttataaatc tagctgcaat atatttaaac tagctatatc gatattgtaa aataaaacta    3900
gctgcattga tactgataaa aaaatatcat gtgctttctg gactgatgat gcagtatact    3960
tttgacattg cctttatttt attttcaga aaagctttct tagttctggg ttcttcatta    4020
tttgtttccc atctccattg tgaattgaat catttgcttc gtgtcacaaa tacaattag    4080 ntaggtacat gcattggtca gattcacggt ttattatgtc atgacttaag ttcatggtag    4140
tacattacct gccacgcatg cattatattg gttagatttg ataggcaaat ttggttgtca    4200
acaatataaa tataaataat gttttatat tacgaaataa cagtgatcaa aacaaacagt    4260
tttatcttta ttaacaagat tttgttttg tttgatgacg ttttttaatg tttacgcttt    4320
cccccttctt ttgaatttag aacactttat catcataaaa tcaaatacta aaaaattac    4380 atatttcata aataataaca caaatatttt taaaaaatct gaataataa tgaacaatat    4440 tacatattat cacgaaaatt cattaataaa aatattatat aaataaaatg taatagtagt    4500
tatatgtagg aaaaaagtac tgcacgcata atatatacaa aaagattaaa atgaactatt    4560
ataaataata acactaaatt aatggtgaat catatcaaaa taatgaaaa gtaaataaaa    4620 tttgtaatta acttctatat gtattacaca cacaaataat aaataatagt aaaaaaaatt    4680
atgataaata tttaccatct cataagatat ttaaaataat gataaaaata tagattattt    4740
tttatgcaac tagctagcca aaaagagaac acgggtatat ataaaaagag tacctttaaa    4800
ttctactgta cttcctttat tcctgacgtt tttatatcaa gtggacatac gtgaagattt    4860
taattatcag tctaaatatt tcattagcac ttaatacttt tctgttttat tcctatccta    4920
taagtagtcc cgattctccc aacattgctt attcacacaa ctaactaaga aagtcttcca    4980
tagcccccca agcggccgca aaccatggca cccaagcgag aggccttgcc catcacgatt    5040
gatggcacaa cctatgatgt gtccgcatgg gtgaaccatc accccggggg cgcagacatc    5100
atggagaatt atcggaaccg agatgccacg gatgtgttca tggtcatgca ctcccacgat    5160
gcgttgaaca agctgaagcg catgcctgtg atggagccca cttcgccacg aagccccaag    5220
actcccaacg acgaggttgc tgaggacttc cgcaagcttc gaaaggacat gattgcaaaa    5280
ggcatgttca acgcatcccc tctcttctac gtgtacaaaa gtgcgaccac agtagccctg    5340
ggcgccctgg ctattctgat ggtgatgcac ctgcagtggt actacatccc agccattttg    5400
ttgggacttt gctaccagca gctggggtgg ttggcacacg attactgcca ccatcaggtg    5460
ttctctaacc gggcgtacaa caattttgct ggacttgtat tcggcaatgt gatgcaagga    5520
tactccggga cttggtggaa ggacaggcac aacggccatc acgccgccac gaacgtgcaa    5580
gggcacgatc ccgacatcga cgacctcccg gtgttggcct ggtccccgga ggacgtcaaa    5640
aacgccggtc ccacgacgcg gaagctcatc aagtggcaac aatactattt cctcccccacc    5700 atcgcaaccc tccgattcat ctggtgcttc cagagcattc tggcggttat ggcatacaag    5760
acagatgcaa ggaatatata ttaccaacgc cagtacgcaa aggaggccgt ggggctggct    5820
ctgcattgga ttctgaaagg ggtattcatg ttctgttaca tgcccggcat actgacgggc    5880
ttggccttct tcctcatctc ggagtgcctg gcgggtttg ggattgccat tgtcgtgttc    5940
ttgaatcact acccattgga gaaggtggag gagtccgtgt gggacagcca cgggttttgc    6000
```

-continued

| | |
|---|---|
| gcggggcaga tccacacgac gatgaacatc caacgcgggg tcatcgttga ctggttcttt | 6060 |
| ggaggcctga actaccaaat cgaacaccat ctgtggccga cgctgccccg gcatcacttg | 6120 |
| aaagctgctt cttttgaggt ggagaaaatt tgccagaagc acaaattgcc atacagagca | 6180 |
| cccccccatgt ccgatggtgt tgctcaattg cttggcttct tggggaagat tgctaagctg | 6240 |
| gcagctgtcc cagtgtaacc ctaaacgtac cacgc | 6275 |

<210> SEQ ID NO 136  
<211> LENGTH: 11467  
<212> TYPE: DNA  
<213> ORGANISM: Artificial Sequence  
<220> FEATURE:  
<223> OTHER INFORMATION: pKR1122  
<220> FEATURE:  
<221> NAME/KEY: misc_feature  
<222> LOCATION: (10270)..(10270)  
<223> OTHER INFORMATION: n is a, c, g, or t

<400> SEQUENCE: 136

| | |
|---|---|
| ggagatccaa gcttttgatc catgcccttc atttgccgct tattaattaa tttggtaaca | 60 |
| gtccgtacta atcagttact tatccttccc ccatcataat taatcttggt agtctcgaat | 120 |
| gccacaacac tgactagtct cttggatcat aagaaaaagc caaggaacaa agaagacaa | 180 |
| aacacaatga gagtatcctt tgcatagcaa tgtctaagtt cataaaattc aaacaaaaac | 240 |
| gcaatcacac acagtggaca tcacttatcc actagctgat caggatcgcc gcgtcaagaa | 300 |
| aaaaaaactg accccaaaa gccatgcaca acaacacgta ctcacaaagg tgtcaatcga | 360 |
| gcagcccaaa acattcacca actcaaccca tcatgagccc tcacatttgt tgtttctaac | 420 |
| ccaacctcaa actcgtattc tcttccgcca cctcattttt gtttatttca acacccgtca | 480 |
| aactgcatgc caccccgtgg ccaaatgtcc atgcatgtta acaagaccta tgactataaa | 540 |
| tagctgcaat ctcggcccag ttttcatca tcaagaacca gttcaatatc ctagtacacc | 600 |
| gtattaaaga atttaagata tactgcggcc gcaccatgga ggtggtgaat gaaatagtct | 660 |
| caattgggca ggaagtttta cccaaagttg attatgccca actctggagt gatgccagtc | 720 |
| actgtgaggt gctttacttg tccatcgcat ttgtcatctt gaagttcact cttggccccc | 780 |
| ttggtccaaa aggtcagtct cgtatgaagt ttgttttcac caattacaac cttctcatgt | 840 |
| ccatttattc gttgggatca ttcctctcaa tggcatatgc catgtacacc atcggtgtta | 900 |
| tgtctgacaa ctgcgagaag gcttttgaca caacgtctt caggatcacc acgcagttgt | 960 |
| tctatttgag caagttcctg gagtatattg actccttcta tttgccactg atgggcaagc | 1020 |
| ctctgacctg gttgcaattc ttccatcatt tgggggcacc gatggatatg tggctgttct | 1080 |
| ataattaccg aaatgaagct gttttggattt ttgtgctgtt gaatggtttc atccactgga | 1140 |
| tcatgtacgg ttattattgg accagattga tcaagctgaa gttccccatg ccaaaatccc | 1200 |
| tgattacatc aatgcagatc attcaattca atgttggttt ctacattgtc tggaagtaca | 1260 |
| ggaacattcc ctgttatcgc caagatggga tgaggatgtt tggctggttc ttcaattact | 1320 |
| tttatgttgg cacagtcttg tgtttgttct tgaatttcta tgtgcaaacg tatatcgtca | 1380 |
| ggaagcacaa gggagccaaa aagattcagt gagcggccgc aagtatgaac taaaatgcat | 1440 |
| gtaggtgtaa gagctcatgg agagcatgga atattgtatc cgaccatgta acagtataat | 1500 |
| aactgagctc catctcactt cttctatgaa taaacaaagg atgttatgat atattaacac | 1560 |
| tctatctatg caccttattg ttctatgata aatttcctct tattattata aatcatctga | 1620 |
| atcgtgacgg cttatggaat gcttcaaata gtacaaaaac aaatgtgtac tataagactt | 1680 |

```
tctaaacaat tctaacctta gcattgtgaa cgagacataa gtgttaagaa gacataacaa    1740
ttataatgga agaagtttgt ctccatttat atattatata ttacccactt atgtattata    1800
ttaggatgtt aaggagacat aacaattata aagagagaag tttgtatcca tttatatatt    1860
atatactacc catttatata ttatacttat ccacttattt aatgtcttta taaggtttga    1920
tccatgatat ttctaatatt ttagttgata tgtatatgaa agggtactat ttgaactctc    1980
ttactctgta taaaggttgg atcatcctta aagtgggtct atttaatttt attgcttctt    2040
acagataaaa aaaaaattat gagttggttt gataaaatat tgaaggattt aaaataataa    2100
taaataacat ataatatatg tatataaatt tattataata taacatttat ctataaaaaa    2160
gtaaatattg tcataaatct atacaatcgt ttagccttgc tggacgaatc tcaattattt    2220
aaacgagagt aaacatattt gacttttttgg ttatttaaca aattattatt taacactata    2280
tgaaattttt ttttttatca gcaaagaata aaattaaatt aagaaggaca atggtgtccc    2340
aatccttata caaccaactt ccacaagaaa gtcaagtcag agacaacaaa aaaacaagca    2400
aaggaaattt tttaatttga gttgtcttgt ttgctgcata attatgcag taaaacacta    2460 cacataaccc ttttagcagt agagcaatgg ttgaccgtgt gcttagcttc tttttatttta    2520 ttttttttatc agcaaagaat aaataaaata aaatgagaca cttcagggat gtttcaacaa    2580
gcttggcgcg ccgttctata gtgtcaccta aatcgtatgt gtatgataca taaggttatg    2640
tattaattgt agccgcgttc taacgacaat atgtccatat ggtgcactct cagtacaatc    2700
tgctctgatg ccgcatagtt aagccagccc cgacacccgc caacccgc tgacgcgccc    2760 tgacgggctt gtctgctccc ggcatccgct tacagacaag ctgtgaccgt ctccgggagc    2820
tgcatgtgtc agaggttttc accgtcatca ccgaaacgcg cgagacgaaa gggcctcgtg    2880
atacgcctat ttttataggt taatgtcatg accaaaatcc cttaacgtga gttttcgttc    2940
cactgagcgt cagaccccgt agaaaagatc aaaggatctt cttgagatcc ttttttttctg    3000 cgcgtaatct gctgcttgca acaaaaaaaa ccaccgctac cagcggtggt ttgtttgccg    3060
gatcaagagc taccaactct ttttccgaag gtaactggct tcagcagagc gcagatacca    3120
aatactgtcc ttctagtgta gccgtagtta ggccaccact tcaagaactc tgtagcaccg    3180
cctacatacc tcgctctgct aatcctgtta ccagtggctg ctgccagtgg cgataagtcg    3240
tgtcttaccg ggttggactc aagacgatag ttaccggata aggcgcagcg gtcgggctga    3300
acggggggtt cgtgcacaca gcccagcttg gagcgaacga cctacaccga actgagatac    3360
ctacagcgtg agcattgaga aagcgccacg cttcccgaag ggagaaaggc ggacaggtat    3420
ccggtaagcg gcagggtcgg aacaggagag cgcacgaggg agcttccagg gggaaacgcc    3480
tggtatcttt atagtcctgt cgggtttcgc cacctctgac ttgagcgtcg attttgtga    3540 tgctcgtcag gggggcggag cctatggaaa aacgccagca acgcggcctt tttacggttc    3600
ctggcctttt gctggccttt tgctcacatg ttctttcctg cgttatcccc tgattctgtg    3660
gataaccgta ttaccgcctt tgagtgagct gataccgctc gccgcagccg aacgaccgag    3720
cgcagcgagt cagtgagcga ggaagcggaa gagcgcccaa tacgcaaacc gcctctcccc    3780
gcgcgttggc cgattcatta atgcaggttg atcgattcga catcgatcta gtaacataga    3840
tgacaccgcg cgcgataatt tatcctagtt tgcgcgctat attttgtttt ctatcgcgta    3900
ttaaatgtat aattgcggga ctctaatcat aaaaacccat ctcataaata acgtcatgca    3960
ttacatgtta attattacat gcttaacgta attcaacaga aattatatga taatcatcgc    4020
```

```
aagaccggca acaggattca atcttaagaa actttattgc caaatgtttg aacgatctgc   4080
ttcgacgcac tccttcttta ggtacctcac tattcctttg ccctcggacg agtgctgggg   4140
cgtcggtttc cactatcggc gagtacttct acacagccat cggtccagac ggccgcgctt   4200
ctgcgggcga tttgtgtacg cccgacagtc ccggctccgg atcggacgat tgcgtcgcat   4260
cgaccctgcg cccaagctgc atcatcgaaa ttgccgtcaa ccaagctctg atagagttgg   4320
tcaagaccaa tgcggagcat atacgcccgg agccgcggcg atcctgcaag ctccggatgc   4380
ctccgctcga agtagcgcgt ctgctgctcc atacaagcca accacggcct ccagaagaag   4440
atgttggcga cctcgtattg ggaatccccg aacatcgcct cgctccagtc aatgaccgct   4500
gttatgcggc cattgtccgt caggacattg ttggagccga atccgcgtg cacgaggtgc    4560
cggacttcgg ggcagtcctc ggcccaaagc atcagctcat cgagagcctg cgcgacggac   4620
gcactgacgg tgtcgtccat cacagtttgc cagtgataca catgggatc agcaatcgcg    4680
catatgaaat cacgccatgt agtgtattga ccgattcctt gcggtccgaa tgggccgaac   4740
ccgctcgtct ggctaagatc ggccgcagcg atcgcatcca tggcctccgc gaccggctgc   4800
agaacagcgg gcagttcggt ttcaggcagg tcttgcaacg tgacaccctg tgcacggcgg   4860
gagatgcaat aggtcaggct ctcgctgaat tccccaatgt caagcacttc cggaatcggg   4920
agcgcggcca tgcaaagtg ccgataaaca taacgatctt tgtagaaacc atcggcgcag    4980
ctatttaccc gcaggacata tccacgccct cctacatcga agctgaaagc acgagattct   5040
tcgccctccg agagctgcat caggtcggag acgctgtcga acttttcgat cagaaacttc   5100
tcgacagacg tcgcggtgag ttcaggcttt ttcatggttt aataagaaga gaaaagagtt   5160
cttttgttat ggctgaagta atagagaaat gagctcgagc gtgtcctctc caaatgaaat   5220
gaacttcctt atatagagga agggtcttgc gaaggatagt gggattgtgc gtcatccctt   5280
acgtcagtgg agatgtcaca tcaatccact tgctttgaag acgtggttgg aacgtcttct   5340
ttttccacga tgctcctcgt gggtgggggt ccatctttgg gaccactgtc ggcagaggca   5400
tcttgaatga tagcctttcc tttatcgcaa tgatggcatt tgtaggagcc accttccttt   5460
tctactgtcc tttcgatgaa gtgacagata gctgggcaat ggaatccgag gaggtttccc   5520
gaaattatcc tttgttgaaa agtctcaata gcccttttggt cttctgagac tgtatctttg   5580
acatttttgg agtagaccag agtgtcgtgc tccaccatgt tgacgaagat tttcttcttg   5640
tcattgagtc gtaaaagact ctgtatgaac tgttcgccag tcttcacggc gagttctgtt   5700
agatcctcga tttgaatctt agactccatg catggcctta gattcagtag gaactacctt   5760
tttagagact ccaatctcta ttacttgcct tggtttatga agcaagcctt gaatcgtcca   5820
tactggaata gtacttctga tcttgagaaa tatgtctttc tctgtgttct tgatgcaatt   5880
agtcctgaat cttttgactg catctttaac cttcttggga aggtatttga tctcctggag   5940
attgttactc gggtagatcg tcttgatgag acctgctgcg taggcctctc taaccatctg   6000
tgggtcagca ttctttctga aattgaagag gctaaccttc tcattatcag tggtgaacat   6060
agtgtcgtca ccttcacctt cgaacttcct tcctagatcg taaagataga ggaaatcgtc   6120
cattgtaatc tccggggcaa aggagatctc ttttggggct ggatcactgc tgggcctttt   6180
ggttcctagc gtgagccagt gggctttttg ctttggtggg cttgttaggg ccttagcaaa   6240
gctcttgggc ttgagttgag cttctccttt ggggatgaag ttcaacctgt ctgtttgctg   6300
acttgttgtg tacgcgtcag ctgctgctct tgcctctgta atagtggcaa atttcttgtg   6360
tgcaactccg ggaacgccgt ttgttgccgc ctttgtacaa ccccagtcat cgtatatacc   6420
```

```
ggcatgtgga ccgttataca caacgtagta gttgatatga gggtgttgaa tacccgattc    6480
tgctctgaga ggagcaactg tgctgttaag ctcagatttt tgtgggattg gaattggatc    6540
gatctcgatc ccgcgaaatt aatacgactc actataggga gaccacaacg gtttccctct    6600
agaaataatt ttgtttaact ttaagaagga gatataccca tggaaaagcc tgaactcacc    6660
gcgacgtctg tcgagaagtt tctgatcgaa aagttcgaca cgtctccga cctgatgcag     6720 ctctcggagg gcgaagaatc tcgtgctttc agcttcgatg taggagggcg tggatatgtc    6780
ctgcgggtaa atagctgcgc cgatggtttc tacaaagatc gttatgttta tcggcacttt    6840
gcatcggccg cgctcccgat tccggaagtg ctttgacattg ggaattcag cgagagcctg     6900 acctattgca tctcccgccg tgcacagggt gtcacgttgc aagacctgcc tgaaaccgaa    6960
ctgcccgctg ttctgcagcc ggtcgcggag gctatggatg cgatcgctgc ggccgatctt    7020
agccagacga gcgggttcgg cccattcgga ccgcaaggaa tcggtcaata cactacatgg    7080
cgtgatttca tatgcgcgat tgctgatccc catgtgtatc actggcaaac tgtgatggac    7140
gacaccgtca gtgcgtccgt cgcgcaggct ctcgatgagc tgatgctttg gccgaggac    7200 tgccccgaag tccggcacct cgtgcacgcg gatttcggct ccaacaatgt cctgacggac    7260
aatggccgca taacagcggt cattgactgg agcgaggcga tgttcgggga ttcccaatac    7320
gaggtcgcca acatcttctt ctggaggccg tggttggctt gtatggagca gcagacgcgc    7380
tacttcgagc ggaggcatcc ggagcttgca ggatcgccgc ggctccgggc gtatatgctc    7440
cgcattggtc ttgaccaact ctatcagagc ttggttgacg gcaatttcga tgatgcagct    7500
tgggcgcagg gtcgatgcga cgcaatcgtc cgatccggag ccgggactgt cgggcgtaca    7560
caaatcgccc gcagaagcgc ggccgtctgg accgatggct gtgtagaagt actcgccgat    7620
agtggaaacc gacgcccag cactcgtccg agggcaaagg aatagtgagg tacagcttgg     7680
atcgatccgg ctgctaacaa agcccgaaag gaagctgagt tggctgctgc caccgctgag    7740
caataactag cataacccct tggggcctct aaacgggtct tgagggggttt tttgctgaaa   7800 ggaggaacta tatccggatg atcgggcgcg ccgtcgacgg atccgtacga gatccggccg    7860
gccagatcct gcaggatata atgagccgta acaaagatg attaagtagt aattaatacg    7920
tactagtaaa agtggcaaaa gataacgaga agaaccaat ttctttgcat tcggccttag     7980
cggaaggcat atataagctt tgattatttt atttagtgta atgatttcgt caaccaaag    8040 catttattta gtactctcac acttgtgtcg cggccgcgtg gtacgtttag ggttacactg    8100
ggacagctgc cagcttagca atcttcccca agaagccaag caattgagca acaccatcgg   8160
acatgggggg tgctctgtat ggcaatttgt gcttctggca aatttctcc acctcaaaag    8220 aagcagcttt caagtgatgc cggggcagcg tcggccacag atggtgttcg atttggtagt    8280
tcaggcctcc aaagaaccag tcaacgatga ccccgcgttg gatgttcatc gtcgtgtgga   8340
tctgccccgc gcaaaacccg tggctgtccc acacggactc ctccaccttc tccaatgggt    8400
agtgattcaa gaacacgaca atggcaatcc caaacccgcc caggcactcc gagatgagga    8460
agaaggccaa gcccgtcagt atgccgggca tgtaacagaa catgaatacc cctttcagaa    8520
tccaatgcag agccagcccc acggcctcct ttgcgtactg gcgttggtaa tatatattcc    8580
ttgcatctgt cttgtatgcc ataaccgcca gaatgctctg gaagcaccag atgaatcgga    8640
gggttgcgat ggtggggagg aaatagtatt gttgccactt gatgagcttc gcgtcgtgg     8700 gaccggcgtt tttgacgtcc tccggggacc aggccaacac cgggaggtcg tcgatgtcgg    8760
```

```
gatcgtgccc ttgcacgttc gtggcggcgt gatggccgtt gtgcctgtcc ttccaccaag   8820
tcccggagta tccttgcatc acattgccga atacaagtcc agcaaaattg ttgtacgccc   8880
ggttagagaa cacctgatgg tggcagtaat cgtgtgccaa ccaccccagc tgctggtagc   8940
aaagtcccaa caaaatggct gggatgtagt accactgcag gtgcatcacc atcagaatag   9000
ccagggcgcc cagggctact gtggtcgcac ttttgtacac gtagaagaga gggatgcgt    9060
tgaacatgcc ttttgcaatc atgtcctttc gaagcttgcg gaagtcctca gcaacctcgt   9120
cgttgggagt cttggggctt cgtggcgaag tgggctccat cacaggcatg cgcttcagct   9180
tgttcaacgc atcgtgggag tgcatgacca tgaacacatc cgtggcatct cggttccgat   9240
aattctccat gatgtctgcg cccccggggt gatggttcac ccatgcggac acatcatagg   9300
ttgtgccatc aatcgtgatg ggcaaggcct ctcgcttggg tgccatggtt tgcggccgct   9360
tgggggggcta tggaagactt tcttagttag ttgtgtgaat aagcaatgtt gggagaatcg  9420
ggactactta taggatagga ataaaacaga aaagtattaa gtgctaatga aatatttaga   9480
ctgataatta aaatcttcac gtatgtccac ttgatataaa aacgtcagga ataaaggaag   9540
tacagtagaa tttaaaggta ctcttttat atatacccgt gttctctttt tggctagcta    9600
gttgcataaa aaataatcta tatttttatc attatttaa atatcttatg agatggtaaa    9660
tatttatcat aattttttttt actattattt attatttgtg tgtgtaatac atatagaagt  9720
taattacaaa ttttatttac ttttttcatta ttttgatatg attcaccatt aatttagtgt   9780
tattatttat aatagttcat tttaatcttt ttgtatatat tatgcgtgca gtactttttt    9840
cctacatata actactatta cattttattt atataatatt tttattaatg aattttcgtg   9900
ataatatgta atattgttca ttattattttc agatttttta aaaatatttg tgttattatt   9960
tatgaaatat gtaattttttt tagtatttga ttttatgatg ataaagtgtt ctaaattcaa  10020
aagaaggggg aaagcgtaaa cattaaaaaa cgtcatcaaa caaaaacaaa atcttgttaa   10080
taaagataaa actgtttgtt ttgatcactg ttatttcgta atataaaaac attatttata   10140
tttatattgt tgacaaccaa atttgcctat caaatctaac caatataatg catgcgtggc   10200
aggtaatgta ctaccatgaa cttaagtcat gacataataa accgtgaatc tgaccaatgc   10260
atgtacctan ctaaattgta tttgtgcacac gaagcaaatg attcaattca caatggagat   10320
gggaaacaaa taatgaagaa cccagaacta agaaagcttt tctgaaaaat aaaataaagg   10380
caatgtcaaa agtatactgc atcatcagtc cagaaagcac atgatatttt tttatcagta   10440
tcaatgcagc tagtttttatt ttacaatatc gatatagcta gtttaaatat attgcagcta   10500
gatttataaa tatttgtgtt attatttatc atttgtgtaa tcctgttttt agtattttag   10560
tttatatatg atgataatgt attccaaatt taaagaagg gaaataaatt taaacaagaa    10620
aaaaagtcat caaacaaaaa acaaatgaaa gggtggaaag atgttaccat gtaatgtgaa   10680
tgttacagta tttctttat tatagagtta acaaattaac taatatgatt ttgttaataa    10740
tgataaaata ttttttttat tattatttca taatataaaa atagtttact taatataaaa   10800
aaaattctat cgttcacaac aaagttggcc acctaattta accatgcatg tacccatgga   10860
ccatattagg taaccatcaa acctgatgaa gagataaaga gatgaagact taagtcataa   10920
cacaaaacca taaaaacaa aaatacaatc aaccgtcaat ctgaccaatg catgaaaaag    10980
ctgcaatagt gagtggcgac acaaagcaca tgatttttctt acaacggaga taaaaccaaa  11040
aaaatatttc atgaacaacc tagaacaaat aaagcttttta tataataaat atataaataa  11100
ataaaggcta tggaataata tacttcaata tatttggatt aaataaaattg ttggcggggt  11160
```

```
tgatatattt atacacacct aaagtcactt caatctcatt ttcacttaac ttttattttt    11220
tttttctttt tatttatcat aaagagaata ttgataatat acttttttaac atatttttat    11280 gacattttt attggtgaaa acttattaaa aatcataaat tttgtaagtt agatttattt     11340
aaagagttcc tcttcttatt ttaaatttttt taataaattt ttaaataact aaaatttgtg   11400
ttaaaaatgt taaaaatgt gttattaacc cttctcttcg aggacgtacg tctagagtcg    11460
acctgca                                                             11467
```

<210> SEQ ID NO 137
<211> LENGTH: 5250
<212> TYPE: DNA
<213> ORGANISM: Artificial Sequence
<220> FEATURE:
<223> OTHER INFORMATION: pKR393

<400> SEQUENCE: 137

```
gatccccgg gctgcaggaa ttcactggcc gtcgttttac aacgtcgtga ctgggaaaac      60
cctggcgtta cccaacttaa tcgccttgca gcacatcccc ctttcgccag ctggcgtaat    120
agcgaagagg cccgcaccga tcgcccttcc caacagttgc gcagcctgaa tggcgaatgg    180
cgcctgatgc ggtattttct ccttacgcat ctgtgcggta tttcacaccg catatggtgc    240
actctcagta caatctgctc tgatgccgca tagttaagcc agccccgaca cccgccaaca    300
cccgctgacg cgccctgacg ggcttgtctg ctcccggcat ccgcttacag acaagctgtg    360
accgtctccg ggagctgcat gtgtcagagg ttttcaccgt catcaccgaa acgcgcgaga    420
cgaaagggcc tcgtgatacg cctatttta taggttaatg tcatgataat aatggtttct    480
tagacgtcag gtggcacttt tcggggaaat gtgcgcggaa cccctatttg tttatttttc    540
taaatacatt caaatatgta tccgctcatg agacaataac cctgataaat gcttcaataa    600
tattgaaaaa ggaagagtat gagtattcaa catttccgtg tcgcccttat tccctttttt    660
gcggcatttt gccttcctgt ttttgctcac ccagaaacgc tggtgaaagt aaaagatgct    720
gaagatcagt tgggtgcacg agtgggttac atcgaactgg atctcaacag cggtaagatc    780
cttgagagtt ttcgccccga agaacgtttt ccaatgatga gcactttta agttctgcta    840 tgtggcgcgg tattatcccg tattgacgcc gggcaagagc aactcggtcg ccgcatacac    900
tattctcaga atgacttggt tgagtactca ccagtcacag aaaagcatct tacggatggc    960
atgacagtaa gagaattatg cagtgctgcc ataaccatga gtgataacac tgcggccaac   1020
ttacttctga caacgatcgg aggaccgaag gagctaaccg cttttttgca acatgggg    1080 gatcatgtaa ctcgccttga tcgttgggaa ccggagctga atgaagccat accaaacgac   1140
gagcgtgaca ccacgatgcc tgtagcaatg gcaacaacgt tgcgcaaact attaactggc   1200
gaactactta ctctagcttc ccggcaacaa ttaatagact ggatggaggc ggataaagtt   1260
gcaggaccac ttctgcgctc ggcccttccg gctggctggt ttattgctga taaatctgga   1320
gccggtgagc gtgggtctcg cggtatcatt gcagcactgg ggccagatgg taagccctcc   1380
cgtatcgtag ttatctacac gacggggagt caggcaacta tggatgaacg aaatagacag   1440
atcgctgaga taggtgcctc actgattaag cattggtaac tgtcagacca agtttactca   1500
tatatacttt agattgattt aaaacttcat ttttaattta aaaggatcta ggtgaagatc   1560 cttttgata atctcatgac caaaatccct taacgtgagt tttcgttcca ctgagcgtca   1620 gacccccgtag aaaagatcaa aggatcttct tgagatcctt ttttctgcg cgtaatctgc    1680
```

```
tgcttgcaaa caaaaaaacc accgctacca gcggtggttt gtttgccgga tcaagagcta   1740
ccaactcttt ttccgaaggt aactggcttc agcagagcgc agataccaaa tactgtcctt   1800
ctagtgtagc cgtagttagg ccaccacttc aagaactctg tagcaccgcc tacatacctc   1860
gctctgctaa tcctgttacc agtggctgct gccagtggcg ataagtcgtg tcttaccggg   1920
ttggactcaa gacgatagtt accggataag gcgcagcggt cgggctgaac gggggggttcg  1980
tgcacacagc ccagcttgga gcgaacgacc tacaccgaac tgagatacct acagcgtgag   2040
ctatgagaaa gcgccacgct tcccgaaggg agaaaggcgg acaggtatcc ggtaagcggc   2100
agggtcggaa caggagagcg cacgagggag cttccagggg gaaacgcctg gtatctttat   2160
agtcctgtcg ggtttcgcca cctctgactt gagcgtcgat ttttgtgatg ctcgtcaggg   2220
gggcggagcc tatggaaaaa cgccagcaac gcggcctttt tacggttcct ggccttttgc   2280
tggccttttg ctcacatgtt ctttcctgcg ttatcccctg attctgtgga taaccgtatt   2340
accgcctttg agtgagctga taccgctcgc cgcagccgaa cgaccgagcg cagcgagtca   2400
gtgagcgagg aagcggaaga gcgcccaata cgcaaaccgc ctctccccgc gcgttggccg   2460
attcattaat gcagctggca cgacaggttt cccgactgga aagcgggcag tgagcgcaac   2520
gcaattaatg tgagttagct cactcattag gcaccccagg ctttacactt tatgcttccg   2580
gctcgtatgt tgtgtggaat tgtgagcgga taacaatttc acacaggaaa cagctatgac   2640
catgattacg ccaagcttgc atgcctgcag gctagcctaa gtacgtactc aaaatgccaa   2700
caaataaaaa aaaagttgct ttaataatgc caaaacaaat taataaaaca cttacaacac   2760
cggattttt ttaattaaaa tgtgccattt aggataaata gttaatattt ttaataatta   2820
tttaaaaagc cgtatctact aaaatgattt ttatttggtt gaaaatatta atatgtttaa   2880
atcaacacaa tctatcaaaa ttaaactaaa aaaaaaataa gtgtacgtgg ttaacattag   2940
tacagtaata taagaggaaa atgagaaatt aagaaattga aagcgagtct aatttttaaa   3000
ttatgaacct gcatatataa aaggaaagaa agaatccagg aagaaaagaa atgaaaccat   3060
gcatggtccc ctcgtcatca cgagtttctg ccatttgcaa tagaaacact gaaacacctt   3120
tctctttgtc acttaattga gatgccgaag ccacctcaca ccatgaactt catgaggtgt   3180
agcacccaag gcttccatag ccatgcatac tgaagaatgt ctcaagctca gcaccctact   3240
tctgtgacgt gtccctcatt caccttcctc tcttccctat aaataaccac gcctcaggtt   3300
ctccgcttca caactcaaac attctctcca ttggtcctta aacactcatc agtcatcacc   3360
gcggccgcca attcaggtgc ccatgatgtt ggccgcaggc tatcttctag tgctctcggc   3420
cgctcgccag agcttccagc aggacattga caacccaac ggggcctact cgacctcgtg   3480
gactggcctg cccattgtga tgtctgtggt ctatctcagc ggtgtgtttg ggctcacaaa   3540
gtacttcgag aaccggaagc ccatgacggg gctgaaggac tacatgttca cttacaatct   3600
ctaccaggtg atcatcaacg tgtggtgcgt ggtggccttt ctcctggagg tgcggcgtgc   3660
gggcatgtca ctcatcggca ataaggtgga ccttgggccc aactccttca ggctcggctt   3720
cgtcacgtgg gtgcactaca caacaagta cgtggagctc ctcgacaccc tatggatggt   3780
gctgcgcaag aagacgcagc aggtctcctt cctccacgtc tatcatcacg tgcttctgat   3840
gtgggcctgt tcgttgtcg tcaagctcgg caatggtggt gacgcatatt ttggcggtct   3900
catgaactcg atcatccacg tgatgatgta ttcctactac accatggcgc tcctgggctg   3960
gtcatgcccc tggaagcgct acctcacgca ggcacagctc gtgcagtttt gcatctgcct   4020
cgcccactcc acatgggcgg cagtaacggg tgcctacccg tggcgaattt gcttggtgga   4080
```

```
ggtgtgggtg atggtgtcca tgctggtgct cttcacacgc ttctaccgcc aggcctatgc   4140
caaggaggcg aaggccaagg aggcgaaaaa gctcgcacag gaggcatcac aggccaaggc   4200
ggtcaaggcg gagtaagtca ctggaggtgg accgcacatg caccacgggc ccggcgagca   4260
gcatggttcg gcgagtcagg cccggtcatg cgtcatggtt ggagtttgca gggcggcagg   4320
tgatcgcctc cgccatgcac ggccacaggc acagccggtc ctctggacgt cccaactttc   4380
aaccgtggtg caaagcacgc tggcgaccgc gagcagcagt cagcgcagcg tgttatcaca   4440
gtgtcgctgg ctgcacgtgc tctctccatc gcggccgcat ttcgcaccaa atcaatgaaa   4500
gtaataatga aaagtctgaa taagaatact taggcttaga tgcctttgtt acttgtgtaa   4560
aataacttga gtcatgtacc tttggcggaa acagaataaa taaaggtgaa attccaatg    4620 ctctatgtat aagttagtaa tacttaatgt gttctacggt tgtttcaata tcatcaaact   4680
ctaattgaaa ctttagaacc acaaatctca atctttcctt aatgaaatga aaatcttaa    4740 ttgtaccatg tttatgttaa acccttaca attggttgga gaggaggacc aaccgatggg    4800
acaacattgg gagaaagaga ttcaatggag atttggatag gaacaacaa ttctttttca    4860 cttcaataca agatgagtgc aacactaagg atatgtatga ctttcaga agctacgaca     4920 acatagatga gtgaggtggt gattcctagc aagaaagaca ttagaggaag ccaaaatcga   4980
acaaggaaga catcaagggc aagagacagg accatccatc tcaggaaaag gagctttggg   5040
atagtccgag aagttgtaca agaaattttt tggagggtga gtgatgcatt gctggtgact   5100
ttaactcaat caaaattgag aaagaaagaa aagggagggg gctcacatgt gaatagaagg   5160
gaaacgggag aattttacag ttttgatcta atgggcatcc cagctagtgg taacatattc   5220
accatgttta accttcacgt acgtctagag                                    5250

<210> SEQ ID NO 138
<211> LENGTH: 4140
<212> TYPE: DNA
<213> ORGANISM: Artificial Sequence
<220> FEATURE:
<223> OTHER INFORMATION: pKR407

<400> SEQUENCE: 138
ggccgcattt cgcaccaaat caatgaaagt aataatgaaa agtctgaata agaatactta     60
ggcttagatg cctttgttac ttgtgtaaaa taacttgagt catgtacctt tggcggaaac    120
agaataaata aaggtgaaa ttccaatgct ctatgtataa gttagtaata cttaatgtgt     180
tctacggttg tttcaatatc atcaaactct aattgaaact ttagaaccac aaatctcaat    240
cttttcttaa tgaaatgaaa atcttaattg taccatgtt tatgttaaac accttacaat     300
tggttggaga ggaggaccaa ccgatgggac aacattggga gaaagagatt caatggagat    360
ttggataggg aacaacatt cttttttcact tcaatacaag atgagtgcaa cactaaggat    420
atgtatgaga ctttcagaag ctacgacaac atagatgagt gaggtggtga ttcctagcaa    480
gaaagacatt agaggaagcc aaaatcgaac aaggaagaca tcaagggcaa gagacaggac    540
catccatctc aggaaaagga gctttgggat agtccgagaa gttgtacaag aaattttttg    600
gagggtgagt gatgcattgc tggtgacttt aactcaatca aaattgagaa agaaagaaa    660 gggaggggc tcacatgtga atagaaggga acgggagaa ttttacagtt ttgatctaat     720
gggcatccca gctagtggta acatattcac catgtttaac cttcacgtac gtctagagga    780
tcccccgggc tgcaggaatt cactggccgt cgttttacaa cgtcgtgact gggaaaaccc    840
```

```
tggcgttacc caacttaatc gccttgcagc catccccct ttcgccagct ggcgtaatag      900
cgaagaggcc cgcaccgatc gcccttccca acagttgcgc agcctgaatg gcgaatggcg      960
cctgatgcgg tattttctcc ttacgcatct gtgcggtatt tcacaccgca tatggtgcac     1020
tctcagtaca atctgctctg atgccgcata gttaagccag ccccgacacc cgccaacacc     1080
cgctgacgcg ccctgacggg cttgtctgct cccggcatcc gcttacagac aagctgtgac     1140
cgtctccggg agctgcatgt gtcagaggtt ttcaccgtca tcaccgaaac gcgcgagacg     1200
aaagggcctc gtgatacgcc tatttttata ggttaatgtc atgataataa tggtttctta     1260
gacgtcaggt ggcacttttc ggggaaatgt gcgcggaacc cctatttgtt tatttttcta     1320
aatacattca aatatgtatc cgctcatgag acaataaccc tgataaatgc ttcaataata     1380
ttgaaaaagg aagagtatga gtattcaaca tttccgtgtc gcccttattc ccttttttgc     1440
ggcattttgc cttcctgttt ttgctcaccc agaaacgctg gtgaaagtaa aagatgctga     1500
agatcagttg ggtgcacgag tgggttacat cgaactggat ctcaacagcg gtaagatcct     1560
tgagagtttt cgccccgaag aacgttttcc aatgatgagc acttttaaag ttctgctatg     1620
tggcgcggta ttatcccgta ttgacgccgg gcaagagcaa ctcggtcgcc gcatacacta     1680
ttctcagaat gacttggttg agtactcacc agtcacagaa aagcatctta cggatggcat     1740
gacagtaaga gaattatgca gtgctgccat aaccatgagt gataacactg cggccaactt     1800
acttctgaca acgatcggag gaccgaagga gctaaccgct tttttgcaca acatggggga     1860
tcatgtaact cgccttgatc gttgggaacc ggagctgaat gaagccatac caaacgacga     1920
gcgtgacacc acgatgcctg tagcaatggc aacaacgttg cgcaaactat taactggcga     1980
actacttact ctagcttccc ggcaacaatt aatagactgg atggaggcgg ataaagttgc     2040
aggaccactt ctgcgctcgg cccttccggc tggctggttt attgctgata aatctggagc     2100
cggtgagcgt gggtctcgcg gtatcattgc agcactgggg ccagatggta agccctcccg     2160
tatcgtagtt atctacacga cggggagtca ggcaactatg gatgaacgaa atagacagat     2220
cgctgagata ggtgcctcac tgattaagca ttggtaactg tcagaccaag tttactcata     2280
tatactttag attgatttaa aacttcattt ttaatttaaa aggatctagg tgaagatcct     2340
ttttgataat ctcatgacca aaatccctta acgtgagttt tcgttccact gagcgtcaga     2400
ccccgtagaa aagatcaaag gatcttcttg agatcctttt tttctgcgcg taatctgctg     2460
cttgcaaaca aaaaaaccac cgctaccagc ggtggtttgt ttgccggatc aagagctacc     2520
aactcttttt ccgaaggtaa ctggcttcag cagagcgcag ataccaaata ctgtccttct     2580
agtgtagccg tagttaggcc accacttcaa gaactctgta gcaccgccta catacctcgc     2640
tctgctaatc ctgttaccag tggctgctgc cagtggcgat aagtcgtgtc ttaccgggtt     2700
ggactcaaga cgatagttac cggataaggc gcagcggtcg ggctgaacgg ggggttcgtg     2760
cacacagccc agcttggagc gaacgaccta caccgaactg agatacctac agcgtgagct     2820
atgagaaagc gccacgcttc ccgaagggag aaaggcggac aggtatccgg taagcggcag     2880
ggtcggaaca ggagagcgca cgagggagct tccaggggga aacgcctggt atctttatag     2940
tcctgtcggg tttcgccacc tctgacttga gcgtcgattt ttgtgatgct cgtcaggggg     3000
gcggagccta tggaaaaacg ccagcaacgc ggcctttta cggttcctgg cttttgctg      3060
gccttttgct cacatgttct ttcctgcgtt atcccctgat tctgtggata accgtattac     3120
cgcctttgag tgagctgata ccgctcgccg cagccgaacg accgagcgca gcgagtcagt     3180
gagcgaggaa gcggaagagc gcccaatacg caaaccgcct ctccccgcgc gttggccgat     3240
```

| | |
|---|---|
| tcattaatgc agctggcacg acaggtttcc cgactggaaa gcgggcagtg agcgcaacgc | 3300 |
| aattaatgtg agttagctca ctcattaggc accccaggct ttacacttta tgcttccggc | 3360 |
| tcgtatgttg tgtggaattg tgagcggata acaatttcac acaggaaaca gctatgacca | 3420 |
| tgattacgcc aagcttgcat gcctgcaggc tagcctaagt acgtactcaa atgccaaca | 3480 |
| aataaaaaaa aagttgcttt aataatgcca aacaaatta ataaaacact tacaacaccg | 3540 |
| gatttttttt aattaaaatg tgccatttag gataaatagt taatattttt aataattatt | 3600 |
| taaaaagccg tatctactaa aatgattttt atttggttga aaatattaat atgttttaaat | 3660 |
| caacacaatc tatcaaaatt aaactaaaaa aaaaataagt gtacgtggtt aacattagta | 3720 |
| cagtaatata agaggaaaat gagaaattaa gaaattgaaa gcgagtctaa tttttaaatt | 3780 |
| atgaacctgc atatataaaa ggaaagaaag aatccaggaa gaaaagaaat gaaaccatgc | 3840 |
| atggtcccct cgtcatcacg agtttctgcc atttgcaata gaaacactga acacccttc | 3900 |
| tctttgtcac ttaattgaga tgccgaagcc acctcacacc atgaacttca tgaggtgtag | 3960 |
| cacccaaggc ttccatagcc atgcatactg aagaatgtct caagctcagc acccctactc | 4020 |
| tgtgacgtgt ccctcattca ccttcctctc ttccctataa ataaccacgc ctcaggttct | 4080 |
| ccgcttcaca actcaaacat tctctccatt ggtccttaaa cactcatcag tcatcaccgc | 4140 |

<210> SEQ ID NO 139
<211> LENGTH: 5414
<212> TYPE: DNA
<213> ORGANISM: Artificial Sequence
<220> FEATURE:
<223> OTHER INFORMATION: pKR1018

<400> SEQUENCE: 139

| | |
|---|---|
| ggccgcattt cgcaccaaat caatgaaagt aataatgaaa agtctgaata agaatactta | 60 |
| ggcttagatg cctttgttac ttgtgtaaaa taacttgagt catgtacctt tggcggaaac | 120 |
| agaataaata aaaggtgaaa ttccaatgct ctatgtataa gttagtaata cttaatgtgt | 180 |
| tctacggttg tttcaatatc atcaaactct aattgaaact ttagaaccac aaatctcaat | 240 |
| cttttcttaa tgaaatgaaa aatcttaatt gtaccatgtt tatgttaaac accttacaat | 300 |
| tggttggaga ggaggaccaa ccgatgggac aacattggga gaaagagatt caatggagat | 360 |
| ttggatagga gaacaacatt cttttttcact tcaatacaag atgagtgcaa cactaaggat | 420 |
| atgtatgaga ctttcagaag ctacgacaac atagatgagt gaggtggtga ttcctagcaa | 480 |
| gaaagacatt agaggaagcc aaaatcgaac aaggaagaca tcaagggcaa gagacaggac | 540 |
| catccatctc aggaaaagga gctttgggat agtccgagaa gttgtacaag aaatttttg | 600 |
| gagggtgagt gatgcattgc tggtgacttt aactcaatca aaattgagaa agaaagaaaa | 660 |
| gggagggggc tcacatgtga atagaaggga acgggagaa ttttacagtt ttgatctaat | 720 |
| gggcatccca gctagtggta acatattcac catgtttaac cttcacgtac gtctagagga | 780 |
| tccccgggc tgcaggaatt cactggccgt cgttttacaa cgtcgtgact gggaaaaccc | 840 |
| tggcgttacc caacttaatc gccttgcagc acatcccct ttcgccagct ggcgtaatag | 900 |
| cgaagaggcc cgcaccgatc gcccttccca acagttgcgc agcctgaatg gcgaatggcg | 960 |
| cctgatgcgg tattttctcc ttacgcatct gtgcggtatt tcacaccgca tatggtgcac | 1020 |
| tctcagtaca atctgctctg atgccgcata gttaagccag ccccgacacc cgccaacacc | 1080 |
| cgctgacgcg ccctgacggg cttgtctgct cccggcatcg gcttacagac aagctgtgac | 1140 |

-continued

```
cgtctccggg agctgcatgt gtcagaggtt ttcaccgtca tcaccgaaac gcgcgagacg   1200
aaagggcctc gtgatacgcc tatttttata ggttaatgtc atgataataa tggtttctta   1260
gacgtcaggt ggcacttttc ggggaaatgt gcgcggaacc cctatttgtt tatttttcta   1320
aatacattca aatatgtatc cgctcatgag acaataaccc tgataaatgc ttcaataata   1380
ttgaaaaagg aagagtatga gtattcaaca tttccgtgtc gcccttattc ccttttttgc   1440
ggcattttgc cttcctgttt ttgctcaccc agaaacgctg gtgaaagtaa agatgctga   1500
agatcagttg ggtgcacgag tgggttacat cgaactggat ctcaacagcg gtaagatcct   1560
tgagagtttt cgccccgaag aacgttttcc aatgatgagc acttttaaag ttctgctatg   1620
tggcgcggta ttatcccgta ttgacgccgg gcaagagcaa ctcggtcgcc gcatacacta   1680
ttctcagaat gacttggttg agtactcacc agtcacagaa aagcatctta cggatggcat   1740
gacagtaaga gaattatgca gtgctgccat aaccatgagt gataacactg cggccaactt   1800
acttctgaca acgatcggag gaccgaagga gctaaccgct tttttgcaca acatggggga   1860
tcatgtaact cgccttgatc gttgggaacc ggagctgaat gaagccatac caaacgacga   1920
gcgtgacacc acgatgcctg tagcaatggc aacaacgttg cgcaaactat taactggcga   1980
actacttact ctagcttccc ggcaacaatt aatagactgg atggaggcgg ataaagttgc   2040
aggaccactt ctgcgctcgg cccttccggc tggctggttt attgctgata atctggagc   2100
cggtgagcgt gggtctcgcg gtatcattgc agcactgggg ccagatggta agccctcccg   2160
tatcgtagtt atctacacga cggggagtca ggcaactatg gatgaacgaa atagacagat   2220
cgctgagata ggtgcctcac tgattaagca ttggtaactg tcagaccaag tttactcata   2280
tatactttag attgatttaa aacttcattt ttaatttaaa aggatctagg tgaagatcct   2340
ttttgataat ctcatgacca aaatccctta acgtgagttt tcgttccact gagcgtcaga   2400
ccccgtagaa aagatcaaag gatcttcttg agatcctttt tttctgcgcg taatctgctg   2460
cttgcaaaca aaaaaaccac cgctaccagc ggtggtttgt ttgccggatc aagagctacc   2520
aactcttttt ccgaaggtaa ctggcttcag cagagcgcag ataccaaata ctgtccttct   2580
agtgtagccg tagttaggcc accacttcaa gaactctgta gcaccgccta catacctcgc   2640
tctgctaatc ctgttaccag tggctgctgc cagtggcgat aagtcgtgtc ttaccgggtt   2700
ggactcaaga cgatagttac cggataaggc gcagcggtcg ggctgaacgg ggggttcgtg   2760
cacacagccc agcttggagc gaacgaccta caccgaactg agatacctac agcgtgagct   2820
atgagaaagc gccacgcttc ccgaagggag aaaggcggac aggtatccgg taagcggcag   2880
ggtcggaaca ggagagcgca cgagggagct tccaggggga aacgcctggt atctttatag   2940
tcctgtcggg tttcgccacc tctgacttga gcgtcgattt ttgtgatgct cgtcaggggg   3000
gcggagccta tggaaaaacg ccagcaacgc ggccttttta cggttcctgg ccttttgctg   3060
gccttttgct cacatgttct ttcctgcgtt atcccctgat tctgtggata accgtattac   3120
cgcctttgag tgagctgata ccgctcgccg cagccgaacg accgagcgca gcgagtcagt   3180
gagcgaggaa gcggaagagc gcccaatacg caaaccgcct ctccccgcgc gttggccgat   3240
tcattaatgc agctggcacg acaggtttcc cgactggaaa gcgggcagtg agcgcaacgc   3300
aattaatgtg agttagctca ctcattaggc accccaggct ttacacttta tgcttccggc   3360
tcgtatgttg tgtggaattg tgagcggata acaatttcac acaggaaaca gctatgacca   3420
tgattacgcc aagcttgcat gcctgcaggc tagcctaagt acgtactcaa aatgccaaca   3480
aataaaaaaa aagttgcttt aataatgcca aaacaaatta ataaaacact tacaacaccg   3540
```

```
gatttttttt aattaaaatg tgccatttag gataaatagt taatattttt aataattatt    3600
taaaaagccg tatctactaa aatgattttt atttggttga aaatattaat atgtttaaat    3660
caacacaatc tatcaaaatt aaactaaaaa aaaataagt gtacgtggtt aacattagta     3720
cagtaatata agaggaaaat gagaaattaa gaaattgaaa gcgagtctaa tttttaaatt    3780
atgaacctgc atatataaaa ggaaagaaag aatccaggaa gaaaagaaat gaaaccatgc    3840
atggtcccct cgtcatcacg agtttctgcc atttgcaata gaaacactga acacctttc    3900 tctttgtcac ttaattgaga tgccgaagcc acctcacacc atgaacttca tgaggtgtag    3960
cacccaaggc ttccatagcc atgcatactg aagaatgtct caagctcagc accctacttc    4020
tgtgacgtgt ccctcattca ccttcctctc ttccctataa ataaccacgc tcaggttct     4080 ccgcttcaca actcaaacat tctctccatt ggtccttaaa cactcatcag tcatcaccgc    4140
ggccgcacca tgtctcctaa gcggcaagct ctgccaatca caattgatgg cgcaacttat    4200
gatgtgtctg cttgggtcaa tcaccaccct ggaggagctg acattatcga gaactatcgc    4260
aaccgcgatg cgaccgatgt cttcatggtg atgcactctc aagaagccgt cgccaagttg    4320
aagagaatgc ctgttatgga gccttcctct cctgacacac ctgttgcacc caagcctaag    4380
cgtgatgagc cccaggagga tttccgcaag ttgcgggagg aattcatctc caagggtatg    4440
ttcgagacga gtttcctttg gtattttac aagacttcaa ctaccgtcgg tttgatggtc      4500
ctttccatct tgatgaccgt gtacacgaat tggtatttca ccgctgcttt ggttcttggc    4560
gtgtgctacc aacagctagg ctggttgtcc cacgactatt gccatcacca ggttttcaca    4620
aaccgcaaga ttaacgacgc tttcggtctc tttttcggta acgtgatgca gggatactca    4680
cagacttggt ggaaggatag gcacaatggt caccatgccg ccaccaatgt ggtcggccat    4740
gacccagata ttgataacct ccccatcctg gcttggtctc ccgaagatgt caagagggct    4800
actccttcga ctcggaatct catcaagtac cagcagtact acttcattcc caccattgca    4860
tcccttaggt tcatctggtg cctccaatcc atcggcggcg tcatgtccta caagagcgag    4920
gagaggaacc tgtactacaa gcgccagtac actaaggagg cgattggtct ggccctccac    4980
tgggtgctca aggccacttt ctattgcagt gccatgccta gctttgccac cggtttggga    5040
tgcttcttga tctccgagct gctcggagga tttggcattg ccatcgttgt gtttctgaat    5100
cactatcctt tggacaaggt tgaggagact gtctgggatg agcacgggtt cagcgccagc    5160
cagatccacg agacgttgaa cattaagccc ggccttctca ccgattgggt ctttggtggt    5220
ctcaactacc agattgagca ccacttgtgg cccaacatgc caggcacaa cctcacggca    5280 gcttccctgg aggtgcagaa gttgtgcgcc aagcacaacc tgccctacag gccccagcc    5340 atcatccccg gggttcagaa attggtcagc ttcttaggcg agattgccca gctggctgct    5400
gtccctgaat gagc                                                      5414
```

<210> SEQ ID NO 140
<211> LENGTH: 7908
<212> TYPE: DNA
<213> ORGANISM: Artificial Sequence
<220> FEATURE:
<223> OTHER INFORMATION: pKR1020R

<400> SEQUENCE: 140

```
ggagatccaa gcttttgatc catgcccttc atttgccgct tattaattaa tttggtaaca      60
gtccgtacta atcagttact tatccttccc ccatcataat taatcttggt agtctcgaat     120
```

```
gccacaacac tgactagtct cttggatcat aagaaaaagc caaggaacaa aagaagacaa    180
aacacaatga gagtatcctt tgcatagcaa tgtctaagtt cataaaattc aaacaaaaac    240
gcaatcacac acagtggaca tcacttatcc actagctgat caggatcgcc gcgtcaagaa    300
aaaaaaactg gaccccaaaa gccatgcaca acaacacgta ctcacaaagg tgtcaatcga    360
gcagcccaaa acattcacca actcaaccca tcatgagccc tcacatttgt tgtttctaac    420
ccaacctcaa actcgtattc tcttccgcca cctcattttt gtttatttca acacccgtca    480
aactgcatgc caccccgtgg ccaaatgtcc atgcatgtta acaagaccta tgactataaa    540
tagctgcaat ctcggcccag ttttcatca tcaagaacca gttcaatatc ctagtacacc     600
gtattaaaga atttaagata tactgcggcc gcaccatgga ggtggtgaat gaaatagtct    660
caattgggca ggaagtttta cccaaagttg attatgccca actctggagt gatgccagtc    720
actgtgaggt gctttacttg tccatcgcat ttgtcatctt gaagttcact cttggccccc    780
ttggtccaaa aggtcagtct cgtatgaagt ttgttttcac caattacaac cttctcatgt    840
ccatttattc gttgggatca ttcctctcaa tggcatatgc catgtacacc atcggtgtta    900
tgtctgacaa ctgcgagaag gcttttgaca acaacgtctt caggatcacc acgcagttgt    960
tctatttgag caagttcctg gagtatattg actccttcta tttgccactg atgggcaagc   1020
ctctgacctg gttgcaattc ttccatcatt tgggggcacc gatggatatg tggctgttct   1080
ataattaccg aaatgaagct gtttggattt ttgtgctgtt gaatggtttc atccactgga   1140
tcatgtacgg ttattattgg accagattga tcaagctgaa gttccccatg ccaaaatccc   1200
tgattacatc aatgcagatc attcaattca atgttggttt ctacattgtc tggaagtaca   1260
ggaacattcc ctgttatcgc caagatggga tgaggatgt tggctggttc ttcaattact    1320
tttatgttgg cacagtcttg tgtttgttct tgaatttcta tgtgcaaacg tatatcgtca   1380
ggaagcacaa gggagccaaa aagattcagt gagcggccgc aagtatgaac taaaatgcat   1440
gtaggtgtaa gagctcatgg agagcatgga atattgtatc cgaccatgta acagtataat   1500
aactgagctc catctcactt cttctatgaa taaacaaagg atgttatgat atattaacac   1560
tctatctatg caccttattg ttctatgata aatttcctct tattattata aatcatctga   1620
atcgtgacgg cttatggaat gcttcaaata gtacaaaaac aaatgtgtac tataagactt   1680
tctaaacaat tctaacctta gcattgtgaa cgagacataa gtgttaagaa gacataacaa   1740
ttataatgga agaagtttgt ctccatttat atattatata ttaccacttt atgtattata   1800
ttaggatgtt aaggagacat aacaattata agagagaag tttgtatcca tttatatatt    1860
atatactacc catttatata ttatacttat ccactatttt aatgtcttta taaggtttga   1920
tccatgatat ttctaatatt ttagttgata tgtatatgaa agggtactat ttgaactctc   1980
ttactctgta taaaggttgg atcatcctta aagtgggtct atttaatttt attgcttctt   2040
acagataaaa aaaaattat gagttggttt gataaaatat tgaaggattt aaaataataa    2100
taaataacat ataatatatg tatataaatt tattataata taacatttat ctataaaaaa   2160
gtaaatattg tcataaatct atacaatcgt ttagccttgc tggacgaatc tcaattattt   2220
aaacgagagt aaacatattt gactttttgg ttatttaaca aattattatt taacactata   2280
tgaaattttt tttttatca gcaaagaata aaattaaatt aagaaggaca atggtgtccc    2340
aatccttata caaccaactt ccacaagaaa gtcaagtcag agacaacaaa aaacaagca    2400 aaggaaattt tttaatttga gttgtcttgt ttgctgcata atttatgcag taaaacacta   2460
cacataaccc ttttagcagt agagcaatgg ttgaccgtgt gcttagcttc ttttatttta   2520
```

```
tttttttatc agcaaagaat aaataaaata aaatgagaca cttcagggat gtttcaacaa    2580
gcttggcgcg ccgttctata gtgtcaccta aatcgtatgt gtatgataca taaggttatg    2640
tattaattgt agccgcgttc taacgacaat atgtccatat ggtgcactct cagtacaatc    2700
tgctctgatg ccgcatagtt aagccagccc cgacacccgc caacacccgc tgacgcgccc    2760
tgacgggctt gtctgctccc ggcatccgct tacagacaag ctgtgaccgt ctccgggagc    2820
tgcatgtgtc agaggttttc accgtcatca ccgaaacgcg cgagacgaaa gggcctcgtg    2880
atacgcctat ttttataggt taatgtcatg accaaaatcc cttaacgtga gttttcgttc    2940
cactgagcgt cagaccccgt agaaaagatc aaaggatctt cttgagatcc ttttttttctg   3000
cgcgtaatct gctgcttgca acaaaaaaaa ccaccgctac cagcggtggt ttgtttgccg    3060
gatcaagagc taccaactct ttttccgaag gtaactggct tcagcagagc gcagatacca    3120
aatactgtcc ttctagtgta gccgtagtta ggccaccact tcaagaactc tgtagcaccg    3180
cctacatacc tcgctctgct aatcctgtta ccagtggctg ctgccagtgg cgataagtcg    3240
tgtcttaccg ggttggactc aagacgatag ttaccggata aggcgcagcg gtcgggctga    3300
acggggggtt cgtgcacaca gcccagcttg gagcgaacga cctacaccga actgagatac    3360
ctacagcgtg agcattgaga aagcgccacg cttcccgaag ggagaaaggc ggacaggtat    3420
ccggtaagcg gcagggtcgg aacaggagag cgcacgaggg agcttccagg gggaaacgcc    3480
tggtatcttt atagtcctgt cgggtttcgc cacctctgac ttgagcgtcg attttttgtga   3540
tgctcgtcag gggggcggag cctatggaaa aacgccagca acgcggcctt tttacggttc    3600
ctggcctttt gctggccttt tgctcacatg ttctttcctg cgttatcccc tgattctgtg    3660
gataaccgta ttaccgcctt tgagtgagct gataccgctc gccgcagccg aacgaccgag    3720
cgcagcgagt cagtgagcga ggaagcggaa gagcgcccaa tacgcaaacc gcctctcccc    3780
gcgcgttggc cgattcatta atgcaggttg atcagatctc gatcccgcga aattaatacg    3840
actcactata gggagaccac aacggtttcc ctctagaaat aattttgttt aactttaaga    3900
aggagatata cccatggaaa agcctgaact caccgcgacg tctgtcgaga gtttctgat    3960
cgaaaagttc gacagcgtct ccgacctgat gcagctctcg gagggcgaag aatctcgtgc    4020
tttcagcttc gatgtaggag ggcgtggata tgtcctgcgg gtaaatagct gcgccgatgg    4080
tttctacaaa gatcgttatg tttatcggca ctttgcatcg gccgcgctcc cgattccgga    4140
agtgcttgac attggggaat tcagcgagag cctgacctat tgcatctccc gccgtgcaca    4200
gggtgtcacg ttgcaagacc tgcctgaaac cgaactgccc gctgttctgc agccggtcgc    4260
ggaggctatg gatgcgatcg ctgcggccga tcttagccag acgagcgggt tcggcccatt    4320
cggaccgcaa ggaatcggtc aatacactac atggcgtgat ttcatatgcg cgattgctga    4380
tccccatgtg tatcactggc aaactgtgat ggacgacacc gtcagtgcgt ccgtcgcgca    4440
ggctctcgat gagctgatgc tttgggccga ggactgcccc gaagtccggc acctcgtgca    4500
cgcggatttc ggctccaaca atgtcctgac ggacaatggc cgcataacag cggtcattga    4560
ctggagcgag gcgatgttcg ggattcccca atacgaggtc gccaacatct tcttctggag    4620
gccgtggttg gcttgtatgg agcagcagac gcgctacttc gagcggaggc atccggagct    4680
tgcaggatcg ccgcggctcc gggcgtatat gctccgcatt ggtcttgacc aactctatca    4740
gagcttggtt gacggcaatt tcgatgatgc agcttgggcg cagggtcgat gcgacgcaat    4800
cgtccgatcc ggagccggga ctgtcggcgc tacacaaatc gcccgcagaa gcgcggccgt    4860
```

```
ctggaccgat ggctgtgtag aagtactcgc cgatagtgga aaccgacgcc ccagcactcg    4920
tccgagggca aaggaatagt gaggtacagc ttggatcgat ccggctgcta acaaagcccg    4980
aaaggaagct gagttggctg ctgccaccgc tgagcaataa ctagcataac cccttgggc     5040 ctctaaacgg gtcttgaggg gttttttgct gaaaggagga actatatccg gatgatcggg    5100
cgcgccgtcg acggatccgt acgagatccg gccggccaga tcctgcagcc cggggggatcc   5160 tctagacgta cgtgaaggtt aaacatggtg aatatgttac cactagctgg gatgcccatt    5220
agatcaaaac tgtaaaattc tcccgttccc cttctattca catgtgagcc ccctcccttt    5280
tctttctttc tcaattttga ttgagttaaa gtcaccagca atgcatcact caccctccaa    5340
aaaatttctt gtacaacttc tcggactatc ccaaagctcc ttttcctgag atggatggtc    5400
ctgtctcttg cccttgatgt cttccttgtt cgattttggc ttcctctaat gtctttcttg    5460
ctaggaatca ccacctcact catctatgtt gtcgtagctt ctgaaagtct catacatatc    5520
cttagtgttg cactcatctt gtattgaagt gaaaagaat gttgttctcc tatccaaatc     5580
tccattgaat ctcttctcc caatgttgtc ccatcggttg gtcctcctct ccaaccaatt     5640
gtaaggtgtt taacataaac atggtacaat taagattttt catttcatta agaaaagatt    5700
gagatttgtg gttctaaagt ttcaattaga gtttgatgat attgaaacaa ccgtagaaca    5760
cattaagtat tactaactta tacatagagc attggaattt caccttttat ttattctgtt    5820
tccgccaaag gtacatgact caagttattt tacacaagta acaaaggcat ctaagcctaa    5880
gtattcttat tcagacttttt cattattact ttcattgatt tggtgcgaaa tgcggccgct   5940
cattcaggga cagcagccag ctgggcaatc tcgcctaaga agctgaccaa tttctgaacc    6000
ccggggatga tggctggggc cctgtagggc aggttgtgct tggcgcacaa cttctgcacc    6060
tccagggaag ctgccgtgag gttgtgcctg gcatgttgg gccacaagtg gtgctcaatc     6120
tggtagttga gaccaccaaa gacccaatcg gtgagaaggc cgggcttaat gttcaacgtc    6180
tcgtggatct ggctggcgct gaacccgtgc tcatcccaga cagtctcctc aaccttgtcc    6240
aaaggatagt gattcagaaa cacaacgatg gcaatgccaa atcctccgag cagctcggag    6300
atcaagaagc atcccaaacc ggtggcaaag ctaggcatgg cactgcaata gaaagtggcc    6360
ttgagcaccc agtggagggc cagaccaatc gcctccttag tgtactgccg cttgtagtac    6420
aggttcctct cctcgctctt gtaggacatg acgccgccga tggattggag gcaccagatg    6480
aacctaaggg atgcaatggt gggaatgaag tagtactgct ggtacttgat gagattccga    6540
gtcgaaggag tagccctctt gacatcttcg ggagaccaag ccaggatggg gaggttatca    6600
atatctgggt catggccgac acattggtg gcggcatggt gaccattgtg cctatccttc     6660
caccaagtct gtgagtatcc ctgcatcacg ttaccgaaaa agagaccgaa agcgtcgtta    6720
atcttgcggt ttgtgaaaac ctggtgatgg caatagtcgt gggacaacca gcctagctgt    6780
tggtagcaca cgccaagaac caaagcagcg gtgaaatacc aattcgtgta cacggtcatc    6840
aagatggaaa ggaccatcaa accgacggta gttgaagtct tgtaaaaata ccaaaggaaa    6900
ctcgtctcga acatcccctt ggagatgaat tcctcccgca acttgcggaa atcctcctgg    6960
ggctcatcac gcttaggctt gggtgcaaca ggtgtgtcag gagaggaagg ctccataaca    7020
ggcattctct tcaacttggc gacggcttct tgagagtgca tcaccatgaa gacatcggtc    7080
gcatcgcggt tgcgatagtt ctcgataatg tcagctcctc cagggtggtg attgacccaa    7140
gcagacacat cataagttgc gccatcaatt gtgattggca gagcttgccg cttaggagac    7200
atggtgcggc cgcggtgatg actgatgagt gtttaaggac caatggagag aatgtttgag    7260
```

```
ttgtgaagcg gagaacctga ggcgtggtta tttataggga agagaggaag gtgaatgagg    7320
gacacgtcac agaagtaggg tgctgagctt gagacattct tcagtatgca tggctatgga    7380
agccttgggt gctacacctc atgaagttca tggtgtgagg tggcttcggc atctcaatta    7440
agtgacaaag agaaaggtgt ttcagtgttt ctattgcaaa tggcagaaac tcgtgatgac    7500
gaggggacca tgcatggttt catttctttt cttcctggat tctttcttcc cttttatata    7560
tgcaggttca taatttaaaa attagactcg ctttcaattt cttaatttct cattttcctc    7620
ttatattact gtactaatgt taaccacgta cacttatttt tttttttagtt taattttgat    7680 agattgtgtt gatttaaaca tattaatatt ttcaaccaaa taaaaatcat tttagtagat    7740
acggcttttt aaataattat taaaaatatt aactatttat cctaaatggc acattttaat    7800
taaaaaaaat ccggtgttgt aagtgtttta ttaatttgtt ttggcattat taaagcaact    7860
ttttttttat tgttggcat tttgagtacg tacttaggct agcctgca    7908

<210> SEQ ID NO 141
<211> LENGTH: 18662
<212> TYPE: DNA
<213> ORGANISM: Artificial Sequence
<220> FEATURE:
<223> OTHER INFORMATION: pKR1022R

<400> SEQUENCE: 141
cgcgccagat cctctagagt cgacctgcag gcatgcaagc ttggcgtaat catggtcata      60
gctgtttcct gtgtgaaatt gttatccgct cacaattcca cacaacatac gagccggaag     120
cataaagtgt aaagcctggg gtgcctaatg agtgagctaa ctcacattaa ttgcgttgcg     180
ctcactgccc gctttccagt cgggaaacct gtcgtgccag ctgcattaat gaatcggcca     240
acgcgcgggg agaggcggtt tgcgtattgg atcgatccct gaaagcgacg ttggatgtta     300
acatctacaa attgcctttt cttatcgacc atgtacgtaa gcgcttacgt ttttggtgga     360
cccttgagga aactggtagc tgttgtgggc ctgtggtctc aagatggatc attaatttcc     420
accttcacct acgatggggg gcatcgcacc ggtgagtaat attgtacggc taagagcgaa     480
tttggcctgt agacctcaat tgcgagcttt ctaatttcaa actattcggg cctaactttt     540
ggtgtgatga tgctgactgg caggatatat accgttgtaa tttgagctcg tgtgaataag     600
tcgctgtgta tgtttgtttg attgtttctg ttggagtgca gcccatttca ccggacaagt     660
cggctagatt gatttagccc tgatgaactg ccgaggggaa gccatcttga gcgcggaatg     720
ggaatggatt tcgttgtaca acgagacgac agaacaccca cgggaccgag cttcgcgagc     780
ttttgtatcc gtggcatcct tggtccgggc gatttgttca cgtccatgag gcgctctcca     840
aaggaacgca tattttccgg tgcaaccttt ccggttcttc ctctactcga cctcttgaag     900
tcccagcatg aatgttcgac cgctccgcaa gcggatcttt ggcgcaacca gccggtttcg     960
cacgtcgatt ctcgcgagcc tgcatacttt ggcaagattg ctgaatgacg ctgatgcttc    1020
atcgcaatct gcgataatgg ggtaagtatc cggtgaaggc cgcaggtcag gccgcctgag    1080
cactcagtgt cttggatgtc cagttccacg gcagctgttg ctcaagcctg ctgatcggag    1140
cgtccgcaag gtcggcgcgg acgtcggcaa gccaggcctg cggatcgatg ttattgagct    1200
tggcgctcat gatcagtgtc gccatgaacg ccgcacgttc agcacaacga tccgatccgg    1260
caaacagcca tgacttcctg ccagtacat agcctctgag cgttcgttcg gcagcattgt    1320
tcgtcaggca aatcgggccg tcatcgagga atgacgtaat gccatccat cgcttgagca    1380
```

```
tgtaatttat cgcctcggcg acgggagaac tgcgcgacaa tttcccccgc tcggtttcga   1440
gccaatcatg cagctcttcg gcgagtgacc ttgatcaggc caccgccacg accgcggaag   1500
acgaacagat gcctgcgcat cggatcgcgc ttcagcgtct cttgcaccat cagcgacaaa   1560
ccgggaaagc ctttgcgcat gtccgtactt atgtcgccac ttgggagggc ttcgtctacg   1620
tggccttcgt gatcgacgtc ttcgcccgtc gcattgtcgg atggcgggcg agccggacag   1680
cacatgcagg ctttgtcctc gatgccctcg aggaggctca tcatgatcgg cgtcccgctc   1740
atggcggcct agtgcatcac tcggatcgcg gtgttcaata cgtgtccttt cgctattccg   1800
agcggttggc agaagcaggt atcgagccat ctatcggaag cgtcggcgac agcacgacaa   1860
cgccctcgca gaagcgatca acggtcttta caaggccgag gtcattcatc ggcgtggacc   1920
atggaggagc ttcgaagcgg tcgagttcgc taccttggaa tggatagact ggttcaacca   1980
cggcggcttt tgaagcccat cggcaatata ccgccagccg aagacgagga tcagtattac   2040
gccatgctgg acgaagcagc catgctgcgc cattttaacg aaatggcctc cggcaaaccc   2100
ggtgcggttc acttgttgcg tgggaaagtt cacgggactc cgcgcacgag ccttcttcgt   2160
aatagccata tcgaccgaat tgacctgcag gggggggggg gaaagccacg ttgtgtctca   2220
aaatctctga tgttacattg cacaagataa aaatatatca tcatgaacaa taaaactgtc   2280
tgcttacata aacagtaata caaggggtgt tatgagccat attcaacggg aaacgtcttg   2340
ctcgaggccg cgattaaatt ccaacatgga tgctgattta tatgggtata atgggctcg    2400 cgataatgtc gggcaatcag gtgcgacaat ctatcgattg tatgggaagc ccgatgcgcc   2460
agagttgttt ctgaaacatg gcaaaggtag cgttgccaat gatgttacag atgagatggt   2520
cagactaaac tggctgacgg aatttatgcc tcttccgacc atcaagcatt ttatccgtac   2580
tcctgatgat gcatggttac tcaccactgc gatccccggg aaaacagcat ccaggtatt    2640 agaagaatat cctgattcag gtgaaaatat tgttgatgcg ctggcagtgt tcctgcgccg   2700
gttgcattcg attcctgttt gtaattgtcc ttttaacagc gatcgcgtat tcgtctcgc    2760 tcaggcgcaa tcacgaatga ataacggttt ggttgatgcg agtgattttg atgacgagcg   2820
taatggctgg cctgttgaac aagtctggaa agaaatgcat aagcttttgc cattctcacc   2880
ggattcagtc gtcactcatg gtgatttctc acttgataac cttatttttg acgaggggaa   2940
attaataggt tgtattgatg ttggacgagt cggaatcgca gaccgatacc aggatcttgc   3000
catcctatgg aactgcctcg gtgagttttc tccttcatta cagaaacggc ttttcaaaa    3060 atatggtatt gataatcctg atatgaataa attgcagttt catttgatgc tcgatgagtt   3120
tttctaatca gaattggtta attggttgta acactggcag agcattacgc tgacttgacg   3180
ggacggcggc tttgttgaat aaatcgaact tttgctgagt tgaaggatca gatcacgcat   3240
cttcccgaca acgcagaccg ttccgtggca aagcaaaagt tcaaaatcac caactggtcc   3300
acctacaaca aagctctcat caaccgtggc tccctcactt tctggctgga tgatggggcg   3360
attcaggcct ggtatgagtc agcaacacct tcttcacgag gcagacctca gcgccccccc   3420
ccccctgcag gtcttttcca atgatgagca cttttaaagt tctgctatgt ggcgcggtat   3480
tatcccgtgt tgacgccggg caagagcaac tcggtcgccg catacactat tctcagaatg   3540
acttggttga gtactcacca gtcacagaaa agcatcttac ggatggcatg acagtaagag   3600
aattatgcag tgctgccata accatgagtg ataacactgc ggccaactta cttctgacaa   3660
cgatcggagg accgaaggag ctaaccgctt ttttgcacaa catgggggat catgtaactc   3720
gccttgatcg ttgggaaccg gagctgaatg aagccatacc aaacgacgag cgtgacacca   3780
```

```
cgatgcctgt agcaatggca acaacgttgc gcaaactatt aactggcgaa ctacttactc   3840
tagcttcccg gcaacaatta atagactgga tggaggcgga taaagttgca ggaccacttc   3900
tgcgctcggc ccttccggct ggctgggtta ttgctgataa atctggagcc ggtgagcgtg   3960
ggtctcgcgg tatcattgca gcactggggc cagatggtaa gccctcccgt atcgtagtta   4020
tctacacgac ggggagtcag gcaactatgg atgaacgaaa tagacagatc gctgagatag   4080
gtgcctcact gattaagcat tggtaactgt cagaccaagt ttactcatat atactttaga   4140
ttgatttaaa acttcatttt taatttaaaa ggatctaggt gaagatcctt tttgataatc   4200
tcatgaccaa aatcccttaa cgtgagtttt cgttccactg agcgtcagac cccgtagaaa   4260
agatcaaagg atcttcttga gatcctttt ttctgcgcgt aatctgctgc ttgcaaacaa   4320
aaaaaccacc gctaccagcg gtggtttgtt tgccggatca agagctacca actcttttc   4380
cgaaggtaac tggcttcagc agagcgcaga taccaaatac tgtccttcta gtgtagccgt   4440
agttaggcca ccacttcaag aactctgtag caccgcctac atacctcgct ctgctaatcc   4500
tgttaccagt ggctgctgcc agtggcgata agtcgtgtct taccgggttg actcaagac   4560
gatagttacc ggataaggcg cagcggtcgg gctgaacggg gggttcgtgc acacagccca   4620
gcttggagcg aacgacctac accgaactga gatacctaca gcgtgagcta tgagaaagcg   4680
ccacgcttcc cgaagggaga aaggcggaca ggtatccggt aagcggcagg gtcggaacag   4740
gagagcgcac gagggagctt ccagggggaa acgcctggta tctttatagt cctgtcgggt   4800
ttcgccacct ctgacttgag cgtcgatttt tgtgatgctc gtcagggggg cggagcctat   4860
ggaaaaacgc cagcaacgcg gcctttttac ggttcctggc cttttgctgg ccttttgctc   4920
acatgttctt tcctgcgtta tcccctgatt ctgtggataa ccgtattacc gcctttgagt   4980
gagctgatac cgctcgccgc agccgaacga ccgagcgcag cgagtcagtg agcgaggaag   5040
cggaagagcg cctgatgcgg tattttctcc ttacgcatct gtgcggtatt tcacaccgca   5100
tatggtgcac tctcagtaca atctgctctg atgccgcata gttaagccag tatacactcc   5160
gctatcgcta cgtgactggg tcatggctgc gccccgacac ccgccaacac ccgctgacgc   5220
gccctgacgg gcttgtctgc tcccggcatc cgcttacaga caagctgtga ccgtctccgg   5280
gagctgcatg tgtcagaggt tttcaccgtc atcaccgaaa cgcgcgaggc agggtgcctt   5340
gatgtgggcg ccggcggtcg agtggcgacg gcgcggcttg tccgcgccct ggtagattgc   5400
ctggccgtag gccagccatt tttgagcggc agcggccgc gataggccga cgcgaagcgg   5460
cggggcgtag ggagcgcagc gaccgaaggg taggcgcttt ttgcagctct tcggctgtgc   5520
gctggccaga cagttatgca caggccaggc gggttttaag agttttaata agttttaaag   5580
agttttaggc ggaaaaatcg ccttttttct cttttatatc agtcacttac atgtgtgacc   5640
ggttcccaat gtacggcttt gggttcccaa tgtacgggtt ccggttccca atgtacggct   5700
ttgggttccc aatgtacgtg ctatccacag gaaagagacc ttttcgacct ttttcccctg   5760
ctagggcaat tgccctagc atctgctccg tacattagga accggcggat gcttcgccct   5820
cgatcaggtt gcggtagcgc atgactagga tcgggccagc ctgccccgcc tcctccttca   5880
aatcgtactc cggcaggtca tttgacccga tcagcttgcg cacggtgaaa cagaacttct   5940
tgaactctcc ggcgctgcca ctgcgttcgt agatcgtctt gaacaaccat ctggcttctg   6000
ccttgcctgc ggcgcggcgt gccaggcggt agagaaaacg gccgatgccg ggatcgatca   6060
aaaagtaatc ggggtgaacc gtcagcacgt ccgggttctt gccttctgtg atctcgcggt   6120
```

```
acatccaatc agctagctcg atctcgatgt actccggccg cccggtttcg ctctttacga    6180
tcttgtagcg gctaatcaag gcttcaccct cggataccgt caccaggcgg ccgttcttgg    6240
ccttcttcgt acgctgcatg gcaacgtgcg tggtgtttaa ccgaatgcag gtttctacca    6300
ggtcgtcttt ctgctttccg ccatcggctc gccggcagaa cttgagtacg tccgcaacgt    6360
gtggacggaa cacgcggccg ggcttgtctc ccttcccttc ccggtatcgg ttcatggatt    6420
cggttagatg ggaaaccgcc atcagtacca ggtcgtaatc ccacacactg gccatgccgg    6480
ccggccctgc ggaaacctct acgtgcccgt ctggaagctc gtagcggatc acctcgccag    6540
ctcgtcggtc acgcttcgac agacggaaaa cggccacgtc catgatgctg cgactatcgc    6600
gggtgcccac gtcatagagc atcggaacga aaaatctgg ttgctcgtcg cccttgggcg    6660
gcttcctaat cgacggcgca ccggctgccg gcggttgccg ggattctttg cggattcgat    6720
cagcggccgc ttgccacgat tcaccggggc gtgcttctgc ctcgatgcgt tgccgctggg    6780
cggcctgcgc ggccttcaac ttctccacca ggtcatcacc cagcgccgcg ccgatttgta    6840
ccgggccgga tggtttgcga ccgctcacgc cgattcctcg ggcttggggg ttccagtgcc    6900
attgcagggc cggcagacaa cccagccgct tacgcctggc caaccgcccg ttcctccaca    6960
catgggcat tccacggcgt cggtgcctgg ttgttcttga ttttccatgc cgcctccttt     7020
agccgctaaa attcatctac tcatttattc atttgctcat ttactctggt agctgcgcga    7080
tgtattcaga tagcagctcg gtaatggtct tgccttggcg taccgcgtac atcttcagct    7140
tggtgtgatc ctccgccggc aactgaaagt tgacccgctt catggctggc gtgtctgcca    7200
ggctggccaa cgttgcagcc ttgctgctgc gtgcgctcgg acggccggca cttagcgtgt    7260
ttgtgctttt gctcattttc tctttacctc attaactcaa atgagttttg atttaatttc    7320
agcggccagc gcctggacct cgcgggcagc gtcgccctcg ggttctgatt caagaacggt    7380
tgtgccggcg gcggcagtgc ctgggtagct cacgcgctgc gtgatacggg actcaagaat    7440
gggcagctcg tacccggcca gcgcctcggc aacctcaccg ccgatgcgcg tgcctttgat    7500
cgcccgcgac acgacaaagg ccgcttgtag ccttccatcc gtgacctcaa tgcgctgctt    7560
aaccagctcc accaggtcgg cggtggccca tatgtcgtaa gggcttggct gcaccggaat    7620
cagcacgaag tcggctgcct tgatcgcgga cacagccaag tccgccgcct ggggcgctcc    7680
gtcgatcact acgaagtcgc gccggccgat ggccttcacg tcgcggtcaa tcgtcgggcg    7740
gtcgatgccg acaacggtta gcggttgatc ttcccgcacg gccgcccaat cgcgggcact    7800
gccctgggga tcggaatcga ctaacagaac atcggccccg gcgagttgca gggcgcgggc    7860
tagatgggtt gcgatggtcg tcttgcctga cccgcctttc tggttaagta cagcgataac    7920
ttcatgcgtt cccttgcgta tttgtttatt tactcatcgc atcatatacg cagcgaccgc    7980
atgacgcaag ctgtttact caaatacaca tcacctttt agacggcggc gctcggtttc      8040
ttcagcggcc aagctggccg gccaggccgc cagcttggca tcagacaaac cggccaggat    8100
ttcatgcagc cgcacggttg agacgtgcgc gggcggctcg aacacgtacc ggccgcgat    8160
catctccgcc tcgatctctt cggtaatgaa aaacggttcg tcctggccgt cctggtgcgg    8220
tttcatgctt gttcctcttg gcgttcattc tcggcggccg ccagggcgtc ggcctcggtc    8280
aatgcgtcct cacggaaggc accgcgccgc ctggcctcgg tgggcgtcac ttcctcgctg    8340
cgctcaagtg cgcggtacag ggtcgagcga tgcacgccaa gcagtgcagc cgcctctttc    8400
acggtgcggc cttcctggtc gatcagctcg cgggcgtgcg cgatctgtgc cggggtgagg    8460
gtagggcggg ggccaaactt cacgcctcgg gccttggcgg cctcgcgccc gctccgggtg    8520
```

```
cggtcgatga ttagggaacg ctcgaactcg gcaatgccgg cgaacacggt caacaccatg   8580
cggccggccg gcgtggtggt gtcggcccac ggctctgcca ggctacgcag gcccgcgccg   8640
gcctcctgga tgcgctcggc aatgtccagt aggtcgcggg tgctgcgggc caggcggtct   8700
agcctggtca ctgtcacaac gtcgccaggg cgtaggtggt caagcatcct ggccagctcc   8760
gggcggtcgc gcctggtgcc ggtgatcttc tcggaaaaca gcttggtgca gccggccgcg   8820
tgcagttcgg cccgttggtt ggtcaagtcc tggtcgtcgg tgctgacgcg gcatagccc    8880
agcaggccag cggcggcgct cttgttcatg gcgtaatgtc tccggttcta gtcgcaagta   8940
ttctacttta tgcgactaaa acacgcgaca agaaaacgcc aggaaaaggg cagggcggca   9000
gcctgtcgcg taacttagga cttgtgcgac atgtcgtttt cagaagacgg ctgcactgaa   9060
cgtcagaagc cgactgcact atagcagcgg aggggttgga ccacaggacg ggtgtggtcg   9120
ccatgatcgc gtagtcgata gtggctccaa gtagcgaagc gagcaggact gggcggcggc   9180
caaagcggtc ggacagtgct ccgagaacgg gtgcgcatag aaattgcatc aacgcatata   9240
gcgctagcag cacgccatag tgactggcga tgctgtcgga atggacgata tcccgcaaga   9300
ggcccggcag taccggcata accaagccta tgcctacagc atccagggtg acggtgccga   9360
ggatgacgat gagcgcattg ttagatttca tacacggtgc ctgactgcgt tagcaattta   9420
actgtgataa actaccgcat taaagctagc ttgcttggtc gttccgcgtg aacgtcggct   9480
cgattgtacc tgcgttcaaa tactttgcga tcgtgttgcg cgcctgcccg gtgcgtcggc   9540
tgatctcacg gatcgactgc ttctctcgca acgccatccg acggatgatg tttaaaagtc   9600
ccatgtggat cactccgttg ccccgtcgct caccgtgttg ggggaaggt gcacatggct   9660
cagttctcaa tggaaattat ctgcctaacc ggctcagttc tgcgtagaaa ccaacatgca   9720
agctccaccg ggtgcaaagc ggcagcggcg gcaggatata ttcaattgta aatggcttca   9780
tgtccgggaa atctacatgg atcagcaatg agtatgatgg tcaatatgga gaaaagaaa    9840
gagtaattac caatttttt tcaattcaaa aatgtagatg tccgcagcgt tattataaaa   9900
tgaaagtaca ttttgataaa acgacaaatt acgatccgtc gtatttatag gcgaaagcaa   9960
taaacaaatt attctaattc ggaaatcttt atttcgacgt gtctacattc acgtccaaat  10020
gggggcttag atgagaaact tcacgatcga tgccttgatt tcgccattcc cagataccca  10080
tttcatcttc agattggtct gagattatgc gaaaatatac actcatatac ataaatactg  10140
acagtttgag ctaccaattc agtgtagccc attacctcac ataattcact caaatgctag  10200
gcagtctgtc aactcggcgt caatttgtcg gccactatac gatagttgcg caaattttca  10260
aagtcctggc ctaacatcac acctctgtcg gcggcgggtc ccatttgtga taaatccacc  10320
atatcgaatt aattcagact cctttgcccc agagatcaca atggacgact tcctctatct  10380
ctacgatcta gtcaggaagt tcgacggaga aggtgacgat accatgttca ccactgataa  10440
tgagaagatt agccttttca atttcagaaa gaatgctaac ccacagatgg ttagagaggc  10500
ttacgcagca ggtctcatca agacgatcta cccgagcaat aatctccagg agatcaaata  10560
ccttcccaag aaggttaaag atgcagtcaa aagattcagg actaactgca tcaagaacac  10620
agagaaagat atatttctca agatcagaag tactattcca gtatgacga ttcaaggctt   10680
gcttcacaaa ccaaggcaag taatagagat tggagtctct aaaaaggtag ttcccactga  10740
atcaaaggcc atggagtcaa agattcaaat agaggaccta acagaactcg ccgtaaagac  10800
tggcgaacag ttcatacaga gtctcttacg actcaatgac aagaagaaaa tcttcgtcaa  10860
```

```
catggtggag cacgacacgc ttgtctactc caaaaatatc aaagatacag tctcagaaga   10920
ccaaagggca attgagactt ttcaacaaag ggtaatatcc ggaaacctcc tcggattcca   10980
ttgcccagct atctgtcact ttattgtgaa gatagtggaa aaggaaggtg gctcctacaa   11040
atgccatcat tgcgataaag gaaaggccat cgttgaagat gcctctgccg acagtggtcc   11100
caaagatgga cccccaccca cgaggagcat cgtggaaaaa gaagacgttc caaccacgtc   11160
ttcaaagcaa gtggattgat gtgatatctc cactgacgta agggatgacg cacaatccca   11220
ctatccttcg caagacccttcctctatata aggaagttca tttcatttgg agaggacacg   11280
ctgaaatcac cagtctccaa gcttgcgggg atcgtttcgc atgattgaac aagatggatt   11340
gcacgcaggt tctccggccg cttgggtgga gaggctattc ggctatgact gggcacaaca   11400
gacaatcggc tgctctgatg ccgccgtgtt ccggctgtca gcgcagggc gcccggttct    11460
ttttgtcaag accgacctgt ccggtgccct gaatgaactg caggacgagg cagcgcggct   11520
atcgtggctg gccacgacgg gcgttccttg cgcagctgtg ctcgacgttg tcactgaagc   11580
gggaagggac tggctgctat tgggcgaagt gccggggcag gatctcctgt catctcacct   11640
tgctcctgcc gagaaagtat ccatcatggc tgatgcaatg cggcggctgc atacgcttga   11700
tccggctacc tgcccattcg accaccaagc gaaacatcgc atcgagcgag cacgtactcg   11760
gatggaagcc ggtcttgtcg atcaggatga tctggacgaa gagcatcagg gctcgcgcc    11820
agccgaactg ttcgccaggc tcaaggcgcg catgcccgac ggcgaggatc tcgtcgtgac   11880
ccatggcgat gcctgcttgc cgaatatcat ggtggaaaat ggccgctttt ctggattcat   11940
cgactgtggc cggctgggtg tggcggaccg ctatcaggac atagcgttgg ctacccgtga   12000
tattgctgaa gagcttggcg gcgaatgggc tgaccgcttc ctcgtgcttt acggtatcgc   12060
cgctcccgat tcgcagcgca tcgccttcta tcgccttctt gacgagttct tctgagcggg   12120
actctggggt tcgaaatgac cgaccaagcg acgcccaacc tgccatcacg agatttcgat   12180
tccaccgccg ccttctatga aaggttgggc ttcggaatcg ttttccggga cgccggctgg   12240
atgatcctcc agcgcgggga tctcatgctg gagttcttcg cccacccccgg atcgatccaa   12300
cacttacgtt tgcaacgtcc aagagcaaat agaccacgaa cgccggaagg ttgccgcagc   12360
gtgtggattg cgtctcaatt ctctcttgca ggaatgcaat gatgaatatg atactgacta   12420
tgaaactttg agggaatact gcctagcacc gtcacctcat aacgtgcatc atgcatgccc   12480
tgacaacatg gaacatcgct attttttctga agaattatgc tcgttggagg atgtcgcggc   12540
aattgcagct attgccaaca tcgaactacc cctcacgcat gcattcatca atattattca   12600
tgcggggaaa ggcaagatta atccaactgg caaatcatcc agcgtgattg gtaacttcag   12660
ttccagcgac ttgattcgtt ttggtgctac ccacgttttc aataaggacg agatggtgga   12720
gtaaagaagg agtgcgtcga agcagatcgt tcaaacattt ggcaataaag tttcttaaga   12780
ttgaatcctg ttgccggtct tgcgatgatt atcatataat ttctgttgaa ttacgttaag   12840
catgtaataa ttaacatgta atgcatgacg ttatttatga gatgggtttt tatgattaga   12900
gtcccgcaat tatacattta atacgcgata gaaaacaaaa tatagcgcgc aaactaggat   12960
aaattatcgc gcgcggtgtc atctatgtta ctagatcgat caaacttcgg tactgtgtaa   13020
tgacgatgag caatcgagag gctgactaac aaaaggtaca tcgcgatgga tcgatccatt   13080
cgccattcag gctgcgcaac tgttgggaag ggcgatcggt gcgggcctct tcgctattac   13140
gccagctggc gaaagggggg atgtgctgcaa ggcgattaag ttgggtaacg ccagggtttt   13200
cccagtcacg acgttgtaaa acgacggcca gtgaattcct gcagcccggg ggatccgccc   13260
```

```
actcgaggcg cgccgtcgac ggatccgtac gagatccggc cggccagatc ctgcagcccg    13320
ggggatcctc tagacgtacg tgaaggttaa acatggtgaa tatgttacca ctagctggga    13380
tgcccattag atcaaaactg taaaattctc ccgtttccct tctattcaca tgtgagcccc    13440
ctcccttttc tttctttctc aattttgatt gagttaaagt caccagcaat gcatcactca    13500
ccctccaaaa aatttcttgt acaacttctc ggactatccc aaagctcctt ttcctgagat    13560
ggatggtcct gtctcttgcc cttgatgtct tccttgttcg attttggctt cctctaatgt    13620
ctttcttgct aggaatcacc acctcactca tctatgttgt cgtagcttct gaaagtctca    13680
tacatatcct tagtgttgca ctcatcttgt attgaagtga aaagaatgt tgttctccta     13740
tccaaatctc cattgaatct ctttctccca atgttgtccc atcggttggt cctcctctcc    13800
aaccaattgt aaggtgttta acataaacat ggtacaatta agattttca tttcattaag     13860
aaaagattga gatttgtggt tctaaagttt caattagagt ttgatgatat tgaaacaacc    13920
gtagaacaca ttaagtatta ctaacttata catagagcat tggaatttca ccttttattt    13980
attctgtttc cgccaaaggt acatgactca agttatttta cacaagtaac aaagcatct     14040
aagcctaagt attcttattc agactttca ttattacttt cattgatttg gtgcgaaatg     14100
cggccgctca ttcagggaca gcagccagct gggcaatctc gcctaagaag ctgaccaatt    14160
tctgaacccc ggggatgatg gctggggccc tgtagggcag gttgtgcttg cgcacaact    14220
tctgcacctc cagggaagct gccgtgaggt tgtgcctggg catgttgggc cacaagtggt    14280
gctcaatctg gtagttgaga ccaccaaaga cccaatcggt gagaaggccg ggcttaatgt    14340
tcaacgtctc gtggatctgg ctggcgctga acccgtgctc atcccagaca gtctcctcaa    14400
ccttgtccaa aggatagtga ttcagaaaca caacgatggc aatgccaaat cctccgagca    14460
gctcggagat caagaagcat cccaaaccgg tggcaaagct aggcatggca ctgcaataga    14520
aagtggcctt gagcacccag tggagggcca gaccaatcgc ctccttagtg tactggcgct    14580
tgtagtacag gttcctctcc tcgctcttgt aggacatgac gccgccgatg gattggaggc    14640
accagatgaa cctaagggat gcaatggtgg gaatgaagta gtactgctgg tacttgatga    14700
gattccgagt cgaaggagta gccctcttga catcttcggg agaccaagcc aggatgggga    14760
ggttatcaat atctgggtca tggccgacca cattggtggc ggcatggtga ccattgtgcc    14820
tatccttcca ccaagtctgt gagtatccct gcatcacgtt accgaaaaag agaccgaaag    14880
cgtcgttaat cttgcggttt gtgaaaacct ggtgatggca atagtcgtgg gacaaccagc    14940
ctagctgttg gtagcacacg ccaagaacca aagcagcggt gaaataccaa ttcgtgtaca    15000
cggtcatcaa gatggaaagg accatcaaac cgacggtagt tgaagtcttg taaaaatacc    15060
aaaggaaact cgtctcgaac atacccttgg agatgaattc ctcccgcaac ttgcggaaat    15120
cctcctgggg ctcatcacgc ttaggcttgg gtgcaacagg tgtgtcagga gaggaaggct    15180
ccataacagg cattctcttc aacttggcga cggcttcttg agagtgcatc accatgaaga    15240
catcggtcgc atcgcggttg cgatagttct cgataatgtc agctcctcca gggtggtgat    15300
tgacccaagc agacacatca taagttgcgc catcaattgt gattggcaga gcttgccgct    15360
taggagacat ggtgcggccg cggtgatgac tgatgagtgt ttaaggacca atggagagaa    15420
tgtttgagtt gtgaagcgga gaacctgagg cgtggttatt tatagggaag agaggaaggt    15480
gaatgaggga cacgtcacag aagtagggtg ctgagcttga gacattcttc agtatgcatg    15540
gctatggaag ccttgggtgc tacacctcat gaagttcatg gtgtgaggtg gcttcggcat    15600
```

```
ctcaattaag tgacaaagag aaaggtgttt cagtgtttct attgcaaatg gcagaaactc    15660
gtgatgacga ggggaccatg catggtttca tttcttttct tcctggattc tttctttcct    15720
tttatatatg caggttcata atttaaaaat tagactcgct ttcaatttct taatttctca    15780
ttttcctctt atattactgt actaatgtta accacgtaca cttattttt ttttagttta     15840
attttgatag attgtgttga tttaaacata ttaatatttt caaccaaata aaaatcattt    15900
tagtagatac ggcttttaa ataattatta aaaatattaa ctatttatcc taaatggcac     15960
attttaatta aaaaaaatcc ggtgttgtaa gtgttttatt aatttgtttt ggcattatta    16020
aagcaacttt tttttattt gttggcattt tgagtacgta cttaggctag cctgcaggag     16080
atccaagctt ttgatccatg cccttcattt gccgcttatt aattaatttg gtaacagtcc    16140
gtactaatca gttacttatc cttcccccat cataattaat cttggtagtc tcgaatgcca    16200
caacactgac tagtctcttg gatcataaga aaagccaag gaacaaaaga agacaaaaca     16260
caatgagagt atcctttgca tagcaatgtc taagttcata aaattcaaac aaaaacgcaa    16320
tcacacacag tggacatcac ttatccacta gctgatcagg atcgccgcgt caagaaaaaa    16380
aaaactggacc ccaaaagcca tgcacaacaa cacgtactca caaggtgtc aatcgagcag     16440
cccaaaacat tcaccaactc aacccatcat gagccctcac atttgttgtt tctaacccaa    16500
cctcaaactc gtattctctt ccgccacctc attttgttt atttcaacac ccgtcaaact     16560
gcatgccacc ccgtggccaa atgtccatgc atgttaacaa gacctatgac tataaatagc    16620
tgcaatctcg gcccaggttt tcatcatcaa gaaccagttc aatatcctag tacaccgtat    16680
taaagaattt aagatatact gcggccgcac catggaggtg gtgaatgaaa tagtctcaat    16740
tgggcaggaa gttttacca agttgatta tgcccaactc tggagtgatg ccagtcactg     16800
tgaggtgctt tacttgtcca tcgcatttgt catcttgaag ttcactcttg gccccttgg    16860
tccaaaaggt cagtctcgta tgaagtttgt tttcaccaat tacaaccttc tcatgtccat    16920
ttattcgttg ggatcattcc tctcaatggc atatgccatg tacaccatcg tgttatgtc     16980
tgacaactgc gagaaggctt ttgacaacaa cgtcttcagg atcaccacgc agttgttcta    17040
tttgagcaag ttcctggagt atattgactc cttctatttg ccactgatgg gcaagcctct    17100
gacctggttg caattcttcc atcatttggg ggcaccgatg gatatgtggc tgttctataa    17160
ttaccgaaat gaagctgttt ggattttgt gctgttgaat ggtttcatcc actggatcat    17220
gtacggttat tattggacca gattgatcaa gctgaagttc cccatgccaa atccctgat     17280
tacatcaatg cagatcattc aattcaatgt tggtttctac attgtctgga agtacaggaa    17340
cattccctgt tatcgccaag atgggatgag gatgtttggc tggttcttca attacttta    17400
tgttggcaca gtcttgtgtt tgttcttgaa tttctatgtg caaacgtata tcgtcaggaa    17460
gcacaaggga gccaaaaaga ttcagtgagc ggccgcaagt atgaactaaa atgcatgtag    17520
gtgtaagagc tcatggagag catggaatat tgtatccgac catgtaacag tataataact    17580
gagctccatc tcacttcttc tatgaataaa caaggatgt tatgatatat taacactcta    17640
tctatgcacc ttattgttct atgataaatt tcctcttatt attataaatc atctgaatcg    17700
tgacggctta tggaatgctt caaatagtac aaaaacaaat gtgtactata agactttcta    17760
aacaattcta accttagcat tgtgaacgag acataagtgt taagaagaca taacaattat    17820
aatggaagaa gtttgtctcc atttatatat tatatattac ccactatgt attatattag     17880
gatgttaagg agacataaca attataaaga gagaagtttg tatccattta tatattatat    17940
actacccatt tatatattat acttatccac ttatttaatg tctttataag gtttgatcca    18000
```

```
tgatatttct aatattttag ttgatatgta tatgaaaggg tactatttga actctcttac  18060
tctgtataaa ggttggatca tccttaaagt gggtctattt aattttattg cttcttacag  18120
ataaaaaaaa aattatgagt tggtttgata aaatattgaa ggatttaaaa taataataaa  18180
taacatataa tatatgtata taaatttatt ataatataac atttatctat aaaaaagtaa  18240
atattgtcat aaatctatac aatcgtttag ccttgctgga cgaatctcaa ttatttaaac  18300
gagagtaaac atatttgact ttttggttat ttaacaaatt attatttaac actatatgaa  18360 atttttttt ttatcagcaa agaataaaat taaattaaga aggacaatgg tgtcccaatc  18420
cttatacaac caacttccac aagaaagtca agtcagagac aacaaaaaaa caagcaaagg  18480 aaattttta atttgagttg tcttgtttgc tgcataattt atgcagtaaa acactacaca  18540 taacccttt agcagtagag caatggttga ccgtgtgctt agcttctttt attttatttt  18600
tttatcagca aagaataaat aaaataaaat gagacacttc agggatgttt caacaagctt  18660
gg                                                                18662
```